United States Patent [19]
Wityak et al.

[11] Patent Number: 6,114,328
[45] Date of Patent: *Sep. 5, 2000

[54] ISOXAZOLINE AND ISOXAZOLE FIBROGEN RECEPTOR ANTAGONISTS

[75] Inventors: John Wityak, West Grove, Pa.; Chu-Biao Xue, Hockessin, Del.; Thais Motria Sielecki-Dzurdz, Newark, Del.; Richard Eric Olson, Wilmington, Del.; William Frank Degrado, Moylan, Pa.; Gary Avonn Cain; Douglas Guy Batt, both of Wilmington, Del.; Donald Pinto, Newark, Del.; Munir Alwan Hussain, Wilmington, Del.; Shaker Ahmed Mousa, Lincoln University, Pa.

[73] Assignee: Dupont Pharmaceuticals Company, Wilmington, Del.

[ * ] Notice: This patent is subject to a terminal disclaimer.

[21] Appl. No.: 08/978,295

[22] Filed: Nov. 25, 1997

Related U.S. Application Data

[60] Division of application No. 08/455,436, May 31, 1995, Pat. No. 5,849,736, which is a continuation-in-part of application No. 08/337,929, Nov. 10, 1994, which is a continuation-in-part of application No. 08/232,961, Apr. 22, 1994, which is a continuation-in-part of application No. 08/157,598, Nov. 24, 1993.

[51] Int. Cl.$^7$ ........................ A61K 31/54; A61K 31/445; C07D 261/02; C07D 217/00
[52] U.S. Cl. ..................................... 514/227.8; 514/236.8; 514/269; 514/307; 514/326; 514/340; 514/365; 514/378; 514/379; 514/380; 544/60; 544/111; 544/137; 544/140; 544/297; 544/298; 544/322; 544/333; 546/141; 546/143; 546/209; 546/275; 548/146; 548/240; 548/243; 548/248
[58] Field of Search ............................. 514/727.8, 236.8, 514/269, 307, 326, 340, 365, 378, 379, 380; 548/146, 240, 245, 248; 546/141, 143, 209, 275; 594/60, 111, 137, 140, 297, 298, 322, 333

[56] References Cited

U.S. PATENT DOCUMENTS

| | | | |
|---|---|---|---|
| 4,267,186 | 5/1981 | Knops et al. | 548/216 |
| 4,283,544 | 8/1981 | Jautelat et al. | 548/216 |
| 4,358,598 | 11/1982 | Jautelat et al. | 548/216 |
| 5,039,805 | 8/1991 | Alig et al. | 546/234 |

FOREIGN PATENT DOCUMENTS

| | | |
|---|---|---|
| 2008311 | 7/1990 | Canada . |
| 2061661 | 9/1992 | Canada . |
| 2074685 | 1/1993 | Canada . |
| 2093770 | 10/1993 | Canada . |
| 381033 | 8/1990 | European Pat. Off. . |
| 445796 | 9/1991 | European Pat. Off. . |
| 478328 | 4/1992 | European Pat. Off. . |
| 478362 | 4/1992 | European Pat. Off. . |
| 478363 | 4/1992 | European Pat. Off. . |
| 0512831 | 11/1992 | European Pat. Off. . |
| 512829 | 11/1992 | European Pat. Off. . |

OTHER PUBLICATIONS

Phillips et al. *Cell* (1991) 65, 359–362.
Hartman et al. *J Mod Chem* (1992) 35 4640–4642.
Alig et al. *J Med Chem* (1992) 35 4393–4407.

*Primary Examiner*—John Kight
*Assistant Examiner*—Raymond Covington
*Attorney, Agent, or Firm*—Norbert F. Reinert

[57] ABSTRACT

This invention relates to novel isoxazolines and isoxazoles which are useful as antagonists of the platelet glycoprotein IIb/IIIa fibrinogen receptor complex or the vitronectin receptor, to pharmaceutical compositions containing such compounds, processes for preparing such compounds, and to methods of using these compounds, alone or in combination with other therapeutic agents, for the inhibition of platelet aggregation, as thrombolytics, and/or for the treatment of thromboembolic disorders.

49 Claims, No Drawings

ISOXAZOLINE AND ISOXAZOLE FIBROGEN RECEPTOR ANTAGONISTS

This is a division of application Ser. No. 08/455,436, filed May 31, 1995 now U.S. Pat. No. 5,849,736.

CROSS REFERENCE TO EARLIER FILED APPLICATION

This application is a continuation-in-part of U.S. patent application Ser. No. 08/337,929, filed Nov. 10, 1994 which is a continuation-in-part of U.S. patent application Ser. No. 08/232,961, filed Apr. 22, 1994 which is a continuation-in-part of U.S. patent application Ser. No. 08/157,598, filed Nov. 24, 1993. The disclosures of these earlier filed applications are hereby incorporated herein by reference.

FIELD OF THE INVENTION

This invention relates to novel isoxazolines and isoxazoles which are useful as antagonists of the platelet glycoprotein IIb/IIIa fibrinogen receptor complex, to pharmaceutical compositions, including those for intranasal administration, containing such compounds, processes for preparing such compounds, and to methods of using these compounds, alone or in combination with other therapeutic agents, for the inhibition of platelet aggregation, as thrombolytics, and/or for the treatment of thromboembolic disorders.

BACKGROUND OF THE INVENTION

Hemostasis is the normal physiological process in which bleeding from an injured blood vessel is arrested. It is a dynamic and complex process in which platelets play a key role. Within seconds of vessel injury, resting platelets become activated and are bound to the exposed matrix of the injured area by a phenomenon called platelet adhesion. Activated platelets also bind to each other in a process called platelet aggregation to form a platelet plug. The platelet plug can stop bleeding quickly, but it must be reinforced by fibrin for long-term effectiveness, until the vessel injury can be permanently repaired.

Thrombosis may be regarded as the pathological condition wherein improper activity of the hemostatic mechanism results in intravascular thrombus formation. Activation of platelets and the resulting platelet aggregation and platelet factor secretion has been associated with a variety of pathophysiological conditions including cardiovascular and cerebrovascular thromboembolic disorders, for example, the thromboembolic disorders associated with unstable angina, myocardial infarction, transient ischemic attack, stroke, atherosclerosis and diabetes. The contribution of platelets to these disease processes stems from their ability to form aggregates, or platelet thrombi, especially in the arterial wall following injury.

Platelets are activated by a wide variety of agonists resulting in platelet shape change, secretion of granular contents and aggregation. Aggregation of platelets serves to further focus clot formation by concentrating activated clotting factors at the site of injury. Several endogenous agonists including adenosine diphosphate (ADP), serotonin, arachidonic acid, thrombin, and collagen, have been identified. Because of the involvement of several endogenous agonists in activating platelet function and aggregation, an inhibitor which acts against all agonists would represent a more efficacious antiplatelet agent than currently available antiplatelet drugs, which are agonist-specific.

Current antiplatelet drugs are effective against only one type of agonist; these include aspirin, which acts against arachidonic acid; ticlopidine, which acts against ADP; thromboxane $A_2$ synthetase inhibitors or receptor antagonists, which act against thromboxane $A_2$; and hirudin, which acts against thrombin.

Recently, a common pathway for all known agonists has been identified, namely platelet glycoprotein IIb/IIIa complex (GPIIb/IIIa), which is the membrane protein mediating platelet aggregation. A recent review of GPIIb/IIIa is provided by Phillips et al. *Cell* (1991) 65: 359–362. The development of a GPIIb/IIIa antagonist represents a promising new approach for antiplatelet therapy.

GPIIb/IIIa does not bind soluble proteins on unstimulated platelets, but GPIIb/IIIa in activated platelets is known to bind four soluble adhesive proteins, namely fibrinogen, von Willebrand factor, fibronectin, and vitronectin. The binding of fibrinogen and von Willebrand factor to GPIIb/IIIa causes platelets to aggregate. The binding of fibrinogen is mediated in part by the Arg-Gly-Asp (RGD) recognition sequence which is common to the adhesive proteins that bind GPIIb/IIIa.

In addition to GPIIb/IIIa, increasing numbers of other cell surface receptors have been identified which bind to extracellular matrix ligands or other cell adhesion ligands thereby mediating cell—cell and cell-matrix adhesion processes. These receptors belong to a gene superfamily called integrins and are composed of heterodimeric transmembrane glycoproteins containing α- and β-subunits. Integrin subfamilies contain a common β-subunit combined with different α-subunits to form adhesion receptors with unique specificity. The genes for eight distinct β-subunits have been cloned and sequenced to date.

Two members of the β1 subfamily, α4/β1 and α5/β1 have been implicated in various inflammatory processes. Antibodies to α4 prevent adhesion of lymphocytes to synovial endothelial cells in vitro, a process which may be of importance in rheumatoid arthritis (VanDinther-Janssen et al., J. Immunol., 1991, 147:4207). Additional studies with monoclonal anti-α4 antibodies provide evidence that α4/β1 may additionally have a role in allergy, asthma, and autoimmune disorders (Walsh et al., J. Immunol., 1991, 146:3419; Bochner et al., J. Exp. Med., 1991 173:1553; Yednock et al., Nature, 1992, 356:63). Anti-α4 antibodies also block the migration of leukocytes to the site of inflammation (Issedutz et al., J. Immunol., 1991, 147:4178).

The $\alpha_v/\beta_3$ heterodimer, commonly referred to as the vitronectin receptor, is another member of the $\beta_3$ integrin subfamily and has been described in platelets, endothelial cells, melanoma, smooth muscle cells and on the surface of osteoclasts (Horton and Davies, J. Bone Min. Res. 1989, 4:803–808; Davies et al., J. Cell. Biol. 1989, 109:1817–1826; Horton, Int. J. Exp. Pathol., 1990, 71:741–759). Like GPIIb/IIIa, the vitronectin receptor binds a variety of RGD-containing adhesive proteins such as vitronectin, fibronectin, VWF, fibrinogen, osteopontin, bone sialo protein II and thrombospondin in a manner mediated by the RGD sequence. Possible roles for $\alpha_v/\beta_3$ in angiogenesis, tumor progression, and neovascularization have been proposed (Brooks et al., Science, 1994, 264:569–571). A key event in bone resorption is the adhesion of osteoclasts to the matrix of bone. Studies with monoclonal antibodies have implicated the $\alpha_v/\beta_3$ receptor in this process and suggest that a selective $\alpha_v/\beta_3$ antagonist would have utility in blocking bone resorption (Horton et al., J. Bone Miner. Res., 1993, 8:239–247; Helfrich et al., J. Bone Miner. Res., 1992, 7:335–343).

Several RGD-peptidomimetic compounds have been reported which block fibrinogen binding and prevent the formation of platelet thrombi.

European Patent Application Publication Number 478363 relates to compounds having the general formula:

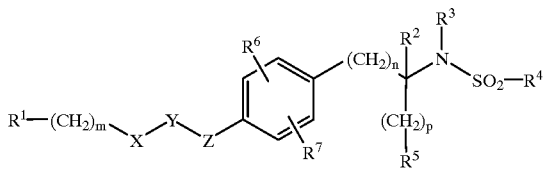

European Patent Application Publication Number 478328 relates to compounds having the general formula:

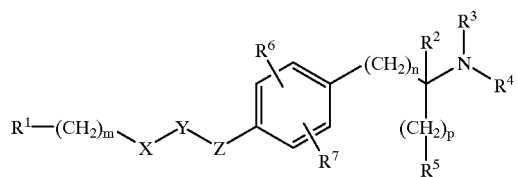

European Patent Application Publication Number 525629 (corresponds to Canadian Patent Application Publication Number 2,074,685) discloses compounds having the general formula:

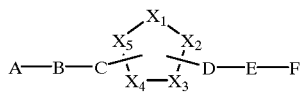

PCT Patent Application 9307867 relates to compounds having the general formula:

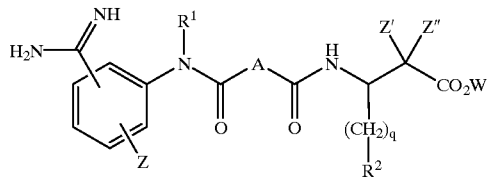

European Patent Application Publication Number 4512831 relates to compounds having the general formula:

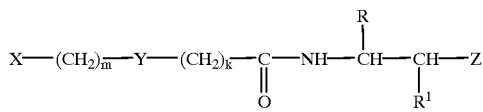

None of the above references teaches or suggests the compounds of the present invention which are described in detail below.

Most peptides and peptidomimetics exhibit very low oral bioavailability due to poor absorption and/or degradation in the GI tract and liver. Therefore, their use is limited to the parenteral route of administration.

Drugs with low bioavailability often have a large variability in pharmacological response due to an associated variability in drug delivery. This large variability in drug delivery may occur when the bioavailability is low because under those conditions, it takes only a small variation in bioavailability to give a large change in plasma drug concentration (W. K. Sietsema, The Absolute Oral Bioavailability of Selected Drug, International Journal of Clinical Pharmacology, Therapy and Toxicology, Vol. 27 No. 4-1989 (179–211)).

Peptides and peptidomimetics have also generally shown relatively low nasal bioavailability. For example, studies with the luteinizing hormone releasing hormone (LHRH) analog, nafarelin acetate, showed that nasal bioavailability was only ~2% (S. T. Anik, G. McRae, C. Nerenberg, A. Worden, J. Foreman, J. Hwang, S. Kushinsky, R. E. Jones, and B. Vickery; J. Pharm., Sci. 73: 684–685 (1984)). Thus, the intranasal administration of peptides and peptidomimetics is generally not recommended.

SUMMARY OF THE INVENTION

The present invention provides novel nonpeptide compounds which bind to integrin receptors thereby altering cell-matrix and cell—cell adhesion processes. The compounds of the present invention are useful for the treatment of inflammation, bone degradation, tumors, metastases, thrombosis, and cell aggregation-related conditions in a mammal.

One aspect of this invention provides novel compounds of Formula I (described below) which are useful as antagonists of the platelet glycoprotein IIb/IIIa complex. The compounds of the present invention inhibit the binding of fibrinogen to platelet glycoprotein IIb/IIIa complex and inhibit the aggregation of platelets. The present invention also includes pharmaceutical compositions containing such compounds of Formula I, and methods of using such compounds for the inhibition of platelet aggregation, as thrombolytics, and/or for the treatment of thromboembolic disorders.

The present invention also includes methods of treating cardiovascular disease, thrombosis or harmful platelet aggregation, reocclusion following thrombolysis, reperfusion injury, or restenosis by administering a compound of Formula I alone or in combination with one or more additional therapeutic agents selected from: anti-coagulants such as warfarin or heparin; anti-platelet agents such as aspirin, piroxicam or ticlopidine; thrombin inhibitors such as boroarginine derivatives, hirudin or argatroban; or thrombolytic agents such as tissue plasminogen activator, anistreplase, urokinase or streptokinase; or combinations thereof.

The present invention also provides novel compounds, pharmaceutical compositions and methods which may be used in the treatment or prevention of diseases which involve cell adhesion processes, including, but not limited to, rheumatoid arthritis, asthma, allergies, adult respiratory distress syndrome, graft versus host disease, organ transplantation, septic shock, psoriasis, eczema, contact dermatitis, osteoporosis, osteoarthritis, atherosclerosis, metastasis, wound healing, diabetic retinopathy, inflammatory bowel disease and other autoimmune diseases.

Also included in the present invention are pharmaceutical kits comprising one or more containers containing pharmaceutical dosage units comprising a compound of Formula I, for the treatment of cell adhesion related disorders, including but not limited to thromboembolic disorders.

DETAILED DESCRIPTION OF THE INVENTION

The present invention provides novel nonpeptide compounds of Formula I (described below) which bind to integrin receptors thereby altering cell-matrix and cell—cell adhesion processes. The compounds of the present invention are useful for the treatment of inflammation, bone degradation, tumors, metastases, thrombosis, and cell aggregation-related conditions in a mammal.

One aspect of this invention provides compounds of Formula I (described below) which are useful as antagonists of the platelet glycoprotein IIb/IIIa complex. The compounds of the present invention inhibit the binding of fibrinogen to the platelet glycoprotein IIb/IIIa complex and inhibit the aggregation of platelets. The present invention also includes pharmaceutical compositions containing such compounds of Formula I, and methods of using such compounds for the inhibition of platelet aggregation, as thrombolytics, and/or for the treatment of thromboembolic disorders.

This invention relates to novel compounds of the Formula I:

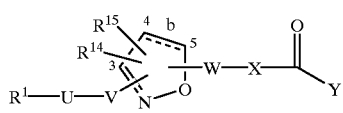

(I)

or a pharmaceutically acceptable salt or prodrug form thereof.

[1] A first embodiment of this invention provides compounds of Formula I:

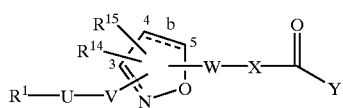

(I)

or pharmaceutically acceptable salt or prodrug forms thereof wherein:

b is a single or double bond;

$R^1$ is selected from $R^2(R^3)N(CH_2)_qZ—$, $R^2(R^3)N(R^2N=)CN(R^2)(CH_2)_qZ—$, piperazinyl-$(CH_2)_qZ—$ or

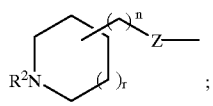

$Z$ is selected from O, S, $S(=O)$, or $S(=O)_2$;

$R^2$ and $R^3$ are independently selected from: H, $C_1-C_{10}$ alkyl, $C_2-C_6$ alkenyl, $C_3-C_{11}$ cycloalkyl, $C_4-C_{11}$ cycloalkylalkyl, $C_6-C_{10}$ aryl, $C_7-C_{11}$ arylalkyl, $C_2-C_7$ alkylcarbonyl, $C_6-C_{10}$ arylcarbonyl, $C_2-C_{10}$ alkoxycarbonyl, $C_4-C_{11}$ cycloalkoxycarbonyl, $C_7-C_{11}$ bicycloalkoxycarbonyl, $C_6-C_{10}$ aryloxycarbonyl, aryl$(C_1-C_{10}$ alkoxy)carbonyl, $C_1-C_6$ alkylcarbonyloxy $(C_1-C_4$ alkoxy)carbonyl, $C_6-C_{10}$ arylcarbonyloxy $(C_1-C_4$ alkoxy)carbonyl, $C_4-C_{11}$ cycloalkylcarbonyloxy$(C_1-C_4$ alkoxy) carbonyl;

U is selected from:
a single bond (i.e., U is not present),
—$(C_1-C_7$ alkyl)-,
—$(C_2-C_7$ alkenyl)-,
—$(C_2-C_7$ alkynyl)-,
—(aryl)-substituted with 0–3 $R^{6a}$, or
-(pyridyl)-substituted with 0–3 $R^{6a}$;

V is selected from:
a single bond (i.e., V is not present);
—$(C_1-C_7$ alkyl)-, substituted with 0–3 groups independently selected from $R^6$ or $R^7$;
—$(C_2-C_7$ alkenyl)-, substituted with 0–3 groups independently selected from $R^6$ or $R^7$;
—$(C_2-C_7$ alkynyl)-, substituted with 0–2 groups independently selected from $R^6$ or $R^7$;
-(aryl)-, substituted with 0–2 groups independently selected from $R^6$ or $R^7$;
-(pyridyl)-, substituted with 0–2 groups independently selected from $R^6$ or $R^7$; or
-(pyridazinyl)-, substituted with 0–2 groups independently selected from $R^6$ or $R^7$;

W is selected from:
a single bond (i.e., W is not present),
—$(C_1-C_7$ alkyl)-,
—$(C_2-C_7$ alkenyl)-,
—$(C_2-C_7$ alkynyl)-, or
—$(C(R^5)_2)_nC(=O)N(R^{5a})$—;

X is selected from:
a single bond (i.e., X is not present);
—$(C_1-C_7$ alkyl)-, substituted with 0–3 groups independently selected from $R^4$, $R^8$ or $R^{14}$;
—$(C_2-C_7$ alkenyl)-, substituted with 0–3 groups independently selected from $R^4$, $R^8$ or $R^{14}$;
—$(C_2-C_7$ alkynyl)-, substituted with 0–2 groups independently selected from $R^4$, $R^8$ or $R^{14}$; or

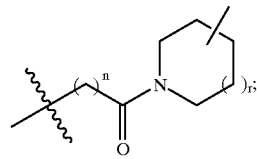

Y is selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ aralkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonyloxyalkyloxy, $C_5$ to $C_{10}$ cycloalkaxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{10}$ alkoxyalkylcarbonyloxyalkyloxy, $C_5$ to $C_{10}$ (5-alkyl-1, 3-dioxa-cyclopenten-2-one-yl)methyloxy, $C_{10}$ to $C_{14}$ (5-aryl-1,3-dioxa-cyclopenten-2-one-yl)methyloxy; or $(R^2)(R^3)N-(C_1-C_{10}$ alkoxy)-;

$R^4$ and $R^{4b}$ are independently selected from H, $C_1-C_{10}$ alkyl, hydroxy, $C_1-C_{10}$ alkoxy, nitro, $C_1-C_{10}$ alkylcarbonyl, or —$N(R^{12})R^{13}$;

$R^5$ is selected from H, $C_1-C_8$ alkyl, $C_2-C_6$ alkenyl, $C_3-C_{11}$ cycloalkyl, $C_4-C_{11}$ cycloalkylmethyl, $C_6-C_{10}$ aryl, $C_7-C_{11}$ arylalkyl, or $C_1-C_{10}$ alkyl substituted with 0–2 $R^{4b}$;

$R^{5a}$ is selected from hydrogen, hydroxy, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_1-C_6$ alkoxy, benzyloxy, $C_6$ to $C_{10}$ aryl, heteroaryl, heteroarylalkyl, $C_7$ to $C_{11}$ arylalkyl, adamantylmethyl or $C_1-C_{10}$ alkyl substituted with 0–2 $R^{4b}$;

alternately, $R^5$ and $R^{5a}$ can be taken together to be 3-azabicyclononyl, 1-piperidinyl, 1-morpholinyl or 1-piperazinyl, each being optionally substituted with $C_1$–$C_6$ alkyl, $C_6$–$C_{10}$ aryl, heteroaryl, $C_7$–$C_{11}$ arylalkyl, $C_1$–$C_6$ alkylcarbonyl, $C_3$–$C_7$ cycloalkylcarbonyl, $C_1$–$C_6$ alkoxycarbonyl, $C_7$–$C_{11}$ arylalkoxycarbonyl, $C_1$–$C_6$ alkylsulfonyl or $C_6$–$C_{10}$ arylsulfonyl;

$R^{5b}$ is selected from $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$;

$R^6$ is selected from H, $C_1$–$C_{10}$ alkyl, hydroxy, $C_1$–$C_{10}$ alkoxy, nitro, $C_1$–$C_{10}$ alkylcarbonyl, —$N(R^{12})R^{13}$, cyano, halo, $CF_3$, CHO, $CO_2R^5$, $C(=O)R^{5a}$, $CONR^5R^{5a}$, $OC(=O)R^{5a}$, $OC(=O)OR^{5b}$, $OR^{5a}$, $OC(=O)NR^5R^{5a}$, $OCH_2CO_2R^5$, $CO_2CH_2CO_2R^5$, $NR^{5a}C(=O)R^{5a}$, $NR^{5a}C(=O)OR^{5b}$, $NR^{5a}C(=O)NR^5R^{5a}$, $NR^{5a}SO_2NR^5R^{5a}$, $NR^{5a}SO_2R^5$, $S(O)_pR^{5a}$, $SO_2NR^5R^{5a}$, $C_2$–$C_6$ alkenyl, $C_3$–$C_{11}$ cycloalkyl, $C_4$–$C_{11}$ cycloalkylmethyl;

$C_6$ to $C_{10}$ aryl optionally substituted with 1–3 groups selected from halogen, $C_1$–$C_6$ alkoxy, $C_1$–$C_6$ alkyl, $CF_3$, $S(O)_m$Me, or —$NMe_2$;

$C_7$ to $C_{11}$ arylalkyl, said aryl being optionally substituted with 1–3 groups selected from halogen, $C_1$–$C_6$ alkoxy, $C_1$–$C_6$ alkyl, $CF_3$, $S(O)_m$Me, or —$NMe_2$;

methylenedioxy when $R^6$ is a substituent on aryl; or a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^{6a}$ is selected from $C_1$–$C_4$ alkyl, $C_1$–$C_4$ alkoxy, halo, $CF_3$, $NO_2$, or $NR^{12}R^{13}$;

$R^7$ is selected from H, $C_1$–$C_{10}$ alkyl, hydroxy, $C_1$–$C_{10}$ alkoxy, nitro, $C_1$–$C_{10}$ alkylcarbonyl, —$N(R^{12})R^{13}$, cyano, halo, $CF_3$, CHO, $CO_2R^5$, $C(=O)R^{5a}$, $CONR^5R^{5a}$, $OC(=O)R^{5a}$, $OC(=O)OR^{5b}$, $OR^{5a}$, $OC(=O)NR^5R^{5a}$, $OCH_2CO_2R^5$, $CO_2CH_2CO_2R^5$, $NO_2$, $NR^{5a}C(=O)R^{5a}$, $NR^{5a}C(=O)OR^{5b}$, $NR^{5a}C(=O)NR^5R^{5a}$, $NR^{5a}SO_2NR^5R^{5a}$, $NR^{5a}SO_2R^5$, $S(O)_pR^{5a}$, $SO_2NR^5R^{5a}$, $C_2$–$C_6$ alkenyl, $C_3$–$C_{11}$ cycloalkyl, $C_4$–$C_{11}$ cycloalkylmethyl, $C_6$–$C_{10}$ aryl, or $C_7$–$C_{11}$ arylalkyl;

$R^8$ is selected from:
H;
$R^6$;
$C_1$–$C_{10}$ alkyl, substituted with 0–3 $R^6$;
$C_2$–$C_{10}$ alkenyl, substituted with 0–3 $R^6$;
$C_2$–$C_{10}$ alkynyl, substituted with 0–3 $R^6$;
$C_3$–$C_8$ cycloalkyl, substituted with 0–3 $R^6$;
$C_5$–$C_6$ cycloalkenyl, substituted with 0–2 $R^6$;
aryl, substituted with 0–2 $R^6$;
5–10 membered heterocyclic ring containing 1–3 N, O, or S heteroatoms, wherein said heterocyclic ring may be saturated, partially saturated, or fully unsaturated, said heterocyclic ring being substituted with 0–2 $R^6$;

$R^{12}$ and $R^{13}$ are independently H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, aryl, $C_2$–$C_6$ alkenyl, $C_3$–$C_{11}$ cycloalkyl, $C_4$–$C_{11}$ cycloalkylalkyl, $C_7$–$C_{11}$ arylalkyl, $C_2$–$C_7$ alkylcarbonyl, $C_7$–$C_{11}$ arylcarbonyl, $C_2$–$C_7$ alkoxycarbonyl, $C_4$–$C_{11}$ cycloalkoxycarbonyl, $C_7$–$C_{11}$ bicycloalkoxycarbonyl, $C_7$–$C_{11}$ aryloxycarbonyl, heteroarylcarbonyl, heteroarylalkylcarbonyl or aryl ($C_1$–$C_{10}$ alkoxy) carbonyl;

$R^{14}$ is selected from H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or $C_1$–$C_{10}$ alkoxycarbonyl, $CO_2R^5$ or —$C(=O)N(R^5)R^{5a}$;

$R^{15}$ is selected from:
H;
$R^6$;
$C_1$–$C_{10}$ alkyl, substituted with 0–8 $R^6$;
$C_2$–$C_{10}$ alkenyl, substituted with 0–6 $R^6$;
$C_1$–$C_{10}$ alkoxy, substituted with 0–6 $R^6$;
aryl, substituted with 0–5 $R^6$;
5–6 membered heterocyclic ring containing 1–2 N, O, or S heteroatoms, wherein said heterocyclic ring may be saturated, partially saturated, or fully unsaturated, said heterocyclic ring being substituted with 0–5 $R^6$;
$C_1$–$C_{10}$ alkoxycarbonyl substituted with 0–8 $R^6$;
$CO_2R^5$; or
—$C(=O)N(R^5)R^{5a}$;

n is 0–4;

q is 2–7;

r is 0–3;

provided that when b is a double bond, only one of $R^{14}$ or $R^{15}$ is present;

provided that n, q, and r are chosen such that the number of in-chain atoms between $R^1$ and Y is in the range of 8–18.

[2] Preferred compounds of this first embodiment are those of Formula II (where W is a single bond (i.e., absent) and U is a single bond (i.e., absent)):

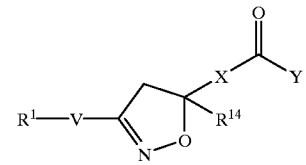

(II)

wherein:

$R^1$ is selected from $R^2HN(CH_2)_qO$—, $R^2HN(R^2N=)CNH(CH_2)_qO$—, piperazinyl-$(CH_2)_qO$—, or

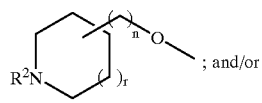

; and/or $R^2$ is selected from H, aryl($C_1$–$C_{10}$ alkoxy)carbonyl, $C_1$–$C_{10}$ alkoxycarbonyl; and/or $R^8$ is selected from H, $C_1$–$C_{10}$ alkyl, $C_2$–$C_{10}$ alkenyl, $C_3$–$C_8$ cycloalkyl, $C_5$–$C_6$ cycloalkenyl, aryl, 5–6 membered heterocyclic ring containing 1–2 N, O, or S heteroatoms, wherein said heterocyclic ring may be saturated, partially saturated, or fully unsaturated; and/or $R^6$ and $R^7$ are selected from H, $C_1$–$C_{10}$ alkyl, hydroxy, $C_1$–$C_{10}$ alkoxy, nitro, $C_1$–$C_{10}$ alkylcarbonyl, —$N(R^{12})R^{13}$, cyano, or halo.

[3] Further preferred compounds of this first embodiment are those of Formula II (where W is a bond/absent and U is a bond/absent):

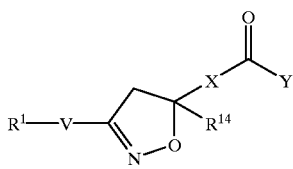

(II)

wherein:
X is selected from:
a single bond (i.e., X is not present);
—($C_1$–$C_7$ alkyl)-, substituted with 0–2 groups independently selected from $R^4$, $R^8$ or $R^{14}$;
—($C_2$–$C_7$ alkenyl)-, substituted with 0–2 groups independently selected from $R^4$, $R^8$ or $R^{14}$;
—($C_2$–$C_7$ alkynyl)-, substituted with 0–2 groups independently selected from $R^4$, $R^8$ or $R^{14}$; and/or
$R^8$ is selected from H, $C_1$–$C_6$ alkyl, $C_2$–$C_6$ alkenyl, $C_3$–$C_8$ cycloalkyl, $C_5$–$C_6$ cycloalkenyl, aryl, 5–6 membered heterocyclic ring containing 1–2 N, O, or S heteroatoms, wherein said heterocyclic ring may be saturated, partially saturated, or fully unsaturated.

[4] Further preferred compounds of this first embodiment are compounds of Formula II wherein:
$R^1$ is

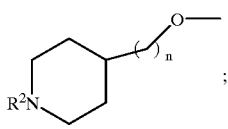

V is phenylene or pyridylene;
n is 1 or 2;
X is —($C_1$–$C_2$)alkyl-substituted with 0–2 $R^4$
Y is selected from:
hydroxy;
$C_1$ to $C_{10}$ alkoxy;
methylcarbonyloxymethoxy-;
ethylcarbonyloxymethoxy-;
t-butylcarbonyloxymethoxy-;
cyclohexylcarbonyloxymethoxy-;
1-(methylcarbonyloxy)ethoxy-;
1-(ethylcarbonyloxy)ethoxy-;
1-(t-butylcarbonyloxy)ethoxy-;
1-(cyclohexylcarbonyloxy)ethoxy-;
i-propyloxycarbonyloxymethoxy-;
t-butyloxycarbonyloxymethoxy-;
1-(i-propyloxycarbonyloxy)ethoxy-;
1-(cyclohexyloxycarbonyloxy)ethoxy-;
1-(t-butyloxycarbonyloxy)ethoxy-;
dimethylaminoethoxy-;
diethylaminoethoxy-;
(5-methyl-1,3-dioxacyclopenten-2-on-4-yl)methoxy-;
(5-(t-butyl)-1,3-dioxacyclopenten-2-on-4-yl) methoxy-;
(1,3-dioxa-5-phenyl-cyclopenten-2-on-4-yl)methoxy-;
1-(2-(2-methoxypropyl)carbonyloxy)ethoxy-;
$R^4$ is —$NR^{12}R^{13}$;
$R^{12}$ is H, $C_1$–$C_4$ alkoxycarbonyl, $C_1$–$C_4$ alkylcarbonyl, $C_1$–$C_4$ alkylsulfonyl, arylalkylsulfonyl, arylsulfonyl, benzyl, benzoyl, phenoxycarbonyl, benzyloxycarbonyl, arylalkylsulfonyl, pyridylcarbonyl, or pyridylmethylcarbonyl; and $R^{13}$ is H.

[5] Specifically preferred compounds of this first embodiment are compounds, or pharmaceutically acceptable salt or prodrug forms thereof, selected from:

5(R,S)-3-[[4-(2-piperidin-4-yl)ethoxyphenyl]isoxazolin-5-yl]acetic acid;

5(R,S)-N-(butanesulfonyl)-L-{3-[4-(2-piperidin-4-yl)ethoxyphenyl]isoxazolin-5-yl}glycine;

5(R,S)-N-(α-toluenesulfonyl)-L-{3-[4-(2-piperidin-4-yl)ethoxyphenyl]isoxazolin-5-yl}glycine;

5(R,S)-N-[(benzyloxy)carbonyl]-L-{3-[4-(2-piperidin-4-yl)ethoxyphenyl]isoxazolin-5-yl}glycine;

5(R,S)-N-(pentanoyl)-L-{3-[4-(2-piperidin-4-yl)ethoxyphenyl]isoxazolin-5-yl}glycine;

5(R,S)-3-{[4-(piperidin-4-yl)methoxyphenyl]isoxazolin-5-yl}propanoic acid;

2(R,S)-5(R,S)-N-(butanesulfonyl)amino-{3-[4-(piperidin-4-yl)methoxyphenyl]isoxazolin-5-yl}propanoic acid;

2(R,S)-5(R,S)-N-(α-toluenesulfonyl)amino-{3-[4-(piperidin-4-yl)methoxyphenyl]isoxazolin-5-yl}propanoic acid;

2(R,S)-5(R,S)-N-[(benzyloxy)carbonyl]amino-{3-[4-(piperidin-4-yl)methoxyphenyl]isoxazolin-5-yl}propanoic acid;

2(R,S)-5(R,S)-N-(pentanoyl)amino-{3-[4-(piperidin-4-yl)methoxyphenyl]isoxazolin-5-yl}propanoic acid.

[6] A second embodiment of this invention provides a compound of Formula I:

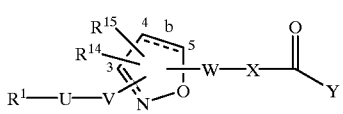

(I)

or a pharmaceutically acceptable salt or prodrug form thereof wherein:

b is a single or double bond;
$R^1$ is selected from $R^{2a}(R^3)N—$, $R^2(R^3)N(R^2N=)C—$, $R^{2a}(R^3)N(CH_2)_qZ—$, $R^2(R^3)N(R^2N=)C(CH_2)_qZ—$, $R^2(R^3)N(R^2N=)CN(R^2)—$, $R^2(R^3)NC(O)—$, $R^2(R^5O)N(R^2N=)C—$, or $R^2(R^3)N(R^5ON=)C—$;

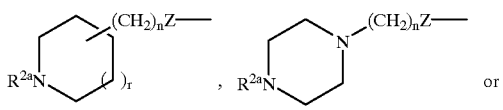

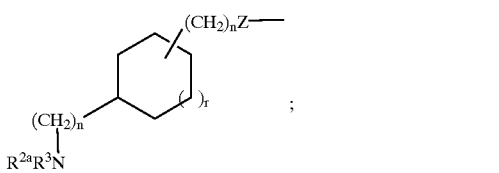

Z is selected from a bond (i.e. is absent), O, S, S(=O), $S(=O)_2$;

$R^2$ and $R^3$ are independently selected from: H; $C_1$–$C_{10}$ alkyl; $C_3$–$C_6$ alkenyl; $C_3$–$C_{11}$ cycloalkyl; $C_4$–$C_{11}$ cycloalkylalkyl; $C_6$–$C_{10}$ aryl optionally substituted with 0–3 groups selected from hydroxy, halogen, $C_1$–$C_6$ alkoxy, $C_1$–$C_6$ alkyl, $CF_3$, $S(O)_mCH_3$, —N(CH$_3$)$_2$, C$_1$–C$_4$ haloalkyl, methylenedioxydiyl, ethylenedioxydiyl; C$_7$–C$_{11}$ arylalkyl optionally substituted with 0–3 groups selected from hydroxy, halogen, C$_1$–C$_6$ alkoxy, C$_1$–C$_6$ alkyl, CF$_3$, S(O)$_m$CH$_3$, —N(CH$_3$)$_2$, C$_1$–C$_4$ haloalkyl, methylenedioxydiyl, ethylenedioxydiyl; C$_2$–C$_7$ alkylcarbonyl; C$_7$–C$_{11}$ arylcarbonyl optionally substituted with 0–3 groups selected from hydroxy, halogen, C$_1$–C$_6$ alkoxy, C$_1$–C$_6$ alkyl, CF$_3$, S(O)$_m$CH$_3$, —N(CH$_3$)$_2$, C$_1$–C$_4$ haloalkyl, methylenedioxydiyl, ethylenedioxydiyl; C$_1$–C$_{10}$ alkoxycarbonyl; C$_4$–C$_{11}$ cycloalkoxycarbonyl; C$_7$–C$_{11}$ bicycloalkoxycarbonyl; C$_7$–C$_{11}$ aryloxycarbonyl optionally substituted with 0–3 groups selected from hydroxy, halogen, C$_1$–C$_6$ alkoxy, C$_1$–C$_6$ alkyl, CF$_3$, S(O)$_m$CH$_3$, —N(CH$_3$)$_2$, C$_1$–C$_4$ haloalkyl, methylenedioxydiyl, ethylenedioxydiyl; aryl(C$_1$–C$_{10}$ alkoxy)carbonyl where the aryl group is optionally substituted with 0–3 groups selected from hydroxy, halogen, C$_1$–C$_6$ alkoxy, C$_1$–C$_6$ alkyl, CF$_3$, S(O)$_m$CH$_3$, —N(CH$_3$)$_2$, C$_1$–C$_4$ haloalkyl, methylenedioxydiyl, ethylenedioxydiyl; C$_1$–C$_6$ alkylcarbonyloxy(C$_1$–C$_4$ alkoxy)carbonyl; C$_6$–C$_{10}$ arylcarbonyloxy(C$_1$–C$_4$ alkoxy)carbonyl where the aryl group is optionally substituted with 0–3 groups selected from hydroxy, halogen, C$_1$–C$_6$ alkoxy, C$_1$–C$_6$ alkyl, CF$_3$, S(O)$_m$CH$_3$, —N(CH$_3$)$_2$, C$_1$–C$_4$ haloalkyl, methylenedioxydiyl, ethylenedioxydiyl; C$_4$–C$_{11}$ cycloalkylcarbonyloxy(C$_1$–C$_4$ alkoxy)carbonyl; heteroaryl optionally substituted with 0–2 groups selected from hydroxy, halogen, C$_1$–C$_6$ alkoxy, C$_1$–C$_6$ alkyl, CF$_3$, S(O)$_m$CH$_3$, —N(CH$_3$)$_2$, C$_1$–C$_4$ haloalkyl, methylenedioxydiyl, ethylenedioxydiyl; or heteroaryl(C$_1$–C$_5$)alkyl where the heteroaryl group is optionally substituted with 0–2 groups selected from hydroxy, halogen, C$_1$–C$_6$ alkoxy, C$_1$–C$_6$ alkyl, CF$_3$, S(O)$_m$CH$_3$, —N(CH$_3$)$_2$, C$_1$–C$_4$ haloalkyl, methylenedioxydiyl, ethylenedioxydiyl;

provided that only one of R$^2$ and R$^3$ may be hydroxy;

R$^{2a}$ is R$^2$ or R$^2$(R$^3$)N(R$^2$N=)C—;

U is selected from:
 a single bond (i.e., U is not present),
 —(C$_1$–C$_7$ alkyl)-,
 —(C$_2$–C$_7$ alkenyl)-,
 —(C$_2$–C$_7$ alkynyl)-,
 -(aryl)-substituted with 0–3 R$^{6a}$, or
 -(pyridyl)-substituted with 0–3 R$^{6a}$;

V is selected from:
 a single bond (i.e., V is not present);
 —(C$_1$–C$_7$ alkyl)-, substituted with 0–3 groups independently selected from R$^6$ or R$^7$;
 —(C$_2$–C$_7$ alkenyl)-, substituted with 0–3 groups independently selected from R$^6$ or R$^7$;
 —(C$_2$–C$_7$ alkynyl)-, substituted with 0–3 groups independently selected from R$^6$ or R$^7$;
 -(phenyl)-Q-, said phenyl substituted with 0–2 groups independently selected from R$^6$ or R$^7$;
 -(pyridyl)-Q-, said pyridyl substituted with 0–2 groups independently selected from R$^6$ or R$^7$; or
 -(pyridazinyl)-Q-, said pyridazinyl substituted with 0–2 groups independently selected from R$^6$ or R$^7$;

Q is selected from:
 a single bond (i.e., Q is not present), —O—, —S(O)$_m$—, —N(R$^{12}$)—, —(CH$_2$)$_m$—, —C(=O)—, —N(R$^{5a}$)C(=O)—, —C(=O)N(R$^{5a}$)—, —CH$_2$O—, —OCH$_2$—, —CH$_2$N(R$^{12}$)—, —N(R$^{12}$)CH$_2$—, —CH$_2$C(=O)—, —C(=O)CH$_2$—, —CH$_2$S(O)$_m$—, or —S(O)$_m$CH$_2$—, provided that when b is a single bond, and R—U—V— is a substituent on C5 of the central 5-membered ring of Formula I, then Q is not —O—, —S(O)$_m$—, —N(R$^{12}$)—, —C(=O)N(R$^{5a}$)—, —CH$_2$O—, CH$_2$N(R$^{12}$)— or —CH$_2$S(O)$_m$—;

W is selected from:
 —(C(R$^4$)$_2$)$_n$C(=O)N(R$^{5a}$)—, or
 —C(=O)—N(R$^{5a}$)—(C(R$^4$)$_2$)$_n$—;

X is selected from:
 a single bond (i.e. X is absent)
 —(C(R$^4$)$_2$)$_n$—C(R$^4$)(R$^8$)—C(R$^4$)(R$^{4a}$)—, with the proviso that when n is 0 or 1, then at least one of R$^{4a}$ or R$^8$ is other than H or methyl;

Y is selected from hydroxy, C$_1$ to C$_{10}$ alkyloxy, C$_3$ to C$_{11}$ cycloalkyloxy, C$_6$ to C$_{10}$ aryloxy, C$_7$ to C$_{11}$ aralkyloxy, C$_3$ to C$_{10}$ alkylcarbonyloxyalkyloxy, C$_3$ to C$_{10}$ alkoxycarbonyloxyalkyloxy, C$_2$ to C$_{10}$ alkoxycarbonylalkyloxy, C$_5$ to C$_{10}$ cycloalkylcarbonyloxyalkyloxy, C$_5$ to C$_{10}$ cycloalkoxycarbonyloxyalkyloxy, C$_5$ to C$_{10}$ cycloalkoxycarbonylalkyloxy, C$_7$ to C$_{11}$ aryloxycarbonylalkyloxy, C$_8$ to C$_{12}$ aryloxycarbonyloxyalkyloxy, C$_8$ to C$_{12}$ arylcarbonyloxyalkyloxy, C$_5$ to C$_{10}$ alkoxyalkylcarbonyloxyalkyloxy, C$_5$ to C$_{10}$ (5-alkyl-1,3-dioxa-cyclopenten-2-one-yl)methyloxy, C$_{10}$ to C$_{14}$ (5-aryl-1,3-dioxa-cyclopenten-2-one-yl)methyloxy, (R$^2$)(R$^3$)N—(C$_1$–C$_{10}$ alkoxy)-;

R$^4$ is selected from H, C$_1$–C$_{10}$ alkyl, C$_1$–C$_{10}$ alkylcarbonyl, aryl, arylalkyl, cycloalkyl, or cycloalkylalkyl;

alternately, two R$^4$ groups on adjacent carbons may join to form a bond (i.e. a carbon—carbon double or triple bond);

R$^{4a}$ is selected from H, hydroxy, C$_1$–C$_{10}$ alkoxy, nitro, N(R$^5$)R$^{5a}$, —N(R$^{12}$)R$^{13}$, —N(R$^{16}$)R$^{17}$, C$_1$–C$_{10}$ alkyl substituted with 0–3 R$^6$, aryl substituted with 0–3 R$^6$, heteroaryl substituted with 0–3 R$^6$ or C$_1$–C$_{10}$ alkylcarbonyl;

R$^{4b}$ is selected from H, C$_1$–C$_6$ alkyl, C$_2$–C$_6$ alkenyl, C$_2$–C$_6$ alkynyl, C$_3$–C$_7$ cycloalkyl, C$_7$–C$_{14}$ bicycloalkyl, hydroxy, C$_1$–C$_6$ alkoxy, C$_1$–C$_6$ alkylthio, C$_1$–C$_6$ alkylsulfinyl, C$_1$–C$_6$ alkylsulfonyl, nitro, C$_1$–C$_6$ alkylcarbonyl, C$_6$–C$_{10}$ aryl, —N(R$^{12}$)R$^{13}$; halo, CF$_3$, CN, C$_1$–C$_6$ alkoxycarbonyl, carboxy, piperidinyl, morpholinyl or pyridinyl;

R$^5$ is selected from H, C$_1$–C$_8$ alkyl, C$_3$–C$_6$ alkenyl, C$_3$–C$_{11}$ cycloalkyl, C$_4$–C$_{11}$ cycloalkylmethyl, C$_6$–C$_{10}$ aryl, C$_7$–C$_{11}$ arylalkyl, or C$_1$–C$_{10}$ alkyl substituted with 0–2 R$^{4b}$;

R$^{5a}$ is selected from hydrogen, hydroxy, C$_1$ to C$_8$ alkyl, C$_3$–C$_6$ alkenyl, C$_3$ to C$_{11}$ cycloalkyl, C$_4$ to C$_{11}$ cycloalkylmethyl, C$_1$–C$_6$ alkoxy, benzyloxy, C$_6$ to C$_{10}$ aryl, heteroaryl, heteroarylalkyl, C$_7$ to C$_{11}$ arylalkyl, adamantylmethyl, or C$_1$–C$_{10}$ alkyl substituted with 0–2 R$^{4b}$;

alternately, R$^5$ and R$^{5a}$ when both are substituents on the same nitrogen atom (as in —NR$^5$R$^{5a}$) can be taken together with the nitrogen atom to which they are attached to form 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl, each being optionally substituted with C$_1$–C$_6$ alkyl, C$_6$–C$_{10}$ aryl, heteroaryl, C$_7$–C$_{11}$ arylalkyl, $C_1$–$C_6$ alkylcarbonyl, $C_3$–$C_7$ cycloalkylcarbonyl, $C_1$–$C_6$ alkoxycarbonyl, $C_7$–$C_{11}$ arylalkoxycarbonyl, $C_1$–$C_6$ alkylsulfonyl or $C_6$–$C_{10}$ arylsulfonyl;

$R^{5b}$ is selected from $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$;

$R^6$ is selected from H, $C_1$–$C_{10}$ alkyl, hydroxy, $C_1$–$C_{10}$ alkoxy, nitro, $C_1$–$C_{10}$ alkylcarbonyl, —N($R^{12}$)$R^{13}$, cyano, halo, $CF_3$, CHO, $CO_2R^5$, C(=O)$R^{5a}$, CONR$^5$R$^{5a}$, OC(=O)$R^{5a}$, OC(=O)OR$^{5b}$, OR$^{5a}$, OC(=O)NR$^5$R$^{5a}$, OCH$_2$CO$_2$R$^5$, CO$_2$CH$_2$CO$_2$R$^5$, NO$_2$, NR$^{5a}$C(=O)R$^{5a}$, NR$^{5a}$C(=O)OR$^{5b}$, NR$^{5a}$C(=O)NR$^5$R$^{5a}$, NR$^{5a}$SO$_2$NR$^5$R$^{5a}$, NR$^{5a}$SO$_2$R$^5$, S(O)$_m$R$^{5a}$, SO$_2$NR$^5$R$^{5a}$, SiMe$_3$, $C_2$ to $C_6$ alkenyl, $C_3$ to $C_{11}$ cycloalkyl, $C_4$ to $C_{11}$ cycloalkylmethyl;

$C_6$ to $C_{10}$ aryl optionally substituted with 1–3 groups selected from halogen, $C_1$–$C_6$ alkoxy, $C_1$–$C_6$ alkyl, $CF_3$, S(O)$_m$Me, or —NMe$_2$;

$C_7$ to $C_{11}$ arylalkyl, said aryl being optionally substituted with 1–3 groups selected from halogen, $C_1$–$C_6$ alkoxy, $C_1$–$C_6$ alkyl, $CF_3$, S(O)$_m$Me, or —NMe$_2$; methylenedioxy when $R^6$ is a substituent on aryl; or a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^{6a}$ is selected from $C_1$–$C_4$ alkyl, $C_1$–$C_4$ alkoxy, halo, $CF_3$, $NO_2$, or NR$^{12}$R$^{13}$;

$R^7$ is selected from H, $C_1$–$C_{10}$ alkyl, hydroxy, $C_1$–$C_{10}$ alkoxy, nitro, $C_1$–$C_{10}$ alkylcarbonyl, —N($R^{12}$)$R^{13}$, cyano, halo, $CF_3$, CHO, $CO_2R^5$, C(=O)$R^{5a}$, CONR$^5$R$^{5a}$, OC(=O)$R^{5a}$, OC(=O)OR$^{5b}$, OR$^{5a}$, OC(=O)NR$^5$R$^{5a}$, OCH$_2$CO$_2$R$^5$, CO$_2$CH$_2$CO$_2$R$^5$, NO$_2$, NR$^{5a}$C(=O)R$^{5a}$, NR$^{5a}$C(O)OR$^{5b}$, NR$^{5a}$C(=O)NR$^5$R$^{5a}$, NR$^{5a}$SO$_2$NR$^5$R$^{5a}$, NR$^{5a}$SO$_2$R$^5$, S(O)$_m$R$^{5a}$, SO$_2$NR$^5$R$^{5a}$, $C_2$ to $C_6$ alkenyl, $C_3$ to $C_{11}$ cycloalkyl, $C_4$ to $C_{11}$ cycloalkylmethyl, $C_6$ to $C_{10}$ aryl, or $C_7$ to $C_{11}$ arylalkyl;

$R^8$ is selected from:
  $R^6$;
  $C_1$–$C_{10}$ alkyl, substituted with 0–3 $R^6$;
  $C_2$–$C_{10}$ alkenyl, substituted with 0–3 $R^6$;
  $C_2$–$C_{10}$ alkynyl, substituted with 0–3 $R^6$;
  $C_3$–$C_8$ cycloalkyl, substituted with 0–3 $R^6$;
  $C_5$–$C_6$ cycloalkenyl, substituted with 0–3 $R^6$;
  aryl, substituted with 0–3 $R^6$;
  5–10 membered heterocyclic ring containing 1–3 N, O, or S heteroatoms, wherein said heterocyclic ring may be saturated, partially saturated, or fully unsaturated, said heterocyclic ring being substituted with 0–2 $R^6$;

$R^{12}$ and $R^{13}$ are independently H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, aryl($C_2$–$C_{10}$ alkenyl)sulfonyl, heteroarylsulfonyl, aryl, $C_2$–$C_6$ alkenyl, $C_3$–$C_{11}$ cycloalkyl, $C_4$–$C_{11}$ cycloalkylalkyl, $C_7$–$C_{11}$ arylalkyl, $C_7$–$C_{11}$ arylcarbonyl, $C_4$–$C_{11}$ cycloalkoxycarbonyl, $C_7$–$C_{11}$ bicycloalkoxycarbonyl, $C_7$–$C_{11}$ aryloxycarbonyl, heteroarylcarbonyl, heteroarylalkylcarbonyl, or aryl ($C_1$–$C_{10}$ alkoxy)carbonyl, wherein said aryls are optionally substituted with 0–3 substituents selected from the group consisting of: $C_1$–$C_4$ alkyl, $C_1$–$C_4$ alkoxy, halo, $CF_3$, and $NO_2$;

$R^{14}$ is selected from H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or $C_1$–$C_{10}$ alkoxycarbonyl, $CO_2R^5$ or —C(=O)N($R^5$)$R^{5a}$;

$R^{15}$ is selected from:
  H; $R^6$; —$CO_2R^5$; —C(=O)N($R^5$)$R^{5a}$;
  $C_1$–$C_{10}$ alkoxycarbonyl substituted with 0–2 $R^6$;
  $C_1$–$C_{10}$ alkyl, substituted with 0–3 $R^6$;
  $C_2$–$C_{10}$ alkenyl, substituted with 0–3 $R^6$;
  $C_1$–$C_{10}$ alkoxy, substituted with 0–3 $R^6$;
  aryl, substituted with 0–3 $R^6$; or
  5–10 membered heterocyclic ring containing 1–3 N, O, or S heteroatoms, wherein said heterocyclic ring may be saturated, partially saturated, or fully unsaturated, said heterocyclic ring being substituted with 0–2 $R^6$;

provided that when b is a double bond, only one of $R^{14}$ or $R^{15}$ is present;

$R^{16}$ is selected from:
  —C(=O)—O—$R^{18a}$,
  —C(=O)—$R^{18b}$,
  —C(=O)N($R^{18b}$)$_2$,
  —C(=O)NHSO$_2$R$^{18a}$,
  —C(=O)NHC(=O)$R^{18b}$,
  —C(=O)NHC(=O)OR$^{18a}$,
  —C(=O)NHSO$_2$NHR$^{18b}$,
  —C(=S)—NH—$R^{18b}$,
  —NH—C(=O)—O—$R^{18a}$,
  —NH—C(=O)—$R^{18b}$,
  —NH—C(=O)—NH—$R^{18b}$,
  —SO$_2$—O—$R^{18a}$,
  —SO$_2$—$R^{18a}$,
  —SO$_2$—N(18$^b$)$_2$,
  —SO$_2$—NHC(=O)O18$^b$,
  —P(=S)(OR$^{18a}$)$_2$,
  —P(=O)(OR$^{18a}$)$_2$,
  —P(=S)(R$^{18a}$)$_2$,
  —P(=O)(R$^{18a}$)$_2$, or

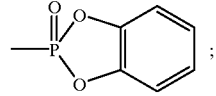
;

$R^{17}$ is selected from: H, $C_1$–$C_{10}$ alkyl, $C_2$–$C_6$ alkenyl, $C_3$–$C_{11}$ cycloalkyl, $C_4$–$C_{15}$ cycloalkylalkyl, aryl, aryl ($C_1$–$C_{10}$ alkyl)-;

$R^{18a}$ is selected from:
  $C_1$–$C_8$ alkyl substituted with 0–2 $R^{19}$, $C_2$–$C_8$ alkenyl substituted with 0–2 $R^{19}$, $C_2$–$C_8$ alkynyl substituted with 0–2 $R^{19}$, $C_3$–$C_8$ cycloalkyl substituted with 0–2 $R^{19}$, aryl substituted with 0–4 $R^{19}$, aryl($C_1$–$C_6$ alkyl)-substituted with 0–4 $R^{19}$,
  a 5–10 membered heterocyclic ring system having 1–3 heteroatoms selected independently from O, S, and N, said heterocyclic ring being substituted with 0–4 $R^{19}$,
  $C_1$–$C_6$ alkyl substituted with a 5–10 membered heterocyclic ring system having 1–3 heteroatoms selected independently from O, S, and N, said heterocyclic ring being substituted with 0–4 $R^{19}$;

$R^{18b}$ is selected from $R^{18a}$ or H;

$R^{19}$ is selected from H, halogen, $CF_3$, CN, $NO_2$, NR$^{12}$R$^{13}$, $C_1$–$C_8$ alkyl, $C_2$–$C_6$ alkenyl, $C_2$–$C_6$ alkynyl, $C_3$–$C_{11}$ cycloalkyl, $C_4$–$C_1$l cycloalkylalkyl, aryl, aryl($C_1$–$C_6$ alkyl)-, $C_1$–$C_6$ alkoxy, or $C_1$–$C_4$ alkoxycarbonyl.;

m is 0–2;
n is 0–4;
q is 1–7;
r is 0–3;

provided that n, q and r are chosen such that the number of atoms connecting $R^1$ and Y is in the range of 8–18.

[7] Preferred compounds of this second embodiment are those compounds of Formula Ia:

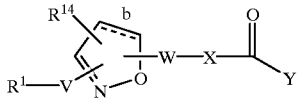

(Ia)

wherein:

Z is selected from a bond (i.e. is absent), O, or S; and/or $R^2$ is selected from H, aryl($C_1$–$C_{10}$ alkoxy)carbonyl, or $C_1$–$C_{10}$ alkoxycarbonyl; and/or W is —$(CH_2)_nC(=O)N(R^{5a})$—; and/or X is —$(C(R^4)_2)_n$—$C(R^4)(R^8)$—$CH(R^4)$—, with the proviso that when n is 0 or 1, then at least one of $R^{4a}$ or $R^8$ is other than H or methyl; and/or $R^5$ is selected from H or $C_1$–$C_{10}$ alkyl substituted with 0–6 $R^{4b}$; and/or $R^6$ is selected from H, $C_1$–$C_{10}$ alkyl, hydroxy, $C_1$–$C_{10}$ alkoxy, nitro, $C_1$–$C_{10}$ alkylcarbonyl, —$N(R^{12})R^{13}$, —$NR^5R^{5a}$, $CO_2R^5$, $S(O)_mR^5$, $OR^5$, cyano, halo;

$C_6$ to $C_{10}$ aryl optionally substituted with 1–3 groups selected from halogen, $C_1$–$C_6$ alkoxy, $C_1$–$C_6$ alkyl, $CF_3$, $S(O)_m$Me, or —$NMe_2$;

$C_7$ to $C_{11}$ arylalkyl, said aryl being optionally substituted with 1–3 groups selected from halogen, $C_1$–$C_6$ alkoxy, $C_1$–$C_6$ alkyl, $CF_3$, $S(O)_m$Me, or —$NMe_2$;

methylenedioxy when $R^6$ is a substituent on aryl; or a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$; and/or $R^7$ is selected from selected from H, $C_1$–$C_{10}$ alkyl, hydroxy, $C_1$–$C_{10}$ alkoxy, nitro, $C_1$–$C_{10}$ alkylcarbonyl, —$N(R^{12})R^{13}$, cyano, or halo; and/or $R^8$ is selected from:
—$CONR^5NR^{5a}$; —$CO_2R^5$;
$C_1$–$C_{10}$ alkyl, substituted with 0–3 $R^6$;
$C_2$–$C_{10}$ alkenyl, substituted with 0–3 $R^6$;
$C_2$–$C_{10}$ alkynyl, substituted with 0–3 $R^6$;
$C_3$–$C_8$ cycloalkyl, substituted with 0–3 $R^6$;
$C_5$–$C_6$ cycloalkenyl, substituted with 0–3 $R^6$;
aryl, substituted with 0–2 $R^6$;
5–10 membered heterocyclic ring containing 1–3 N, O, or S heteroatoms, wherein said heterocyclic ring may be saturated, partially saturated, or fully unsaturated, said heterocyclic ring being substituted with 0–2 $R^6$; and/or $R^{12}$ and $R^{13}$ are each independently selected from H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, aryl, heteroarylcarbonyl, or heteroarylalkylcarbonyl, wherein said aryls are optionally substituted with 0–3 substituents selected from the group consisting of: $C_1$–$C_4$ alkyl, $C_1$–$C_4$ alkoxy, halo, $CF_3$, and $NO_2$.

[8] Further preferred compounds of this second embodiment are those compounds of Formula Ia:

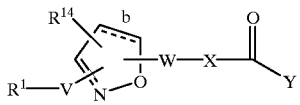

(Ia)

wherein:

Z is selected from a bond (i.e. is absent) or O; and/or

W is —$(CH_2)_nC(=O)N(R^{12})$—; and/or

X is —$C(R^4)(R^8)$—$C(R^4)_2$—.

[9] Further preferred compounds of this second embodiment are compounds of Formula Ia, wherein:

$R^1$ is $R^2NHC(=NR^2)$—, $R^2NHC(=NR^2)NH$— and V is phenylene or pyridylene, or $R^1$ is

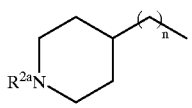

and V is a single bond (i.e. V is absent);

n is 1 or 2;

X is —$CHR^8CH_2$—;

Y is selected from:
hydroxy;
$C_1$ to $C_{10}$ alkoxy;
methylcarbonyloxymethoxy-;
ethylcarbonyloxymethoxy-;
t-butylcarbonyloxymethoxy-;
cyclohexylcarbonyloxymethoxy-;
1-(methylcarbonyloxy)ethoxy-;
1-(ethylcarbonyloxy)ethoxy-;
1-(t-butylcarbonyloxy)ethoxy-;
1-(cyclohexylcarbonyloxy)ethoxy-;
i-propyloxycarbonyloxymethoxy-;
t-butyloxycarbonyloxymethoxy-;
1-(i-propyloxycarbonyloxy)ethoxy-;
1-(cyclohexyloxycarbonyloxy)ethoxy-;
1-(t-butyloxycarbonyloxy)ethoxy-;
dimethylaminoethoxy-;
diethylaminoethoxy-;
(5-methyl-1,3-dioxacyclopenten-2-on-4-yl)methoxy-;
(5-(t-butyl)-1,3-dioxacyclopenten-2-on-4-yl)methoxy-;
(1,3-dioxa-5-phenyl-cyclopenten-2-on-4-yl)methoxy-;
1-(2-(2-methoxypropyl)carbonyloxy)ethoxy-;

$R^6$ is selected from H, $C_1$–$C_4$ alkyl, hydroxy, $C_1$–$C_4$ alkoxy, nitro, $C_1$–$C_{10}$ alkylcarbonyl, —$N(R^{12})R^{13}$, —$NR^5R^{5a}$, $CO_2R^5$, $S(O)_mR^5$, $OR^5$, cyano, halo;

$C_6$ to $C_{10}$ aryl optionally substituted with 1–3 groups selected from halogen, $C_1$–$C_6$ alkoxy, $C_1$–$C_6$ alkyl, $CF_3$, $S(O)_m$Me, or —$NMe_2$;

methylenedioxy when $R^6$ is a substituent on aryl; or a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, benzimidazolyl, piperidinyl, tetrahydrofuranyl, pyranyl, pyridinyl, 3H-indolyl, carbazolyl, pyrrolidinyl, piperidinyl, indolinyl, isoxazolinyl or morpholinyl;

$R^8$ is selected from:
—CONR$^5$NR$^{5a}$; —CO$_2$R$^5$;
C$_1$–C$_{10}$ alkyl, substituted with 0–3 R$^6$;
C$_2$–C$_{10}$ alkenyl, substituted with 0–3 R$^6$;
C$_2$–C$_{10}$ alkynyl, substituted with 0–3 R$^6$,
C$_3$–C$_8$ cycloalkyl, substituted with 0–3 R$^6$; aryl, substituted with 0–2 R$^6$;
a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolinyl, benzimidazolyl, piperidinyl, tetrahydrofuranyl, pyranyl, pyridinyl, 3H-indolyl, carbazolyl, pyrrolidinyl, piperidinyl, indolinyl, or morpholinyl, said heterocyclic ring being substituted with 0–2 R$^6$;
$R^{12}$ is selected from H, C$_1$–C$_6$ alkyl, C$_1$–C$_4$ alkoxycarbonyl, C$_1$–C$_6$ alkylcarbonyl, C$_1$–C$_6$ alkylsulfonyl, aryl(C$_1$–C$_4$ alkyl)sulfonyl, arylsulfonyl, aryl, pyridylcarbonyl or pyridylmethylcarbonyl, wherein said aryls are optionally substituted with 0–3 substituents selected from the group consisting of: C$_1$–C$_4$ alkyl, C$_1$–C$_4$ alkoxy, halo, CF$_3$, and NO$_2$; and
$R^{13}$ is H.

[10], [35] Specifically preferred compounds of this second embodiment are compounds, or enantiomeric or diasteriomeric forms thereof, or mixtures of enantiomeric or diasteriomeric forms thereof, or a pharmaceutically acceptable salt or prodrug forms thereof, selected from:

3(R,S)-{5(R,S)-N-[3-(4-amidinophenyl)isoxazolin-5-ylacetyl]amino}-3-phenylpropanoic acid;

3(R,S)-{5(R,S)-N-[3-(4-amidinophenyl)isoxazolin-5-ylacetyl]amino}-pentanoic acid;

3(R)-{5(R,S)-N-[3-(4-amidinophenyl)isoxazolin-5-ylacetyl]amino}heptanoic acid;

3(R,S)-{5(R,S)-N-[3-(4-amidinophenyl)isoxazolin-5-ylacetyl]amino}-4-(phenylthio)butanoic acid;

3(R,S)-{5(R,S)-N-[3-(4-amidinophenyl)isoxazolin-5-ylacetyl]amino}-4-(phenylsulfonamido)butanoic acid;

3(R,S)-{5(R,S)-N-[3-(4-amidinophenyl)isoxazolin-5-ylacetyl]amino}-4-(n-butylsulfonamido)butanoic acid;

3(S)-{5(R,S)-N-[3-(4-amidinophenyl)isoxazolin-5-ylacetyl]amino}-3-(adamantylmethylaminocarbonyl)propanoic acid;

3(S)-{5(R,S)-N-[3-(4-amidinophenyl)isoxazolin-5-ylacetyl]amino}-3-(1-azabicyclo[3.2.2]nonylcarbonyl)propanoic acid;

3(S)-{5(R,S)-N-[3-(4-amidinophenyl)isoxazolin-5-ylacetyl]amino}-3-(phenethylaminocarbonyl)propanoic acid;

3(R)-{5(R,S)-N-[3-(4-amidinophenyl)isoxazolin-5-ylacetyl]amino}-3-(3-pyridylethyl)propanoic acid;

3(R)-{5(R,S)-N-[3-(4-amidinophenyl)isoxazolin-5-ylacetyl]amino}-3-(2-pyridylethyl)propanoic acid;

3(R)-{5(R,S)-N-[3-(4-amidinophenyl)isoxazolin-5-ylacetyl]amino}-3-(phenylpropyl)propanoic acid;

N$^3$-[2-{3-(4-formamidinophenyl)-isoxazolin-5-yl}-acetyl]-N$^2$-(phenylsulfonyl)-2,3-diaminopropanoic acid;

N$^3$-[2-{3-(4-formamidinophenyl)-isoxazolin-5-yl}-acetyl]-N$^2$-(4-methyl-phenyl-sulfonyl)-2,3-diaminopropanoic acid;

N$^3$-[2-{3-(4-formamidinophenyl)-isoxazolin-5-yl}-acetyl]-N$^2$-(butanesulfonyl)-2,3-diaminopropanoic acid;

N$^3$-[2-{3-(4-formamidinophenyl)-isoxazolin-5-yl}-acetyl]-N$^2$-(propanesulfonyl)-2,3-diaminopropanoic acid;

N$^3$-[2-{3-(4-formamidinophenyl)-isoxazolin-5-yl}-acetyl]-N$^2$-(ethanesulfonyl)-2,3-diaminopropanoic acid;

N$^3$-[2-{3-(4-formamidinophenyl)-isoxazolin-5-yl}-acetyl]-N$^2$-(methyloxycarbonyl)-2,3-diaminopropanoic acid;

N$^3$-[2-{3-(4-formamidinophenyl)-isoxazolin-5-yl}-acetyl]-N$^2$-(ethyloxycarbonyl)-2,3-diaminopropanoic acid;

N$^3$-[2-{3-(4-formamidinophenyl)-isoxazolin-5-yl}-acetyl]-N$^2$-(1-propyloxycarbonyl)-2,3-diaminopropanoic acid;

N$^3$-[2-{3-(4-formamidinophenyl)-isoxazolin-5-yl}-acetyl]-N$^2$-(2-propyloxycarbonyl)-2,3-diaminopropanoic acid;

N$^3$-[2-{3-(4-formamidinophenyl)-isoxazolin-5-yl}-acetyl]-N$^2$-(n-butyloxycarbonyl)-2,3-diaminopropanoic acid;

N$^3$-[2-{3-(4-formamidinophenyl)-isoxazolin-5-yl}-acetyl]-N$^2$-(1-(2-methyl)-propyloxycarbonyl)-2,3-diaminopropanoic acid;

N$^3$-[2-{3-(4-formamidinophenyl)-isoxazolin-5-yl}-acetyl]-N$^2$-(2-(2-methyl)-propyloxycarbonyl)-2,3-diaminopropanoic acid;

N$^3$-[2-{3-(4-formamidinophenyl)-isoxazolin-5-yl}-acetyl]-N$^2$-(benzyloxycarbonyl)-2,3-diaminopropanoic acid;

N$^3$-[2-{3-(4-formamidinophenyl)-isoxazolin-5-yl}-acetyl]-N$^2$-(4-methylbenzyloxycarbonyl)-2,3-diaminopropanoic acid;

N$^3$-[2-{3-(4-formamidinophenyl)-isoxazolin-5-yl}-acetyl]-N$^2$-(4-methoxybenzyloxycarbonyl)-2,3-diaminopropanoic acid;

N$^3$-[2-{3-(4-formamidinophenyl)-isoxazolin-5-yl}-acetyl]-N$^2$-(4-chlorobenzyloxycarbonyl)-2,3-diaminopropanoic acid;

N$^3$-[2-{3-(4-formamidinophenyl)-isoxazolin-5-yl}-acetyl]-N$^2$-(4-bromobenzyloxycarbonyl)-2,3-diaminopropanoic acid;

N$^3$-[2-{3-(4-formamidinophenyl)-isoxazolin-5-yl}-acetyl]-N$^2$-(4-fluorobenzyloxycarbonyl)-2,3-diaminopropanoic acid;

N$^3$-[2-{3-(4-formamidinophenyl)-isoxazolin-5-yl}-acetyl]-N$^2$-(4-phenoxybenzyloxycarbonyl)-2,3-diaminopropanoic acid;

N$^3$-[2-{3-(4-formamidinophenyl)-isoxazolin-5-yl}-acetyl]-N$^2$-(2-(methyloxyethyl)-oxycarbonyl)-2,3-diaminopropanoic acid;

N$^3$-[2-{3-(4-formamidinophenyl)-isoxazolin-5-yl}-acetyl]-N$^2$-(2-pyridinylcarbonyl)-2,3-diaminopropanoic acid;

N$^3$-[2-{3-(4-formamidinophenyl)-isoxazolin-5-yl}-acetyl]-N$^2$-(3-pyridinylcarbonyl)-2,3-diaminopropanoic acid;

N$^3$-[2-{3-(4-formamidinophenyl)-isoxazolin-5-yl}-acetyl]-N$^2$-(4-pyridinyl-carbonyl)-2,3-diaminopropanoic acid;

N$^3$-[2-{3-(4-formamidinophenyl)-isoxazolin-5-yl}-acetyl]-N$^2$-(2-(2-pyridinyl)-acetyl)-2,3-diaminopropanoic acid;

N$^3$-[2-{3-(4-formamidinophenyl)-isoxazolin-5-yl}-acetyl]-N$^2$-(2-(3-pyridinyl)-acetyl)-2,3-diaminopropanoic acid;

$N^3$-[2-{3-(4-formamidinophenyl)-isoxazolin-5-yl}-acetyl]-$N^2$-(2-(4-pyridinyl)-acetyl)-2,3-diaminopropanoic acid;

$N^3$-[2-{3-(4-formamidinophenyl)-isoxazolin-5-yl}-acetyl]-$N^2$-(2-pyridyl-methyloxycarbonyl)-2,3-diaminopropanoic acid;

$N^3$-[2-{3-(4-formamidinophenyl)-isoxazolin-5-yl}-acetyl]-$N^2$-(3-pyridyl-methyloxycarbonyl)-2,3-diaminopropanoic acid;

$N^3$-[2-{3-(4-formamidinophenyl)-isoxazolin-5-yl}-acetyl]-$N^2$-(4-pyridyl-methyloxycarbonyl)-2,3-diaminopropanoic acid;

$N^3$-[2-{3-(4-formamidinophenyl)-isoxazolin-5-yl}-acetyl]-$N^2$-(4-butyloxyphenylsulfonyl)-2,3-diaminopropanoic acid;

$N^3$-[2-{3-(4-formamidinophenyl)-isoxazolin-5-yl}-acetyl]-$N^2$-(2-thienylsulfonyl)-2,3-diaminopropanoic acid;

$N^3$-[2-{3-(4-formamidinophenyl)-isoxazolin-5-yl}-acetyl]-$N^2$-(3-methylphenylsulfonyl)-2,3-diaminopropanoic acid;

$N^3$-[2-{3-(4-formamidinophenyl)-isoxazolin-5-yl}-acetyl]-$N^2$-(4-iodophenylsulfonyl)-2,3-diaminopropanoic acid;

$N^3$-[2-{3-(4-formamidinophenyl)-isoxazolin-5-yl}-acetyl]-$N^2$-(3-trifluoromethylphenylsulfonyl)-2,3-diaminopropanoic acid;

$N^3$-[2-{3-(4-formamidinophenyl)-isoxazolin-5-yl}-acetyl]-$N^2$-(3-chlorophenylsulfonyl)-2,3-diaminopropanoic acid;

$N^3$-[2-{3-(4-formamidinophenyl)-isoxazolin-5-yl}-acetyl]-$N^2$-(3-2-methoxycarbonylphenylsulfonyl)-2,3-diaminopropanoic acid;

$N^3$-[2-{3-(4-formamidinophenyl)-isoxazolin-5-yl}-acetyl]-$N^2$-(2,4,6-trimethylphenylsulfonyl)-2,3-diaminopropanoic acid;

$N^3$-[2-{3-(4-formamidinophenyl)-isoxazolin-5-yl}-acetyl]-$N^2$-(2-chlorophenylsulfonyl)-2,3-diaminopropanoic acid;

$N^3$-[2-{3-(4-formamidinophenyl)-isoxazolin-5-yl}-acetyl]-$N^2$-(4-trifluoromethylphenylsulfonyl)-2,3-diaminopropanoic acid;

$N^3$-[2-{3-(4-formamidinophenyl)-isoxazolin-5-yl}-acetyl]-$N^2$-(2-trifluoromethylphenylsulfonyl)-2,3-diaminopropanoic acid;

$N^3$-[2-{3-(4-formamidinophenyl)-isoxazolin-5-yl}-acetyl]-$N^2$-(2-fluorophenylsulfonyl)-2,3-diaminopropanoic acid;

$N^3$-[2-{3-(4-formamidinophenyl)-isoxazolin-5-yl}-acetyl]-$N^2$-(4-fluorophenylsulfonyl)-2,3-diaminopropanoic acid;

$N^3$-[2-{3-(4-formamidinophenyl)-isoxazolin-5-yl}-acetyl]-$N^2$-(4-methoxyphenylsulfonyl)-2,3-diaminopropanoic acid;

$N^3$-[2-{3-(4-formamidinophenyl)-isoxazolin-5-yl}-acetyl]-$N^2$-(2,3,5,6-tetramethylphenylsulfonyl)-2,3-diaminopropanoic acid;

$N^3$-[2-{3-(4-formamidinophenyl)-isoxazolin-5-yl}-acetyl]-N2-(4-cyanophenylsulfonyl)-2,3-diaminopropanoic acid;

$N^3$-[2-{3-(4-formamidinophenyl)-isoxazolin-5-yl}-acetyl]-$N^2$-(4-chlorophenylsulfonyl)-2,3-diaminopropanoic acid;

$N^3$-[2-{3-(4-formamidinophenyl)-isoxazolin-5-yl}-acetyl]-$N^2$-(4-propylphenylsulfonyl)-2,3-diaminopropanoic acid;

$N^3$-[2-{3-(4-formamidinophenyl)-isoxazolin-5-yl}-acetyl]-$N^2$-(2-phenylethylsulfonyl)-2,3-diaminopropanoic acid;

$N^3$-[2-{3-(4-formamidinophenyl)-isoxazolin-5-yl}-acetyl]-$N^2$-(4-isopropylphenylsulfonyl)-2,3-diaminopropanoic acid;

$N^3$-[2-{3-(4-formamidinophenyl)-isoxazolin-5-yl}-acetyl]-$N^2$-(3-phenylpropylsulfonyl)-2,3-diaminopropanoic acid;

$N^3$-[2-{3-(4-formamidinophenyl)-isoxazolin-5-yl}-acetyl]-$N^2$-(3-pyridylsulfonyl)-2,3-diaminopropanoic acid;

$N^3$-[2-{3-(4-formamidinophenyl)-isoxazolin-5-yl}-acetyl]-$N^2$-(phenylaminosulfonyl)-2,3-diaminopropanoic acid;

$N^3$-[2-{3-(4-formamidinophenyl)-isoxazolin-5-yl}-acetyl]-$N^2$-(benzylaminosulfonyl)-2,3-diaminopropanoic acid;

$N^3$-[2-{3-(4-formamidinophenyl)-isoxazolin-5-yl}-acetyl]-$N^2$-(dimethylaminosulfonyl)-2,3-diaminopropanoic acid;

$N^3$-[2-{3-(2-fluoro-4-formamidinophenyl)-isoxazolin-5-yl}-acetyl]-$N^2$-(3-methylphenylsulfonyl)-2,3-diaminopropanoic acid;

$N^3$-[2-{3-(2-formamidino-5-pyridinyl)-isoxazolin-5-yl}-acetyl]-$N^2$-(n-butyloxycarbonyl)-2,3-diaminopropanoic acid;

$N^3$-[2-{3-(2-formamidino-5-pyridinyl)-isoxazolin-5-yl}-acetyl]-$N^2$-(3-methylphenylsulfonyl)-2,3-diaminopropanoic acid;

$N^3$-[2-{3-(3-formamidino-6-pyridinyl)-isoxazolin-5-yl}-acetyl]-$N^2$-(n-butyloxycarbonyl)-2,3-diaminopropanoic acid;

$N^3$-[2-{3-(3-formamidino-6-pyridinyl)-isoxazolin-5-yl}-acetyl]-$N^2$-(3-methylphenylsulfonyl)-2,3-diaminopropanoic acid;

$N^3$-[2-{3-(4-formamidinophenyl)-isoxazolin-5-yl}-acetyl]-$N^2$-(phenylaminocarbonyl)-2,3-diaminopropanoic acid;

$N^3$-[2-{3-(4-formamidinophenyl)-isoxazolin-5-yl}-acetyl]-$N^2$-(4-fluorophenylaminocarbonyl)-2,3-diaminopropanoic acid;

$N^3$-[2-{3-(4-formamidinophenyl)-isoxazolin-5-yl}-acetyl]-$N^2$-(1-naphthylaminocarbonyl)-2,3-diaminopropanoic acid;

$N^3$-[2-{3-(4-formamidinophenyl)-isoxazolin-5-yl}-acetyl]-$N^2$-(benzylaminocarbonyl)-2,3-diaminopropanoic acid;

$N^3$-[2-{3-(4-formamidinophenyl)-isoxazolin-5-yl}-acetyl]-$N^2$-(3-bromo-2-thienylsulfonyl)-2,3-diaminopropanoic acid;

$N^3$-[2-{3-(4-formamidinophenyl)-isoxazolin-5-yl}-acetyl]-$N^2$-(3-methyl-2-benzothienylsulfonyl)-2,3-diaminopropanoic acid;

$N^3$-[2-{3-(4-formamidinophenyl)-isoxazolin-5-yl}-acetyl]-$N^2$-(isobutyloxycarbonyl)-2,3-diaminopropanoic acid;

$N^3$-[2-{3-(4-formamidinophenyl)-isoxazolin-5-yl}-acetyl]-$N^2$-(isobutyloxycarbonyl)-2,3-diaminopropanoic acid;

N³-[2-{3-(4-formamidinophenyl)-isoxazolin-5-yl}-acetyl]-N²-(isobutyloxycarbonyl)-2,3-diaminopropanoic acid;

N³-[2-{3-(4-formamidinophenyl)-isoxazolin-5-yl}-acetyl]-N²-(2-cyclopropylethoxycarbonyl)-2,3-diaminopropanoic acid;

N³-[2-{3-(4-guanidinophenyl)-isoxazolin-5-yl}-acetyl]-N²-(n-butyloxycarbonyl)-2,3-diaminopropanoic acid;

N³-[2-{3-(4-guanidinophenyl)-isoxazolin-5-yl}-acetyl]-N²-(3-methylphenylsulfonyl)-2,3-diaminopropanoic acid;

N³-[2-{5-(4-formamidinophenyl)-isoxazolin-3-yl}-acetyl]-N²-(n-butyloxycarbonyl)-2,3-diaminopropanoic acid;

N³-[2-{3-(4-formamidinophenyl)-isoxazolin-5-yl}-acetyl]-N²-(2-bromo-phenylsulfonyl)-2,3-diaminopropionic acid;

N³-[2-{3-(4-formamidinophenyl)-isoxazolin-5-yl}-acetyl]-N²-(2-methyl-phenylsulfonyl)-2,3-diaminopropionic acid;

N³-[2-{3-(3-formamidino-6-pyridinyl)-isoxazolin-5-yl}-acetyl]-N²-(3-methylphenylsulfonyl)-2,3-diaminopropionic acid;

N³-[2-{3-(2-formamidino-5-pyridinyl)-isoxazolin-5-yl}-acetyl]-N²-(3-methylphenylsulfonyl)-2,3-diaminopropionic acid;

N³-[2-{3-(2-fluoro-4-formamidinophenyl)-isoxazolin-5-yl}-acetyl]-N²-(3-methylphenylsulfonyl)-2,3-diaminopropionic acid;

N³-[2-{3-(4-formamidinophenyl)-isoxazolin-5-yl}-acetyl]-N²-(3-bromo-phenylsulfonyl)-2,3-diaminopropionic acid;

N³-[2-{3-(4-formamidinophenyl)-isoxazolin-5-yl}-acetyl]-N²-(4-bromo-phenylsulfonyl)-2,3-diaminopropionic acid;

said enantiomeric and diasteriomeric forms being selected from:
(R,S), (R,S);
(R), (R,S);
(S), (R, S);
(R), (R);
(S), (R);
(R), (S);
(S), (S).

The prodrug forms of the compounds of the second embodiment include the following esters:
methyl;
ethyl;
isopropyl;
methylcarbonyloxymethyl-;
ethylcarbonyloxymethyl-;
t-butylcarbonyloxymethyl-;
cyclohexylcarbonyloxymethyl-;
1-(methylcarbonyloxy)ethyl-;
1-(ethylcarbonyloxy)ethyl-;
1-(t-butylcarbonyloxy)ethyl-;
1-(cyclohexylcarbonyloxy)ethyl-;
i-propyloxycarbonyloxymethyl-;
cyclohexylcarbonyloxymethyl-;
t-butyloxycarbonyloxymethyl-;
1-(i-propyloxycarbonyloxy)ethyl-;
1-(cyclohexyloxycarbonyloxy)ethyl-;
1-(t-butyloxycarbonyloxy)ethyl-;
dimethylaminoethyl-;
diethylaminoethyl-;
(5-methyl-1,3-dioxacyclopenten-2-on-4-yl)methyl-;
(5-(t-butyl)-1,3-dioxacyclopenten-2-on-4-yl)methyl-;
(1,3-dioxa-5-phenyl-cyclopenten-2-on-4-yl)methyl-;
1-(2-(2-methoxypropyl)carbonyloxy)ethyl-.

[11] Also preferred compounds of the second embodiment are those compounds of Formula Ic:

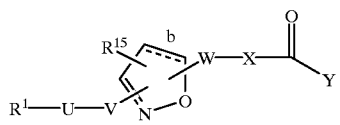

(Ic)

wherein:
b is a single or double bond;
R¹ is selected from R²ᵃ(R³)N—, R²(R³)N(R²N=)C—, R²ᵃ(R³)N(CH₂)qZ—, R²(R³)N(R²N=)C(CH₂)qZ—, R²(R³)N(R²N=)CN(R²)—, R²(R³)NC(O)—, R²(R⁵O)N(R²N=)C—, or R²(R³)N(R⁵ON=)C—;

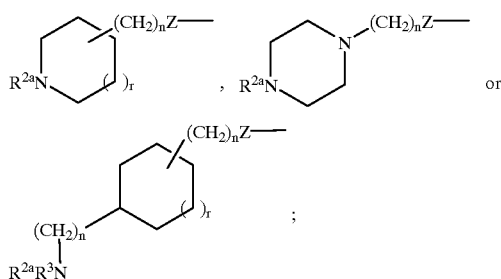

Z is selected from a bond (i.e. is absent), O, or S;
R² and R³ are independently selected from: H; $C_1$–$C_6$ alkyl; $C_7$–$C_{11}$ arylalkyl optionally substituted with 0–3 groups selected from hydroxy, halogen, $C_1$–$C_6$ alkoxy, $C_1$–$C_6$ alkyl, $CF_3$, $S(O)_m CH_3$, —$N(CH_3)_2$, $C_1$–$C_4$ haloalkyl, methylenedioxydiyl, ethylenedioxydiyl; $C_1$–$C_{10}$ alkoxycarbonyl; aryl($C_1$–$C_{10}$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_m CH_3$, —$N(CH_3)_2$, $C_1$–$C_4$ haloalkyl, methylenedioxydiyl, ethylenedioxydiyl; or heteroaryl($C_1$–$C_5$)alkyl where the heteroaryl group is optionally substituted with 0–2 groups selected from hydroxy, halogen, $C_1$–$C_6$ alkoxy, $C_1$–$C_6$ alkyl, $CF_3$, $S(O)_m CH_3$, —$N(CH_3)_2$, $C_1$–$C_4$ haloalkyl, methylenedioxydiyl, ethylenedioxydiyl;

R²ᵃ is R² or R²(R³)N(R²N=)C;

U is a single bond (i.e., U is not present),

V is selected from:
a single bond (i.e., V is not present);
—($C_1$–$C_7$ alkyl)-, substituted with 0–3 groups independently selected from R⁶ or R⁷;
—($C_2$–$C_7$ alkenyl)-, substituted with 0–3 groups independently selected from R⁶ or R⁷;
—($C_2$–$C_7$ alkynyl)-, substituted with 0–3 groups independently selected from R⁶ or R⁷;
—(phenyl)-Q-, said phenyl substituted with 0–2 groups independently selected from R⁶ or R⁷;
—(pyridyl)-Q-, said pyridyl substituted with 0–2 groups independently selected from R⁶ or R⁷; or -(pyridazinyl)-Q-, said pyridazinyl substituted with 0–2 groups independently selected from $R^6$ or $R^7$, Q is selected from a single bond (i.e., Q is not present), —O—, —S(O)$_m$—, —N($R^{12}$)—, —(CH$_2$)$_m$—, —C(=O)—, —N($R^{5a}$)C(=O)—, —C(=O)N($R^{5a}$)—, —CH$_2$O—, —OCH$_2$—, —CH$_2$N($R^{12}$)—, —N($R^{12}$)CH$_2$—, —CH$_2$C(=O)—, —C(=O)CH$_2$—, —CH$_2$S(O)$_m$—, or —S(O)$_m$CH$_2$—, provided that when b is a single bond, and $R^1$—U—V— is a substituent on $C_5$ of the central 5-membered ring in Formula I, then Q is not —O—, —S(O)$_m$—, —N($R^{12}$)—, —C(=O)N($R^{5a}$)—, —CH$_2$O—, CH$_2$N($R^{12}$)— or —CH$_2$S(O)$_m$—;

W is selected from:

—(C($R^4$)$_2$)—C(=O)—N($R^{5a}$)—, or —C(=O)—N($R^{5a}$)—(C($R^4$)$_2$)—;

X is —C($R^4$)$_2$—CHR$^{4a}$—;

$R^4$ is selected from H, $C_1$–$C_{10}$ alkyl, $C_1$–$C_{10}$ alkylcarbonyl, aryl, arylalkyl, cycloalkyl, or cycloalkylalkyl;

$R^{4a}$ is selected from hydroxy, $C_1$–$C_{10}$ alkoxy, nitro, —N($R^5$)$R^{5a}$, —N($R^{12}$)$R^{13}$, or —N($R^{16}$)$R^{17}$, $C_1$–$C_{10}$ alkyl substituted with 0–3 $R^6$, aryl substituted with 0–3 $R^6$, heteroaryl substituted with 0–3 $R^6$, or $C_1$–$C_{10}$ alkylcarbonyl;

$R^{4b}$ is selected from H, $C_1$–$C_6$ alkyl, $C_2$–$C_6$ alkenyl, $C_2$–$C_6$ alkynyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, $C_1$–$C_6$ alkylcarbonyl, $C_6$–$C_{10}$ aryl, —N($R^{12}$)$R^{13}$, halo, CF$_3$, CN, $C_1$–$C_6$ alkoxycarbonyl, carboxy, piperidinyl, morpholinyl or pyridyl;

$R^5$ is selected from H or $C_1$–$C_{10}$ alkyl substituted with 0–6 $R^{4b}$;

$R^{5a}$ is selected from hydrogen, hydroxy, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_1$–$C_6$ alkoxy, benzyloxy, $C_6$ to $C_{10}$ aryl, heteroaryl, heteroarylalkyl, $C_7$ to $C_{11}$ arylalkyl, or adamantylmethyl, $C_1$–$C_{10}$ alkyl substituted with 0–2 $R^{4b}$;

alternately, $R^5$ and $R^{5a}$ can be taken together to be 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl, each being optionally substituted with $C_1$–$C_6$ alkyl, $C_6$–$C_{10}$ aryl, heteroaryl, $C_7$–$C_{11}$ arylalkyl, $C_1$–$C_6$ alkylcarbonyl, $C_3$–$C_7$ cycloalkylcarbonyl, $C_1$–$C_6$ alkoxycarbonyl or $C_7$–$C_{11}$ arylalkoxycarbonyl;

$R^{5b}$ is selected from $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$ Y is selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ aralkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{10}$ alkoxyalkylcarbonyloxyalkyloxy, $C_5$ to $C_{10}$ (5-alkyl-1,3-dioxa-cyclopenten-2-one-yl)methyloxy, or $C_{10}$ to $C_{14}$ (5-aryl-1,3-dioxa-cyclopenten-2-one-yl) methyloxy;

$R^6$ and $R^7$ are each independently selected from H, $C_1$–$C_{10}$ alkyl, hydroxy, $C_1$–$C_{10}$ alkoxy, nitro, $C_1$–$C_{10}$ alkylcarbonyl, —N($R^{12}$)$R^{13}$, cyano, or halo;

$R^{12}$ and $R^{13}$ are each independently selected from H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, heteroarylcarbonyl, heteroarylalkylcarbonyl or aryl, wherein said aryls are optionally substituted with 0–3 substituents selected from the group consisting of: $C_1$–$C_4$ alkyl, $C_1$–$C_4$ alkoxy, halo, CF$_3$, and NO$_2$;

$R^{15}$ is selected from H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or $C_1$–$C_{10}$ alkoxycarbonyl, CO$_2$$R^5$ or —C(=O)N($R^5$)$R^{5a}$;

$R^{16}$ is selected from:
—C(=O)—O—$R^{18a}$,
—C(=O)—$R^{18b}$,
—C(=O)N($R^{18b}$)$_2$,
—SO$_2$—$R^{18a}$, or
—SO$_2$—N($R^{18b}$)$_2$;

$R^{17}$ is selected from: H or $C_1$–$C_4$ alkyl;

$R^{18a}$ is selected from:
$C_1$–$C_8$ alkyl substituted with 0–2 $R^{19}$,
$C_2$–$C_8$ alkenyl substituted with 0–2 $R^{19}$,
$C_2$–$C_8$ alkynyl substituted with 0–2 $R^{19}$,
$C_3$–$C_8$ cycloalkyl substituted with 0–2 $R^{19}$,
aryl substituted with 0–4 $R^{19}$,
aryl($C_1$–$C_6$ alkyl)-substituted with 0–4 $R^{19}$,
a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolinyl, benzimidazolyl, piperidinyl, tetrahydrofuranyl, pyranyl, pyrimidinyl, 3H-indolyl, carbazolyl, pyrrolidinyl, piperidinyl, indolinyl, or morpholinyl, said heterocyclic ring being substituted with 0–4 $R^{19}$;

$C_1$–$C_6$ alkyl substituted with a heterocyclic ring system selected from pyridinyl, furanyl, thiazolyl, thienyl, pyrrolyl, pyrazolyl, imidazolyl, isoxazolyl, benzofuranyl, indolyl, indolenyl, quinolinyl, isoquinolinyl,.benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, said heterocyclic ring being substituted with 0–4 $R^{19}$;

$R^{18b}$ is selected from $R^{18a}$ or H;

$R^{19}$ is selected from H, halogen, CF$_3$, CN, NO$_2$, N$R^{12}R^{13}$, $C_1$–$C_8$ alkyl; $C_2$–$C_6$ alkenyl, $C_2$–$C_6$ alkynyl, $C_1$–$C_6$ alkoxy, $C_3$–$C_{11}$ cycloalkyl, $C_4$–$C_{11}$ cycloalkylalkyl, aryl, heteroaryl, aryl($C_1$–$C_6$ alkyl)-, or $C_1$–$C_4$ alkoxycarbonyl;

n is 0–4;

q is 1–7;

r is 0–3;

provided that n, q, and r are chosen such that the number of atoms between $R^1$ and Y is in the range of 8–17.

[12] Further preferred compounds of the second embodiment of Formula Ic are those compounds of Formula Ib:

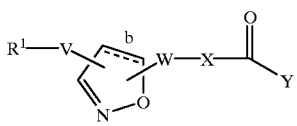

(Ib)

wherein:

R[1] is selected from: R[2](R[3])N—, R[2]NH(R[2]N=)C—, R[2]NH(R[2]N=)CNH—, R[2]R[3]N(CH$_2$)$_{p'}$Z—, R[2]NH(R[2]N=)CNH(CH$_2$)$_{p'}$Z—, R[2](R[3])NC(O)—, R[2](R[5]O)N(R[2]N=)C—, or R[2](R[3])N(R[5]ON=)C—;

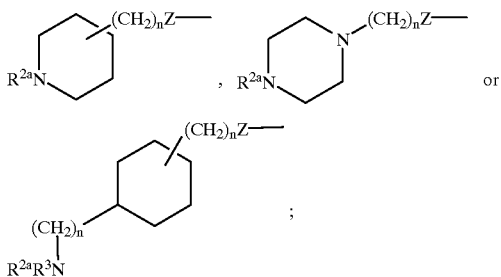

n is 0–1;
p' is 4–6;
p" is 2–4;
Z is selected from a bond (i.e. is absent) or O;
V is a single bond (i.e., V is not present), -(phenyl)- or -(pyridyl)-;
W is selected from:
  —(C(R[4])$_2$)—C(=O)—N(R[5a])—,
  —C(=O)—N(R[5a])—CH$_2$—;
X is selected from:
  —CH$_2$—CHN(R[16])R[17]—, or
  —CH$_2$—CHNR[5]R[5a]—;
Y is selected from:
  hydroxy;
  $C_1$ to $C_{10}$ alkoxy;
  methylcarbonyloxymethoxy-;
  ethylcarbonyloxymethoxy-;
  t-butylcarbonyloxymethoxy-;
  cyclohexylcarbonyloxymethoxy-;
  1-(methylcarbonyloxy)ethoxy-;
  1-(ethylcarbonyloxy)ethoxy-;
  1-(t-butylcarbonyloxy)ethoxy-;
  1-(cyclohexylcarbonyloxy)ethoxy-;
  i-propyloxycarbonyloxymethoxy-;
  t-butyloxycarbonyloxymethoxy-;
  1-(i-propyloxycarbonyloxy)ethoxy-;
  1-(cyclohexyloxycarbonyloxy)ethoxy-;
  1-(t-butyloxycarbonyloxy)ethoxy-;
  dimethylaminoethoxy-;
  diethylaminoethoxy-;
  (5-methyl-1,3-dioxacyclopenten-2-on-4-yl)methoxy-;
  (5-(t-butyl)-1,3-dioxacyclopenten-2-on-4-yl)methoxy-;
  (1,3-dioxa-5-phenyl-cyclopenten-2-on-4-yl)methoxy-;
  1-(2-(2-methoxypropyl)carbonyloxy)ethoxy-;
R[16] is selected from:
  —C(=O)—O—R[18a],
  —C(=O)—R[18b],
  —S(=O)$_2$—R[18a] or
  —SO$_2$—N(R[18b])$_2$;
R[17] is selected from H or $C_1$–$C_5$ alkyl;
R[18a] is selected from:
  $C_1$–$C_8$ alkyl substituted with 0–2 R[19],
  $C_2$–$C_8$ alkenyl substituted with 0–2 R[19],
  $C_2$–$C_8$ alkynyl substituted with 0–2 R[19],
  $C_3$–$C_8$ cycloalkyl substituted with 0–2 R[19],
  aryl substituted with 0–4 R[19],
  aryl($C_1$–$C_6$ alkyl)-substituted with 0–4 R[19],
  a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolinyl, benzimidazolyl, piperidinyl, tetrahydrofuranyl, pyranyl, pyrimidinyl, 3H-indolyl, carbazolyl, pyrrolidinyl, piperidinyl, indolinyl, or morpholinyl, said heterocyclic ring being substituted with 0–4 R[19];
  $C_1$–$C_6$ alkyl substituted with a heterocyclic ring system selected from pyridinyl, furanyl, thiazolyl, thienyl, pyrrolyl, pyrazolyl, imidazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, said heterocyclic ring being substituted with 0–4 R[19].

[13] Further preferred compounds of Formula Ib are those compounds wherein:
  R[1] is R[2]NH(R[2]N=)C— or R[2]HN(R[2]N=)CNH— and V is phenylene or pyridylene; or
  R[1] is

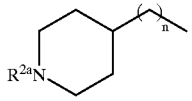

and V is a single bond (i.e. V is absent);
n is 1 or 2;
R[18a] is selected from:
  $C_1$–$C_4$ alkyl substituted with 0–2 R[19],
  $C_2$–$C_4$ alkenyl substituted with 0–2 R[19],
  $C_2$–$C_4$ alkynyl substituted with 0–2 R[19],
  $C_3$–$C_7$ cycloalkyl substituted with 0–2 R[19],
  aryl substituted with 0–4 R[19],
  aryl($C_1$–$C_4$ alkyl)-substituted with 0–4 R[19],
  a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolinyl, benzimidazolyl, piperidinyl, tetrahydrofuranyl, pyranyl, pyrimidinyl, 3H-indolyl, carbazolyl, pyrrolidinyl, piperidinyl, indolinyl, isoxazolinyl or morpholinyl, said heterocyclic ring being substituted with 0–4 R[19];
  $C_1$–$C_4$ alkyl substituted with a heterocyclic ring system selected from pyridinyl, furanyl, thiazolyl, thienyl, pyrrolyl, pyrazolyl, imidazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, isoxazolinyl or morpholinyl, said heterocyclic ring being substituted with 0–4 R[19].

[14] Specifically preferred compounds of Formula Ib are compounds, or pharmaceutically acceptable salt forms thereof, selected from:

$N^3$-[2-{3-(4-formamidinophenyl)-isoxazolin-5(R,S)-yl}-acetyl]-N2-(phenylsulfonyl)-2,3-(S)-diaminopropanoic acid;

$N^3$-[2-{3-(4-formamidinophenyl)-isoxazolin-5(R,S)-yl}-acetyl]-N2-(4-methyl-phenyl-sulfonyl)-2,3-(S)-diaminopropanoic acid;

$N^3$-[2-{3-(4-formamidinophenyl)-isoxazolin-5(R,S)-yl}-acetyl]-N2-(butanesulfonyl)-2,3-(S)-diaminopropanoic acid;

$N^3$-[2-{3-(4-formamidinophenyl)-isoxazolin-5(R,S)-yl}-acetyl]-N2-(propanesulfonyl)-2,3-(S)-diaminopropanoic acid;

$N^3$-[2-{3-(4-formamidinophenyl)-isoxazolin-5(R,S)-yl}-acetyl]-N2-(ethanesulfonyl)-2,3-(S)-diaminopropanoic acid;

$N^3$-[2-{3-(4-formamidinophenyl)-isoxazolin-5(R,S)-yl}-acetyl]-N2-(methyloxycarbonyl)-2,3-(S)-diaminopropanoic acid;

$N^3$-[2-{3-(4-formamidinophenyl)-isoxazolin-5(R,S)-yl}-acetyl]-N2-(ethyloxycarbonyl)-2,3-(S)-diaminopropanoic acid;

$N^3$-[2-{3-(4-formamidinophenyl)-isoxazolin-5(R,S)-yl}-acetyl]-N2-(1-propyloxycarbonyl)-2,3-(S)-diaminopropanoic acid;

$N^3$-[2-{3-(4-formamidinophenyl)-isoxazolin-5(R,S)-yl}-acetyl]-N2-(2-propyloxycarbonyl)-2,3-(S)-diaminopropanoic acid;

$N^3$-[2-{3-(4-formamidinophenyl)-isoxazolin-5(R,S)-yl}-acetyl]-N2-(n-butyloxycarbonyl)-2,3-(S)-diaminopropanoic acid;

$N^3$-[2-{3-(4-formamidinophenyl)-isoxazolin-5(R)-yl}-acetyl]-N2-(n-butyloxycarbonyl)-2,3-(S)-diaminopropanoic acid;

$N^3$-[2-{3-(4-formamidinophenyl)-isoxazolin-5(S)-yl}-acetyl]-N2-(n-butyloxycarbonyl)-2,3-(S)-diaminopropanoic acid;

$N^3$-[2-{3-(4-formamidinophenyl)-isoxazolin-5(R)-yl}-acetyl]-N2-(n-butyloxycarbonyl)-2,3-(R)-diaminopropanoic acid;

$N^3$-[2-{3-(4-formamidinophenyl)-isoxazolin-5(S)-yl}-acetyl]-N2-(n-butyloxycarbonyl)-2,3-(R)-diaminopropanoic acid;

$N^3$-[2-{3-(4-formamidinophenyl)-isoxazolin-5(R,S)-yl}-acetyl]-N2-(2-butyloxycarbonyl)-2,3-(S)-diaminopropanoic acid;

$N^3$-[2-{3-(4-formamidinophenyl)-isoxazolin-5(R,S)-yl}-acetyl]-N2-(1-(2-methyl)-propyloxycarbonyl)-2,3-(S)-diaminopropanoic acid;

$N^3$-[2-{3-(4-formamidinophenyl)-isoxazolin-5(R,S)-yl}-acetyl]-N2-(2-(2-methyl)-propyloxycarbonyl)-2,3-(S)-diaminopropanoic acid;

$N^3$-[2-{3-(4-formamidinophenyl)-isoxazolin-5(R,S)-yl}-acetyl]-N2-(benzyloxycarbonyl)-2,3-(S)-diaminopropanoic acid;

$N^3$-[2-{3-(4-formamidinophenyl)-isoxazolin-5(R)-yl}-acetyl]-N2-(benzyloxycarbonyl)-2,3-(S)-diaminopropanoic acid;

$N^3$-[2-{3-(4-formamidinophenyl)-isoxazolin-5(S)-yl}-acetyl]-N2-(benzyloxycarbonyl)-2,3-(S)-diaminopropanoic acid;

$N^3$-[2-{3-(4-formamidinophenyl)-isoxazolin-5(R,S)-yl}-acetyl]-N2-(4-methylbenzyloxycarbonyl)-2,3-(S)-diaminopropanoic acid;

$N^3$-[2-{3-(4-formamidinophenyl)-isoxazolin-5(R,S)-yl}-acetyl]-N2-(4-methoxybenzyloxycarbonyl)-2,3-(S)-diaminopropanoic acid;

$N^3$-[2-{3-(4-formamidinophenyl)-isoxazolin-5(R,S)-yl}-acetyl]-N2-(4-chlorobenzyloxycarbonyl)-2,3-(S)-diaminopropanoic acid;

$N^3$-[2-{3-(4-formamidinophenyl)-isoxazolin-5(R,S)-yl}-acetyl]-N2-(4-bromobenzyloxycarbonyl)-2,3-(S)-diaminopropanoic acid;

$N^3$-[2-{3-(4-formamidinophenyl)-isoxazolin-5(R,S)-yl}-acetyl]-N2-(4-fluorobenzyloxycarbonyl)-2,3-(S)-diaminopropanoic acid;

$N^3$-[2-{3-(4-formamidinophenyl)-isoxazolin-5(R,S)-yl}-acetyl]-N2-(4-phenoxybenzyloxycarbonyl)-2,3-(S)-diaminopropanoic acid;

$N^3$-[2-{3-(4-formamidinophenyl)-isoxazolin-5(R,S)-yl}-acetyl]-N2-(2-(methyloxyethyl)-oxycarbonyl)-2,3-(S)-diaminopropanoic acid;

$N^3$-[2-{3-(4-formamidinophenyl)-isoxazolin-5(R,S)-yl}-acetyl]-N2-(2-pyridinylcarbonyl)-2,3-(S)-diaminopropanoic acid;

$N^3$-[2-{3-(4-formamidinophenyl)-isoxazolin-5(R,S)-yl}-acetyl]-N2-(3-pyridinylcarbonyl)-2,3-(S)-diaminopropanoic acid;

$N^3$-[2-{3-(4-formamidinophenyl)-isoxazolin-5(R,S)-yl}-acetyl]-N2-(4-pyridinyl-carbonyl)-2,3-(S)-diaminopropanoic acid;

$N^3$-[2-{3-(4-formamidinophenyl)-isoxazolin-5(R,S)-yl}-acetyl]-N2-(2-(2-pyridinyl)-acetyl)-2,3-(S)-diaminopropanoic acid;

$N^3$-[2-{3-(4-formamidinophenyl)-isoxazolin-5(R,S)-yl}-acetyl]-N2-(2-(3-pyridinyl)-acetyl)-2,3-(S)-diaminopropanoic acid;

$N^3$-[2-{3-(4-formamidinophenyl)-isoxazolin-5(R,S)-yl}-acetyl]-N2-(2-(4-pyridinyl)-acetyl)-2,3-(S)-diaminopropanoic acid;

$N^3$-[2-{3-(4-formamidinophenyl)-isoxazolin-5(R,S)-yl}-acetyl]-N2-(2-pyridyl-methyloxycarbonyl)-2,3-(S)-diaminopropanoic acid;

$N^3$-[2-{3-(4-formamidinophenyl)-isoxazolin-5(R,S)-yl}-acetyl]-N2-(3-pyridyl-methyloxycarbonyl)-2,3-(S)-diaminopropanoic acid;

$N^3$-[2-{3-(4-formamidinophenyl)-isoxazolin-5(R,S)-yl}-acetyl]-N2-(4-pyridyl-methyloxycarbonyl)-2,3-(S)-diaminopropanoic acid.

$N^3$-[2-{3-(4-formamidinophenyl)-isoxazolin-5(R,S)-yl}-acetyl]-N2-(4-butyloxyphenylsulfonyl)-2,3-(S)-diaminopropanoic acid;

$N^3$-[2-{3-(4-formamidinophenyl)-isoxazolin-5(R,S)-yl}-acetyl]-N2-(2-thienylsulfonyl)-2,3-(S)-diaminopropanoic acid;

$N^3$-[2-{3-(4-formamidinophenyl)-isoxazolin-5(R,S)-yl}-acetyl]-N2-(3-methylphenylsulfonyl)-2,3-(R,S)-diaminopropanoic acid;

$N^3$-[2-{3-(4-formamidinophenyl)-isoxazolin-5(R,S)-yl}-acetyl]-N2-(3-methylphenylsulfonyl)-2,3-(S)-diaminopropanoic acid;

$N^3$-[2-{3-(4-formamidinophenyl)-isoxazolin-5(R,S)-yl}-acetyl]-N2-(3-methylphenylsulfonyl)-2,3-(R)-diaminopropanoic acid;

$N^3$-[2-{3-(4-formamidinophenyl)-isoxazolin-5(R)-yl}-acetyl]-N2-(3-methylphenylsulfonyl)-2,3-(S)-diaminopropanoic acid;

$N^3$-[2-{3-(4-formamidinophenyl)-isoxazolin-5(S)-yl}-acetyl]-N2-(3-methylphenylsulfonyl)-2,3-(S)-diaminopropanoic acid;

$N^3$-[2-{3-(4-formamidinophenyl)-isoxazolin-5(S)-yl}-acetyl]-N2-(3-methylphenylsulfonyl)-2,3-(R)-diaminopropanoic acid;

$N^3$-[2-{3-(4-formamidinophenyl)-isoxazolin-5(R)-yl}-acetyl]-N2-(3-methylphenylsulfonyl)-2,3-(R)-diaminopropanoic acid;

$N^3$-[2-{3-(4-formamidinophenyl)-isoxazolin-5(R,S)-yl}-acetyl]-N2-(4-iodophenylsulfonyl)-2,3-(S)-diaminopropanoic acid;

$N^3$-[2-{3-(4-formamidinophenyl)-isoxazolin-5(R,S)-yl}-acetyl]-N2-(3-trifluoromethylphenylsulfonyl)-2,3-(S)-diaminopropanoic acid;

$N^3$-[2-{3-(4-formamidinophenyl)-isoxazolin-5(R,S)-yl}-acetyl]-N2-(3-chlorophenylsulfonyl)-2,3-(S)-diaminopropanoic acid;

$N^3$-[2-{3-(4-formamidinophenyl)-isoxazolin-5(R,S)-yl}-acetyl]-N2-(3-2-methoxycarbonylphenylsulfonyl)-2,3-(S)-diaminopropanoic acid;

$N^3$-[2-{3-(4-formamidinophenyl)-isoxazolin-5(R,S)-yl}-acetyl]-N2-(2,4,6-trimethylphenylsulfonyl)-2,3-(S)-diaminopropanoic acid;

$N^3$-[2-{3-(4-formamidinophenyl)-isoxazolin-5(R,S)-yl}-acetyl]-N2-(2-chlorophenylsulfonyl)-2,3-(S)-diaminopropanoic acid;

$N^3$-[2-{3-(4-formamidinophenyl)-isoxazolin-5(R,S)-yl}-acetyl]-N2-(4-trifluoromethylphenylsulfonyl)-2,3-(S)-diaminopropanoic acid;

$N^3$-[2-{3-(4-formamidinophenyl)-isoxazolin-5(R,S)-yl}-acetyl]-N2-(2-trifluoromethylphenylsulfonyl)-2,3-(S)-diaminopropanoic acid;

$N^3$-[2-{3-(4-formamidinophenyl)-isoxazolin-5(R,S)-yl}-acetyl]-N2-(2-fluorophenylsulfonyl)-2,3-(S)-diaminopropanoic acid;

$N^3$-[2-{3-(4-formamidinophenyl)-isoxazolin-5(R,S)-yl}-acetyl]-N2-(4-fluorophenylsulfonyl)-2,3-(S)-diaminopropanoic acid;

$N^3$-[2-{3-(4-formamidinophenyl)-isoxazolin-5(R,S)-yl}-acetyl]-N2-(4-methoxyphenylsulfonyl)-2,3-(S)-diaminopropanoic acid;

$N^3$-[2-{3-(4-formamidinophenyl)-isoxazolin-5(R,S)-yl}-acetyl]-N2-(2,3,5,6-tetramethylphenylsulfonyl)-2,3-(S)-diaminopropanoic acid;

$N^3$-[2-{3-(4-formamidinophenyl)-isoxazolin-5(R,S)-yl}-acetyl]-N2-(4-cyanophenylsulfonyl)-2,3-(S)-diaminopropanoic acid;

$N^3$-[2-{3-(4-formamidinophenyl)-isoxazolin-5(R,S)-yl}-acetyl]-N2-(4-chlorophenylsulfonyl)-2,3-(S)-diaminopropanoic acid;

$N^3$-[2-{3-(4-formamidinophenyl)-isoxazolin-5(R,S)-yl}-acetyl]-N2-(4-propylphenylsulfonyl)-2,3-(S)-diaminopropanoic acid;

$N^3$-[2-{3-(4-formamidinophenyl)-isoxazolin-5(R,S)-yl}-acetyl]-N2-(2-phenylethylsulfonyl)-2,3-(S)-diaminopropanoic acid;

$N^3$-[2-{3-(4-formamidinophenyl)-isoxazolin-5(R,S)-yl}-acetyl]-N2-(4-isopropylphenylsulfonyl)-2,3-(S)-diaminopropanoic acid;

$N^3$-[2-{3-(4-formamidinophenyl)-isoxazolin-5(R,S)-yl}-acetyl]-N2-(3-phenylpropylsulfonyl)-2,3-(S)-diaminopropanoic acid;

$N^3$-[2-{3-(4-formamidinophenyl)-isoxazolin-5(R,S)-yl}-acetyl]-N2-(3-pyridylsulfonyl)-2,3-(S)-diaminopropanoic acid;

$N^3$-[2-{3-(4-formamidinophenyl)-isoxazolin-5(R,S)-yl}-acetyl]-N2-(phenylaminosulfonyl)-2,3-(S)-diaminopropanoic acid;

$N^3$-[2-{3-(4-formamidinophenyl)-isoxazolin-5(R,S)-yl}-acetyl]-N2-(benzylaminosulfonyl)-2,3-(S)-diaminopropanoic acid;

$N^3$-[2-{3-(4-formamidinophenyl)-isoxazolin-5(R,S)-yl}-acetyl]-N2-(dimethylaminosulfonyl)-2,3-(S)-diaminopropanoic acid;

$N^3$-[2-{3-(2-fluoro-4-formamidinophenyl)-isoxazolin-5(R,S)-yl}-acetyl]-N2-(3-methylphenylsulfonyl)-2,3-(S)-diaminopropanoic acid, $N^3$-[2-{3-(2-formamidino-5-pyridinyl)-isoxazolin-5(R,S)-yl}-acetyl]-N2-(n-butyloxycarbonyl)-2,3-(S)-diaminopropanoic acid, $N^3$-[2-{3-(2-formamidino-5-pyridinyl)-isoxazolin-5(R,S)-yl}-acetyl]-N2-(3-methylphenylsulfonyl)-2,3-(S)-diaminopropanoic acid, $N^3$-[2-{3-(3-formamidino-6-pyridinyl)-isoxazolin-5(R,S)-yl}-acetyl]-N2-(n-butyloxycarbonyl)-2,3-(S)-diaminopropanoic acid, $N^3$-[2-{3-(3-formamidino-6-pyridinyl)-isoxazolin-5(R,S)-yl}-acetyl]-N2-(3-methylphenylsulfonyl)-2,3-(S)-diaminopropanoic acid, $N^3$-[2-{3-(4-formamidinophenyl)-isoxazolin-5(R,S)-yl}-acetyl]-N2-(phenylaminocarbonyl)-2,3-(S)-diaminopropanoic acid;

$N^3$-[2-{3-(4-formamidinophenyl)-isoxazolin-5(R,S)-yl}-acetyl]-N2-(4-fluorophenylaminocarbonyl)-2,3-(S)-diaminopropanoic acid;

$N^3$-[2-{3-(4-formamidinophenyl)-isoxazolin-5(R,S)-yl}-acetyl]-N2-(1-naphthylaminocarbonyl)-2,3-(S)-diaminopropanoic acid;

$N^3$-[2-{3-(4-formamidinophenyl)-isoxazolin-5(R,S)-yl}-acetyl]-N2-(benzylaminocarbonyl)-2,3-(S)-diaminopropanoic acid;

$N^3$-[2-{3-(4-formamidinophenyl)-isoxazolin-5(R,S)-yl}-acetyl]-N2-(3-bromo-2-thienylsulfonyl)-2,3-(S)-diaminopropanoic acid;

$N^3$-[2-{3-(4-formamidinophenyl)-isoxazolin-5(R,S)-yl}-acetyl]-N2-(3-methyl-2-benzothienylsulfonyl)-2,3-(S)-diaminopropanoic acid, $N^3$-[2-{3-(4-formamidinophenyl)-isoxazolin-5(R,S)-yl}-acetyl]-N2-(isobutyloxycarbonyl)-2,3-(S)-diaminopropanoic acid, $N^3$-[2-{3-(4-formamidinophenyl)-isoxazolin-5(R)-yl}-acetyl]-N2-(isobutyloxycarbonyl)-2,3-(S)-diaminopropanoic acid, $N^3$-[2-{3-(4-formamidinophenyl)-isoxazolin-5(S)-yl}-acetyl]-N2-(isobutyloxycarbonyl)-2,3-(S)-diaminopropanoic acid, $N^3$-[2-{3-(4-formamidinophenyl)-isoxazolin-5(R,S)-yl}-acetyl]-N2-(2-cyclopropylethoxycarbonyl)-2,3-(S)-diaminopropanoic acid, $N^3$-[2-{3-(4-formamidinophenyl)-isoxazolin-5(R)-yl}-acetyl]-N2-(2-cyclopropylethoxycarbonyl)-2,3-(S)-diaminopropanoic acid, and $N^3$-[2-{3-(4-formamidinophenyl)-isoxazolin-5(S)-yl}-acetyl]-N2-(2-cyclopropylethoxycarbonyl)-2,3-(S)-diaminopropanoic acid.

N³-[2-{3-(4-guanidinophenyl)-isoxazolin-5(R,S)-yl}-acetyl]-N2-(n-butyloxycarbonyl)-2,3-(S)-diaminopropanoic acid.

N³-[2-{3-(4-guanidinophenyl)-isoxazolin-5(R)-yl}-acetyl]-N2-(n-butyloxycarbonyl)-2,3-(S)-diaminopropanoic acid.

N³-[2-{3-(4-guanidinophenyl)-isoxazolin-5(R)-yl}-acetyl]-N2-(3-methylphenylsulfonyl)-2,3-(S)-diaminopropanoic acid.

N³-[2-{5-(4-formamidinophenyl)-isoxazolin-3(R,S)-yl}-acetyl]-N2-(n-butyloxycarbonyl)-2,3-(S)-diaminopropanoic acid;

[15] Also specifically preferred are prodrug esters of the specifically preferred compounds of Formula Ib, said esters being chosen from the group consisting of:

methyl;
ethyl;
isopropyl;
methylcarbonyloxymethyl-;
ethylcarbonyloxymethyl-;
t-butylcarbonyloxymethyl-;
cyclohexylcarbonyloxymethyl-;
1-(methylcarbonyloxy)ethyl-;
1-(ethylcarbonyloxy)ethyl-;
1-(t-butylcarbonyloxy)ethyl-;
1-(cyclohexylcarbonyloxy)ethyl-;
i-propyloxycarbonyloxymethyl-;
cyclohexyloxycarbonyloxymethyl-;
t-butyloxycarbonyloxymethyl-;
1-(i-propyloxycarbonyloxy)ethyl-;
1-cyclohexyloxycarbonyloxy)ethyl-;
1-(t-butyloxycarbonyloxy)ethyl-;
dimethylaminoethyl-;
diethylaminoethyl-;
(5-methyl-1,3-dioxacyclopenten-2-on-4-yl)methyl-;
(5-(t-butyl)-1,3-dioxacyclopenten-2-on-4-yl)methyl-;
(1,3-dioxa-5-phenyl-cyclopenten-2-on-4-yl)methyl-;
1-(2-(2-methoxypropyl)carbonyloxy)ethyl-.

[16] A third embodiment of this invention provides a compound of Formula Id:

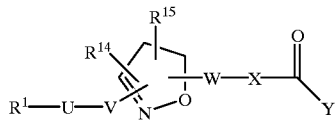

(Id)

or a pharmaceutically acceptable salt or prodrug form thereof wherein:

R¹ is selected from is selected from R²(R³)N—, R²(R³)N(R²N=)C—, R²(R³)N(R²N=)CN(R²)—, R²(R³)N(CH₂)qZ—, R²(R³)N(R²N=)C(CH₂)qZ—, R²(R³)N(R²N=)CN(R²)(CH₂)qZ—, piperazinyl-(CH₂)qZ—, R²(R³)NC(O)—, R²(R⁵O)N(R²N=)C—, R²(R³)N(R⁵ON=)C—,

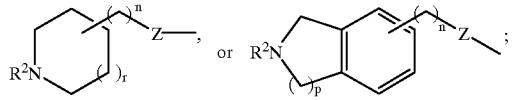

Z is selected from a bond (i.e., is absent), O, S, S(=O), or S(=O)₂;

R² and R³ are independently selected from: H; $C_1$–$C_{10}$ alkyl; $C_3$–$C_6$ alkenyl; $C_3$–$C_{11}$ cycloalkyl; $C_4$–$C_{11}$ cycloalkylalkyl; $C_6$–$C_{10}$ aryl optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; , $C_7$–$C_{11}$ arylalkyl optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; $C_2$–$C_7$ alkylcarbonyl; $C_7$–$C_{11}$ arylcarbonyl optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; $C_1$–$C_{10}$ alkoxycarbonyl; $C_4$–$C_{11}$ cycloalkoxycarbonyl; $C_7$–$C_{11}$ bicycloalkoxycarbonyl; $C_7$–$C_{11}$ aryloxycarbonyl optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; aryl($C_1$–$C_{10}$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; $C_1$–$C_6$ alkylcarbonyloxy($C_1$–$C_4$ alkoxy)carbonyl; $C_6$–$C_{10}$ arylcarbonyloxy($C_1$–$C_4$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; $C_4$–$C_{11}$ cycloalkylcarbonyloxy($C_1$–$C_4$ alkoxy)carbonyl; heteroaryl optionally substituted with 0–2 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; or heteroaryl($C_1$–$C_5$)alkyl where the heteroaryl group is optionally substituted with 0–2 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl;

provided that only one of R² and R³ may be hydroxy;

U is selected from:
a single bond (i.e., U is absent)
$C_1$–$C_7$ alkylene,
$C_2$–$C_7$ alkenylene,
$C_2$–$C_7$ alkynylene,
arylene substituted with 0–3 $R^{6a}$,, or
pyridylene substituted with 0–3 $R^{6a}$;

V is selected from:
a single bond (i.e., V is absent);
$C_1$–$C_7$ alkylene substituted with 0–6 $R^6$ or $R^7$;
$C_2$–$C_7$ alkenylene substituted with 0–4 $R^6$ or $R^7$;
$C_2$–$C_7$ alkynylene substituted with 0–4 $R^6$ or $R^7$;
phenylene substituted with 0–4 $R^6$ or $R^7$;
pyridylene substituted with 0–3 $R^6$ or $R^7$;
pyridazinylene substituted with 0–3 $R^6$ or $R^7$;

X is selected from:
  a single bond (i.e., X is absent);
  —(CH$_2$)$_n$C(=O)N(R$^{12}$)—;
  C$_1$–C$_7$ alkylene substituted with 0–6 R$^4$, R$^8$ or R$^{15}$;
  C$_2$–C$_7$ alkenylene substituted with 0–4 R$^4$, R$^8$ or R$^{15}$;
  C$_2$–C$_7$ alkynylene substituted with 0–4 R$^4$, R$^8$ or R$^{15}$;
Y is selected from:
  hydroxy,
  C$_1$ to C$_{10}$ alkyloxy,
  C$_3$ to C$_{11}$ cycloalkyloxy,
  C$_6$ to C$_{10}$ aryloxy,
  C$_7$ to C$_{11}$ aralkyloxy,
  C$_3$ to C$_{10}$ alkylcarbonyloxyalkyloxy,
  C$_3$ to C$_{10}$ alkoxycarbonyloxyalkyloxy,
  C$_2$ to C$_{10}$ alkoxycarbonylalkyloxy,
  C$_5$ to C$_{10}$ cycloalkylcarbonyloxyalkyloxy,
  C$_5$ to C$_{10}$ cycloalkoxycarbonyloxyalkyloxy,
  C$_5$ to C$_{10}$ cycloalkoxycarbonylalkyloxy,
  C$_7$ to C$_{11}$ aryloxycarbonylalkyloxy,
  C$_8$ to C$_{12}$ aryloxycarbonyloxyalkyloxy,
  C$_8$ to C$_{12}$ arylcarbonyloxyalkyloxy,
  C$_5$ to C$_{10}$ alkoxyalkylcarbonyloxyalkyloxy,
  C$_5$ to C$_{10}$ (5-alkyl-1,3-dioxa-cyclopenten-2-one-yl) methyloxy,
  C$_{10}$ to C$_{14}$ (5-aryl-1,3-dioxa-cyclopenten-2-one-yl) methyloxy;
  (R$^2$)(R$^3$)N—(C$_1$–C$_{10}$ alkoxy)-;
R$^{14}$ and W are attached to the same carbon and taken together to form a spiro-fused, 5–7 membered ring structure of the formula:

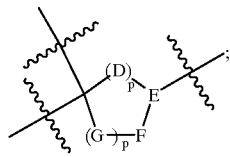

D, E, F and G are each independently selected from:
  C(R$^{6a}$)$_2$;
  carbonyl;
  a heteroatom moiety selected from N, N(R$^{12}$), O, provided that no more than 2 of D, E, F and G are N, N(R$^{12}$), O, S, or C(=O);
  alternatively, the bond between D and E, E and F, or F and G in such spiro-fused ring may be a carbon-nitrogen double bond or a carbon—carbon double bond;
R$^4$ is selected from H, C$_1$–C$_{10}$ alkyl, hydroxy, C$_1$–C$_{10}$ alkoxy, nitro, C$_1$–C$_{10}$ alkylcarbonyl, or —N(R$^{12}$)R$^{13}$;
R$^6$ and R$^7$ are each independently selected from H, C$_1$–C$_{10}$ alkyl, hydroxy, C$_1$–C$_{10}$ alkoxy, nitro, C$_1$–C$_{10}$ alkylcarbonyl, —N(R$^{12}$)R$^{13}$, cyano, halo, CF$_3$, CHO, CO$_2$R$^{5a}$, C(=O)R$^{5a}$, CONHR$^{5a}$, CON(R$^{12}$)$_2$, OC(=O)R$^{5a}$, OC(=O)OR$^{5a}$, OR$^{5a}$, OC(=O)N(R$^{12}$)$_2$, OCH$_2$CO$_2$R$^{5a}$, CO$_2$CH$_2$CO$_2$R$^{5a}$, N(R$^{12}$)$_2$, NO$_2$, NR$^{12}$C(=O)R$^{5a}$, NR$^{12}$C(=O)OR$^{5a}$, NR$^{12}$C(=O)N(R$^{12}$)$_2$, NR$^{12}$SO$_2$N(R$^{12}$)$_2$, NR$^{12}$SO$_2$R$^{5a}$, S(O)$_p$R$^{5a}$, SO$_2$N(R$^{12}$)$_2$, C$_2$ to C$_6$ alkenyl, C$_3$ to C$_{11}$ cycloalkyl, C$_4$ to C$_{11}$ cycloalkylmethyl;
  C$_6$ to C$_{10}$ aryl optionally substituted with 1–3 groups selected from halogen, C$_1$–C$_6$ alkoxy, C$_1$–C$_6$ alkyl, CF$_3$, S(O)$_m$Me, or —NMe$_2$;
  C$_7$ to C$_{11}$ arylalkyl, said aryl being optionally substituted with 1–3 groups selected from halogen, C$_1$–C$_6$ alkoxy, C$_1$–C$_6$ alkyl, CF$_3$, S(O)$_m$Me, or —NMe$_2$;
  methylenedioxy when R$^6$ is a substituent on aryl;
R$^{6a}$ is selected from C$_1$–C$_4$ alkyl, C$_1$–C$_4$ alkoxy, halo, CF$_3$, NO$_2$, or NR$^{12}$R$^{13}$;
R$^8$ is selected from:
  H;
  R$^6$;
  C$_1$–C$_{10}$ alkyl, substituted with 0–8 R$^6$;
  C$_2$–C$_{10}$ alkenyl, substituted with 0–6 R$^6$;
  C$_2$–C$_{10}$ alkynyl, substituted with 0–6 R$^6$;
  C$_3$–C$_8$ cycloalkyl, substituted with 0–6 R$^6$;
  C$_5$–C$_6$ cycloalkenyl, substituted with 0–5 R$^6$;
  aryl, substituted with 0–5 R$^6$;
  5–6 membered heterocyclic ring containing 1–2 N, O, or S heteroatoms, wherein said heterocyclic ring may be saturated, partially saturated, or fully unsaturated, said heterocyclic ring being substituted with 0–5 R$^6$;
R$^{12}$ and R$^{13}$ are independently H, C$_1$–C$_{10}$ alkyl, C$_1$–C$_{10}$ alkoxycarbonyl, C$_1$–C$_{10}$ alkylcarbonyl, C$_1$–C$_{10}$ alkylsulfonyl, aryl(C$_1$–C$_{10}$ alkyl)sulfonyl, arylsulfonyl, aryl, C$_2$–C$_6$ alkenyl, C$_3$–C$_{11}$ cycloalkyl, C$_4$–C$_{11}$ cycloalkylalkyl, C$_7$–C$_{11}$ arylalkyl, C$_2$–C$_7$ alkylcarbonyl, C$_7$–C$_{11}$ arylcarbonyl, C$_2$–C$_{10}$ alkoxycarbonyl, C$_4$–C$_{11}$ cycloalkoxycarbonyl, C$_7$–C$_{11}$ bicycloalkoxycarbonyl, C$_7$–C$_{11}$ aryloxycarbonyl, heteroarylcarbonyl, heteroarylalkylcarbonyl or aryl (C$_1$–C$_{10}$ alkoxy)carbonyl, wherein said aryls or heteroaryls are optionally substituted with 0–3 substituents selected from the group consisting of: C$_1$–C$_4$ alkyl, C$_1$–C$_4$ alkoxy, halo, CF$_3$, and NO$_2$;
R$^5$ and R$^{5a}$ are selected independently from H, C$_1$ to C$_8$ alkyl, C$_2$ to C$_6$ alkenyl, C$_3$ to C$_{11}$ cycloalkyl, C$_4$ to C$_{11}$ cycloalkylmethyl, C$_6$ to C$_{10}$ aryl, C$_7$ to C$_{11}$ arylalkyl, or C$_1$–C$_{10}$ alkyl substituted with 0–8 R$^4$;
R$^{15}$ is selected from:
  H;
  R$^6$;
  C$_1$–C$_{10}$ alkyl, substituted with 0–8 R$^6$;
  C$_2$–C$_{10}$ alkenyl, substituted with 0–6 R$^6$;
  C$_1$–C$_{10}$ alkoxy, substituted with 0–6 R$^6$;
  aryl, substituted with 0–5 R$^6$;
  5–6 membered heterocyclic ring containing 1–2 N, O, or S heteroatoms, wherein said heterocyclic ring may be saturated, partially saturated, or fully unsaturated, said heterocyclic ring being substituted with 0–5 R$^6$;
  C$_1$–C$_{10}$ alkoxycarbonyl substituted with 0–8 R$^6$;
  CO$_2$R$^5$; or
  —C(=O)N(R$^{12}$)R$^{13}$;
n is 0–4;
p is 1–3;
q is 1–7;
r is 0–3;
provided that n, p, q and r are chosen such that the number of atoms between R$^1$ and Y is in the range of 8–17.

[47] Also preferred compounds of the second embodiment are those compounds of Formulae Ie or If:

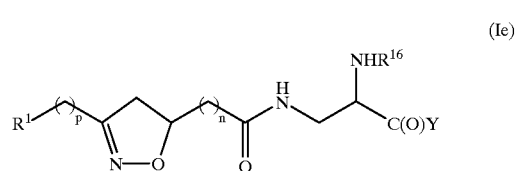
(Ie)

-continued

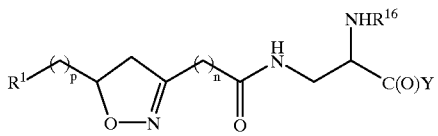
(If)

or enantiomeric or diasteriomeric forms thereof, or mixtures of enantiomeric or diasteriomeric forms thereof, or a pharmaceutically acceptable salt form thereof, wherein:

$R^1$ is $R^2(R^3)N(R^2N=)C-$, $R^2(R^3)N(R^2N=)CN(R^2)-$, or $R^2(R^3)N-$;

$R^2$ and $R^3$ are independently selected from: H; $C_1-C_{10}$ alkyl; $C_3-C_6$ alkenyl; $C_3-C_{11}$ cycloalkyl; $C_4-C_{11}$ cycloalkylalkyl; $C_6-C_{10}$ aryl optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; $C_7-C_{11}$ arylalkyl optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; $C_2-C_7$ alkylcarbonyl; $C_7-C_{11}$ arylcarbonyl optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; $C_1-C_{10}$ alkoxycarbonyl; $C_4-C_{11}$ cycloalkoxycarbonyl; $C_7-C_{11}$ bicycloalkoxycarbonyl; $C_7-C_{11}$ aryloxycarbonyl optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; aryl($C_1-C_{10}$ alkoxy)carbonyl where the aryl group is optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; $C_1-C_6$ alkylcarbonyloxy($C_1-C_4$ alkoxy)carbonyl; $C_6-C_{10}$ arylcarbonyloxy($C_1-C_4$ alkoxy)carbonyl where the aryl group is optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; $C_4-C_{11}$ cycloalkylcarbonyloxy($C_1-C_4$ alkoxy)carbonyl; heteroaryl optionally substituted with 0–2 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; or heteroaryl($C_1-C_5$)alkyl where the heteroaryl group is optionally substituted with 0–2 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl;

provided that only one of $R^2$ and $R^3$ may be hydroxy;

$R^{12}$ and $R^{13}$ are independently H, $C_1-C_{10}$ alkyl, $C_1-C_{10}$ alkoxycarbonyl, $C_1-C_{10}$ alkylcarbonyl, $C_1-C_{10}$ alkylsulfonyl, aryl($C_1-C_{10}$ alkyl)sulfonyl, arylsulfonyl, aryl($C_2-C_{10}$ alkenyl)sulfonyl, heteroarylsulfonyl, aryl, $C_2-C_6$ alkenyl, $C_3-C_{11}$ cycloalkyl, $C_4-C_{11}$ cycloalkylalkyl, $C_7-C_{11}$ arylalkyl, $C_7-C_{11}$ arylcarbonyl, $C_4-C_{11}$ cycloalkoxycarbonyl, $C_7-C_{11}$ bicycloalkoxycarbonyl, $C_7-C_{11}$ aryloxycarbonyl, heteroarylcarbonyl, heteroarylalkylcarbonyl, or aryl ($C_1-C_{10}$ alkoxy)carbonyl, wherein said aryls are optionally substituted with 0–3 substituents selected from the group consisting of: $C_1-C_4$ alkyl, $C_1-C_4$ alkoxy, halo, $CF_3$, and $NO_2$;

$R^{16}$ is selected from:
 $-C(=O)-O-R^{18a}$,
 $-C(=O)-R^{18b}$,
 $-C(=O)N(R^{18b})_2$,
 $-C(=O)NHSO_2R^{18a}$,
 $-C(=O)NHC(=O)R^{18b}$,
 $-C(=O)NHC(=O)OR^{18a}$,
 $-C(=O)NHSO_2NHR^{18b}$,
 $-C(=S)-NH-R^{18b}$,
 $-NH-C(=O)-O-R^{18a}$,
 $-NH-C(=O)-R^{18b}$,
 $-NH-C(=O)-NH-R^{18b}$,
 $-SO_2-O-R^{18a}$,
 $-SO_2-R^{18a}$,
 $-SO_2-N(18^b)_2$,
 $-SO_2-NHC(=O)O18^b$,
 $-P(=S)(OR^{18a})_2$,
 $-P(=O)(OR^{18a})_2$,
 $-P(=S)(R^{18a})_2$,
 $-P(=O)(R^{18a})_2$, or

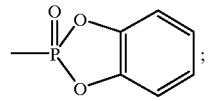

$R^{18a}$ is selected from:
 $C_1-C_8$ alkyl substituted with 0–2 $R^{19}$,
 $C_2-C_8$ alkenyl substituted with 0–2 $R^{19}$,
 $C_2-C_8$ alkynyl substituted with 0–2 $R^{19}$,
 $C_3-C_8$ cycloalkyl substituted with 0–2 $R^{19}$,
 aryl substituted with 0–4 $R^{19}$,
 aryl($C_1-C_6$ alkyl)-substituted with 0–4 $R^{19}$,
 a 5–10 membered heterocyclic ring system having 1–3 heteroatoms selected independently from O, S, and N, said heterocyclic ring being substituted with 0–4 $R^{19}$,
 $C_1-C_6$ alkyl substituted with a 5–10 membered heterocyclic ring system having 1–3 heteroatoms selected independently from O, S, and N, said heterocyclic ring being substituted with 0–4 $R^{19}$;

$R^{18b}$ is selected from $R^{18a}$ or H;

$R^{19}$ is selected from H, halogen, $CF_3$, CN, $NO_2$, $NR^{12}R^{13}$, $C_1-C_8$ alkyl, $C_2-C_6$ alkenyl, $C_2-C_6$ alkynyl, $C_3-C_{11}$ cycloalkyl, $C_4-C_{11}$ cycloalkylalkyl, aryl, aryl($C_1-C_6$ alkyl)-, $C_1-C_6$ alkoxy, or $C_1-C_4$ alkoxycarbonyl;

Y is selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ aralkyloxy, $C_3$ to $C_{11}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{10}$ alkoxyalkylcarbonyloxyalkyloxy, $C_5$ to $C_{10}$ (5-alkyl-1, 3-dioxa-cyclopenten-2-one-yl)methyloxy, $C_{10}$ to $C_{14}$ (5-aryl-1,3-dioxa-cyclopenten-2-one-yl)methyloxy, $(R^2)(R^3)N-(C_1-C_{10}$ alkoxy)-;

m is 0–2;
n is 0–2; and
p is 1–5.

[17] Preferred compounds of this third embodiment are compounds of Formula III:

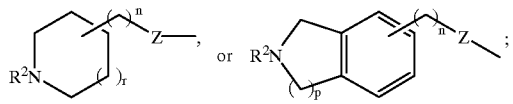
(III)

wherein:
$R^1$ is selected from $R^2HN-$, $H_2N(R^2N=)C-$, $H_2N(R^2N=)CNH-$, $R^2HN(CH_2)_qO-$, $H_2N(R^2N=)CNH(CH_2)_qO-$, piperazinyl-$(CH_2)_qO-$, $R^2(R^3)NC(O)-$, $R^2(R^5O)N(R^2N=)C-$, $R^2(R^3)N(R^5ON=)C-$,

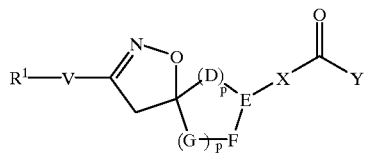

$R^2$ and $R^3$ are selected from H; $C_1-C_6$ alkyl; $C_7-C_{11}$ arylalkyl optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; aryl($C_1-C_{10}$ alkoxy)carbonyl where the aryl group is optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; heteroaryl($C_1-C_5$)alkyl where the heteroaryl group is optionally substituted with 0–2 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; or $C_1-C_{10}$ alkoxycarbonyl;

$R^4$ is selected from H, $C_1-C_{10}$ alkyl, hydroxy, $C_1-C_{10}$ alkoxy, nitro, $C_1-C_{10}$ alkylcarbonyl, or $-N(R^{12})R^{13}$;

V is selected from:
  a single bond (i.e., V is absent);
  $C_1-C_7$ alkylene substituted with 0–6 $R^6$ or $R^7$;
  $C_2-C_7$ alkenylene substituted with 0–4 $R^6$ or $R^7$;
  $C_2-C_7$ alkynylene substituted with 0–4 $R^6$ or $R^7$;
  phenylene substituted with 0–3 $R^6$ or $R^7$;
  pyridylene substituted with 0–3 $R^6$ or $R^7$;
  pyridazinylene substituted with 0–3 $R^6$ or $R^7$;

X is selected from $-(CH_2)_nC(=O)N(R^{12})-$, $C_1-C_7$ alkylene substituted with 0–1 $R^4$, $C_2-C_7$ alkenylene, or $C_2-C_7$ alkynylene;

Y is selected from:
  hydroxy,
  $C_1$ to $C_{10}$ alkyloxy,
  $C_3$ to $C_{11}$ cycloalkyloxy,
  $C_6$ to $C_{10}$ aryloxy,
  $C_7$ to $C_{11}$ aralkyloxy,
  $C_3$ to $C_{10}$ alkylcarbonyloxyalkyloxy,
  $C_3$ to $C_{10}$ alkoxycarbonyloxyalkyloxy,
  $C_2$ to $C_{10}$ alkoxycarbonylalkyloxy,
  $C_5$ to $C_{10}$ cycloalkylcarbonyloxyalkyloxy,
  $C_5$ to $C_{10}$ cycloalkoxycarbonyloxyalkyloxy,
  $C_5$ to $C_{10}$ cycloalkoxycarbonylalkyloxy,
  $C_7$ to $C_{11}$ aryloxycarbonylalkyloxy,
  $C_8$ to $C_{12}$ aryloxycarbonyloxyalkyloxy,
  $C_8$ to $C_{12}$ arylcarbonyloxyalkyloxy,
  $C_5$ to $C_{10}$ alkoxyalkylcarbonyloxyalkyloxy,
  $C_5$ to $C_{10}$ (5-alkyl-1,3-dioxa-cyclopenten-2-one-yl)methyloxy, or
  $C_{10}$ to $C_{14}$ (5-aryl-1,3-dioxa-cyclopenten-2-one-yl)methyloxy;

Z is selected from O or $CH_2$;

D, E, F and G are each independently selected from:
  $CH_2$;
  carbonyl;
  a heteroatom moiety selected from N, NH, O, provided that no more than 2 of D, E, F and G are N, NH, O or S;
  alternatively, the bond between D and E, E and F, or F and G in such spiro-fused ring may be a carbon-nitrogen double bond or a carbon—carbon double bond;

$R^6$ and $R^7$ are each independently selected from H, $C_1-C_{10}$ alkyl, hydroxy, $C_1-C_{10}$ alkoxy, nitro, $C_1-C_{10}$ alkylcarbonyl, $-N(R^{12})R^{13}$, cyano, or halo;

$R^{12}$ and $R^{13}$ are each independently selected from H, $C_1-C_{10}$ alkyl, $C_1-C_{10}$ alkoxycarbonyl, $C_1-C_{10}$ alkylcarbonyl, $C_1-C_{10}$ alkylsulfonyl, aryl($C_1-C_{10}$ alkyl)sulfonyl, arylsulfonyl, heteroarylcarbonyl, heteroaryalkylcarbonyl or aryl;

n is 0–4;
p is 1–3;
q is 1–7;
r is 0–3;

provided that n, p, q and r are chosen such that the number of atoms between $R^1$ and Y is in the range of 8–17.

[18] Further preferred compounds of this third embodiment are compounds of Formula II wherein:
$R^1$ is $R^2NHC(=NR^2)-$ and V is phenyl or pyridyl or $R^1$ is

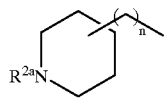

and V is a single bond (i.e. V is absent);
n is 1 or 2;
X is $C_1-C_4$ alkylene substituted with 0–1 $R^4$;
Y is selected from:
  hydroxy;
  $C_1$ to $C_{10}$ alkoxy;
  methylcarbonyloxymethoxy-;
  ethylcarbonyloxymethoxy-;
  t-butylcarbonyloxymethoxy-;
  cyclohexylcarbonyloxymethoxy-;
  1-(methylcarbonyloxy)ethoxy-;
  1-(ethylcarbonyloxy)ethoxy-;
  1-(t-butylcarbonyloxy)ethoxy-;
  1-(cyclohexylcarbonyloxy)ethoxy-;
  i-propyloxycarbonyloxymethoxy-;
  t-butyloxycarbonyloxymethoxy-;
  1-(i-propyloxycarbonyloxy)ethoxy-;
  1-(cyclohexyloxycarbonyloxy)ethoxy-;
  1-(t-butyloxycarbonyloxy)ethoxy-;
  dimethylaminoethoxy-;
  diethylaminoethoxy-;

(5-methyl-1,3-dioxacyclopenten-2-on-4-yl)methoxy-;
(5-(t-butyl)-1,3-dioxacyclopenten-2-on-4-yl) methoxy-;
(1,3-dioxa-5-phenyl-cyclopenten-2-on-4-yl)methoxy-;
1-(2-(2-methoxypropyl)carbonyloxy)ethoxy-;

$R^{12}$ and $R^{13}$ are each independently selected from H, $C_1$–$C_6$ alkyl, $C_1$–$C_4$ alkoxycarbonyl, $C_1$–$C_4$ alkylcarbonyl, $C_1$–$C_4$ alkylsulfonyl, aryl($C_1$–$C_4$ alkyl)sulfonyl, arylsulfonyl, heteroarylcarbonyl, heteroarylalkylcarbonyl or aryl; and $R^{13}$ is H.

[19] Specifically preferred compounds of this third embodiment are compounds, or pharmaceutically acceptable salt or prodrug forms thereof, selected from:

5(R,S)-3-(4-amidinophenyl)-8-(2-carboxyethyl)-1-oxa-2,8-diazaspiro[4.4]non-2-ene-7,9-dione;

5(R,S)-3-(4-amidinophenyl)-8-(3-carboxypropyl)-1-oxa-2,8-diazaspiro[4.4]non-2-ene-7,9-dione;

5(R,S)-3-(4-amidinophenyl)-8-(2-carboxyethyl)-1-oxa-2,8-diazaspiro[4.4]non-2-ene-5-one;

5(R,S)-3-(4-amidinophenyl)-8-(3-carboxypropyl)-1-oxa-2,8-diazaspiro[4.4]non-2-ene-5-one;

5(R,S)-3-(4-amidinophenyl)-8-(2-carboxyethyl)-1-oxa-2-azaspiro[4.4]nona-2,8-diene-5-one;

5(R,S)-3-(4-amidinophenyl)-8-(3-carboxypropyl)-1-oxa-2-azaspiro[4.4]nona-2,8-diene-5-one;

5(R,S)-3-(4-amidinophenyl)-8-(2-carboxyethyl)-1-oxa-2,8-diazaspiro[4.4]dec-2-ene-7,9-dione;

5(R,S)-3-(4-amidinophenyl)-8-(3-carboxypropyl)-1-oxa-2,8-diazaspiro[4.4]dec-2-ene-7,9-dione;

5(R,S)-3-(4-amidinophenyl)-8-(2-carboxyethyl)-1-oxa-2,8-diazaspiro[4.4]dec-2-ene-5-one;

5(R,S)-3-(4-amidinophenyl)-8-(3-carboxypropyl)-1-oxa-2,8-diazaspiro[4.4]dec-2-ene-5-one;

5(R,S)-3-(4-amidinophenyl)-8-(2-carboxyethyl)-1-oxa-2-azaspiro[4.4]deca-2,8-diene-5-one;

5(R,S)-3-(4-amidinophenyl)-8-(3-carboxypropyl)-1-oxa-2-azaspiro[4.4]deca-2,8-diene-5-one;

5(R,S)-3-(4-amidinophenyl)-8-(2-carboxyethyl)-1-oxa-2,8-diazaspiro[4.4]undec-2-ene-7,9-dione;

5(R,S)-3-(4-amidinophenyl)-8-(3-carboxypropyl)-1-oxa-2,8-diazaspiro[4.4]undec-2-ene-7,9-dione;

5(R,S)-3-(4-amidinophenyl)-8-(2-carboxyethyl)-1-oxa-2,8-diazaspiro[4.4]undec-2-ene-5-one;

5(R,S)-3-(4-amidinophenyl)-8-(3-carboxypropyl)-1-oxa-2,8-diazaspiro[4.4]undec-2-ene-5-one;

5(R,S)-3-(4-amidinophenyl)-8-(2-carboxyethyl)-1-oxa-2-azaspiro[4.4]undeca-2,8-diene-5-one;

5(R,S)-3-(4-amidinophenyl)-8-(3-carboxypropyl)-1-oxa-2-azaspiro[4.4]undeca-2,8-diene-5-one;

5(R,S)-3-[2-(piperidin-4-yl)ethyl]-8-(2-carboxyethyl)-1-oxa-2,8-diazaspiro[4.4]non-2-ene-7,9-dione;

5(R,S)-3-[2-(piperidin-4-yl)ethyl]-8-(3-carboxypropyl)-1-oxa-2,8-diazaspiro[4.4]non-2-ene-7,9-dione;

5(R,S)-3-[2-(piperidin-4-yl)ethyl]-8-(2-carboxyethyl)-1-oxa-2,8-diazaspiro[4.4]non-2-ene-5-one;

5(R,S)-3-[2-(piperidin-4-yl)ethyl]-8-(3-carboxypropyl)-1-oxa-2,8-diazaspiro[4.4]non-2-ene-5-one;

5(R,S)-3-[2-(piperidin-4-yl)ethyl]-8-(2-carboxyethyl)-1-oxa-2-azaspiro[4.4]nona-2,8-diene-5-one;

5(R,S)-3-[2-(piperidin-4-yl)ethyl]-8-(3-carboxypropyl)-1-oxa-2-azaspiro[4.4]nona-2,8-diene-5-one;

5(R,S)-3-[2-(piperidin-4-yl)ethyl]-8-(2-carboxyethyl)-1-oxa-2,8-diazaspiro[4.4]dec-2-ene-7,9-dione;

5(R,S)-3-[2-(piperidin-4-yl)ethyl]-8-(3-carboxypropyl)-1-oxa-2,8-diazaspiro[4.4]dec-2-ene-5,7-dione;

5(R,S)-3-[2-(piperidin-4-yl)ethyl]-8-(2-carboxyethyl)-1-oxa-2,8-diazaspiro[4.4]dec-2-ene-5-one;

5(R,S)-3-[2-(piperidin-4-yl)ethyl]-8-(3-carboxypropyl)-1-oxa-2,8-diazaspiro[4.4]dec-2-ene-5-one;

5(R,S)-3-[2-(piperidin-4-yl)ethyl]-8-(2-carboxyethyl)-1-oxa-2-azaspiro[4.4]deca-2,8-diene-5-one;

5(R,S)-3-[2-(piperidin-4-yl)ethyl]-8-(3-carboxypropyl)-1-oxa-2-azaspiro[4.4]deca-2,8-diene-5-one;

5(R,S)-3-[2-(piperidin-4-yl)ethyl]-8-(2-carboxyethyl)-1-oxa-2,8-diazaspiro[4.4]undec-2-ene-7,9-dione;

5(R,S)-3-[2-(piperidin-4-yl)ethyl]-8-(3-carboxypropyl)-1-oxa-2,8-diazaspiro[4.4]undec-2-ene-7,9-dione;

5(R,S)-3-[2-(piperidin-4-yl)ethyl]-8-(2-carboxyethyl)-1-oxa-2,8-diazaspiro[4.4]undec-2-ene-5-one;

5(R,S)-3-[2-(piperidin-4-yl)ethyl]-8-(3-carboxypropyl)-1-oxa-2,8-diazaspiro[4.4]undec-2-ene-5-one;

5(R,S)-3-[2-(piperidin-4-yl)ethyl]-8-(2-carboxyethyl)-1-oxa-2-azaspiro[4.4]undeca-2,8-diene-5-one;

5(R,S)-3-[2-(piperidin-4-yl)ethyl]-8-(3-carboxypropyl)-1-oxa-2-azaspiro[4.4]undeca-2,8-diene-5-one;

5(R,S)-3-(4-amidinophenyl)-8-[2-(benzyloxycarbonylamino)-2-carboxyethyl]-1-oxa-2,8-diazaspiro[4.5]dec-2-ene.

[20] A fourth embodiment of this invention provides compounds of Formula I:

(I)

or pharmaceutically acceptable salt or prodrug forms thereof, wherein:

$R^1$ is selected from:
$R^2(R^3)N(CH_2)_qZ$—, $R^2(R^3)N(R^2N$=$)C(CH_2)_qZ$—, $R^2(R^3)N(R^2N$=$)CN(R^2)(CH_2)_qZ$—, piperazinyl-$(CH_2)_qZ$— or Z is selected from O, S, S(=O), S(=O)$_2$;

$R^2$ and $R^3$ are independently selected from: H, $C_1$–$C_{10}$ alkyl, $C_2$–$C_6$ alkenyl, $C_3$–$C_{11}$ cycloalkyl, $C_4$–$C_{11}$ cycloalkylalkyl, $C_6$–$C_{10}$ aryl, $C_7$–$C_{11}$ arylalkyl, $C_2$–$C_7$ alkylcarbonyl, $C_7$–$C_{11}$ arylcarbonyl, $C_2$–$C_{10}$ alkoxycarbonyl, $C_4$–$C_{11}$ cycloalkoxycarbonyl $C_7$–$C_{11}$ bicycloalkoxycarbonyl, $C_7$–$C_{11}$ aryloxycarbonyl, or aryl($C_1$–$C_{10}$ alkoxy)carbonyl, $C_1$–$C_6$ alkylcarbonyloxy ($C_1$–$C_4$ alkoxy)carbonyl, $C_6$–$C_{10}$ arylcarbonyloxy ($C_1$–$C_4$ alkoxy)carbonyl, $C_4$–$C_{11}$ cycloalkylcarbonyloxy ($C_1$–$C_4$ alkoxy)carbonyl;

U is optionally present and is selected from $C_1$–$C_7$ alkylene, $C_2$–$C_7$ alkenylene, $C_2$–$C_7$ alkynylene, arylene, or pyridylene;

V is selected from:

a single bond (i.e., V is absent);
$C_1$–$C_7$ alkylene substituted with 0–6 $R^6$ or $R^7$;
$C_2$–$C_7$ alkenylene substituted with 0–4 $R^6$ or $R^7$;
$C_2$–$C_7$ alkynylene substituted with 0–4 $R^6$ or $R^7$;
phenylene substituted with 0–4 $R^6$ or $R^7$;
pyridylene substituted with 0–3 $R^6$ or $R^7$;
pyridazinylene substituted with 0–3 $R^6$ or $R^7$;

W is -(aryl)-$Z^1$-, wherein said aryl is substituted with 0–6 $R^6$ or $R^7$;

$Z^1$ is selected from a single bond (i.e., $Z^1$ is absent), —$CH_2$—, O or S;

X is selected from:
a single bond (i.e., X is absent);
$C_1$–$C_7$ alkylene substituted with 0–6 $R^4$, $R^8$ or $R^{15}$;
$C_2$–$C_7$ alkenylene substituted with 0–4 $R^4$, $R^8$ or $R^{15}$;
$C_2$–$C_7$ alkynylene substituted with 0–4 $R^4$, $R^8$ or $R^{15}$;

Y is selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ aralkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{10}$ alkoxyalkylcarbonyloxyalkyloxy, $C_5$ to $C_{10}$ (5-alkyl-1,3-dioxa-cyclopenten-2-one-yl)methyloxy, $C_{10}$ to $C_{14}$ (5-aryl-1,3-dioxa-cyclopenten-2-one-yl)methyloxy; ($R^2$)($R^3$)N—($C_1$–$C_{10}$ alkoxy)-;

$R^4$ is selected from H, $C_1$–$C_{10}$ alkyl, hydroxy, $C_1$–$C_{10}$ alkoxy, nitro, $C_1$–$C_{10}$ alkylcarbonyl, or —N($R^{12}$)$R^{13}$;

$R^6$ and $R^7$ are each independently selected from H, $C_1$–$C_{10}$ alkyl, hydroxy, $C_1$–$C_{10}$ alkoxy, nitro, $C_1$–$C_{10}$ alkylcarbonyl, —N($R^{12}$)$R^{13}$, cyano, halo, $CF_3$, CHO, $CO_2R^{5a}$, C(=O)$R^{5a}$, CONHR$^{5a}$, CON($R^{12}$)$_2$, OC(=O)$R^{5a}$, OC(=O)O$R^{5a}$, O$R^{5a}$, OC(=O)N($R^{12}$)$_2$, OCH$_2$CO$_2$$R^{5a}$, CO$_2$CH$_2$CO$_2$$R^{5a}$, N($R^{12}$)$_2$, NO$_2$, NR$^{12}$C(=O) $R^{5a}$, NR$^{12}$C(=O)OR$^{5a}$, NR$^{12}$C(=O)N($R^{12}$)$_2$, NR$^{12}$SO$_2$N($R^{12}$)$_2$, NR$^{12}$SO$_2$R$^{5a}$, S(O)$_p$R$^{5a}$, SO$_2$N($R^{12}$)$_2$, $C_2$ to $C_6$ alkenyl, $C_3$ to $C_{11}$ cycloalkyl, $C_4$ to $C_{11}$ cycloalkylmethyl;
$C_6$ to $C_{10}$ aryl optionally substituted with halogen, alkoxy, alkyl, —$CF_3$, S(O)$_m$Me, or —NMe$_2$; or
$C_7$ to $C_{11}$ arylalkyl said aryl being optionally substituted with halogen, alkoxy, alkyl, —$CF_3$, S(O)$_m$Me, or —NMe$_2$;

$R^8$ is selected from:
H;
$R^6$;
$C_1$–$C_{10}$ alkyl, substituted with 0–8 $R^6$;
$C_2$–$C_{10}$ alkenyl, substituted with 0–6 $R^6$;
$C_2$–$C_{10}$ alkynyl, substituted with 0–6 $R^6$;
$C_3$–$C_8$ cycloalkyl, substituted with 0–6 $R^6$;
$C_5$–$C_6$ cycloalkenyl, substituted with 0–5 $R^6$;
aryl, substituted with 0–5 $R^6$;
5–6 membered heterocyclic ring containing 1–2 N, O, or S heteroatoms, wherein said heterocyclic ring may be saturated, partially saturated, or fully unsaturated, said heterocyclic ring being substituted with 0–5 $R^6$;

$R^{12}$ and $R^{13}$ are independently H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, aryl, $C_2$–$C_6$ alkenyl, $C_3$–$C_{11}$ cycloalkyl, $C_4$–$C_{11}$ cycloalkylalkyl, $C_7$–$C_{11}$ arylalkyl, $C_2$–$C_7$ alkylcarbonyl, $C_7$–$C_{11}$ arylcarbonyl, $C_2$–$C_{10}$ alkoxycarbonyl, $C_4$–$C_{11}$ cycloalkoxycarbonyl, $C_7$–$C_{11}$ bicycloalkoxycarbonyl, $C_7$–$C_{11}$ aryloxycarbonyl, heteroarylcarbonyl, heteroarylalkylcarbonyl or aryl ($C_1$–$C_{10}$ alkoxy)carbonyl;

$R^{14}$ is selected from H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or $C_1$–$C_{10}$ alkoxycarbonyl, $CO_2R^5$ or —C(=O)N($R^{12}$)$R^{13}$;

$R^5$ and $R^{5a}$ are selected independently from H, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_6$ to $C_{10}$ aryl, $C_7$ to $C_{11}$ arylalkyl, or $C_1$–$C_{10}$ alkyl substituted with 0–8 $R^4$;

$R^{15}$ is selected from:
H;
$R^6$;
$C_1$–$C_{10}$ alkyl, substituted with 6–8 $R^6$;
$C_2$–$C_{10}$ alkenyl, substituted with 0–6 $R^6$;
$C_1$–$C_{10}$ alkoxy, substituted with 0–6 $R^6$;
aryl, substituted with 0–5 $R^6$;
5–6 membered heterocyclic ring containing 1–2 N, O, or S heteroatoms, wherein said heterocyclic ring may be saturated, partially saturated, or fully unsaturated, said heterocyclic ring being substituted with 0–5 $R^6$;
$C_1$–$C_{10}$ alkoxycarbonyl substituted with 0–8 $R^6$;
$CO_2R^5$; or
—C(=O)N($R^{12}$)$R^{13}$;

n is 0–4;

q is 2–7;

r is 0–3;

provided that n, q, and r are chosen such that the number of atoms between $R^1$ and Y is about 8–17.

[21] Preferred compounds of this fourth embodiment are those of Formula IV:

(IV)

wherein:
$R^1$ is selected from $R^2$HN(CH$_2$)$_q$O—, $R^2$HN($R^2$N=C)NH(CH$_2$)$_q$O—, piperazinyl-(CH$_2$)$_q$O—, or Z is O;
$R^2$ is selected from H, aryl($C_1$–$C_{10}$)alkoxycarbonyl, $C_1$–$C_{10}$ alkoxycarbonyl;
V is selected from:
a single bond (i.e., V is absent);
$C_1$–$C_7$ alkylene substituted with 0–6 $R^6$ or $R^7$;
$C_2$–$C_7$ alkenylene substituted with 0–4 $R^6$ or $R^7$;
$C_2$–$C_7$ alkynylene substituted with 0–4 $R^6$ or $R^7$;
phenylene substituted with 0–3 $R^6$ or $R^7$;
pyridylene substituted with 0–3 $R^6$ or $R^7$;
pyridazinylene substituted with 0–3 $R^6$ or $R^7$;

$Z^1$ is selected from a single bond (i.e., $Z^1$ is absent), O or S;

X is selected from:
 a single bond (i.e., X is absent);
 $C_1-C_7$ alkylene substituted with 0–4 $R^4$, $R^8$ or $R^{15}$;
 $C_2-C_7$ alkenylene substituted with 0–3 $R^4$, $R^8$ or $R^{15}$;
 $C_2-C_7$ alkynylene substituted with 0–3 $R^4$, $R^8$ or $R^{15}$;

Y selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ aralkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{10}$ alkoxyalkylcarbonyloxyalkyloxy, $C_5$ to $C_{10}$ (5-alkyl-1,3-dioxa-cyclopenten-2-one-yl)methyloxy, or $C_{10}$ to $C_{14}$ (5-aryl-1,3-dioxa-cyclopenten-2-one-yl) methyloxy;

$R^4$ is selected from H, $C_1-C_{10}$ alkyl, hydroxy, $C_1-C_{10}$ alkoxy, nitro, $C_1-C_{10}$ alkylcarbonyl, or $-N(R^{12})R^{13}$;

$R^6$ and $R^7$ are selected from H, $C_1-C_{10}$ alkyl, hydroxy, $C_1-C_{10}$ alkoxy, nitro, $C_1-C_{10}$ alkylcarbonyl, $-N(R^{12})R^{13}$, cyano, or halo;

$R^8$ is selected from H, $C_1-C_{10}$ alkyl, $C_2-C_{10}$ alkenyl, $C_3-C_8$ cycloalkyl, $C_5-C_6$ cycloalkenyl, aryl, 5–6 membered heterocyclic ring containing 1–2 N, O, or S, where said heterocyclic ring may be saturated, partially saturated, or fully unsaturated;

$R^{12}$ and $R^{13}$ are independently selected from H, $C_1-C_{10}$ alkyl, $C_1-C_{10}$ alkoxycarbonyl, $C_1-C_{10}$ alkylcarbonyl, $C_1-C_{10}$ alkylsulfonyl, aryl($C_1-C_{10}$ alkyl)sulfonyl, arylsulfonyl, heteroarylcarbonyl, heteroarylalkylcarbonyl or aryl;

$R^{14}$ is selected from H, $C_1-C_{10}$ alkyl, $C_2-C_{10}$ alkenyl, $C_2-C_{10}$ alkynyl, $C_1-C_{10}$ alkoxy, aryl, heteroaryl or $C_1-C_{10}$ alkoxycarbonyl, $CO_2R^5$ or $-C(=O)N(R^{12})R^{13}$;

$R^5$ is selected from H or $C_1-C_{10}$ alkyl substituted with 0–6 $R^4$;

n is 0–4;

q is 2–7;

provided that n and q are chosen such that the number of atoms between $R^1$ and Y is in the range of 8–17.

[22] Further preferred compounds of this fourth embodiment are compounds of Formula IV wherein:
$R^1$ is $R^2HN(CH_2)_qO-$ or

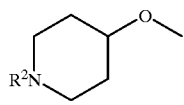

V is $C_1-C_3$ alkylene;
$Z^1$ is a single bond (i.e. $Z^1$ is absent) or O;
X is $C_1-C_3$ alkylene substituted with 0–1 $R^4$;
Y is selected from:
 hydroxy;
 $C_1$ to $C_{10}$ alkoxy;
 methylcarbonyloxymethoxy-;
 ethylcarbonyloxymethoxy-;
 t-butylcarbonyloxymethoxy-;
 cyclohexylcarbonyloxymethoxy-;
 1-(methylcarbonyloxy)ethoxy-;
 1-(ethylcarbonyloxy)ethoxy-;
 1-(t-butylcarbonyloxy)ethoxy-;
 1-(cyclohexylcarbonyloxy)ethoxy-;
 i-propyloxycarbonyloxymethoxy-;
 t-butyloxycarbonyloxymethoxy-;
 1-(i-propyloxycarbonyloxy)ethoxy-;
 1-(cyclohexyloxycarbonyloxy)ethoxy-;
 1-(t-butyloxycarbonyloxy)ethoxy-;
 dimethylaminoethoxy-;
 diethylaminoethoxy-;
 (5-methyl-1,3-dioxacyclopenten-2-on-4-yl)methoxy-;
 (5-(t-butyl)-1,3-dioxacyclopenten-2-on-4-yl) methoxy-;
 (1,3-dioxa-5-phenyl-cyclopenten-2-on-4-yl)methoxy-;
 1-(2-(2-methoxypropyl)carbonyloxy)ethoxy-;

$R^{12}$ and $R^{13}$ are independently selected from H, $C_1-C_6$ alkyl, $C_1-C_4$ alkoxycarbonyl, $C_1-C_4$ alkylcarbonyl, $C_1-C_6$ alkylsulfonyl, aryl($C_1-C_4$ alkyl)sulfonyl, arylsulfonyl, heteroarylcarbonyl, heteroarylalkylcarbonyl or aryl;

$R^{13}$ is H.

[23] Specifically preferred compounds of this fourth embodiment are compounds, or pharmaceutically acceptable salt or prodrug forms thereof, selected from:
5(R,S)-4-[3-(piperidin-4-yl)oxymethylisoxazolin-5-yl] hydrocinnamic acid;
5(R,S)-4-[3-(2-aminoethoxymethyl)isoxazolin-5-yl] hydrocinnamic acid;
5(R,S) -4-[3-(3-aminopropyloxymethyl)isoxazolin-5-yl] hydrocinnamic acid;
5(R,S)-4-[3-(piperidin-4-yl)oxymethylisoxazolin-5-yl] phenoxyacetic acid;
5(R,S)-4-[3-(2-aminoethoxymethyl)isoxazolin-5-yl] phenoxyacetic acid;
5(R,S)-4-[3-(3-aminopropyloxymethyl)isoxazolin-5-yl] phenoxyacetic acid.

[24] A fifth embodiment of this invention provides a compound of Formula I:

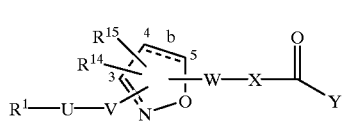

(I)

or a pharmaceutically acceptable salt or prodrug form thereof wherein:
b is a single or double bond;
$R^1$ is selected from $R^{2a}(R^3)N-$, $R^2(R^3)N(R^2N=)C-$, $R^{2a}(R^3)N(CH_2)_qZ-$, $R^2(R^3)N(R^2N=)C(CH_2)_qZ-$, $R^2(R^3)NC(O)-$, $R^2(R^5O)N(R^2N=)C-$, $R^2(R^3)N(R^5ON=)C-$;

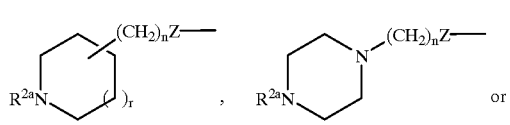

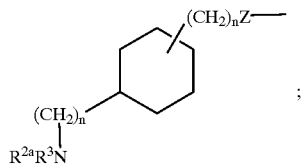

Z is selected from a bond (i.e. is absent), O, S, S(=O), $S(=O)_2$;

R² and R³ are independently selected from: H; $C_1$–$C_{10}$ alkyl; $C_3$–$C_6$ alkenyl; $C_3$–$C_{11}$ cycloalkyl; $C_4$–$C_{11}$ cycloalkylalkyl; $C_6$–$C_{10}$ aryl optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; $C_7$–$C_{11}$ arylalkyl optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; $C_2$–$C_7$ alkylcarbonyl; $C_7$–$C_{11}$ arylcarbonyl optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; $C_1$–$C_{10}$ alkoxycarbonyl; $C_4$–$C_{11}$ cycloalkoxycarbonyl; $C_7$–$C_{11}$ bicycloalkoxycarbonyl; $C_7$–$C_{11}$ aryloxycarbonyl optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; aryl($C_1$–$C_{10}$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; $C_1$–$C_6$ alkylcarbonyloxy($C_1$–$C_4$ alkoxy)carbonyl; $C_6$–$C_{10}$ arylcarbonyloxy($C_1$–$C_4$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; $C_4$–$C_{11}$ cycloalkylcarbonyloxy($C_1$–$C_4$ alkoxy)carbonyl; heteroaryl optionally substituted with 0–2 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; or heteroaryl($C_1$–$C_5$)alkyl where the heteroaryl group is optionally substituted with 0–2 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl;

provided that only one of R² and R³ may be hydroxy;

$R^{2a}$ is R² or $R^2(R^3)N(R^2N=)C$;

U is selected from:
  a single bond (i.e., U is not present),
  —($C_1$–$C_7$ alkyl)-,
  —($C_2$–$C_7$ alkenyl)-,
  —($C_2$–$C_7$ alkynyl)-,
  -(aryl)-substituted with 0–3 $R^{6a}$, or
  -(pyridyl)-substituted with 0–3 $R^{6a}$;

V is selected from:
  a single bond (i.e., V is not present);
  —($C_1$–$C_7$ alkyl)-, substituted with 0–3 groups independently selected from $R^6$ or $R^7$;
  —($C_2$–$C_7$ alkenyl)-, substituted with 0–3 groups independently selected from $R^6$ or $R^7$;
  —($C_2$–$C_7$ alkynyl)-, substituted with 0–3 groups independently selected from $R^6$ or $R^7$;
  -(phenyl)-, substituted with 0–2 groups independently selected from $R^6$ or $R^7$;
  -(pyridyl)-, substituted with 0–2 groups independently selected from $R^6$ or $R^7$; or
  -(pyridazinyl)-, substituted with 0–2 groups independently selected from $R^6$ or $R^7$;

W is selected from:

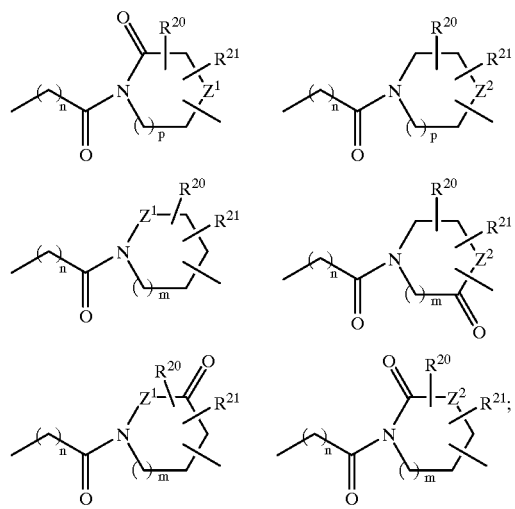

X is selected from:
  a single bond (i.e. X is absent) —$(C(R^4)_2)_n$—$C(R^4)$ $(R^8)$—$C(R^4)(R^{4a})$—, with the proviso that when n is 0 or 1, then at least one of $R^{4a}$ or $R^8$ is other than H or methyl;

Y is selected from:
  hydroxy,
  $C_1$ to $C_{10}$ alkyloxy,
  $C_3$ to $C_{11}$ cycloalkyloxy,
  $C_6$ to $C_{10}$ aryloxy,
  $C_7$ to $C_{11}$ aralkyloxy,
  $C_3$ to $C_{10}$ alkylcarbonyloxyalkyloxy,
  $C_3$ to $C_{10}$ alkoxycarbonyloxyalkyloxy,
  $C_2$ to $C_{10}$ alkoxycarbonylalkyloxy,
  $C_5$ to $C_{10}$ cycloalkylcarbonyloxyalkyloxy,
  $C_5$ to $C_{10}$ cycloalkoxycarbonyloxyalkyloxy.
  $C_5$ to $C_{10}$ cycloalkoxycarbonylalkyloxy,
  $C_7$ to $C_{11}$ aryloxycarbonylalkyloxy,
  $C_7$ to $C_{12}$ aryloxycarbonyloxyalkyloxy,
  $C_8$ to $C_{12}$ arylcarbonyloxyalkyloxy,
  $C_5$ to $C_{10}$ alkoxyalkylcarbonyloxyalkyloxy,
  $C_5$ to $C_{10}$ (5-alkyl-1,3-dioxa-cyclopenten-2-one-yl) methyloxy,
  $C_{10}$ to $C_{14}$ (5-aryl-1,3-dioxa-cyclopenten-2-one-yl) methyloxy,
  $(R^2)(R^3)N$—$(C_1$–$C_{10}$ alkoxy)-;

$Z^1$ is —C—, —O—, or —$NR^{22}$—;
$Z^2$ is —O—, or —$NR^{22}$—;

R⁴ is selected from H, $C_1$–$C_{10}$ alkyl, $C_1$–$C_{10}$ alkylcarbonyl, aryl, arylalkylene cycloalkyl, or cycloalkylalkylene;

alternately, two R⁴ groups on adjacent carbons may join to form a bond (i.e. a carbon—carbon double or triple bond);

$R^{4a}$ is selected from H, hydroxy, $C_1$–$C_{10}$ alkoxy, nitro, $N(R^5)R^{5a}$, —$N(R^{12})R^{13}$, —$N(R^{16})R^{17}$, $C_1$–$C_{10}$ alkyl substituted with 0–3 $R^6$, aryl substituted with 0–3 $R^6$, or $C_1$–$C_{10}$ alkylcarbonyl;

$R^{4b}$ is selected from H, $C_1$–$C_6$ alkyl, $C_2$–$C_6$ alkenyl, $C_2$–$C_6$ alkynyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, $C_1$–$C_6$ alkylcarbonyl, $C_6$–$C_{10}$ aryl, —$N(R^{12})R^{13}$; halo, $CF_3$, CN, $C_1$–$C_6$ alkoxycarbonyl, carboxy, piperidinyl, or pyridyl;

$R^5$ is selected from H, $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$;

$R^{5a}$ is selected from hydrogen, hydroxy, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_1$–$C_6$ alkoxy, benzyloxy, $C_6$ to $C_{10}$ aryl, heteroaryl, $C_7$ to $C_{11}$ arylalkyl, or $C_1$–$C_{10}$ alkyl substituted with 0–2 $R^{4b}$;

alternately, $R^5$ and $R^{5a}$ when both are substituents on the same nitrogen atom (as in —$NR^5R^{5a}$) can be taken together with the nitrogen atom to which they are attached to form 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl, each being optionally substituted with $C_1$–$C_6$ alkyl, $C_6$–$C_{10}$ aryl, heteroaryl, $C_7$–$C_{11}$ arylalkyl, $C_1$–$C_6$ alkylcarbonyl, $C_3$–$C_7$ cycloalkylcarbonyl, $C_1$–$C_6$ alkoxycarbonyl, $C_7$–$C_{11}$ arylalkoxycarbonyl, $C_1$–$C_6$ alkylsulfonyl or $C_6$–$C_{10}$ arylsulfonyl;

$R^{5b}$ is selected from $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$;

$R^6$ is selected from H, $C_1$–$C_{10}$ alkyl, hydroxy, $C_1$–$C_{10}$ alkoxy, nitro, $C_1$–$C_{10}$ alkylcarbonyl, —$N(R^{12})R^{13}$, cyano, halo, $CF_3$, CHO, $CO_2R^5$, $C(=O)R^{5a}$, $CONR^5R^{5a}$, $OC(=O)R^{5a}$, $OC(=O)OR^{5b}$, $OR^5$, $OC(=O)NR^5R^{5a}$, $OCH_2CO_2R^5$, $CO_2CH_2CO_2R^5$, $NO_2$, $NR^{5a}C(=O)R^{5a}$, $NR^{5a}C(=O)OR^{5b}$, $NR^{5a}C(=O)NR^5R^{5a}$, $NR^{5a}SO_2NR^5R^{5a}$, $NR^{5a}SO_2R^5$, $S(O)_pR^5$, $SO_2NR^5R^{5a}$, $C_2$ to $C_6$ alkenyl, $C_3$ to $C_{11}$ cycloalkyl, $C_4$ to $C_{11}$ cycloalkylmethyl;

$C_6$ to $C_{10}$ aryl optionally substituted with 1–3 groups selected from halogen, $C_1$–$C_6$ alkoxy, $C_1$–$C_6$ alkyl, $CF_3$, $S(O)_mMe$, or —$NMe_2$;

$C_7$ to $C_{11}$ arylalkyl, said aryl being optionally substituted with 1–3 groups selected from halogen, $C_1$–$C_6$ alkoxy, $C_1$–$C_6$ alkyl, $CF_3$, $S(O)_mMe$, or —$NMe_2$;

methylenedioxy when $R^6$ is a substiuent on aryl; or a 5–6 membered heterocyclic ring containing 1–2 N, O, or S heteroatoms, wherein said heterocyclic ring may be saturated, partially saturated, or fully unsaturated, said heterocyclic ring being substituted with 0–2 $R^7$;

$R^{6a}$ is selected from $C_1$–$C_4$ alkyl, $C_1$–$C_4$ alkoxy, halo, $CF_3$, $NO_2$, or $NR^{12}R^{13}$;

$R^7$ is selected from H, $C_1$–$C_{10}$ alkyl, hydroxy, $C_1$–$C_{10}$ alkoxy, nitro, $C_1$–$C_{10}$ alkylcarbonyl, —$N(R^{12})R^{13}$, cyano, halo, $CF_3$, CHO, $CO_2R^5$, $C(=O)R^{5a}$, $CONR^5R^{5a}$, $OC(=O)R^{5a}$, $OC(=O)OR^{5b}$, $OR^{5a}$, $OC(=O)NR^5R^{5a}$, $OCH_2CO_2R^5$, $CO_2CH_2CO_2R^5$, $NO_2$, $NR^{5a}C(=O)R^{5a}$, $NR^{5a}C(=O)OR^{5b}$, $NR^{5a}C(=O)NR^5R^{5a}$, $NR^{5a}SO_2NR^5R^{5a}$, $NR^{5a}SO_2R^5$, $S(O)_mR^{5a}$, $SO_2NR^5R^{5a}$, $C_2$ to $C_6$ alkenyl, $C_3$ to $C_{11}$ cycloalkyl, $C_4$ to $C_{11}$ cycloalkylmethyl, $C_6$ to $C_{10}$ aryl, or $C_7$ to $C_{11}$ arylalkyl;

$R^8$ is selected from:
$R^6$;
$C_2$–$C_{10}$ alkyl, substituted with 0–3 $R^6$;
$C_2$–$C_{10}$ alkenyl, substituted with 0–3 $R^6$;
$C_2$–$C_{10}$ alkynyl, substituted with 0–3 $R^6$;
$C_3$–$C_8$ cycloalkyl, substituted with 0–3 $R^6$;
$C_5$–$C_6$ cycloalkenyl, substituted with 0–3 $R^6$;
aryl, substituted with 0–3 $R^6$;
5–6 membered heterocyclic ring containing 1–2 N, O, or S heteroatoms, wherein said heterocyclic ring may be saturated, partially saturated, or fully unsaturated, said heterocyclic ring being substituted with 0–2 $R^6$;

$R^{12}$ and $R^{13}$ are independently H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, aryl, $C_2$–$C_6$ alkenyl, $C_3$–$C_{11}$ cycloalkyl, $C_4$–$C_{11}$ cycloalkylalkyl, $C_7$–$C_{11}$ arylalkyl, $C_7$–$C_{11}$ arylcarbonyl, $C_4$–$C_{11}$ cycloalkoxycarbonyl, $C_7$–$C_{11}$ bicycloalkoxycarbonyl, $C_7$–$C_{11}$ aryloxycarbonyl, or aryl($C_1$–$C_{10}$ alkoxy)carbonyl, wherein said aryls are optionally substituted with 0–3 substituents selected from the group consisting of: $C_1$–$C_4$ alkyl, $C_1$–$C_4$ alkoxy, halo, $CF_3$, and $NO_2$;

$R^{14}$ is selected from H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or $C_1$–$C_{10}$ alkoxycarbonyl, $CO_2R^5$ or —$C(=O)N(R^5)R^{5a}$;

$R^{15}$ is selected from:
H;
$R^6$;
$C_1$–$C_{10}$ alkyl, substituted with 0–3 $R^6$;
$C_2$–$C_{10}$ alkenyl, substituted with 0–3 $R^6$;
$C_1$–$C_{10}$ alkoxy, substituted with 0–3 $R^6$;
aryl, substituted with 0–3 $R^6$;
5–6 membered heterocyclic ring containing 1–2 N, O, or S heteroatoms, wherein said heterocyclic ring may be saturated, partially saturated, or fully unsaturated, said heterocyclic ring being substituted with 0–2 $R^6$;
$C_1$–$C_{10}$ alkoxycarbonyl substituted with 0–2 $R^6$;
-$CO_2R^5$; or
—$C(=O)N(R^{12})R^{13}$;

provided that when b is a double bond, only one of $R^{14}$ or $R^{15}$ is present;

$R^{16}$ is selected from:
—$C(=O)$—O—$R^{18a}$,
—$C(=O)$—$R^{18b}$,
—$C(=O)N(R^{18b})_2$,
—$C(=O)NHSO_2R^{18a}$,
—$C(=O)NHC(=O)R^{18b}$,
—$C(=O)NHC(=O)OR^{18a}$,
—$C(=O)NHSO_2NHR^{18b}$,
—$C(=S)$—NH—$R^{18b}$,
—NH—$C(=O)$—O—$R^{18a}$,
—NH—$C(=O)$—$R^{18b}$,
—NH—$C(=O)$—NH—$R^{18b}$,
—$SO_2$—O—$R^{18a}$,
—$SO_2$—$R^{18a}$,
—$SO_2$—N$(18^b)_2$,
—$SO_2$—NHC(=O)O$18^b$,
—P(=S)(O$R^{18a}$)$_2$,
—P(=O)(O$R^{18a}$)$_2$,
—P(=S)($R^{18a}$)$_2$,
—P(=O)($R^{18a}$)$_2$, or

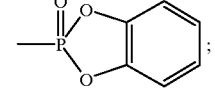

$R^{17}$ is selected from: H, $C_1$–$C_{10}$ alkyl, $C_2$–$C_6$ alkenyl, $C_3$–$C_{11}$ cycloalkyl, $C_4$–$C_{15}$ cycloalkylalkyl, aryl, aryl ($C_1$–$C_{10}$ alkyl)-;

$R^{18a}$ is selected from:
$C_1$–$C_8$ alkyl substituted with 0–2 $R^{19}$,
$C_2$–$C_8$ alkenyl substituted with 0–2 $R^{19}$, $C_2$–$C_8$ alkynyl substituted with 0–2 $R^{19}$,
$C_3$–$C_8$ cycloalkyl substituted with 0–2 $R^{19}$,
aryl substituted with 0–4 $R^{19}$,
aryl($C_1$–$C_6$ alkyl)-substituted with 0–4 $R^{19}$,
a 5–10 membered heterocyclic ring system having 1–3 heteroatoms selected independently from O, S, and N, said heterocyclic ring being substituted with 0–4 $R^{19}$,
$C_1$–$C_6$ alkyl substituted with a 5–10 membered heterocyclic ring system having 1–3 heteroatoms selected independently from O, S, and N, said heterocyclic ring being substituted with 0–4 $R^{19}$;

$R^{18b}$ is selected from $R^{18a}$ or H;

$R^{19}$ is selected from H, halogen, $CF_3$, CN, $NO_2$, $NR^{12}R^{13}$, $C_1$–$C_8$ alkyl, $C_2$–$C_6$ alkenyl, $C_2$–$C_6$ alkynyl, $C_3$–$C_{11}$ cycloalkyl, $C_4$–$C_{11}$ cycloalkylalkyl, aryl, aryl($C_1$–$C_6$ alkyl)-, $C_1$–$C_6$ alkoxy, or $C_1$–$C_4$ alkoxycarbonyl;

$R^{20}$ and $R^{21}$ are each independently selected from H, $C_1$–$C_{10}$ alkyl, $CO_2R^5$, $C(=O)R^{5a}$, $CONR^5R^{5a}$, $NR^5C(=O)R^{5a}$, $NR^{12}R^{13}$, $C_2$–$C_6$ alkenyl, $C_3$–$C_{11}$ cycloalkyl, $C_4$–$C_{11}$ cycloalkylmethyl, $C_6$–$C_{10}$ aryl, or $C_7$–$C_{11}$ arylalkyl;

$R^{22}$ is selected from $C_1$–$C_{10}$ alkyl, $C_2$–$C_6$ alkenyl, $C_3$–$C_{11}$ cycloalkyl, $C_4$–$C_{15}$ cycloalkylalkyl, aryl, aryl ($C_1$–$C_{10}$ alkyl)-; $C(=O)R^{5a}$, $CO_2R^{5b}$, $—C(=O)N(R^5)R^{5a}$, or a bond to X;

m is 0–2;
n is 0–2;
p is 1–2;
q is 1–7;
r is 0–3;

provided that n, q and r are chosen such that the number of atoms connecting $R^1$ and Y is in the range of 8–17.

[25] Preferred compounds of this embodiment are those compounds of Formula Ic:

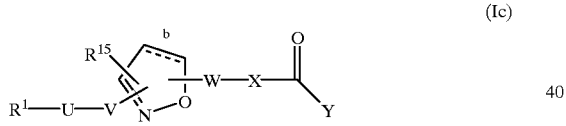

(Ic)

wherein:
Z is selected from a bond (i.e. is absent), O, or S;
$R^2$ and $R^3$ are independently selected from: H; $C_1$–$C_6$ alkyl; $C_7$–$C_{11}$ arylalkyl optionally substituted with 0–3 groups selected from hydroxy, halogen, $C_1$–$C_6$ alkoxy, $C_1$–$C_6$ alkyl, $CF_3$, $S(O)_mCH_3$, $—N(CH_3)_2$, $C_1$–$C_4$ haloalkyl, methylenedioxydiyl, ethylenedioxydiyl; $C_1$–$C_{10}$ alkoxycarbonyl; aryl($C_1$–$C_{10}$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, $—N(CH_3)_2$, $C_1$–$C_4$ haloalkyl, methylenedioxydiyl, ethylenedioxydiyl; or heteroaryl($C_1$–$C_5$)alkyl where the heteroaryl group is optionally substituted with 0–2 groups selected from hydroxy, halogen, $C_1$–$C_6$ alkoxy, $C_1$–$C_6$ alkyl, $CF_3$, $S(O)_mCH_3$, $—N(CH_3)_2$, $C_1$–$C_4$ haloalkyl, methylenedioxydiyl, ethylenedioxydiyl;
U is a single bond (i.e., U is not present);
X is $—CHR^{4a}—$;
$R^5$ is selected from H or $C_1$–$C_{10}$ alkyl substituted with 0–6 $R^{4b}$;
$R^6$ and $R^7$ are each independently selected from H, $C_1$–$C_{10}$ alkyl, hydroxy, $C_1$–$C_{10}$ alkoxy, nitro, $C_1$–$C_{10}$ alkylcarbonyl, $—N(R^{12})R^{13}$, cyano, or halo;

$R^{12}$ and $R^{13}$ are each independently selected from H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, or aryl, wherein said aryls are optionally substituted with 0–3 substituents selected from the group consisting of: $C_1$–$C_4$ alkyl, $C_1$–$C_4$ alkoxy, halo, $CF_3$, and $NO_2$;

$R^{15}$ is selected from H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or $C_1$–$C_{10}$ alkoxycarbonyl, $CO_2R^5$ or $—C(=O)N(R^5)R^{5a}$;

$R^{16}$ is selected from:
—$C(=O)$—$O$—$R^{18a}$,
—$C(=O)$—$R^{18b}$,
—$S(=O)_2$—$R^{18a}$;

$R^{17}$ is selected from: H or $C_1$–$C_4$ alkyl;

$R^{18a}$ is selected from:
$C_1$–$C_8$ alkyl substituted with 0–2 $R^{19}$,
$C_2$–$C_8$ alkenyl substituted with 0–2 $R^{19}$,
$C_2$–$C_8$ alkynyl substituted with 0–2 $R^{19}$,
$C_3$–$C_8$ cycloalkyl substituted with 0–2 $R^{19}$,
aryl substituted with 0–2 $R^{19}$,
aryl($C_1$–$C_6$ alkyl)-substituted with 0–2 $R^{19}$,
a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolinyl, benzimidazolyl, piperidinyl, tetrahydrofuranyl, pyranyl, pyridinyl, 3H-indolyl, carbazolyl, pyrrolidinyl, piperidinyl, indolinyl, or morpholinyl, said heterocyclic ring being substituted with 0–2 $R^{19}$;
$C_1$–$C_6$ alkyl substituted with a heterocyclic ring system selected from pyridinyl, furanyl, thiazolyl, thienyl, pyrrolyl, pyrazolyl, imidazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, said heterocyclic ring being substituted with 0–2 $R^{19}$.

[26] Further preferred compounds of this embodiment are compounds of Formula Ib:

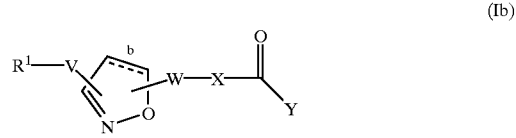

(Ib)

wherein:
$R^1$ is selected from: $R^2(R^3)N—$, $R^2NH(R^2N=)C—$, $R^2R^3N(CH_2)_{p''}Z—$, $R^2NH(R^2N=)CNH(CH_2)_{p''}Z—$, $R^2(R^3)NC(O)—$, $R^2(R^5O)N(R^2N=)C—$, $R^2(R^3)N(R^5ON=)C—$;

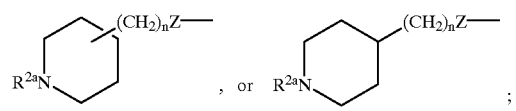

n is 0–1;
p' is 2–4;
p'' is 4–6;

Z is selected from a bond (i.e. is absent) or O;

$R^3$ is H or $C_1$–$C_5$ alkyl;

V is a single bond (i.e., V is not present), or -(phenyl)-;

X is selected from:
—$CH_2$—,
—$CHN(R^{16})R^{17}$—, or
$CHNR^5R^{5a}$—;

Y is selected from:
hydroxy;
$C_1$ to $C_{10}$ alkoxy;
methylcarbonyloxymethoxy-;
ethylcarbonyloxymethoxy-;
t-butylcarbonyloxymethoxy-;
cyclohexylcarbonyloxymethoxy-;
1-(methylcarbonyloxy)ethoxy-;
1-(ethylcarbonyloxy)ethoxy-;
1-(t-butylcarbonyloxy)ethoxy-;
1-(cyclohexylcarbonyloxy)ethoxy-;
i-propyloxycarbonyloxymethoxy
t-butyloxycarbonyloxymethoxy-;
1-(i-propyloxycarbonyloxy)ethoxy-;
1-(cyclohexyloxycarbonyloxy)ethoxy-;
1-(t-butyloxycarbonyloxy)ethoxy-;
dimethylaminoethoxy-;
diethylaminoethoxy-;
(5-methyl-1,3-dioxacyclopenten-2-on-4-yl)methoxy-;
(5-(t-butyl)-1,3-dioxacyclopenten-2-on-4-yl)methoxy-;
(1,3-dioxa-5-phenyl-cyclopenten-2-on-4-yl)methoxy-;
1-(2-(2-methoxypropyl)carbonyloxy)ethoxy-;

$R^{18a}$ is selected from:
$C_1$–$C_4$ alkyl substituted with 0–2 $R^{19}$,
$C_2$–$C_4$ alkenyl substituted with 0–2 $R^{19}$,
$C_2$–$C_4$ alkynyl substituted with 0–2 $R^{19}$,
$C_3$–$C_4$ cycloalkyl substituted with 0–2 $R^{19}$,
aryl substituted with 0–2 $R^{19}$,
aryl($C_1$–$C_4$ alkyl)-substituted with 0–2 $R^{19}$,
a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolinyl, benzimidazolyl, piperidinyl, tetrahydrofuranyl, pyranyl, pyridinyl, 3H-indolyl, carbazolyl, pyrrolidinyl, piperidinyl, indolinyl, or morpholinyl, said heterocyclic ring being substituted with 0–2 $R^{19}$;
$C_1$–$C_6$ alkyl substituted with a heterocyclic ring system selected from pyridinyl, furanyl, thiazolyl, thienyl, pyrrolyl, pyrazolyl, imidazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, said heterocyclic ring being substituted with 0–2 $R^{19}$.

[27] Further preferred compounds of this fifth embodiment are compounds of Formula Ib wherein:

$R^1$ is $R^2NH(R^2N=)C$— or $R^2NH(R^2N=)CNH$— and V is phenyl or pyridyl; or $R^1$ is

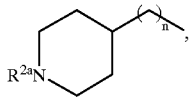

and V is a single bond (i.e. V is absent)

n is 1–2;

X is selected from:
—$CH_2$—,
—$CHN(R^{16})R^{17}$—, or
—$CHNR^5R^{5a}$—;

W is selected from:

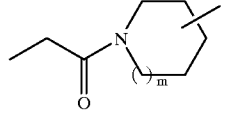

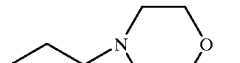

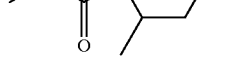

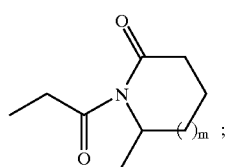

m is 1–3;

Y is selected from:
hydroxy;
$C_1$ to $C_{10}$ alkoxy;
methylcarbonyloxymethoxy-;
ethylcarbonyloxymethoxy-;
t-butylcarbonyloxymethoxy-;
cyclohexylcarbonyloxymethoxy-;
1-(methylcarbonyloxy)ethoxy-;
1-(ethylcarbonyloxy)ethoxy-;
1-(t-butylcarbonyloxy)ethoxy-;
1-(cyclohexylcarbonyloxy)ethoxy-;
i-propyloxycarbonyloxymethoxy-;
t-butyloxycarbonyloxymethoxy-;
1-(i-propyloxycarbonyloxy)ethoxy-;
1-(cyclohexyloxycarbonyloxy)ethoxy-;
1-(t-butyloxycarbonyloxy)ethoxy-;
dimethylaminoethoxy-;
diethylaminoethoxy-;
(5-methyl-1,3-dioxacyclopenten-2-on-4-yl)methoxy-;
(5-(t-butyl)-1,3-dioxacyclopenten-2-on-4-yl)methoxy-;
(1,3-dioxa-5-phenyl-cyclopenten-2-on-4-yl)methoxy-;
1-(2-(2-methoxypropyl)carbonyloxy)ethoxy-;

$R^{19}$ is H, halogen, $C_1$–$C_4$ alkyl, $C_3$–$C_7$ cycloalkyl, cyclopropylmethyl, aryl, or benzyl;

$R^{20}$ and $R^{21}$ are both H;

$R^{22}$ is H, $C_1$–$C_4$ alkyl or benzyl.

[28] Specifically preferred compounds of this fifth embodiment are compounds of Formula Ib, or pharmaceutically acceptable salt forms thereof, selected from:

2-(R,S)-2-carboxymethyl-1-{5-(R,S)-N-[3-(4-amidinophenyl)isoxazolin-5-yl acetyl]piperidine;

2-(R,S)-2-carboxymethyl-1-{5-(R,S)-N-[3-(4-amidinophenyl)isoxazolin-5-yl acetyl]azepine;

2-(R,S)-2-carboxymethyl-1-{5-(R,S)-N-[3-(4-amidinophenyl)isoxazolin-5-yl acetyl]pyrrolidine;

3-(R,S)-carboxymethyl-4-{5-(R,S)-N-[3-(4-amidinophenyl)isoxazolin-5-yl acetyl]piperazine-2-one;

6-(R,S)-carboxymethyl-1-{5-(R,S)-N-[3-(4-amidinophenyl)isoxazolin-5-yl acetyl]piperidine-2-one;

5-(R,S)-carboxymethyl-1-{5-(R,S)-N-[3-(4-amidinophenyl)isoxazolin-5-yl acetyl]pyrrolidine-2-one;

7-(R,S)-carboxymethyl-1-{5-(R,S)-N-[3-(4-amidinophenyl)isoxazolin-5-yl acetyl]azetidine-2-one;

2-(R,S) -carboxymethyl-1-{5-(R,S)-N-[3-(4-amidinophenyl)isoxazolin-5-yl acetyl]pyrazolidine;

3-(R,S)-carboxymethyl-4-{5-(R,S)-N-[3-(4-amidinophenyl)isoxazolin-5-yl acetyl]morpholine.

In the present invention it has been discovered that the compounds of Formula I above are useful as inhibitors of cell-matrix and cell—cell adhesion processes. The present invention includes novel compounds of Formula I and methods for using such compounds for the prevention or treatment of diseases resulting from abnormal cell adhesion to the extracellular matrix which comprises administering to a host in need of such treatment a therapeutically effective amount of such compound of Formula I.

In the present invention it has also been discovered that the compounds of Formula I above are useful as inhibitors of glycoprotein IIb/IIIa (GPIIb/IIIa). The compounds of the present invention inhibit the activation and aggregation of platelets induced by all known endogenous platelet agonists.

The present invention also provides pharmaceutical compositions comprising a compound of Formula I and a pharmaceutically acceptable carrier.

The compounds of Formula I of the present invention are useful for the treatment (including prevention) of thromboembolic disorders. The term "thromboembolic disorders" as used herein includes conditions involving platelet activation and aggregation, such as arterial or venous cardiovascular or cerebrovascular thromboembolic disorders, including, for example, thrombosis, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolisms, pulmonary embolisms, or such disorders associated with diabetes, comprising administering to a mammal in need of such treatment a therapeutically effective amount of a compound of Formula I described above.

The compounds of Formula I of the present invention may be useful for the treatment or prevention of other diseases which involve cell adhesion processes, including, but not limited to, infammation, bone degradation, rheumatoid arthritis, asthma, allergies, adult respiratory distress syndrome, graft versus host disease, organ transplantation rejection, septic shock, psoriasis, eczema, contact dermatitis, osteoporosis, osteoarthritis, atherosclerosis, tumors, metastasis, diabetic retinopathy, inflammatory bowel disease and other autoimmune diseases. The compounds of Formula I of the present invention may also be useful for wound healing.

The compounds of the present invention are useful for inhibiting the binding of fibrinogen to blood platelets, inhibiting aggregation of blood platelets, treating thrombus formation or embolus formation, or preventing thrombus or embolus formation in a mammal. The compounds of the invention may be used as a medicament for blocking fibrinogen from acting at its receptor site in a mammal.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption, and where the aggregated platelets may form thrombi and thromboemboli. The compounds of the present invention may be administered to these surgical patients to prevent the formation of thrombi and thromboemboli.

Extracorporeal circulation is routinely used during cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the extracorporeal circuit. Platelets released from artificial surfaces show impaired homeostatic function. The compounds of the invention may be administered to prevent such ex vivo adhesion.

The compounds of the present invention may be used for other ex vivo applications to prevent cellular adhesion in biological samples.

Other applications of these compounds include prevention of platelet thrombosis, thromboembolism, and reocclusion during and after thrombolytic therapy and prevention of platelet thrombosis, thromboembolism and reocclusion after angioplasty of coronary and other arteries and after coronary artery bypass procedures. The compounds of the present invention may also be used to prevent myocardial infarction. The compounds of the present invention are useful as thrombolytics for the treatment of thromboembolic disorders.

The compounds of the present invention can also be administered in combination with one or more additional therapeutic agents select from: anti-coagulant or coagulation inhibitory agents, such as heparin or warfarin; anti-platelet or platelet inhibitory agents, such as aspirin, piroxicam, or ticlopidine; thrombin inhibitors such as boropeptides, hirudin or argatroban; or thrombolytic or fibrinolytic agents, such as plasminogen activators, anistreplase, urokinase, or streptokinase.

The compounds of Formula I of the present invention can be administered in combination with one or more of the foregoing additional therapeutic agents, thereby to reduce the doses of each drug required to achieve the desired therapeutic effect. Thus, the combination treatment of the present invention permits the use of lower doses of each component, with reduced adverse, toxic effects of each component. A lower dosage minimizes the potential of side effects of the compounds, thereby providing an increased margin of safety relative to the margin of safety for each component when used as a single agent. Such combination therapies may be employed to achieve synergistic or additive therapeutic effects for the treatment of thromboembolic disorders.

By "therapeutically effective amount" it is meant an amount of a compound of Formula I that when administered alone or in combination with an additional therapeutic agent to a cell or mammal is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term anti-coagulant agents (or coagulation inhibitory agents), as used herein, denotes agents that inhibit blood coagulation. Such agents include warfarin (available as Coumadin™) and heparin.

The term anti-platelet agents (or platelet inhibitory agents), as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam. Piroxicam is commercially available from Pfizer Inc. (New York, N.Y.), as Feldane™. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include thromboxane-A2-receptor antagonists and thromboxane-A2-synthetase inhibitors, as well as pharmaceutically acceptable salts or prodrugs thereof.

The phrase thrombin inhibitors (or anti-thrombin agents), as used herein, denotes inhibitors of the serine protease thrombin and other inhibitors of thrombin synthesis such as Factor XA. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. Such inhibitors include boroarginine derivatives and boropeptides, hirudin and argatroban, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471 651 A2, the disclosures of which are hereby incorporated herein by reference, in their entirety.

The phrase thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. Tissue plasminogen activator (tPA) is commercially available from Genentech Inc., South San Francisco, Calif. The term anistreplase, as used herein, refers to anisoylated plasminogen streptokinase activator complex, as described, for example, in European Patent Application No. 028,489, the disclosures of which are hereby incorporated herein by reference herein, in their entirety. Anistreplase is commercially available as Eminase™. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

GPIIb/IIIa is known to be overexpressed in metastatic tumor cells. The compounds or combination products of the present invention may also be useful for the treatment, including prevention, of metastatic cancer.

The compounds of the present invention are also useful as standard or reference compounds, for example as a quality standard or control, in tests or assays involving the binding of fibrinogen to platelet GPIIb/IIIa. Such compounds may be provided in a commercial kit, for example, for use in pharmaceutical research involving GPIIb/IIIa. The compounds of the present invention may also be used in diagnostic assays involving platelet GPIIb/IIIa.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable (for example but not limited to, $R^2$, $R^4$, $R^6$, $R^7$, $R^8$, $R^{12}$, and $R^{14}$, n, etc.) occurs more than one time in any constituent or in any formula, its definition on each occurrence is independent of its definition at every other occurrence. Thus, for example, if a group is shown to be substituted with 0–2 $R^4$, then said group may optionally be substituted with up to two $R^4$ and $R^4$ at each occurrence is selected independently from the defined list of possible $R^4$. Also, by way of example, for the group —N($R^{5a}$)$_2$, each of the two $R^{5a}$ substituents on N is independently selected from the defined list of possible $R^{5a}$. Similarly, by way of example, for the group —C($R^7$)$_2$—, each of the two $R^7$ substituents on C is independently selected from the defined list of possible $R^7$.

When a bond to a substituent is shown to cross the bond connecting two atoms in a ring, then such substituent may be bonded to any atom on the ring. When a bond joining a substituent to another group is not specifically shown or the atom in such other group to which the bond joins is not specifically shown, then such substituent may form a bond with any atom on such other group.

When a substituent is listed without indicating the atom via which such substituent is bonded to the rest of the compound of Formula I, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of Formula I via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "alkyl" is intended to include both branched and straight-chain saturated aliphatic hydrocarbon groups having the specified number of carbon atoms (for example, "$C_1$–$C_{10}$" denotes alkyl having 1 to 10 carbon atoms); "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-, bi-, or poly-cyclic ring systems, such as cyclopropyl, cyclobutyl, cyclopentyl, cyclohexyl, cycloheptyl, cyclooctyl, and adamantyl; and "bicycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon—carbon bonds which may occur in any stable point along the chain, such as ethenyl, propenyl and the like; and "alkynyl" is intended to include hydrocarbon chains of either a straight or branched configuration and one or more triple carbon—carbon bonds which may occur in any stable point along the chain, such as ethynyl, propynyl and the like.

The terms "alkylene", "alkenylene", "phenylene", and the like, refer to alkyl, alkenyl, and phenyl groups, respectively, which are connected by two bonds to the rest of the structure of Formula I. Such "alkylene", "alkenylene", "phenylene", and the like, may alternatively and equivalently be denoted herein as "-(alkyl)-", "-(alkenyl)-" and "-(phenyl)-", and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl optionally substituted with 0–3 groups independently selected from methyl, methoxy, amino, hydroxy, halogen, $C_1$–$C_6$ alkoxy, $C_1$–$C_6$ alkyl, $CF_3$, $S(O)_mCH_3$, —$N(CH_3)_2$, $C_1$-$C_4$ haloalkyl, methylenedioxydiyl, ethylenedioxydiyl; the term "arylalkyl" represents an aryl group attached through an alkyl bridge.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, isoxazolinyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolyl, oxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl or oxazolidinyl. Also included are fused ring and spiro compounds containing, for example, the above heterocycles.

As used herein, the term "heteroaryl" refers to aromatic heterocyclic groups. Such heteroaryl groups are preferably 5–6 membered monocylic groups or 8–10 membered fused bicyclic groups. Examples of such heteroaryl groups include, but are not limited to pyridyl (pyridinyl), pyrimidinyl, furanyl (furyl), thiazolyl, thienyl, pyrrolyl, pyrazolyl, imidazolyl, indolyl, isoxazolyl, oxazolyl, pyrazinyl, pyridazinyl, benzofuranyl, benzothienyl, benzimidazolyl, quinolinyl, or isoquinolinyl.

As used herein, the term "chiral amine" refers to any amine containing compound that also contains a chiral center. Such compounds include, by way of example and without limitation, either enantiomer of cinchonidine, ephedrine, 2-phenylglycinol, 2-amino-3-methoxy-1-propanol, quinidine and pseudoephedrine.

As used herein, "pharmaceutically acceptable salts" refer to derivatives of the disclosed compounds wherein the parent compound of Formula I is modified by making acid or base salts of the compound of Formula I. Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to Formula I in vivo when such prodrug is administered to a mammalian subject. Prodrugs of the compounds of Formula I are prepared by modifying functional groups present in the compounds in such a way that the modifications are cleaved, either in routine manipulation or in vivo, to the parent compounds. Prodrugs include compounds of Formula I wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of Formula I, and the like. Examples of representative carboxyl and amino prodrugs are included under the definition of $R^2$, $R^3$, and Y.

The pharmaceutically acceptable salts of the compounds of Formula I include the conventional non-toxic salts or the quaternary ammonium salts of the compounds of Formula I formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa.; 1985; p. 1418, the disclosure of which is hereby incorporated by reference.

The disclosures of all of the references cited herein are hereby incorporated herein by reference in their entirety.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The following abbreviations are used herein:

| | |
|---|---|
| β-Ala | 3-aminopropionic acid |
| Boc | tert-butyloxycarbonyl |
| Boc$_2$O | di-tert-butyl dicarbonate |
| BOP | benzotriazolyl-N-oxytris(dimethylamino)-phosphonium hexafluorophosphate |
| BSTFA | N,O-bis(trimethylsilyl)triflouoromethyl-acetamide |
| Cbz | benzyloxycarbonyl |
| DCC | 1,3-dicyclohexylcarbodiimide |
| DEAD | diethyl azodicarboxylate |
| DEC | 1-(3-dimethylaminopropyl)-3-ethylcarbodiimide hydrochloride |
| DIEA | diisopropylethylamine |
| DCHA | dicyclohexylamine |
| DCM | dichloromethane |
| DMAP | 4-dimethylaminopyridine |
| DMF | N,N-dimethyl formamide |
| EtOAc | ethyl acetate |
| EtOH | ethyl alcohol |
| HOBt | 1-hydroxybenzotriazole |
| IBCF | iso-butyl chloroformate |
| LAH | lithium aluminum hydride |
| NCS | N-chlorosuccinimide |
| NMM | N-methylmorpholine |
| PPh$_3$ | triphenylphosphine |
| pyr | pyridine |
| TBTU | 2-(1H-Benzotriazol-1-yl)-1,1,3,3-tetramethyluronium tetrafluoroborate |
| TFA | trifluoroacetic acid |
| THF | tetrahydrofuran |

A convenient method for the synthesis of the compounds of this invention utilizes a dipolar cycloaddition of nitrile oxides with appropriate dipolarophiles to prepare the isoxazoline rings present in compounds of Formula I (for reviews of 1,3-dipolar cycloaddition chemistry, see 1,3-Dipolar Cycloaddition Chemistry (Padwa, ed.), Wiley, New York, 1984; Kanemasa and Tsuge, *Heterocycles* 1990, 30, 719).

Scheme I describes one synthetic sequence to the compounds of the second embodiment of this invention. An appropriately substituted hydroxylamine is treated with NCS in DMF according to the method of Liu, et al. (*J. Org. Chem.* 1980, 45, 3916). The resulting hydroximinoyl chloride is then dehydrohalogenated in situ using TEA to give a nitrile oxide, which undergoes a 1,3-dipolar cycloaddition to a suitably substituted alkene to afford the isoxazoline. Alternatively, the oxime may be oxidatively chlorinated, dehydrochlorinated and the resulting nitrile oxide trapped by a suitable alkene under phase transfer conditions according to the method of Lee (*Synthesis* 1982, 508). Hydrolysis of the ester using conventional methods known to one skilled in the art of organic synthesis gives the desired acids. Intermediates containing alkali-sensitive functionality, such as nitrile, may be deesterified with excellent chemoselectivity using sodium trimethylsilanolate according to the procedure of Laganis and Ehenard (*Tetrahedron Lett.* 1984, 25, 5831). Coupling of the resulting acids to an appropriately substituted α- or β-amino ester using standard coupling reagents, such as DCC/HOBt, affords a nitrile-amide. The nitrile is then converted to the amidine via the imidate or thioimidate under standard conditions followed by ester saponification (LiOH, THF/H$_2$O).

Scheme I

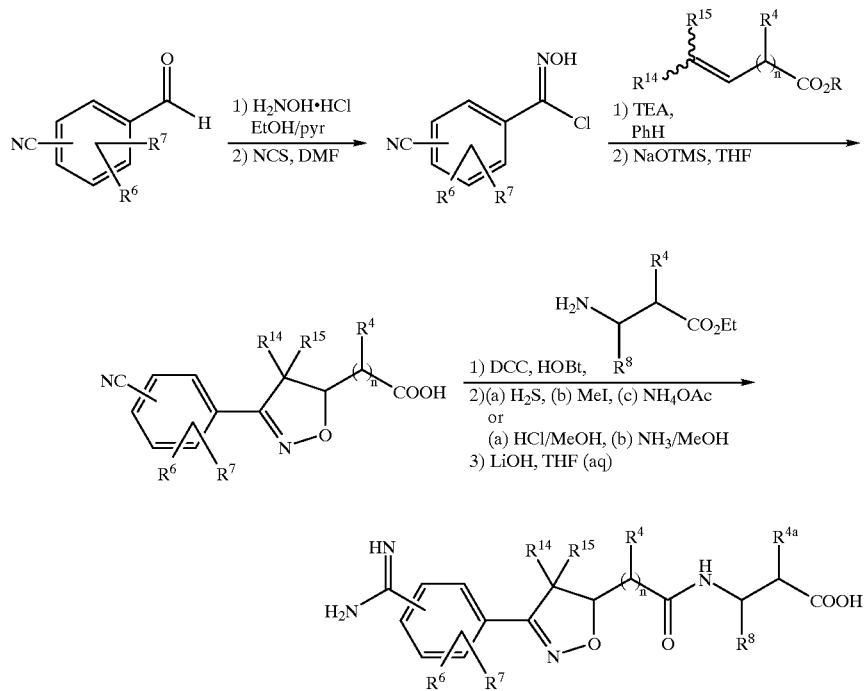

An example of a related method of preparation for compounds within the second embodiment of the present invention is illustrated in Scheme Ia. Conversion of 3-(4-cyanophenyl)isoxazolin-5-ylacetic acid to the corresponding amidine, followed by protection as the Boc- derivative and saponification provides 3-(4-Boc-amidinophenyl)isoxazolin-5-ylacetic acid which is coupled with P-amino acid esters as shown. Deprotection provides the desired isoxazolinylacetyl-β-aminoalaninyl esters. Saponification as described above gives the free acids.

Scheme Ia

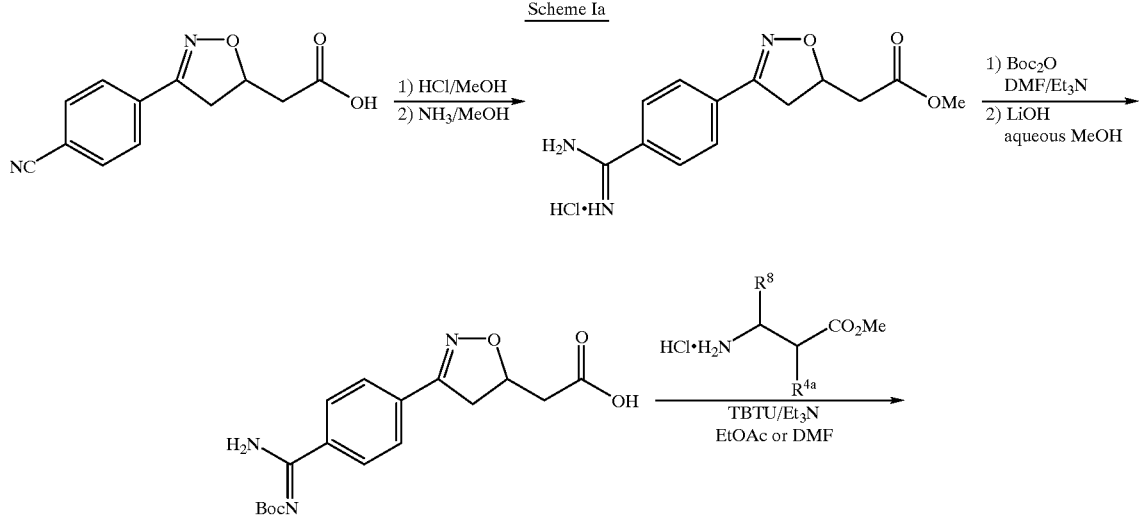

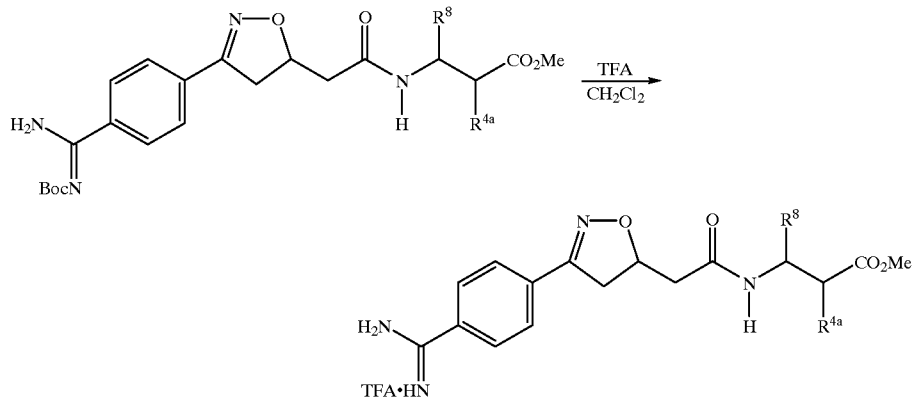

A further example of the synthesis of compounds within the second embodiment is shown in Scheme Ib. Cycloaddition of commerically available 4-cyanostyrene and t-butyl-3-oxoproprionate oxime using the method -described by Gree et al. (Bioorganic and Med. Chem. Lett. 1994, 253) provides t-butyl [5-(4-cyanophenyl)isoxazolin-3-yl]acetate. Using the procedures described above, this intermediate is converted to compounds of formula I wherein the isoxazoline ring is in the reverse orientation with respect to the compounds prepared via Schemes I and Ia.

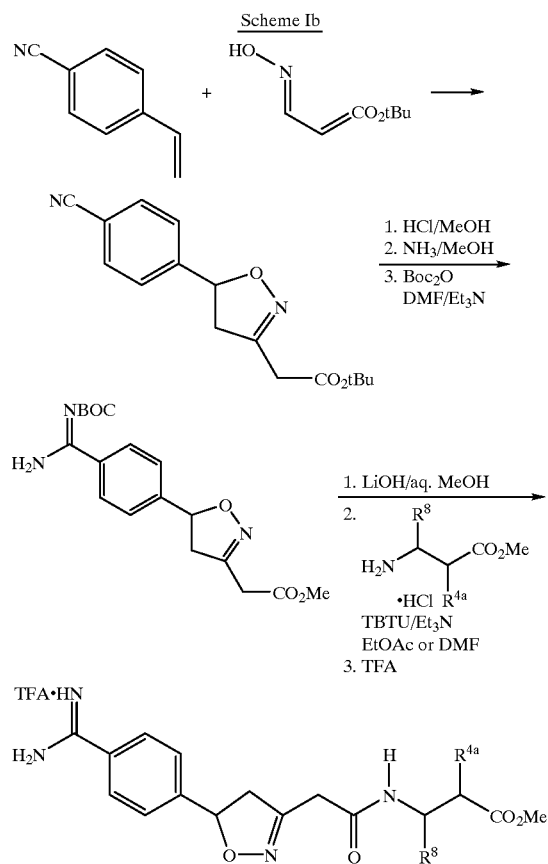

Additional isoxazolinyl acetates useful as starting materials for the preparation of compounds of Formula I, wherein V is -(phenyl)-Q- and Q is other than a single bond, can be prepared by cycloaddition of a suitably substituted chloro or bromooxime with an ester of vinyl acetic acid as shown in Scheme Ic using literature methods or modifications thereof. (D. P. Curran & J. Chao, J. Org. Chem. 1988, 53, 5369–71; J. N. Kim & E. K. Ryu, Heterocycles 1990, 31, 1693–97).

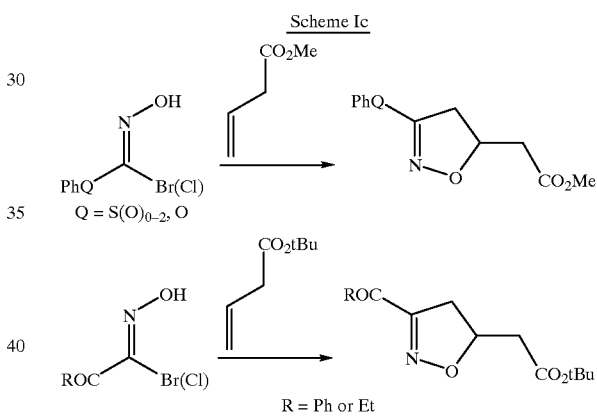

The compounds of the present invention where $R^2$ or $R^3$ is e.g. alkoxycarbonyl may be prepared by reacting the free amidines, amines or guanidines with an activated carbonyl derivative, such as an alkyl chloroformate. In compounds of the second embodiment, the conversion of the free amines, amidines and guanidines to such acyl-nitrogen groups may optionally be performed prior to coupling an isoxazoline acetic acid with e.g β-amino acids, as illustrated in Scheme Ia.

The compounds of the present invention wherein Y is an oxyalkoxy group, e.g. alkoxycarbonyloxyalkoxy, may be prepared by reacting a suitably protected carboxylic acid of Formula I with an alkoxycarbonyloxyalkyl chloride in the presence of an iodide source, such as tetrabutylammonium iodide or potassium iodide, and an acid scavenger, such as triethylamine or potassium carbonate, using procedures known to those skilled in the art.

The appropriately substituted racemic β-amino acids may be purchased commercially or, as is shown in Scheme II, Method 1, prepared from the appropriate aldehyde, malonic acid and ammonium acetate according to the procedure of Johnson and Livak (J. Am. Chem. Soc. 1936, 58, 299). Racemic β-substituted-β-amino esters may be prepared through the reaction of dialkylcuprates or alkyllithiums with 4-benzoyloxy-2-azetidinone followed by treatment with anhydrous acid in ethanol (Scheme I, Method 2) or by reductive amination of β-keto esters as is described in WO9316038. (Also see Rico et al., J. Org. Chem. 1993, 58, 7948–51.) Enantiomerically pure β-substituted-β-amino acids can be obtained through the optical resolution of the racemic mixture or can be prepared using numerous methods, including: Arndt-Eistert homologation of the corresponding α-amino acids as shown in Scheme II, Method 3 (see Meier, and Zeller, Angew. Chem. Int. Ed. Engl. 1975, 14, 32; Rodriguez, et al. Tetrahedron Lett. 1990, 31, 5153; Greenlee, J. Med. Chem. 1985, 28, 434 and references cited within); and through an enantioselective hydrogenation of a dehydroamino acid as is shown in Scheme II, Method 4 (see Asymmetric Synthesis, Vol. 5, (Morrison, ed.) Academic Press, New York, 1985). A comprehensive treatise on the preparation of β-amino acid derivatives may be found in patent application WO 9307867, the disclosure of which is hereby incorporated by reference.

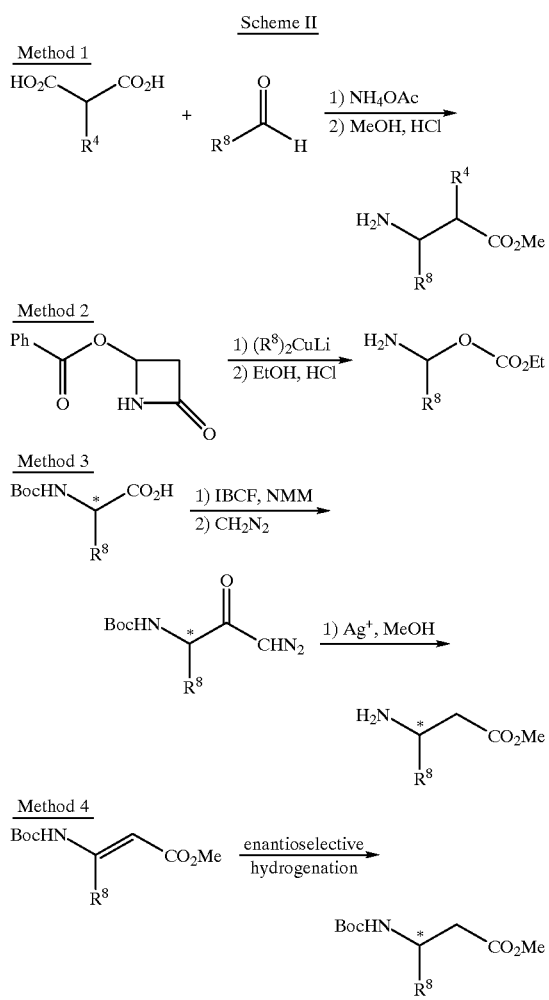

The synthesis of $N^2$-substituted diaminopropionic acid derivatives can be carried out via Hoffman rearrangement of a wide variety of asparagine derivatives as described in Synthesis, 266–267, (1981).

The appropriately substituted pyrrolidine-, piperidine- and hexahydroazepineacetic acids may be prepared using a number of methods. The pyrrolidines are conveniently prepared using an Arndt-Eistert homologation of the corresponding proline as shown in Scheme III, Method 1 (see Meier, and Zeller, Angew. Chem. Int. Ed. Engl. 1975, 14, 32; Rodriguez, et al. Tetrahedron Lett. 1990, 31, 5153; Greenlee, J. Med. Chem. 1985, 28, 434 and references cited within). The piperidines can be prepared by reduction of the corresponding pyridine as shown in Scheme III, Method 2. The hexahydroazepines are prepared by reduction of the corresponding vinylogous amide using sodium cyanoborohydride as depicted in Scheme III, Method 3.

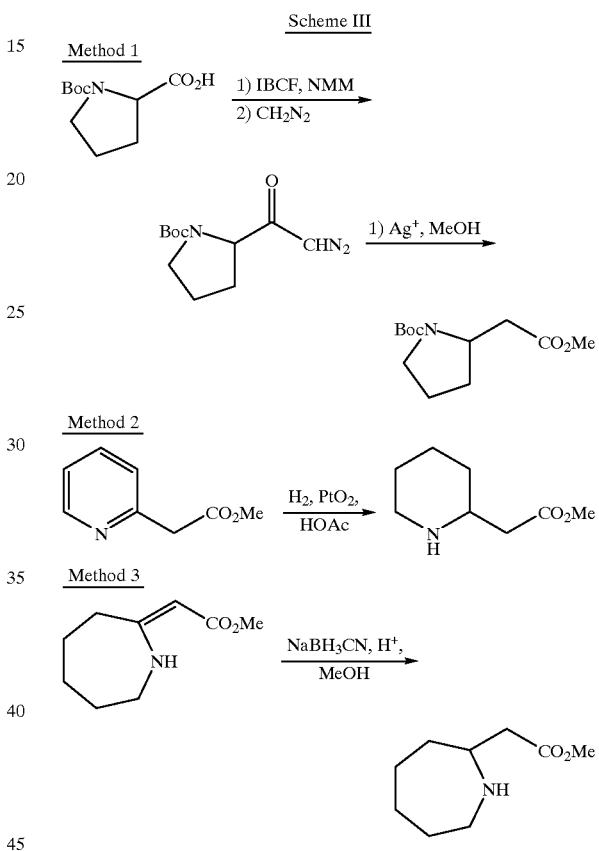

Many additional appropriately substituted heterocycles are available commercially or can be readily modified by procedures known by one skilled in the art. Appropriately substituted morpholines can be prepared from amino acids via the sequence of steps depicted in Scheme IIIa, method 1 (see Brown, et. al. J. Chem. Soc. Perkin Trans I 1987, 547; Bettoni, et. al. Tetrahedron 1980, 36, 409; Clarke, F. H. J. Org. Chem. 1962, 27, 3251 and references therein.) N-ethoxycarbonylmethyl-1,2-diazaheterocyles are prepared by condensation of suitably substituted dibromides with benzylhydrazine followed by Mitsunobu reaction with ethyl hydroxyacetate and deprotection as shown in Scheme IIIa, method 2 (see Kornet, et. al. J. Pharm. Sci. 1979, 68, 377.; Barcza, et. al. J. Org. Chem. 1976, 41, 1244 and references therein.)

Scheme IIIa

Method 1

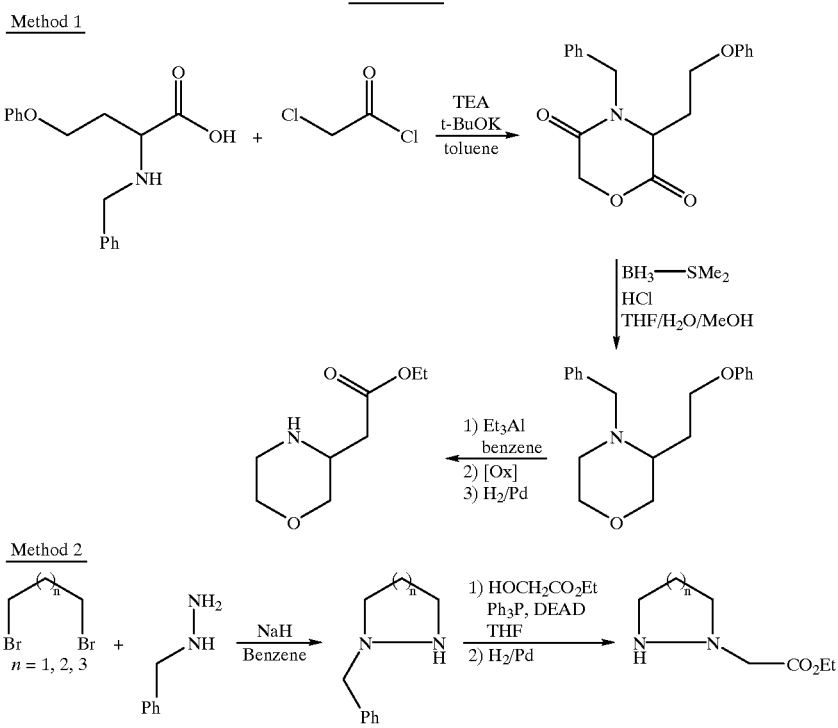

Method 2

A general synthetic protocol to the compounds of the first embodiment of this invention is depicted in Scheme IV. Coupling of a suitable Boc-protected amino alcohol to an appropriately substituted phenol under Mitsunobu conditions (see Mitsunobu, *Synthesis* 1981, 1) is followed by oximation using hydroxylamine hydrochloride in 1:1 ethanol/pyridine. Isoxazoline formation, ester saponification and Boc-deprotection (33% TFA/DCM) then affords the compounds of this invention in good overall yield.

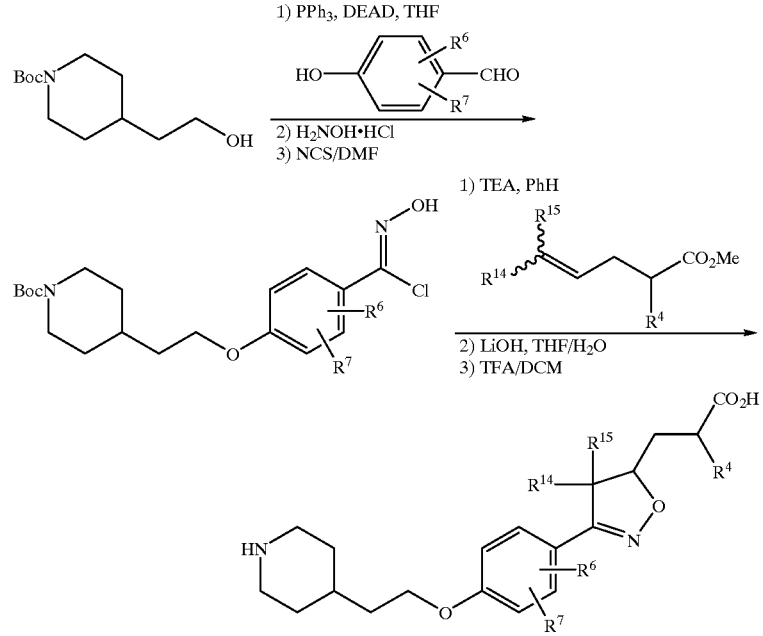

The synthesis of the spiro-fused isoxazolinyl imides of the third embodiment of the present invention is exemplified by the general protocol depicted in Scheme V. Dipolar cycloaddition of an oximinoyl chloride with a α-methylene diester affords an isoxazolinyl diester, which is deesterified using the silanolate method. Dehydration to the anhydride according to Ishihara, et al. (*Chem. Pharm. Bull.* 1992, 40, 1177–85) followed by imide formation using an appropriately substituted amino ester affords the spirocycle. Alternatively, the imide may be prepared directly from the isoxazoline diester according to Culbertson, et al. (*J. Med. Chem.* 1990, 33, 2270–75). Amidine formation or Boc deprotection followed by ester saponification then affords the compounds of this invention in good overall yield.

Scheme V

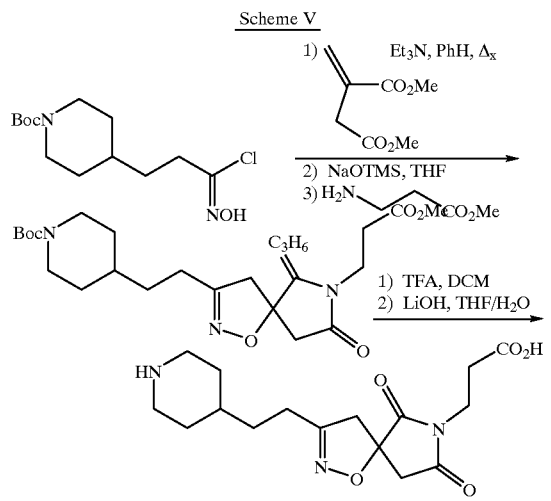

The synthesis of the spiro-fused isoxazolinyl amides of the third embodiment of the present invention is exemplified by the general protocol depicted in Scheme VI. Dipolar cycloaddition of an oximinoyl chloride with a α-methylene lactone affords the isoxazolinyl lactone, which is reacted with an appropriate amino ester to afford the amide (see The Chemistry of the Amides (Zabicky, ed.), p 96, Interscience, New York, 1970; Prelog, et al., *Helv. Chim. Acta* 1959, 42, 1301; Inubushi, et al., *J. Chem. Soc., Chem. Commun.* 1972, 1252). Amidine formation or Boc deprotection followed by ester saponification then affords the compounds of this invention in good overall yield.

Scheme VI

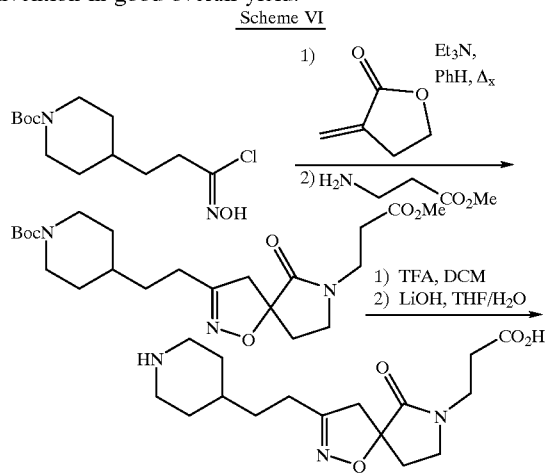

The synthesis of the spiro-fused isoxazolinyl cycloalkenes of the third embodiment of the present invention is exemplified by the general protocol depicted in Scheme VII. Dipolar cycloaddition of an oximinoyl chloride with an appropriately substituted α-methylene lactone affords the isoxazolinyl lactone. The lactone is then reacted with an appropriate lithium dimethyl alkylphosphonate, followed by PCC oxidation. The resulting diketophosphonate undergoes an intramolecular Wittig reaction in the presence of $K_2CO_3$/ 18-crown-6 according to the method described by Lim and Marquez (*Tetrahedron Lett.* 1983, 21, 5559). Amidine formation or Boc deprotection followed by ester saponification then affords the compounds of this invention in good overall yield.

Scheme VII

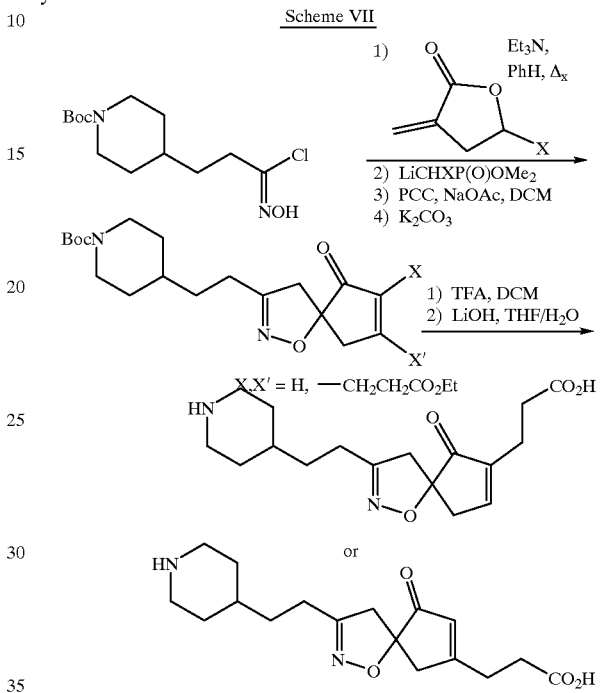

The dipolarophiles used to prepare the compounds of this invention may be prepared by numerous methods. The ω-alkenoic ester class of dipolarophile may be purchased commercially or prepared by oxidation of the corresponding ω-alkenols by the method of Corey and Schmidt (*Tetrahedron Lett.* 1979, 399, Scheme VIII, Method 1). The α-methylene diester and α-methylene lactone class of dipolarophile may be purchased commercially or can be prepared by numerous methods from the corresponding diester (see Osbond, *J. Chem. Soc.* 1951, 3464; Ames and Davey, *J. Chem,. Soc* 1958, 1794; Vig, et al., *Ind. J. Chem.* 1968, 6, 60; Grieco and Hiroi, *J. Chem, Soc., Chem, Commun.* 1972, 1317, Scheme VIII, Method 2). The 3-(styryl)propionic ester class of dipolarophile may be prepared by palladium-catalyzed cross coupling of the appropriately substituted bromo- or iodohydrocinnamic acid to a vinylmetal species according to methods cited within Mitchell (*Synthesis* 1992, 803) and Stille (*Angew. Chem. Int. Ed. Engl.* 1986, 25, 508, Scheme VIII, Method 3).

Scheme VIII

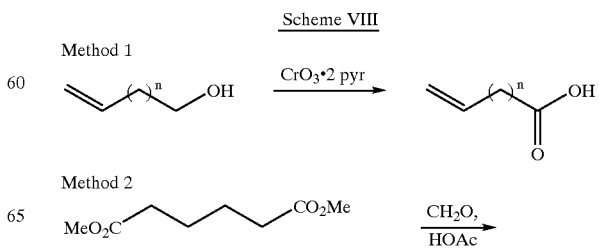

-continued

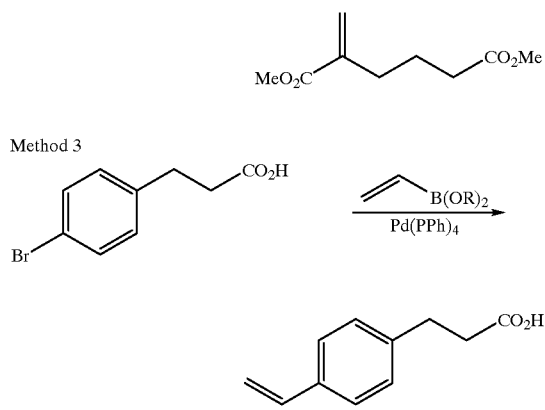

Method 3

Compounds of Formula I wherein b is a double bond can be prepared using one of the routes depicted in Scheme IX. Bromination followed by subsequent dehydrobromination of a suitably substituted methyl 3-(cyanophenyl)isoxazolin-5-ylacetate, prepared as described above, using the method of Elkasaby & Salem (Indian J. Chem. 1980, 19B, 571–575) provides the corresponding isoxazole intermediate. Alternately, this intermediate can be obtained by 1,3-dipolar cycloaddition of a cyanophenylnitrile oxide (prepared from the corresponding chlorooxime as described in Scheme I) with an appropriate alkyne to give the isoxazole directly. Hydrolysis of the ester using conventional methods known to one skilled in the art of organic synthesis gives the acetic acids. Coupling of the resulting acids to an appropriately substituted α- or β-amino ester using standard coupling reagents, such as TBTU, affords a nitrile-amide. The nitrile is then converted to the amidine via the imidate or thioimidate under standard conditions to give the prodrug esters. Saponification gives the acids.

Scheme IX

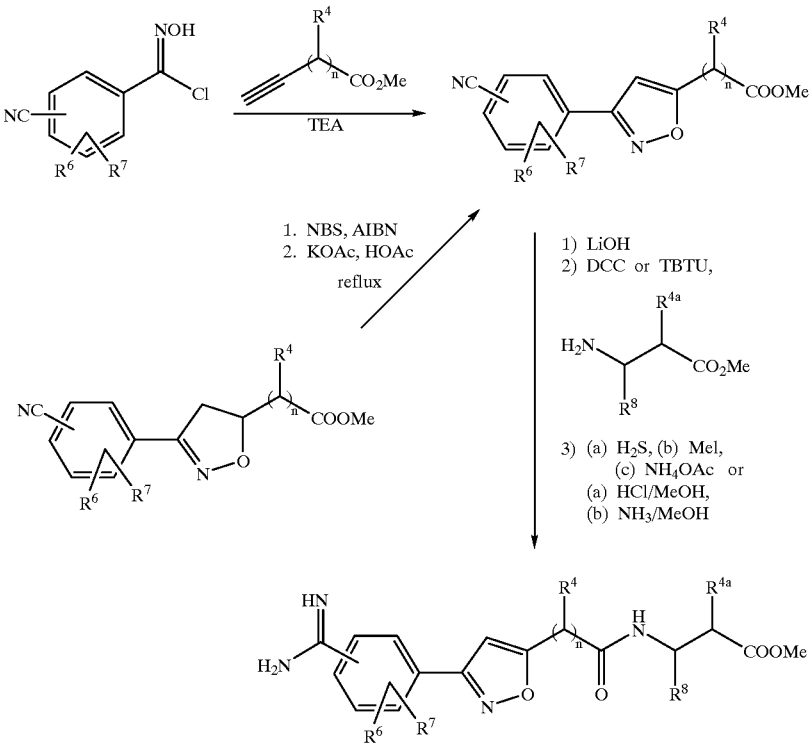

Compounds of Formula I wherein $R^1$ is $(R^2)(R^3)N(R^2N=)CN(R^2)$— and V is phenylene are prepared as illustrated in Scheme X. Cycloaddition of an appropriately N-protected aminophenylaldoxime with vinyl acetic acid, t-butyl ester, using the conditions described above provides t-butyl [3-(4-t-butyloxycarbonylaminophenyl)isoxazolin-5-yl]acetate. Hydrolysis of the ester with lithium hydroxide provides the free acid which can be coupled with a suitably substituted methyl 3-aminopropionate as previously described. After deprotection, the aniline is converted to the corresponding guanidine using the method described by Kim et al. (Tetrahedron Lett. 1993, 48, 7677). A final deprotection step to remove the BOC groups provides guanidino compounds of Formula I.

An example of the preparation of compounds of the second embodiment wherein $R^1$-U is a benzamide is illustrated in Scheme XI. Conversion of the 3-(4-cyanophenyl)isoxazolin-5-yl-β-aminoalaninyl esters to the amides can be accomplished by reaction of the nitrile with an appropriate alcohol under acidic conditions. (J. Med. Chem. 1991, 34, 851.) The substituted amides can be accessed by allowing the 3-(4-cyanophenyl)isoxazolin-5-yl-β-aminoalaninyl esters to react with an appropriate halogenated compound (Synthesis, 1978, 303. Saponification as described above gives the free acids.

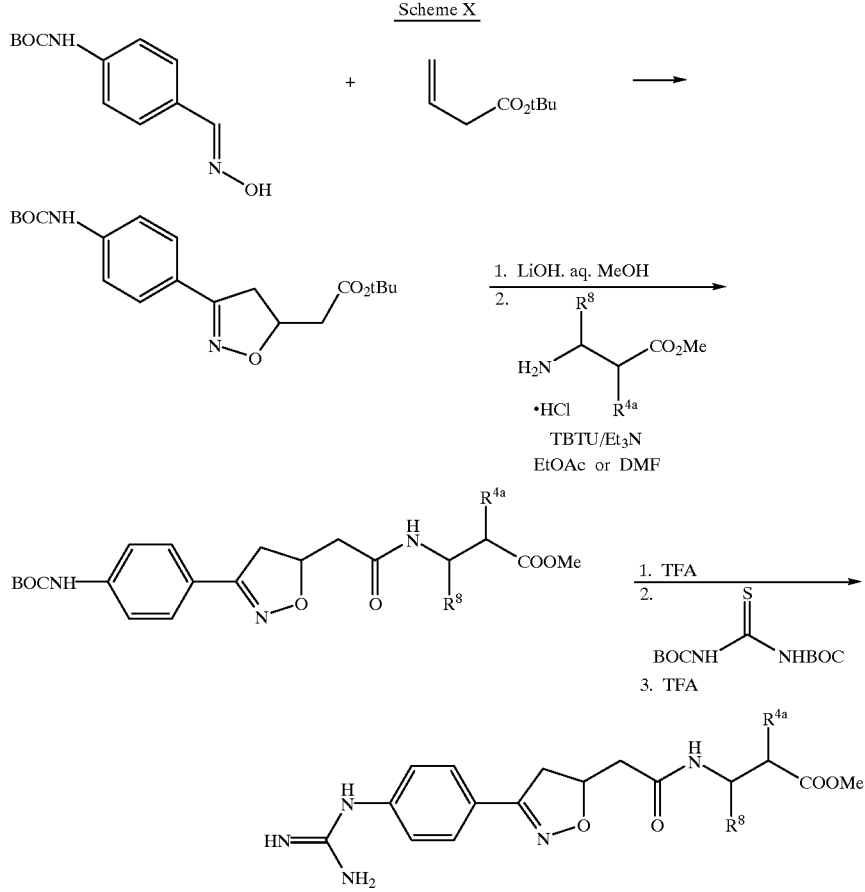

Scheme X

Scheme XI

A:

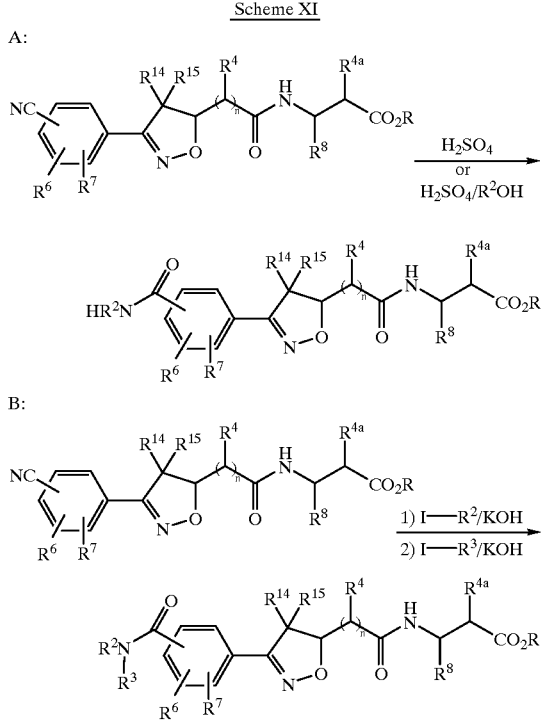

B:

The compounds of the invention where U is a pyridyl may be prepared by several methods. 2-Amino-4-pyridyl analogs can be easily accessed from readily available 2-bromo-4-pyridylcarboxaldehyde (Corey, E. J. et. al. Tetrahedron Lett. 1983, 32, 3291). The desired amino compound can be suitably introduced by displacement of the bromo substituent with a suitable ammonia source or alternatively with sodium azide followed by reduction via standard techniques known to those in the art. 2-Amidino-5-pyridyl analogs can be accessed from 2-bromo-5-pyridylcarboxaldehyde by displacement of the bromide at an appropriate stage in the synthesis with KCN. Conversion of the nitrile to the requisite amidine then affords the desired products. 6-Amino-3-pyridyl analogs can be easily accessed (according to the method described for the preparation of 2-amino-5-pyridyl analogs) from 6-chloro-3-pyridylcarboxaldehyde. This was obtained in part from 6-chloro-3-pyridylcarboxylic acid (Aldrich) via techinques known in the art. 6-Amidino-3-pyridyl analogs can be readily accessed from 6-chloro-3-pyridylcarboxaldehyde via techniques described for 2-amidino-5-pyridylanalogs.

The preparation of quinuclidine carboxaldehyde starting materials may be done as follows. 4-Cyanoquinuclidine prepared by the method of Kanai, T. et al, (Het., 1992, 34, 2137), can be converted to quinuclidine-4-carboxaldehyde by standard conditions and homologated by the method of (Tetrahedron Lett. 1987, 28, 1847) to the desired aldehyde. Conversion of the aldehyde to the oxime followed by chlorination to the chlorooxime should then afford the key quinuclidine chlorooxime which can then be further elaborated to the desired compounds.

The synthesis of spiro-fused isoxazolinyl amines of the third embodiment of the present invention is exemplified by the general protocol depicted in Scheme XII. Dipolar cycloaddition of a suitable oxime with a suitably protected methylenecycloamine, prepared by methods known in the literature (De Amici, M.; Frolund, B.; Hjeds, H.; Krogsgaard-Larson, P. Eur. J. Med. Chem. 1991, 26, 625; Mimura, M., et. al. Chem. Pharm. Bull. 1993, 41, 1971; Labouta, I. M.; Jacobsen, P.; Thorbek, P.; Krogsgaard-Larson, P.; Hjeds, H. Acta Chem. Scand., Ser. B 1982, 36, 669), yields the spirocyclic amine after deprotection. This amine can be functionalized with a serine beta-lactone (Arnold, L. D.; Kalantar, T. H.; Vederas, J. C. J. Am. Chem. Soc. 1985, 107, 7105) providing an optically active product. Alternatively, the amine can be reacted with a 3-iodo or 3-chloroalanine derivative (I: Marki, W.; Schwyzer, R. Helv. Chim. Acta 1975, 58, 1471; Cl: Bigge, C. F.; Wu J.-P.; Druumond, J. R. Tetrahedron Lett. 1991, 32, 7659; Benoiton, L. Can. J. Chem. 1968, 46, 1549) to give a racemic product.

Scheme XII

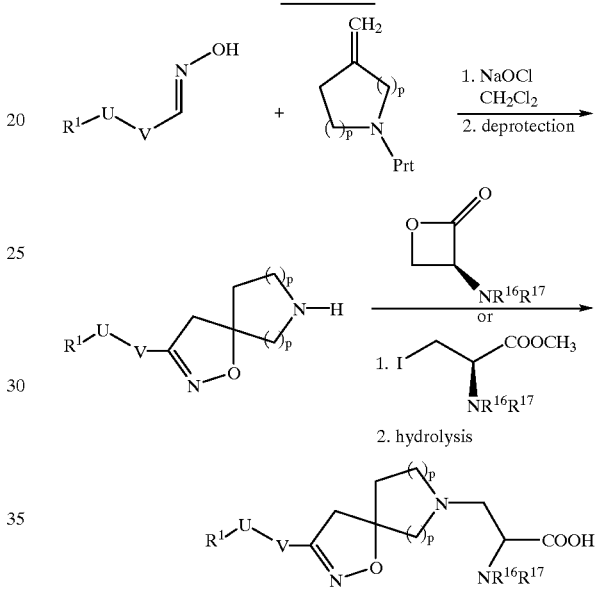

The cycloaddition can also be performed after the introduction of the propionyl side chain as shown in Scheme XIII.

Scheme XIII

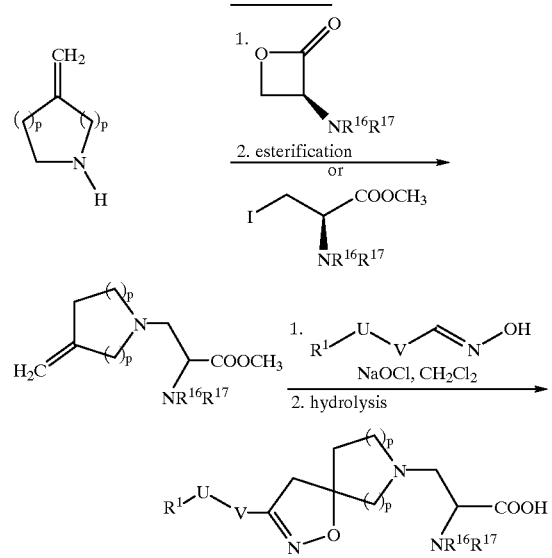

The compounds of Tables 12 and 13 were made using combinatorial synthetic methodology as shown in Scheme XIV. Thus, a resin was derivatized and to it was coupled the protected 2,3-diaminoproprionate. Following deprotection of $N^3$, the desired isoxazoline carboxylic acid was coupled to $N^3$. The final product was removed from once the terminal amine of the isoxazoline carboxylic acid was converted to its desired form.
Scheme XIV
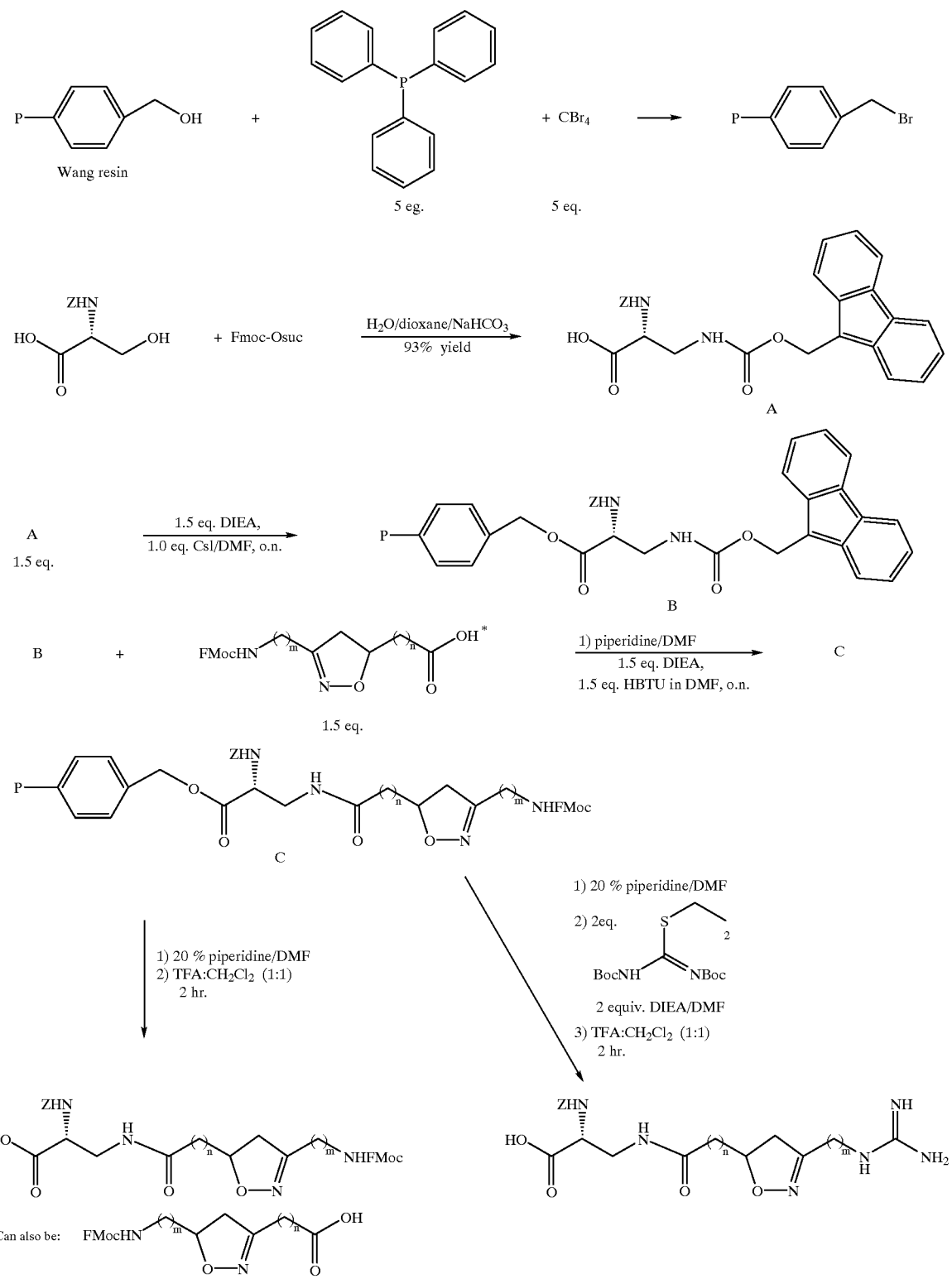

The compounds of this invention and their preparation can be further understood by the following procedures and examples, which exemplify but do not constitute a limit of their invention.

EXAMPLE 1

3-(4-[2-Piperidin-4-yl)ethoxy]-phenyl]-(5R,S)-isoxazolin-5-ylacetic Acid, Trifluoroacetic Acid Salt Part A. Preparation of 2-(4-N-t-Butyloxycarbonylpiperidinyl)ethanol This material was prepared from 4-piperidine-2-ethanol according to European Patent Application Publication Number 478363 A2.

Part B. 4-[2-(N-t-Butyloxycarbonylpiperidinyl-4-yl)ethoxy]benzaldehyde

To a solution of 2-(4-N-t-Butyloxycarbonylpiperidinyl)ethanol (7.71 g, 33.6 mmol), 4-hydroxybenzaldehyde (4.11 g, 33.6 mmol) and PPh$_3$ (8.82 g, 33.6 mmol) in THF (60 mL) at −20° C. was added a solution of DEAD (5.3 mL, 33.7 mmol) in THF (30 mL) over 2 hours. During the addition, a deep red solution resulted, which changed to a golden color upon warming to room temperature overnight (18 hours). At this time the solution was concentrated and redissolved in EtOAc. It was then washed with water, 0.1M HCl, 1M NaOH, sat. NaCl and dried (MgSO$_4$). Concentration gave a solid (~20 g), which was purified using flash chromatography (10–20–30–40–50% EtOAc/hexanes step gradient), affording 7.82 g (70%) of the desired ether after pumping to constant weight; mp 76.4–79.7° C.; $^1$H NMR (300 MHz, CDCl$_3$) δ 9.88 (s 1H), 7.83 (d, J=8.4 Hz, 2H), 6.98 (d, J=8.4 Hz, 2H), 4.10 (bd, J=12.8 Hz, 2H), 4.04 (t, J=6.6 Hz 2H), 2.69 (bt, 2H), 1.84 (m, 2H), 1.70 (bd J=14.3 Hz, 2H), 1.46 (s, 9H, overlapped with m, 2H), 1.10 (m, 2H).

Part C. 4-[2-(N-t-Butyloxycarbonylpiperidin-4-yl)ethoxy]benzaldoxime

To a solution of 4-[2-(N-t-butyloxycarbonylpiperidin-4-yl)ethoxy]benzaldehyde (3.16 g, 9.48 mmol) in MeOH (20 mL) was added hydroxylamine hydrochloride (1.27 g, 18.3 mmol) and 2M NaOH (7 mL, 14 mmol). The resulting suspension was stirred overnight at room temperature (18 hours). The mixture was brought to pH 4 using 1M HCl, followed by filtration and water wash. The crystals were dried under vacuum over P$_2$O$_5$, affording 2.88 g (87%); mp: 114.4–116.1° C.; $^1$H NMR (300 MHz, CDCl$_3$) δ 8.09 (s, 2H), 7.51 (d, J=8.8 Hz, 2H), 6.89 (d, J=8.8 Hz, 2H), 4.10 (b, 2H), 4.03 (t, J=6.2 Hz 2H), 2.71 (bt, 2H), 1.73 (m, 4H), 1.46 (s, 9H), 1.19 (m, 2H).

Part D. 4-[2-(N-t-Butyloxycarbonylpiperidin-4-yl)ethoxy]benzaldoximinoyl Chloride To a solution of 4-[2-(N-t-butyloxycarbonylpiperidin-4-yl)ethoxy]benzaldoxime (955 mg, 2.74 mmol) in DMF (5 mL) was added NCS (366 mg, 2.74 mmol) in 3 portions. After 3 hours, the solution was diluted with EtOAc and washed with water, sat. NaCl, dried (MgSO$_4$) and concentrated. The resulting solid was crystallized from ether/hexanes to give 548 mg (52%) of the oximinoyl chloride; mp. 119.3–119.9° C.; $^1$H NMR (300 MHz, CDCl$_3$) δ 8.37 (bs 1H), 7.77 (d, J=8.8 Hz, 2H), 6.88 (d, J=8.8 Hz, 2H), 4.12 (bd, J=13.2 Hz, 2H), 4.04 (t, J=6.2 Hz 2H), 2.72 (bt, J=12.1 Hz, 2H), 1.70 (m, 5H), 1.46 (s, 9H), 1.10 (m, 2H).

Part E. Methyl 3-[4-{2-(N-t-Butyloxycarbonylpiperidin-4-yl)ethoxy}phenyl]-(5R, S)-isoxazolin-5-ylacetate To a solution of 4-[2-(N-t-butyloxycarbonylpiperidin-4-yl)ethoxy]benzaldoximinoyl chloride (400 mg, 1.045 mmol) and methyl 3-butenoate (200 mg, 2.00 mmol) was added TEA (0.15 mL, 1.1 mmol). The resulting suspension was heated at reflux for 5 hours, cooled to room temperature and diluted with EtOAc. It was then washed with 0.1M HCl, water, sat. NaCl, dried (MgSO$_4$) and concentrated. The resulting solid was crystallized from DCM/hexanes to give 357 mg (77%) of the isoxazoline; mp: 139.1–140.9° C.; $^1$H NMR (300 MHz, CDCl$_3$) δ 7.59 (d, J=8.8 Hz, 2H), 6.90 (d, J=8.8 Hz, 2H), 5.08 (m, 1H), 4.10 (bd, J=13.2 Hz, 2H), 4.04 (t, J=5.9 Hz 2H), 3.73 (s, 3H), 3.53 (dd, J=16.5, 10.1 Hz, 1H), 3.10 (dd, J=16.8, 7.1 Hz, 1H), 2.88 (dd, J=16.1, 5.9 Hz, 1H), 2.71 (bt, J=12.8 Hz, 2H), 2.64 (dd, J=15.8, 7.7 Hz, 1H), 1.72 (m, 5H), 1.46 (s, 9H), 1.08 (m, 2H).

Part F. 3-[4-{2-(N-t-Butyloxycarbonylpiperidin-4-yl)ethoxy}phenyl]-(5R,S)-isoxazolin-5-ylacetic Acid To a solution of methyl 3-[4-{2-(N-t-butyloxycarbonylpiperidin-4-yl)ethoxy}phenyl]-(5R,S)-isoxazolin-5-ylacetate (47 mg, 0.105 mmol) in THF (2 mL) was added 0.5M LiOH (1 mL, 0.5 mmol). The reaction was stirred at room temperature for 5 hours, then was acidified to pH 3 using 0.1M HCl. The mixture was washed with DCM and the combined organic fraction dried (MgSO$_4$) and concentrated. The resulting solid was crystallized from EtOAc/hexanes to give 34 mg (74%) of the carboxylic acid; mp: 169.1–170.6° C.; $^1$H NMR (300 MHz, CDCl$_3$) δ 7.60 (d, J=8.8 Hz, 2H), 6.91 (d, J=8.8 Hz, 2H), 5.10 (m, 1H), 4.08 (bd, 2H, overlapped with t, J=5.9 Hz 2H), 3.55 (dd, J=16.5, 10.2 Hz, 1H), 3.11 (dd, J=16.8, 7.0 Hz, 1H), 2.93 (dd, J=16.1, 6.2 Hz, 1H), 2.71 (m, 3H), 2.00 (m, 2H), 1.72 (m, 5H), 1.46 (s, 9H).

Part G. 3-(4-[2-(Piperidin-4-yl)ethoxylphenyl]-(5R,S)-isoxazolin-5-ylacetic Acid, Trifluoroacetic Acid Salt To a solution of 3-[4-{2-(N-t-Butyloxycarbonylpiperidin-4-yl)ethoxy}phenyl]-(5R,S)-isoxazolin-5-ylacetic acid (53 mg, 0.12 nmol) in DCM (2 mL) was added TFA (1 mL, 13 mmol). After 1.5 hours, the product was crystallized by the addition of ether, affording 33 mg (60%) of the amino acid; mp: 142.4–143.1° C.; $^1$H NMR (300 MHz, CDCl$_3$) δ 7.59 (dd, J=8.8, 2.6 Hz, 2H), 6.96 (dd, J=8.8, 2.6 Hz, 2H), 5.03 (m, 1H), 4.10 (m, 2H), 3.55 (ddd, J=16.8, 10.3, 2.2.Hz, 1H), 3.38 (bd, J=12.4 Hz, 2H), 3.16 (ddd, J=17.2, 7.7, 2.2 Hz, 1H), 2.98 (bt, J=13.2 Hz, 2H), 2.69 (m, 2H), 2.01 (bd, J=14.3 Hz, 2H), 1.91 (m, 1H), 1.80 (m, 2H), 1.46 (m, 2H).

EXAMPLE 4

2-[3-(4-[2-(Piperidin-4-yl)ethoxy]phenyl)isoxazolin-5-yl]-2-(S)-(benzyloxycarbonylamino)acetate, Trifluoroacetic Acid Salt Part A. Benzyl 2-(S)-[[(benzyloxy)carbonyl]amino]-3-butenoate This material was prepared from N-Cbz-l-glutamic acid α-benzyl ester according to Krol, et al. (*J. Org. Chem*, 1991, 728).

Part B. Benzyl (2S)-(5R,S)-[3-[4-{(2-N-t-Butyloxycarbonylpiperidin-4-yl)ethoxy}phenyl]isoxazolin-5-yl{[(benzyloxy)carbonyl]amino}]acetate To a solution of 4-[(2-N-t-butyloxycarbonylpiperidin-4-yl)ethoxy]benzaldoxime (852 mg, 2.44 mmol) and benzyl l-2-[[(benzyloxy)carbonyl]amino]-3-butenoate (612 mg, 1.88 mmol) in DCM (10 mL) was added 5% NaOCl (common household bleach, 4 mL, 2.8 mmol). The mixture was rapidly stirred at room temperature for 22 hours, after which time it was diluted with water and DCM. After separation of the layers, the aqueous was washed with DCM (3x). The combined organic extracts were dried (MgSO$_4$) and concentrated in vacuo, giving 1.4 g. Purification using flash chromatography (10% EtOAc/hexanes—30% EtOAc/hexanes) then afforded 886 mg (70%) of an oily product as a 2.5:1 mixture of the erythro and threo isomers; $^1$H NMR (400 MHz, CDCl$_3$) δ 7.50 (m, 2H), 7.34 (m, 5H), 7.23 (m, 5H), 6.87 (d, J=8.8 Hz, 2H), 5.47 (bd, 1H), 5.12 (m, 5H), 4.60 (m, 1H), 4.07 (m, overlapped with 4.03 (t, J=6.1 Hz, 4H) , 3.36 (m, 2H), 2.71 (bt, J=12.7 Hz, 2H), 1.70 (m, 5H), 1.45 (s, 9H), 1.18 (m, 2H); Anal. Calc. for $C_{38}H_{45}N_3O_8$: C, 67.93; H, 6.76; N, 6.26. Found: C, 67.95; H, 6.77; N, 6.17.

Part C. (2S)-(5R,S)-[3-[4-{(2-N-t-Butyloxycarbonylpiperidin-4-yl)ethoxy}phenyl]isoxazolin-5-yl{[(benzyloxy)carbonyl]amino}]acetic Acid A solution of benzyl (2S)-(5R,S)-[3-[4-{(2-N-t-butyloxycarbonylpiperidin-4-yl)ethoxy}phenyl]isoxazolin-5-yl{[(benzyl-oxy)carbonyl]amino}]acetate (875 mg, 1.302 mmol) in THF (5 mL) was saponified over 5 hours using 0.5M LiOH (3.5 mL) according to Example 1, Part F. To the crude product was added methanol, causing crystallization of one of the diastereomers. Filtration and pumping to constant weight gave 295 mg (39%); mp: 216.1° C.; $^1$H NMR (400 MHz, DMSO-$d_6$, 80° C.) δ 7.50 (d, J=8.9 Hz, 2H), 7.23 (s, 5H), 6.96 (d, J=8.9 Hz, 2H), 6.17 (bs, 1H), 4.99 (m, 3H), 4.07 (t, J=6.1 Hz, 2H), 3.90 (m, 3H), 3.35 (d, J=9.3 Hz, 2H), 2.72 (bt, J=12.4 Hz, 2H), 1.67 (m, 5H), 1.39 (s, 9H), 1.08 (m, 2H). The filtrate was concentrated in vacuo and pumped until constant weight was achieved, giving 200 mg (26%) of the carboxylic acids as a mixture of erythro- and threo-isomers; TLC (silica gel 60, 20% MeOH/CHCl$_3$) $R_f$=0.23, Mass Spectrum (ESI, e/z, relative abundance) 582 (M+H)$^+$, 32%; 526 (M−$C_4H_9$+$H_2$)$^+$, 100%; 482 (M−Boc+$H_2$)$^+$, 91%).

Part D. (2S)-(5R,S)-[3-[4-{(2-Piperidin-4-yl)ethoxyl}phenyl]isoxazolin-5-yl{[(benzyloxy)carbonyl]amino}]acetic Acid (isomer A)

(2S)-(5R,S)-[3-[4-{(2-N-t-Butyloxycarbonylpiperidin-4-yl)ethoxy}phenyl]isoxazolin-5-yl{[(benzyloxy)carbonyl]amino}]acetic acid (23 mg, 0.039 mmol) was Boc-deprotected using 33% TFA/DCM according to Example 1, Part G, giving 15 mg (79%); mp: 302° C. (dec); $^1$H NMR (400 MHz, DMSO-$d_6$, 60° C.) δ 7.57 (d, J=8.8 Hz, 2H), 7.30 (s, 5H), 6.99 (d, J=8.8 Hz, 2H), 5.05 (s, 2H, coincident with m, 1H), 4.35 (d, J=4.9 Hz,, 1H), 4.09 (t, J=6.1 Hz, 2H), 3.52 (dd, J=17.3, 10.7 Hz, 1H), 3.26 (m, 3H), 2.88 (dt, J=12.7, 2.7 Hz, 2H), 1.88 (bd, J=14.4 Hz, 2H), 1.80 (m, 1H), 1.72 (m, 2H), 1.38 (m, 2H).

Part D'. (2S)-(5R,S)-[3-[4-{(2-Piperidin-4-yl)ethoxy}phenyl]isoxazolin-5-yl{[(benzyloxy)carbonyl]amino}]acetic Acid, Trifluoroacetic Acid Salt (isomer B)

(2S)-(5R,S)-[3-[4-{(2-N-t-Butyloxycarbonylpiperidin-4-yl)ethoxy}phenyl]isoxazolin-5-yl{[(benzyloxy)carbonyl]amino}]acetic acid (177 mg, 0.304 nmol) was Boc-deprotected using 33% TFA/DCM according to Example 1, Part G, giving 3 mg (2%) of the TFA salt; mp: >400° C.; $^1$H NMR (400 MHz, DMSO-$d_6$, 60° C.) δ 8.48 (bs,0.5H) , 8.15 (bs, 0.5H), 7.55 (d, J=8.9 Hz, 2H), 7.30 (m, 5H), 6.97 (d, J=8.9 Hz, 2H), 5.05 (s, 2H), 4.96 (m, 1H), 4.33 (m, 1H) , 4.07 (t, J=6.3 Hz, 2H) , 3.38 (m, 2H) , 3.26 (bd, J=12.0 Hz, 2H), 2.87 (m, 2H), 1.86 (bd, J=14.2 Hz, 2H), 1.78 (m, 1H), 1.70 (apparent q, J=6.3 Hz, 2H), 1.36 (bq, J=13.2 Hz, 2H).

EXAMPLE 6

3-(3-[4- (Piperidin-4-ylmethoxy)phenyl]-(5R,S)-isoxazolin-5-yl)propionic Acid, Trifluoroacetic Acid Salt Part A. Ethyl N-t-Butyloxycarbonylpiperidine-4-carboxylate To a stirred solution of ethyl isonipecotate (20.01 g, 0.1273 mol) in EtOAc (100 mL) at 0° C. was added dropwise a solution of Boc$_2$O (27.76 g, 0.1272 mol) in EtOAc (50 mL). The mixture was allowed to warm to room temperature overnight. After 20 hours, the mixture was washed with water, 0.1M HCl, sat. NaHCO$_3$, sat. NaCl and dried (MgSO$_4$). Concentration and pumping under vacuum to constant weight gave 32.54 g (99%) of the desired carbamate as a mobile oil; $^1$H NMR (300 MHz, CDCl$_3$) δ 4.13 (q, J=7.0 Hz, 2H), 4.03 (dm, J=13.6 Hz 2H), 2.81 (m, 2H), 2.41 (m, 1H), 1.86 (dm, J=13.6 Hz, 2H), 1.62 (m, 2H), 1.44 (s, 9H), 1.24 (t, J=7.0 Hz, 3H).

Part B. N-t-Butyloxycarbonylpiperidin-4-ylmethanol

To a solution of ethyl N-t-butyloxycarbonylpiperidine-4-carboxylate (32.34 g, 0.1257 mol) in THF (100 mL) at 0° C. was added dropwise 1M LAH in THF (87.9 mL, 0.0879 mol). After 2 hours, excess hydride was quenched by the addition of water (3.2 mL), 2M NaOH (3.2 mL) and water (10 mL). The mixture was filtered, washed with EtOAc and the filtrate washed with water, sat. NaCl, dried (MgSO$_4$) and concentrated. Pumping to constant weight gave 22.72 g (84%); mp: 79.2–81.1° C.; $^1$H NMR (300 MHz, CDCl$_3$) δ 4.12 (bd, J=12.8 Hz 2H), 3.49 (d, J=6.2 Hz, 2H), 2.68 (dt, J=13.2, 1.8 Hz, 2H), 1.69 (m, 3H), 1.44 (s, 9H, overlapped with m, 1H), 1.14 (m, 2H).

Part C. 4-(N-t-Butyloxycarbonylpiperidin-4-ylmethoxy)-benzaldehyde

To N-t-butyloxycarbonylpiperidin-4-ylmethanol (7.87 g, 36.5 mmol), p-hydroxybenzaldehyde (4.46 g, 36.5 mmol) and PPh$_3$ (9.59 g, 36.5 mmol) in THF (100 mL) at −20° C. was added DEAD (5.75 mL, 36.5 mmol) in THF (50 mL) according to Example 1, Part B, affording 8.14 g (70%); mp: 115.6–116.8° C.; $^1$H NMR (300 MHz, CDCl$_3$) δ 9.86 (s, 1H), 7.81 (d, J=8.8 Hz, 2H), 6.96 (d, J=8.8 Hz, 2H), 4.15 (bd, J=13.2 Hz 2H), 3.87 (d, J=6.6 Hz, 2H), 2.74 (dt, J=12.4, 1.8 Hz, 2H), 1.97 (m, 1H), 1.81 (bd, J=12.8 Hz, 2H), 1.45 (s, 9H), 1.27 (dq, J=12.1, 4.0 Hz, 2H).

Part D. 4-(N-t-Butyloxycarbonylpiperidin-4-ylmethoxy)-benzaldoxime

A mixture of 4-(N-t-butyloxycarbonylpiperidin-4-ylmethoxy)benzaldehyde (3.16 g, 9.89 mmol) and hydroxylamine hydrochloride (1.27 g, 18.3 mmol) in 9:1 MeOH/pyridine (30 mL) was heated at reflux for 18 hours. The mixture was cooled to room temperature and concentrated to dryness. The residue was dissolved in EtOAc and washed with 0.1M HCl (3x), water, sat. CuSO$_4$ (2x), water, sat. NaCl, dried (MgSO$_4$) and concentrated, giving 3.19 g (96%) of the oxime; mp: 140.1–141.8° C.; $^1$H NMR (300 MHz, CDCl$_3$) δ 8.07 (s, 1H), 7.48 (d, J=8.8 Hz, 2H), 6.86 (d, J=8.8 Hz, 2H), 4.14 (bs, 2H), 3.80 (d, J=6.2 Hz, 2H), 2.71 (bt, J=12.4 Hz, 2H), 1.95 (m, 1H), 1.80 (bd, J=12.4 Hz, 2H), 1.45 (s, 9H), 1.26 (m, 2H).

Part E. 4-(N-t-Butyloxycarbonylpiperidin-4-ylmethoxy)-benzaldoximinoyl Chloride 4-(N-t-Butyloxycarbonylpiperidin-4-ylmethoxy)-benzaldoxime (3.19 g, 9.54 mmol) in DMF (10 mL) was reacted with NCS (1.27 g, 9.51 mmol) for 18 hours according to Example 1, Part D to afford the hydroximinoyl chloride (1.17 g, 33%); mp: 178.0–179.8° C.; $^1$H NMR (300 MHz, CDCl$_3$) δ 7.75 (d, J=9.0 Hz, 2H), 6.86 (d, J=9.0 Hz, 2H), 4.17 (bd, J=12.4 Hz, 2H), 3.80 (d, J=6.2 Hz, 2H), 2.74 (dt, J=12.8, 1.8 Hz, 2H), 1.95 (m, 1H), 1.81 (bd, J=12.1 Hz, 2H), 1.46 (s, 9H), 1.27 (dq, J=12.5, 4.0 Hz, 2H).

Part F. Methyl 3-(3-[4-(N-t-Butyloxycarbonylpiperidin-4-ylmethoxy)phenyl]-(5R,S)-isoxazolin-5-yl)propionate 4-(N-t-Butyloxycarbonylpiperidin-4-ylmethoxy)benzaldoximinoyl chloride (738 mg, 2.00 mmol), methyl 4-pentenoate (230 mg, 2.02 mmol) and TEA (0.28 mL, 2.0 mmol) were heated at reflux for 1 hour according to Example 1, Part E. Crystallization from ether/hexanes afforded 537 mg (60%). mp: 97.9–99.9° C.; $^1$H NMR (300 MHz, CDCl$_3$) δ 7.57 (d, J=9.0 Hz, 2H), 6.87 (d, J=9.0

Hz,2H), 4.74 (m, 1H), 4.15 (bd, J=13.2 Hz, 2H), 3.81 (d, J=6.2 Hz, 2H), 3.67 (s, 3H), 3.40 (dd, J=16.5, 10.2 Hz, 1H), 2.95 (dd, J=16.5, 7.3 Hz, 1H), 2.73 (dt, J=13.2, 1.1 Hz, 2H), 2.52 (t, J=7.3 Hz, 2H), 1.98 (q, J=7.0 Hz, 2H, overlapping m, 1H), 1.81 (bd, J=12.8 Hz, 2H), 1.45 (s, 9H), 1.26 (dq, J=12.4, 3.7 Hz, 2H).

Part G. 3-(3-[4-(N-t-Butyloxycarbonylpiperidin-4-ylmethoxy)phenyl]-(5R,S)-isoxazolin-5-yl)propionic Acid Methyl 3-(3-[4-(N-t-butyloxycarbonylpiperidin-4-ylmethoxy)phenyl]-(5R,S)-isoxazolin-5-yl)propionate (250 mg, 0.560 mmol) was saponified using 0.5M LiOH (2 mL, 1 mmol) in THF (2 mL). The reaction was stirred at room temperature for 3 hours, according to Example 1, Part F. The resulting solid was crystallized from DCM/hexanes to give 163 mg (67%) of the carboxylic acid; mp: 146.5–147.7° C.; $^1$H NMR (300 MHz, CDCl$_3$) δ 7.57 (d, J=8.8 Hz, 2H), 6.88 (d, J=8.8 Hz, 2H), 4.75 (m, 1H), 3.81 (d, J=6.2 Hz, 2H), 3.41 (dd, J=16.5, 10.3 Hz, 1H), 2.95 (dd, J=16.5, 7.3 Hz, 1H), 2.75 (bt, J=12.4 Hz, 2H), 2.57 (t, J=7.3 Hz, 2H), 1.97 (m, 3H), 1.81 (bd, J=12.1 Hz, 2H), 1.45 (s, 9H), 1.24 (m, 2H).

Part H. 3-(3-[4-(Piperidin-4-ylmethoxy)phenyl]-(5R,S)-isoxazolin-5-yl)propionic Acid, Trifluoroacetic Acid Salt 3-(3-[4-(N-t-Butyloxycarbonylpiperidin-4-ylmethoxy)phenyl]-(5R,S)-isoxazolin-5-yl)propionic acid (103 mg, 0.238 mmol) was Boc-deprotected using 33% TFA/DCM according to Example 1, Part G, giving 88 mg (83%) of the TFA salt; mp: 179.1–181.8° C.; $^1$H NMR (400 MHz, MeOH-d$_4$) δ 7.60 (d, J=9.0 Hz, 2H), 6.97 (d, J=9.0 Hz, 2H), 4.73 (m, 1H), 3.94 (d, J=6.1 Hz, 2H), 3.46 (m, 3H), 3.06 (m, 3H), 2.45 (dt, J=7.3, 1.2 Hz, 2H), 2.16 (m, 1H), 2.08 (bd, J=15.4 Hz, 2H), 1.94 (q, J=6.6 Hz, 1H), 1.64 (dq, J=14.2, 4.2 Hz, 2H).

EXAMPLE 7

3-[4-(Piperidin-4-ylmethoxy)phenyl]-(5R,S)-isoxazolin-5-ylacetic Acid, Trifluoroacetic Acid Salt Part A. Methyl 3-[4-(N-t-Butyloxycarbonylpiperidin-4-ylmethoxy)phenyl]-(5R,S)-isoxazolin-5-ylacetate 4-(N-t-Butyloxycarbonylpiperidin-4-ylmethoxy) benzaldoximinoyl chloride (412 mg, 1.12 mmol), methyl 3-butenoate (200 mg, 2.00 mmol) and TEA (0.18 mL, 1.3 mmol) were heated at reflux for 2 hours according to Example 1, Part E. Crystallization from chloroform/cyclohexane afforded 329 mg (68%). mp: 97.9–99.9° C.; $^1$H NMR (300 MHz, CDCl$_3$) δ 7.58 (d, J=8.8 Hz, 2H), 6.88 (d, J=8.8 Hz,2H), 5.04 (m, 1H), 4.15 (bd, J=13.2 Hz, 2H), 3.81 (d, J=6.2 Hz, 2H), 3.71 (s, 3H), 3.54 (dd, J=16.8, 10.3 Hz, 1H), 3.08 (dd, J=16.8, 7.3 Hz, 1H), 2.86 (dd, J=16.1, 5.9 Hz, 1H), 2.73 (dt, J=12.8, 1.8 Hz, 2H), 2.62 (dd, J=15.8, 7.7 Hz, 1H), 1.95 (m, 1H), 1.81 (bd, J=13.2 Hz, 2H), 1.45 (s, 9H), 1.25 (dq, J=12.8, 4.4 Hz, 2H).

Part B. 3-[4-(N-t-Butyloxycarbonylpiperidin-4-ylmethoxy)phenyl]-(5R,S)-isoxazolin-5-ylacetic Acid Methyl 3-[4-(N-t-butyloxycarbonylpiperidin-4-ylmethoxy)phenyl]-(5R,S)-isoxazolin-5-ylacetate (329 mg, 0.762 mmol) was saponified using 0.5M LiOH (3 mL, 1.5 mmol) in THF (5 mL). The reaction was stirred at reflux for 4 hours, according to Example 1, Part F to give 72 mg (22%) of the carboxylic acid; mp: 164.0–164.8° C.; $^1$H NMR (300 MHz, CDCl$_3$) δ 7.58 (d, J=8.8 Hz, 2H), 6.88 (d, J=8.8 Hz, 2H), 5.07 (m, 1H), 4.15 (bd, J=13.6 Hz, 2H), 3.82 (d, J=6.2 Hz, 2H), 3.53 (dd, J=16.8, 10.3 Hz, 1H), 3.10 (dd, J=16.8, 7.0 Hz, 1H), 2.91 (dd, J=16.1, 5.9 Hz, 1H), 2.73 (dt, J=14.6, 1.8 Hz, 2H), 2.68 (dd, J=16.1, 7.3 Hz, 1H), 1.97 (m, 1H), 1.81 (bd, J=13.2 Hz, 2H), 1.45 (s, 9H), 1.26 (dq, J=12.8, 4.4 Hz, 2H).

Part C. 3-[4-(Piperidin-4-ylmethoxy)phenyl]-(5R,S)-isoxazolin-5-ylacetic Acid, Trifluoroacetic Acid Salt 3-[4-(N-t-Butyloxycarbonylpiperidin-4-ylmethoxy)phenyl]-(5R,S)-isoxazolin-5-ylacetic acid (72 mg, 0.172 mmol) was Boc-deprotected using 33% TFA/DCM according to Example 1, Part G, giving 64 mg (94%) of the TFA salt; mp: 220° C. (dec); $^1$H NMR (300 MHz, MeOH-d$_4$) δ 7.61 (d, J=9.2 Hz, 2H), 6.97 (d, J=9.2 Hz, 2H), 5.04 (m, 1H), 3.95 (d, J=5.9 Hz, 2H), 3.56 (dd, J=17.2, 10.2 Hz, 1H), 3.45 (bd, J=12.8 Hz, 2H), 3.18 (dd, J=17.2, 7.3 Hz, 1H), 3.04 (dt, J=10.2, 2.9 Hz, 2H), 2.69 (m, 2H), 2.18 (m, 1H), 2.08 (bd, J=14.6 Hz, 2H) 1.63 (bq, 2H).

EXAMPLE 8

3-[4-(2-Piperidin-4-yl)ethoxyphenyl]-(5R,S)-isoxazolin-5-ylpropionic Acid, Trifluoroacetic Acid Salt This material was prepared analogously to Example 1, giving the desired material; mp: 114.8–115.7° C.; $^1$H NMR (300 MHz, CD$_3$OD) δ 7.59 (d, J=8.4 Hz, 2H), 6.95 (d, J=8.4 Hz, 2H), 4.72 (m, 1H), 4.07 (t, J=5.9 Hz, 2H), 3.47 (dd, J=16.8. 10.2 Hz, 1H), 3.37 (dd, J=16.8, 7.7 Hz, 1H), 2.98 (m, 2H), 2.44 (t, J=7.3 Hz, 2H), 2.01 (bd, J=15.0 Hz, 2H), 1.93 (m, 3H), 1.80 (m, 2H), 1.44 (m, 2H).

EXAMPLE 9 erythro- and-threo-3-[3-[4-[(piperidin-4-yl)methoxy]phenyl]isoxazolin-5-yl{[butanesulfonyl]amino}propionate, Trifluoroacetic Acid Salt Part A. Dicyclohexylammonium d,l-2-[(Butanesulfonyl)-aminol-4-pentenoic acid, To a suspension of d,l-2-amino-4-pentenoic acid (2.54 g, 22.06 mmol) in acetonitrile (35 mL) was added BSTFA (7.3 mL, 27.5 mmol). The suspension was heated at 55° C. for 2 hours, after which time a golden yellow solution resulted. To this solution was added pyridine (2.2 mL, 27.2 mmol) and n-butanesulfonyl chloride (3.0 mL, 23.1 mmol). The mixture was heated at 70° C. for 20 hours, then cooled to room temperature. Concentration in vacuo afforded a brown oil, to which was added 15% KHSO$_4$ (5 mL). The mixture was stirred for 1 hour and shaken with EtOAc (3x). The combined organic extracts were washed with sat. NaCl, dried (MgSO$_4$), concentrated and the resulting oil dissolved in ether (5 mL). To this solution was added DCHA (4.38 mL, 22.0 mmol), causing immediate precipitation of the dicyclohexylammonium salt. The solid was collected by filtration and pumped to constant weight, giving 8.42 g (92%); mp: 207.1–208.6° C.; $^1$H NMR (400 MHz, MeOH-d$_4$) δ 5.84 (m, 1H), 5.09 (dm, J=17.1.Hz, 1H), 5.04 (dm, J=10.2 Hz, 1H), 3.80 (dd, J=7.1, 5.1 Hz, 1H), 3.18 (m, 2H), 3.02 (m, 2H), 2.49 (m, 2H), 2.06 (m, 4H), 1.78 (m, 8H), 1.55 (m, 12H), 0.94 (t, J=7.3 Hz).

Part B. Methyl d,l-2-[(Butanesulfonyl)amino]-4-pentenoate

To a solution of dicyclohexylammonium d,l-2-[(butanesulfonyl)amino]-4-pentenoate (8.36 g, 20.07 mmol) in MeOH (50 mL) was added HCl-saturated MeOH (50 mL). The resulting suspension was stirred at room temperature for 18 hours, diluted with ether, and filtered. Concentration of the filtrate in vacuo was followed by the addition of ether, a second filtration, and washing of the filtrate with 0.1M HCl, sat. NaHCO$_3$, sat. NaCl. The solution was dried over anhydrous MgSO$_4$, concentrated and placed under vacuum until constant weight to give 4.49 g (90%) of the desired ester as a light brown oil; $^1$H NMR (300 MHz, CDCl$_3$) δ 5.68 (m, 1H), 5.19 (bd, J=1.5 Hz, 1H), 5.15 (m, 1H), 4.78 (bd, J=8.4 Hz, 1H), 4.20 (dt, J=8.8, 5.8 Hz, 1H), 3.77 (s, 3H), 2.99 (m, 2H), 2.54,(t, J=6.6 Hz, 2H), 1.76 (m, 2H), 1.42 (sextuplet, J=7.3 Hz, 2H), 0.93 (t, J=7.3 Hz, 3H)

Part C. Methyl erythro- and-threo-3-(3-[4-{(Butyloxycarbonylpiperidin-4-yl)methoxy}phenyl]isoxazolin-5-yl{(butanesulfonyl]amino})propionate To a solution of 4-[(N-t-butyloxycarbonylpiperidin-4-yl)methoxy]benzaldoxime (2.680 g, 8.01 mmol), methyl d,l-2-[(butanesulfonyl)amino]-4-pentenoate (2.000 g, 8.02 mmol) and TEA (0.11 mL, 0.79 mmol) in THF (10 mL) was added a 5% solution of NaOCl (common household bleach, 15 mL, 10.5 mmol). The resulting mixture was rapidly stirred at room temperature for 20 hours. The mixture was diluted with EtOAc and water and the layers were separated. The aqueous portion was washed with EtOAc, and the combined organic fraction washed with sat. NaCl and dried over $MgSO_4$. Concentration in vacuo afforded a light brown oil (4.8 g), which was purified using flash chromatography (0–50% EtOAc/hexanes in 5 steps), giving four components. The least polar of these materials (fractions 8–11) was determined by $^1$H NMR to be the starting olefin (1.520 g, 76%). The next component isolated in order of increasing polarity (fractions 12–15) was determined by $^1$H NMR to be the starting oxime (1.423 g, 53%). The next component off of the column (fraction 20) was determined to be the faster of the two diastereomers (317 mg). This material had co-eluted with an impurity having a $^1$H NMR profile similar to the starting oxime and appeared to be approximately 50% pure. The most polar component isolated (fractions 22–25) was assigned as the second diastereomer (395 mg, 8%); mp:.127.5–129.3° C.; $^1$H NMR (300 MHz, $CDCl_3$) δ 7.56 (d, J=8.6 Hz, 2H), 6.87 (d, J=8.6 Hz, 2H), 5.25 (d, J=9.5 Hz, 1H), 4.87 (m, 1H), 4.35 (dt, J=9.2, 3.7 Hz, 1H), 4.15 (bs, 2H), 3.81, (d, J=6.2 Hz, 2H), 3.78 (s, 3H), 3.49 (dd, J=16.5, 10.3 Hz, 1H), 3.05 (t, J=7.7 Hz, 2H), 2.97 (dd, J=16.5, 7.0 Hz, 1H), 2.73 (bt, J=12.1 Hz, 2H), 2.21 (m, 1H), 1.94 (m, 2H), 1.82 (m, 4H), 1.45 (s, 9H), 1.24 (m, 3H), 0.92 (t, J=7.3 Hz, 3H).

Part D. 3-(3- [4-{(Butyloxycarbonylpiperidin-4-yl)methoxy}phenyl]isoxazolin-5-yl{[butanesulfonyl]amino})-propionic Acid (More Polar Diastereomer)

A solution of methyl 3-(3-[4-{(butyloxycarbonylpiperidin-4-yl)methoxy}phenyl]isoxazolin-5-yl{[butanesulfonyl]amino})propionate more polar diastereomer (200 mg, 0.344 mmol) in THF (1 mL) was saponified using 0.5M LiOH (1 mL, 0.5 mmol) over 4 hours as per Example 1, Part F. The crude carboxylic acid was crystallized from EtOAc/hexanes, affording 77 mg (39%) of the desired material; mp: 137.3–139.0° C.; $^1$H NMR (300 MHz, $CDCl_3$) δ 7.55 (d, J=8.8 Hz, 2H), 6.87 (d, J=8.8 Hz, 2H), 5.45 (d, J=9.5 Hz, 1H), 4.92 (m, 1H), 4.37 (m, 1H), 4.15 (b, 2H), 3.81, (d, J=6.2 Hz, 2H), 3.47 (dd, J=16.5, 9.9 Hz, 1H), 3.08 (t, J=8.1 Hz, 2H), 3.01 (dd, J=16.5, 7.0 Hz, 1H), 2.74 (bt, J=12.1 Hz, 2H), 2.26 (m, 1H), 2.01 (m, 2H), 1.81 (m, 4H), 1.45 (s, 9H, overlapped with m, 1H), 1.24 (m, 3H) , 0.91 (t, J=7.3 Hz, 3H).

Part D'. 3-(3-[4-{(Butyloxycarbonylpiperidin-4-yl)methoxy}phenyl]isoxazolin-5-yl{[butanesulfonyl]amino})-propionic Acid (Less Polar Diastereomer)

A solution of the impure methyl 3-(3-[4-{(butyloxycarbonylpiperidin-4-yl)methoxy}phenyl]isoxazolin-5-yl{[butanesulfonyl]amino})propionate less polar diastereomer (309 mg) in THF (5 mL) was saponified using 0.5M LiOH (2 mL, 1 mmol) over 6 hours as per Example 1, Part F. The crude carboxylic acid was purified using flash chromatography ($CHCl_3$—5–15% MeOH/$CHCl_3$ step gradient) followed by crystallization from EtOAc/hexanes, affording 169 mg of the desired material; mp: 155° C. (dec); $^1$H NMR (400 MHz, DMSO-$d_6$, 80° C.) δ 7.56 (d, J=8.8 Hz, 2H), 6.98 (d, J=8.8 Hz, 2H), 4.80 (m, 1H), 3.96 (bd, J=13.2 Hz, 2H), 3.90 (d, J=6.3 Hz, 2H), 3.77 (bs, 3H), 3.52 (t, J=7.8 Hz, 1H), 3.38 (dd, J=14.4, 10.0 Hz, 1H), 2.98 (t, J=7.8 Hz, 2H), 2.76 (dt, J=12.2, 1.7 Hz, 2H), 1.95 (m, 2H), 1.75 (m, 4H), 1.41 (s, 9H), 1.38 (d, J=7.6 Hz, 1H), 1.25 (m, 4H), 0.88 (t, J=7.3 Hz, 3H).

Part E. 3-(3-[4-{(Piperidin-4-yl)methoxy}phenyl]isoxazolin-5-yl{[butanesulfonyl]amino})propionic Acid, Trifluoroacetic Acid Salt (More Polar Diastereomer)

3-(3-[4-{(Butyloxycarbonylpiperidin-4-yl)methoxy}phenyl]isoxazolin-5-yl{[butanesulfonyl]amino}) propionic acid more polar diastereomer(40 mg, 0.070 mmol) was Boc-deprotected using 33% TFA/DCM according to Example 1, Part G. Recrystallization from methanol then afforded 4 mg (10%) of the TFA salt; mp: 263.5° C. (dec).

Part E'. 3-(3-[4-{(Piperidin-4-yl)methoxy}phenyl]isoxazolin-5-yl{[butanesulfonyl]amino}propionic Acid, Trifluoroacetic Acid Salt (Less Polar Diastereomer)

3-(3-[4-{(Butyloxycarbonylpiperidin-4-yl)methoxy}phenyl]isoxazolin-5-yl{[butanesulfonyl]amino}) propionic acid less polar diastereomer(98 mg, 0.173 mmol) was Boc-deprotected using 33% TFA/DCM according to Example 1, Part G, giving 40 mg of the TFA salt. Recrystallization from methanol then afforded 28 mg (29%) of the pure amino acid; mp: 239.4–240.7° C.

EXAMPLE 33

4-Carboxymethyl-3-[4- (2-piperidin-4-yl)ethoxyphenyl]-(5R,S)-isoxazolin-5-ylacetic Acid, Trifluoroacetic Acid Salt This material was prepared analogously to Example 1, giving the desired material; mp: 141.4° C. (dec); $^1$H NMR (400 MEz, $CD_3OD$, 60° C.) δ7.60 (d, J=8.8 Hz, 2H), 6.96 (d, J=8.8 Hz, 2H), 3.84 (d, J=17.3 Hz, 1H), 3.66 (s, 3H), 3.59 (d, J=17.3 Hz, 1H), 3.38 (bd, J=12.9 Hz, 1H), 3.24 (t, J=1.7 Hz, 2H), 3.21 (dm, J=20.3 Hz, 1H), 3.04 (d, J=1.5 Hz, 2H), 3.00 (dt, J=12.9, 2.9 Hz, 2H), 2.02 (bd, J=14.4 Hz, 2H), 1.95 (m, 1H), 1.81 (m, 2H), 1.48 (m, 2H).

EXAMPLE 43

N-[3-(4-Amidinophenyl)isoxazolin-5(R,S)-ylacetyl]-(R,S)-3-amino-3-phenylpropanoic Acid Part A: 4-Cyanobenzaldoxime This material was prepared from 4-cyanobenzaldehyde according to Kawase and Kikugawa (*J. Chem. Soc., Perkin Trans I* 1979, 643). To a solution of 4-cyanobenzaldehyde (1.31 g, 10 mmol) in 1:1 EtOH:pyridine (10 mL) was added hydroxylamine hydrochloride (0.70 g, 10 mmol). The resulting solution was stirred at room temperature for 18 h and was concentrated in vacuo to one-half volume. To this solution was added ice water, causing the product to crystallize from solution. Recrystallization from EtOH—water followed by drying over $P_2O_5$ afforded 1.46 g (100%) of the desired oxime; mp: 167.8–169.4° C.

Part B: Methyl 3-(3-Butenoyl)amino-3-phenylpropionate

To a solution of vinylacetic acid (861 mg, 10.0 mmol), methyl 3-amino-3-phenylpropionate hydrochloride (2.37 g, 11.0 mmol) and TEA (1.6 mL, 12 mmol) in DCM (20 mL) at −10° C. was added DEC (2.11 g, 11.0 mmol). The resulting mixture was stirred at −10° C. for 15 hours. The mixture was then washed with water, 0.1 M HCl, sat. $NaHCO_3$, sat. NaCl and dried over anhydrous $MgSO_4$. Concentration in vacuo followed by pumping until constant weight gave 2.36 g (95%) of the desired amide as a golden oil of suitable purity for further reaction; $^1$H NMR (300 MHz, $CDCl_3$) δ7.28 (m, 5H), 6.78 (bd, J=7.7 Hz, 1H), 5.95 (m, 1H), 5.43 (dt, J=8.4, 5.9 Hz, 1H), 5.25 (m, 2H), 3.61 (s, 3H), 3.04 (d, J=7.0 Hz, 2H), 2.88 (dq, J=15.0, 5.9 Hz, 2H).

Part C: Methyl 3(R,S)-{5(R, S)-N-[3-(4-Cyanophenyl)isoxazolin-5-ylacetyl]amino)-3-phenylpropanoate To a solution of methyl 3-(3-butenoyl)amino-3-phenylpropionate (816 mg, 3.30 mmol) and 4-cyanobenzaldoxime (prepared according to Example 1, Part A, 438 mg, 3.00 mmol) in $CH_2Cl_2$ (10 mL) was added a 5% solution of sodium hypochlorite ("Clorox", 5.3 mL, 3.5 mmol). The resulting mixture was stirred rapidly overnight (15 h), the layers separated and the aqueous washed with $CH_2Cl_2$. The combined organic was dried (MgSO4) and concentrated in vacuo. The crude product was then purified using flash chromatography (70% EtOAc/hexanes), affording 731 mg (62%) of the desired isoxazoline as a 1:1 mixture of diastereomers; $^1$H NMR (300 MHz, CDCl$_3$) δ7.74 (m, 8H), 7.29 (m, 10H), 6.92 (bm, 2H), 5.42 (m, 2H), 5.16 (m, 2H), 3.64 (s, 3H), 3.60 (s, 3H), 3.48 (m, 2H), 3.26 (dd, J=17.3, 7.7 Hz, 1H), 3.15 (dd, J=16.8, 8.1 Hz, 1H), 2.85 (m, 2H), 2.69 (m, 2H).

Part D: Methyl 3(R,S)-{5(R,S)-N-[3-(4-Amidinophenyl)isoxazo-lin-5-ylacetyl]amino}-3-phenylpropanoate Into a solution of methyl 3(R,S)-{5(R,S)-N-[3-(4-cyanophenyl)isoxazolin-5-ylacetyl]amino}-3-phenylpropanoate (587 mg, 1.50 mmol) in 10% DCM/methanol (55 mL) was bubbled dry HCl gas for 2 hours. The mixture was stirred for 18 hours, then concentrated in vacuo. The crude imidate was dissolved in methanol (20 mL) and ammonium carbonate added. The resulting mixture was stirred for 18 hours, then filtered. The filtrate was concentrated in vacuo and the residue purified using flash chromatography (CHCl$_3$—20% methanol/CHCl$_3$). Concentration of the appropriate fractions in vacuo followed by placing the residue under vacuum until constant weight afforded 193 mg (32%) of the desired amidines; CIMS (NH$_3$, e/z, relative abundance): 409 (M+H)$^+$, 100%.

Part E: 3(R,S)-{5(R,S)-N-[3-(4-Amidinophenyl)isoxazolin-5-ylacetyl]amino}-3-phenylpropanoic Acid, Trifluoroacetic Acid Salt Methyl 3(R,S)-{5(R,S)-N-[3-(4-amidinophenyl)isoxazolin-5-ylacetyl]amino}-3-phenylpropanoate (45 mg, 0.113 mmol) was saponified using 0.5 M LiOH (0.6 mL, 0.3 mmol) according to Example 1, Part F, affording 28 mg (49%); CIMS (NH$_3$, e/z, relative abundance): 412 (M+H)$^+$, 100%.

EXAMPLE 43A

5(R,S)-N-[3-(4-Amidinophenyl)isoxazolin-5-ylacetyl]aminopropanoic Acid

Part A: Ethyl 3-(3-Butenoyl)aminopropionate

To an ice cold solution of vinylacetic acid (4.39 g, 51.0 mmol), ethyl 3-aminopropionate hydrochloride (8.49 g, 55.3 mmol) and TEA (7.8 mL, 56 mmol) in DCM (50 mL) was added DEC (10.54 g, 55.0 mmol). The resulting mixture was warmed to room temperature overnight (18 h). The mixture was then washed with water, 0.1 M HCl, sat. NaHCO$_3$, sat. NaCl and dried (MgSO$_4$). Concentration in vacuo followed by pumping until constant weight was achieved gave 6.34 g (67%) of the desired amide as a golden oil of purity suitable for further reaction; $^1$H NMR (300 MHz, CDCl$_3$) δ6.26 (bs, 1H), 5.98–5.85 (m, 1H), 5.25–5.17 (m, 2H), 4.16 (q, J=7.0 Hz, 2H), 3.52 (q, J=5.9 Hz, 2H), 2.99 (dt, J=7.0, 1.1 Hz, 2H), 2.53 (t, J=5.9 Hz, 2H), 1.27 (t, J=7.0 Hz, 3H).

Part B: Ethyl 5(R,S)-N-[3-(4-Cyanophenyl)isoxazolin-5-ylacetyl]aminopropanoate

To a solution of ethyl 3-(3-butenoyl)aminopropionate (556 mg, 3.00 mmol) and 4-cyanobenzaldoxime (prepared according to Example 1, Part A, 292 mg, 2.00 mmol) in $CH_2Cl_2$ (7 mL) was added a 5% solution of sodium hypochlorite ("Clorox", 4.2 mL, 2.8 mmol). The resulting mixture was stirred rapidly overnight (15 h), the layers separated and the aqueous washed with $CH_2Cl_2$. The combined organic was dried (MgSO4) and concentrated in vacuo. The crude product was then purified using flash chromatography (EtOAc), affording 386 mg (58%) of the desired isoxazoline; mp: 102.0–102.9° C.

Part C: Ethyl 5(R,S)-3-[3-(4-Amidinophenyl)isoxazolin-5-ylacetyl]aminopropanoate Into a solution of ethyl 5(R,S)-3-[3-(4-cyanophenyl)isoxazolin-5-ylacetyl]aminopropanoate (1.65 mg, 5.00 mmol) in 10% DCM/EtOH (165 mL) was bubbled HCl gas for 2 hours. After 18 hours, the solvent was evaporated in vacuo, the residue dissolved in EtOH (100 mL) and ammonium carbonate (14.41 g, 150 mmol) added. The resulting suspension was stirred at room temperature for 18 hours, then filtered and the resulting filtrate concentrated in vacuo. The residue was then crystallized from EtOH/ether, giving 713 mg (41%) of the desired amidine; $^1$H NMR (300 MHz, CD$_3$OD) δ7.88 (AB quartet, Δ=16.8 Hz, J=8.4 Hz, 4H), 5.13 (m, 1H), 4.12 (q, J=7.3 Hz, 2H), 3.58 (dd, J=17.2, 10.6 Hz, 1H), 3.44 (m, 2H), 3.26 (dd, J=17.2, 7.3 Hz, 1H, coincident with solvent), 2.57 (m, 4H), 1.25 (t, J=7.3 Hz, 2H).

Part H: 5(R,S)-3-[3-(4-Amidinophenyl)isoxazolin-5-ylacetyl]aminopropanoic Acid

To a solution of ethyl 5(R,S)-3-[3-(4-amidinophenyl)isoxazolin-5-ylacetyl]aminopropanoate (346 mg, 1.00 mmol) in EtOH (6 mL) was added 0.5 M LiOH. Upon mixing, a precipitate of the zwitterionic product began to form. After stirring for 18 hours at room temperature, the solid was collected by filtration, affording 365 mg of the title compound; $^1$H NMR (300 MHz, CD$_3$OD) δ7.86 (AB quartet, Δ=18.3 Hz, J=8.4 Hz, 4H), 5.21 (m, 1H), 3.57 (dd, J=17.2, 10.6 Hz, 1H), 3.43 (m, 2H), 3.25 (dd, J=17.2, 7.3 Hz, 1H, coincident with solvent), 2.64 (dd, J=14.6, 6.8 Hz, 1H), 2.52 (m, 3H).

EXAMPLE 120a

Methyl 3 (R)-{5(R,S)-N-[3-(4-amidinophenyl)isoxazolin-5-ylacetyl]amino}-3-phenethylpropanoate Part A. Methyl (E)-5-phenyl-2-pentenoate A solution of hydrocinnamaldehyde (13.42 g, 0.1 mol) and methyl(triphenylphosphoranylidene)acetate (33.44 g, 0.1 mol) in THF was stirred at reflux for 20 hours. The reaction mixture was concentrated under vacuum and the residue was purified by flash chromatography using hexane:EtOAc::9:1. The desired product was obtained as a clear, pale yellow oil (8.0 g, 0.042 mol, 42%); $^1$H NMR (300 MHz, CDCl$_3$) δ 7.3–7.2 (m, 2H), 7.2–7.1 (m, 3H), 7.1–6.9 (m, 1H), 5.85 (d, 1H, J=5.8 Hz), 3.75 (s, 3H), 2.8 (t, 2H, J=7.7 Hz), 2.55 (q, 2H, J=7.4 Hz); MS (NH$_3$-DCI) 191 (M+H)$^+$.

Part B. Methyl 3-(R)-[N-(1-(R)-1-phenylethyl)amino]-5-phenylpentanoate

A mixture of methyl (E)-5-phenyl-2-pentenoate (5.70 g, 0.03 mol) and R-methylbenzylamine (14.54 g, 0.12 mol) was heated at 110° C. over 94 hours. The cooled reaction mixture was purified by flash chromatography using hexane:EtOAc::8:2 to afford 1.18 g (0.0038 mol, 12%) of the desired product as a clear liquid; $^1$H NMR (300 MHz, CDCl$_3$) δ7.4–7.0 (m, 11H), 3.9 (q, 1H, J=6.5 Hz), 3.65 (s, 3H), 2.9–2.65 (m, 2H), 2.6–2.35 (m, 3H), 1.75–1.6 (m, 2H), 1.35 (d, 3H, J=6.2 Hz); MS (NH$_3$-DCI) 312 (M+H)$^+$.

Part C. Methyl 3-(R)-amino-5-phenylpentanoate ● acetic acid salt

A mixture of methyl,3-(R)-[N-(1-(R)-1-phenylethyl)amino]-5-phenylpentanoate (0.72 g, 2.3 mmol), 20% Pd(OH)$_2$/C (0.38 g), cyclohexene (8.2 mL), glacial HOAc (0.13 mL, 2.3 mmol), and MeOH (15 mL) was heated at reflux under N$_2$ for 20 hours. After cooling, the catalyst was removed by filtration through a Celite plug, rinsed with MeCH, and the solution concentrated under vacuum. The residue was triturated with hexane to afford 0.46 g (96%) of a white solid, mp=73–75° C.; $^1$H NMR (300 MHz, DMSO) δ 8.3 (bs, 2H), 7.35–7.15 (m, 5H), 3.65 (s, 3H), 3.45–3.35 (m, 1H), 2.8–2.6 (m, 4H), 2.0–1.7 (m, 2H); $[\alpha]_D^{25}$—12.50° (c=0.0032, MeOH).

Part D. Methyl 3(R)-{5(R,S)-N-[3-(4-cyanophenyl) isoxazolin-5-ylacetyl]amino}-3-phenethylpropanoate To a suspension of 3-(4-cyanophenyl)isoxazolin-5-ylacetic acid (460 mg, 2.0 mmol) in EtOAc (15 ml) was added methyl 3-(R)-amino-5-phenylpentanoate acetic acid salt (410 mg, 2.0 mmol), TBTU (640 mg, 2.0 mmol), and Et$_3$N (0.56 mL, 400 mg, 4.0 mmol). After stirring at room temp for 16 hours, the reaction mixture was concentrated under vacuum then purified by flash chromatography using EtOAc to afford 690 mg (83%) of a colorless oil. $^1$H NE (300 MHz, DMSO) δ 8.05 (brs, 1H), 7.95–7.9 (m, 2H), 7.85–7.8 (m, 2H), 7.3–7.25 (m, 2H), 7.2–7.1 (m, 2H), 5.15–5.0 (m, 1H), 4.15–4.0 (m, 1H), 3.6 (d, 3H, J=9.9 Hz), 3.3 (d, 2H, J=6.9 Hz), 3.25–3.15 (m, 1H), 2.75–2.35 (m, 6H), 1.8–1.6 (m, 2H); MS (NH$_3$-DCI) 420 (M+H)$^+$.

Part E Methyl 3(R)-{5(R,S)-N-[3-(4-amidinophenyl) isoxazolin-5-ylacetyl]amino}-3-phenethylpropanoate This material was prepared from methyl 3(R)-{5(R,S)-N-[3-(4-cyanophenyl)isoxazolin-5-ylacetyl]amino}-3-phenethylpropanoate (670 mg, 1.6 nmol) according to Example 43, Part D. The crude product was triturated with cold ether to afford 272 mg (39%) of a white solid of the title compound as a 1:1 mixture of diastereomers, mp=76–78° C.; $^1$H NMR (300 MHz, DMSO) δ 8.1–8.0 (m, 1H), 8.0–7.8 (m, 4H), 7.95–7.85 (m, 5H), 7.35–7.2 (m, 5H), 5.1–5.0 (m, 1H), 4.1–4.0 (m, 1H), 3.6 (s, 3H), 3.3–3.15 (m, 2H), 2.7–2.4 (m, 6H), 1.8–1.7 (m, 2H), 1.1–1.0 (m, 2H); Mass Spectrum (NH$_3$-ESI,) 437 (M+H)$^+$.

EXAMPLE 120b

Methyl 3(S)-{5(R,S)-N-[3-(4-amidinophenyl) isoxazolin-5-ylacetyl]amino}-3-phenethylpropanoate Part A. Methyl 3-(S)-[N-(1-(R)-1-phenylethyl)amino]-5-phenylpentanoate A mixture of (E)-methyl-5-phenyl-2-pentenoate (5.70 g, 0.03 mol) and R-methylbenzylamine (14.54 g, 0.12 mol) was heated at 110° C. over 94 hours. The cooled reaction mixture was purified by flash chromatography using hexane:EtOAc::8:2 to afford 1.20 g (0.0039 mol, 13%) of the desired product as a clear liquid; $^1$H NMR (300 MHz, CDCl$_3$) δ 7.35–7.0 (m, 11H), 3.9 (q, 1H, J=6.6 Hz), 3.65 (s, 3H), 2.95–2.8 (m, 1H), 2.75–2.5 (m, 2H), 2.45–2.35 (m, 2H), 1.9–1.65 (m, 2H), 1.3 (d, 3H, J=6.6 Hz); MS (NH$_3$-DCI) 312 (M+H)$^+$.

Part B. Methyl 3-(S)-amino-5-phenylpentanoate ● acetic acid salt

Methyl 3-(S)-[N-benzyl-N-(1-(R)-1-phenylethyl)amino] heptanoate (0.93 g, 2.9 mmol), 20% Pd(OH)$_2$/C (0.47 g), cyclohexene (10.1 mL), glacial HOAc (0.17 mL, 2.9 mmol), and MeOH (20 mL) were heated at reflux under N$_2$ for 48 hours. After cooling, the catalyst was removed by filtration through a Celite plug, rinsed with MeOH, and the solution concentrated under vacuum. The residue was triturated with hexane to afford 0.65 g (80%) of a white solid, mp=86–88° C.; $^1$H NMR (300 MHz, CDCl$_3$) δ 7.35–7.15 (m, 5H), 5.3 (brs, 2H), 3.65 (s, 3H), 3.35–3.2 (m, 1H), 2.8–2.55 (m, 3H), 2.5–2.4 (m, 1H), 2.0 (s, 3H), 1.8 (q, 2H, J=7.4 Hz); $[\alpha]D^{25}$+9.55° (c=0.220, MeOH).

Part C. Methyl 3(S-{5(R,S)-N-[3-(4-cyanophenyl) isoxazolin-5-ylacetyl]amino}-3-phenethylpropanoate To a suspension of 3-(4-cyanophenyl)isoxazolin-5-ylacetic acid (700 mg, 2.6 mmol) in EtOAc (15 ml) was added methyl 3-(S)-amino-5-phenylpentanoate acetic acid salt (600 mg, 2.6 mmol), TBTU (830 mg, 2.6 mmol), and Et$_3$N (1.09 mL, 790 mg, 7.8 mmol). After stirring at room temperature 16 hours, the reaction mixture was concentrated under vacuum then purified by flash chromatography using EtOAc to afford 420 mg (38%) of a colorless oil. $^1$H NMR (300 MHz, CDCl$_3$) δ 8.05–8.0 (m, 1H), 7.95–7.9 (m, 2H), 7.85–7.8 (m, 2H), 7.3–7.2 (m, 2H), 7.2–7.1 (m, 3H), 5.15–5.0 (m, 1H), 4.15–4.0 (m, 1H), 3.6–3.55 (m, 3H), 3.3–3.1 (m, 1H), 2.7–2.4 (m, 6H), 1.8–1.6 (m, 2H); MS (NH$_3$-DCI) 420 (M+H)$^+$.

Part D. Methyl 3(S)-{5(R,S)-N-[3-(4-amidinophenyl) isoxazolin-5-ylacetyl]amino}-3-phenethylpropanoate This material was prepared from methyl 3(S)-{5(R,S)-N-[3-(4-cyanophenyl)isoxazolin-5-ylacetyl]amino}-3-phenethylpropanoate (360 mg, 0.86 mmol) according to Example 43, Part D. The crude product was triturated with cold ether to afford 230 mg (62%) of an amorphous solid of the title compound as a 1:1 mixture of diastereomers, mp=84–86° C.; $^1$H NMR (300 MHz, DMSO) δ 8.1–8.0 (m, 1H), 8.0–7.8 (m, 4H), 7.75–7.7 (m, 1H), 7.3–7.1 (m, 6H), 5.1–5.0 (m, 1H), 4.15–4.0 (m, 1H), 3.65 (s, 3H), 3.3–3.1 (m, 1H), 2.7–2.6 (m, 3H), 2.5–2.4 (m, 3H), 1.8–1.65 (m, 2H), 1.1–1.0 (m, 2H); Mass Spectrum (NH$_3$-ESI) 437 (M+H)$^+$.

EXAMPLE 189

5(R,S)-(2-Piperidin-4-yl)ethyl-8-(2-carboxyethyl)-1-oxa-2,8-diazaspiro[4,4]non-2-ene-7,9-dione Part A. 3-(N-t-Butyloxycarbonylpiperidin-4-yl)propanal To a suspension of PCC (11.52 g, 53.44 mmol) and sodium acetate (4.38 g, 53.4 mmol) in DCM (60 mL) was added a solution of 3-(N-t-butyloxycarbonylpiperidin-4-yl) propanol (10.00 g, 41.09 mmol) in DCM (20 mL). After 4 hours at room temperature, the mixture was diluted with ether and passed though a short column of fluorisil® using ether as an eluent. The eluate was concentrated in vacuo and placed under vacuum until constant weight was achieved, affording 8.32 g (84%) of the desired aldehyde as a colorless oil; $^1$H NMR (300 MHz, CDCl$_3$) δ 9.76 (t, J=1.5 Hz, 1H), 4.05 (bs, 2H), 2.64 (bt, J=11.7 Hz, 2H), 2.45 (dt, J=7.3, 1.5 Hz, 2H), 1.60 (m, 3H), 1.43 (s, 9H, overlapped with m, 2H), 1.08 (dq, J=12.1, 4.0 Hz, 2H).

Part B. (E,Z)-3-(N-t-Butyloxycarbonylpiperidin-4-yl) propanal Oxime

To a solution of 3-(N-t-butyloxycarbonylpiperidin-4-yl) propanal (3.905 g, 16.18 mmol) in EtOH : pyr=1:1 (20 mL) was added hydroxylamine hydrochloride (1.701 g, 24.48 mmol) and the resulting solution stirred at room temperature for 20 hours. Concentration in vacuo, resulted in an oil, which was dissolved in EtOAc and washed with 0.1 M HCl (3x), water, sat. CUSO$_4$ (2x), water and brine. The solution was dried over MgSO$_4$, concentrated in vacuo and placed under vacuum until constant weight was achieved, affording 4.071 g (98%) of a 1:1 mixture of the (E,Z)-oxime as a colorless oil; $^1$H NMR (300 MHz, CDCl$_3$) δ 7.42 (t, J=6.2 Hz, 0.5H), 6.70 (t, J=5.5 Hz, 0.5H), 4.06 (bs, 2H), 2.67 (bt, J=12.8 Hz, 2H), 2.41 (m, 1H), 2.23 (m, 1H), 1.66 (b, 2H), 1.45 (s, 9H, overlapped with m, 4H), 1.08 (m, 2H).

Part C. Methyl (5R,S)-3-{[2-(N-t-Butyloxycarbonylpiperidin-4-yl)ethyl]-5-carboxymethylisoxazolin-5-yl}acetate To a solution of (E,Z)-3-(N-t-butyloxycarbonylpiperidin-4-yl)propanal oxime (503 mg, 1.96 mol) and dimethyl itaconate (620 mg, 3.92 mmol) in DCM (3 mL) was added a 5% solution of sodium hypochlorite (common household bleach, 3 mL, 2 mmol). The resulting mixture was stirred overnight (19 hours) at room temperature. The layers were separated and the aqueous washed with DCM (2x). The combined DCM fraction was dried over $MgSO_4$ and concentrated in vacuo. Purification using flash chromatography (hexanes—10% EtOAc/hexanes—50% EtOAc/hexanes) followed by concentration and pumping to constant weight afforded the desired isoxazoline (510 mg, 63%) as a colorless oil; $^1$H NMR (300 MHz, $CDCl_3$) δ 4.06 (bd, J=13.6 Hz, 2H), 3.78 (s, 3H), 3.67 (s, 3H), 3.57 (d, J=17.6 Hz, 1H), 3.15 (d, J=16.5 Hz), 3.06 (d, J=17.6 Hz, 1H), 2.86 (d, J=16.5 Hz, 1H), 2.65 (bt, J=12.1 Hz, 2H), 2.36 (m, 2H), 1.65 (m, 2H, overlapped with $H_2O$, 2H), 1.43 (s, 9H), 1.07 (m, 2H).

Part D. (5R,S)-3-{[2-(N-t-Butyloxycarbonylpiperidin-4-yl) ethyl]-5-carboxyisoxazolin-5-yl}acetic Acid To a solution of methyl (5R,S)-3-{[2-(N-t-butyloxycarbonylpiperidin-4-yl)ethyl]-5-carboxymethylisoxazolin-5-yl}acetate (380 mg, 0.921 mmol) was saponified using 0.5M LiOH (5 mL, 2.5 mmol) in THF (5 mL). The reaction was stirred at ambient temperature for 5 hours, according to Example 1, Part F to give 240 mg (68%) of the diacid; mp: 154.4–154.9° C.; $^1$H NMR (300 MHz, MeOH-$d_4$) δ 4.04 (bd, J=13.2 Hz, 2H), 3.52 (d, J=17.8 Hz, 1H), 3.18 (d, J=17.8 Hz, 1H), 2.97 (AB quartet, Δ=32.6, J=16.8 Hz, 2H), 2.72 (b, 2H), 2.39 (m, 2H), 1.71 (bd, J=13.2 Hz, 2H), 1.51 (m, 3H), 1.43 (s, 9H), 1.05 (m, 2H).

Part E. 5(R,S)-2-(N-t-Butyloxycarbonylpiperidin-4-yl) ethyl-8-[(2-(1,1-dimethylethoxycarbonyl)ethyl]-1-oxa-2,8-diazaspiro[4,4]non-2-ene-7,9-dione To a solution of (5R,S)-3-{[2-(N-t-butyloxycarbonylpiperidin-4-yl)ethyl]-5-carboxyisoxazolin-5-yl}acetic acid (700 mg, 1.82 mmol) in THF (5 mL) was added DCC (378 mg, 1.83 mmol), and the resulting suspension was stirred for 30 min at room temperature. To this mixture was added a suspension of β-alanine t-butyl ester hydrochloride (372 mg, 2.05 mmol) and TEA (300 μL, 2.15 mmol) in THF (5 mL). The mixture was stirred overnight (18 hours) at room temperature. Following dilution with EtOAc, the mixture was filtered and the filtrate washed with 0.1M HCl, sat. $NaHCO_3$ and sat. NaCl. It was dried over anhydrous MgSO4, concentrated and placed under vacuum until constant weight was reached, giving 430 mg (46%) of the crude amide. A portion of this material (420 mg, 0.821 mmol) was dissolved in THF (4 mL). To this solution was added HOSuc (100 mg, 0.869 mmol) followed by DCC (180 mg, 0.872 mmol). The resulting suspension was stirred at room temperature for 18 hours. Following dilution with ether, the mixture was cooled to 0° C. and filtered. The filtrate was dried over anhydrous MgSO4, concentrated and placed under vacuum until constant weight was reached, giving 430 mg (86%) of the crude active ester. A portion of this material (402 mg, 0.660 mmol) was dissolved in DMF (5 mL) at 0° C. To this solution was added NaH (16 mg, 0.66 mmol). After 3 hours at 0° C., the reaction was quenched with HOAc. After dilution with EtOAc, the mixture was washed with water (4x), sat. $NaHCO_3$, water, 0.1M HCl and sat. NaCl. It was dried over anhydrous MgSO4, concentrated and placed under vacuum until constant weight was reached, giving 230 mg (70%) of the crude imide. The crude material was purified using flash chromatography ($CHCl_3$—5% MeOH/$CHCl_3$), affording 149 mg (46%) of a colorless oil after concentration of the appropriate fractions and pumping to constant weight; $^1$H NMR (300 MHz, $CDCl_3$) δ 4.09 (b, 2H), 3.82 (t, J=7.3 Hz, 2H), 3.54 (d, J=17.2 Hz, 1H), 3.12 (d, J=18.7 Hz, 1H), 2.98 (d, J=17.2 Hz, 1H), 2.83 (d, J=18.7 Hz, 1H), 2.69 (m, 2H), 2.57 (t, J=7.3 Hz, 2H), 2.42 (m, 2H), 1.68 (m, 2H), 1.57 (m, 2H), 1.45 (s, 9H, coincident with m, 1H), 1.11 (m, 2H).

Part F. 5(R,S)-(2-Piperidin-4-yl)ethyl-8-(2-carboxyethyl)-1-oxa-2,8-diazaspiro[4,4]non-2-ene-7,9-dione To a solution of 5(R,S)-2-(N-t-butyloxycarbonylpiperidin-4-yl)ethyl-8-[(2-(1,1-dimethylethoxycarbonyl)ethyl]-1-oxa-2,8-diazaspiro[4.4] non-2-ene-7,9-dione (75 mg, 0.152 mmol) in DCM (1 mL) was added TFA (0.5 mL, 8 mmol). The reaction was stirred at room temperature for 2 hours, then was concentrated in vacuo. Excess TFA was chased by rotary evaporation with toluene (2x). Crystallization from MeOH/ether gave 10 mg (15%) of the desired amino acid after pumping to constant weight; mp: 178.0–179.1° C.; $^1$H NMR (400 MHz, DMSO-$d_6$, 60° C.) δ 12.15 (bs, 1H). 8.26 (bs, 2H), 3.64 (m, 2H), 3.39 (d, J=17.8 Hz, 1H), 3.26 (m, 3H), 2.98 (AB quartet, Δ=71.3 Hz, J=18.3 Hz, 2H), 2.85 (m, 2H), 2.50 (m, 1H, coincident with DMSO-$d_5$), 2.37 (t, J=7.6 Hz, 2H), 1.84 (bd, J=11.7 Hz, 2H), 1.58 (m, 1H), 1.52 (t, J=7.6 Hz, 2H), 1.29 (m, 2H).

EXAMPLE 275

$N^3$-[3-(4-amidinophenyl)isoxazolin-5(R, S)-ylacetyl]-L-2,3-diaminopropionic Acid TFA Salt Part A. 3-(4-cyanophenyl)isoxazolin-5(R, S)-ylacetic acid.

To a solution of 4-cyanobenzaldoxime (see Ex 43, Part A) (312 g, 2.13 mol) in tetrahydrofuran (3000 ml) at room temperature was added vinyl acetic acid (552 g, 6.41 mol). The yellow solution was cooled in an ice bath and sodium hypochlorite solution (5200 ml) was added in a dropwise fashion over 2h. After stirring overnight at room temperature the reaction was quenched with a 5% citric acid solution and diluted with 200 ml ether. The layers were separated and the aqueous acidified to pH 4 using citric acid. The acid layer was washed twice with 200 ml ether, the ether layers combined and extracted with saturated sodium bicarbonate solution. After acidifying the basic layer with citric acid, the product was extracted into 400 ml ether. The organic phase was washed three times with 150 ml water, once with brine, dried ($MgSO_4$) and concentrated to give 220 g of 3-(4-cyanophenyl)isoxazolin-5-ylacetic acid as a white solid. Recrystallization from 25% water/ethanol yielded 165 g of analytically pure material. Anal. Calcd for $C_{12}H_{10}N_2O_3$: C,62.61; H,4.38; N, 12.17. Found: C. 62.37; H 4.47; N, 11.71. $^1$H NMR(300 MHz, $CDCl_3$): δ 7.77–7.76 (d, 2H, J=1.8 Hz); 7.72–7.71 (d, 2H, J=1.8 Hz); 5.22–5.14 (m, 1H); 3.63–3.54 (dd, 1H, J=10.6 Hz, 16.8 Hz); 3.19–3.11 (dd, 1H, J=7.3Hz, 16.8 Hz); 3.00–2.93 (dd, 1H, J=6.2 Hz, 16.5 Hz); 2.79–2.72 (dd, 1H, J=7.3 Hz, 16.5 Hz). IR(KBr pellet): 3202, 2244, 1736, 1610, 1432, 1416, 1194, 1152, 928, 840, 562 $cm^{-1}$.

Part B. Methyl $N^2$-Cbz-L-2,3-diaminopropionate HCl salt.

$N^2$-Cbz-L-2,3-diaminopropionic acid (10 mmol, 2.39 g) was dissolved in 20 mL methanol and 20 mL 4 N HCl in dioxane and the solution was stirred for 4 hours and then concentrated to give a solid. The solid was washed with ether several times to give 2.50 g (87%) product. NMR (DMSO-$d_6$): δ 8.38 (b, 3H); 7.96 (d, 1H); 7.38 (m, 5H); 5.05 (s, 2H); 4.44 (m, 1H); 3.66 (s, 3H); 3.14 (m, 2H).

Part C. Methyl $N^2$-Cbz-$N^3$-[3-(4-cyanophenyl)isoxazolin-5(R, S)-ylacetyl]-L-2,3-diaminopropionate.

To a solution of 3-(4-cyanophenyl)isoxazolin-5(R, S)-ylacetic acid. (19 mmol, 4.37 g), methyl $N^2$-Cbz-L-2,3-diaminopropionate HCl salt (20 mmol, 5.76 g) and triethylamine (60 mmol, 8.36 mL) was added TBTU (20 mmol, 6.42 g) and the solution was stirred for 2 hours. Ethyl acetate was added and the solution was washed with dilute citric acid, brine, $NaHCO_3$ and brine, dried ($MgSO_4$), and concentrated. Crystallization from ethyl acetate/ether gave 6.85 g (78%) product. NMR (DMSO-$d_6$): δ 8.16 (t, 1H); 7.92 (d, 2H); 7.82 (d, 2H); 7.68 (d, 1H); 7.36 (m, 5H); 5.04 (m, 3H); 4.20 (m, 1H); 3.64 (s, 3H); 3.50 (m, 2H); 3.26 (m, 2H); 2.50 (m, 2H).

Part D. Methyl $N^3$-[3-(4-amidinophenyl)isoxazolin-5(R, S)-ylacetyl]-L-2,3-diaminopropionate HCl salt.

HCl gas was bubbled into a solution of methyl $N^2$-Cbz-$N^3$-[3-(4-cyanophenyl)isoxazolin-5(R, S)-ylacetyl]-L-2,3-diaminopropionate (2.1 mmol, 1.0 g) for 1 hour and the solution was stirred overnight and concentrated. The residue was dissolved in 30 mL 2 M ammonia in methanol and the solution was stirred overnight. and concentrated to give 1.2 g crude product.

Part E. $N^3$-[3- (4-amidinophenyl)isoxazolin-5(R,S)-ylacetyl]-L-2,3-diaminopropionic acid TFA salt.

Methyl $N^3$-[3-(4-amidinophenyl)isoxazolin-5(R, S)-ylacetyl]-L-2,3-diaminopropionate HCl salt (200 mg) was saponified with 1 mL methanol and 1 mL 1 N NaOH for 1 hour and acidified with acetic acid. Purification on reversed phase HPLC gave 40 mg product. ESI (M+H)$^+$: Calcd 334.2; Found 334.2.

EXAMPLE 276

$N^2$-Cbz-$N^3$-[3-(4-amidinophenyl)isoxazolin-5(R, S)-ylacetyl]-L-2,3-diaminopropionic acid TFA salt Part A. Methyl $N^2$-Cbz-$N^3$-[3-(4-amidinophenyl)isoxazolin-5(R, S)-ylacetyl]-L-2,3-diaminopropionate TFA salt.

To a solution of the compound of Ex. 275, part D (1.0 mmol, 385 mg) and sodium bicarbonate (5.0 mmol, 400 g) in 2 mL water, 2 mL acetonitrile and 1 mL DMF was added benzyl chloroformate (1 mmol, 143 μL) and the mixture was stirred for 2 hours at room temperature. The solution was filtered, acidified with TFA and purified on reversed phase HPLC to give 150 mg (25%) product. NMR (DMSO-$d_6$): δ 9.40 (s, 2H); 9.20 (s, 2H); 8.18 (t, 1H); 7.86 (m, 4H); 7.68 (d, 1H); 7.35 (m, 5H); 5.02 (m, 3H); 4.20 (m, 1H); 3.64 (s, 3H); 3.52 (m, 2H); 3.26 (m, 2H); 2.50 (m, 2H).

Part B. $N^2$-Cbz-$N^3$-[3-(4-amidinophenyl)isoxazolin-5(R, S)-ylacetyl]-L-2,3-diaminopropionic acid TFA salt Methyl $N^2$-Cbz-$N^3$-[3-(4-amidinophenyl)isoxazolin-5(R, S)-ylacetyl]-L-2,3-diaminopropionate TFA salt (0.12 mmol, 70 mg) was dissolved in 2 mL methanol and 1 mL 1 N NaOH and after 1 hour, the solution was acidified with acetic acid. Purification on reversed phase HPLC gave 50 mg (74%) product. ESI (M+H)$^+$: Calcd 468.2; Found 468.2.

EXAMPLE 278

$N^2$-n-butyloxycarbonyl-$N^3$-[3-(4-amidinophenyl) isoxazolin-5(R, S)-ylacetyl]-L-2,3-diaminopropionic acid TFA salt Part A. Methyl $N^2$-n-butyloxycarbonyl-$N^3$-[3-(4-amidinophenyl)isoxazolin-5(R, S)-ylacetyl]-L-2,3-diaminopropionate TFA salt.

To a solution of the compound of Ex. 275, part E (1.0 mmol, 385 mg) and sodium bicarbonate (2.5 mmol, 200 mg) in 2 mL water, 2 mL acetonitrile and 1 mL DMF cooled in an ice bath was added n-butyl chloroformate (1 mmol, 127 μL). After stirring for 1 hour, the solution was acidified with acetic acid and purified on reversed phase HPLC to give 150 mg (27%) product. NMR (DMSO-$d_6$): δ 9.40 (s, 2H); 9.20 (s, 2H); 8.16 (t, 1H); 7.86 (m, 4H); 7.47 (d, 1H); 5.02 (m, 1H); 4.16 (m, 1H); 3.94 (t, 2H); 3.62 (s, 3H); 3.50 (m, 2H); 3.26 (m, 2H); 2.50 (m, 2H); 1.52 (m, 2H); 1.32 (m, 2H); 0.88 (t, 3H). ESI (M+H)$^+$: Calcd 448.3; Found 448.3.

Part B. $N^2$-n-butyloxycarbonyl-$N^3$-[3-(4-amidinophenyl) isoxazolin-5(R, S)-ylacetyl]-(S)-2,3-diaminopropionic acid TFA salt.

Methyl N2-n-butyloxycarbonyl-N3-[3-(4-amidinophenyl)isoxazolin-5(R, S)-ylacetyl]-(S)-2,3-diaminopropionate TFA salt (0.107 mmol, 60 mg) was dissolved in 2 mL methanol and 2 mL 1 N NaOH and after 1 hour, the solution was acidified with acetic acid. Purification on reversed phase HPLC gave 53 mg (89%) product. ESI (M+H)$^+$: Calcd 434.3; Found 434.3.

EXAMPLE 278a

Methyl $N^2$-n-butyloxycarbonyl-$N^3$-[3-(4-amidinophenyl)isoxazolin-5(R)-ylacetyl]-(S)-2,3-diaminopropionate Mesylate salt.

Methyl $N^2$-n-butyloxycarbonyl-$N^3$-[3-(4-amidinophenyl) isoxazolin-5(R)-ylacetyl]-(S)-2,3-diaminopropionate (500 mg, 1.03 mmol) was dissolved in 20 mL methanol and methanesulfonic acid (0.335 mL, 5 mmol) was added. The solution was allowed to stand at room temperature overnight and the solvent was removed by concentration. The residue was taken up in 20 mL methanol and the solution was allowed to stand at room temperature overnight. The solvent was removed by concentration and the residue was triturated with 8 mL 2-propanol. The solid product was isolated by filtration and dissolved in 12 mL 2-propanol by warming. After cooling to room temperature, crystalline solid formed. The mixture was allowed to stand in a refrigerator overnight. The crystal was filtered, washed with cold 2-propanol and dried. Yield 230 mg (41%). ES-MS (M+1): calcd 448.3; found 448.3. Analysis for $C_{22}H_{33}N_5O_9S$: calcd C 48.61, H 6.13, N 12.88; found C 48.38, H 5.91, N12.65.

EXAMPLE 278b $N^2$-n-butyloxycarbonyl-$N^3$-[3-(4-amidinophenyl) isoxazolin-5(R)-ylacetyl]-(S)-2,3-diaminopropionic acid TFA salt.

To a solution of methyl $N^2$-n-butyloxycarbonyl-$N^3$-[3-(4-amidinophenyl)isoxazolin-5(R)-ylacetyl]-(S)-2,3-diaminopropionate hydrochloride salt (600 mg, 1.24 mmol) in 20 mL MeOH and 20 mL water cooled in an ice bath was added 1 N LiOH (1.3 mL, 1.3 mmol) over 5 min and the solution was stirred at room temperature for 5 hours. The solvents were removed by concentration at 25° C. The residue was taken up in 3 mL water, 3 mL acetonitrile, and 0.2 mL TFA. Purification by reversed phase HPLC gave 610 mg (89%) product. ES-MS (M+1): calcd 434.3; found 434.3.

EXAMPLE 298

$N^2$-n-Butanesulfonyl-$N^3$-[3-(4-amidino-phenyl) isoxazolin-5(R,S)-ylacetyl]-(S)-2,3-diaminopropionic Acid TFA Salt Prepared according to Example 490a. MS (ESI, e/z, relative intensity): 454 (M+H)$^+$, (100%).

EXAMPLE 299

$N^2$-Phenylsulfonyl-$N^3$-[3-(4-amidinophenyl) isoxazolin-5(R,S)-ylacetyl]-(S)-2,3-diaminopropionic Acid TFA Salt Prepared according to Example 490a. MS (ESI, e/z, relative intensity): 474 (M+H)$^+$, (100%).

EXAMPLE 314A

Methyl $N^2$-n-butyloxycarbonl-$N^3$-[3-(4-amidinophenyl)isoxazolin-5(S)-ylacetyl]-(S)-2,3-diaminopropionate TFA salt Part A: Methyl $N^2$-Cbz-$N^3$-Boc-L-2,3-diaminopropionate.

To a solution of methyl $N^2$-Cbz-(S)-2,3-diaminopropionate HCl salt (16.3 mmol, 4.7 g) and ditert-butyl dicarbonate (16.3 mmol, 3.56 g) in 30 mL chloroform cooled in an ice bath was added triethylamine (34 mmol, 4.7 mL) and the solution was stirred in the ice bath for 1 hour and at room temperature for 3 hours and concentrated. The residue was taken up in ethyl acetate and the solution was washed with dilute citric acid, brine, $NaHCO_3$ and brine, dried ($MgSO_4$), and concentrated. Crystallization from ether/petroleum ether gave 5.2 g (92%) product. NMR (DMSO-$d_6$): δ 7.60 (d, 1H); 7.35 (m, 5H); 6.88 (t, 1H); 5.02 (s, 2H); 4.14 (m, 1H); 3.60 (s, 3H); 3.28 (m, 2H); 1.37 (s, 9H).

Part B: Methyl $N^3$-Boc-(S)-2,3-diaminopropionate Formic acid salt.

A mixture of methyl $N^2$-Cbz-$N^3$-Boc-(S)-2,3-diaminopropionate. (14 mmo, 5.0 g), formic acid (42 mmol, 1.6 mL) and 10% Pd/C (500 mg) in 40 mL methanol was stirred at room temperature for 1 hour and filtered through a celite. The filtrate was concentrated and the residue was triturated with ether-petroleum ether to give 3.7 g (100%) solid product. NMR (DMSO-$d_6$): δ8.20(s, 1H); 6.90 (t, 1H); 5.36 (b, 3H); 3.61 9s, 3H); 3.51 (t, 1H); 3.18 (t, 2H); 1.38 (s, 9H).

Part C: Methyl $N^2$-n-butyloxycarbonyl-$N^3$-Boc-(S)-2,3-diaminopropionate.

To a mixture of methyl $N_3$-Boc-(S)-2,3-diaminopropionate $HCO_2H$ salt (14 mmol, 3.7 g) and $NaHCO_3$ (40 mmol, 3.4 g) in 10 mL water and 10 mL THF cooled in an ice bath was added slowly butyl chloroformate (16 mmol, 2 mL) over 15 min. After stirring for 1 hour, ethyl acetate was added and the solution was washed with dilute citric acid, brine, $NaHCO_3$ and brine, dried ($MgSO_4$), and concentrated to give 4.4 g (100%) oily product. NMR (DMSO-$d_6$): δ 7.37 (d, 1H); 6.84 (t, 1H); 4.10 (m, 1H); 3.96 (t, 2H); 3.60 (s, 3H); 3.26 (m, 2H); 1.52 (m, 2H); 1.38 (s, 9H); 1.36 (m, 2H); 0.88 (t, 3H).

Part D: Methyl $N^2$-butyloxycarbonyl-(S)-2,3-diaminopropionate TFA salt.

Methyl $N^2$-n-butyloxycarbonyl-$N^3$-Boc-(S)-2,3-diaminopropionate (13.9 mmol, 4.4 g) was dissolved in 25 mL methylene chloride and 35 mL TFA and after 1 hour, the solution was concentrated to give an oily product. Yield 4.8 g (100%). NMR (DMSO-$d_6$): δ 8.02 (b, 3H); 7.68 (d, 2H); 4.38 (m, 1H); 3.99 (t, 2H); 3.68 (s, 3H); 3.22 (m, 1H); 3.06 (m, 1H); 1.55 (m, 2H); 1.34 (m, 2H); 0.89 (t, 3H).

Part E: Methyl-$N^2$-n-butyloxycarbonyl-$N^3$-[3-(4-cyanophenyl)isoxazolin-5(S)-ylacetyl]-(S)-2,3-diaminopropionate To a solution of 3-(4-cyanophenyl)isoxazolin-5(S)-ylacetic acid (5.2 mmol, 1.2 g) [Chiral starting material was prepared from the racemic compound of Ex. 275, Part A by resolution on a 50 X 2 cm Chiralpak AD column using 0.1% TFA/EtOH at 10° C. to give S-isomer (faster eluting) and R-isomer (slower eluting). Alternately, the isomers were resolved by crystallization of the chinconidine salt of the 5-S isomer of the isoxazolines from acetone, leaving the 5(R), isomer in the mother liquor. The absolute stereochemistry of the crystalline salt was determined by X-ray crystallography to be the 5(S) isoxazoline.] and methyl $N^2$-butyloxycarbonyl-(S)-2,3-diaminopropionate TFA salt (6 mmol, 1.53 g) in 20 ml DMF cooled in an ice bath was added diisopropylethylamine (20 mmol, 3.5 mL) followed by BOP (5.5 mmol, 2.43 g). After stirring at room temperature for 3 hours, ethyl acetate was added and the solution was washed with 0.5 N HCl, brine, NaHCO3 and brine, dried (MgSO4), and concentrated to give 1.9 g (87%) product. NMR (DMSO-$d_6$): δ 8.12 (t, 1H); 7.94 (d, 2H); 7.83 (d, 2H); 7.46 (d, 1H); 5.04 (m, 1H); 4.16 (m, 1H); 3.96 (t, 2H); 3.64 (s, 3H); 3.58 (dd, 1H); 3.40 (m, 2H); 3.20 (dd, 1H); 2.56 (dd, 1H); 2.43 (dd, 1H); 1.52 (m, 2H); 1.32 (m, 2H); 0.88 (t, 3H).

Part F: Methyl-$N^2$-n-butyloxycarbonyl-$N^3$[3-(4-amidinophenyl)isoxazolin-5(S)-ylacetyl]-(S)-2,3-diaminopropionate TFA salt.

To a solution of methyl-$N^2$-n-butyloxycarbonyl-$N^3$-[3-(4-cyanophenyl)isoxazolin-5(S)-ylacetyl]-(S)-2,3-diaminopropionate (4.4 mmol, 1.9 g) in 50 mL methanol was bubbled with HCl gas at 0° C. for 1 hour and the solution was stirred at room temperature for 5 hours and concentrated. The residue was taken up in 20 mL methanol and ammonium carbonate (11 mmol, 1.1 g) was added. The mixture was stirred at room temperature overnight and concentrated. The solid was dissolved in ethanol/water/TFA and purification on reversed phase HPLC gave 1.0 g (40%) product. ESI (M+H)$^+$: Calcd 448.3; Found 448.3.

EXAMPLE 314B

Methyl-$N^2$-n-butyloxycarbonyl-$N^3$-[3-(4-amidinophenyl)isoxazolin-5(R)-ylacetyl]-(S)-2,3-diaminopropionate TFA salt Part A: 3-(4-cyanophenyl)-5(R)-ylacetic acid This material was resolved from 3-(4-cyanophenyl) isoxazolin-5(R,S)-ylacetic acid as described above in the proceudure for Example 314A, Part E.

Part B: Methyl-$N^2$-n-butyloxycarbonyl-$N^3$-[3-(4-cyanophenyl)isoxazolin-5(R)-ylacetyl]-(S)-2,3-diaminopropionate.

This material was synthesized from 3-(4-cyanophenyl)-5(R)-ylacetic acid (4.3 mmol, 1.0 g), Methyl $N^2$-butyloxycarbonyl-(S)-2,3-diaitinopropionate TFA salt (5 mmol, 1.27 g), BOP (4.5 mmol, 2 g) and diisopropylethylamine (16 mmol, 2.8 mL) using the same procedure as for XVI. Yield 1.75 g (95%). NMR (DMSO-$d_6$): δ 8.12 (t, 1H); 7.94 (d, 2H); 7.83 (d, 2H); 7.46 (d, 1H); 5.04 (m, 1H); 4.16 (m, 1H); 3.96 (t, 2H); 3.64 (s, 3H); 3.58 (dd, 1H); 3.40 (m, 2H); 3.20 (dd, 1H); 2.56 (dd, 1H); 2.43 (dd, 1H); 1.52 (m, 2H); 1.32 (m, 2H); 0.88 (t, 3H).

Part C: Methyl-$N^2$-n-butyloxycarbonyl-$N^3$-[3-(4-amidinophenyl)isoxazolin-5(R)-ylacetyl]-(S)-2,3-diaminopropionate TFA salt This compound was synthesized from Methyl-$N^2$-n-butyloxycarbonyl-$N^3$-[3-(4-cyanophenyl)isoxazolin-5(R)-ylacetyl]-(S)-2,3-diaminopropionate (4.0 mmol, 1.7 g) using the same procedure as for Example 314A, Part G. Yield 1.0 g (45%). ESI (M+H)$^+$: Calcd 448.3; Found 448.3.

EXAMPLE 317

$N^2$-(2-Phenylethylsulfonyl)-$N^3$-[3-(4-amidinophenyl)isoxazolin-5(R,S)-ylacetyl]-(S)-2,3-diaminopropionic Acid TFA Salt Prepared according to Example 490a. MS (ESI, e/z, relative intensity): 502 (M+H)$^+$, (100%).

EXAMPLE 344

Methyl 3(R)-{5(R,S)-N-[3-(4-Amidinophenyl)
isoxazolin-5-ylacetyl]amino}heptanoate Part A. (E)-Methyl 2-heptenoate To a solution of diethyl methylphosphonoacetate (19 ml, 104 mmol) in dry THF (800 ml) at −4° C. was added 64 ml of n-BuLi (1.6 M in hexane, 102 mmol) dropwise over 45 min. The resulting solution was stirred 1 h at room temp. Valeraldehyde (10.0 ml, 94 mmol) was added and stirred 3.5 h at room temp. The reaction was quenched with 25 ml sat. $NH_4Cl$. Solvents were distilled at atmospheric pressure, and the resulting solids were taken up in EtOAc, extracted with water and brine, and dried with $Na_2SO_4$. The solvents were again distilled at atmospheric pressure, and the resulting yellow liquid was distilled under house vacuum to yield 7.2 g clear liquid, boiling range under house vacuum 90–125° C.; HRMS, e/z Calc. for $(M+H)^+$: 143.1072. Found: 143.1070; IR(film) 1728, 1658 $cm^{-1}$.

Part B. N-(1-(R)-1-Phenylethyl)benzamide

A solution of benzoyl chloride (22.5 mL, 0.19 mole) in dichloromethane (10 mL) was added dropwise over 1.5 h to a 0° C. solution of (R)-(+)-α-methylbenzylamine (25 mL, 0.19 mole), triethylamine (31 mL, 0.22 mole), and 4-DMAP (100 mg), in dichloromethane (1 L). After 1.75 h at 0° C. the mixture was concentrated in vacuo, then diluted with EtOAc. This mixture was extracted with water, 1 M HCl, water, and brine, then dried ($MgSO_4$) and concentrated to yield 43.4 g of a colorless crystalline solid; mp 121.0–121.5° C.; IR(KBr) 3332, 1636 $cm^{-1}$; $[\alpha]_D^{25}$−2.30° (c=1.002, $CH_2Cl_2$); Anal. Calc. for $C_{15}H_{15}NO$: C, 79.97; H, 6.71; N, 6.22. Found: C, 79.88; H, 6.65; N, 6.17.

Part C. N-(1-(R)-1-Phenylethyl)-N-benzylamine $BH_3$/THF (1 M in THF, 220 mL, 220 mmol) was added dropwise over 1 h to a 0° C. solution of the above benzamide (20 g, 89 mmol) in dry THF (200 mL). The ice bath was removed, and the mixture was heated to reflux for 40 h. A TLC analysis indicated incomplete reaction, so more $BH_3$/THF (1 M in THF, 30 mL, 30 mmol) was added, and heating resumed for 22.5 h. After cooling, MeOH (250 mL) was added dropwise cautiously over 5 h. The resulting mixture was boiled for 2 h, then cooled and concentrated in vacuo. Reconcentration from MeOH (2×500 mL) and drying under high vacuum gave 19.3 g of an oil containing a small amount of a precipitate. This crude product was stirred with hot 2 M HCl (140 mL) to generate a clear solution, then slowly cooled to RT, and ultimately in an ice bath to yield a crystalline solid, as described by Simpkins (*Tetrahedron* 1990, 46(2), 523). The solid was collected by filtration and rinsed with a small amount of water. After air drying for 3 d, 16.35 g of the hydrochloride salt was obtained; mp 178.5–179.5° C.; $[\alpha]_D^{21}$+18.9° (c=4.0, EtOH). The salt was converted to the free base by extraction with $Et_2O$ and aq. KOH, then Kugelrohr distilled, oven temp. 120–140° C. (1.1 mm Hg) to give 12.5 g of an oil; $[\alpha]_D^{21}$+61.2° (c=3.98, EtOH); Anal. Calc. for $C_{15}H_{17}N$: C, 85.26; H, 8.11; N, 6.63. Found: C, 84.93; H, 7.75; N, 6.58.

Part D. Methyl 3-(R)-[N-benzyl-N-(1-(R)-1-phenylethyl)amino]heptanoate

Following the asymmetric Michael addition method of Davies (*Tetrahedron:Asymmetry* 1991, 2(3), 183), n-butyllithium (1.6 M in hexanes, 4.4 mL, 7.0 mmol) was added dropwise over 3 min to a 0° C. solution of N-(1-(R)-1-phenylethyl)-N-benzylamine (1.5 g, 7.0 mmol) in dry THF (35 mL). After 30 min, the resulting dark pinkish-red solution was cooled to −78° C., and a solution of methyl 2-heptenoate (0.50 g, 3.5 mmol) in THF (10 mL) was added dropwise over 10 min. After 13 min, the cold reaction was quenched with saturated $NH_4Cl$ (7 mL). After warming to RT, the mixture was extracted with $Et_2O$ and brine, dried (MgSO4), and concentrated in vacuo. The product was purified by chromatography over silica gel, eluting with 0% to 50% EtOAc in hexane. The cleanest major product fractions (apart from a few mixed fractions) were concentrated in vacuo to give 0.91 g of a pale yellow oil which by NMR is a single diastereomer, with the newly generated asymmetric center assigned as 3(R) by analogy with the Davies reference above; $^{13}$C NMR (300 MHz, $CDCl_3$) δ 173.31, 143.40, 141.78, 128.40, 128.27, 128.11, 128.00, 126.91, 126.67, 57.90, 54.22, 51.32, 50.05, 36.83, 33.28, 29.32, 22.72, 19.40, 14.12; $[\alpha]_D^{25}$+12.96° (c=0.602, MeOH).

Part E. Methyl 3-(R)-aminoheptanoate ● acetic acid salt

Methyl 3-(R)-[N-benzyl-N-(1-(R)-1-phenylethyl)amino]heptanoate (0.70 g, 2.0 mmol), 20% $Pd(OH)_2$/C (0.35 g), cyclohexene (7 mL), glacial HOAc (0.12 mL, 2.1 mmol), and MeOH (14 mL) were heated at reflux under $N_2$ for 20.5 h. After cooling, the catalyst was removed by filtration thru a Celite plug, rinsed with MeOH, and the solution concentrated in vacuo. Drying overnight under high vacuum yielded 0.43 g of a viscous oil; $^{13}$C NMR (300 MHz, $CDCl_3$) δ 177.64, 171.52, 51.97, 48.22, 37.24, 33.08, 27.50, 23.31, 22.29, 13.76; $[\alpha]_D^{25}$−10.6° (c=0.602, MeOH).

Part F. Methyl 3(R)-[5(R,S)-N-[3-(4-cyanophenyl)isoxazolin-5-ylacetyl]amino}heptanoate To a suspension of 3-(4-cyanophenyl)isoxazolin-5-ylacetic acid (300 mg, 1.3 mmol) in EtOAc (10 ml) was added methyl 3-(R)-aminoheptanoate acetic acid salt (287 mg, 1.3 mmol), TBTU (420 mg, 1.3 mmol), and Et3N (600 μl, 4.3 mmol). After stirring at room temp 2.5 h, the reaction mixture was extracted with 5% $KHSO_4$, sat $NaHCO_3$, and brine, then dried with $Na_2SO_4$. Evaporation, followed by chromatography over silica gel in 50–100% EtOAc/hexanes yielded 245 mg colorless glass. MS ($NH_3$-DCI) Calc. for $(M+H)^+$: 372, $(M+NH_4)^+$: 389. Found: 372, 389.

Part G. Methyl 3(R)-{5(R,S)-N-[3-(4-Amidinophenyl)isoxazolin-5-ylacetyl]amino}heptanoate To a solution of methyl 3(R)-{5(R,S)-N-[3-(4-cyanophenyl)isoxazolin-5-ylacetyl]amino}heptanoate (179 mg, 0.48 mmol) in 15 ml dry MeOH at 0° C., was added a stream of HCl gas generated from dropping two 20 ml portions of $H_2SO_4$ into solid NaCl over 35 min. After stirring 20 h at room temp, the solvent was removed with a rapid stream of $N_2$. $Et_2O$ was added and removed with a rapid stream of $N_2$. The resulting gummy oil was taken up in 15 ml dry MeOH, to which was added $(NH_4)_2CO_3$ (1.1 g, 11.4 mmol). After stirring 19.5 h at room temp, the solvent was removed with a rapid stream of $N_2$, and the resulting white solid was purified by chromatography over silica gel, eluting with 0–20% MeOH/$CHCl_3$. Purified product was taken up in 5% MeOH/$CHCl_3$ and filtered. Concentration of the filtrate yielded 100 mg white solid. IR(KBr) 3600–2800, 1734, 1676, 1640 $cm^{-1}$; HRMS, e/z Calc. for $(M+H)^+$: 389.2189. Found: 389.2192.

EXAMPLE 348

Ethyl 3(R)-{5(R,S)-N-[3-(4-amidinophenyl)
isoxazolin-5-ylacetyl]amino}-5-methylhexanoate ●
trifluoroacetic Acid Salt Part A. (E)-Ethyl 5-methyl-2-hexenoate Prepared in analogous fashion to rethyl 2-heptenoate, using triethyl phosphonoacetate, stirring 17 h at room temp upon addition of isovaleraldehyde. Distillation under house vacuum yielded 72% clear oil, boiling range under house vacuum 80–130° C.; IR(film) 1724, 1656 $cm^{-1}$.

Part B. Ethyl 3-(R)-[N-benzyl-N-(1-(R)-1-phenylethyl)amino]-5-methylhexanoate Prepared in analogous fashion via the asymmetric Michael addition of Ex. 344, part D above. Yield a viscous pale yellow oil (65%); $^{13}$C NMR (300 MHz, CDCl$_3$) δ 172.83, 143.56, 142.17, 128.27, 128.21, 128.15, 128.03, 126.96, 126.60, 60.10, 58.56, 52.43, 50.09, 3.23, 36.72, 24.76, 23.48, 22.13, 20.20, 14.21; $[\alpha]_D^{25}$+5.12° (c=0.606, EtOH).

Part C. Ethyl 3-(R)-amino-5-methylhexanoate ● acetic acid salt

Prepared as previously described except EtOH was used as solvent. Yield a waxy solid (94%); mp 57–61° C.; HRMS, e/z Calc. for (M+H)$^+$: 174.1494. Found: 174.1485.

Part D. Ethyl 3-(R)-amino-5-methylhexanoate ● hydrochloric acid salt

The above acetic acid salt (1.1 g, 4.7 mmol) was stirred 4 min in 4 M HCl/dioxane (5.0 ml). The resulting solution was triturated with Et$_2$O, cooled, and the clear liquid decanted, leaving an orange oil which solidified to 960 mg waxy solid on high vacuum; $^1$H NMR (300 MHz, CDCl$_3$) ∂ 8.49 (br, 3H), 4.20 (q, J=7.3, 2H), 3.70–3.65 (m, 1H), 2.86–2.80 (m, 2H), 1.83–1.80 (m, 2H), 1.58–1.54 (m, 1H), 1.30–1.26 (t, J=7.3, 3H), 0.99–0.91 (m, 6H).

Part E. Ethyl 3(R)-{5(R,S)-N-[3-(4-(N-t-butoxycarbonylamidino)phenyl)isoxazolin-5-ylacetyl]amino}-5-methylhexanoate To a suspension of 3-(4-(N-t-butoxycarbonylamidino)phenyl]isoxazolin-5-ylacetic acid (78 mg, 0.22 mmol) in EtOAc (5 ml) was added ethyl 3-(R)-amino-5-methylhexanoate hydrochloride salt (47 mg, 0.22 mmol), TBTU (72 mg, 0.22 mmol), and Et$_3$N (100 μl, 0.72 mmol). After stirring 6 h at room temp, the reaction mixture was extracted with pH 4 buffer (potassium hydrogen phthalate), sat NaHCO$_3$, and brine, then dried with Na$_2$SO$_4$. Evaporation, followed by chromatography over silica gel in 100% EtOAc yielded 33 mg colorless glass; $^1$H NMR (300 MHz, CDCl$_3$) ∂ 7.90 (d, J=8.4, 2H), 7.70 (dd, J=8.5, J'=1.9, 2H), 6.32–6.28 (m, 1H), 5.13–5.11 (m, 1H), 4.34–4.33 (m, 1H), 4.17–4.09 (m, 2H), 3.56–3.47 (m, 1H), 3.25–3.17 (m, 1H), 2.71–2.46 (m, 4H), 1.66–1.47 (m, 2H), 1.56 (s, 9H), 1.31–1.23 (m, 4H), 0.92 (dd, J=6.6, J'=1.8, 3H), 0.84 (d, J=6.6, 3H).

Part F. Ethyl 3(R)-{5(R,S) -N-[3-(4-amidinophenyl)isoxazolin-5-ylacetyl]amino}-5-methyl hexanoate ● trifluoroacetic acid salt The product from Part E above (29 mg, 0.058 mmol) was dissolved in DCM (300 μl), to which was added TFA (100 μl). The resulting solution was stirred at room temp under a CaSO$_4$ drying tube for 3.5 h, and triturated with Et$_2$O. 24 mg white solid were collected by filtration; $^1$H NMR (300 MHz, CDCl$_3$) ∂ 9.4 (br, 1H), 9.0 (br, 1H), 7.8 (s, 4H), 5.0 (m, 1H), 4.2 (m, 1H), 4.0 (q, 2H), 3.6 (m, 1H), 3.3 (m, 2H), 2.4 (m, 3H), 1.6 (m, 1H), 1.4 (m, 1H), 1.2 (m, 4H), 0.8 (m, 6H); HRMS, e/z Calc. for (M+H)$^+$: 403.2345. Found: 403.2363.

EXAMPLE 350

Methyl 3(R,S)-{5(R,S)-N-[3-(4-amidinophenyl)isoxazolin-5-ylacetyl]amino}-4-(phenylthio)butanoate ● hydrochloric acid salt;

Part A. Methyl phenylthioacetoacetate

To a solution of thiophenol (5.00 ml, 48.6 mmol) in DMF (20 ml), K$_2$CO$_3$ (10.09 g, 73 mmol) and methyl chloroacetoacetate (5.93 ml, 48.6 mmol) were added. The reaction mixture was stirred 6 h at 50° C., diluted with EtOAc, and extracted with saturated Na$_2$SO$_4$, water, and brine, then dried (Na$_2$SO$_4$) and concentrated. The resulting oil was chromatographed with 20% EtOAc in Hexane to yield 9.40 g yellow oil; MS (CH4-DCI) Calc. for (M+H)$^+$: 224. Found: 224; IR(KBr) 2954, 1656, 1438, 626 cm$^{-1}$.

Part B. Methyl-3(R,S)-amino-4-penylthiobutanoate

To a solution of methyl phenylthioacetoacetate (1.00 g, 4.5 mmol) in MeOH (20 ml), ammonium formate (4.26 g, 6.75 mmol) and sodium cyanoborohydride (0.42 g, 6.7 mmol) were added. The reaction mixture was stirred at room temperature for 18 h, then diluted with EtOAc and partitioned into 1 M HCl. The aqueous layer was then basified to pH=8.0 with NaOH. The desired product was extracted out with EtOAc, washed with water and brine, dried over Na$_2$SO$_4$ and concentrated to yield 0.61 g yellow oil; MS (NH3-CI/DDIP) Calc. for (M+H)$^+$: 226. Found: 226; $^1$H NMR (300 MHz, CDCl$_3$) δ 7.39 (d, J=7, 2H), 7.32–7.26 (m, 3H), 7.22 (d, J=10, 1H), 3.74 (s, 3H), 3.39–3.31 (m, 1H), 3.13–3.07 (dd, J=13, J'=9, 1H), 2.91–2.83 (dd, J=12, J'=6, 1H), 2.65–2.58 (dd, J=12, J'=6, 1H), 2.46–2.38 (dd, J=16, J'=8, 1H).

Part C. Methyl-3(R,S)-{5(R,S)-N-[3-(4-cyanophenyl)isoxazolin-5-ylacetyl]amino}-4-(phenylthio)butanoate To a suspension of 3-(4-cyanophenyl)isoxazolin-5-ylacetic acid (0.50 g, 2 mmol) in EtOAc (10 ml), methyl-3(R,S)amino-4-(phenylthio)butanoate (0.51 g, 2 mmol), TBTU (0.71 g, 2 mmol), and Et$_3$N (1.24 ml, 8.9 mmol) were added. The reaction mixture was stirred 2 h at room temperature, diluted with EtOAc, washed with 5% citric acid, saturated NaHCO$_3$, and brine, dried over Na$_2$SO$_4$, concentrated, and the resulting oil was chromatographed over silica gel in 100% EtOAc to yield 0.61 g of a yellow glass: MS (NH$_3$-CI/DDIP) Calc. for (M+H)$^+$: 438.1. Found: 438.1; Anal. Calc. for C$_{32}$H$_{23}$N$_3$O$_4$S$_1$: C, 63.31; H, 5.30; N, 9.60; S, 7.33. Found: C, 62.99; H, 5.22; N, 9.53; S, 7.30.

Part D. Methyl 3(R,S)-{5(R,S)-N-[3-(4-amidinophenyl)isoxazolin-5-ylacetyl]amino}-4-(phenylthio)butanoate ● hydrochloric acid salt The product from Part C above (0.30 g,0.68 mmol) was dissolved in dry MeOH (20 ml) at 0° C. To the resulting solution, HCl gas was bubbled in from a generator as described in Example 344, Part G, over a period of 2 h. The generator was removed and the reaction mixture stirred at 0° C. for 18 h, then concentrated and triturated with CHCl$_3$. The resulting precipitate was collected by filtration and redissolved in dry MeOH (20 ml). To this solution, ammonium carbonate (0.99 g, 10 mmol) was added and the mixture stirred at room temperature for 18 h. The solution was concentrated and recrystallized from DCM/MeOH to yield 0.14 g white solid; HRMS, e/z Calc. for (M+H)$^+$: 455.1753. Found: 455.175; $^1$H NMR (300 MHz, d$_6$-DMSO) δ 9.44 (br s, 1H), 9.18 (br s, 1H), 8.22 (d, J=10, 1H), 7.86 (m, 4H), 7.41–7.25 (m, 4H), 7.2 (m, 1H), 5.03 (m, 1H), 4.2 (m, 1H), 3.59 (s, 3H), 3.29–3.05 (m, 4H), 2.8–2.39 (m, 4H).

EXAMPLE 359

Methyl 3(R,S)-{5(R,S)-N-[3-(4-amidinophenyl)isoxazolin-5-ylacetyl]amino}-4-(phenylsulfonamido)butanoate ● Trifluoroacetic Acid Salt;

Part A. Methyl 3-(R,S)-hydroxy-4-aminobutanoate ● hydrochloric acid salt

Chlorotrimethylsilane (100 mL, 0.79 mol) was added dropwise over 1.5 h to a stirred 0° C. suspension of 4-amino-3-(R,S)-hydroxybutyric acid (25 g, 0.21 mol) in MeOH (1 L). The resulting clear solution was allowed to slowly warm to room temperature overnight. The solvent was evaporated in vacuo, and the resulting residue was reconcentrated from more MeOH (2×500 mL). Drying under high vacuum produced 37 g of a-viscous oil; $^{13}$C NMR (300 MHz, d$_6$-DMSO) δ 171.42, 90.14, 64.67, 51.89, 44.39; Anal. Calc. for C$_5$H$_{16}$ClNO$_3$: C, 35.41; H, 7.13; N, 8.26; Cl, 20.90. Found: C, 35.18; H, 7.09; N, 8.18; Cl, 20.77.

Part B. Methyl 3-(R,S)-hydroxy-4-(phenylsulfonamido) butanoate

A solution of benzenesulfonyl chloride (7.5 mL, 59 mmol) in dichloromethane (10 mL) was added dropwise over 55 min to a 0° C. solution of the Part A amine salt (10 g, 50 mmol), and Et$_3$N (17 mL, 120 mol) in dichloromethane (110 mL). The mixture was allowed to slowly warm to room temperature, and stirring was continued over the weekend. After solvent removal in vacuo, the mixture was diluted with EtOAc and extracted with H$_2$O, 0.1 M HCl, and brine. Drying (MgSO$_4$) and solvent removal in vacuo yielded 14.6 g of a viscous oil; $^{13}$C NMR (300 MHz, CDCl$_3$) δ 172.67, 139.79, 132.78, 129.22, 127.02, 66.77, 52.01, 47.72, 38.31; Anal. Calc. for C$_{11}$H$_{15}$NO$_5$S: C, 48.34; H, 5.53; N, 5.13; S, 11.73. Found: C, 48.44; H, 5.61; N, 4.90; S, 11.34.

Part C. Methyl 3-oxo-4-(phenylsulfonamido)butanoate

The Part B alcohol (2.8 g, 10 mmol) was oxidized with Jones reagent under standard conditions. The ketone was purified by chromatography on silica gel, eluting with 0% to 100% EtOAc in hexane, to yield 1.11 g of a waxy solid; mp 94.5–95.5° C.; $^{13}$C NMR (300 MHz, CDCl$_3$) δ 197.08, 166.80, 139.17, 133.08, 129.29, 127.17, 52.71, 51.91, 46.15; Anal. Calc. for C$_{11}$H$_{13}$NO$_5$S: C, 48.70; H, 4.83; N, 5.16; S, 11.82. Found: C, 48.77; H, 4.69; N, 5.08; S, 11.88.

Part D. Methyl 3-(R,S)-3-amino-4-(phenylsulfonamido) butanoate

To a room temperature solution of the Part C ketone (0.71 g, 2.6 mmol) in MeOH (7 mL) and THF (3 mL) was added ammonium formate (2.5 g, 39 mmol) and sodium cyanoborohydride (0.25 g, 3.9 mmol). After 45.5 h, solvent was evaporated, and the residue was diluted with EtOAc (70 mL). This solution was extracted with 1.0 M NaOH, H$_2$O, and brine. After concentration, the product was purified by chromatography on silica gel, eluting with 0% to 100% EtOAc in hexane, then 1% to 20% MeOH in EtOAc to yield 0.16 g of a viscous oil, which eventually solidified; $^1$H NMR (300 MHz, CDCl$_3$) ∂ 9.79 (br, 2H), 7.84 (d, 2H, J=8 Hz), 7.81 (br, 1H), 7.68–7.53 (m, 3H), 4.05–3.92 (m, 1H), 3.75 (s, 3H), 3.33–3.17 (m, 2H), 2.89–2.72 (m, 2H); HRMS, e/z Calc. for (M+H)$^+$: 273.0909. Found: 273.0916.

Part E. Methyl 3-(R,S)-{5(R,S)-N-[3-(4-(N-t-butoxycarbonylamidino)phenyl)isoxazolin-5-ylacetyl] amino}-4-(phenylsulfonamido)butanoate This compound was prepared analogous to Example 348, Part E, stirring 24 h in 5 ml EtOAc and 1 ml DMF. Chromatography in 5% MeOH/CHCl$_3$ yielded 80% of an orange solid; IR(KBr) 3296, 2338, 1736, 1660, 1618 cm$^{-1}$; HRMS, e/z Calc. for (M+H)$^+$: 602.2285. Found: 602.2270.

Part F. Methyl 3(R,S)-{5(R,S)-N-[3-(4-amidinophenyl) isoxazolin-5-ylacetyl]amino}-4-(phenylsulfonamido) butanoae ● trifluoroacetic acid salt The product from Part E was deprotected analogously to Example 348, Part F, yielding 86% pink solid; IR(KBr) 3312, 3104, 1734, 1670; HRMS, e/z Calc. for (M+H)$^+$: 502.1760. Found: 502.1761. The more active diastereomer (based on PRP assay) was isolated from the above mixture by SFC HPLC, Chiralpak AD—2×25 cm, eluted with 0.1% TFA/25% MeOH/75% CO$_2$. Under these conditions, the more active diastereomer eluted last.

EXAMPLE 362

Methyl 3(R,S)-{5(R,S)-N-[3-(4-amidinophenyl) isoxazolin-5-ylacetyl]amino}-4-(n-butylsulfonamido)butanoate ● trifluoroacetic acid salt;

Part A. Methyl 3-(R,S)-hydroxy-4-(n-butylsulfonamido) butanoate

This compound was prepared entirely analogously to Ex.359, Part B, using n-butylsulfonylchloride instead. A colorless, waxy solid of excellent purity was obtained in 65% yield without purification; mp 46–50° C.; $^{13}$C NMR (300 MHz, CDCl$_3$) δ 172.64, 67.29, 52.56, 51.99, 47.83, 38.40, 25.57, 21.52, 13.55; Anal. Calc. for C$_9$H$_{19}$NO$_5$S: C, 42.67; H, 7.56; N, 5.53; S, 12.66. Found: C, 42.69; H, 7.59; N, 5.36; S, 12.78.

Part B. Methyl 3-oxo-4-(n-butylsulfonamido)butanoate

The immediately preceeding alcohol was oxidized as described for Example 359, Part C, to give a 57% yield of a colorless solid; mp 53–55° C.; Anal. Calc. for C$_9$H$_{17}$NO$_5$S: C, 43.02; H. 6.82; N, 5.57; S, 12.76. Found: C, 42.68; H, 7.03; N, 5.74; S, 13.06.

Part C. Methyl 3(R,S)-3-amino-4-(n-butylsulfonamido) butanoate

This compound was prepared analogous to Example 350, Part B, using the product from Part B above (1.20 g, 4.8 mmol) yielding 0.26 g yellow oil; 1H NMR (300 MHz, CDCl$_3$) δ 3.70 (s, 3H), 3.38 (m, 1H), 3.24–3.13 (m, 1H), 3.02 (m, 4H), 2.58–2.52 (dd, J=16, J'=11, 1H), 1.79 (m, 2H), 1.24 (m, 2H), 0.95 (t, 3H); MS (NH4-DCI) Calc. for (M+H)$^+$: 271. Found: 271.

Part D. Methyl-3(R,S)-{5(R,S)-N-[3-(4-(N-t-butoxycarbonylamidine)phenyl)isoxazolin-5-ylacetyl] amino}-4-(n-butylsulfonylamidc)butanoate To a solution 3-[4-(N-t-butoxycarbonylamidine)phenyl] isoxazolin-5-ylacetic acid (0.24 g, 0.83 mmol) in DMF (20 ml), the product from Part C above (0.29 gr, 0.83 mmol), TBTU (0.27 g, 0.83 mmol), and Et$_3$N (0.46 ml, 3.3 mmol) was added. After stirring 4 h at room temperature, the reaction mixture was diluted with EtOAc, extracted with pH 4 buffer (potassium hydrogen phthalate), saturated NaHCO$_3$, brine, then dried (NaSO$_4$). Concentration, followed by chromatography over silica gel in 100% EtOAc, yielded 1.17 g of a white foam; MS (NH3-DCI) Calc. for (M+H)$^+$: 582.3. Found: 582; IR(KBr) 3312, 2338, 1620, 1144 cm$^{-1}$.

Part E. Methyl 3(R,S)-{5(R,S)-N-[3-(4-amidinophenyl) isoxazolin-5-ylacetyl]amino}-4-(n-butylsulfonylamido) butanoate ● trifluoroacetic acid To a solution of the product from Part D above (0.22 g, 0.37 mmol) in DCM (10 ml), trifluoroacetic acid (2.2 ml) was added. The reaction mixture was stirred 2 h at room temperature, triturated with Et$_2$O, and the resulting precipitate was chromatographed over silica gel in 20% MeOH in CHCl$_3$ to yield 0.20 g white solid; HRMS, e/z Calc. for (M+H)$^+$: 482.2073. Found: 482.2090; mp=178–184° C.

EXAMPLE 365

Methyl {5(R,S)-N-[3-(4-amidinophenyl)isoxazolin-5-ylacetyl]amino}-4-(methoxycarbonyl)butanoate ● trifluoroacetic Acid Salt Part A. Dimethyl 3-aminoglutarate ● hydrochloric acid salt This product was prepared similarly to Example 359, Part A, from β-glutamic acid to yield the diester as a colorless gum in quantitative yield; HRMS, e/z Calc. for (M+H)$^+$: 176.0923. Found: 176.0933.

Part B. Methyl {5(R,S)-N-[3-(4-(N-t-butoxycarbonylamidino)phenyl)isoxazolin-5-ylacetyl] amino}-4-(methoxycarbonyl)butanoate Prepared analogous to Example 359, Part E, to yield 32% of a white solid; IR(KBr) 3306, 2338, 1738, 1656, 1620 cm$^{-1}$; HRMS, e/z Calc. for (M+H)$^+$: 505.2298. Found: 505.2283.

Part C. Methyl {5(R,S)-N-[3-(4-amidinophenyl)isoxazolin-5-ylacetyl]amino}-4-(methoxycarbonyl)butanoate ● trifluoroacetic acid salt Prepared analogous to Example 348, Part F, yielding 83% white solid; IR(KBr) 3316, 3102, 2340, 1736, 1670 cm$^{-1}$; HRMS, e/z Calc. for (M+H)$^+$: 405.1774. Found: 405.1775.

EXAMPLE 368

Methyl 3(R,S)-{5(RS)-N-[3-(4-amidinophenyl) isoxazolin-5-ylacetyl]amino}-4-(methoxycarbonyl)-pentanoate ● trifluoroacetic Acid Salt Part A. Dimethyl 3-(R,S)-aminoadipate ● hydrochloric acid salt This product was prepared as in Example 359, Part A, from β-aminoadipic acid to yield a colorless gum in quantitative yield; HRMS, e/z Calc. for (M+H)$^+$: 190.1079. Found: 190.1080.

Part B. Methyl-3(R,S)-{5(R,S)-N-[3-(4-(N-t-butoxycarhonylamidine)phenyl)isoxzalin-5-ylacetyl] amino}-4-(methoxycarbonyl)pentanoate This product was prepared similarly as in Example 362, Part D, using the product from Part B above (0.70 g, 3.1 mmol) instead to yield 1.17 g of a white foam; HRMS, e/z Calc. for (M+H)$^+$: 519.2454. Found: 519.2459; Anal. Calc. for $C_{25}H_{34}N_4O_8$: C, 57.90; H, 6.61; N,10.80. Found: C, 57.73; H, 6.51; N, 10.86.

Part C. Methyl-3(R,S)-{5(R,S)-N-[3-(4-amidinophenyl) isoxazolin-5-ylacetyl]amine}-4-(methoxyacarbonyl) pentanoate ● trifluoroacetic acid salt This product was prepared as in Example 362, Part E, using the product from Part C above (1.00 g, 1.9 mmol) to yield 0.9 g white solid; HRMS, e/z Calc. for (M+H)$^+$: 419.1930. Found: 419.1921; mp=214–215° C. (decomposes).

EXAMPLE 375

Preparation of 2-(R,S)-2-Carboxymethyl-1-{5-(R, S)-N-[3-(4-amidinophenyl)isoxazolin-5-yl acetyl] }piperidine Part A. Preparation of 2-(Methoxy-2-oxoethyl)piperidine Pyridylacetic acid hydrochloride (10.00 g, 57.6 mmol) and platinum(IV) oxide (1.00 g, 4.4 mmol) were shaken in a mixture of 75 ml acetic acid, 75 ml methanol, and 10 ml conc. HCl on Parr under 60 psi hydrogen at room temperature overnight. The mixture was then filtered through Celite, and the filtrate evaporated under reduced pressure to yield 8.42 g (75.9%) of the title compound as an off-white solid. MS (NH$_3$-CI/DDIP): m/e 158 (M+H)$^+$. $^1$H NMR (300 MHz, CDCl$_3$): δ 1.50–1.96 (m, 6H); 2.80 (m, 2H); 3.20–3.60 (m, 3H); 3.76 (s, 3H). $^{13}$C NMR (60 MHz, d$_6$-DMSO): δ 21.94; 28.05; 37.46; 40.49; 44.12; 57.33; 52.74; 170.39.

Part B. Preparation of 2-(R,S)-2-(Methoxy-2-oxoethyl)-1-{5-(R,S)-N-[3-(4-cyanophenyl)isoxazolin-5-yl acetyl] }piperidine To 2.00 g (8.69 mmol) of 3-(4-cyanophenyl)-isoxazolin-5-yl acetic acid in 100 ml anhydrous DMF was added 1.36 g (8.69 mmol) of 2-(methoxy-2-oxoethyl)piperidine, 2.80 g (8.69 mmol) of TBTU, and 6.05 ml (34.7 mmol) of diisopropylethylamine. After stirring for 6 hrs, the reaction mixture was diluted with ethyl acetate and washed with 5% aqueous citric acid solution, water, 5% aqueous NaHCO$_3$ solution, and saturated NaCl solution. The organic layer was dried over Na$_2$SO$_4$ and filtered. The filtrate was evaporated under reduced pressure to give the crude product as a yellow foam. Purification by flash column chromatography on silica gel using 25–75% ethyl acetate in hexane yielded 1.54 g (48%) of the title compound as a yellow foam. One diastereomer (racemic) was isolated from the mixture. MS (NH$_3$-CI/DDIP): m/e 370 (M+H)$^+$. $^1$H NMR (300 MHz, CDCl$_3$): δ 1.42–1.76 (m, 6H); 2.60 (m, 2H); 2.77–3.01 (m, 3H); 3.05–3.26 (m, 2H); 3.56–3.70 (m, 4H); 4.50 (m, 1H); 5.20 (m, 1H); 7.69 (d, J=8.4 Hz, 2H); 7.77 (d, J=8.4 Hz, 2H).

Part C. Preparation of 2-(Methoxy-2-oxoethyl)-1-{N- [3-(4-amidinophenyl)isoxazolin-5-yl acetyl]}piperidine, (racemic diastereomer A)

HCl gas was bubbled for 2 hrs through a solution of 1.02 g (2.80 mmol) of the product of part B above in 30 ml of anhydrous MeOH cooled in an ice bath. The reaction flask was then sealed with Teflon tape and warmed to room temperature while stirring overnight. MeOH was evaporated under reduced pressure and then under vacuum to give the intermediate imidate as a yellow foam. MS (ESI): m/e 402 (M+H)$^+$. It was then stirred with 8.07 g (84.0 mmol) of (NH$_4$)$_2$CO$_3$ in 30 ml anhydrous EtOH overnight in a sealed reaction flask. After filtering, the filtrate was evaporated under reduced pressure to give the crude product as a yellow foam, which was then purified by flash column chromatography using 5–17% MeOH in CH$_2$Cl$_2$ to give 0.29 g (26.8%) of the title compound as a yellow solid. MS (ESI): m/e 387 (M+H)$^+$. $^1$H NMR (300 MHz, d$_6$-DMSO): δ 1.57–1.67 (br., 6H); 2.46–2.90 (m, 5H); 3.16 (m, 2H); 3.53–3.64 (m, 4H); 4.36 (br. m, 1H); 5.07 (br. m, 1H); 7.89 (m, 4H); 9.38 (br. s, 3H).

Part D. Preparation of 2-Carboxymethyl-1-{N-[3-(4-amidinophenyl)isoxazolin-5-yl acetyl]}piperidine, (Racemic Isomer A)

To a solution of 0.08 g (0.2 mmol) of the product isolated in Part C above in 5 ml anhydrous THF at ambient temperature was added 0.5 ml (0.5 mmol) of 1.0 M solution of NaOTMS in THF. After stirring overnight, solvent was evaporated under reduced-pressure to give a yellow solid, which was recrystallized from MeOH and Et$_2$O to give 0.05 g (64.9%) of the title compound as a yellow powder. MS (ESI): m/e 373 (M+H)$^+$. $^1$H NMR (300 MHz, CD$_3$OD): δ 1.68 (br., 6H); 2.56 (m, 2H); 2.72 (m, 3H); 2.94 (m, 2H); 3.57 (m, 4H); 4.46 (br., 1H); 5.18 (br., 1H); 7.84 (m, 4H).

EXAMPLE 377

Preparation of 2-(R,S)-2-Carboxymethyl-1-{5-(R, S)-N-[3-(4-amidinophenyl)isoxazolin-5-yl acetyl] }azepine Part A. Preparation of 2-(R,S)-2-(Ethoxy-2-oxoethyl)-1-{5-(R,S)-N-[3-(4-cyanophenyl)isoxazolin-5-yl acetyl]}azepine From 0.50 g (2.17 mmol) of 3-(4-cyanophenyl) isoxazolin-5-yl acetic acid, using 0.40 g (2.17 mmol) of 2-(ethoxy-2-oxoethyl)azepine, 0.70 g (2.17 mmol) TBTU, and 1.51 ml (8.70 mmol) diisopropylethylamine, 0.73 g (84.6 %) of the title compound was obtained following the procedure of Example 375, Part B. MS (NH$_3$-CI/DDIP): m/e 398 (M+H)$^+$. $^1$H NMR (300 MHz, CDCl$_3$): δ 1.26 (m, 11H); 1.83 (br., 2H); 2.05 (m, 1H); 2.18–2.65 (m, 2H); 2.76–2.85 (m, 1H); 3.04 (m, 2H); 3.62 (s, 1H); 4.08 (m, 2H); 5.22 (m, 1H); 7.68 (d, J=8.4 Hz, 2H); 7.78 (d, J=8.4 Hz, 2H).

Part B. Preparation of 2-(R,S)-2-(Ethoxy-2-oxoethyl)-1-{5-(R,S) -N-[3-(4-amidinophenyl)isoxazolin-5-yl acetyl] }azepine From 0.73 g (1.84 mmol) of 2-(R,S)-2-(ethoxy-2-oxoethyl)-1-{5-(R,S)-N-[3-(4-cyanophenyl)isoxazolin-5-yl acetyl]}azepine, using EtOH as the solvent, 0.42 g (61.6%)

of the title compound was obtained following the procedure of Example 375, Part C. MS (NH3-CI/DDIP): m/e 415(M+H)$^+$. $^1$H NMR (300 MHz, d$_6$-DMSO): δ 1.18 (m, 3H); 1.38 (m, 2H); 1.70 (m, 4H); 2.08 (br., 2H); 2.66 (m, 2H); 3.02–3.26 (m, 2H); 3.60 (br. m, 2H); 4.05 (m, 2H); 4.58 (,m, 1H); 5.10 (m, 1H); 7.90 (m, 4H); 9.38 (br. s, 3H).

Part C. Preparation of 2-(R,S)-2-Carboxymethyl-1-{5-(R,S)-N-[3-(4-amidinophenyl)isoxazolin-5-yl acetyl]}azepine From 0.16 g (0.35 mmol) of 2-(R,S)-2-(ethoxy-2-oxoethyl)-1-{5-(R,S)-N-[3-(4-amidinophenyl)isoxazolin-5-yl acetyl]}azepine and using 0.89 ml (0.89 mmol) of 1.0 M solution of NaOTMS in THF, 0.12 g (82.9%) of the title compound was obtained following the procedure of Example 375, Part D. MS (NH$_3$-DCI): m/e 387 (M+H)$^+$.

EXAMPLE 400

Preparation of 3-(R,S)-(Methoxy-2-oxoethyl)-4-{5-(R,S)-N-[3-(4-amidinophenyl)isoxazolin-5-yl acetyl]}piperazin-2-one Part A. Preparation of 3-(R,S)-(Ethoxy-2-oxoethyl)-4-{5-(R,S)-N-[3-(4-cyanophenyl)isoxazolin-5-yl acetyl]}piperazin-2-one From 1.00 g (4.34 mmol) of 3-(4-cyanophenyl)isoxazolin-5-yl acetic acid, using 0.81 g (4.34 mmol) of ethyl 2-piperazin-3-one acetate, 1.39 g (4.34 nmol) TBTU, and 3.02 ml (17.40 mmol) diisopropylethylamine, 1.08 g (62.4%) of the title compound was obtained following the procedure of Example 375, Part B. MS (NH$_3$-CI/DDIP): m/e 399 (M+H)$^+$. $^1$H NMR (300 MHz, CDCl$_3$): δ 1.26 (m, 3H); 2.71–3.65 (br., 9H); 3.87 (br. m, 1H); 4.16 (m, 2H); 5.01 & 5.09 (two t, J=5.0, 5.1 Hz, 1H); 5.20 (m, 1H); 7.00 & 7.12 (two br., 1H); 7.77 (m, 4H).

Part B. Preparation of 3-(R,S)-(Methoxy-2-oxoethyl)-4-{5-(R,S)-N-[3-(4-amidinophenyl)isoxazolin-5-yl acetyl]}piperazin-2-one From 1.08 g (2.71 mmol) of 3-(R,S)-(ethoxy-2-oxoethyl)-4-{5-(R,S)-N-[3-(4-cyanophenyl)isoxazolin-5-yl acetyl]}piperazin-2-one, 0.30 g (27.6%) of the title compound was obtained, following the procedure of Example 375, Part C. MS (ESI): m/e 402 (M+H)$^+$. $^1$H NMR (300 MHz, d$_6$-DMSO): δ 2.70–3.67 (m, 12H); 3.91 (br., 1H); 4.87 & 4.64 (two m, 1H); 5.06 (m., 1H); 7.88 (m, 4H); 8.16 (br., 1H); 9.40 (br. s, 3H).

EXAMPLE 434

Preparation of (S)-N$^α$-[3-(4-Amidinoehenyl)-isoxazolin-5-(R,S) -ylacetyl]-α-aspart-N-(2-phenylethyl)amide, trifluoroacetic Acid Salt Part A. Preparation of (S)-N$^α$-(Benzyloxycarbonyl)-β-(O-t-butyl)-α-aspart-N-(2-phenylethyl)amide To a solution of (S)-N-(Benzyloxycarbonyl)-β-(O-t-butyl)-aspartic acid (BACHEM-Bioscience Inc) (3.20 g, 9.9 mmol) in DCM (25 mL), was added phenethylamine (1.34 g, 11.1 mmol); followed by DEC (2.10 g, 10.9 nmol). The reaction mixture was stirred overnight at room temperature, affording a pale yellow solution. This solution was washed with water, 1M HCl, 5% NaHCO$_3$ and sat. NaCl, dried over anhydrous MgSO$_4$, filtered, and concentrated in vacuo to give 4.28 g (100%) of amide, which was of sufficient purity to be carried on to the next step; $^1$H NMR (300 MHz, CDCl$_3$) δ 7.35 (s, 5H), 7.17–7.35 (bm, 5H), 6.52 (bs, 1H), 5.93 (bd, J=8.1 Hz, 1H), 5.10 (s, 2H), 4.46 (bm, 1H), 3.50 (dd, J=13.9, 6.2 Hz, 2H), 2.92 (dd, J=17.0, 4.2 Hz, 1H), 2.78 (t, J=7.1 Hz, 2H), 2.57 (dd, J=17.0, 6.4 Hz, 1H), 1.42 (s, 9H); Mass Spectrum (NH$_3$-DCI, e/z, relative abundance) 444, (M+NH$_4$)$^+$, 100%; 427, (M+H)$^+$, 4%.

Part B. Preparation of (S)-β-(O-t-butyl)-α-aspart-N-(2-phenylethyl)amide

A solution of (S)-N-(benzyloxycarbonyl)-β-(O-t-butyl)-α-aspart-N-(2-phenylethyl)amide (4.09 g, 9.58 mmol) in ethyl alcohol (30 mL) was hydrogenated under atmospheric pressure using 10% palladium on carbon catalyst (1.0 g) for 90 minutes. The catalyst was filtered and the filtrate concentrated in vacuo to give 2.80 g of an amber oil, which was purified by flash chromatography (5% MeOH/DCM), affording 2.13 g (76%) of the free amine as a solid product; $^1$H NMR (300 MHz, CDCl$_3$) δ 7.44(bs, 1H), 7.20–7.35 (m, 5H), 3.61 (dd, J=8.4, 3.7 Hz, 1H), 3.52 (dd, J=13.2, 7.0 Hz, 1H), 2.80–2.90 (m, 3H), 2.46 (dd, J=16.7, 8.4 Hz, 1H), 1.58 (bs, 2H), 1.45 (s, 9H); Mass Spectrum (ESI, e/z, relative abundance) 293, (M+H)$^+$, 37%; 237, (M+H−C$_4$H$_8$)$^+$, 100%.

Part C. Preparation of Methyl 3-(4-methoxyiminophenyl)-(5R,S)-isoxazolin-5-ylacetate. Hydrochloride Salt A suspension of 3-(4-cyanophenyl)-(5R,S)-isoxazolin-5-ylacetic acid (23.1 g, 100 mmol) in 200 mL of anhydrous methanol was chilled in an ice bath and dry HCl gas was bubbled through the reaction mixture until a clear solution was obtained. The total addition time was about three hours. The reaction flask was sealed and the reaction mixture was allowed to warm to room temperature, with stirring, over a period of about 24 hrs. At this point, the methanolic solution was poured into 600 mL of anhydrous ether, precipitating the product, and the resulting slurry was chilled to −25° C. for 2½ hours. The slurry was then diluted with an additional 100 mL of chilled anhydrous ether. The precipitate was filtered, washed with two 100 mL portions of chilled anhydrous ether, and suction dried under nitrogen to afford 23.3 g (73%) of the hydrochloride salt; $^1$H NMR (300 MHz, CDCl$_3$) δ 12.9 (bs, 1H) 12.2 (bs, 1H), 8.46 (d, J=8.8 Hz, 2H), 7.86 (d, J=8.8 Hz, 2H), 5.20 (bm, 1H), 4.59 (s, 3H), 3.74 (s, 3H), 3.53 (dd, J=16.8, 10.6 Hz, 1H), 3.15 (dd, J=16.8, 7.7 Hz, 1H), 2.90 (dd, J=16.1, 6.2 Hz, 1H), 2.70 (dd, J=16.1, 7.3 Hz, 1H), 1.77 (bs, 1H); Mass Spectrum (NH$_3$-CI/DDIP, e/z, relative abundance) 277, (M+H)$^+$, 100%.

Part D. Preparation of methyl 3-(4-amidinophenyl)-5R,S)-isoxazolin-5-ylacetate. Hydrochloride Salt A suspension of methyl 3-(4-methoxyiminophenyl)-(5R,S)-isoxazolin-5-ylacetate hydrochloride (22.9 g, 73.0 mmol) in 500 mL of 1M ammonia in anhydrous methanol was stirred at room temperature for 14 hours during which time all solids dissolved. The solution was concentrated in vacuo to give 22.1 g (100%) of crude hydrochloride salt as a tan solid; $^1$H NMR (300 MHz, CDCl$_3$) δ 9.6–9,2 (b), 7.91 (d, J=8.8, 2H), 7.87 (d, J=8.8, 2H), 5.08 (bm, 1H), 3.64 (s, 3H), 3.3–3.1 (m, 2H), 2.8 (m, 2H); Mass Spectrum (ESI, e/z, relative abundance) 264, (M+H)$^+$, 100%.

Part E. Preparation of Methyl 3-(4-N-Boc-amidinophenyl)isoxazolin-5-ylacetate

To a solution of 21.6 g (72.5 mmol) of methyl 3-(4-amidinophenyl)isoxazolin-5-ylacetate (prepared using the procedure of Example 434, Part D) in 350 ml DMF cooled with an ice bath was added 20.2 ml (145 mmol) of triethylamine and 17.4 g (79.8 mmol) of di-tert-butyl dicarbonate. The mixture was warmed to room temperature and stirred for 16 hours. The reaction mixture was poured into 1500 ml water while stirring. A while precipitate formed and was then filtered and dried on the filter under nitrogen to give 19.6 g (74.8%) of the title compound as a white solid. MS (ESI): m/e 362 (M+H)$^+$; 306 (M+H−tBu)$^+$. $^1$H NMR (300 MHz, d$_6$-DMSO): δ 1.56 (s, 9H); 2.68 (dd, J=6.1, 6.1 Hz, 1H); 2.90 (dd, J=6.1, 6.1 Hz, 1H); 3.14 (dd, J=6.8, 6.8 Hz, 1H); 3.56 (dd, J=6.8, 6.8 Hz, 1H); 3.74 (s, 3H); 5.14 (m, 1H); 7.70 (d, J=8.4 Hz, 2H); 7.90 (d, J=8.4 Hz, 2H). $^{13}$C NMR (60

MHz, $d_6$-DMSO): δ 28.46; 39.31; 39.58; 51.98; 77.89; 78.35; 126.91; 128.51; 132.79; 136.24; 156.86; 164.04; 165.76; 170.93.

Part F. Preparation of 3-(4-N-Boc-amidinophenyl) isoxazolin-5ylacetic Acid

To a solution of 18.95 g (52.4 mmol) of methyl 3-(4-N-Boc-amidinophenyl)isoxazolin-5-ylacetate (prepared using the procedure of Example 434, Part E) in 500 ml methanol was added 2.42 g (57.7 mmol) of lithium hydroxide monohydrate in 75 ml water at 22° C. The mixture was stirred at 22° C. for 16 hours and then filtered; the filtrate was then evaporated under reduced pressure to remove methanol. The residual aqueous phase was cooled with an ice bath and acidified with 6 N and 1 N HCl to pH=4. A white solid precipitated and it was left at −4° C. overnight. The solid was filtered and dried on the filter under nitrogen to give 17.74 g (97.4%) of the title compound as an off-white powder. MS (ESI): m/e 348 (M+H)$^+$; 292 (M+H−tBu)$^+$. $^1$H NMR (300 MHz, $d_6$-DMSO): δ 1.50 (s, 9H); 2.68 (d, J=7.0 Hz, 2H); 3.22 (dd, J=7.2, 7.2 Hz, 1H); 3.62 (dd, J=6.8, 7.2 Hz, 1H); 5.04 (m, 1H); 7.78 (d, J=8.4 Hz, 2H); 7.94 (d, J=8.4 Hz, 2H). $^{13}$C NMR (60 MHz, $d_6$-DMSO): δ 28.27; 39.30; 40.44; 78.39; 81.55; 126.87; 129.43; 132.78; 133.87; 156.76; 158.61; 165.58; 171.91.

Part G. Preparation of (S)-N-[α-(4-N-Boc-Amidinophenyl)-isoxazolin-5-(R,S)-ylacetyl]-β-(O-t-butyl)-α-aspart-N-(2-phenylethyl)amide To a suspension of (S)-β-(O-t-butyl)-α-aspart-N-(2-phenylethyl)amide (0.30 g, 1.0 mmol), 3-(4-N-Boc-amidinophenyl)-isoxazolin-5-ylacetic acid (0.35 g, 1.0 mmol), and TBTU (0.32 g, 1.0 mmol) in EtOAc (20 mL), was added triethyl amine (460 μL, 0.33 g, 1.0 mmol). The reaction mixture was stirred at room temperature for 4.5 hr. It was diluted with EtOAc (20 mL), washed with pH 4 buffer, water, 5% NaHCO$_3$ and sat. NaCl, dried over anhydrous MgSO$_4$, filtered, and concentrated in vacuo to give 0.58 g of solid. The crude product was purified by flash chromatography (100% EtOAc), affording 0.51 g (81%); $^1$H NMR (300 MHz, CDCl$_3$) δ 7.89 (t, J=8.1 Hz, 2H), 7.69 (m, 2H), 7.25–7.3 (m, 3H), 7.15–7.25 (m, 4H), 7.04 (d, J=8.4 Hz, 1H), 6.65–6.80 (dt, 1H), 5.10 (bm, 1H), 4.71 (bm, 1H), 3.4–3.7 (bm, 3H), 3.1–3.3 (octet, 1H), 2.75–2.95 (m, 3H), 2.5–2.65 (m, 3H), 1.56 (s, 9H), 1.44, (d, 9H); Mass Spectrum.(ESI, e/z, relative abundance) 622, (M+H)$^+$, 100%.

EXAMPLE 435

Preparation of (S)-N$^α$-[3-(4-Amidinophenyl)-isoxazolin-5-(R,S)-ylacetyl]-α-aspart-N-(2-phenylethyl)amide, Trifluoroacetic Acid Salt A solution of (S)-N-[3-(4-N$^α$-Boc-amidinophenyl)-isoxazolin-5-ylacetyl]-β-(O-t-butyl)-α-aspart-N-(2-phenylethyl)amide (160 mg, 0.26 mmol) in trifluoroacetic acid (10 mL) and DCM (10 mL) was stirred at room temperature for three days. The solution was concentrated in vacuo to give 150 mg of product; $^1$H NMR (300 MHz, CDCl$_3$) δ 9.40 (bs, 2H), 9.26 (bs, 2H), 8.33 (t, J=8.6, 1H), 7.85–8.0 (m, 1H), 7.88 (s, 4H), 7.3 (m, 1H), 7.28 (d, J=7.1, 2H), 7.20 (d, J=7.1, 2H), 5.07 (bm, 1H), 4.56 (bm, 1H), 3.5–3.6 (octet, 1H), 3.26 (bt, J=7.0, 2H), 3.2 (m, 1H), 2.70 (bt, J=7.0, 2H), 2.6–2.65 (bm, 2H), 2.4–2.5 (m, 2H); Mass Spectrum (ESI, e/z, relative abundance) 466, (M+H)$^+$, 100%.

EXAMPLE 445

N$^2$-(β-Styrylsulfonyl)-N$^3$-[3-(4-amidino-phenyl) isoxazolin-5(R,S)-ylacetyl]-(S)-2,3-diaminopropionic Acid TFA Salt Prepared according to Example 490a. MS (ESI, e/z, relative intensity): 500 (M+H)$^+$, (100%).

EXAMPLES 473A AND 473B

Resolution of Methyl N$^2$-3-methylphenylsulfonyl-N$^3$-[3-(4-amidinophenyl)-5S-ylacetyl]-S-2,3-diaminopropionate Trifluoroacetic Acid Salt and Methyl N$^2$-3-methylphenylsulfonyl-N$^3$-[3-(4-amidinophenyl)isoxazolin-5R-ylacetyl]-S-2,3-diaminopropionate Trifluoroacetic Acid Salt The mixture was initially purified on a Pirkle DNBPG column using 10%HOAc/20%EtOH/70% hexane as the eluting solvent. The column temperature was maintained at 45° C., the flow rate at 1.5 ml/min, and the detector set at 280 nm. The diastereomers were then separated on a chiralcel OD-25×2cm column using an eluting solvent of 0.1%TFA/20%MeOH/80%CO$_2$. The column temperature was maintained at 30° C., the flow rate at 13 ml/min, the pressure at 175 atm, and the detector was set at 280 nm. Injections were made on 23mg of sample. Over the two columns a total of 300 mg was injected giving 59 mg of the R isomer, Ex. 473A (HRMS calc'd for C$_{23}$H$_{27}$N$_5$O$_6$S 502.176031 Found: 502.175508) and 85 mg of the S isomer, Ex. 473B (HRMS calc'd for C$_{23}$H$_{27}$N$_5$O$_6$S 502.176031 Found: 502.176358).

EXAMPLE 473C

N$^2$-3-methylphenylsulfonyl-N$^3$-[3-(4-amidinophenyl)isoxazolin-5S-ylacetyl]-S-2,3-diaminopropionic Acid Part A: Methyl-N$^2$-3-methylphenylsulfonyl-N$^3$-[3-(4-cyanophenyl)isoxazolin-5S-ylacetyl]-S-2,3-diaminoprotionate Into a solution of 3-(4-cyanophenyl)isoxazolin-5-S-ylacetic acid (1.82 g, 7.90 mmol, obtained as described in Es. 314A, part F) in DMF (50 ml) was added methyl-N$^2$-3-methylphenylsulfonyl-L-2,3-diaminopropionate HCl salt (2.77 g, 7.90 mmol), TBTU (2.53 g, 7.90 mmol), and Hunigs base (2.75 ml, 15.8 mmol). After stirring at room temperature for 16 hours, the reaction mixture was diluted with EtOAc (500 ml) and washed one time with water (200 ml), one time with sat'd NaHCO$_3$ (200 ml), one time with 0.1N HCl (200 ml), dried (MgSO$_4$), filtered, and concentrated. Column chromatography on silica gel using 10% EtOAc/hexane as the eluting solvent gave 1.99 g (52%) of the desired material as an off-white foam. $^1$H NMR: (CDCl$_3$): δ 7.81–7.78 (d, 2H, J=8.4 Hz); 7.16–7.67 (d, 2H, J=8.8 Hz); 7.61–7.58 (m, 2H); 7.39–7.37 (d, 2H, J=5.1 Hz); 6.35–6.30 (m, 1H); 5.54–5.52 (d, 1H, J=7.7 Hz); 5.18–5.17 (m, 1H); 4.00–3.96 (m, 1H); 3.62–3.50 (m, 3H); 3.57 (s, 3H); 3.27–3.19 (dd, 1H, J-7.7, 17.0 Hz); 2.78–2.70 (dd, 1H, J=5.9, 14.8 Hz); 2.64–2.57 (dd, 1H, J=6.6, 14.6 Hz); 2.42 (s, 3H).

Part B: Methyl-N$^2$-3-methylphenylsulfonyl-N$^3$-[3-(4-amidinophenyl)isoxazolin-5S-ylacetyl]-S-2,3-diaminopropionate hydrochloride Methyl-N$^2$-3-methylphenylsulfonyl-N$^3$-[3-(4-cyanophenyl)-5S-ylacetyl]-S-2,3-diaminopropionate was dissolved in 100 ml absolute ethanol at 0° C. and a stream of HCl gas was bubbled through the solution for two hours. The reaction vessel was sealed and after sitting at room temperature for 16 hours the volatiles were removed in vacuo. The residue was then diluted with 100 ml of absolute ethanol, ammonium carbonate (9.6 g, 0.123 mol) was added and after stirring for 16 hours the reaction mixture was filtered and concentrated in vacuo. Column chromatography on silica using a gradient elution from 5%MeOH/CH$_2$Cl$_2$ to 20%MeOH/CH$_2$Cl$_2$ gave 0.762 g (37%) of the desired amidine as a white solid. $^1$H NMR (CDCl$_3$): δ 8.23–8.20 (m, 1H); 7.91–7.85 (m, 4H); 7.57–7.54 (m, 2H); 7.49–7.46 (m, 2H); 5.00–4.94 (m, 1H); 4.08–3.86 (m, 1H); 3.59–3.49 (m, 1H); 3.39 (s, 3H); 3.38–3.29 (m, 3H); 2.49 (s, 3H); 2.50–2.45 (m, 2H). HRMS: calc'd for $C_{23}H_{27}N_5O_6S$ 502.176031 found 502.175992. $[\alpha]_D=+48.88°$ (c=0.180, MeOH).

Part C: $N^2$-3-methylphenylsulfonyl-$N^3$-[3-(4-amidinophenyl)5(S)-yl]acetyl-S-2,3-diaminopropionic acid The compound of Ex 473C, part B (0.077 g., 0.14 mmol) was dissolved in MeOH (4 ml). To the resulting solution was added a solution of lithium hydroxide (0.0066 g., 0.158 mmol) in water (4 ml) and the mixture was stirred overnight at room temperature. The methanol was removed by evaporation in vacuo, and the product precipitated from the aqueous as a white solid (0.026 g., 35%). HRMS calcd for $C_{22}H_{25}N_5O_6S$: 488.160381; found: 488.160827.

EXAMPLE 473D

Methyl-$N^2$-3-methylphenylsulfonyl-$N^3$-[3-(4-amidinophenyl)isoxazolin-5R-ylacetyl]-S-2,3-diaminopropionate Hydrochloride Part A: Methyl-$N^2$-3-methylphenylsulfonyl-$N^3$-[3-(4-cyanophenyl)-5R-ylacetyl]-S-2,3-diaminopropionate This compound was synthesized from 3-(4-cyanophenyl)isoxazolin-5-(R)-ylacetic acid (3.07 g, 0.011 mol, obtained as described in Ex. 314B, part B) using the same procedure as for example 473C, part A. Yield 41%. Theory: C 57.02, H 4.99, N 11.56 Found: C 56.83, H 4.87, N 11.45.

Part B: Methyl-$N^2$-3-methylphenylsulfonyl-$N^3$-[3-(4-amidinophenyl)isoxazolin-5R-ylacetyl]-S-2,3-diaminopropionate hydrochloride This compound was synthesized from Methyl-$N^2$-3-methylphenylsulfonyl-$N^3$-[3-(4-cyanophenyl)isoxazolin-5R-ylacetyl]-S-2,3-diaminopropionate using the same procedure as for example 473C, part B. Yield 49%. HRMS Calc'd for $C_{23}H_{27}N_5O_6S$ 502.176031 Found: 502.174103.

EXAMPLE 478a $N^2$-2,4,6-trimethylphenylsulfonyl-$N^3$-[3-(4-amidinophenyl)-isoxazolin-5-(R,S)-ylacetyl]-(S)-2,3-diaminopropionic Acid TFA Salt $^1$H NMR (DMSO-$d_6$) δ: 9.37 (s, 2H), 9.06 (s,2H), 8.10 (q,J=6.22 Hz, 1H), 7.98(d, J=9.52 Hz, 1H), 7.87 (s,4H),6.98 (d, J=4.40 Hz, 2H), 4.99(m, 1H), 3.85 (m, 1H), 3.59–3.0 (m, 4H), 2.55 (s, 6H), 2.41 ( m,2H), 2.23 (s, 3H) ppm; Mass Spectrum (ESI) m/z (M+H)$^+$516.3 (100)%, High Res Mass Spectrum (M+H)$^+$ calculated 516.190344, found 516.189999.

EXAMPLE 479a $N^2$-2-chlorophenylsulfonyl-$N^3$-[3-(4-amidinophenyl)-isoxazolin-5-(R,S)-ylacetyl]-(S)-2,3-diaminopropionic Acid M.P. 138–140° C. $^1$H NMR (DMSO-$d_6$) δ: 9.39 (s, 2H), 9.27 (s, 2H) 8.30 (dd, J=4.40, 9.15 Hz 1H), 8.22 (m, 1H), 7.96 (d, J=6.95 Hz, 1H), 7.88 (s, 4H), 7.65 ( m,2H), 7.59 (m 1H), 5.04 (m, 1H), 4.03 (m 1H), 3.58 ( m 1H), 3.38 (m, 1H), 3.24 (m, 2H), 2.59 (dd, j=6.22, 14.28 Hz, 1H), 2.43 (m, 1H) ppm Mass Spectrum (ESI) m/z (M+H)$^+$ 508.1 (100%), High Res Mass Spectrum (M+H)$^+$ calculated 508.107096, found 508.106929.

EXAMPLE 485a $N^\alpha$-2,3,5,6-tetramethylthenylsulfonyl-$N^3$-[3-(4-amidinophenyl)-isoxazolin-5-(R,S)-ylacetyl]-(S)-2,3-diaminopropionic Acid TFA Salt M.P.148–150° C., $^1$H NMR (DMSO-$d_6$) δ: 9.38 (s, 2H), 9.29 (s,2H), 8.09 (m, 1H), 7.97 (dd, J=4.40, 9.15 Hz, 1H), 7.85 (s, 4H), 7.15 ( d, J=7.32 Hz, 1H), 4.98 (m, 1H), 3.88 (q, J=6.96, 15.75 Hz, 1H), 3.56 (m, 1H), 3.34–3.08 (m, 4H), 2.43 (s,6H), 2.39 (m, 1H), 2.19 (s,3H), 2.18 (s, 3H) ppm. Mass Spectrum (ESI) m/z (M+H)$^+$ 530.2 (100%); High Res Mass Spectrum (M+H)$^+$ calculated 530.208668; found 530.208357.

EXAMPLE 490a $N^2$-n-Propanesulfonyl-$N^3$-[3-(4-amidinophenyl) isoxazolin-5(R,S)-ylacetyl]-(S)-2,3-diaminopropionic Acid TFA Salt Part A: Methyl $N^2$-n-Propanesulfonyl-$N^3$-Boc-(S)-2,3-diaminopropionate To a solution of methyl $N^3$-Boc-(S)-2,3-diaminopropionate (prepared in Ex 20, Part C, 410 mg, 1.88 mmol)-in $CH_2Cl_2$ (5 mL) at 0° C. was added propanesulfonyl chloride (0.21 mL, 1.9 mmol) and $Et_3N$ (0.35 mL, 2.5 mmol) and the resulting mixture allowed to warm to room temperature overnight (18 h). The mixture was washed with 0.1 M HCl, sat. $NaHCO_3$ and brine, dried ($MgSO_4$), and concentrated to give 530 mg (87%) of the desired sulfonamide as a viscous oil; CIMS (e/z, relative intensity): 342 (M+H)$^+$, 100%.

Part B: Methyl $N^2$-n-Propanesulfonyl-(S)-2,3-diaminopropionate Hydrochloride Salt To neat methyl $N^2$-n-propanesulfonyl-$N^3$-Boc-(S)-2,3-diaminopropionate (520 mg, 1.60 mmol) was added 4 M HCl/dioxane (5 mL, 20 mmol). The resulting solution was stirred at room temperature for 4 h, then it was concentrated in vacuo, giving an oil. Trituration with ether (3×10 mL) followed by drying under vacuum afforded 383 mg (92%) of the desired amine; CIMS (e/z, relative intensity): 225 (M+H)$^+$, 100%.

Part C: Methyl $N^2$-n-propanesulfonyl-$N^3$-[3-(4-(N-t-butoxycarbonylamidino)phenyl)isoxazolin-5(R,S)-ylacetyl]-(S)-2,3-diaminopropionate To a suspension of 3-(4-N-Boc-amidinophenyl)isoxazolin-5-ylacetic acid (prepared in Example 32, 252 mg, 0.725 mmol), methyl $N^2$-n-propanesulfonyl-(S)-2,3-diaminopropionate hydrochloride (189 mg, 0.726 mmol) in DMF (5 mL) was added $Et_3N$ (0.30 mL, 2.2 mmol) and TBTU (233 mg, 0.726 mmol). The resulting mixture was stirred for 4 h at room temperature, then was diluted with EtOAc (30 mL). It was washed with water (4×20 mL), sat. $NaHCO_3$ (30 mL), sat. NaCl and dried ($MgSO_4$). Concentration in vacuo followed by placing the material under vacuum until constant weight was achieved afforded 292 mg (73%) of the desired amide; MS (ESI, e/z, relative intensity): 554 (M+H)$^+$, 100%.

Part D: Methyl $N^2$-n-Propanesulfonyl-$N^3$-[3-(4-amidinophenyl)isoxazolin-5(R,S)-ylacetyl]-(S)-2,3-diaminopropionate TFA Salt To a solution of methyl $N^2$-n-propanesulfonyl-$N^3$-[3-(4-(N- t-butoxycarbonylamidino)phenyl)isoxazolin-5(R,S)-ylacetyl]-(S)-2,3-diaminopropionate (284 mg, 0.513 mmol) in $CH_2Cl_2$ (4 mL) was added TFA (2 mL, 26 mmol). After 2 h at room temperature, the solution was concentrated in vacuo and the residue triturated with ether (3×5 mL). The resulting white powder was then placed under vacuum until constant weight was achieved, giving 260 mg (89%) of the desired benzamidine; MS (ESI, e/z, relative intensity): 454 (M+H)$^+$, 100%.

Part E: $N^2$-n-Propanesulfonyl-$N^3$-[3-(4-amidinophenyl) isoxazolin-5(R,S)-ylacetyl]-(g)-2,3-diaminopropionic Acid TFA Salt To a solution of methyl $N^2$-n-propanesulfonyl-$N^3$[3-(4-amidinophenyl)isoxazolin-5(R,S)-ylacetyl]-(S)-2,3- diaminopropionate (100 mg, 0.176 mmol) in MeOH (1 mL) was added 0.5 M LiOH (0.5 mL, 0.25 mmol) and the reaction stirred at room temperature overnight (18 h). The resulting mixture was concentrated in vacuo, redissolved in water and the pH adjusted to 4 using 1 M HCl. Purification on reversed phase HPLC gave 10 mg (10%) of the desired carboxylic acid; MS (ESI, e/z, relative intensity): 440 (M+H)$^+$, (100%).

EXAMPLE 492a $N^2$-p-isopropylphenylsulfonyl-$N^3$-[3-(4-amidinophenyl)isoxazolin-5-(R,S)-ylacetyl]-(S)-2,3-diaminopropionic Acid TFA Salt $^1$HNMR (DMSO) δ: 9.37(1H, s), 9.09(1H, s), 8.15(2H, m), 8.78(4H, d, J=1.465 Hz), 7.09(2H, d, J=8.423 Hz), 7.44(2H, m), 4.98(1H, m), 3.93(1H, m), 3.59(2H, m), 3.50 (2H, m), 3.22(2H, m), 2.98(1H, m),2.45(2H, m), 1.22(6H, m)ppm; ESI mass spectrum 516.3 (M+H, 100)$^+$ free base.

EXAMPLE 496

Methyl $N_2$-(2,2-diphenyl-1-ethenesulfonyl)-$N^3$-[3-(4-amidinophenyl)isoxazolin-5-(R,S)-ylacetyl]-(S)-2,3-diaminoeropionate, Trifluoroacetic Acid Salt Part A: Methyl $N^2$-(2,2-diphenyl-1-ethenesulfonyl)-$N^3$-Boc-(S)-2,3-diaminopropionate.

To a mixture of methyl $N^3$-Boc-(S)-2,3-diaminopropionate (255 mg, 1.17 mmol) and 2,2-diphenylethylenesulfonyl chloride (Hasegawa and Hirooka, J. Chem. Soc. Japan 48, 1513–1518 (1975); 391 mg, 1.40 mmol) in methylene chloride (10 mL) cooled in an ice bath was added triethylamine (0.25 mL, 1.76 mmol). After 22 h, the mixture was concentrated and flash chromatographed (6:4 toluene/ethyl acetate) to provide 240 mg (46%) of product. NMR (CDCl$_3$) δ 7.42–7.20 (10H), 6.81 (s, 1H), 5.24 (bd, 1H), 4.87 (bs, 1H), 3.95 (q, 1H), 3.72 (s, 3H), 3.50–3.42 (2H), 1.44 (s, 9H); mass spec (NH$_3$-CI) m/z 466.54 (M+NH4$^+$, 100%).

Part B: Methyl $N^2$-(2,2-diphenyl-1-ethenesulfonyl)-(S)-2,3-diaminopropionate TFA salt.

The product of Part A (210 mg, 0.468 mmol) was dissolved in 5 mL of methylene chloride and 3 mL TFA. After 1 hour, the solution was concentrated to give an oily product. (222 mg, 100%). NMR (DMSO-d$_6$) δ 8.02 (bs, 3H), 7.40 (m, 5H), 7.23 (m, 4H), 7.00 (s, 1H), 4.26 (m, 1H), 3.71 (s, 3H), 3.20 (m, 1H), 2.98 (m, 1H).

Part C: Methyl $N^2$-(2,2-diphenyl-1-ethenesulfonyl)-$N^3$-[3-(4-N-Boc-amidinophenyl)isoxazolin-5-(R,S)-ylacetyl]-(S)-2,3-diaminopropionate.

The product of part B (220 mg, 0.46 mmol) was reacted with 3-(4-N-Boc-amidinophenyl)-isoxazolin-5-ylacetic acid (from Example 434 , part F; 160 mg, 0.46 mmol), according to the procedure of example 651, Part A, to provide the title product (215 mg, 68%). NMR (CDCl$_3$) δ 7.84 (m, 2H), 7.64 (m,2H), 7.40–7.18 (10H), 6.75 (s, 1H), 6.30 (m, 1H), 5.30 (m, 1H), 5.04 (m,1H), 4.00 (1H), 3.78 (s,3H), 3.62–3.40 (4H), 3.10 (m, 2H), 2.70–2.50 (2H), 2.04 (s, 1H), 1.58 (s, 9H); mass spec (ESI) m/z 690.2 (M+H$^+$, 100%).

Part D: Methyl $N^2$-(2,2-diphenyl-1-ethenesulfonyl)-$N^3$-[3-(4-amidinophenyl)isoxazolin-5-(R,S)-ylacetyl]-(S)-2,3-diaminopropionate, trifluoroacetic acid salt The product of part C (210 mg, 0.30 mmol) was dissolved in methylene chloride (3 mL) and treated with trifluoroacetic acid (1 mL) according to the procedure of example 651, Part B, to provide the title product (150 mg, 80%). NMR (DMSO-d$_6$) δ 9.39 (bs,2H), 9.05 (bs,2H), 8.22 (m, 1H), 8.00 (m, 1H), 7.85 (s,4H), 7.40 (m,6H), 7.20 (m,4H), 6.89 (s, 1H), 5.00 (m, 1H), 4.00 (m, 1H), 3.70–3.18 (5H), 3.62 (2s,3H); mass spec (ESI) m/z 590.2 (M+H$^+$, 100%)

EXAMPLE 511

Methyl $N^2$-(N,N-dimethylsulfamoyl)-$N^3$-[3-(4-amidinophenyl)isoxazolin-5-(R,S)-ylacetyl]-(S)-2,3-diaminopropionate, Trifluoroacetic Acid Salt Part A: Methyl $N^2$-(N,N-dimethyl sulfamoyl)-$N^3$-Boc-(S)-2,3-diaminopropionate.

To a mixture of methyl $N^3$-Boc-(S)-2,3-diaminopropionate (400 mg, 1.80 mmol) and Dimethylsulfamoyl chloride (0.24 mL, 2.20 mmol) in methylene chloride (10 mL) cooled in an ice bath was added triethylamine (0.38 mL, 2.20 mmol). After 18 h, the mixture was concentrated and flash chromatographed (6:4 toluene/ethyl acetate) to provide 283 mg (49%) of product. NMR (CDCl$_3$) δ 5.23 (bd, 1H), 4.90 (m, 1H), 4.06 (m, 1H), 3.80 (s, 3H), 3.52 (bt, 2H), 2.80 (s,6H), 1.42 (s, 9H); mass spec (NH$_3$-CI) m/z 343.0 (M+NH$_4^+$, 100%).

Part B: Methyl $N^2$-(N,N-dimethyl sulfamoyl)-(S)-2,3-diaminopropionate TFA salt.

The Product of Part A was dissolved in 5 mL of methylene chloride and 3 mL TFA. After 1 hour, the solution was concentrated to give an oily product (294 mg, 100%). NMR (DMSO-d$_6$) δ 6.52 (bs, 2H), 4.4–3.9 (2H), 3.8 (bs, 3H), 2.93 (bs, 6H).

Part C: Methyl $N^2$-(N,N-dimethyl sulfamoyl)-$N^3$-[3-(4-N-Boc-amidinophenyl)isoxazolin-5-(R,S)-ylacetyl]-L-2,3-diaminoiroDionate.

The product of part B (200 mg, 0.61 mmol) was reacted with 3-(4-N-Boc-amidinophenyl)isoxazolin-5-ylacetic acid (from Example 434, part F; 212 mg, 0.61 mmol), according to the procedure of Example 651, Part A, to provide the title product (203 mg, 61%). NMR (CDCl$_3$) δ 7.78 (m, 2H), 7.42 (bt, 2H), 7.00 (m, 1H), 5.92 (m, 1H), 5.04 (m, 1H), 3.80 (2s, 3H), 3.64 (m, 2H), 3.40 (m, 1H), 3.05 (m, 1H), 2.80 (2s, 6H), 2.74 (m, 1H), 2.60 (m, 1H), 2.02 (s, 3H), 1.60 (s, 9H); mass spec (ESI) m/z 555.1 (M+H$^+$, 100%).

Part D: Methyl $N^2$-(N,N-dimethyl sulfamoyl)-$N^3$-[3-(4-amidinophenyl)isoxazolin-5-(R,S)-ylacetyl]-L-2,3-diaminopropionate, trifluoroacetic acid salt The product of part C (183 mg, 0.329 mmol) was dissolved in methylene chloride (3 mL) and treated with trifluoroacetic acid (1 mL) according to the procedure of example 651, Part B, to provide the title product (159 mg, 85%). NMR (DMSO-d$_6$) δ 9.40 (bs, 2H), 9.00 (bs, 2H), 8.22 (m, 1H), 7.82 (s, 4H), 5.00 (m, 1H), 3.95 (m, 1H), 3.68 (2s, 3H), 3.60 (m, 2H), 3.20 (m, 4H), 2.80 (s, 6H); mass spec (ESI) m/z 455.1 (M+H$^+$, 100%).

EXAMPLE 512

Methyl $N^2$-(m-toluenesulfonyl)-$N^3$-[3-(4-amidino-2-fluorophenyl)isoxazolin-5-ylacetyl]-S-2,3-diaminopropionate Hydrochloric Acid Salt Part A: 3-Fluoro-4-methylbenzamide 3-Fluoro-4-methylbenzoic acid (10 g, 65 mmol) was boiled in thionyl chloride (100 ML) under a drying tube for 2.5 h. The excess SOCl$_2$ was removed by distillation. The oily acid chloride product was diluted with CH$_2$Cl$_2$ (100 mL) and cooled in an ice bath. Conc. aq. NH$_3$ (20 mL) was added dropwise, and stirring continued at 0° C. for 0.5 h. The CH$_2$Cl$_2$ was removed in vacuo, then the residue was diluted with EtOAc. The mixture was extracted with sat. aq. Na$_2$CO$_3$ (2x), H$_2$O, and brine, dried (MgSO$_4$), and concentrated to yield 9.9 g of a pale yellow solid; mp 161°–163° C.;

IR(KBr) 3382, 1654 cm$^{-1}$; Anal. Calc. for $C_8H_8FNO$: C, 62.74; H, 5.27; N, 9.15; F, 12.40. Found: C, 62.66; H, 5.17; N, 9.12; F, 12.28.

Part B: 3-Fluoro-4-methylbenzonitrile

A solution of trichloroacetyl chloride (7.3 mL, 65 mmol) in $CH_2Cl_2$ (20 mL) was added dropwise over 0.5 h to a solution/suspension of the Part A amide (9.0 g, 59 mmol) and $Et_3N$ (17 mL, 120 mmol) in $CH_2Cl_2$ (80 mL) at 0° C. After 40 min, the mixture was concentrated in vacuo, then diluted with $Et_2O$. This solution was extracted with 1 M HCl, sat. aq. $NaHCO_3$, $H_2O$, and brine, then dried ($MgSO_4$), and concentrated to yield 7.8 g of a tan solid; mp 45–47° C.; IR(KBr) 2232 cm$^{-1}$; HRMS, e/z Calc. for (M+H)$^+$: 135.0484. Found: 135.0482.

Part C: 2-Fluoro-4-cyanobenzylbromide

N-Bromosuccinimide (9.6 g, 54 mmol) and the part B substrate (7.3 g, 54 mmol) were heated under reflux in $CCl_4$ (100 mL) under $N_2$ with irradiation with a high intensity visible lamp for 2 h. After cooling to ambient temp., the mixture was filtered through a Celite pad and concentrated in vacuo. The crude product was recrystallized from hot cyclohexane (4x) to yield 4.5 g of off-white needles; mp 75–77° C.; IR(KBr) 2236 cm$^{-1}$. RMS, e/z Calc. for (M+H)$^+$: 213.9668. Found: 213.9660.

Part D: 2-Fluoro-4-cyanobenzaldehyde

The part C benzyl bromide (3.68 g, 17 mmol), trimethylamine N-oxide dihydrate (7.6 g, 68 mmol), $CH_2Cl_2$ (15 mL), and DMSO (30 mL) were stirred at 0° C. for a few h, slowly warming to ambient T overnight. The mixture was diluted with water (30 mL) and brine (30 mL), and extracted with $Et_2O$ (4x). The combined organics were washed with brine, dried ($MgSO_4$), and concentrated to yield 1.1 g of a yellow solid; IR(KBr) 2238, 1706 cm$^{-1}$; HRMS, e/z Calc. for (M+H)$^+$: 150.0355. Found: 150.0341.

Part E: 2-Fluoro-4-cyanobenzaldoxime

The part D aldehyde (1.1 g, 7.4 mmol), hydroxylamine hydrochloride (1.0 g, 15 mmol), $K_2CO_3$ (1.0 g, 7.4 mmol), water (1 mL) and MeOH (10 mL) were heated under reflux for 2.25 h. After brief cooling, the mixture was diluted with water, and the insoluble product was collected by filtration, then rinsed with more water. Drying under high vacuum provided 0.94 g of a pale yellow amorphous solid; mp 179–182° C.; IR(KBr) 3256, 2236, 1556 cm$^{-1}$; HRMS, e/z Calc. for (M+H)$^+$: 165.0464. Found: 165.0455.

Part F: Methyl 3-(4-cyano-2-fluorophenyl)isoxazolin-5-ylacetate

The part E oxime was allowed to react with Clorox and methyl vinylacetate in the usual way to afford the isoxazoline as a yellow solid in 32% yield; mp 92–94° C.; IR(KBr) 2240, 1746 cm$^{-1}$; HRMS, e/z Calc. for (M+H)$^+$: 263.0832. Found: 263.0818. Anal. Calc. for $C_{13}H_{11}FN_2O_3$: C, 59.54; H, 4.23; N, 10.68; F, 7.24. Found: C, 59.84; H, 4.31; N, 10.53; F, 7.26.

Part G: Methyl N$^2$-(m-toluenesulfonyl)-N$^3$-[3-(4-tert-butyloxycarbonylamidino-2-fluorophenyl)isoxazolin-(R,S)-5-ylacetyl-(S)-2,3-diaminopropionate.

The part F intermediate was converted to the title compound by the usual sequence of steps: Pinner amidine synthesis, amidine BOC protection, ester saponification, and condensation with the 2,3-diaminopropionate sulfonamide ester; MS (DCI, $NH_3$) 620 (M+H), 520.

Part H: Methyl N$^2$-(m-toluenesulfonyl)-N$^3$-[3- (4-amidino-2-fluorophenyl)isoxazolin-(R,S)-5-ylacetyl-(S)-2,3-diaminoeropionate hydrochloric acid salt.

The BOC group was removed from the part G intermediate by treatment with 4M HCl in dioxane to provide a yellow gum; HRMS, e/z Calc. for (M+H)$^+$: 520.1666. Found: 520.1675.

EXAMPLE 512A

N$^2$-(m-Toluenesulfonyl)-N$^3$-[3- (4-amidino-2-fluorophenyl)isoxazolin-(R)-5-ylacetyl-(S)-2,3-diaminopropionate Hydrochloric Acid Salt Part A: N$^2$-(m-Toluenesulfonyl)-N$^3$-[3-(4-tert-butyloxycarbonylamidino-2-fluorophenyl)isoxazolin-(R,S)-5-ylacetyl-(S)-2,3-diaminopropionate.

The intermediate from Example 512, Part G (0.60 g, 0.97 mmol) was saponified using lithium hydroxide hydrate (61 mg, 1.45 mmol) in water (1 mL) and methanol (1 mL) at room temperature for 3 d. The mixture was extracted with ethyl acetate, the aqueous layer was acidified with pH 4 buffer, and it was extracted with ethyl acetate. The extracts were dried and concentrated to 0.427 g of a clear glass. This material was flashed chromatographed using a methanol/chloroform gradient solvent system, starting with chloroform and progressing through 2%, 10%, 15%, and 20% methanol/chloroform to give 0.360 g (57%) of a clear glass. $^1$H NMR (DMSO-d$_6$, 300 MHz) δ 9.09 (br, 1H), 7.88–7.80 (m, 3H), 7.60–7.56 (m, 2H), 7.47–7.42 (m, 2H), 5.00–4.97 (m, 1H), 3.62–3.57 (m, 1H), 3.29–3.16 (m, 4H), 2.58–2.43 (m, 2H), 2.37 (s, 3H), 1.45 (s, 9H). HRMS (FAB, glycerol) Calc. for (M+H)$^+$: 606.2034. Found: 606.2043.

Part B: N$^2$-(m-Toluenesulfonyl)-N$^3$-[3-(4-amidino-2-fluorophenyl)isoxazolin-(R)-5-ylacetyl-(S)-2,3-diaminopropionate hydrochloric acid salt.

The intermediate from Part A (0.344 g, 0.57 mmol) was dissolved in 4M HCl in dioxane and stirred at room temperature for 21.5 h. The solution was diluted with ether and the precipitated white solid was collected and dried, yielding 0.367 g. This material was subjected to super critical fluid chiral Prep HPLC on a Chiral OG 2 in×25 cm column using 0.1% TFA, 25% methanol, 75% carbon dioxide as eluent at a flow rate of 20 mL/min to separate the isoxazoline isomers. The second eluting, (R,S), isomer was obtained as a white solid. $^1$H NMR (DMSO-d$_6$, 300 MHz) δ 12.81 (br, 1H), 9.53 (s, 1.5H), 9.29 (s, 1.5H), 8.17 (m, 2H), 7.95 (t, J=7.7 Hz, 1H), 7.86 (d, J=12.0 Hz, 1H), 7.40 (d, J=9.5 Hz, 1H), 7.60–7.56 (m, 2H), 7.46–7.41 (m, 2H), 4.97–4.93 (m, 1H), 3.88–3.86 (m, 1H), 3.59–3.55 (m, 1H), 3.42–3.14 (m, 3H), 2.52–2.45 (m, 1H), 2.41–2.33 (m, 4H). HRMS (FAB, glycerol) Calc. for (M+H)$^+$: 506.1510. Found: 506.1494.

EXAMPLE 513

Methyl N$^2$-(n-butyloxycarbonyl)-N$^3$-[3-(3-amidinopyrid-6-yl)isoxazolin-5-ylacetyl]-S-2,3-diaminopropionate Hydrochloric Acid Salt Prepared using methods described in Ex. 514 to provide a pale yellow powder; mp 90–110° C. (dec); HRMS, e/z Calc. for (M+H)$^+$: 449.2149. Found: 449.2140.

EXAMPLE 514

Methyl N$^2$-(m-toluenesulfonyl)-N$^3$-[3-(3-amidinopyrid-6-yl)isoxazolin-5-ylacetyl]-S-2,3-diaminopropionate Hydrochloric Acid Salt Part A: 3-cyano-6-pyridaldoxime 5-Cyano-2-picoline (25 g, 0.21 mol) and $I_2$ were heated under reflux in DMSO (200 mL) for 1 h. After cooling to RT, hydroxylamine hydrochloride (16 g, 0.23 mol), $K_2CO_3$ (29 g, 0.21 mol), and water (21 mL) were added. The resulting mixture was heated to 80° C. for 2.5 h, cooled, diluted with water (100 mL) and much acetone, and absorbed onto silica gel by concentration. Chromatography on silica gel, eluting with 0% to 50% EtOAc in hexane, afforded 12.2 g of a tan solid; mp 204–207° C. (dec); HRMS, e/z Calc. for (M+H)⁺: 148.0511. Found: 148.0516.

Part B: Methyl 3-(3-cyanoeyrid-6-yl)isoxazolin-5-ylacetate

The oxime of Ex. 514, part A was converted to the isoxazoline as described in Ex. 516, part B in 76% yield as a yellow solid; mp 97–98° C.; HRMS, e/z Calc. for (M+H)⁺: 246.0879. Found: 246.0881. Anal. Calc. for $C_{12}H_{11}N_3O_3$: C, 58.77; H, 4.52; N, 17.13. Found: C, 58.74; H, 4.51; N, 17.11.

Part C: Methyl 3-(3-t-butyloxycarbonylamidinoyrid-6-yl)isoxazolin-5-ylacetate

The nitrile of Ex. 514, part B was converted to the amidine as described in the method of Ex. 516, parts D & E (except that 0.6 eq. NaOMe was required), and BOC protected in standard fashion to afford, after purification, a yellow solid; mp 143° C. (gas evolves); HRMS, efz Calc. for (M+H)⁺: 363.1668. Found: 363.1675. Anal. Calc. for $C_{17}H_{22}N_4O_5$: C, 56.35; H, 6.12; N, 15.46. Found: C, 56.35; H, 6.10; N, 15.39.

Part D: Lithium 3-(3-t-butyloxycarbonylamidinopyrid-6-yl)isoxazolin-5-ylacetate

The ester of Ex. 514, part C was saponified and lyophilized as described in the method of Ex. 516, part F to give a colorless amorphous solid quantitatively; mp >230° C.; HRMS, e/z Calc. for conjugate acid (M+H)⁺: 349.1512. Found: 349.1527.

Part E: Methyl $N^2$-(m-toluenesulfonyl)-$N^3$-[3-(3-tert-butyloxycarbonylamidinopyrid-6-yl)isoxazolin-(R,S)-5-ylacetyl]-(S)-2,3-diaminopropionate.

The Part D lithium carboxylate was condensed with methyl $N^2$-(m-toluenesulfonyl)-(S)-2,3-diaminopropionate hydrochloride using conditions described above to give a yellow foam. HRMS, e/z Calc for (M+H)⁺: 603.2237. Found: 603.2223.

Part F: Methyl $N^2$-(m-toluenesulfonyl)-$N^3$-[3-(3-amidinopyrid-6-yl)isoxazolin-(R,S)-5-ylacetyl]-(S)-2,3-diaminopropionate hydrochloric acid salt.

The protected amidine of Part E was treated with 4M HCl in dioxane to provide a yellow solid; mp 90° C. (dec); HRMS, e/z Calc. for (M+H)⁺: 503.1713. Found: 503.1718.

EXAMPLE 514A $N^2$-(m-Toluenesulfonyl)-$N^3$-[3-(3-amidinopyrid-6-yl)isoxazolin-(R)-5-ylacetyl]-(S)-2,3-diaminopropionic Acid Trifluoroacetic Acid Salt Part A: Lithium $N^2$-(m-toluenesulfonyl)-$N^3$-[3-(3-tert-butyloxycarbonylamidinopyrid-6-yl)isoxazolin-(R,S)-5-ylacetyl]-(S)-2,3-diaminopropionate.

The methyl ester of Example 514, Part E (0.16 g, 0.27 mmol) was saponified by stirring with 0.5 M LiOH (0.54 mL, 0.27 mmol) in methanol (2 mL) at room temperature. The mixture was concentrated in vacuo to give 0.16 g (99%) of a tan solid; HRMS, e/z Calc for (M+H)⁺: 589.2081. Found: 589.2086.

Part B: $N^2$-(m-Toluenesulfonyl)-$N^3$-[3-(3-amidinopyrid-6-yl)isoxazolin-(R)-5-ylacetyl]-(S)-2,3-diaminopropionic acid trifluoroacetic acid salt.

The lithium salt of Part A was treated with 4M HCl in dioxane to give a tan foam. This material was purified by Prep reverse phase HPLC on a Vydac C18 2×25 cm column using a gradient solvent system starting with 0.05% TFA in water progressing to 80:20 0.05% TFA in water: 0.05% TFA in acetonitrile over 50 m, the purified material was subjected to super critical fluid Prep chiral HPLC on a Chiral OG 2 in×25 cm column using 0.1% TFA, 25% methanol, 75% carbon dioxide as elutant at a flow rate of 20 mL/min to separate the isoxazoline isomers. The second eluting, (R,S), isomer was resubmitted to reverse phase Prep HPLC as above to give the title compound as a tan solid. ¹H NMR (DMSO-d₆, 300 MHz) δ 2.31 (dd, J=15.0, 7.0 Hz, 1H, partially obscured), 2.37 (s, 3H), 2.48–2.59 (m, 1H, under DMSO), 3.02–3.15 (m, 1H), 3.22 (dd, J=17.6, 10.6 Hz, 1H), 3.32–3.42 (m, 1H, under water peak), 3.55 (dd, J=17.6, 10.6 Hz, 1H), 3.82–3.92 (m, 1H), 4.98–5.11 (m, 1H), 7.39–7.49 (m, 2H), 7.54–7.61 (m, 2H), 8.08–8.15 (m, 3H), 8.25 (dd, J=8.4, 2.2 Hz, 1H), 9.01 (d, J=1.8 Hz, 1H), 9.24 (br s, 2H), 9.53 (br s, 2H), 12.78 (very br s, 1H). MS (ESI) 489 (M+H, 65), 288 (100), 245 (27).

EXAMPLE 515

Methyl $N^2$-(n-butyloxycarbonyl)-$N^3$-[3-(2-amidinopyrid-5-yl)isoxazolin-5-ylacetyl]-S-2,3-diaminopropionate Hydrochloric Acid Salt In similar fashion to the method described in Ex. 516, the compound of Ex. 514, part E was coupled with methyl $N^2$-(n-butyloxycarbonyl)-2,3-diaminopropionate hydrochloride using-conditions described above, followed by BOC deprotection with 4 M HCl/dioxane to yield a pale yellow powder; HRMS, e/z Calc. for (M+H)⁺: 449.2149. Found: 449.2154.

EXAMPLE 516

Methyl $N^2$-(m-toluenesulfonyl)-$N^3$-[3- (2-amidinopyrid-5-yl)isoxazolin-5-ylacetyl]-S-2,3-diaminopropionate Hydrochloric Acid Salt Part A: 2-Chloro-5-pyridaldoxime 2-Chloro-5-formylpyridine (2.1 g, 15 mmol) was condensed with hydroxylamine hydrochloride in the usual way to give the oxime, 1.5 g, as a yellow crystalline solid; mp 171–175° C. (dec); HRMS, e/z Calc. for (M+H)⁺: 157.0169. Found: 157.0175.

Part B: Methyl 3-(2-chloropyrid-5-yl)isoxazolin-5-ylacetate

Sodium hypochlorite (5% wt, 20 mL) was added dropwise over 1.75 h to a mixture of the part A oxime (1.13 g, 7.2 mmol), methyl vinylacetate (70% purity, 3.0 g, 21 mmol), $CH_2Cl_2$ (40 mL), and DMF (4 mL) with stirring at ambient temperature. The $CH_2Cl_2$ was evaporated, and the mixture was diluted with EtOAc, extracted with water (5x) and brine, then dried (MgSO₄), filtered, and concentrated. Chromatography on silica gel, eluting with 0% to 70% EtOAc in hexane, afforded 1.4 g of a solid; mp 94–96° C.; HRMS, e/z Calc. for (M+H)⁺: 255.0536. Found: 255.0531.

Part C: Methyl 3-(2-cyanopyrid-5-yl)isoxazolin-5-ylacetate

The part B chloropyridine (0.51 g, 2.0 mmol), zinc cyanide (0.23 g, 2.0 imol), Pd(PPh₃)₄ (0.12 g, 0.10 mmol), and DMF (2 mL) were heated to 80° C. under N₂ for 3 days. After cooling and concentration, the mixture was preabsorbed onto silica gel by concentration from CHCl₃. Chromatography on silica gel, eluting with 0% to 90% EtOAc in hexane afforded 0.28 g of a pale yellow solid; mp 115–116° C.; HRMS, e/z Calc. for (M+H)⁺: 246.0879. Found: 246.0880. Anal. Calc. for $C_{12}H_{11}N_3O_3$: C, 58.77; H, 4.52; N, 17.13. Found: C, 58.68; H, 4.48; N, 16.90.

Part D: Methyl 3-(2-amidinopyrid-5-yl)isoxazolin-5-ylacetate formic acid salt

The part C cyanopyridine (0.47 g, 1.9 mmol) and sodium methoxide (prepared in situ from Na metal, 4 mg, 0.2 mmol were stirred in dry MeOH (6 mL) at ambient temperature for 16 h, after which ¹H NMR analysis of a reaction aliquot indicated complete formation of methyl imidate [note 9.25 (s, 1H) and 3.92 (s, 3H)]. Ammonium formate (0.60 g, 9.5 mmol) was added to the reaction mixture, and stirring continued for 7 h. The mixture was absorbed onto silica gel by concentration in vacuo. Chromatography on silica gel, eluting with 0% to 20% MeOH in CHCl$_3$, and concentration afforded 0.61 g of the amidine as an off-white solid; mp 180–182° C. (dec); HRMS, e/z Calc. for (M+H)$^+$: 263.1144. Found: 263.1148.

Part E: Methyl 3-(2-t-butyloxycarbonylamidinopyrid-5-yl) isoxazolin-5-ylacetate

The part D amidine was BOC protected in standard fashion to afford, after silica gel chromatographic purification, a 41% yield of a colorless foam; HRMS, e/z Calc. for (M+H)$^+$: 363.1668. Found: 363.1682.

Part F: Lithium 3-(2-t-butyloxycarbonylamidinopyrid-5-yl) isoxazolin-5-ylacetate The part E methyl ester (0.37 g, 1.0 mmol) was saponified by stirring with 0.5 $\underline{M}$ LiOH in MeOH at RT. The MeOH was removed in vacua, then the aqueous mixture was frozen and lyophilized to produce a pale yellow solid quantitatively; HRMS, e/z Calc. for conjugate acid (M+H)$^+$: 349.1512. Found: 349.1531.

Part G: Methyl N$^2$-(m-toluenesulfonyl)-N$^3$-[3-(2-amidinopyrid-5-yl)isoxazolin-5-ylacetyl]-S-2,3-diaminopropionate hydrochloric acid salt The part F lithium carboxylate was condensed with methyl N$^2$-(m-toluenesulfonyl)-2,3-diaminopropionate hydrochloride using conditions described above, followed by standard BOC deprotection with 4 $\underline{M}$ HCl/dioxane to yield a yellow amorphous solid; HRMS, e/z Calc. for (M+H)$^+$: 503.1713. Found: 503.1707.

EXAMPLE 516A

N$^2$-(m-Toluenesulfonyl)-N$^3$-[3-(2-amidinopyrid-5-yl)isoxazolin-(R,S)-5-ylacetyl]-(S)-2,3-diaminopropionic Acid Trifluoroacetic Acid Salt The methyl ester of Example 516, Part G (31.4 mg, 54.6 nmol) was dissolved in 6M aqueous hydrochloric acid (1 mL) and the mixture was stirred at room temperature for 44 h. The yellow solution was concentrated and subjected to Prep reverse phase HPLC as described in Example 514A, Part B to give 25.0 mg (75%) of a white solid. mp 158.5–161.5° C. $^1$H NMR (DMSO-d$_6$, 300 MHz) δ 2.31–2.44 (m, 1H), 2.37, 2.38 (singlets, 3H), 2.50–2.60 (m, 1H, under DMSO), 3.00–3.10 (m, 0.5H), 3.12–3.36 (m, 2H), 3.38–3.48 (m, 0.5H), 3.60 (ddd, J=17.2, 10.6, 5.9 Hz, 1H), 3.85–3.95 (m, 1H), 4.95–5.11 (m, 1H), 7.39–7.45 (m, 2H), 7.52–7.60 (m, 2H), 8.10–8.22 (m, 2H), 8.28–8.40 (m, 2H), 9.06 (s, 1H), 9.37 (br s, 2H), 9.60 (br s, 2H). MS (ESI) 489 (M+H, free base, 100), 214 (17).

EXAMPLE 528a

N$^2$-o-Bromophenylcarbonyl-N$^3$-[3-(4-amidinophenyl)isoxazolin-5-(R,S)-ylacetyl]-(S)-2,3-diaminopropionic Acid The title compound was obtained as its TFA salt from readily accessible N$^2$-amino-3-[(4-tertbutyloxycarbonylamidino)phenylisoxazolin-5-(R,S)-ylacetyl]-(S)-2,3-diamino-tertbutylpropionate by common acylation techniques with 2-bromobenzoyl chloride. Removal of the tert-butyl protecting groups with TFA afforded the desired product as colorless crystals. M.P. 172–174° C.; $^1$H NMR (DMSO d6) δ: 7.80(d, J=8Hz, 2H), 7.51–7.63(m, 3H), 7.28 (m, 2H), 7.12 (dd, 1H), 6.61 (m, 1H), 5.05 (m, 1H), 4.81(q, 1H), 3.80 (d, 3H), 3.06 (m, 1H), 2.53 (m, 2H), 1.53 (s, 9H)ppm; ESI mass spectrum 516(M+H, 100 free base); HRMS calcd. for C$_{22}$H$_{23}$BrN$_5$O$_5$ 516.088255, found 516.086811 (free base).

EXAMPLE 536

N$^2$-(2,5-Dimethyl-4-chlorobenzenesulfonyl)-N$^3$-[3-(4-amidinophenyl)isoxazolin-5(R,S)-ylacetyl]-(S)-2,3-diaminopropionic Acid TFA Salt Prepared according to Example 490a. MS (ESI, e/z, relative intensity): 536 (M+H)$^+$, (100%).

EXAMPLE 540

N$^2$-methylphenylcarbonyl-N$^3$-[3-(4-amidinophenyl) isoxazolin-5-(R,S)-ylacetyl]-(S)-2,3-diaminopropionic Acid Obtained as colorless crystals, M.P. 166–168° C.; $^1$H NMR (DMSO d6) δ: 9.38 (b, 2H), 9.18 (b, 2H), 8.42 (t, 1H), 8.20 (m, 1H), 7.21 (d, J=10.2 Hz, 4H), 5.00 (m, 1H), 4.50 (m, 1H), 3.30–3.73 (m. 3H), 2.58–2.65 (dd, 1H), 2.41–2.50 (dd, 1H), 2.34 (s, 3H)ppm; ESI mass spectrum 452(M+H, 100 free base); HRMS calcd for C$_{23}$H$_{26}$N$_5$O$_5$ 452.193394, found 452.1922251(free base).

EXAMPLE 540a

N$^2$-methylphenylsulfonyl-N$^3$-[3-(4-amidinophenyl) isoxazolin-5-(R,S)-ylacetyl]-(S)-2,3-diaminopropionic Acid Obtained as colorless crystals M.P. 136–138° C.; $^1$H NMR (DMSO d$_6$) δ: 9.39 (b, 2H), 9.27 (s, 2H), 8.18 (m, 2H), 7.80 (d, J=7.7 Hz, 1H), 7.44(t, 1H), 7.32(q, 2H), 4.96 (m, 1H), 3.90 (b, 1H), 3.81 (q, 1H), 3.40–3.60 (m, 2H), 3.04 (m, 2H), 2.60 (s, 2H), 2.24 (dd, J=7.7 and 15.6 Hz)ppm; ESI mass spectrum 488(M+H, 100 free base). HRMS calcd for. C$_{22}$H$_{25}$N$_5$SO$_6$ 488.160381, found 488.16292 (free base).

EXAMPLE 548

Preparation of 3-bromothiophene-2-sulfonyl Chloride

A solution of chlorosulfonic acid (14.3 g, 0.12 mol) in 35 mL of 1,2-dichloroethane was chilled to –10° C. and protected from moisture. Phosphorus pentachloride (20.8 g, 0.1 mol) was added in small portions while maintaining the temperature between –5° and –10° C. The resulting slurry was stirred at –10° C. for 30 minutes. Then, 3-bromothiophene (16.3 g, 0.1 mol) was added dropwise over a period of 45 minutes, maintaining the temperature between –5° and +5° C. During the addition of the 3-bromothiophene, hydrogen chloride gas was evolved; the reaction mixture became thick and pasty, and difficult to stir. Upon complete addition of the 3-bromothiophene, the reaction temperature was held at 0° C. for two hours. The reaction was then heated to 80° C. and kept there for one hour; during which the solids dissolved, and hydrogen chloride gas was evolved once more. The reaction mixture was chilled in an ice bath, poured over 250 g crushed ice, and stirred for one hour as the ice melted. The resulting two phase system was separated and the aqueous layer washed three times with 125 mL of chloroform. The combined organic phases were dried over anhydrous MgSO$_4$, filtered, and concentrated in vacuo to give 24.1 g (92%) of crude product as a dark amber oil; $^1$H NMR (300 MHz, CDCl$_3$) δ 7.22 (d, J=5.3, 1H), 7.73 (d, J=5.3, 1H); Mass Spectrum (CH$_4$-DCI/GC-MS, e/z, relative abundance) 262.8, (M+H)$^+$, 100%; 226.9, (M+H–HCl)$^+$, 89.7%.

EXAMPLE 587A

N$^2$-3-methylphenylsulfonyl-N$^3$-[3-(4-amidinophenyl)isoxazolin-5S-ylacetyl]-S-2,3-diaminopropionic Acid The compound of Example 473C, Part B (0.077 g, 0.14 mmol) was dissolved in MeOH (4 ml), LiOH (0.0066 g, 0.158 mmol) in H$_2$O (4 ml) was added and the reaction mixture left to stir overnight. After evaporation of methanol the product precipitated from the aqueous as a white solid (0.027 g, 35% yield). HRMS calc'd for C$_{22}$H$_{25}$N$_5$O$_6$S: 488.160381 found: 488.160827.

EXAMPLE 602

Methyl N$^2$-n-butyloxycarbonyl-N$^3$-[3-(4-guanidinophenyl)isoxazolin-5-(R,S)-ylacetyl]-(S)-2, 3-diaminopropionate, Trifluoroacetic Acid Salt Part A: [3-[(4-t-butyloxycarbonylamino)phenyl]-isoxazolin-5-yl]acetic acid: This compound was prepared in 49% yield from 4-t-butyloxycarbonylaminobenzaldoxime and t-butyl vinyl acetate using the procedure described above for Ex. 275, Part A. $^1$HNMR(CDCl$_3$) δ 0.99 (t, 3H), 1.35 (m, 2H), 1.50 (s, 9H), 1.61 (m, 2H), 2.60 (dd, J=7.7 and 16.5 Hz, 1H) 2.84 (dd, J=5.9 & 16 Hz, 1H), 3.06 (dd, J=7.4 & 16.9 Hz, 1H), 3.48 (dd, J=10.3 & 16.5 Hz, 1H), 4.10 (t, 2H), 5.03 (m, 1H), 6.60 (broad s, 1H), 7.38 (d, J=8.4 Hz, 2H), 7.58 (J=8.3 Hz, 2H); IR(KBr): 2966, 1734, 1740, 1610, 1578, 1528, 1508, 1458, 1442, 1412, 1392, 1368 1234, 1160, 1058, 916, 878, 828, 772, 612 cm$^{-1}$; HRMS calcd. for $C_{20}H_{28}N_2O_5$: 377.207647, Found 377.207278. Standard LiOH saponification conditions then afforded the corresponding carboxylic acid compound as colorless crystals in 88% yield. mp 178–180° C.; $^1$HNMR(CDCl$_3$) δ 1.52 (s, 9H), 2.67 (dd, J=7.8 and 16 Hz, 1H), 2.89 (dd, J=8.3 & 16 Hz, 1H), 3.06 (dd, J=9.5 & 16.9 Hz, 1H), 3.48 (dd, J=10.3 & 16.5 z, 1H), 5.03(m, 1H).

Part B: Methyl $N^2$-n-butyloxycarbonyl-$N^3$-[3-[(4-t-butyloxycarbonylamino)phenyl]isoxazolin-5-yl acetyl]-(S)-2,3-diaminopropionate: The compound of Example 602, Part A was condensed with methyl $N^2$-tBoc-(S)-2,3-diaminopropionate using the procedure described for Ex. 275, Part C above to provide the desired product. mp 80–82° C.; $^1$HNMR(CDCl$_3$) δ 1.88 (t,3H), 1.30 (m,2H), 1.47 (sm, 20H), 2.50 (dd, 1H), 2.61 (dd, 1H), 3.07 (dd, 1H), 3.40 (dd, 1H), 3.63 (t, 2H), 3.74 (s, 3H), 4.00 (m, 2H), 4.38 (m, 1H), 5.00 (m, 1H), 5.88 (dd, 1H), 6.77 (t, 1H), 7.58 (d, 2H), 7.84 (d, 2H), 10.4 (s, 1H), 11.6 (s, 1H); IR(KBr):3286, 2964, 1722, 1646, 1546, 1414, 1368, 1340, 1312, 1294, 1240, 1156, 1122, 1100, 1058, 1030, 844, 776 cm$^{-1}$. Mass spectrum (CI/NH$_4$) 663 (M+H, 20),563(7), 549(78), 506(81),463 (100).

Part C: Methyl $N^2$-n-butyloxycarbonyl-$N^3$-(3-(4-quanidinophenyl)isoxazolin-5-yl acetyl]-(S)-2,3-diaminopropionate: The compound of Ex 602, part B was treated with TFA in dichloromethane to afford the corresponding aniline as its TFA salt. This intermediate was converted to the corresponding bis-BOC protected quanidino compound in 59% yield using the method of Kim et al. (Tet. Lett. 1993, 48, 7677). Deprotection under standard conditions (TFA/CH$_2$Cl$_2$) provided the title compound as its TFA salt (90%). $^1$HNMR(DMSO-d$_6$) δ 1.89 (t, 3H), 1.34 (m, 2H), 1.57 (m, 2H), 2.44 (dd, 1H), 2.58 (t, 2H), 2.64 (m, 1H), 3.17 (m, 1H), 3.40 (m,2H), 3.65 (m, 1H), 3.70 (s, 3H), 4.00 (t, 2H), 4.31 (m, 1H), 5.02 (m, 1H), 6.80 (m, 1H), 7.28 (d, 2H), 7.64 (broads, 3H), 7.68 (d, 2H), 7.84 (broad, 1H) ; Mass spectrum(ES) m/z 463 (M+H, 100).

EXAMPLE 606

Methyl $N^2$-p-toluylsulfonyl-$N^3$-[3-(4-quanidinophenyl)isoxazolin-5-(R,S)-ylacetyl]-(S)-2,3-diaminopropionic Acid TFA Salt Part A: The methyl di-Boc-quanidino-α-toluyl ester was prepared according to the procedure for example 602. Deprotection of the Boc-protecting groups then afforded example 606 as the TFA salt. $^1$HNMR (DMSO) δ: 8.30 (dd, 2H), 8.09 (m, 1H), 7.68 (d, J=8.2 Hz, 2H), 7.60 (d, J=8.0 Hz, 2H), 7.35 (d, J=8.2 Hz, 2H), 7.28 (d, J=8.4 Hz, 2H), 4.88 (m, 1H), 4.00 (m, 1H), 3.42 (dt, 1H), 3.38 ((d, 3H), 3.05–3.33 (m, 3H), 2.40 (m, 1H), 2.36 (s, 3H), 2.25 (m, 1H) ppm; HR MS calcd. for $C_{23}H_{29}N_6O_6S$ 517.186930; Found 517.186911.

Part B: Lithium hydroxide saponification on the product of part A then afforded example 605 in 39% yield after recrystallization from dichloromethane and ether. 1HNMR (CD$_3$OD) δ: 8.29(brd, S, 2H), 8.05 (brd, s, 1H), 7.75 (d, J=8.1 Hz, 2H), 7.70 (d, J=8.4 Hz, 2H), 7.31 (d, 4H), 5.02 (m, 1H), 3.85 (m, 1H), 3.60 (m, 2H), 3.41 (m, 1H), 3.20 (m, 1H), 2.64 (dd, 1H), 2.43 (dd, 1H), 2.40 (s, 3H);HR MS calcd. for $C_{22}H_{27}N_6O_6S$ 503.171280; Found 503.170531.

EXAMPLE 625

$N^2$-p-methylphenylsulfonyl-$N^3$-[3- (4-amidinophenylmethyl)-isoxazolin-5-(R,S)-ylacetyl]-(S)-2,3-diaminopropionic Acid TFA Salt Part A: 1-β-nitroethene-4-benzonitrile (Bourgvignon, J.et al., Can, J. Chem., 1985, 63, 2354) (0.9 g, 5.17 mmol) was reduced according to the method of Nakamura, et al. (Chem. Lett., 1985, 523) to afford 0.73 g (80%) of desired product. $^1$H NMR (CDCl$_3$) δ: 7.73 (d, J=8.42 Hz, 2H), 7.43 (d, J=8.42 Hz, 2H), 4.75 (d, J=6.96 Hz, 2H), 3.48 (d, J=6.96 Hz, 2H) ppm; Mass Spectrum (CH$_4$-CI) m/z (M+H)$^+$177 (100%).

Part B: 1-β-nitroethane-4-benzonitrile (1.38 g, 7.8 mmol) was condensed with tert-butyl acrylate (1.4 ml, 9.4 mmol) according to the method of Curran, D. P., et al (J. Org. Chem., 1988, 53, 5369) to afford the crude ester. The ester was difficult to purify so the ester was hydrolyzed in 30 ml of 30% TFA/CH$_2$Cl$_2$ for 48 h. The crude acid was extracted into aqueous NaHCO$_3$. The aqueous layer was acidified and extracted with CH$_2$Cl$_2$ and dried (MgSO$_4$) to afford 1.48 g (80%) orange solid. $^1$H NMR (CDCl$_3$) δ: 7.97 (brd, 1H), 7.64 (d, J=8.42 Hz, 2H), 7.36 (d, J=8.42 Hz, 2H), 5.07 (dd, J=6.59,10.98 Hz, 1H), 3.79 (s, 2H), 3.20 (m,. 2H) ppm.

Part C: The product of Part B (366 mg, 1.6 mmol) was coupled with methyl-L-$N^\alpha$-p-toluylsulfonyl-2,3-diaminoproprionate using procedure described in Example 43D. Chromatography on silica gel (2%MeOH/CH$_2$Cl$_2$) afforded 388 mg (50%).mp 141–144° C; $^1$H NMR (CDCl$_3$) δ: 7.75–7.65 (m, 2H), 7.60 (d, 2H), 7.45 (d, 2H), 7.30 (dd, 2H), 7.20 (m, 1H), 5.50 (dd, 1H), 4.99 (m, 1H), 4.20–3.99 (m, 1H), 3.90–3.70 (m, 3H), 3.55 (s, 3H), 3.30 (m, 3H), 2.42 (s, 3H) ppm; Mass Spectrum (NH$_3$-CI) m/z (M+H)$^+$ 485.2 (100%); IR (KBr) 3276, 1738, 1666, 1538, 1338, 1162, 862, 822 cm$^{-1}$.

Part D: The product of Part C (360 mg, 0.74 mmol) was subjected to the Pinner reaction previously described. Chromatography on silica gel (5–15% MeOH/CH$_2$Cl$_2$) afforded 313 mg (75%) .mp 133–137° C.; $^1$H NMR (DMSO-d$_6$) δ: 9.20 (brd, 2H), 8.26 (t, J=5.86 Hz, 1H), 7.80 (d, J=8.06 Hz, 2H), 7.63 (d, J=8.06 Hz, 2H), 7.51 (d, J=8.06 Hz, 2H), 7.38 (d, J=8.06 Hz, 2H), 4.87–4.73 (m, 1H), 3.98–3.89 (m, 1H), 3.80 (s, 2H), 3.34 (s, 3H), 3.34–3.31 (m, 3H), 3.28 (m, 2H), 2.98 (dd, J=6.23, 17.21 Hz, 1H), 2.37 (s, 3H) ppm; Mass Spectrum (ESI) m/z (M+H)$^+$ 502.2 (100%).

Part E: To the product of Part D (182 mg, 0.338 mmol) was added 1 ml MeOH, followed by lithium hydroxide (31 mg, 0.74 mmol). The mix ture was stirred for 18 h and the solvent was removed in vacuo and water added. HCl was added until a precipitate formed. The solid was filtered off and stirred in 2 ml HCl for 1 h. The acid was removed in vacuo to afford 72 mg of product which contained 15% methyl ester. Purification via standard HPLC techniques then afforded the desire product. $^1$H NMR (DMSO-d$_6$) δ: 9.35 (s, 2H), 9.08 (s, 2H), 8.14–8.07 (m, 2H), 7.78 (d, J=7.32 Hz, 2H), 7.66 (dd, J=2.19, 8.42 Hz, 2H), 7.51 (d, J=7.69 Hz, 2H), 7.36 (d, J=8.42 Hz, 2H), 4.86–4.69 (m, 1H), 3.92–3.80 (m, 1H), 3.79 (s, 2H), 3.30–2.90 (m, 4H), 2.49 (s, 3H) ppm; Mass Spectrum (ESI) m/z (M+H)+488.3 (100%).

EXAMPLE 651

Methy $N^2$-benzyloxycarbonyl-$N^3$-methyl-$N^3$-[3-(4-amidinophenyl)isoxazolin-5-(R,S)-ylacetyl]-(S)-2,3-diaminopropionate, Trifluoroacetic Acid Salt Part A. Preparation of methyl $N^2$-benzyloxycarbonyl-$N^3$-methyl-[3-(4-N-Boc-amidinophenyl)isoxazolin-5-(R,S)-ylacetyl]-(S)-2,3-diaminopropionate.

To a mixture of 3-(4-N-Boc-amidinophenyl)-isoxazolin-5-ylacetic acid (prepared according to the procedure of Example 434, part F; 189 mg, 0.54 mmol), methyl $N^3$-methyl-$N^2$-Cbz-L-2,3-diaminopropionate (prepared according to Sakai and Ohfune, J. Am. Chem. Soc. 114, 998 (1992); 145 mg, 0.54 mmol) and TBTU (175 mg, 0.54 mmol) in ethyl acetate (10 mL) was added triethylamine (0.15 mL, 1.09 mmol). After stirring for 26 h, the mixture was diluted with ethyl acetate, washed with pH 4 buffer, then with saturated aqueous sodium bicarbonate, then with saturated brine. The organic phase was dried (MgSO$_4$) and concentrated. The residue was flash chromatographed (ethyl acetate) to provide the product as a colorless glass (279 mg, 86%): NMR (CDCl$_3$) δ 7.88 (m, 2H), 7.69 (m, 2H), 5.79 (bd, 1H), 5.09 (m, 3H), 4.58 (m, 1H), 3.86 (m, 1H), 3.77 (2s, 3H), 3.63 (m, 2H), 3.14 (dd, 1H), 3.01 (2s, 3H), 2.9 (m, 1H), 2.53 (m, 1H), 1.66 (b, 2H), 1.56 (s, 9H); mass spec (ESI) m/z 596.2 (M+H$^+$, 100%).

Part B. Preparation of Methyl $N^2$-benzyloxycarbonyl-$N^3$-methyl-$N^3$-[3-(4-amidinophenyl)isoxazolin-5-(R,S)-ylacetyl]-(S)-2,3-diaminopropionate, trifluoroacetic acid salt The product of part A (226 mg, 0.38 mmol) was dissolved in dichloromethane (3 mL) and treated with trifluoroacetic acid (1 mL). After stirring at room temperature for 4 h, the mixture was diluted with ether and stirred. The resulting white solid was collected by filtration to provide the title product as a white solid (201 mg, 87%): NMR (DMSO-d$_6$) δ 9.39 (bs, 2H), 9.19 (bs, 2H), 7.87 (s, 4H), 7.79 (t, 1H), 7.32 (m, 5H), 5.03 (3H), 4.40 (m, 2H), 3.90 (m, 1H), 3.65 (2s, 3H), 2.95 and 2.82 (4s, 3H), 3.6–2.8 (4H); mass spec (ESI) m/z 496.3 (M+H$^+$, 100%).

EXAMPLE 666

$N^2$-(methyl)-$N^2$-m-toluylsulfonyl-$N^3$[-3-(4-amidinophenyl)-isoxazoline-5-(R,S)-ylacetyl]-(S)-2,3-diaminopropionic Acid TFA Salt Part A: Methyl $N^3$-[3-(4-cyanophenyl)isoxazolin-5-(R,S)-ylacetyl]-$N^2$-m-toluyl-(S)-2,3-diaminopropionate obtained as the precursor to Example 300 was subjected to a selective Mitsonubo-N-methylation of the sulfonamide (Acta. chem. scand. 1994, 48, 324333),to afford methyl $N^2$-(methyl)-$N^2$-m-toluyl-$N^3$-[3-(4-cyanophenyl)isoaxzolin-5-(R,S)-ylacetyl]-(S)-2,3-diaminopropionate as colorless crystals. M.P=148–149° C. $^1$HNMR(CDCl$_3$) δ: 7.77 (d, 2H), 7.60 (m, 2H), 7.46 (m, 2H), 7.41 (d, 2H), 6.07 (t, 1H), 5.21 (m, 1H), 4.80 (dd, J=4.8 & 10.6 Hz, 1H), 3.81 (m, 1H), 3.56 (s, 3H), 3.43 (m, 2H), 3.25 (dd, J=7.4 & 17.4 Hz, 1H), 2.80 (dd, J=8 & 17.1 Hz, 1H), 2.77 (s, 3H), 2.56 (dd, J=7.7 & 15.1 Hz, 1H), 2.44 (s, 1H) ppm; IR (KBr) 3340, 2224, 1726, 1644, 1610, 1596, 1534, 1440, 1414, 1402, 1366, 1336, 1284, 1258, 1212, 1144, 1012, 934, 918, 896, 844, 812, 784, 690, cm$^{-1}$. ESI mass spectrum 499 (M+H, 48), 359(63), 279(53), 198(100). HR MS calcd. for $C_{24}H_{27}N_4O_6S$ 499.165132 found 499.164946.

Part B: The cyano procursor from part A was then subjected to the Pinner amidine reaction conditions as per example 275E to obtain the desired compound as the methyl ester in 60% overall yield. Saponification with 6N HCl followed by HPLC purification [solvent A: CH$_3$CN: H$_2$O: TFA/2%:98%:0.05%, solvent B: CH$_3$CN:H$_2$O:TFA/80%:20%:0.05%] afforded the desired amidine acid compound 666 as its TFA salt. $^1$HNMR (CDCl$_3$) δ: 9.35 (s, 1H), 9.23 (s, 1H), 8.20 (brd, 2H), 7.89 (brd, 4H), 7.57 (d, J=8 Hz, 2H), 7.40 (d, J=8 Hz, 2H), 5.05 (m, 1H), 4.67 (m, 1H), 3.50–3.66 (m, 3H), 3.20–3.40 (m, 2H), 2.80 (s, 3H), 2.55 (m, 1H), 2.35 (m/s, 4H) ppm; ESI mass spectrum 502(M+H, 100), HRMS calcd for $C_{23}H_{27}N_5SO_6$ 502.176031 found 502.176612.

EXAMPLE 703

Methyl $N^2$-n-butyloxycarbonyl-$N^3$-[3-(4-amidinophenyl)isoxazol-5-yl acetyl]-L-2,3-diaminopropionate TFA Salt Part A. Preparation of Methyl 3-(4-cyanophenyl)isoxazo-5-yl acetate To a suspension of methyl 3-(4-cyanophenyl)-(5R,S)-isoxazolin-5-yl acetate (5.28 g, 21.62 mmol) in chloroform (150 mL) were added N-bromosuccinimide (4.23 g, 23.78 mmol) and AIBN (100 mg) and the mixture was refluxed. Small amounts of AIBN (100 mg–200 mg) were added at one hour intervals until TLC showed a complete reaction. Potassium acetate (17.3 g) and acetic acid (6.5 mL) were added and the reaction mixture was refluxed for 1 hour, cooled, then poured into 1N NaOH (325 mL). The organic layer was separated and the aqueous layer was extracted with EtOAc (3×100 mL). The organic layers were combined and washed with sat. NaCl, dried over Na$_2$SO$_4$, filtered, and concentrated in vacuo. The residue was chromatographed on silica gel (15% to 35% EtOAc in Hexane) to yield 2.2 g (42%) of an off-white solid as product; $^1$H NMR (300 MHz, CDCl$_3$) δ: 7.93 (dd, 2H), 7.76 (dd, 2H), 6.67 (s, 1H), 3.92 (s, 2H), 3.8 (s, 3H).

Part B. Preparation of Methyl 3-(4-methoxyiminophenyl)isoxazo-5-yl acetate HCl salt.

A suspension of methyl 3-(4-cyanophenyl)isoxazo-5-yl acetate (2.19 g, 9.04 mmol) in 100 mL of anhydrous methanol was chilled in an ice bath and dry HCl gas was bubbled through the reaction mixture until a solution was obtained. The total addition time was two hours. The reaction flask was sealed and the reaction mixture was allowed to warm to room temperature, with stirring, over a period of about 24 hrs. At this point, the methanolic solution was poured into 500 mL of anhydrous ether, precipitating the product, and the resulting slurry was chilled to −25° C. for 3 hours. The precipitate was filtered, washed with two 100 mL portions of chilled anhydrous ether, and suction dried under nitrogen to afford 2.3 g (82%) of the hydrochloride salt; $^1$H NMR (300 MHz, suspension in CDCl$_3$) δ 8.52 (d, J=8.06 Hz, 2H), 8.03 (d, J=8.4 Hz, 2H), 6.67 (s, 1H), 4.6 (s, 3H), 3.93 (s, 2H), 3.8 (s, 3H).

Part C. Preparation of Methyl 3-(4-amidinophenyl)isoxazo-5-yl acetate HCl salt.

A solution of methyl 3-(4-methoxyiminophenyl)isoxazo-5-yl acetate HCl salt (2.3 g, 7.4 mmol) in 50 mL of anhydrous methanol was chilled in an ice bath and 2M ammonia in methanol (18.5 mL, 37 mmol) was added. The reaction flask was sealed and the reaction mixture was allowed to warm to room temperature, with stirring, over a period of 24 hrs. The amber solution was then concentrated in vacuo to give 2.2 g (quant. yield) of a yellow foam; $^1$H NMR (300 MHz, d$_6$-DMSO) δ 9.6–9.2 (b), 8.12 (d, J=8.4 Hz, 2H), 7.97 (d, J=8.4 Hz, 2H), 7.14 (s, 1H), 4.15 (s, 2H), 3.7 (s, 3H).

Part D. Preparation of Methyl 3-(4-N-Boc-amidinophenyl) isoxazo-5-yl acetate.

To a solution of methyl 3-(4-amidinophenyl)isoxazo-5-yl acetate HCl salt (2.2 g, 7.4 mmol) in 30 mL DMF cooled with an ice bath was added triethylamine (2.06 mL, 14.8 mmol) and di-tert-butyl dicarbonate (1.78 g, 8.14 mmol). The reaction mixture was warmed to room temperature and stirred for 64 hrs. The reaction mixture was then partitioned between EtOAc and water. The aqueous layer was washed with EtOAc. The organic layers were combined and washed with water, sat. NaCl, dried over $Na_2SO_4$, filtered, and concentrated in vacuo. The residue was chromatographed on silica gel (15% to 25% EtOAc in Hexane) to afford 1.45 g (54%) of product; $^1$H NMR (300 MHz, $CDCl_3$) δ 7.96 (d, J=8.4 Hz, 2H), 7.87 (d, J=8.4 Hz, 2H), 6.65 (s, 1H), 3.91 (s, 2H), 3.8 (s, 3H), 1.56 (s, 9H).

Part E. Preparation of 3-(4-N-Boc-amidinophenyl)isoxazo-5-yl acetic acid.

To a solution of methyl 3-(4-N-Boc-amidinophenyl) isoxazo-5-yl acetate (1.45 g, 4.03 mmol) in 30 mL of methanol was added a solution of lithium hydroxide monohydrate (0.195 g, 4.64 mmol) in water (5 mL). The mixture was stirred at room temperature for 16 hours. The reaction mixture was then concentrated in vacuo and the residue was diluted with water and the resulting mixture was cooled using an ice bath. 1N HCl was slowly added to a pH of 3–4 and the resulting acidic aqueous mixture was extracted repeatedly with EtOAc. The organic layers were combined and washed with sat. NaCl, dried over $Na_2SO_4$, filtered and concentrated in vacuo to yield 0.97 g (70%) of an off-white powdery solid as product; $^1$H NMR (300 MHz, $d_6$-DMSO) δ 8.07 (d, J=8.79 Hz, 2H), 7.97 (d, J=8.4 Hz, 2H), 7.03 (s, 1H), 3.99 (s, 2H), 1.45 (s, 9H).

Part F. Preparation of Methyl $N^2$-n-butyloxycarbonyl-$N^3$-[3-(4-N-Boc-amidinophenyl)isoxazo-5-yl acetyl]-L-2,3-diaminopropionate.

To a solution of 3-(4-N-Boc-amidinophenyl)isoxazo-5-yl acetic acid (0.262 g, 0.76 mmol), methyl $N^2$-n-butyloxycarbonyl-L-2,3-diaminopropionate HCl salt (0.193 g, 0.76 mmol), and TBTU (0.256 g, 0.8 mmol) in DMF (15 mL) was added triethylamine (0.45 mL, 3.23 mmol) and the resulting reaction mixture was allowed to stir at room temperature for 16 hours. The reaction mixture was partitioned between EtOAc and water. The water layer was washed twice with EtOAc. The organic layers were combined and washed with water, pH 4 buffer, 5% $NaHCO_3$, and sat. NaCl, dried over $Na_2SO_4$, filtered, and evaporated in vacuo. The residue was chromatographed on silica gel (100% EtOAc) to yield 0.315 g (76%) of a slightly amber foam; $^1$H NMR (300 MHz, $CDCl_3$) δ 7.93 (d, J=8.42 Hz, 2H), 7.83 (d, J=8.42 Hz, 2H), 6.6 (s, 1H), 6.57 (bm, 1H), 5.66 (bm, 1H), 4.45 (bm, 1H), 4.05 (m, 2H), 3.77 (s, 5H), 3.7 (m, 2H), 1.57 (s, 9H), 1.56 (m, 2H), 1.35 (m, 2H), 0.9 (t, J=7.32 Hz, 3H).

Part G. Preparation of Methyl $N^2$-n-butyloxycarbonyl-$N^3$-[3-(4-amidinophenyl)isoxazo-5-yl acetyl]-L-2,3-diaminopropionate TFA salt.

A solution of methyl $N^2$-n-butyloxycarbonyl-$N^3$-[3-(4-N-Boc-amidinophenyl)isoxazo-5-yl acetyl]-L-2,3-diaminopropionate (0.215 g, 0.39 mmol) in 1:1 methylene chloride/trifluoroacetic acid (20 mL total) was stirred at room temperature for 16 hours. The reaction mixture was then concentrated in vacuo and the residue chromatographed on silica gel (10% to 30% methanol in chloroform) to yield 0.11 g (50%) of a white solid; $^1$H NMR (300 MHz, $d_6$-DMSO) δ 9.4 (bs, 2H), 9.15 (bs, 2H), 8.45 (t, 1H), 8.11 (d, J=8.42 Hz, 2H), 7.94 (d, J=8.42 Hz, 2H), 7.53 (d, J=8.06 Hz, 1H), 7.01 (s, 1H), 4.21 (m, 1H), 3.95 (t, 2H), 3.81 (s, 2H), 3.62 (s, 3H), 3.55 (m, 1H), 3.34 (m, 1H), 1.5 (m, 2H), 1.3 (m, 2H), 0.87 (t, J=7.32 Hz, 3H).; Mass Spectrum (ESI, e/z, relative abundance) 446.3, (M+H)$^+$, 100%.

EXAMPLE 717

$N^2$-Phenylmethylsulfonyl-$N^3$-[3-(4-amidinophenyl) isoxazolin-5(R,S)-ylacetyl]-(S)-2,3-diaminopropionic Acid TFA Salt Prepared according to Example 490a. MS (ESI, e/z, relative intensity): 488 (M+H)$^+$, (100%).

EXAMPLE 816

$N^2$-p-toluylsulfonyl-$N^3$-[5-(4-amidinophenyl) isoxazolin-3-(R,S)-yl-acetyl]-(S)-2,3-diaminopropionic Acid TFA Salt The title compound was prepared in a manner similar to example 829. Saponification of the methyl ester via standard techniques then afforded crude compound 816, which was purified via HPLC [graduant flow, solvent A $CH_3CN(2\%)$ :$H_2O(98\%)$:TFA(0.05%), solvent B: $CH_3CN(80\%)$:$H_2O$ (20%):TFA(0.05%),] to afford colorless crystals of compound 816 as its TFA salt. $^1$HNMR($CDCl_3$) δ:

9.30(brds, 4H), 8.34 (t, 1H), 8.12 (d,J=9.2 Hz, 1H), 7.81 (d, J=8.3 Hz, 1H), 7.60 (d, J=8.0 Hz, 1H), 5.60 (dt, 1H), 3.81 (q, 1H), 3.43 (dt, 1H), 3.25 (m, 1H), 3.20 (d, 1H), 3.03 (m, 1H), 2.89 (m, 1H), 2.50 (s, 1H), 2.34(s,3H) ppm; ESI mass spectrum 488 (M+H,100), HRMS calcd. for $C_{22}H_{26}N_5O_6S$ 488.160381; found 488.158785.

EXAMPLE 829

Methyl $N^2$-n-butyloxycarbonyl-$N^3$-[5-(4-amidinophenyl)isoxazolin-3-yl acetyl]-(2S)-2,3-diaminopropionate Part A: t-Butyl [5-(4-cyanophenyl)isoxazolin-3-yl]acetate:

Cycloaddition of 4-cyanophenylethylene (MP & D chemical Co.) and tert-butyl-3-oxopropionate oxime was carried out following the procedure of Gree et. al. (Bioorganic & Medicinal Chemistry letters 1994, 253) to provide the desired isoxazoline in 72% yield. $^1$HNMR ($CDCl_3$) δ: 1.40 (s, 9H), 3.00 (dd, J=8.3 and 17 Hz, 1H), 3.35 (dd(AB) J=18 and 8.3 Hz, 2H),3.48 (m, 1H), 5.60 (dd, J=9 and 4.5 Hz, 1H), 7.47 (d, J=8 Hz, 2H), 7.65 (d, J=8 Hz, 2H); IR 2235, 1718, 1610 cm$^{-1}$. Mass spectrum m/z 287 (M+H, 100).

Part B: [5-(4-cyanophenyl)isoxazolin-3-yl]acetic acid:

Hydrolysis of the compound of Ex.829, Part A with excess TFA in dichloromethane afforded the acid in 90% yield. $^1$HNMR ($CDCl_3$) δ 3.00 (dd, J=8 and 17.2 Hz, 1H), 3.55 (s, 2H), 3.59 (m, 1H), 5.66 (dd, J=8 and 11 Hz, 1H), 7.45 (d, J=8.4 Hz, 2H), 7.66 (d, J=8.0 Hz, 2H); IR(KBr) 3325, 2235, 1718, 1605 cm$^{-1}$; Mass spectrum m/z 231 (M+H, 100).

Part C: Methyl [5- (4-Boc-amidinophenyl)isoxazolin-3-yl] Acetate:

The compound of Ex. 829, Part B compound was then subjected to the standard Pinner reaction conditions described in Ex. 275, Part D to afford an amidino compound, which, without purification, was subjected to treatment with di-tert-butyldicarbonate in dioxane/water (9:1) and excess triethylamine to afford the desired compound in 28% yield. $^1$HNMR($CDCl_3$) δ 1.54 (s,9H), 2.98 (dd, J=8 and 17 HZ, 1H), 3.49 (s, 2H), 3.53 (m, 1H), 3.71 (s, 3H), 5.63 (dd, J=8 & 11.4 Hz, 1H), 7.38 (d, 8.2 Hz, 2H), 7.82 ((d, 8.2 Hz, 2H); Mass spectrum m/z 362(M+H, 8), 306(18), 262(M+H-Boc, 100).

Part D: [5-(4-Boc-amidinophenyl)isoxazolin-3-yl]acetic acid:

Hydrolysis of the ester using standard LiOH conditions afforded the desired acid in 5% yield. $^1$HNMR($CDCl_3$) δ 1.54 (s,9H), 3.00 (dd, J=8 and 17 HZ, 1H), 3.51 (s, 2H), 3.53 (m, 1H), 5.63 (dd, J=8 & 11.4 Hz, 1H), 7.38 (d, 8.2 Hz, 2H), 7.82 ((d, 8.2 Hz, 2H); Mass spectrum m/z 348(M+H,12), 248(M+H-Boc, 100).

Part E: Methyl $N^2$-n-butyloxycarbonyl-$N^3$-[5-(4-amidinophenyl)isoxazolin-3-yl-acetyl](S)-2,3-diaminopropionate, trifluoroacetate:

The compound of Ex. 829, Part D was coupled with methyl-(S)-$N^2$-n-butyloxycarbonyl-2,3-diaminopropionate following the procedure described in Ex. 275, Part C to give the Boc protected intermediate in 80% yield. $^1$HNMR (CDCl$_3$) δ 0.89 (t, 3H), 1.32 (m, 2H), 1.53 (s, 9H), 1.17 (m, 2H), 2.95 (dd, J=8 and 17 HZ, 1H), 3.33 (s, 2H), 3.46 (m, 1H), 3.60 (m, 2H), 3.73 (s, 3H), 4.00 (m, 2H), 4.31 (m, 1H), 5.60 (dd, J=8 & 11.4 Hz, 1H), 5.70 (bd, 1H), 6.70 (broad, 1H), 7.33 (d, 8.2 Hz, 2H), 7.89 ((d, 8.2 Hz, 2H); Mass spectrum m/z 534 (M+H, 30), 434 (M+H-Boc, 100). Deprotection by treatment of the above Boc-amidine with excess TFA in dichloromethane provided the title compound as the TFA salt. $^1$HNMR(CDCl$_3$/DMSO-d$_6$) δ 1.88 (t, 3H), 1.30 (m, 2H), 1.53 (m, 2H), 3.00 (dd, J=8 and 17 HZ, 1H), 3.32 (s, 2H), 3.40–3.63 (m, 3H), 3.63 (d, 3H), 3.98 (t, 2H), 4.29 (m, 1H), 5.60 (dd, J=8 & 11 Hz, 1H), 6.80 (d, 1H), 7.50 (d, J=8 Hz, 2H), 7.80 (d, J=8.2 Hz, 2H), 8.03 (broad s, 1H), 9.05 (broad s, 2H); IR(KBr): 3388, 1718, 1664, 1620, 1528, 1456, 1436, 1384, 1366, 1280, 1254, 1168, 1144, 1074, 980, 882, 778 cm$^{-1}$; Mass spectrum(ES) m/z 448 (M+H, 100)

EXAMPLE 952

Methyl $N^2$-m-toluenesulfono-$N^3$-[3-(4-N-isopropylamidophenyl)isoxazolin-5R-ylacetyl]-S-2,3-diaminopropionate Methyl $N^2$-m-toluenesulfono-$N^3$-[3-(4-cyanophenyl)isoxazolin-5R-ylacetyl]-S-2,3-diaminopropionate (prepared as in example 473 part C above) (0.098 g, 0.0002 mol) was stirred with isopropyl alcohol (0.018 ml, 0.0002 mol) and sulfuric acid (5 ml) for 12 hours. The reaction mixture was poured over ice and diluted to three times its' volume with water. The title compound was filtered as a pale brown solid. $^1$H NMR (CDCl$_3$) δ: 7.79–7.61 (m, 6H); 7.38–7.36 (m, 2H); 6.49–6.40 (m, 1H); 6.01–5.99 (m, 1H); 5.62–5.55 (m, 1H); 5.19–5.08(m, 1H); 4.31–4.28(m, 1H); 4.11–3.99(m, 1H); 3.56 (s, 3H); 3.72–3.48 (m, 4H); 3.24–3.16 (dd, 1H, J=7.3, 17.0); 2.41 (s, 3H); 1.29–1.27 (d, 6H, J=6.59 Hz). MS(ESI) calc'd for C$_{26}$H$_{32}$N$_4$SO$_7$ 545.3 found 545.2 (M+H)$^+$

EXAMPLE 954

$N^2$-3-(n-butylcarbamoyl)-$N^3$-[3- (4-amidophenyl) isoxazolin-5R-ylacetyl]-S-2,3-diaminopropionic Acid Following the procedure outlined for example 1945 above, Methyl $N^2$-3-(n-butylcarbamoyl)-$N^3$-[3-(4-cyanophenyl)isoxazolin-5R-ylacetyl]-S-2,3-diaminopropionate (0.87 g, 0.002 mol) gave a 66% yield of $N^2$-3-(n-butylcarbamoyl)-$N^3$-[3-(4-amidophenyl) isoxazolin-5R-ylacetyl]-S-2,3-diaminopropionic acid. $^1$H NMR (CDCl3) δ: 12.7 (bs, 1H); 8.12–8.09 and 7.28–7.26 (2m, 1H); 8.05 and 7.43 (2s, 1H); 7.94–7.92 (d, 2H, J=8.54); 7.87 (s, 1H); 7.73–7.70 (d, 2H, J=8.5 Hz); 6.51–6.49 (m, 1H); 5.02–4.95 (m, 1H); 3.95–3.90 (m, 1H); 3.58–3.47 (m, 2H); 3.29–3.13 (m, 2H); 2.72–2.38 (m, 4H); 1.52–1.46 (m, 2H); 1.34–1.25 (m, 2H); 0.87–0.85 (t, 3H, J=4.3 Hz). MS(ESI): Cacl'd for C20H26N4O7 435.2 found 435.2 (M+H)$^+$.

EXAMPLE 956

$N^2$-3-methylphenylsulfonyl-$N^3$-[3-(4-amidophenyl)-5R-ylacetyl]-S-2,3-diaminopropionic Acid
Part A: Methyl $N^2$-m-toluenesulfono-$N^3$-[3-(4-amidophenyl)-5S-ylacetyl]-S-2,3-diaminopropionate hydrochloride.

Methyl $N^2$-m-toluenesulfono-$N^3$-[3-(4-cyanophenyl)-5R-ylacetyl]-S-2,3-diaminopropionate (0.19 g, 0.00039 mol) was dissolved in 10 ml concentrated sulfuric acid. After stirring for 12 hours the reaction mixture was poured over 10 g of ice and 20 ml of water was added. The white solid was filtered, washed once with water and dried under vacuum overnight to give methyl-$N^2$-m-toluenesulfono-$N^3$-[3-(4-amidophenyl)-5S-ylacetyl]-S-2,3-diaminopropionate as a white powder. IR(neat) cm$^{-1}$: 3404, 3340, 3274, 3202, 2930, 1710, 1652, 1612, 1526, 1320, 1286, 1238, 1174, 1100, 1086, 1070, 886, 850, 614, 574. MS(ESI): calc'd for C$_{23}$H$_{26}$N$_4$O$_7$S 503.2 found 503.3(M+H)$^+$.
Part B: $N^2$-m-toluenesulfono-$N^3$-[3-(4-amidophenyl)-5R-ylacetyl]-S-2,3-diaminopropionic acid Methyl $N^2$-m-toluenesulfono-$N^3$-[3-(4-amidophenyl)-5R-ylacetyl]-S-2,3-diaminopropionate hydrochloride (0.146 g, 0.29 mmol) was dissolved in MeOH (5 ml), LiOH (0.013 g, 0.32 mmol) in H$_2$O (5 ml) was added and the reaction mixture left to stir overnight. Purification was done by HPLC on a Vyadek column using a gradient of 0.05%TFA/water to 0.05%TFA/acetonitrile over 45 min. The flow was set to 10 ml/min and the detector at 254 nm. The peak eluted at 25 min, the volatiles were evaporated in vacuo, and the solid dried under vacuum. MS(ESI) calc'd for C$_{22}$H$_{24}$N$_4$O$_7$S: 489.2 found: 489.2.

EXAMPLE 978

Methyl $N^2$-m-toluenesulfono-$N^3$-[3-(5-amidopyrid-2-yl)isoxazolin-5S-ylacetyl]-2,3-diaminopropionate mp 192–195.5° C. (dec). $^1$H NMR (DMSO-d$_6$, 300 MHz) δ 2.28 (dd, J=14.6, 7.0 Hz, 1H), 2.36 (s, 3H), 2.44–2.54 (m, 1H, under DMSO), 3.04–3.15 (m, 1H), 3.20 (dd, J=17.6, 7.3 Hz, 1H), 3.30–3.40 (m, 1H, under water), 3.53 (dd, J=17.6, 10.6 Hz, 1H), 3.80–3.89 (m, 1H), 4.92–5.05 (m, 1H), 7.38–7.48 (m, 2H), 7.54–7.61 (m, 2H), 7.68 (br s, 1H), 7.98 (d, J=8.1 Hz, 1H), 8.04–8.10 (m, 2H), 8.23 (br s, 1H), 8.27 (dd, J=8.1, 2.2 Hz, 1H), 9.06 (d, J=1.5 Hz, 1H), 12.76 (br s, 1H). IR (KBr) 3388, 3314, 3274, 3186, 1712, 1662, 1584, 1546, 1418, 1344, 1160, 934, 794, 712, 688, 620, 576 cm$^{-1}$. MS (ESI) 490 (M+H, 100).

EXAMPLE 979

$N^2$-[(p-ethyl)phenylsulfonyl]-$N^3$-[3-(4-carboxamidophenyl)isoxazolin-5-(R,S)-ylacetyl]-(S)-2,3-diaminopropionate $^1$HNMR (DMSO) δ 8.12 (2H,m), 7.94 (2H, d, J=8.423 Hz), 7.74 (2H, m), 7.70 (2H, d, J=8.423 Hz), 7.46 (1H, s),7.40 (2H, m), 4.94 (1H, m), 3.92 (1H, m), 3.56 (2H, m), 3.37 (3H, m), 2.70 (2H, m), 2.45 (3H, m), 1.22 (3H, m) ppm; MS (ESI) m/z 503.3 (M+H)$^+$.

EXAMPLE 996

$N^2$-o-toluenesulfonyl-$N^3$-[5-(4-amidinophenyl)isoxazolin-3(R,S)-ylformyl]-(S)-2,3-diaminopropionic Acid TFA Salt Standard cycloaddition techniques using ethylchlorooximido acetate(Aldrich) and 4-cyanostyrene agfforded the desired precursor ethyl-5-(4-cyanophenyl)-isoxazoline carboxylate. Saponification followed by coupling with methyl $N^2$-o-toluylsulfonyl-(S)-2,3-diaminopropionate via standard techniques afforded the desired cyanoprecursor. Formation of the amidine via standard Pinner reaction conditions afforded the desired compound as colorless crystals after HPLC purification; M.P. 84–86° C.; $^1$HNMR(DMSO d$_6$) δ: 9.45 (b, 1H), 9.35 (b, 1H), 8.40 (q, 1H), 8.21 (dd, 1H), 7.81 (t,2H), 7.77 ( d, J=8.5 Hz, 2H), 7.55 (d, J=8.5 Hz, 2H), 7.38–7.49 (t, 1H), 7.25 (m, 2H), 5.83 (m, 1H), 3.89 (q, 1H), 3.23–3.71 (m, 3H), 2.98(q, 1H), 2.57 (s,3H) ppm; ESI mass spectrum 474 (M=H, 100 free base); HRMS calcd for C$_{21}$H$_{24}$N$_5$O$_6$S 474.144731, found 474.143847.

EXAMPLE 1540

2-(n-Butyloxycarbonylamino)-3-[3-(4-amidinophenyl)-1-oxo-2,8-diazaspiro[4,5]dec-2-en-8-yl]propionic Acid Bis Trifluoroacetic Acid Salt Part A: 3-(4-Cyanophenyl)-8-benzyloxycarbonyl-1-oxyo-2,8-diazaspiro[4,5]dec-2-ene.

The title material was prepared from 4-cyanobenzaldoxime (7.0 g, 48 mmol) and 1-benzyloxycarbonyl-4-methylenepiperidine (De Amici, M.; Frølund, B.; Hjeds, H. Krogsgaard-Larsen, P. *Eur. J. Med. Chem.* 1991, 26, 625) (11.0 g, 48 mmol) as described in Example 4, Part B. The crude adduct was purified by flash chromatography using a gradient hexane/ethyl acetate solvent system, starting with hexane and progressing to 65% ethyl acetate/hexane in 5% increments to give 14.4 g (86%) of a pale yellow gum. $^1$H NMR (DMSO-d$_6$, 300 MHz) δ 7.75 (d, J=8 Hz, 2H), 7.69 (d, J=8 Hz, 2H), 7.37–7.29 (m, 5H), 5.15 (s, 2H), 3.95–3.83 (m, 2H), 3.51–3.44 (m, 2H), 3.09 (s, 2H), 2.00–1.89 (m, 2H), 1.83–1.70 (m, 2H). IR (KBr) 2228, 1698 cm$^{-1}$. HRMS (DEP, NH$_3$) Calc. for (M+H)$^+$: 376.1661. Found: 376.1646.

Part B: 3-(4-Amidinophenyl)-1-oxo-2,8-diazastiro[4.5]dec-2-ene dihydrochloric acid salt.

The intermediate of Part A (4.18 g, 11.1 nmol) was subjected to standard Pinner conditions to give a crude amidine-amine salt, which was purified by flash chromatography using a graduated solvent system starting with chloroform and progressing to 30% methanol in chloroform to give 1.8 g (48%) of the title compound. $^1$H NMR (DMSO-d$_6$, 300 MHz) δ 9.56 (br s, 1.5H), 9.36 (br s, 1.5H), 7.95 (d, J=8.7 Hz, 2H), 7.86 (d, J=8.4 Hz, 2H), 4.15–4.14 (m, 1H), 3.43 (s, 2H), 3.36 (s, 4H), 2.05–2.04 (m, 4H). HRMS (DEP, NH$_3$) Calc. for (M+H)$^+$: 259.1559. Found: 259.1562.

Part C: Methyl 2-(R,S)-(benyloxycarbonylamino)-3-[3(4-amidinothenyl)-1-oxo-2,8-diazaspiro[4,5]dec-2-en-8-yl]-propionate dihydroiodic acid salt.

The intermediate of Part B (1.67 g, 5.0 mmol) was dissolved in dimethylformamide (20 mL) and sodium bicarbonate (1.27 g, 15.1 mmol) was added. A solution of N-benzyloxycarbonyl-3-iodo-L-alanine methyl ester (M arki, W.; Schwyzer, R. *Helv. Chim. Acta* 1975, 58, 1471) (2.0 g, 5.5 mmol) in dimethylformamide (6 mL) was added and the mixture was stirred at room temperature for 7 d. The solvent was evaporated and the residue was flash chromatographed using a graduated solvent system starting with chloroform and progressing to 20% methanol/chloroform in 5% steps to give 1.78 g of impure material. It was chromatographed a second time as above to give 1.72 g (45%) of pure material. $^1$H NMR (DMSO-d$_6$, 300 MHz) δ 9.16 (br s, 4H), 7.87 (s, 4H), 7.71 (d, J=7.7 Hz, 1H), 7.39–7.30 (m, 5H), 5.10–5.05 (m, 2H), 4.29–4.27 (m, 1H), 3.65 (s, 3H), 3.23 (s, 2H), 2.66–2.60 (m, 4H), 2.46 (m, 2H), 1.75 (m, 4H). IR (KBr) 3300–2950 (br), 1718, 1674 cm$^{-1}$. HRMS (FAB, glycerol) Calc for (M+H)$^+$: 494.2403. Found: 494.2401.

Part D: Methyl 2-(R,S)-amino-3-[3-(4-amidinophenyl)-1-oxo-2,8-diazaspiro[4,5]dec-2-en-8-yl]propionate trihydrobromic acid salt.

The intermediate of Part C (1.2 g, 1.6 mol) was dissolved in 30% hydrogen bromide in acetic acid (10 mL) and the solution was stirred at room temperature for 17.5 h. The mixture was diluted with ether and filtered. The solid was washed with ether and dried to give 0.872 g (89%) of a gray solid. $^1$H NMR (DMSO-d$_6$+TFA-d, 300 MHz) δ 9.43 (s, 2H), 9.14 (s, 2H), 7.94–7.85 (m, 4H), 4.84 (m, 1H), 3.84 (s, 4H), 3.55–3.42 (m, 6H), 2.16 (br m, 4H). MS (ESI) 360 (M+H).

Part E: Methyl 2-(n-butyloxycarbonylamino)-3-[3-(4-amidinophenyl)-1-oxo-2,8-diazaspiro[4.5]dec-2-en-8-yl] propionate hydrobromic acid salt.

n-Butylchloroformate (45 μL, 0.35 nmol) was added to a solution of the intermediate of Part D (0.200 g, 0.33 mmol) and triethylamine (0.14 mL, 1.0 mmol) in dimethylformamide (2 mL) and the mixture was stirred at room temperature for 2 h. The solution was flash chromatographed using a gradient solvent system starting with chloroform and progressing to 20% methanol/chloroform in 5% steps to give 0.249 g of the title compound. MS (ESI) 460 (M+H).

Part F: 2-(n-Butyloxycarbonylamino)-3-[3-(4-amidinophenyl)-1-oxo-2,8-diazaspiro[4,5]dec-2-en-8-yl] propionic acid bis trifluoroacetic acid salt.

The intermediate of Part E (229 mg, 0.33 mmol) was dissolved in methanol (7 mL) and water (7 mL) and lithium hydroxide hydrate (33 mg, 0.79 mmol). The mixture was stirred at room temperature for 24 h and additional lithium hydroxide hydrate (18 mg, 0.43 mmol) was added. The mixture was stirred for 24 h and the methanol was evaporated. The aqueous residue was diluted with trifluoroacetic acid (0.15 mL) and the mixture was purified by Prep HPLC as described in Example 514A, Part B to give 31 mg (11%) of the title compound. $^1$H NMR (DMSO-d$_6$, 300 MHz) δ 9.40 (br s, 2H), 9.12 (br s, 2H), 7.91–7.86 (m, 4H), 7.61 (br, 1H), 6.56 (br, 1H), 4.44 (br, 1H), 4.00 (t, J=6.2 Hz, 2H), 3.38 (m, 6H, under water peak), 2.03 (br, 4H), 1.58–1.54 (m, 2H), 1.36–1.34 (m, 2H), 0.90 (t, J=7.4 Hz, 3H). HRMS (FAB, glycerol) Calc. for (M+H)$^+$: 446.2403. Found: 446.2394.

EXAMPLE 1541

2-(R,S)-(3-methylphenylsulfonylamino)-3-[3-(4-amidinophenyl)-1-oxo-2,8-diazaspiro[4,5]dec-2-en-8-yl]propionic Acid Bis Trifluoroacetic Acid Salt Part A: Methyl 2-(R,S)-(m-toluenesulfonylamino)-3-[3-(4-amidinophenyl)-1-oxo-2,8-diazaspiro[4,5]dec-2-en-8-yl] propionate hydrobromic acid salt.

m-Toluenesulfonyl chloride (63 mg, 0.33 mmol) was added to a mixture of the intermediate in Example SP1, Part D (0.200 g, 0.33 mmol) and triethylamine (0.14 mL, 1.0 mmol) in dimethylformamide (2 mL) and the mixture was stirred at room temperature for 19 h. Additional m-toluenesulfonyl chloride (14 mg, 0.07 mmol) was added and the mixture was stirred for 24 h. The solution was flash chromatographed using a graduated solvent system starting with chloroform and progressing to 30% methanol/ chloroform to give 0.309 g of a tan solid. HRMS (FAB, glycerol) Calc. for (M+H)$^+$: 514.2124. Found: 514.2137.

Part B: 2- (R,S)-(m-Toluenesulfonylamino)-3-[3-(4-amidinophenyl)-1-oxo-2,8-diazaspiro[4,5]dec-2-en-8-yl] propionic acid bis trifluoroacetic acid salt.

The intermediate of Part A (0.277 g, 0.46 mmol) was suspended in 6M hydrochloric acid and the mixture was stirred at room temperature for 2 d. The mixture was concentrated and the residue was purified by Prep HPLC as described in Example 514A, Part B to give 16 mg of the title compound. HRMS (FAB, glycerol) Calc. for (M+H)$^+$: 500.1968. Found: 500.1956.

EXAMPLE 1552

5 (R,S)-(2-Piperidin-4-yl)ethyl-8-(3-carboxypropyl)-1-oxa-2,8-diazaspiro[4,4]non-2-ene-7,9-dione This material was prepared using the procedures outlined in Example 189, giving the title compound; mp:

133.4–135.1° C.; $^1$H NMR (400 MHz, CD$_3$OD, 55° C.) δ 3.59 (t, J=6.8 Hz, 2H), 3.50 (d, J=17.7 Hz, 1H), 3.38 (bd, J=12.9 Hz, 2H), 3.18 (d, J=17.7 Hz, 1H), 2.98 (m, 4H), 2.85 (m, 2H), 2.50 (m, 1H, coincident with DMSO-d$_5$), 2.45 (m, 2H), 2.31 (t, J=7.1 Hz, 2H), 2.00 (m, 2H), 1.98 (pentuplet, J=7.1 Hz., 2H), 1.40 (m, 2H).

EXAMPLE 1585A

N$^2$-n-butyloxycarbonyl-N$^3$-[3-(4-piperidinylmethyl)-isoxazolin-5-(R,S)-yl-acetyl]-(S)-2,3-diaminopropionic Acid TFA Salt $^1$HNMR (DMSO) δ 8.5 (1H, brd), 8.2 (1H, brd), 8.0 (1H, m), 7.4 (1H, d), 4.7 (1H, m), 3.9 (3H, m), 3.6 (1H, m), 3.25 (2H, m), 3.1 (3H, m), 2.9 (2H, m), 2.7 (1H, m), 2.4 (2H, m), 2.2 (3H; m), 1.8 (2H, m), 1.7 (1H, m), 1.5 (2H, m), 1.3 (4H, m), 0.9 (3H, t) ppm; ESI mass spectrum 427.1 (M+H)$^+$ free base.

EXAMPLE 1603

Methyl N$^2$-n-butyloxycarbonyl-N$^3$-[3-(4-piperidinylpropyl)-isoxazolin-5(R,S)-yl-acetyl]-(S)-2,3-diaminopropionate TFA Salt $^1$HNMR (CDCl$_3$) δ 6.29 (1H, brd), 4.9 (1H, m), 4.45 (1H, m), 4.05 (2H, m), 3.78 (3H, s), 3.68 (1H, m), 3.5 (3H, m), 3.1 (1H, m), 2.96 (2H, m), 2.78 (1H, m), 2.55 (2H, m), 2.36 (2H, m), 1.95 (2H, m), 1.6 (6H, m), 1.5 (2H, m), 1.35 (5H, m), 0.94 (3H, m) ppm; ESI mass spectrum 455 (M+H)$^+$ free base.

EXAMPLE 1609

Methyl N$^2$-p-toluenesulfonyl-N$^3$-[3-(4-piperidinylpropyl)-isoxazolin-5-(R,S)-yl-acetyl]-(S)-2,3-diaminopropionate TFA Salt $^1$HNMR (CDCl$_3$) δ 7.7 (2H, d), 7.3 (2H, d), 7.18 (1H, m), 6.4 (1H, m), 4.92 (1H, m), 4.0 (2H,m), 3.7 (1H, m), 3.58 (3H, d), 3.35 (2H, m), 3.1 (1H, m), 2.9 (2H, m), 2.75 (1H, m), 2.55 (1H, m), 2.4 (6H, m), 1.9 (2H, m), 1.6 (5H, m), 1.35 (2H, m) ppm; ESI mass spectrum 509.3 (M+H)$^+$ free base

EXAMPLE 1619

N$^2$-(2-methylphenylsulfonyl)-N$^3$-[3-(4-piperidinylethyl)-isoxazolin-5-(R,S)-ylacetyl]-(S)-2,3-diaminopropionic Acid IFA Salt $^1$HNMR (DMSO) δ: 8.5(1H, m), 8.18 (1H, m), 8.05 (1H, m), 7.79 (1H, d J=8.057 Hz), 7.51 (1H, t, J=6.958 & 7.324 Hz), 7.37 (2H, m), 4.65 (1H, m), 3.83(1H, m), 3.4 (1H, m), 3.27 (3H, m), 3.07 (1H, m), 2.84 (2H, m), 2.68 (1H, m), 2.59 (3H, s), 2.4 (1H, m), 2.32 (3H, m), 2.08 (1H, m), 1.83 (2H, m), 1.45 (3H, m), 1.26 (2H, m) ppm; ESI mass spectrum 481.4 (M+H, 100)$^+$ free base.

EXAMPLE 1621

N$^2$-p-toluenesulfonyl-N$^3$-[3-(4-pieridinylethyl)-isoxazolin-5-(R,S)-ylacetyl]-(S)-2,3-diaminopropionic Acid TFA Salt $^1$HNMR (DMSO) δ 7.73 (2H, d), 7.35 (2H, d), 4.85 (2H, m), 4.05 (1H, m), 3.63 (1H, m), 3.2 (2H, m), 3.0 (4H, m), 2.6 (1H, m), 2.4 (3H, s), 2.42 (2H, m), 2.0 (2H, m), 1.7 (1H, d), 1.6 (3H, m), 1.4 (3H, m) ppm; ESI mass spectrum 481 (M+H, 100)$^+$ free base

EXAMPLE 1622

N$^2$-(2-bromophenylsulfonyl)-N$^3$-[3-(4-piperidinylethyl)-isoxazolin-5-(R,S)-ylacetyl]-(S)-2,3-diaminopropionic Acid TFA Salt $^1$HNMR (DMSO) δ: 8.5 (1H, brd), 8.2 (1H, m), 8.1 (1H, m), 7.95 (1H, m), 7.8 (1H, m), 7.5 (2H, m), 4.7 (1H, m), 3.9 (1H, m), 3.4 (1H, m), 3.25 (2H, m), 3.2 (1H, m), 3.0 (1H, m), 2.8 (2H, m), 2.7 (1H, m), 2.4 (2H, m), 2.3 (2H, m), 2.2 (1H, m), 1.8 (2H, m), 1.5 (2H, m), 1.2 (2H, m) ppm; ESI mass spectrum 545.2 (M+H, 100)$^+$ free base.

EXAMPLE 1623

N$^2$-(3,5-dimethylisoxazoylsulfonyl)-N$^3$-[3-(4-piperidinylethyl)-isoxazolin-5-(R,S)-ylacetyl]-(S)-2,3-diaminopropionic Acid TFA Salt $^1$HNMR (DMSO) δ: 8.5 (1H, d), 8.08 (1H, m), 4.65 (1H, m), 3.9 (1H, m), 3.4 (1H, m), 3.25 (3H, m), 3.15 (2H, m), 2.85 (2H, m), 2.7 (1H, m), 2.52 (3H, s), 2.4 (1H, m), 2.3 (3H, m), 2.2 (3H, m), 1.8 (2H, brd, d), 1.45 (3H, m), 1.25 (2H, m) ppm; ESI mass spectrum 486.3 (M+H, 100)$^+$ free base.

EXAMPLE 1624

N$^2$-(3,4-dimethylthiazoylsulfonyl)-N$^3$-[3-(4-piperidinylethyl)-isoxazolin-5-(R,S)-ylacetyl]-(S)-2,3-diaminopropionic Acid TFA Salt $^1$HNMR (DMSO) δ: 8.6 (1H, d), 8.45 (1H, brd), 8.1 (1H, m), 4.65 (1H, m), 3.9 (1H, m), 3.5 (4H, m), 3.05 (2H, m), 2.9 (3H, m), 2.6 (3H, s), 2.45 (3H, s), 2.4 (5H, m), 1.8 (2H, brd. d), 1.5 (2H, m), 1.2 (2H, m) ppm; ESI mass spectrum 502.4 (M+H, 100)$^+$ free base.

EXAMPLE 1625

N$^2$-n-butylsulfonyl-N$^3$-[3-(4-piperidinylethyl)-isoxazolin-5-(R,S)-ylacetyl]-(S)-2,3-diaminopropionic Acid TFA Salt $^1$HNMR (DMSO) δ 8.5 (1H, m), 8.2 (2H, m), 7.55 (1H, m), 4.7 (1H, m), 3.9 (1H, m), 3.4 (1H, m), 3.2 (3H, brd, d), 3.1 (1H, m), 2.98 (2H, m), 2.9 (4H, m), 2.4 (1H, d), 2.3 (3H, m), 1.8 (2H, brd, d), 1.7 (2H, m), 1.5 (6H, m), 0.9 (3H, t) ppm; ESI mass spectrum 447.3 (M+H, 100)$^+$free base

EXAMPLE 1627

N$^2$-n-butyloxycarbonyl-N$^3$-[3-(4-piperidinylpropyl)-isoxazolin-5-(R,S)-yl-acetyl]-(S)-2,3-diaminopropionic Acid TFA Salt $^1$HNMR (DMSO) δ 8.5 (1H, m), 8.2 (2H, brd),7.3 (1H, m), 4.7 (1H, m), 4.05 (1H, m), 3.9 (2H, t), 3.5 (1H, m), 3.2 (3H, brd, d), 3.0 (1H, m), 2.8 (2H, m), 2.7 (1H, m), 2.4 (1H, d), 2.25 (3H, m), 1.8 (2H, d), 1.6 (6H, m), 1.4 (7H, m), 0.9 (3H, t) ppm; ESI mass spectrum 441.3 (M+H, 100)$^+$ free base.

EXAMPLE 1631

N$^2$-p-toluenesulfonyl-N$^3$-[3-(4-piperidinylpropyl)-isoxazolin-5-(R,S)-ylacetyl]-(S)-2,3-diaminopropionic Acid TFA Salt $^1$HNMR (CD$_3$OD) δ: 7.7 (2H, m), 7.35 (2H, m), 4.85 (1H, m), 4.05 (2H, m), 3.72 (1H, m), 3.66 (2H, m), 3.56 (1H, m), 3.35 (2H, m), 3.25 (1H, m), 3.14 (1H, m), 2.94 (2H, m), 2.84

(1H, m), 2.55 (1H, m), 2.4 (3H, m), 2.35 (3H, m), 1.95 (2H, m), 1.62 (3H, m), 1.32 (4H, m), ppm; ESI mass spectrum 495.3 (M+H)$^+$ free base

EXAMPLE 1656

$N^2$-m-toluenesulfonyl-$N^3$-[3-(4-amidinopiperidinyl)-isoxazolin-5-(R,S)-ylacetyl]-(S)-2,3-diaminoproprionic Acid M.P. 70–74° C.; $^1$H NMR (DMSO-d$_6$) δ 8.13 (m,2H), 7.58 (m,2H), 7.44–7.38 (m, 5H), 4.74 (m, 1H), 3.88–3.80 (m, 5H), 3.40 (m, 1H), 3.14–2.99 (m, 4H), 2.74 (m,2H), 2.37 (s,3H), 2.17 (dd, J=7.32, 14.28 Hz), 1.88 (d, J=13.18 Hz, 2H), 1.53 (q, J=11.35 Hz, 2H) ppm; High Res Mass Spectrum calculated (M+H)$^+$ 495.202580; found (M+H)$^+$ 495.200904.

EXAMPLE 1657

$N^2$-p-toluenesulfonyl-$N^3$-[3-(4-amidinopiperidinyl)-isoxazolin-5-(R,S)-ylacetyl]-(S)-2,3-diaminoproprionic Part A: The isoxazoline acetic acid was prepared starting from 1-t-butylcarbamate-4-piperidine carboxaldehyde (Jacobs, R., et al, EP 532177) through methods previously described. $^1$H NMR (CDCl$_3$) δ 4.94 (m, 1H), 4.18–4.05 (m, 2H), 3.18 (dd, J=10.25, 17.20 Hz, 1H), 2.90–2.67 (m, 4H), 2.63 (m, 2H), 1.87 (m, 2H), 1.56–1.45 (s, 9H), 1.46 (s, 9H) ppm; Mass Spectrum (NH$_3$-CI) m/z (M+NH$_4$)$^+$ 330 (100%); IR (KBr) 3100, 1734, 1690, 1648, 1430, 1276, 1168, 758 cm$^{-1}$.

Part B: The acid from Part A (360 mg, 1.2 mmol) was coupled with methyl L-$N^2$-p-toluylsulfonyl-diaminopropionate using procedure described in Example 43D. The crude product was chromatographed on silica gel (2% MeOH/CH$_2$Cl$_2$) to afford 270 mg (41%) of a white foam. M.P. 55–60° C.; $^1$H NMR (CDCl$_3$) δ 7.72 (d, J=8.06 Hz, 2H), 7.30 (d, J=8.06 Hz, 2H), 6.45 (m, 1H), 5.73 (dd, J=8.42, 16.11 Hz, 1H), 4.90 (m, 1H), 4.13 (m, 2H), 4.01 (m, 1H), 3.58 (s, 3H), 3.60–3.49 (m, 2h), 3.10 (m, 1H), 2.84–2.72 (m, 3H), 2.57 (m, 2H), 2.48 (m, 1H), 2.42 (s, 3H), 1.85 (d, 2H), 1.55–1.46 (brd m, 2H), 1.46 (s, 9H) ppm; Mass Spectrum (NH$_3$-CI) m/z (M+NH$_4$)$^+$ 584 (100%); IR (KBr) brd 3300, 1746, 1688, 1428, 1238, 1164 cm$^{-1}$.

Part C: To the product from Part B (230 mg, 0.41 mmol) was added 10 ml of 30% TFA/CH$_2$Cl$_2$ and the mixture was stirred for 3h. The solvents were removed in vacuo. To the residue was added 2 ml DMF, triethylamine (0.39 ml, 2.8 mmol), and bis-tertbutyloxycarbonyl-3,5-dimethylpyrazole-1-carboxamidine (165 mg, 0.49 mmol) (Kim, et al, Tet. Lett.,1993, 34, 7677) and the mixture was stirred for 24 h. The reaction was partitioned with EtOAc/water. The organic layer was washed successively with water, brine and dried (MgSO$_4$). Chromatography on silica gel (2% MeOH/CH$_2$Cl$_2$) afforded 203 mg (71%) of a white foam. M.P. 69–75° C.; $^1$H NMR (CDCl$_3$) δ 10.18 (brd m, 1H), 7.72 (d, J=8.05 Hz, 2H), 7.30 (d, J=8 Hz, 2H), 6.40 (m, 1H), 5.65 (m, 1H), 4.87 (m, 1H), 4.30 (brd, 1H), 4.05 (brd, 1H), 3.60–3.51 (s+m, 5H), 3.09 (m, 3H), 2.78 (m, 3H), 2.42 (s, 3H), 1.89 (m, 2H), 1.73 (m, 2H), 1.63 brd m, 2H), 1.49 (s, 18H) ppm; Mass Spectrum (ESI) m/z (M+H)$^+$ 709.5 (100%); IR (KBr) 3300–2800, 2210, 1742, 1660, 1600, 1546, 1446, 1332, 1162, 1092 cm$^{-1}$.

Part D: To the product from Part C (160 mg, 0.23 mmol) was added 6 ml of 1:1 MeOH/water and lithium hydroxide (28 mg, 0.67 mmol). The mixture was stirred for 18 h and the solvents were removed in vacuo. The residue was taken up in water and acidified with 1N HCl and extracted with EtOAc. The organic layer was dried (MgSO$_4$), filtered and concentrated to afford 118 mg (76%) of the acid. To the acid was added 10 ml 30% TFA/CH$_2$Cl$_2$ and the mixture was stirred 24h. The solvents were removed and the TFA salt was purified by HPLC to afford 20 mg product. M.P. 134–140° C.; $^1$HNMR (DMSO-d$_6$) δ 7.9 (q, 1H), 7.66 (d, j=8.06 Hz, 2H), 7.46 (s, 3H), 7.36 (d, j=8.06 Hz, 2H), 4.72 (m, 1H), 3.80 (d, j=13.18 Hz, 2H) 3.61 (m, 1H), 3.41–3.18 (m, 5H), 3.13–2.99 (m, 3H), 2.75 (m 2H), 2.36 (s,3H), 2.22 (m, 1H), 1.88 (d, j=12.8 Hz, 2H), 1.53 (m, 2H) ppm ; Mass spectrum (ESI) m/z 495.2 (100%), high res Mass Spectrum (M+H)$^+$ calculated 495.20258, found 495.202476

EXAMPLE 1673

$N^2$-p-toluenesulfonyl-$N^3$-[3-(4-amidinopiperidinylmethyl)-isoxazolin-5-(R,S)-ylacetyl]-(S)-2,3-diaminopropionic Acid TFA Salt $^1$HNMR (DMSO) δ: 8.1 (2H, m), 7.65 (2H, d), 7.35 (2H, d), 4.7 (1H, m), 3.8 (3H, m), 3.4 (2H, m), 3.1 (1H, m), 3.0 (3H, m), 2.7 (1H, m), 2.4 (1H, m), 2.35 (3H, s), 2.25 (1H, m), 2.2 (3H, m), 1.85 (1H, m), 1.7 (2H, m), 1.6 (1H, m), 1.2 (3H, m) ppm; ESI mass spectrum 509.4 (M+H, 100)$^+$ free base.

EXAMPLE 1704

$N^2$-n-butyloxycarbonyl-$N^3$-[3-(quanidinopropyl)-isoxazolin-5-(R,S)-ylacetyl]-(S)-2,3-diaminopropionic Acid TFA Salt Part A: The title compound was prepared following the [3+2] cycloaddition methodology employed for example 4 from the readily accessible Boc-aminopropylchlorooxime (obtained from a sequence of steps from commerical (Aldrich) aminopropanol (aldehyde obtained via Moffat et. al. J. C. S. Perk. Trans. 1. 1991, 5, 1041–1051)) and butylvinyl ester. LiOH saponification in methanol:water (9:1), then afforded the desired acetic acid compound in 90% yield. $^1$HNMR (CDCl$_3$) δ 4.90 (m, 1H), 4.70 (brd, s, 1H), 3.08 (m, 3H), 2.68 (m, 2H), 2.57 (dd, 1H), 2.34 (t,2H), 1.75 (m, 2H), 1.41 (s, 9H) ppm; ESI mass spectrum 287(M+H, 100).

Part B: The product from part A was then coupled to methyl $N^2$-n-butyloxycarbonyl-(S)-2,3-diaminopropionate via the procedure used in example 4, to obtain Methyl $N^2$-n-butyloxycarbonyl-$N^3$-[3-(Boc-aminopropyl) isoxazolin-5-(R,S)-ylacetyl]-(S)-2,3-diaminopropionate in 50% yeild. Treatment with trifluoroaceticacid in dichloromethane, evaporation of solvent then afforded the anilino intermediate as the TFA salt. Standard guanidine formation techniques then afforded the di-Bocguanidinopropyl analog in 90% yield. Removal of the Boc-protecting groups with TFA afforded example 601 as the TFA salt. Alternatively, saponification of the methyl ester followed by removal of the Boc-protecting groups with TFA also afforded the desired product as the TFA salt in 80% overall yield. $^1$H NMR (CD$_3$OD) δ: 4.93 (m, 1H), 4.29 (brd.m, 1H), 4.02 (t, 2H), 3.65 (m, 1H), 3.32 (m, 1H), 3.21 (m, 2H), 3.09 (dd, J=10.2 & 17.6 Hz, 1H), 2.79 (dd, J=7.32 & 17.1 Hz, 1H), 2.52 (dd, J=2.2 & 8.8 Hz, 1H), 1.84 (m, 2H), 2.39 (m, 3H), 1.58 (m, 2H), 1.36 (m, 2H), 0.9 (t, 3H,) ppm; HR MS calcd. for ESI mass spectrum 529 (M+H, 100) for free base.

EXAMPLE 1756

$N^2$-p-toluylsulfonyl-$N^3$-[3-(4-piperidinylmethylaminocarbonyl)-isoxazolin-5-(R,S)-ylacetyl]-(S)-2,3-diaminoproprionic Acid Part A: To a mixture of tert-butyl vinylacetic acid (11.2 g, 0.079 mol) and ethylchlorooximidoacetate (11.37 g, 0.075 mol, Aldrich) in a mixture of 2:1 THF/water at 0° C. was added sodium bicarbonate (19.9 g, 0.237 mol). The reaction was stirred for 3d at room temperature, the layers were separated and the aqueous layer was extracted with EtOAc. The combined organic layers were washed with brine and dried with $MgSO_4$. The crude oil was chromatographed on silica gel (7:1 hexanes/ EtOAc) to afford 7.46 g (39%) of product as a colorless oil; $^1$H NMR ($CDCl_3$) δ 5.15 (m, 1H), 4.39 (q, J=7.32 Hz, 2H),3.43 (dd, J=10.99, 17.58 Hz, 1H), 3.03 (dd, J=7.69, 17.58 Hz, 1H), 2.81 (dd, J=5.86, 16.11 Hz, 1H), 2.59 (dd, J=7.69, 16.11 Hz, 1H),1.46 (s, 9H), 1.39 (t, J=7.32 Hz, 3H); Mass Spectrum ($NH_3$-CI) m/z (M+H)$^+$ 258 (12%), (M+$NH_4$)$^+$ 275 (100%).

Part B: The ethyl ester (3 g, 0.012 mol) from Part 1A was selectively hydrolyzed with LiOH (0.64 g, 0.015 mol) in 1.5:1 methanol/water at 0° C. for 1.5 h. The methanol was removed in vacuo. The aqueous residue was acidified with 10% citric acid and extracted with EtOAc and dried with $MgSO_4$. The crude solid was recrystallized with $CH_2Cl_2$/hexanes to afford 2 g (75%) white crystals. mp 83–86° C.; $^1$H NMR ($CDCl_3$) δ 5.23 (m, 1H), 3.44 (dd, J=10.98, 17.58 Hz, 1H), 3.05 (dd, J=8.05, 17.95 Hz, 1H), 2.82 (dd, J=5.85, 16.11 Hz, 1H), 2.64 (dd, J=7.32, 16.11 Hz, 1H), 1.46 (s, 9H) ppm; Mass spectrum ($NH_3$-CI) m/z (M+$NH_4$)$^+$ 247 (90%).

Part C: 4-Aminomethyl piperidine (3.8 g, 0.034 mol, Aldrich) was selectively protected in 68% yield with carbobenzoxyimidazole using the method of Sharma, et al. (J. Med. Chem. 1989, 32, 357). To the crude 4-Cbz-aminomethyl piperidine (3 g, 0.012 mol) in 30 ml dioxane at 0° C. was added 13 ml of 1N sodium hydroxide and di-t-butyl dicarbonate (2.7 g, 0.013 mol). The reaction was stirred at room temperature for 48 h. The dioxane was removed in vacuo and the residue was suspended in EtOAc and washed successively with 10% citric acid, sat'd $NaHCO_3$, brine and dried ($MgSO_4$). Recrystallization with $CH_2Cl_2$/hexane afforded 1 g of white crystals (24%) mp 91–96°C.; $^1$H NMR ($CDCl_3$) δ 7.32 (s, 5H), 5.10 ( s, 2H), 4.60 (t, 1H), 4.20 (brd, 2H), 3.0 (brd, 2H), 2.75 (brd, 2H), 1.65 (d, 2H), 1.45 (s, 9H), 1.12 (brd, 2H) ppm; Mass spectrum ($NH_3$-CI) m/z (M+H)+349 (31%), (M+H–56)+ 293 (100%); IR (KBr) 1698, 1530 cm$^{-1}$; Analysis for C19H28N2O4 calc'd C:65.49, H:8.10, N:8.04; found C:65.78, H:7.82, N:8.06.

Part D: To the compound from part C (94 mg, 2.7 mmol) was added 50 ml EtOH and 100 mg of 10% Pd/C and the mixture was hydrogenated at 40 PSI for 18 h. Filtration and removal of the solvent afforded 569 mg (98%) solid. mp 84–88° C.; $^1$H NMR ($CDCl_3$) δ 4.70 (brd, 1H), 3.10 (d, 2H), 3.0 (t, 2H), 2.95 (brd, 2H), 2.64 (t, 2H), 1.70 (d, 2H), 1.46 (s, 9H), 1.20 (m, 2H) ppm; Mass spectrum ($NH_3$-CI) m/z (M+H)$^+$ 215 (100%); IR (KBr) 2972–2800, 1694 cm$^{-1}$.

Part E: To the acid from Part B (360 mg, 1.6 mmol) in 5 ml EtOAc was added triethylamine (0.67 ml, 4.80 mmol) followed by TBTU (560 mg, 1.73 mmol). After 15 minutes the amine from Part D (370 mg, 1.7 mmol) was added and the reaction was stirred for 24 h. The reaction mixture was washed successively with 10% citric acid, water, sat'd $NaHCO_3$, brine and dried ($MgSO_4$). The residue was chromatogrphed on silica gel (3:2 Hexanes/EtOAc) to afford 0.41 g (61%) white foam. $^1$H NMR ($CDCl_3$) δ 5.04 (m, 1H), 4.63 (d, J=13.18 Hz, 2H), 4.53 (d, J=13.18 Hz, 1H), 3.52–3.38 (m, 1H), 3.15–2.99 (m, 4H), 2.77 (m, 2H), 2.59–2.49 (m, 5H),1.78 (t, J=10.0 Hz 3H), 1.46 (s, 9H), 1.44 (s, 9H), 1.25 (m, 2H); Mass Spectrum (NH3-CI) m/z (M+H)+426.3 (29%), (M+H–56)+370.2 (43%); IR (KBr) 2976, 2930, 1714, 1632, 1592, 1522, 1476, 1452, 1392, 1366, 1168 cm$^{-1}$.

Part F: To the product of Part E (380 mg, 0.89 mmol) was added 10 ml of 30% TFA/$CH_2Cl_2$ and stirred for 4 h. The solvents were removed and 10 ml dioxane was added. The mixture was cooled to 0° C. and 2 ml of 1N NaOH was added followed by di-t-butyldicarbonate (0.22 g, 0.98 mmol). The reaction was stirred for 48 h at room temperature. The reaction was concentrated and partitioned with EtOAc and water. The aqueous layer was acidified with 10% citric acid, extracted with EtOAc and dried ($MgSO_4$). The crude residue was chromatographed on silica gel (10% MeOH/$CH_2Cl_2$) to afford 0.23 g (69%) of a white foam. mp 159–165° C. $^1$H NMR (DMSO-$d_6$) δ 6.95 (t, J=5.86 Hz, 1H), 4.87 (m, 1H), 4.33 (d, J=13.18 Hz, 1H), 4.09 (d, J=13.90 Hz, 1H), 3.31 (m, 1H), 3.07 (t, J=12.82 Hz, 1H), 2.99 (dd, J=3.66, 8.05 Hz, 1H), 2.93 (dd, J=3.66, 7.70 Hz, 1H), 2.82 (t, J=5.86 Hz, 2H), 2.69 (t, 12.82 Hz, 1H), 2.39 (m, 1H), 2.27 (dd, J=7.69, 14.6 Hz, 1H), 1.67–1.60 (m, 3H), 1.37 (s, 9H), 1.04 (t, J=13.5 Hz, 1H) ppm; Mass Spectrum (NH3-CI) m/z (M+$NH_4$)$^+$ 387 (100%); IR (KBr) 3352, 1692, 1630, 1588, 1518, 1448, 1210, 1176, 1140 cm$^{-1}$.

Part G: The product of Part F (217 mg, 0.59 imol) was coupled with methyl L-$N^2$-p-toluylsulfonyl-diaminoproprionate according to procedure in Example 43D. The crude material was chromatographed on silica gel (2% MeOH/$CH_2Cl_2$) to afford 230 mg (63%) foam. $^1$H NMR ($CDCl_3$) δ 7.72 (d, 2H), 7.30 (d, 2H), 6.40–6.32 (m, 1H), 5.1 (m, 1H), 4.70 (brd, 2H), 4.50 (d, 1H), 3.99 (brd, 1H), 3.65 (s, 3H), 3.50 (m, 2H), 3.15–2.99 (m, 3H), 2.85–2.55 (m 2H), 2.45 (s,3H), 1.85 (brd, 4H), 1.46 (s, 9H), 1.29 (m, 2H) ppm; Mass Spectrum (ESI) m/z (M+H)$^+$ 624.5 (72%), (M+H–56)$^+$ 568.3 (98%).

Part H: The product of Part G (200 mg, 0.32 nmol) was hydrolyzed with lithium hydroxide (20 mg, 0.48 mmol) in 1:1 MeOH/water for 48 h. The solvents were removed in vacuo and the residue dissolved in water, acidified with 10% citric acid, extracted with EtOAc and dried ($MgSO_4$). The crude acid was treated with 15 ml of 30% TFA/$CH_2Cl_2$ for 24 h. The crude TFA salt was purified via HPLC to give 21 mg (11%) foamy solid. $^1$HNMR (DMSO-$d_6$) δ8.15 (m,1H), 7.73 (m,1H), 7.63 (d,j=8.06 Hz, 2H), 7.35 (d,j=8.05 Hz, 2H), 4.90 (m,1H), 4.37 (d,j=13.5 Hz, 2H), 4.14 (d,j=2H, j=10.9 Hz), 3.83 (q,j=9 Hz,1H), 3.35 (m,2H), 3.12–2.90 (m,3H), 2.74 (m, 2H), 2.33 (s,3H), 2.50–2.20 (m, 3H), 1.90–1.70 (m,4H), 1.35 (m,2H) ppm; High Res Mass Spectrum (M+H)$^+$ calculated 510.202246, found 510.203464.

EXAMPLE 1769

$N^2$-p-toluenesulfonyl-$N^3$-[3-(N-(4-piperidinylmethyl)-N-(methyl)aminocarbonyl) isoxazolin-5-(R,S)-ylacetyl]-(S)-2,3-diaminopronrionic Acid Trifluoroacetic Acid Salt Part A: To 4-tertButyloxycarbonyl-piperidinyl-methyl amine described previously (1.93 g, 0.009 mol) in 20 ml $CH_2Cl_2$ at 0° C. was added pyridine (1.1 ml, 0.014 mol) followed by slow addition of trifluoroacetic anhydride (1.4 ml, 0.009 mol). The reaction was stirred at 0° C. for 1 h, then it was diluted with $CH_2Cl_2$ washed successively with 10% citric acid, water, sat'd $NaHCO_3$, brine and dried ($MgSO_4$). Recrystallization from $CH_2Cl_2$/Hexanes afforded 2.4 g (86%) of a bright yellow solid. mp 123–125° C.; $^1$H NMR ($CDCl_3$) δ 4.74 (m, 1H), 4.56 (d, J=13 Hz, 2H), 4.0 (d, J=12 Hz, 1H), 3.14 (m, 3H), 2.75 (t, J=13 Hz, 1H), 1.82 (d, 3H), 1.45 (s, 9H) 1.28 (m, 2H) ppm; Mass Spectrum ($NH_3$–CI) m/z (M+$NH_4$)$^+$ 328 (100%), (M+$NH_4$ –56)+272.1 (100%); IR (KBr) 3354, 1686, 1526, 1200, 1140 cm$^{-1}$.

Part B: To the product of Part A (400 mg, 1.29 mmol) in 2 ml DMF was added NaH (62 mg, 1.6 mmol) After 1 h, methyl iodide (0.1 ml, 1.6 mmol) was added and the reaction was immersed in a 60° C. oil bath for 24 h. The reaction was cooled and partioned between EtOAc and water. The organic layer was washed with water, brine and dried (MgSO$_4$). The reaction had not gone to completion and was resubjected to the above conditions and after work up afforded 322 mg (77%) yellow oil. The crude trifluoroacetate was placed in 20 ml of 1:1 MeOH/water and K$_2$CO$_3$ (150 mg, 1.1 mmol) was added and the reaction was stirred for 36 h. The solvents were removed in vacuo and the residue partioned with EtOAc/water. The aqueous layer was extracted with EtOAc and the combined organic layers were washed with brine and dried (MgSO$_4$), filtered and concentrated to yield 194 mg (89%) oil. $^1$H NMR (CDCl$_3$) δ 3.15 (m, 4H), 2.85 (s, 3H), 2.80 (brd s, 1H), 2.61 (t, J=12Hz, 2H), 1.63 (d, J=10.6 Hz, 2H), 1.45 (s, 9H), 1.25 (m, 2H), 0.87 (m, 1H) ppm; Mass Spectrum (NH$_3$–CI) m/z (M+H)$^+$ 229 (100%), (M+NH$_4$)$^+$ 246 (15%); IR (KBr) 2924,1696,1160 cm$^{-1}$.

Part C: The product of Part B (173 mg, 0.76 mmol) was coupled with the acid (from Part B previous example) according to procedure in Example 43D to yield 177 mg (54%) yellow oil. $^1$H NMR (CDCl$_3$) δ 5.02 (m, 1H), 4.59–4.50 (brd m, 2H), 3.48 (dd, J=10.62,17.58 Hz, 1H), 3.15–3.02 (m, 4H), 2.86 (s, 3H), 2.77 (m, 2H), 2.59 (m, 1H), 2.0–1.91 (brd m, 1H), 1.73 (t, J=11.72 Hz, 2H), 1.46 (s, 18H), 1.28 (m, 2H) ppm; Mass Spectrum (NH$_3$–CI) m/z (M+H)$^+$ 440.2 (100%), (M+NH$_4$)$^+$ 457.3 (23%), (M+H–56)$^+$ 384.2 (73%); IR (KBr) 2976, 2932, 1730, 1694, 1634, 1162 cm$^{-1}$ Part D: The product of Part C (170 mg, 0.387 mmol) was deprotected and selectively reprotected as in Part 1F to afford a yellow foam. $^1$H NMR (CDCl$_3$) δ 5.10 (m, 1H), 4.60 (m, 1H), 4.50 (m, 1H), 3.50 (m, 1H), 3.12 (m, 4H), 2.80 (s, 3H), 2.78 (m, 1H), 2.70 (m, 2H), 1.90 (brd m, 1H), 1.75 (brd m, 2 H), 1.45 (s, 9H), 1.25 (brd m, 2H) ppm; Mass Spectrum (NH$_3$–CI) m/z (M+NH$_4$)$^+$ 401 (100%).

Part E: The product of Part D (148 mg, 0.386 mmol) was coupled with methyl L-N$^2$-p-toluylsulfonyl-diaminoproprionate according to the procedure in Example 43D. The crude material was chromatographed on silica gel (3% MeOH/CH$_2$Cl$_2$) to afford 230 mg clear glass containing minor impurities. $^1$H NMR (CDCl$_3$) δ 7.72 (d,2H), 7.33 (d,2H), 6.35 (m, 1H), 5.10 (m,1H), 4.61 (brd m, 1H), 4.45 (brd m, 1H), 3.97 (brd m, 1H), 3.63–3.54 (s+m, 5H), 3.48–3.30 (m, 2H), 3.15 (brd m,4H), 2.85 (s, 3H), 2.75–2.5 (m, 4H), 2.45 (s, 3H), 1.78 (brd m, 2H), 1.46 (s,9H), 1.30 (m, 2H) ppm; Mass Spectrum (ESI) m/z (M+H)$^+$ 638.5 (100%)

Part F: The product of Part E (230 mg, 0.36 mmol) was subjected to hydrolysis and deprotection and purification by HPLC to afford 134 mg (58%) of a white powder. mp 69–72° C.; $^1$HNMR (DMSO-d$_6$) δ 8.35 (brd m, 2H), 8.10 (brd m, 2H), 7.65 (d, J=6.96 Hz, 2H), 7.35 (d, j=8.05 Hz, 2H), 4.83 (m,1H), 4.36 (d,j=13.6 Hz, 1H), 4.12 (d,j=10 Hz, 1H), 4.0–3.5 (m,6H), 3.35 (m,1H), 3.14 (t,j=10.98 Hz, 1H),2.83 (m,1H), 2.59 (s, 3H), 2.55 (m,1H), 2.36 (s, 3H), 2.35 (m,1H), 2.0 (brd m,1H), 1.80–1.74 (brd m, 2H), 1.18 (m, 2H) ppm; Mass Specturm (ESI) m/z (m+H)$^+$ 524.4 (100%); IR (KBr) 3300–2800 brd, 1736,1632, 1202,1162 cm$^{-1}$.

EXAMPLE 1774

N$^2$-p-toluylsulfonyl-N$^3$-[3-(4-piperidinylaminocarbonyl)isoxazolin-5-(R,S)-ylacetyl]-(S)-2,3-diaminoproprionate Part A: The acid (from Part B described previously, 225 mg, 0.98 mmol) was coupled with 1-tertbutyloxycarbonyl-4-aminopiperidine (Obase, H; et al, J.Het. Chem. 1983, 20, 565) as described in Example 43D.A white foam was obtained in 78% yield. $^1$H NMR (CDCl$_3$) δ 6.50 (d, J=8.05 Hz, 1H), 5.13 (m, 1H), 3.43 (dd, J=10.62, 17.95 Hz, 1H), 3.04 (dd, J=7.69, 18.3 Hz, 1H), 2.87 (t, J=12.45 Hz, 2H), 2.76 (dd, J=6.22, 16.11 Hz, 1H), 2.57 (dd, J=6.95, 16.11 Hz, 1H), 1.94 (d, J=9.88 Hz, 2H), 1.46 (s,18H), 1.41 (m, 2H) ppm; Mass Spectrum (NH$_3$–CI) m/z (M+H)$^+$ 412.2 (69%), (M+NH$_4$)$^+$ 429.3 (50%), (M+NH$_4$–56)$^+$ 373.2 (100%); IR (KBr) 3424,2866,1728,1692,1536,1426,1368,1238,1162 cm$^{-1}$.

Part B: The product of Part A (300 mg, 0.73 mmol) was deprotected with TFA and selectively reprotected with di-t-butyldicarbonate to afford 270 mg of a white foam. $^1$H NMR (CDCl$_3$) δ 6.64 (d, J=8.05 Hz, 1H), 5.2 (m, 1H), 4.10–3.95 (m, 3H), 3.47 (dd, J=10.99, 17.96 Hz, 1H), 3.08 (dd, J=7.69, 17.95 Hz, 1H), 2.89 (t+dd, 3H), 2.72 (dd, J=6.95, 16.11 Hz, 1H), 1.94 (d, J=12.82 Hz, 2H), 1.46 (s, 9H), 1.46 (brd m, 2H) ppm; Mass Spectrum (NH$_3$–CI) m/z (M+NH$_4$)$^+$ 373 (100%).

Part C: The product of Part B (260 mg, 0.73 mmol) was coupled with methyl L-N$^2$-p-toluylsulfonyl-diaminoproprionate according to the procedure in Example 43D. The crude foam was chromatographed on silica gel (2% MeOH/CH$_2$Cl$_2$) to afford 289 mg (65%) of a white foam. $^1$H NMR (CDCl$_3$) δ 7.71 (d, J=8.06 Hz, 2H), 7.31 (d, J=8.42 Hz, 2H), 6.65 (dd, J=6.59 Hz, 1H), 6.36 (t, J=5.86 Hz, 1H), 5.15 (m, 1H), 4.10–3.96 (m, 4H), 3.63–3.56 (s+m, 5H), 3.45–3.35 (m, 1H), 3.09 (m,1H), 2.85 (t, J=12.45 Hz, 2H), 2.62 (m, 2H), 2.43 (s, 3H), 1.94 (d, J=12.82 Hz, 2H), 1.45 (s+m, 9+2H) ppm; Mass Spectrum (ESI) m/z (M+H)$^+$ 610.3 (100%).

Part D: The product of Part C (289 mg, 0.47 mmol) was subjected to hydrolysis and deprotection and purification as previously described to afford 224 mg (78%) white powder. mp 88–91° C.; $^1$HNMR (DMSO-d$_6$) δ 8.66–8.57 (d+m, j=7.69Hz, 2H), 8.30 (brd m, 1H), 8.07 (m, 2H), 7.64 (d,j=8.06 Hz, 2H), 7.35 (d,j=8.06 Hz, 2H), 4.94 (m,1H), 3.96 (m, 1H), 3.87 (q,j=6.95 Hz, 1H), 3.30–3.24 (m,4H), 3.08–2.89 (m,4H), 2.46 (m,1H), 2.37 (s,3H), 2.37 (m,1H), 1.87 (d,j=10.9 Hz,2H), 1.73 (q,j=10.6 Hz,2H) ppm; Mass Spectrum (ESI) m/z (M+H)$^+$ 496.3 (100%); IR (KBr) 3300–2800 brd, 1736,1666, 1544 1162 cm$^{-1}$

EXAMPLE 1945

N$^2$-3-Methylphenylsulfonyl-N$^3$-[3-[2-(piperidin-4-yl)ethyl]isoxazolin-5(R,S)-ylacetyl)-(S)-2,3-diaminopropionic Acid TFA Salt Part A: Methyl (3-(2-N-t-Butyloxycarbonylpiperidin-4-yl) ethyl)isoxazolin-5(R,S)-ylacetate To a solution of Methyl Vinylacetate 352 g, 0.35 mol) in CH$_2$Cl$_2$ (175 mL) was added a 5% solution of sodium hypochlorite (210 mL, 0.15 mol). The mixture was stirred rapidly at room temperature and a solution of (3-N-t-butyloxycarbonylpiperidin-4-yl)propanal oxime (Example 189, Part B, 17.60 g, 68.6 mmol) in CH$_2$Cl$_2$ (50 mL) was added over 15 h. The mixture was diluted with water and CH$_2$Cl$_2$, the layers separated, and the aqueous washed with CH$_2$Cl$_2$. The combined organic was dried (MgSO$_4$), concentrated in vacuo, and the oily residue purified using flash chromatography (10–50% EtOAc/hexanes step gradient), giving 10.35 g (42%) of the desired isoxazoline as a golden oil; Anal. Calcd for C$_{18}$H$_{30}$N$_2$O$_5$: C, 61.00; H, 8.53; N, 7.90. Found: C, 61.07; H, 8.50; N, 7.80.

Part B: (3-(2-N-t-Butyloxycarbonylpiperidin-4-yl)ethyl) isoxazolin-5(R,S)-ylacetic Acid To a solution of methyl (3-(2-N-t-butyloxycarbonylpiperidin-4-yl)ethyl)isoxazolin-5(R,S)ylacetate (10.35 g, 29.20 mmol) in THF (100 mL) was added 0.5 M LiOH (80 mL, 40 mmol). The resulting solution was stirred at room temperature overnight (18 h) and then concentrated in vacuo to one-half volume. The pH was adjusted to 4, and the resulting cloudy solution washed with $CH_2Cl_2$ (4×30 mL). The combined organic was dried ($MgSO_4$), concentrated in vacuo, and placed under vacuum until constant weight was achieved, affording 9.74 g (98%) of the desired acid; Anal. Calcd for $C_{17}H_{28}N_2O_5$: C, 59.98; H, 8.29; N, 8.23. Found: C, 60.19; H, 8.42; N, 7.87.

Part C: t-Butyl $N^2$-3-Methylphenylsulfonyl-$N^3$-[(3-(N-t-butyloxycarbonyl-2-piperidin-4-yl)ethyl)isoxazolin-5(R,S)-ylacetyl]-(S)-2,3-diaminopropionate To a solution of (3-(2-N-t-butyloxycarbonylpiperidin-4-yl)ethyl)isoxazolin-5(R,S)-ylacetic acid (165 mg, 0.485 mmol) and t-butyl $N^2$-3-methylphenylsulfonyl-(S)-2,3-diaminopropionate hydrochloride (170 mg, 0.485 mmol) in DMF (5 mL) was added $Et_3N$ (0.2 mL, 1.4 mmol) followed by TBTU (160 mg, 0.498 mmol). The resulting mixture was stirred for 4 h at room temperature, then was diluted with EtOAc (50 mL). It was washed with water (4×20 mL), sat. $NaHCO_3$ (30 mL), sat. NaCl and dried ($MgSO_4$). Concentration in vacuo followed by placing the material under vacuum until constant weight was achieved afforded 271 mg (88%) of the desired amide; MS (ESI, e/z, relative intensity): 637 $(M+H)^+$, 20%, 537 $(M+H-C_4H_9CO_2)^+$, 51%.

Part D: $N^2$-3-Methylphenylsulfonyl-$N^3$-[(3-(2-piperidin-4-yl)ethyl)isoxazolin-5(R,S)-ylacetyl]-(S)-2,3-diaminopropionic Acid TFA Salt To a solution of t-butyl $N^2$-3-methylphenylsulfonyl-$N^3$-[(3-(N-t-butyloxycarbonyl-2-piperidin-4-yl)ethyl)isoxazolin-5(R,S)-ylacetyl]-(S)-2,3-diaminopropionate (261 mg, 0.410 mmol) in $CH_2Cl_2$ (2 mL) was added TFA (2 mL, 26 mmol). After 2 h at room temperature, the solution was concentrated in vacuo and the residue triturated with ether (3×5 mL). The resulting white powder was purified using reverse phase HPLC, giving 202 mg (83%) of the desired piperidine; MS (ESI, e/z, relative intensity): 481 $(M+H)^+$, 100%.

EXAMPLE 2103

$N^2$-(3,5-dimethylisoxazole-4-sulfonyl)-$N^3$-[3-(4-amidinophenyl)isoxazolin-5(R,S)-ylacetyl]-(S)-2,3-diaminopropionate Trifluoroacetate Salt Part A: Methyl $N^2$-(3,5-Dimethylisoxazole-4-sulfonyl)-$N^3$[3-(4-N-t-butoxycarbonylamidinophenyl)isoxazolin-5(R S)-ylacetyl]-(S)-2,3-diaminopropionate Methyl $N^2$-(3,5-dimethylisoxazole-4-sulfonyl)-$N^3$-Boc-(S)-2,3-diaminopropionate (1.40 mmole) was stirred with 4 M HCl/dioxane (10 mL, 40 mmol) at 25° C. After 2.5 h, the volatiles were removed in vacuo, and residual HCl/dioxane was removed by repeated addition of toluene and evaporation. To the residue was added 3-(4-N-t-butoxycarbonylamidinophenyl)isoxazolin-5(R,S)-ylacetic acid (510 mg, 1.47 nmol), TBTU (480 mg, 1.50 mmole) and DMF (15 mL). Triethylamine (0.830 mL, 603 mg, 5.97 mmole) was added and the reaction mixture was stirred at 25° C. overnight. The mixture was diluted with water (70 mL) extracted with 3× ethyl acetate. The combined organic extracts were washed with 2× water, 5% pH 4 potassium hydrogen phthalate buffer (25 mL), 5% aqueous sodium bicarbonate (25 mL) and brine. After drying over MgSO4, removal of volatiles and purification by flash chromatography (ethyl acetate) provided 0.598 g of the desired product in 96% purity, as assessed by analytical HPLC (4.6 mm×25 cm C18 reverse phase, 1 mL/min, 0.05% TFA/10–90% AcCN/water gradient over 20 min, product at 12.9 min); $^1$H NMR (300 MHz, $CDCl_3$) δ 7.84 (m, 2H), 7.63 (m, 2H), 6.52 (bm, 1H), 6.07 (bd, 1H), 5.11 (bm, 1H), 4.02 (bm, 1H), 3.66/3.67 (2s, 3H, diastereomers, methyl ester), 3.67–3.45 (m, 3H), 3.15 (m, 1H), 2.60/2.61 (2s, 3H, diastereomers, isoxazole methyl), 2.76–2.55 (m, 2H), 2.38/2.41 (2s, 3H, diastereomers, isoxazole methyl), 1.56 (s, 9H, t-Bu); MS (ESI): m/e 607.2 $(M+H)^+$.

Part B: $N^2$-(3,5-Dimethylisoxazole-4-sulfonyl)-$N^3$-[3-(4-N-t-butoxycarbonylamidinophenyl)isoxazolin-5(R,S)-ylacetyl]-(S)-2.3-diaminopropionate To a solution of 200 mg (0.329 mmole) of methyl $N^2$-(3,5-dimethylisoxazole-4-sulfonyl)-$N^3$[3-(4-N-t-butoxycarbonyl-amidinophenyl)isoxazolin-5(R,S)-ylacetyl]-(S)-2,3-diamino-propionate in 15 mL of THF/MeOH/water 1:1:1 was added 138 mg (3.29 mmole) of LiOH. After 2 h, analytical HPLC (see conditions in Part A, product at 11.7 min) indicated the reaction was 97% complete. Removal of volatiles and purification by flash chromatography provided 0.164 g 91% pure (see HPLC conditions in Part A) of the desired product as a mixture of free acid and lithium salt (as indicated by 0.55% Li by elemental analysis); $^1$H NMR (300 MHz, DMSO-$d_6$) δ 8.02 (d, J=8.0 Hz, 2H), 7.96 (m, 1H), 7.75 (dd, J=1.5, 8.4 Hz, 2H), 5.02 (m, 1H), 3.58–3.08 (m, 5H), 2.55 (s, 3H, isoxazole methyl), 2.60–2.37 (m, 2H), 2.34 (s, 3H, isoxazole methyl), 1.45 (s, 9H, t-Bu); MS (ESI): m/e 593.3 $(M+H)^+$, m/e 493.2 (M-Boc)$^+$.

Part C: $N^2$-(3,5-dimethylisoxazole-4-sulfonyl)-$N^3$-[3-(4-amidinophenyl)isoxazolin-5(R,S)-ylacetyl]-(S)-2,3-diaminopropionate Trifluoroacetate Salt A solution of 137 mg (0.231 mmole) of $N^2$-(3,5-dimethylisoxazole-4-sulfonyl)-$N^3$[3-(4-N-t-butoxycarbonyl-amidinophenyl)isoxazolin-5(R,S)-ylacetyl]-(S)-2,3-diamino-propionate in 4 mL of $CH_2Cl_2$ and 2 mL of TFA was stirred for 4 h, then diluted with 60 mL of ether. The precipitate was dried to give 0.103 g of the desired product as a white solid, which was determined to be 96% pure by analytical HPLC (see HPLC conditions in Part A); $^1$H NMR (300 MHz, DMSO-$d_6$) δ 9.79 (bs, 1H), 9.72 (bs, 1H), 9.29 (bs, 2H), 8.25 (bs, 1H), 8.16 (m, 1H), 7.87 (s, 4H), 5.02 (bm, 1H), 3.78 (bs, 1H), 3.60–3.08 (m, 4H), 2.54 (s, 3H, isoxazole methyl), 2.34 (s, 3H, isoxazole methyl), 2.62–2.34 (m, 2H); MS (ESI): m/e 493.3 $(M+H)^+$; HRMS (FAB): m/e calculated for $C_{20}H_{25}N_6O_7S$ $(M+H)^+$ 493.150544; found 493.148681.

EXAMPLE 2103a $N^2$-(3,5-dimethylisoxazole-4-sulfonyl)-$N^3$-[3-(4-amidinophenyl)isoxazolin-5(R)-ylacetyl]-(S)-2,3-diaminopropionate Trifluoroacetate Salt (Alternative Hydrolysis Procedure)

Methyl $N^2$-(3,5-dimethylisoxazole-4-sulfonyl)-$N^3$-[3-(4-amidinophenyl)isoxazolin-5(R)-ylacetyl]-(S)-2,3-diaminopropionate hydrochloride salt (Part B, replacing ammonium acetate with ammonium chloride, 1.3 g, 2.6 mmol) was stirred in 6N HCl (150 ml) at room temperature for 20 hours. Solvent was evaporated under reduced pressure to give the crude hydrochloride salt as a white solid (1.1 g, 87%). Purification of 0.17 g crude product by preparative HPLC (Vydac C18 reverse phase column; 2×25 cm; 10 ml/min flow rate; 254 nM; gradient: from 100% $H_2O$ with 0.05% TFA to 20% $H_2O$ and 80% $CH_3CN$ with 0.05% TFA in 50 minutes) yielded 0.12 g (70.6%) of the title compound as a white powder. Chiral HPLC analysis (SFC, Chiralcel OD; 0.46×25 cm; 30° C.; 2.0 ml/min flow rate; 0.1% TFA/22% MeOH/78% $CO_2$; 280 nM; 150 atm) showed >99% d.e. with respect to the (S,S)-diastereomer and >98% chemical purity. MS (ESI): m/e 493 (M+H)$^+$. HRMS (FAB): m/e calculated for $C_{20}H_{24}N_6O_7S$ (M+H)$^+$ 493.150649; Found 493.150544.

EXAMPLE 2103b $N^2$-(3,5-Dimethylisoxazole-4-sulfonyl)-$N^3$-[3-(4-amidinophenyl)isoxazolin-5(R)-ylacetyl]-(S)-2,3-diaminopropionic Acid Methanesulfonate Salt Part A: Methyl $N^2$-(3,5-Dimethylisoxazole-4-sulfonyl)-$N^3$ [3-(4-(cyanophenyl)isoxazolin-5(R)-ylacetyl]-(S)-2,3-diaminopropionate To a suspension of 3-(4-cyanophenyl)isoxazolin-5(R)-ylacetic acid (252 mg, 0.725 mmol), methyl $N^2$-(3,5-dimethylisoxazole-4-sulfonyl-(S)-2,3-diaminopropionate hydrochloride (28.24 g, 70% purity, 63.0 mmol) in DMF (200 mL) was added TBTU (28.90 g, 90 mmol). The mixture was cooled to 0° C. and Et$_3$N (31.4 mL, 225 mmol) was added dropwise. The resulting mixture was allowed to warm to room temperature overnight (18 h), then was diluted with EtOAc (500 mL). It was washed with water (4×200 mL), sat. NaHCO$_3$ (100 mL), sat. NaCl (100 mL) and dried (MgSO$_4$). Concentration in vacuo followed by placing the material under vacuum until constant weight was achieved afforded 25.06 g (81%) of the desired amide; $^1$H NMR (300 MHz, CDCl$_3$) δ 8.77 (bs, 1H), 8.22 (t, J=5.9 Hz, 1H), 5.02 (m, 1H), 3.98 (t, J 7.0 Hz, 1H), 3.55 (dd, J=17.2, 10.6 Hz, 1H), 3.48 (s, 3H), 3.42 (m, 1H), 3.16 (m, 2H), 2.54 (s, 3H, coincident with m, 1H, DMSO-d$_5$), 2.37 (dd, J=14.6, 7.0 Hz, 1H), 2.33 (s, 3H).

Part B: Methyl $N^2$-(3,5-Dimethylisoxazole-4-sulfonyl)-$N^3$-[3-(4-amidinophenyl)isoxazolin-5(R)-ylacetyl]-(S)-2,3-diaminopropionate Acetate Salt Into a solution of methyl $N^2$-(3,5-dimethylisoxazole-4-sulfonyl)-$N^3$[3-(4-(cyanophenyl)isoxazolin-5(R)-ylacetyl]-(S)-2,3-diaminopropionate (25.06 g, 51.17 mmol) in anhydrous MeOH (750 mL) at 0° C. was bubbled HCl gas for 3 hours. The resulting solution was then allowed to warm to room temperature overnight (18 h), after which the solvent was evaporated in vacuo, to give an oil. The oily residue was triturated with ether (3×100 mL) and the resulting solid placed under vacuum until constant weight was achieved. The crude imidate was then dissolved in MeOH (1 L) and ammonium acetate (20.0 g, 259 mmol) added. The resulting mixture was stirred at room temperature for 18 h, then concentrated in vacuo. The residue was then crystallized from EtOH, giving 21.75 g of crude amidine. A portion of this material (8.5 g) was purified using flash chromatography (20% MeOH-EtOAc) to give 3.77 g (33%) of 97.6% pure amidine (analytical HPLC: 4.6 mm×25 cm C18 reverse phase, 1 mL/min, 0.05% TFA/10–90% AcCN/water gradient over 20 min); $^1$H NMR (300 MHz, DMSO-d$_6$) δ 8.26 (bt, 1H), 7.86 (m, 4H), 5.01 (m, 1H), 3.96 (t, J=6.6 Hz, 1H), 3.56 (dd, J=17.2, 10.6 Hz, 1H), 3.48 (s, 3H, coincident with m, 1H), 3.18 (m, 2H), 2.53 (s, 3H, coincident with m, 1H, DMSO-d$_5$), 2.54 (s, 3H), 2.36 (dd, J=14.6, 7.0 Hz, 1H), 2.32 (s, 3H), 1.74 (s, 3H); MS (ESI): m/e 507.3 (M+H)$^+$.

Part C: $N^2$-(3,5-Dimethylisoxazole-4-sulfonyl)-$N^3$[3-(4-amidinophenyl)isoxazolin-5(R)-ylacetyl]-(S)-2,3-diaminopropionic Acid (Enzymatic Hydrolysis)

To a solution of methyl $N^2$-(3,5-dimethylisoxazole-4-sulfonyl-$N^3$[3-(4-amidinophenyl)isoxazolin-5(R)-ylacetyl]-(S)- 2,3-diaminopropionate HOAc salt (1.866 g, 3.29 mmol) in 0.4 N Hepes buffer (pH 7.1, 220 mL, 15 mmol) was added rabbit liver esterase (3.6 M crystalline suspension in ammonium sulfate, 2000 units, Sigma). The resulting solution was incubated at 37° C. for 60 hours. Protein was removed from the reaction mixture by ultra filtration (Amicon YM-10 membrane), and the filtrate was then concentrated in vacuo and lyophilized. Purification using a reverse phase silica column (5×9.5 cm in water; crude product loaded as an aqueous solution followed by elution with water (1200 mL) and by 500 mL each of 5, 10, 20 and 30% CH$_3$CN-H$_2$O. Fractions containing the desired product were pooled, acetonitrile was removed and the aqueous solution lyophilized to yield 1.5 g (93%) of pure zwitterion; $^1$H NMR (300 MHz, DMSO-d$_6$) δ 7.93 (t, 1H), 7.76 (s, 4H), 4.98 (m, 1H), 3.17–3.50 (m, 5H, coincident with water), 2.66 (dd, 1H), 2.56 (s, 3H), 2.35 (s, 3H), 2.36 (dd, 1H); MS (ESI): m/e 493.3 (M+H)$^+$.

Part D: $N^2$-(3,5-Dimethylisoxazole-4-sulfonyl)-$N^3$[3-(4-amidinophenyl)isoxazolin-5(R)-ylacetyl]-(S)-2,3-diaminopropionic Acid Methanesulfonic Acid Salt To a solution of the zwitterion (2.75 g, 5.43 mmol) in 50% CH$_3$CN—H$_2$O (135 mL) was added methanesulfonic acid (0.57 g, 5.97 mmol). The reaction mixture was stirred at room temperature for 1 h, resulting in a clear solution. Solvents were removed in vacuo and the residue placed under vacuum for several hours. The crude mesylate was dissolved in hot acetone and water until the solution was clear (120 mL total volume). After hot filtration the solution was allowed to cool slowly and was then refrigerated for 24 h. The resulting white precipitate was filtered and dried under vacuum, affording 1.72 g (52%) of the title compound; $^1$H NMR (300 MHz, DMSO-d$_6$) δ 9.37 (bs, 2H), 9.03 (bs, 2H), 8.57 (d, J=9.5 Hz, 1H), 8.23 (t, J=5.9 Hz, 1H), 7.88 (s, 4H), 5.03 (m, 1H), 3.91 (m, 2H), 3.57 (dd, J=17.2, 10.6 Hz, 1H), 3.44 (m, 1H), 3.21 (dd, J=17.6, 7.7 Hz, 1H), 3.09 (m, 1H), 2.58 (dd, J=14.6, 6.6 Hz, 1H), 2.54 (s, 3H), 2.38 (dd, J=14.6, 7.3 Hz, 1H), 2.33 (s, 3H, MsOH); MS (ESI): m/e 493.2 (M+H)$^+$; Anal. Calcd. for $C_{21}H_{28}N_6O_{10}S_2$: C, 42.85; H, 4.79; N, 14.05; S, 10.89. Found: C, 42.45; H, 4.74; N, 14.05; S, 11.19.

EXAMPLE 2420

Methyl $N^2$-n-butyloxycarbonyl-$N^3$-[3-(4-piperidinylpropyl)isoxazolin-5-(R,S)-ylformyl]-(S)-2,3-diaminopropionate TFA salt $^1$HNMR (CDCl$_3$) δ 7.38 (1H, brd), 6.95 (1H, brd), 5.65 (1H, m), 4.98 (1H, m), 4.42 (1H, m), 4.06 (2H, m), 3.76 (3H, s), 3.65 (2H, m), 3.48 (2H, m), 3.25 (2H, m), 2.95 (2H, m), 2.4 (2H, m), 1.95 (2H, brd), 1.6 (5H, m), 1.48 (2H, m), 1.35 (4H, m), 0.94 (3H, m) ppm; ESI mass spectrum 441 (M+H)$^+$ free base

EXAMPLE 2421

Methyl $N^2$-p-toluenesulfonyl-$N^3$-[3-(4-piperidinylpropyl)-isoxazolin-5-(R,S)-ylformyl]-(S)-2,3-diaminopropionate TFA salt $^1$HNMR (CDCl$_3$) δ: 7.8 (1H, m), 7.68 (2H, m), 7.3 (3H, m), 5.7 (1H, m), 4.92 (1H, m), 4.1 (1H, m), 4.0 (1H, m), 3.7 (2H, m), 3.55 (3H, s), 3.45 (3H, m), 2.9 (2H, brd), 2.4 (3H, s), 2.38 (2H, m), 1.9 (3H, m), 1.65 (2H, m), 1.54 (2H, m), 1.35 (2H, m) ppm; ESI mass spectrum 495.3 (M+H)$^+$ free base.

EXAMPLE 2422

$N^2$-p-toluenesulfonyl-$N^3$-[3-(4-piperidinylpropyl) isoxazolin-5-(R,S)-ylformyl]-(S)-2,3-diaminopropionic acid TFA salt $^1$HNMR (CD$_3$OD) δ: 7.7 (2H, m), 7.32 (2H, m), 4.85 (1H m), 4.1 (1H, m), 3.75 (1H, m), 3.65 (2H, m), 3.32 (3H, m), 3.2 (2H, m), 2.9 (2H, m), 2.4 (5H, m), 1.95 (2H, m), 1.62 (3H, m), 1.35 (4H, m),ppm; ESI mass spectrum 481.3 $(M+H)^+$ free base

EXAMPLE 2423

$N^2$-n-butyloxycarbonyl-$N^3$-[3-(4-piperidinylpropyl) isoxazolin-5-(R,S)-ylformyl]-(S)-2,3-diaminopropionic acid TFA salt $^1$HNMR (CD$_3$OD) δ: 4.92 (1H, m), 4.3 (1H, m), 4.05 (2H, m), 3.6 (2H, m), 3.38 (3H, m), 3.15 (1H, m), 2.95 (2H, m), 2.35 (2H, m), 1.95 (2H, m), 1.6 (5H, m), 1.35 (6H, m), 0.95 (3H, m) ppm; ESI mass spectrum 427.3 $(M+H)^+$ free base.

EXAMPLE 2500

Methyl $N^3$-Boc-(S)-2,3-diaminopropionate

Part A: Methyl $N^2$-Cbz-L-2,3-diaminopropionate HCl Salt

To a solution of $N^2$-Cbz-L-2,3-diaminopropionic acid (Bachem, 220 g, 0.923 mol) in MeOH (2 L) at 0° C. was added thionyl chloride (76 mL, 1.04 mol) over 20 min. The solution was warmed to room temperature overnight (18 h) and then concentrated to give a solid. The solid was crystallized from CHCl$_3$-MeOH to give 172 g (64%) of the desired ester; $^1$H NMR (DMSO-d$_6$) δ 8.38 (b, 3H), 7.96 (d, 1H), 7.38 (m, 5H), 5.05 (s, 2H), 4.44 (m, 1H), 3.66 (s, 3H), 3.14 (m, 2H).

Part B: Methyl $N^2$-Cbz-$N^3$-Boc-L-2,3-diaminopropionate

To a solution of methyl $N^2$-Cbz-(S)-2,3-diaminopropionate HCl salt (172 g, 0.596 mol) and di-tert-butyl dicarbonate (129.05 g, 0.591 mol) in CH$_2$Cl$_2$ (2 L) cooled in an ice bath was added a saturated solution of NaHCO$_3$ (1200 mL, 0.96 mol) and the solution was warmed to room temperature overnight (18 h). The layers were separated and the aqueous washed with CH$_2$Cl$_2$ (2×500 mL). The combined organic was washed with brine, dried (MgSO$_4$), and concentrated. The resulting white solid was triturated with hexanes (3×500 mL) and dried under vacuum, giving 195.99 g (93%) of the desired material; $^1$H NMR (DMSO-d$_6$): δ 7.60 (d, 1H), 7.35 (m, 5H), 6.88 (t, 1H), 5.02 (s, 2H), 4.14 (m, 1H), 3.60 (s, 3H), 3.28 (m, 2H), 1.37 (s, 9H).

Part C: Methyl $N^3$-Boc-(S)-2,3-diaminopropionate

To a solution of methyl $N^2$-Cbz-$N^3$-Boc-(S)-2,3-diaminopropionate. (54.7 g, 0.155 mol) in EtOH (300 mL) was added 10% Pd/C (4.0 g). The mixture was placed on a Parr apparatus and hydrogenated at 50 p.s.i. overnight (18 h). The catalyst was filtered through Celite®, the filter cake washed with EtOH (3×50 mL) and the filtrate was concentrated in vacuo and placed under vacuum to give 32.63 g (96%) of the free base amine as a golden, viscous liquid; $^1$H NMR (DMSO-d$_6$): δ 8.20 (s, 1H), 6.90 (t, 1H), 5.36 (b, 3H), 3.61 9s, 3H), 3.51 (t, 1H), 3.18 (t, 2H), 1.38 (s, 9H).

EXAMPLE 2502

Resolution of 3-(4-cyanophenyl)isoxazolin-5(R,S)-ylacetic acid by Crystallization 3-(4-Cyanophenyl)isoxazolin-5(S)-ylacetic acid (127 g, 0.55 moles) and (+)-cinchonidine (180.37 g, 0.55 mol) were added to acetone (2.0 L) and stirred at ambien temperature for at least 1.5 hrs. The resulting precipitate (169.21 g) was collected by filtration. The precipitate was dissolved in hot acetone (4.0 L) while stirring. After complete dissolution, the solution was allowed to stand overnight. The crystals formed were collected by filtration and recrystallized with acetone gain to yield the 3-(4-cyanophenyl)isoxazolin-5(S)-ylacetic acid/(+)-cinchonidine salt in 33% overall yield and >99 % diastereomeric excess. The 3-(4-cyanophenyl) isoxazolin-5(S)-ylacetic acid was liberated from its cinchonidine salt complex by suspending the salt in ethereal HCL (1 N), filtering the solid after equilibration and evaporating the ether solution to provide the solid 3-(4-cyanophenyl)isoxazolin-5(S)-ylacetic acid. The R-isomer could be obtained from the mother liquor. Other chiral bases used include ephedrine, 2-phenylglycinol, 2-amino-3-methoxy-1-propanol, quinidine and pseudoephedrine.

EXAMPLE 2503

General Procedure for the Preparation of Compounds of the Formula (Ie) and (If)

Part A.

Z-2,3-diaminopropionic acid (2.5 g, Fluka) was combined with Fmoc-N-Hydroxysuccinimide (1.1 eq., 3.89 g) and NaHCO$_3$ (3 eq., 2.65 g), in dioxane (24 ml) and H$_2$O (21 ml). After stirring at room temperature overnight, the pH was adjusted with Na$_2$CO$_3$ to pH 9. The solution was extracted three times with ethyl ether, then the aqueous layer was acidified with conc. HCl, with stirring. At pH 4–5, a solid precipitated out. This was filtered, rinsed with 1 N HCl, and dried. (93% yield)

Part B.

Wang resin (2.0 g, 1.16 mmole/g, Advanced Chem Tech) was added to triphenylphosphine (5 eq, 3.0 g) in 20 ml DMF. CBr$_4$ (5 eq, 3.85 g) was then added and the solution was stirred at room temperature 3 hours. The resin was filtered and rinsed with DMF. Fmoc-Z-2,3-diaminopropionic acid (1.60 g, 1.5 equiv.) was dissolved in 20 ml DMF and the above resin was added, with 1.5 equiv. DIEA (0.60 ml) and 1.0 equiv. CsI (0.60 g) and stirred at room temperature overnight. The resin was filtered and rinsed with DMF and MeOH. Weight gain, IR, elemental analysis, and picric acid determination were used to establish the substitution level of the resin as approx. 0.8 mmole/g.

Part C.

The above derivatized resin (150 mg) was deprotected by mixing 10 min. with 20% piperidine/DMF. of The Fmoc-isoxazolin derivative (1.5 eq., 0.18 mmole) was dissolved in 1.5 ml DMF and added to the resin with HBTU (1.5 eq, 68 mg) and DIEA (1.5 eq, 32 ul). The tubes were mixed overnight, then drained, rinsed with DMF and MeOH, and the resin split into two portions. One portion was deprotected with 20% piperidine/DMF and then cleaved to produce the primary amine analogs. The other portion was deprotected with 20% piperidine/DMF and then coupled overnight with bis Boc-S-ethyl isothiourea (2 eq., 37 mg) and DEA (2 eq., 21 ul) in DMF.

Part D.

After rinsing, the compounds were cleaved from the resin by mixing with 1:1 TFA:CH$_2$Cl$_2$ for two hours. The filtrate was rotovapped under reduced pressure to an oil, dissolved in 1:1 acetonitrile:H$_2$O, and lyophilized. The crude material was analyzed by mass spec and HPLC. They were then purified by reverse phase HPLC (ACN:H$_2$O:0.1% TFA, C 18 column).

Using the above methods and variations thereof known in the art of organic synthesis, the additional examples in Tables 1-2, 2A-2D, 3–14 can be prepared.

TABLE 1

(V)

| Ex. No. | $R^2$ | $R^4$ | Y | n | $R^{14}$ | n' |
|---|---|---|---|---|---|---|
| 1 | H | H | OH | 2 | H | 0 |
| 2 | H | NHSO$_2$nC$_4$H$_9$ | OH | 2 | H | 0 |
| 3 | H | NHSO$_2$CH$_2$Ph | OH | 2 | H | 0 |
| 4 | H | NHCO$_2$CH$_2$Ph | OH | 2 | H | 0 |
| 5 | H | NHCOnC$_4$H$_9$ | OH | 2 | H | 0 |
| 6 | H | H | OH | 1 | H | 1 |
| 7 | H | H | OH | 1 | H | 0 |
| 8 | H | H | OH | 2 | H | 1 |
| 9 | H | NHSO$_2$nC$_4$H$_9$ | OH | 1 | H | 1 |
| 10 | H | NHSO$_2$CH$_2$Ph | OH | 1 | H | 1 |
| 11 | H | NHCO$_2$CH$_2$Ph | OH | 1 | H | 1 |
| 12 | H | NHCOnC$_4$H$_9$ | OH | 1 | H | 1 |
| 13 | H | NHSO$_2$nC$_4$H$_9$ | OMe | 2 | H | 0 |
| 14 | H | NHCO$_2$CH$_2$Ph | OMe | 2 | H | 0 |
| 15 | H | NHSO$_2$nC$_4$H$_9$ | OMe | 1 | H | 1 |
| 16 | H | NHCO$_2$CH$_2$Ph | OMe | 1 | H | 1 |
| 17 | H | NHSO$_2$nC$_4$H$_9$ | OEt | 2 | H | 0 |
| 18 | H | NHCO$_2$CH$_2$Ph | OEt | 2 | H | 0 |
| 19 | H | NHSO$_2$nC$_4$H$_9$ | OEt | 1 | H | 1 |
| 20 | H | NHCO$_2$CH$_2$Ph | OEt | 1 | H | 1 |
| 21 | Boc | NHSO$_2$nC$_4$H$_9$ | OH | 2 | H | 0 |
| 22 | Boc | NHCO$_2$CH$_2$Ph | OH | 2 | H | 0 |
| 23 | Boc | NHSO$_2$nC$_4$H$_9$ | OH | 1 | H | 1 |
| 24 | Boc | NHCO$_2$CH$_2$Ph | OH | 1 | H | 1 |
| 25 | Cbz | NHSO$_2$nC$_4$H$_9$ | OH | 2 | H | 0 |
| 26 | Cbz | NHCO$_2$CH$_2$Ph | OH | 2 | H | 0 |
| 27 | Cbz | NHSO$_2$nC$_4$H$_9$ | OH | 1 | H | 1 |
| 28 | Cbz | NHCO$_2$CH$_2$Ph | OH | 1 | H | 1 |
| 29 | H | NHSO$_2$nC$_4$H$_9$ | -OCH$_2$OC(O)O-cyclohexyl | 2 | H | 0 |
| 30 | H | NHSO$_2$nC$_4$H$_9$ | -OCH$_2$OC(O)Me | 2 | H | 0 |
| 31 | H | NHSO$_2$nC$_4$H$_9$ | (5-methyl-2-oxo-1,3-dioxol-4-yl)methoxy | 2 | H | 0 |
| 32 | H | NHSO$_2$nC$_4$H$_9$ | -OCH$_2$C(O)OEt | 2 | H | 0 |
| 31 | H | NHSO$_2$nC$_4$H$_9$ | -OCH$_2$CH$_2$N(Et)$_2$ | 2 | H | 0 |
| 33 | H | H | OH | 2 | CO$_2$Me | 0 |
| 34 | H | H | OMe | 2 | H | 0 |
| 35 | H | NHSO$_2$CH$_2$Ph | OMe | 2 | H | 0 |
| 36 | H | NHCOnC$_4$H$_9$ | OMe | 2 | H | 0 |
| 37 | H | H | OMe | 1 | H | 1 |
| 38 | H | H | OMe | 1 | H | 0 |
| 39 | H | H | OMe | 2 | H | 1 |

TABLE 1-continued (V)

| Ex. No. | R² | R⁴ | Y | n | R¹⁴ | n' |
|---|---|---|---|---|---|---|
| 40 | H | NHSO₂CH₂Ph | OMe | 1 | H | 1 |
| 41 | H | NHCOnC₄H₉ | OMe | 1 | H | 1 |
| 42 | H | H | OMe | 2 | CO₂Me | 0 |

TABLE 2

(VI)

| Example Number | R² | R⁸ | Y | MS (M + H)⁺ |
|---|---|---|---|---|
| 43 | H | Ph | OH | 412 |
| 43A | H | Ph | OH | HNMR |
| 44 | H | 3-hydroxyphenyl | OH | |
| 45 | H | 4-bromophenyl | OH | |
| 46 | H | 2-fluorophenyl | OH | |
| 47 | H | 3-fluorophenyl | OH | |
| 48 | H | 4-fluorophenyl | OH | |
| 49 | H | 3-methoxyphenyl | OH | |

TABLE 2-continued (VI)

| Example Number | R² | R⁸ | Y | MS (M + H)⁺ |
|---|---|---|---|---|
| 50 | H | 3-(OEt)phenyl | OH | |
| 51 | H | 4-(OPh)phenyl | OH | |
| 52 | H | 3-(OPh)phenyl | OH | |
| 53 | H | 4-Cl-phenyl | OH | |
| 54 | H | 3-CN-phenyl | OH | |
| 55 | H | 4-CN-phenyl | OH | |
| 56 | H | 3-CF₃-phenyl | OH | |
| 57 | H | 4-CF₃-phenyl | OH | |
| 58 | H | 3,5-diCl-phenyl | OH | |
| 59 | H | 3,4-diCl-phenyl | OH | |

TABLE 2-continued
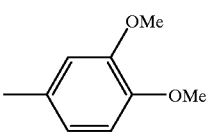
(VI)
| Example Number | R² | R⁸ | Y | MS (M + H)⁺ |
|---|---|---|---|---|
| 60 | H | 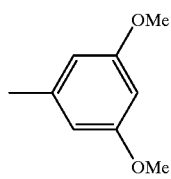 | OH | |
| 61 | H | 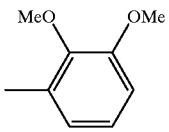 | OH | |
| 62 | H | 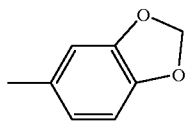 | OH | |
| 63 | H | 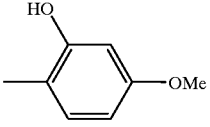 | OH | |
| 64 | H | 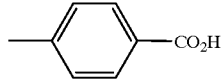 | OH | |
| 65 | H | 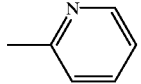 | OH | |
| 66 | H | 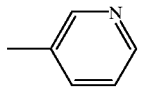 | OH | |
| 67 | H | 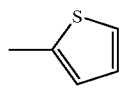 | OH | |
| 68 | H |  | OH | |
| 69 | H | Et | OH | |
| 70 | H | n-Pr | OH | |
| 71 | H | —C≡CH | OH | |
| 72 | H | CO₂H | OH | |
| 73 | H | CH₂Ph | OH | |
| 74 | H | CH₂CH₂Ph | OH | |

TABLE 2-continued
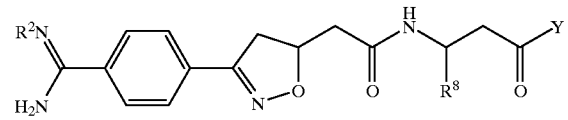
(VI)
| Example Number | R² | R⁸ | Y | MS (M + H)⁺ |
|---|---|---|---|---|
| 75 | H | —C≡CH₂ | OH | |
| 76 | H | 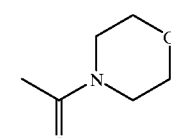 | OH | |
| 80 | Cbz | Ph | OH | |
| 81 | Cbz | 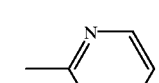 | OH | |
| 82 | Boc | Ph | OH | |
| 83 | Boc | 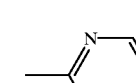 | OH | |
| 84 | H | 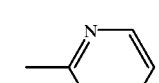 | 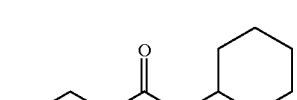 | |
| 85 | H | 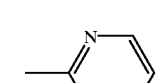 | 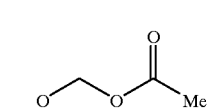 | |
| 86 | H | 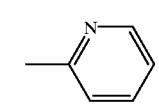 | 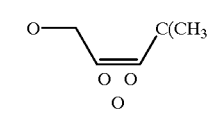 | |
| 87 | H | 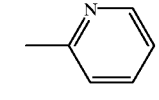 | 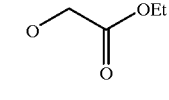 | |
| 88 | H | 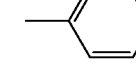 |  | |
| 89 | H | Ph | OMe | |
| 90 | H | 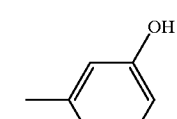 | OMe | |

TABLE 2-continued
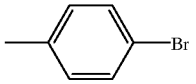
(VI)
| Example Number | R² | R⁸ | Y | MS (M + H)⁺ |
|---|---|---|---|---|
| 91 | H | 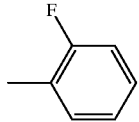 4-Br-phenyl | OMe | |
| 92 | H | 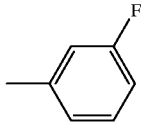 2-F-phenyl | OMe | |
| 93 | H |  3-F-phenyl | OMe | |
| 94 | H | 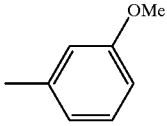 4-F-phenyl | OMe | |
| 95 | H | 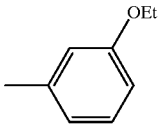 3-OMe-phenyl | OMe | |
| 96 | H | 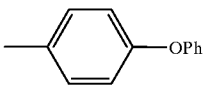 3-OEt-phenyl | OMe | |
| 97 | H | 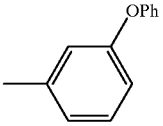 4-OPh-phenyl | OMe | |
| 98 | H | 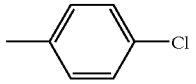 3-OPh-phenyl | OMe | |
| 99 | H | 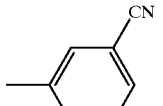 4-Cl-phenyl | OMe | |
| 100 | H | 3-CN-phenyl | OMe | |

TABLE 2-continued (VI)

| Example Number | R² | R⁸ | Y | MS (M + H)⁺ |
|---|---|---|---|---|
| 101 | H | 4-cyanophenyl | OMe | |
| 102 | H | 3-trifluoromethylphenyl | OMe | |
| 103 | H | 4-trifluoromethylphenyl | OMe | |
| 104 | H | 3,5-dichlorophenyl | OMe | |
| 105 | H | 3,4-dichlorophenyl | OMe | |
| 106 | H | 3,4-dimethoxyphenyl | OMe | |
| 107 | H | 3,5-dimethoxyphenyl | OMe | |
| 108 | H | 2,3-dimethoxyphenyl | OMe | |
| 109 | H | 3,4-methylenedioxyphenyl | OMe | |

TABLE 2-continued (VI)

| Example Number | R² | R⁸ | Y | MS (M + H)⁺ |
|---|---|---|---|---|
| 110 | H | 2-methyl-5-methoxy-4-hydroxyphenyl (HO, OMe substituted phenyl) | OMe | |
| 111 | H | 4-carboxyphenyl (CO₂H substituted phenyl) | OMe | |
| 112 | H | 2-pyridyl | OMe | |
| 113 | H | 3-pyridyl | OMe | |
| 114 | H | 2-thienyl | OMe | |
| 115 | H | Et | OMe | 361 |
| 116 | H | n-Pr | OMe | |
| 117 | H | —C≡H | OMe | |
| 118 | H | CO₂H | OMe | |
| 119 | H | CH₂Ph | OMe | 423 |
| 120 | H | CH₂CH₂Ph | OMe | 437 |
| 121 | H | —C=CH₂ | OMe | |
| 122 | H | morpholinyl-C(O)-CH₂- | OMe | |
| 126 | Cbz | Ph | OMe | |
| 127 | Cbz | 2-pyridyl | OMe | |
| 128 | Boc | Ph | OMe | |
| 129 | Boc | 2-pyridyl | OMe | |
| 130 | H | Ph | OEt | |

TABLE 2-continued (VI)

| Example Number | R² | R⁸ | Y | MS (M + H)⁺ |
|---|---|---|---|---|
| 131 | H | 3-hydroxyphenyl | OEt | |
| 132 | H | 4-bromophenyl | OEt | |
| 133 | H | 2-fluorophenyl | OEt | |
| 134 | H | 3-fluorophenyl | OEt | |
| 135 | H | 4-fluorophenyl | OEt | |
| 136 | H | 3-methoxyphenyl | OEt | |
| 137 | H | 3-ethoxyphenyl | OEt | |
| 138 | H | 4-phenoxyphenyl | OEt | |
| 139 | H | 3-phenoxyphenyl | OEt | |
| 140 | H | 4-chlorophenyl | OEt | |

TABLE 2-continued (VI)

Structure: R²N(H₂N)C-[phenyl]-[isoxazoline]-CH₂-C(O)-NH-CH(R⁸)-CH₂-C(O)-Y

| Example Number | R² | R⁸ | Y | MS (M + H)⁺ |
|---|---|---|---|---|
| 141 | H | 3-cyanophenyl-CH₂- | OEt | |
| 142 | H | 4-cyanophenyl-CH₂- | OEt | |
| 143 | H | 3-(CF₃)phenyl-CH₂- | OEt | |
| 144 | H | 4-(CF₃)phenyl-CH₂- | OEt | |
| 145 | H | 3,5-dichlorophenyl-CH₂- | OEt | |
| 146 | H | 3,4-dichlorophenyl-CH₂- | OEt | |
| 147 | H | 3,4-dimethoxyphenyl-CH₂- | OEt | |
| 148 | H | 3,5-dimethoxyphenyl-CH₂- | OEt | |
| 149 | H | 2,3-dimethoxyphenyl-CH₂- | OEt | |

TABLE 2-continued (VI)

[Structure: R²N(H₂N)C-phenyl-isoxazoline-CH₂-C(O)-NH-CH(R⁸)-CH₂-C(O)-Y]

| Example Number | R² | R⁸ | Y | MS (M + H)⁺ |
|---|---|---|---|---|
| 150 | H | 6-methyl-benzo[1,3]dioxole | OEt | |
| 151 | H | 2-hydroxy-5-methoxy-methylphenyl | OEt | |
| 152 | H | 4-carboxyphenylmethyl | OEt | |
| 153 | H | 2-pyridylmethyl | OEt | |
| 154 | H | 3-pyridylmethyl | OEt | |
| 155 | H | 2-thienylmethyl | OEt | |
| 156 | H | Et | OEt | |
| 157 | H | n-Pr | OEt | |
| 158 | H | —C=H | OEt | |
| 159 | H | CO₂H | OEt | |
| 160 | H | CH₂Ph | OEt | |
| 161 | H | CH₂CH₂Ph | OEt | |
| 162 | H | —C≡CH₂ | OEt | |
| 163 | H | CH₂-C(O)-morpholine | OEt | |
| 164 | H | CH₂N(Me)Ph | OEt | |
| 165 | H | CH₂NEt₂ | OEt | |
| 166 | H | CH₂NMe₂ | OEt | |
| 167 | Cbz | Ph | OEt | |
| 168 | Cbz | 2-pyridylmethyl | OEt | |
| 169 | Boc | Ph | OEt | |

TABLE 2-continued

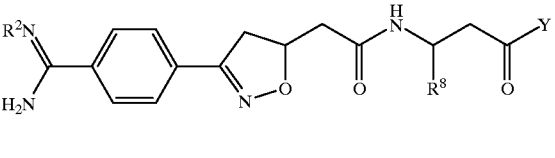

(VI)

| Example Number | R² | R⁸ | Y | MS (M + H)⁺ |
|---|---|---|---|---|
| 170 | Boc | 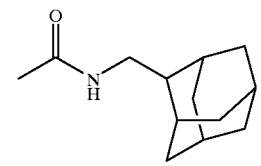 | OEt | |
| 338 | H | CO₂Me | OMe | mp 160° |
| 339 | H | CO₂Me | H | 363 |
| 340 | H | CONMe₂ | OMe | 404 |
| 341 | H | 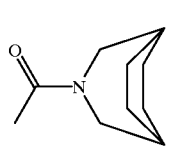 | OMe | 524 |
| 343 | H | n-butyl | OH | |
| 344 | H | n-butyl | OMe | 389 |
| 345 | H | n-butyl | OEt | |
| 346 | H | isobutyl | OH | |
| 347 | H | isobutyl | OMe | 389 |
| 348 | H | isobutyl | OEt | 403 |
| 349 | H | CH₂SPh | OH | |
| 350 | H | CH₂SPh | OMe | 455 |
| 351 | H | CH₂SPh | OEt | |
| 352 | H | CH₂OPh | OH | |
| 353 | H | CH₂OPh | OMe | |
| 354 | H | CH₂OPh | OEt | |
| 355 | H | CH₂SO₂Ph | OH | |
| 356 | H | CH₂SO₂Ph | OMe | |
| 357 | H | CH₂SO₂Ph | OEt | |
| 358 | H | CH₂NHSO₂Ph | OH | |
| 359 | H | CH₂NHSO₂Ph | OMe | 502 |
| 360 | H | CH₂NHSO₂Ph | OEt | |
| 361 | H | CH₂NHSO₂n-Bu | OH | |
| 362 | H | CH₂NHSO₂n-Bu | OMe | 482 |
| 363 | H | CH₂NHSO₂n-Bu | OEt | |
| 364 | H | CH₂COOH | OH | 377 |
| 365 | H | CH₂COOMe | OMe | 405 |
| 366 | H | CH₂COOEt | OEt | |
| 367 | H | CH₂CH₂COOH | OH | |
| 368 | H | CH₂CH₂COOMe | OMe | 419 |
| 369 | H | CH₂CH₂COOEt | OEt | |
| 370 | H | CH₂NMe₂ | OH | |
| 371 | H | CH₂NMe₂ | OMe | 390 |
| 372 | H | CH₂NMe₂ | OEt | |
| 434 | BOC | —C(=O)NH—(CH₂)₂C₆H₅ | OtBu | 622 |
| 435 | H | —C(=O)NH—(CH₂)₂C₆H₅ | OH | 466 |
| 439 | H | —C(=O)OC₂H₅ | OEt | 419 |
| 441 | H |  | OH | 484 |
| 446 | H | (CH₂)₃Ph | OMe | |
| 447 | H | CH₂-(2-pyr) | OMe | |
| 448 | H | (CH₂)₂-(2-pyr) | OMe | |
| 449 | H | (CH₂)₂-(3-pyr) | OMe | 438 |
| 450 | H | (CH₂)₂-(4-pyr) | OMe | 438 |
| 452 | H | —C(=O)NH—(CH₂)₂C₆H₅ | OMe | 480 |

TABLE 2-continued (VI)

| Example Number | R² | R⁸ | Y | MS (M + H)⁺ |
|---|---|---|---|---|
| 453 | BOC | C(O)-(4-piperidyl)-N-CH₂Ph | OMe | 635 |
| 454 | H | C(=O)N(CH₃)—(CH₂)₂C₆H₅ | OMe | |
| 455 | H | C(O)-(4-piperidyl)-N-CH₂Ph | OMe | |
| 456 | H | i-hexyl | OEt | 431 |
| 457 | H | —C≡CSiMe₃ | OMe | 429 |
| 458 | H | —(CH₂)₂-(3-pyr) | OH | 424 |
| 459 | H | —(CH₂)₂-(2-pyr) | OH | 424 |
| 460 | H | —(CH₂)₃—C₆H₅ | OH | 437 |
| 461 | H | —(CH₂)₃—C₆H₅ | OMe | 451 |
| 462 | H | C(=O)NH-CH₂-adamantyl | OEt | 538 |
| 463 | H | C(=O)NH-CH₂-adamantyl | OH | 510 |
| 464 | H | C(=O)NH-CH₂-adamantyl | OMe | 492 |
| 465 | H | C(=O)-tetrahydroisoquinolinyl | OMe | 492 |
| 466 | H | C(=O)NH-adamantyl | OMe | 510 |

TABLE 2-continued

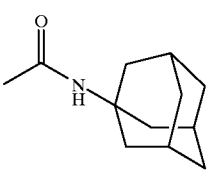

(VI)

| Example Number | R² | R⁸ | Y | MS (M + H)⁺ |
|---|---|---|---|---|
| 467 | H | 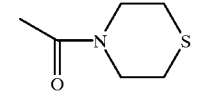 | OMe | 510 |
| 468 | H | 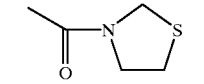 | OMe | 462 |
| 469 | H | 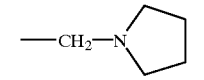 | OMe | 448 |
| 587 | H | —(CH$_2$)$_3$-(4-pyr) | OH | 424 |
| 611 | H | —CH$_2$NHSO$_2$NMe$_2$ | OMe | 469 |
| 612 | H | —CH$_2$—N(pyrrolidine) | OMe | 416 |

TABLE 2A

| Example Number | R¹-V | R¹⁶ | Y | MS (M + H)⁺ |
|---|---|---|---|---|
| 275 | 4-amidinophenyl | H | OH | 334 |
| 276 | 4-amidinophenyl | benzyloxycarbonyl | OH | 468 |
| 277 | 4-amidinophenyl | t-butyloxycarbonyl | OH | |
| 278 | 4-amidinophenyl | n-butyloxycarbonyl | OH | 434 |
| 278a | 4-amidinophenyl | n-butyloxycarbonyl | OMe | 448 |
| 278b | 4-amidinophenyl | n-butyloxycarbonyl | OH | 434 |
| 279 | 4-amidinophenyl | ethyloxycarbonyl | OH | |
| 280 | 4-amidinophenyl | methyloxycarbonyl | OH | |
| 290 | 4-amidinophenyl | phenylethylcarbonyl | OH | 510 |
| 291 | 4-amidinophenyl | 2,2-dimethyl-propyl carbonyl | OH | |
| 292 | 4-amidinophenyl | n-pentylcarbonyl | OH | |
| 293 | 4-amidinophenyl | n-butylcarbonyl | OH | |
| 294 | 4-amidinophenyl | propionyl | OH | |
| 295 | 4-amidinophenyl | acetyl | OH | |
| 296 | 4-amidinophenyl | methylsulfonyl | OH | |
| 297 | 4-amidinophenyl | ethylsulfonyl | OH | |
| 298 | 4-amidinophenyl | n-butylsulfonyl | OH | |
| 299 | 4-amidinophenyl | phenylsulfonyl | OH | 474 |
| 300 | 4-amidinophenyl | 4-methylphenyl-sulfonyl | OH | 488 |
| 301 | 4-amidinophenyl | benzylsulfonyl | OH | |
| 302 | 4-amidinophenyl | 2-pyridylcarbonyl | OH | |
| 303 | 4-amidinophenyl | 3-pyridylcarbonyl | OH | |
| 304 | 4-amidinophenyl | 4-pyridylcarbonyl | OH | |
| 305 | 4-amidinophenyl | 2-pyridylmethyl-carbonyl | OH | |
| 306 | 4-amidinophenyl | 3-pyridylmethyl carbonyl | OH | |
| 307 | 4-amidinophenyl | 4-pyridylmethyl-carbonyl | OH | |

TABLE 2A-continued

| Example Number | R$^1$-V | R$^{16}$ | Y | MS (M + H)$^+$ |
|---|---|---|---|---|
| 308 | 4-amidinophenyl | 2-pyridylmethoxycarbonyl | OH | |
| 309 | 4-amidinophenyl | 3-pyridylmethoxycarbonyl | OH | |
| 310 | 4-amidinophenyl | 4-pyridylmethoxycarbonyl | OH | |
| 311 | 4-amidinophenyl | H | OMe | |
| 312 | 4-amidinophenyl | benzyloxycarbonyl | OMe | 482 |
| 313 | 4-amidinophenyl | t-butyloxycarbonyl | OMe | |
| 314 | 4-amidinophenyl | n-butyloxycarbonyl | OMe | 448 |
| 315 | 4-amidinophenyl | ethyloxycarbonyl | OMe | |
| 316 | 4-amidinophenyl | methyloxycarbonyl | OMe | |
| 317 | 4-amidinophenyl | phenylethylsulfonyl | OH | 502 |
| 318 | 4-amidinophenyl | 2,2-dimethylpropylcarbonyl | OMe | |
| 319 | 4-amidinophenyl | n-pentylcarbonyl | OMe | |
| 320 | 4-amidinophenyl | n-butylcarbonyl | OMe | |
| 321 | 4-amidinophenyl | propionyl | OMe | |
| 322 | 4-amidinophenyl | acetyl | OMe | |
| 323 | 4-amidinophenyl | methylsulfonyl | OMe | 426 |
| 324 | 4-amidinophenyl | ethylsulfonyl | OMe | 440 |
| 325 | 4-amidinophenyl | n-butylsulfonyl | OMe | |
| 326 | 4-amidinophenyl | phenylsulfonyl | OMe | 488 |
| 327 | 4-amidinophenyl | 4-methylphenylsulfonyl | OMe | 502 |
| 328 | 4-amidinophenyl | benzylsulfonyl | OMe | 502 |
| 329 | 4-amidinophenyl | 2-pyridylcarbonyl | OMe | |
| 330 | 4-amidinophenyl | 3-pyridylcarbonyl | OMe | |
| 331 | 4-amidinophenyl | 4-pyridylcarbonyl | OMe | |
| 332 | 4-amidinophenyl | 2-pyridylmethylcarbonyl | OMe | |
| 333 | 4-amidinophenyl | 3-pyridylmethylcarbonyl. | OMe | |
| 334 | 4-amidinophenyl | 4-pyridylmethylcarbonyl | OMe | |
| 335 | 4-amidinophenyl | 2-pyridylmethoxycarbonyl | OMe | |
| 336 | 4-amidinophenyl | 3-pyridylmethoxycarbonyl | OMe | |
| 337 | 4-amidinophenyl | 4-pyridylmethoxycarbonyl | OMe | |
| 374 | 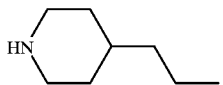 | benzyloxycarbonyl | OMe | 475 |
| 440 | 4-(BOCamidino)phenyl | benzyloxycarbonyl | OMe | 582 |
| 442 | 4-(BOCamidino)phenyl | n-butyloxycarbonyl | OMe | 594 |
| 443 | 4-amidinophenyl | 1-naphthylsulfonyl | OMe | 538 |
| 444 | 4-amidinophenyl | 2-naphthylsulfonyl | OMe | 538 |
| 445 | 4-amidinophenyl | styrylsulfonyl | OMe | 514 |
| 445a | 4-amidinophenyl | styrylsulfonyl | OH | 500 |
| 451 | 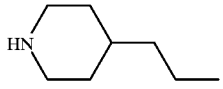 | n-butyloxycarbonyl | OMe | 441 |
| 471 | 4-amidinophenyl | 4-butyloxyphenylsulfonyl | OMe | 560 |
| 472 | 4-amidinophenyl | 2-thienylsulfonyl | OMe | 494 |
| 473 | 4-amidinophenyl | 3-methylphenylsulfonyl | OMe | 502 |
| 474 | 4-amidinophenyl | 4-iodophenyl | OMe | 614 |
| 475 | 4-amidinophenyl | 3-trifluoromethylphenylsulfonyl | OMe | 556 |
| 476 | 4-amidinophenyl | 3-chlorophenylsulfonyl | OMe | 522 |
| 477 | 4-amidinophenyl | 2-methoxycarbonylphenylsulfonyl | OMe | 546 |
| 478 | 4-amidinophenyl | 2,4,6-trimethylphenylsulfonyl | OMe | 530 |
| 478a | 4-amidinophenyl | 2,4,6-trimethylphenylsulfonyl | OH | 516 |

TABLE 2A-continued

| Example Number | R¹-V | R¹⁶ | Y | MS (M + H)⁺ |
|---|---|---|---|---|
| 479 | 4-amidinophenyl | 2-chlorophenylsulfonyl | OMe | 522 |
| 479a | 4-amidinophenyl | 2-chlorophenylsulfonyl | OH | 508 |
| 480 | 4-amidinophenyl | 2-trifluoromethyl-phenylsulfonyl | OMe | 556 |
| 481 | 4-amidinophenyl | 4-trifluoromethyl-phenylsulfonyl | OMe | 556 |
| 482 | 4-amidinophenyl | 2-fluorophenylsulfonyl | OMe | 506 |
| 483 | 4-amidinophenyl | 4-fluorophenylsulfonyl | OMe | 506 |
| 484 | 4-amidinophenyl | 4-methoxyphenylsulfonyl | OMe | 518 |
| 485 | 4-amidinophenyl | 2,3,5,6-tetramethyl-phenylsulfonyl | OMe | 544 |
| 485a | 4-amidinophenyl | 2,3,5,6-tetramethyl-phenylsulfonyl | OH | 530 |
| 486 | 4-amidinophenyl | 4-cyanophenylsulfonyl | OMe | 513 |
| 487 | 4-amidinophenyl | 4-chlorophenylsulfonyl | OMe | 522 |
| 488 | 4-amidinophenyl | 4-ethylphenylsulfonyl | OMe | 516 |
| 489 | 4-amidinophenyl | 4-propylphenylsulfonyl | OMe | 530 |
| 490 | 4-amidinophenyl | n-propylsulfonyl | OMe | 454 |
| 490a | 4-amidinophenyl | n-propylsulfonyl | OH | 440 |
| 491 | 4-amidinophenyl | 2-phenylethylsulfonyl | OMe | 516 |
| 492 | 4-amidinophenyl | 4-isopropylphenylsulfonyl | OMe | 530 |
| 492a | 4-amidinophenyl | 4-isopropylphenylsulfonyl | OH | 516 |
| 493 | 4-amidinophenyl | 3-phenylpropylsulfonyl | OMe | 530 |
| 494 | 4-amidinophenyl | 3-pyridylsulfonyl | OMe | 489 |
| 495 | 4-amidinophenyl | 2-pyridylsulfonyl | OMe | 489 |
| 496 | 4-amidinophenyl | 2,2-diphenyl-1-ethenylsulfonyl | OMe | 590 |
| 497 | 4-amidinophenyl | 2-pyrimidinylsulfonyl | OMe | |
| 498 | 4-amidinophenyl | 4-methyl-2-pyrimidinylsulfonyl | OMe | |
| 499 | 4-amidinophenyl | 4,6-dimethyl-2-pyrimidinylsulfonyl | OMe | |
| 500 | 4-amidinophenyl | 1,2,4-triazol-3-ylsulfonyl | OMe | |
| 501 | 4-amidinophenyl | 1-methyl-1,3,4-triazol-5-ylsulfonyl | OMe | |
| 502 | 4-amidinophenyl | 3,5-dimethyl-4-pyrazolylsulfonyl | OMe | |
| 503 | 4-amidinophenyl | 1-phenyl-4-pyrazolylsulfonyl | OMe | |
| 504 | 4-amidinophenyl | n-butylaminosulfonyl | OMe | 483 |
| 505 | 4-amidinophenyl | i-butylaminosulfonyl | OMe | 483 |
| 506 | 4-amidinophenyl | t-butylaminosulfonyl | OMe | 483 |
| 507 | 4-amidinophenyl | i-propylaminosulfonyl | OMe | 469 |
| 508 | 4-amidinophenyl | cyclohexylaminosulfonyl | OMe | 509 |
| 509 | 4-amidinophenyl | phenylaminosulfonyl | OMe | 503 |
| 510 | 4-amidinophenyl | benzylaminosulfonyl | OMe | 517 |
| 511 | 4-amidinophenyl | dimethylaminosulfonyl | OMe | 455 |
| 512 | 4-amidino-2-fluoro-phenyl | 3-methylphenylsulfonyl | OMe | 520 |
| 512A | 4-amidino-2-fluoro-phenyl | 3-methylphenylsulfonyl | OH | 506 |
| 514 | 2-amidino-5-pyridyl | 3-methylphenylsulfonyl | OMe | 503 |
| 514A | 2-amidino-5-pyridyl | 3-methylphenylsulfonal | OH | 489 |
| 516 | 3-amidino-6-pyridyl | 3-methylphenylsulfonyl | OMe | 503 |
| 516A | 3-amidino-6-pyridyl | 3-methylphenylsulfonyl | OH | 489 |

TABLE 2A-continued

| Example Number | R¹-V | R¹⁶ | Y | MS (M + H)⁺ |
|---|---|---|---|---|
| 518 | 4-amidinophenyl | 4-fluorophenylaminocarbonyl | OMe | 485 |
| 519 | 4-amidinophenyl | 1-naphthylaminocarbonyl | OMe | 517 |
| 520 | 4-amidinophenyl | benzylaminocarbonyl | OMe | |
| 521 | 4-amidinophenyl | n-butylaminocarbonyl | OMe | 435 |
| 522 | 4-amidinophenyl | 4-ethylphenylcarbonyl | OMe | 480 |
| 523 | 4-amidinophenyl | biphenylcarbonyl | OMe | 528 |
| 524 | 4-amidinophenyl | 2-naphthylcarbonyl | OMe | 502 |
| 525 | 4-amidinophenyl | (2-chlorophenyl)methoxycarbonyl | OMe | 516 |
| 526 | 4-amidinophenyl | (2-chlorophenyl)methoxycarbonyl | OH | 502 |
| 527 | 4-amidinophenyl | (2-bromophenyl)methoxycarbonyl | OMe | 562 |
| 528 | 4-ainidinophenyl | (2-bromophenyl)methoxycarbonyl | OH | 548 |
| 528a | 4-amidinophenyl | (2-bromophenyl)carbonyl | OH | 516 |
| 529 | 4-amidinophenyl | n-hexyloxycarbonyl | OMe | 476 |
| 530 | 4-amidinophenyl | n-hexyloxycarbonyl | OH | 460 |
| 531 | 4-amidinophenyl | isobutyloxycarbonyl | OMe | 448 |
| 532 | 4-amidinophenyl | isobutyloxycarbonyl | OH | 434 |
| 533 | 4-amidinophenyl | 2-cyclopropylethoxycarbonyl | OMe | 460 |
| 534 | 4-amidinophenyl | 2-cyclopropylethoxycarbonyl | OH | 446 |
| 535 | 4-amidinophenyl | 2-cyclopentylethoxycarbonyl | OMe | 488 |
| 536 | 4-amidinophenyl | 2-cyclopentylethoxycarbonyl | OH | 474 |
| 537 | 4-amidinophenyl | 4,4,4-trifluorobutyloxycarbonyl | OMe | 502 |
| 538 | 4-amidinophenyl | 4,4,4-trifluorobutyloxycarbonyl | OH | 488. |
| 539 | 4-amidinophenyl | n-propylsulfonyl | OMe | |
| 540 | 4-amidinophenyl | 2-methylphenylcarbonyl | OH | 452 |
| 540a | 4-amidinophenyl | 2-methylphenylsulfonyl | OH | 488 |
| 541 | 4-amidinophenyl | 4-chloro-2,5-dimethylphenylsulfonyl | OMe | 550 |
| 541a | 4-amidinophenyl | 4-chloro-2,5-dimethylphenylsulfonyl | OMe | 536 |
| 542 | 4-amidinophenyl | 2,3-dichlorophenylsulfonyl | OMe | 556 |
| 543 | 4-amidinophenyl | 2-bromophenylsulfonyl | OMe | 568 |
| 544 | 4-amidinophenyl | 3-bromophenylsulfonyl | OMe | 568 |
| 545 | 4-amidinophenyl | 4-bromophenylsulfonyl | OMe | 568 |
| 546 | 4-amidinophenyl | biphenylsulfonyl | OMe | 564 |
| 547 | 4-amidinophenyl | 5-chloro-1,3-dimethyl-4-pyrazolyl | OMe | 540 |
| 548 | 4-amidinophenyl | 3-bromo-2-thienylsulfonyl | OMe | 574 |
| 549 | 4-amidinophenyl | 5-bromo-2-thienylsulfonyl | OMe | 574 |
| 550 | 4-amidinophenyl | 5-[1-methyl-5-trifluoromethyl-3-pyrazolyl]-2-thienylsulfonyl | OMe | 642 |
| 551 | 4-amidinophenyl | 5-(3-isoxazolyl)-2-thienylsulfonyl | OMe | 561 |
| 552 | 4-amidinophenyl | 5-(2-pyridinyl)-2-thienylsulfonyl | OMe | 571 |
| 553 | 4-amidinophenyl | 4-methyl-2-methylcarbonylamino-5-thiazolylsulfonyl | OMe | 566 |
| 554 | 4-amidinophenyl | 2-benzothienylsulfonyl | OMe | 628 |
| 555 | 4-amidinophenyl | 2-benzothienylsulfonyl | OMe | 544 |
| 556 | 4-amidinophenyl | 3-methyl-2-benzothienylsulfonyl | OMe | 558 |

TABLE 2A-continued

| Example Number | R¹-V | R¹⁶ | Y | MS (M + H)⁺ |
|---|---|---|---|---|
| 557 | 4-amidinophenyl | 8-quinolinylsulfonyl | OMe | 539 |
| 558 | 4-amidinophenyl | 8-quinolinylsulfonyl | OH | 525 |
| 559 | 4-amidinophenyl | 2,1,3-benzo-thiadiazol-4-ylsulfonyl | OMe | 546 |
| 560 | 4-amidinophenyl | 2,1,3-benzo-thiadiazol-4-ylsulfonyl | OH | 532 |
| 561 | 4-amidinophenyl | 4-N,N-dimethylamino-1-naphthylsulfonyl | OMe | |
| 562 | 4-amidinophenyl | 4-N,N-dimethylamino-1-naphthylsulfonyl | OH | |
| 563 | 4-amidinophenyl | 2,1,3-benzoxadiazol-4-ylsulfonyl | OMe | |
| 564 | 4-amidinophenyl | 2,1,3-benzoxadiazol-4-ylsulfonyl | OH | |
| 565 | 4-amidinophenyl | 2,2,5,7,8-pentamethyl 3,4-dihydro-2Hbenzo-pyran-6-ylsulfonyl | OMe | |
| 566 | 4-amidinophenyl | 2,2,5,7,8-pentamethyl 3,4-dihydro-2Hbenzo-pyran-6-ylsulfonyl | OH | |
| 567 | 4-N-methylamidino phenyl | 3-methylphenylsulfonyl | OMe | |
| 568 | 4-N-ethylamidino phenyl | 3-methylphenylsulfonyl | OMe | 530 |
| 569 | 4-N-n-propylamidino phenyl | 3-methylphenylsulfonyl | OMe | |
| 570 | 4-N-benzylamidino phenyl | 3-methylphenylsulfonyl | OMe | |
| 571 | 4-N-n-butylamidino phenyl | 3-methylphenylsulfonyl | OMe | 558 |
| 572 | 4-N-methylamidino phenyl | 3-methylphenylsulfonyl | OH | |
| 573 | 4-N-ethylamidino phenyl | 3-methylphenylsulfonyl | OH | 516 |
| 574 | 4-N-n-propylamidino phenyl | 3-methylphenylsulfonyl | OH | |
| 575 | 4-N-benzylamidino phenyl | 3-methylphenylsulfonyl | OH | |
| 576 | 4-N-n-butylamidino phenyl | 3-methylphenylsulfonyl | OH | 544 |
| 577 | 4-N-methylamidino-phenyl | n-butyloxycarbonyl | OMe | |
| 578 | 4-N-ethylamidinophenyl | n-butyloxycarbonyl | OMe | |
| 579 | 4-N-npropylamidino-phenyl | n-butyloxycarbonyl | OMe | |
| 580 | 4-N-n-butylamidino-phenyl | n-butyloxycarbonyl | OMe | 504 |
| 581 | 4-N-benzylamidino-phenyl | n-butyloxycarbonyl | OMe | |
| 582 | 4-N-methylamidino-phenyl | n-butyloxycarbonyl | OH | |
| 583 | 4-N-ethylamidino-phenyl | n-butyloxycarbonyl | OH | |
| 584 | 4-N-n-propylamidino-phenyl | n-butyloxycarbonyl | OH | |
| 585 | 4-N-n-butylamidino-phenyl | n-butyloxycarbonyl | OH | |
| 586 | 4-N-benzylamidino-phenyl | n-butyloxycarbonyl | OH | |
| 589 | 4-(acetoxyamidino)-phenyl | n-butyloxycarbonyl | OMe | |
| 590 | 4-(acetoxyamidino)-phenyl | n-butyloxycarbonyl | OH | |
| 591 | 4-(acetoxyamidino)-phenyl | isobutyloxycarbonyl | OMe | |
| 592 | 4-(acetoxyamidino) phenyl | isobutyloxycarbonyl | OH | |
| 593 | 4-(acetoxyamidino)-phenyl | cyclopropylethoxy-carbonyl | OMe | |
| 594 | 4-(acetoxyamidino)-phenyl | cyclopropylethoxy-carbonyl | OH | |
| 595 | 4-(acetoxyamidino)-phenyl | benzyloxycarbonyl | OMe | |
| 596 | 4-(acetoxyamidino)-phenyl | benzyloxycarbonyl | | |
| 597 | 4-(acetoxyamidino)-phenyl | 4-methylphenylsulfonyl | OMe | |

TABLE 2A-continued

| Example Number | R¹-V | R¹⁶ | Y | MS (M + H)⁺ |
|---|---|---|---|---|
| 598 | 4-(acetoxyamidino)-phenyl | 4-methylphenylsulfonyl | OH | |
| 599 | 4-(acetoxyamidino)-phenyl | 3-methylphenylsulfonyl | OMe | |
| 600 | 4-(acetoxyamidino)-phenyl | 3-methylphenylsulfonyl | OH | |
| 601 | 4-guanidinophenyl | n-butyloxycarbonyl | OH | |
| 602 | 4-guanidinophenyl | n-butyloxycarbonyl | OMe | 463 |
| 603 | 4-guanidinophenyl | benzyloxycarbonyl | OH | |
| 604 | 4-guanidinophenyl | benzyloxycarbonyl | OMe | |
| 605 | 4-guanidinophenyl | 4-methylphenylsulfonyl | OH | 503 |
| 606 | 4-guanidinophenyl | 4-methylphenylsulfonyl | OMe | 517 |
| 607 | 4-guanidinophenyl | 3-methylphenylsulfonyl | OH | |
| 608 | 4-guanidinophenyl | 3-methylphenylsulfonyl | OMe | |
| 609 | 4-guanidinophenyl | n-butylsulfonyl | OH | |
| 610 | 4-guanidinophenyl | n-butylsulfonyl | OMe | |
| 613 | 4-amidino-2-fluoro-phenyl | n-butyloxycarbonyl | OMe | 466 |
| 614 | 4-piperidinyl | n-butyloxycarbonyl | OMe | 412 |
| 615 | 4-piperidinylmethyl | n-butyloxycarbonyl | OMe | 426 |
| 616 | 4-piperidinylpropyl | n-butyloxycarbonyl | OMe | 454 |
| 617 | 4-quanidinophenyl | n-butyloxycarbonyl | OH | 449 |
| 618 | 4-amidinophenylmethyl | benzyloxycarbonyl | OMe | |
| 619 | 4-amidinophenylmethyl | benzyloxycarbonyl | OH | |
| 220 | 4-amidinophenylmethyl | n-butyloxycarbonyl | OMe | |
| 621 | 4-amidinophenylmethyl | n-butyloxycarbonyl | OH | |
| 622 | 4-amidinophenylmethyl | cyclopropylethoxy carbonyl | OMe | |
| 623 | 4-amidinophenylmethyl | cyclopropylethoxy carbonyl | OH | |
| 624 | 4-amidinophenylmethyl | 4-methylphenylsulfonyl | OMe | |
| 625 | 4-amidinophenylmethyl | 4-methylphenylsulfonyl | OH | 488 |
| 626 | 4-amidinophenylmethyl | 3-methylphenylsulfonyl | OMe | |
| 627 | 4-amidinophenylmethyl | 3-methylphenylsulfonyl | OH | |
| 628 | 4-amidinophenylmethyl | n-butylsulfonyl | OMe | |
| 629 | 4-amidinophenylmethyl | n-butylsulfonyl | OH | |
| 630 | 4-amidinophenylmethoxy | benzyloxycarbonyl | OMe | |
| 631 | 4-amidinophenylmethoxy | benzyloxycarbonyl | OH | |
| 632 | 4-amidinophenylmethoxy | n-butyloxycarbonyl | OMe | |
| 633 | 4-amidinophenylmethoxy | n-butyloxycarbonyl | OH | |
| 634 | 4-amidinophenylmethoxy | cyclopropylethoxy carbonyl | OMe | |
| 635 | 4-amidinophenylmethoxy | cyclopropylethoxy carbonyl | OH | |
| 636 | 4-amidinophenylmethoxy | 4-methylphenylsulfonyl | OMe | |
| 637 | 4-amidinophenylmethoxy | 4-methylphenylsulfonyl | OH | |
| 638 | 4-amidinophenylmethoxy | 3-methylphenylsulfonyl | OMe | |
| 639 | 4-amidinophenylmethoxy | 3-methylphenylsulfonyl | OH | |
| 640 | 4-amidinophenylmethoxy | n-butylsulfonyl | OMe | |
| 641 | 4-amidinophenylmethoxy | n-butylsulfonyl | OH | |
| 642 | 4-amidinophenyl | 5-chloro-1,3-dimethyl-4-pyrazolyl | OMe | 526 |
| 643 | 4-amidinophenyl | 1-methylimidazol-4-ylsulfonyl | OH | 478 |
| 644 | 4-amidinophenyl | 3,5-dimethyl-1,3-thioimidazole-2-ylsulfonyl | OH | 509 |
| 645 | N-t-butyloxycarbonyl-4-amidinophenyl | 5-(2-pyridinyl)-2-thienylsulfonyl | OMe | 671 |
| 646 | N-t-butyloxycarbonyl-4-amidinophenyl | 3,5-dimethyl-1,3 thioimidazole-2-ylsulfonyl | OMe | 623 |
| 647 | N-t-butyloxycarbonyl-4-amidinophenyl TFA salt, 5(R),N²(S) isomer | 3,5-dimethylisoxazol-4-ylsulfonyl | OMe | 607 |

TABLE 2B

| Example Number | R¹-V | R$^{5a}$ | R$^{16}$ | Y | MS (M + H)$^+$ |
|---|---|---|---|---|---|
| 651 | 4-amidinophenyl | methyl | benzyloxycarbony | OMe | 496 |
| 652 | 4-amidinophenyl | methyl | n-butyloxycarbony | OMe | |
| 653 | 4-amidinophenyl | methyl | 3-methylphenylsulfonyl | OMe | |
| 654 | 4-amidinophenyl | methyl | benzyloxycarbonyl | OH | |
| 655 | 4-amidinophenyl | methyl | n-butyloxycarbonyl | OH | |
| 656 | 4-amidinophenyl | methyl | 3-methylphenylsulfonyl | OH | |
| 657 | 4-amidinophenyl | methyl | 4-methylphenylsulfonyl | OH | |
| 658 | 4-amidinophenyl | methyl | 4-methylphenylsulfonyl | OMe | |
| 659 | 4-amidinophenyl | methyl | n-butylsulfonyl | OH | |
| 660 | 4-amidinophenyl | methyl | n-butylsulfonyl | OMe | |

TABLE 2C

| Example Number | R¹-V | R$^{16}$ | R$^{17}$ | Y | MS (M + H)$^+$ |
|---|---|---|---|---|---|
| 661 | 4-amidinophenyl | benzyloxycarbonyl | methyl | OMe | |
| 662 | 4-amidinophenyl | benzyloxycarbonyl | methyl | OH | |
| 663 | 4-amidinophenyl | n-butyloxycarbonyl | methyl | OMe | |
| 664 | 4-amidinophenyl | n-butyloxycarbonyl | methyl | OH | |
| 665 | 4-amidinophenyl | 3-methylphenylsulfonyl | methyl | OMe | |
| 666 | 4-amidinophenyl | 3-methylphenylsulfonyl | methyl | OH | 502 |
| 667 | 4-amidinophenyl | 4-methylphenylsulfonyl | methyl | OMe | |
| 668 | 4-amidinophenyl | 4-methylphenylsulfonyl | methyl | OH | |
| 669 | 4-amidinophenyl | n-butylsulfonyl | methyl | OMe | |
| 670 | 4-amidinophenyl | n-butylsulfonyl | methyl | OH | |

TABLE 2D

| Example Number | R¹—V | R$^{16}$ | Y | MS (M + H)$^+$ |
|---|---|---|---|---|
| 701 | 4-amidinophenyl | benzyloxycarbonyl | OH | |
| 702 | 4-amidinophenyl | t-butyloxycarbonyl | OH | |
| 703 | 4-amidinophenyl | n-butyloxycarbonyl | OH | |
| 704 | 4-amidinophenyl | ethyloxycarbonyl | OH | |
| 705 | 4-amidinophenyl | methyloxycarbonyl | OH | |
| 706 | 4-amidinophenyl | phenylethylcarbonyl | OH | |
| 707 | 4-amidinophenyl | 2,2-dimethyl-propylcarbonyl | OH | |
| 708 | 4-amidinophenyl | n-pentylcarbonyl | OH | |
| 709 | 4-amidinophenyl | n-butylcarbonyl | OH | |
| 710 | 4-amidinophenyl | propionyl | OH | |
| 711 | 4-amidinophenyl | acetyl | OH | |
| 712 | 4-amidinophenyl | methylsulfonyl | OH | |
| 713 | 4-amidinophenyl | ethylsulfonyl | OH | |
| 714 | 4-amidinophenyl | n-butylsulfonyl | OH | |
| 715 | 4-amidinophenyl | phenylsulfonyl | OH | |
| 716 | 4-amidinophenyl | 4-methylphenyl-sulfonyl | OH | |
| 717 | 4-amidinophenyl | benzylsulfonyl | OH | 488 |
| 718 | 4-amidinophenyl | 2-pyridylcarbonyl | OH | |
| 719 | 4-amidinophenyl | 3-pyridylcarbonyl | OH | |
| 720 | 4-amidinophenyl | 4-pyridylcarbonyl | OH | |
| 721 | 4-amidinophenyl | 2-pyridylmethyl-carbonyl | | |

TABLE 2D-continued

| Example Number | R¹—V | R$^{16}$ | Y | MS (M + H)$^+$ |
|---|---|---|---|---|
| 722 | 4-amidinophenyl | 3-pyridylmethylcarbonyl | OH | |
| 723 | 4-amidinophenyl | 4-pyridylmethylcarbonyl | OH | |
| 724 | 4-amidinophenyl | 2-pyridylmethoxycarbonyl | OH | |
| 725 | 4-amidinophenyl | 3-pyridylmethoxycarbonyl | OH | |
| 726 | 4-amidinophenyl | 4-pyridylmethoxycarbonyl | OH | |
| 727 | 4-amidinophenyl | benzyloxycarbonyl | OMe | 480 |
| 728 | 4-amidinophenyl | t-butyloxycarbonyl | OMe | |
| 729 | 4-amidinophenyl | n-butyloxycarbonyl | OMe | 446 |
| 730 | 4-amidinophenyl | ethyloxycarbonyl | OMe | |
| 731 | 4-amidinophenyl | methyloxycarbonyl | OMe | |
| 732 | 4-amidinophenyl | phenylethylcarbonyl | OMe | |
| 733 | 4-amidinophenyl | 2,2-dimethyl-propylcarbonyl | OMe | |
| 734 | 4-amidinophenyl | n-pentylcarbonyl | OMe | |
| 735 | 4-amidinophenyl | n-butylcarbonyl | OMe | |
| 736 | 4-amidinophenyl | propionyl | OMe | |
| 737 | 4-amidinophenyl | acetyl | OMe | |
| 738 | 4-amidinophenyl | methylsulfonyl | OMe | |
| 739 | 4-amidinophenyl | ethylsulfonyl | OMe | |
| 740 | 4-amidinophenyl | n-butylsulfonyl | OMe | |
| 741 | 4-amidinophenyl | phenylsulfonyl | OMe | |
| 742 | 4-amidinophenyl | 4-methylphenyl-sulfonyl | OMe | |
| 743 | 4-amidinophenyl | benzylsulfonyl | OMe | |
| 744 | 4-amidinophenyl | 2-pyridylcarbonyl | OMe | |
| 745 | 4-amidinophenyl | 3-pyridylcarbonyl | OMe | |
| 746 | 4-amidinophenyl | 4-pyridylcarbonyl | OMe | |
| 747 | 4-amidinophenyl | 2-pyridylmethylcarbonyl | OMe | |
| 748 | 4-amidinophenyl | 3-pyridylmethylcarbonyl | OMe | |
| 749 | 4-amidinophenyl | 4-pyridylmethylcarbonyl | OMe | |
| 750 | 4-amidinophenyl | 2-pyridylmethoxycarbonyl | OMe | |
| 751 | 4-amidinophenyl | 3-pyridylmethoxycarbonyl | OMe | |
| 752 | 4-amidinophenyl | 4-pyridylmethoxycarbonyl | OMe | |
| 753 | 4-piperidinylethyl | benzylcarbonyl | OMe | |
| 754 | 4-(BOCamidino)phenyl | benzyloxycarbonyl | OMe | |
| 755 | 4-(BOCamidino)phenyl | n-butyloxycarbonyl | OMe | |
| 756 | 4-amidinophenyl | 1-naphthylsulfonyl | OMe | |
| 757 | 4-amidinophenyl | 2-naphthylsulfonyl | OMe | |
| 758 | 4-piperidinylethyl | n-butyloxycarbonyl | OMe | 440 |
| 759 | 4-amidinophenyl | 2-thienylsulfonyl | OMe | |
| 760 | 4-amidinophenyl | 3-methylphenyl-sulfonyl | OMe | |
| 761 | 4-amidinophenyl | 4-fluorophenyl-sulfonyl | OMe | |
| 762 | 4-amidinophenyl | 4-methoxyphenyl-sulfonyl | OMe | |
| 763 | 4-amidinophenyl | n-propylsulfonyl | OMe | |
| 764 | 4-amidinophenyl | 2-phenylethyl-sulfonyl | OMe | |
| 765 | 4-amidinophenyl | 4-isopropylphenyl-sulfonyl | OMe | |
| 766 | 4-amidinophenyl | 3-phenylpropyl-sulfonyl | OMe | |
| 767 | 4-amidinophenyl | 3-pyridylsulfonyl | OMe | |
| 768 | 4-amidinophenyl | 2-pyridylsulfonyl | OMe | |
| 769 | 4-amidinophenyl | n-butylamino-sulfonyl | OMe | |
| 770 | 4-amidinophenyl | i-butylamino-sulfonyl | OMe | |
| 771 | 4-amidinophenyl | t-butylamino-sulfonyl | OMe | |
| 772 | 4-amidinophenyl | i-propylamino-sulfonyl | OMe | |
| 773 | 4-amidinophenyl | cyclohexylamino-sulfonyl | OMe | |
| 774 | 4-amidinophenyl | phenylamino-sulfonyl | OMe | |
| 775 | 4-amidinophenyl | benzylamino-sulfonyl | OMe | |
| 776 | 4-amidinophenyl | dimethylamino-sulfonyl | OMe | |
| 777 | 2-fluoro-4-amidinophenyl | 3-methylphenyl-sulfonyl | OMe | |
| 778 | 5-amidino-2-pyridyl | n-butyloxycarbonyl | OMe | |
| 779 | 5-amidino-2-pyridyl | 3-methylphenyl-sulfonyl | OMe | |
| 780 | 6-amidino-3-pyridyl | n-butyloxycarbonyl | OMe | |
| 781 | 6-amidino-3-pyridyl | 3-methylphenyl-sulfonyl | OMe | |
| 782 | 4-amidinophenyl | phenylamino-carbonyl | OMe | |
| 783 | 4-amidinophenyl | benzylamino-carbonyl | OMe | |
| 784 | 4-amidinophenyl | n-butylamino-carbonyl | OMe | |
| 785 | 4-amidinophenyl | n-hexyloxycarbonyl | OMe | |
| 786 | 4-amidinophenyl | n-hexyloxycarbonyl | OH | |
| 787 | 4-amidinophenyl | isobutyloxycarbonyl | OMe | |
| 788 | 4-amidinophenyl | isobutyloxycarbonyl | OH | |
| 789 | 4-amidinophenyl | 2-cyclopropyl-ethoxycarbonyl | OMe | |
| 790 | 4-amidinophenyl | 2-cyclopropyl-ethoxycarbonyl | OH | |
| 791 | 4-amidinophenyl | 2-cyclopentyl-ethoxycarbonyl | OMe | |
| 792 | 4-amidinophenyl | 2-cyclopentyl-ethoxycarbonyl | OH | |
| 793 | 4-amidinophenyl | n-propylsulfonyl | OMe | |
| 794 | 4-amidinophenyl | 2-methylphenyl-sulfonyl | OMe | |
| 795 | 4-amidinophenyl | 2-benzothienyl-sulfonyl | OMe | |
| 796 | 4-amidinophenyl | 2-benzothienyl-sulfonyl | OMe | |
| 797 | 4-amidinophenyl | 2,2,5,7,8-pentamethyl 3,4-dihydro-2Hbenzo-pyran-6-ylsulfonyl | OH | |
| 798 | 4-amidinophenyl | 3-methylphenyl-sulfonyl | OH | 486 |

TABLE 2E

| Example Number | R¹—V | R¹⁶ | Y | MS (M + H)⁺ |
|---|---|---|---|---|
| 801 | 4-amidinophenyl | benzyloxycarbonyl | OH | |
| 802 | 4-amidinophenyl | t-butyloxycarbonyl | OH | |
| 803 | 4-amidinophenyl | n-butyloxycarbonyl | OH | |
| 804 | 4-amidinophenyl | ethyloxycarbonyl | OH | |
| 805 | 4-amidinophenyl | methyloxycarbonyl | OH | |
| 806 | 4-amidinophenyl | phenylethylcarbonyl | OH | |
| 807 | 4-amidinophenyl | 2,2-dimethyl-propylcarbonyl | OH | |
| 808 | 4-amidinophenyl | n-pentylcarbonyl | OH | |
| 809 | 4-amidinophenyl | n-butylcarbonyl | OH | |
| 810 | 4-amidinophenyl | propionyl | OH | |
| 811 | 4-amidinophenyl | acetyl | OH | |
| 812 | 4-amidinophenyl | methylsulfonyl | OH | |
| 813 | 4-amidinophenyl | ethylsulfonyl | OH | |
| 814 | 4-amidinophenyl | n-butylsulfonyl | OH | |
| 815 | 4-amidinophenyl | phenylsulfonyl | OH | |
| 816 | 4-amidinophenyl | 4-methylphenyl-sulfonyl | OH | 488 |
| 817 | 4-amidinophenyl | benzylsulfonyl | OH | |
| 818 | 4-amidinophenyl | 2-pyridylcarbonyl | OH | |
| 819 | 4-amidinophenyl | 3-pyridylcarbonyl | OH | |
| 820 | 4-amidinophenyl | 4-pyridylcarbonyl | OH | |
| 821 | 4-amidinophenyl | 2-pyridylmethyl-carbonyl | OH | |
| 822 | 4-amidinophenyl | 3-pyridylmethyl-carbonyl | OH | |
| 823 | 4-amidinophenyl | 4-pyridylmethyl-carbonyl | OH | |
| 824 | 4-amidinophenyl | 2-pyridylmethoxy-carbonyl | OH | |
| 825 | 4-amidinophenyl | 3-pyridylmethoxy-carbonyl | OH | |
| 826 | 4-amidinophenyl | 4-pyridylmethoxy-carbonyl | OH | |
| 827 | 4-amidinophenyl | benzyloxycarbonyl | OMe | |
| 828 | 4-amidinophenyl | t-butyloxycarbonyl | OMe | |
| 829 | 4-amidinophenyl | n-butyloxycarbonyl | OMe | 448 |
| 830 | 4-amidinophenyl | ethyloxycarbonyl | OMe | |
| 831 | 4-amidinophenyl | methyloxycarbonyl | OMe | |
| 832 | 4-amidinophenyl | phenylethylcarbonyl | OMe | |
| 833 | 4-amidinophenyl | 2,2-dimethyl-propylcarbonyl | OMe | |
| 834 | 4-amidinophenyl | n-pentylcarbonyl | OMe | |
| 835 | 4-amidinophenyl | n-butylcarbonyl | OMe | |
| 836 | 4-amidinophenyl | propionyl | OMe | |
| 837 | 4-amidinophenyl | acetyl | OMe | |
| 838 | 4-amidinophenyl | methylsulfonyl | OMe | |
| 839 | 4-amidinophenyl | ethylsulfonyl | OMe | |
| 840 | 4-amidinophenyl | n-butylsulfonyl | OMe | |
| 841 | 4-amidinophenyl | phenylsulfonyl | OMe | |
| 842 | 4-amidinophenyl | 4-methylphenyl-sulfonyl | OMe | |
| 843 | 4-amidinophenyl | benzylsulfonyl | OMe | |
| 844 | 4-amidinophenyl | 2-pyridylcarbonyl | OMe | |
| 845 | 4-amidinophenyl | 3-pyridylcarbonyl | OMe | |
| 846 | 4-amidinophenyl | 4-pyridylcarbonyl | OMe | |
| 847 | 4-amidinophenyl | 2-pyridylmethyl-carbonyl | OMe | |
| 848 | 4-amidinophenyl | 3-pyridylmethyl-carbonyl | OMe | |
| 849 | 4-amidinophenyl | 4-pyridylmethyl-carbonyl | OMe | |
| 850 | 4-amidinophenyl | 2-pyridylmethoxy-carbonyl | OMe | |
| 851 | 4-amidinophenyl | 3-pyridylmethoxy-carbonyl | OMe | |
| 852 | 4-amidinophenyl | 4-pyridylmethoxy-carbonyl | OMe | |
| 853 | 4-piperidinylethyl | benzylcarbonyl | OMe | |
| 854 | 4-(BOCamidino)phenyl | benzyloxycarbonyl | OMe | |
| 855 | 4-(BOCamidino)phenyl | n-butyloxycarbonyl | OMe | |
| 856 | 4-amidinophenyl | 1-naphthylsulfonyl | OMe | |
| 857 | 4-amidinophenyl | 2-naphthylsulfonyl | OMe | |
| 858 | 4-piperidinylethyl | n-butyloxycarbonyl | OMe | |
| 859 | 4-amidinophenyl | 2-thienylsulfonyl | OMe | |
| 860 | 4-amidinophenyl | 3-methylphenyl-sulfonyl | OMe | |
| 861 | 4-amidinophenyl | 4-fluorophenyl-sulfonyl | OMe | |
| 862 | 4-amidinophenyl | 4-methoxyphenyl-sulfonyl | OMe | |
| 863 | 4-amidinophenyl | n-propylsulfonyl | OMe | |
| 864 | 4-amidinophenyl | 2-phenylethyl-sulfonyl | OMe | |
| 865 | 4-amidinophenyl | 4-isopropylphenyl-sulfonyl | OMe | |
| 866 | 4-amidinophenyl | 3-phenylpropyl-sulfonyl | OMe | |
| 867 | 4-amidinophenyl | 3-pyridylsulfonyl | OMe | |
| 868 | 4-amidinophenyl | 2-pyridylsulfonyl | OMe | |
| 869 | 4-amidinophenyl | n-butylamino-sulfonyl | OMe | |
| 870 | 4-amidinophenyl | i-butylamino-sulfonyl | OMe | |
| 871 | 4-amidinophenyl | t-butylamino-sulfonyl | OMe | |
| 872 | 4-amidinophenyl | i-propylamino-sulfonyl | OMe | |
| 873 | 4-amidinophenyl | cyclohexylamino-sulfonyl | OMe | |
| 874 | 4-amidinophenyl | phenylamino-sulfonyl | OMe | |
| 875 | 4-amidinophenyl | benzylamino-sulfonyl | OMe | |
| 876 | 4-amidinophenyl | dimethylamino-sulfonyl | OMe | |
| 877 | 2-fluoro-4-amidino-phenyl | 3-methylphenyl-sulfonyl | OMe | |
| 878 | 5-amidino-2-pyridyl | n-butyloxycarbonyl | OMe | |
| 879 | 5-amidino-2-pyridyl | 3-methylphenyl-sulfonyl | OMe | |
| 880 | 6-amidino-3-pyridyl | n-butyloxycarbonyl | OMe | |
| 881 | 6-amidino-3-pyridyl | 3-methylphenyl-sulfonyl | OMe | |
| 882 | 4-amidinophenyl | phenylamino-carbonyl | OMe | |
| 883 | 4-amidinophenyl | benzylamino-carbonyl | OMe | |
| 884 | 4-amidinophenyl | n-butylamino-carbonyl | OMe | |
| 885 | 4-amidinophenyl | n-hexyloxycarbonyl | OMe | |
| 886 | 4-amidinophenyl | n-hexyloxycarbonyl | OH | |
| 887 | 4-amidinophenyl | isobutyloxycarbonyl | OMe | |
| 888 | 4-amidinophenyl | isobutyloxycarbonyl | OH | |
| 889 | 4-amidinophenyl | 2-cyclopropyl-ethoxycarbonyl | OMe | |
| 890 | 4-amidinophenyl | 2-cyclopropyl-ethoxycarbonyl | OH | |
| 891 | 4-amidinophenyl | 2-cyclopentyl-ethoxycarbonyl | OMe | |
| 892 | 4-amidinophenyl | 2-cyclopentyl-ethoxycarbonyl | OH | |

TABLE 2E-continued

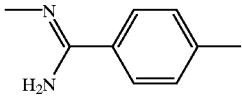

| Example Number | R¹—V | R¹⁶ | Y | MS (M + H)⁺ |
|---|---|---|---|---|
| 893 | 4-amidinophenyl | n-propylsulfonyl | OMe | |
| 894 | 4-amidinophenyl | 2-methylphenyl sulfonyl | OMe | |
| 895 | 4-amidinophenyl | 2-benzothienyl-sulfonyl | OMe | |
| 896 | 4-amidinophenyl | 2-benzothienyl sulfonyl | OMe | |
| 897 | 4-amidinophenyl | 2,2,5,7,8-penta-methyl 3,4-dihydro-2Hbenzo-pyran-6-ylsulfonyl | OH | |

TABLE 3

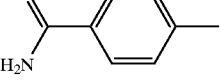

(VII)

| Ex. No. | R² | R¹—V | —F—E< | p | n' | Y | MS (M + H)⁺ |
|---|---|---|---|---|---|---|---|
| 171 | H | 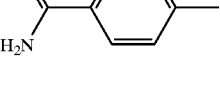 | —C(=O)—N< | 1 | 1 | OH | |
| 172 | H | 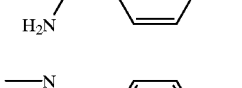 | —C(=O)—N< | 1 | 2 | OH | |
| 173 | H |  | —C(H₂)—N< | 1 | 1 | OH | |
| 174 | H | 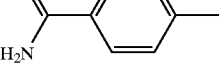 | —C(H₂)—N< | 1 | 2 | OH | |
| 175 | H | 4-amidinophenyl | —C(H)=C< | 1 | 1 | OH | |
| 176 | H | 4-amidinophenyl | —C(H)=C< | 1 | 2 | OH | |

TABLE 3-continued
(VII)
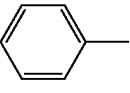
| Ex. No. | R² | R¹—V | —F—E< | p | n' | Y | MS (M + H)⁺ |
|---|---|---|---|---|---|---|---|
| 177 | H | 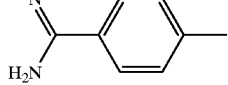 | —C(=O)—N< | 2 | 1 | OH | |
| 178 | H | 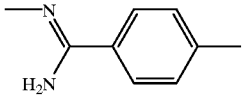 | —C(=O)—N< | 2 | 2 | OH | |
| 179 | H | 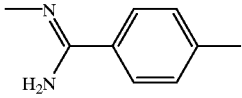 | —C(H₂)—N< | 2 | 1 | OH | |
| 180 | H | 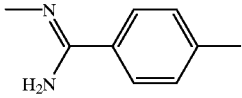 | —C(H₂)—N< | 2 | 2 | OH | |
| 181 | H | 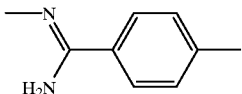 | —C(H)=C< | 2 | 1 | OH | |
| 182 | H | 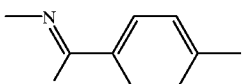 | —C(H)=C< | 2 | 2 | OH | |
| 183 | H | 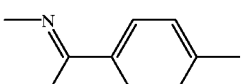 | —C(=O)—N< | 3 | 1 | OH | |
| 184 | H | 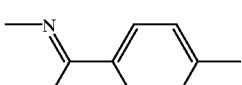 | —C(=O)—N< | 3 | 2 | OH | |
| 185 | H | 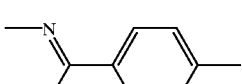 | —C(H₂)—N< | 3 | 1 | OH | |
| 186 | H | | —C(H₂)—N< | 3 | 2 | OH | |
| 187 | H | 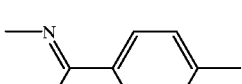 | —C(H)=C< | 3 | 1 | OH | |

TABLE 3-continued (VII)

| Ex. No. | R² | R¹—V | —F—E< | p | n' | Y | MS (M + H)⁺ |
|---|---|---|---|---|---|---|---|
| 188 | H | 4-(H₂N-C(=NH)-N<)-phenyl (amidine) | —C(H)=C< | 3 | 2 | OH | |
| 189 | H | N-methylpiperidin-4-yl-ethyl | —C(=O)—N< | 1 | 1 | OH | 338 |
| 190 | H | N-methylpiperidin-4-yl-ethyl | —C(=O)—N< | 1 | 2 | OH | 352 |
| 191 | H | N-methylpiperidin-4-yl-ethyl | —C(H₂)—N< | 1 | 1 | OH | |
| 192 | H | N-methylpiperidin-4-yl-ethyl | —C(H₂)—N< | 1 | 2 | OH | |
| 193 | H | N-methylpiperidin-4-yl-ethyl | —C(H)=C< | 1 | 1 | OH | |
| 194 | H | N-methylpiperidin-4-yl-ethyl | —C(H)=C< | 1 | 2 | OH | |
| 195 | H | N-methylpiperidin-4-yl-ethyl | —C(=O)—N< | 2 | 1 | OH | |
| 196 | H | N-methylpiperidin-4-yl-ethyl | —C(=O)—N< | 2 | 2 | OH | |
| 197 | H | N-methylpiperidin-4-yl-ethyl | —C(H₂)—N< | 2 | 1 | OH | |
| 198 | H | N-methylpiperidin-4-yl-ethyl | —C(H₂)—N< | 2 | 2 | OH | |
| 199 | H | N-methylpiperidin-4-yl-ethyl | —C(H)=C< | 2 | 1 | OH | |

TABLE 3-continued
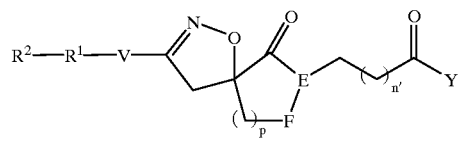
(VII)
| Ex. No. | R² | R¹—V | —F—E< | p | n' | Y | MS (M + H)⁺ |
|---|---|---|---|---|---|---|---|
| 200 | H | ![piperidine] | —C(H)=C< | 2 | 2 | OH | |
| 201 | H | ![piperidine] | —C(=O)—N< | 3 | 1 | OH | |
| 202 | H | ![piperidine] | —C(=O)—N< | 3 | 2 | OH | |
| 203 | H | ![piperidine] | —C(H₂)—N< | 3 | 1 | OH | |
| 204 | H | ![piperidine] | —C(H₂)—N< | 3 | 2 | OH | |
| 205 | H | ![piperidine] | —C(H)=C< | 3 | 1 | OH | |
| 206 | H | ![piperidine] | —C(H)=C< | 3 | 2 | OH | |
| 207 | Boc | ![piperidine] | —C(=O)—N< | 1 | 1 | OH | |
| 208 | Cbz | ![piperidine] | —C(=O)—N< | 1 | 1 | OH | |
| 209 | H | ![piperidine] | —C(=O)—N< | 1 | 1 | —OCH₂OC(=O)O-cyclohexyl | |
| 210 | H | ![piperidine] | —C(=O)—N< | 1 | 1 | —OCH₂OC(=O)Me | |

TABLE 3-continued (VII)

| Ex. No. | R² | R¹—V | —F—E< | p | n' | Y | MS (M + H)⁺ |
|---|---|---|---|---|---|---|---|
| 211 | H | 1-methyl-4-propylpiperidine | —C(=O)—N< | 1 | 1 | (4-methyl-5-(propan-2-yl)-2-oxo-1,3-dioxol-4-yl)methoxy | |
| 212 | H | 1-methyl-4-propylpiperidine | —C(=O)—N< | 1 | 1 | OCH₂C(=O)OEt | |
| 213 | H | 1-methyl-4-propylpiperidine | —C(=O)—N< | 1 | 1 | OCH₂CH₂N(Et)₂ | |
| 214 | H | 4-amidinophenyl | —C(=O)—N< | 1 | 1 | OEt | |
| 215 | H | 4-amidinophenyl | —C(=O)—N< | 1 | 2 | OEt | |
| 216 | H | 4-amidinophenyl | —C(H₂)—N< | 1 | 1 | OEt | |
| 217 | H | 4-amidinophenyl | —C(H₂)—N< | 1 | 2 | OEt | |
| 218 | H | 4-amidinophenyl | —C(H)=C< | 1 | 1 | OEt | |
| 219 | H | 4-amidinophenyl | —C(H)=C< | 1 | 2 | OEt | |
| 220 | H | 4-amidinophenyl | —C(=O)—N< | 2 | 1 | OEt | |

TABLE 3-continued
(VII)
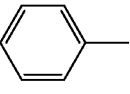
| Ex. No. | R² | R¹—V | —F—E< | p | n' | Y | MS (M + H)⁺ |
|---|---|---|---|---|---|---|---|
| 221 | H | 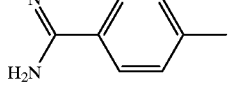 | —C(=O)—N< | 2 | 2 | OEt | |
| 222 | H | 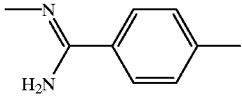 | —C(H₂)—N< | 2 | 1 | OEt | |
| 223 | H | 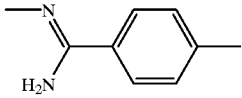 | —C(H₂)—N< | 2 | 2 | OEt | |
| 224 | H | 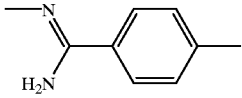 | —C(H)=C< | 2 | 1 | OEt | |
| 225 | H | 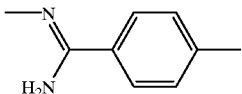 | —C(H)=C< | 2 | 2 | OEt | |
| 226 | H | 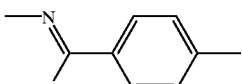 | —C(=O)—N< | 3 | 1 | OEt | |
| 227 | H | 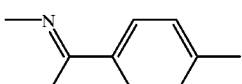 | —C(=O)—N< | 3 | 2 | OEt | |
| 228 | H | 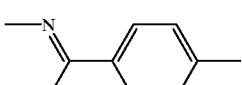 | —C(H₂)—N< | 3 | 1 | OEt | |
| 229 | H | 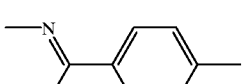 | —C(H₂)—N< | 3 | 2 | OEt | |
| 230 | H | 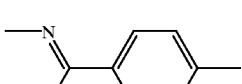 | —C(H)=C< | 3 | 1 | OEt | |
| 231 | H |  | —C(H)=C< | 3 | 2 | OEt | |

TABLE 3-continued (VII)

$$R^2-R^1-V-\text{[spiro isoxazoline structure]}-E-(\phantom{x})_{n'}-Y$$
$$(\phantom{x})_p-F$$

| Ex. No. | R² | R¹—V | —F—E< | p | n' | Y | MS (M + H)⁺ |
|---|---|---|---|---|---|---|---|
| 232 | H | N-methylpiperidin-4-yl-propyl | —C(=O)—N< | 1 | 1 | OEt | |
| 233 | H | N-methylpiperidin-4-yl-propyl | —C(=O)—N< | 1 | 2 | OEt | |
| 234 | H | N-methylpiperidin-4-yl-propyl | —C(H₂)—N< | 1 | 1 | OEt | |
| 235 | H | N-methylpiperidin-4-yl-propyl | —C(H₂)—N< | 1 | 2 | OEt | |
| 236 | H | N-methylpiperidin-4-yl-propyl | —C(H)=C< | 1 | 1 | OEt | |
| 237 | H | N-methylpiperidin-4-yl-propyl | —C(H)=C< | 1 | 2 | OEt | |
| 238 | H | N-methylpiperidin-4-yl-propyl | —C(=O)—N< | 2 | 1 | OEt | |
| 239 | H | N-methylpiperidin-4-yl-propyl | —C(=O)—N< | 2 | 2 | OEt | |
| 240 | H | N-methylpiperidin-4-yl-propyl | —C(H₂)—N< | 2 | 1 | OEt | |
| 241 | H | N-methylpiperidin-4-yl-propyl | —C(H₂)—N< | 2 | 2 | OEt | |
| 242 | H | N-methylpiperidin-4-yl-propyl | —C(H)=C< | 2 | 1 | OEt | |
| 243 | H | N-methylpiperidin-4-yl-propyl | —C(H)=C< | 2 | 2 | OEt | |

TABLE 3-continued (VII)

| Ex. No. | R² | R¹—V | —F—E< | p | n' | Y | MS (M + H)⁺ |
|---|---|---|---|---|---|---|---|
| 244 | H | N-methylpiperidine-4-propyl | —C(=O)—N< | 3 | 1 | OEt | |
| 245 | H | N-methylpiperidine-4-propyl | —C(=O)—N< | 3 | 2 | OEt | |
| 246 | H | N-methylpiperidine-4-propyl | —C(H₂)—N< | 3 | 1 | OEt | |
| 247 | H | N-methylpiperidine-4-propyl | —C(H₂)—N< | 3 | 2 | OEt | |
| 248 | H | N-methylpiperidine-4-propyl | —C(H)=C< | 3 | 1 | OEt | |
| 249 | H | N-methylpiperidine-4-propyl | —C(H)=C< | 3 | 2 | OEt | |
| 250 | Boc | N-methylpiperidine-4-propyl | —C(=O)—N< | 1 | 1 | OEt | |
| 251 | Cbz | N-methylpiperidine-4-propyl | —C(=O)—N< | 1 | 1 | OEt | |
| 373 | H | N-methylpiperidine-4-butyl | —C(=O)—N< | 1 | 2 | OH | 366 |

TABLE 4

(VIII)

Structure: R²-O-R¹ª attached to isoxazoline ring connected to phenyl-Z¹-CH₂-C(=O)-Y

| Example Number | R² | R¹ª | Z¹ | Y |
|---|---|---|---|---|
| 252 | H | N-methylpiperidin-4-yl | CH₂ | OH |
| 253 | H | —NHCH₂)₂— | CH₂ | OH |
| 254 | H | —NHCH₂)₃— | CH₂ | OH |
| 255 | H | N-methylpiperidin-4-yl | O | OH |
| 256 | H | —NHCH₂)₂— | O | OH |
| 257 | H | —NHCH₂)₃— | O | OH |
| 258 | Boc | N-methylpiperidin-4-yl | CH₂ | OH |
| 259 | Cbz | N-methylpiperidin-4-yl | CH₂ | OH |
| 260 | H | N-methylpiperidin-4-yl | CH₂ | —OCH₂OC(=O)O-cyclohexyl |
| 261 | H | N-methylpiperidin-4-yl | CH₂ | —OCH₂OC(=O)Me |
| 262 | H | N-methylpiperidin-4-yl | CH₂ | —OCH₂-(4-t-butyl-5-methyl-1,3-dioxol-2-one) |
| 263 | H | N-methylpiperidin-4-yl | CH₂ | —OCH₂C(=O)OEt |
| 264 | H | N-methylpiperidin-4-yl | CH₂ | —OCH₂CH₂N(Et)₂ |
| 265 | H | N-methylpiperidin-4-yl | CH₂ | OEt |

TABLE 4-continued (VIII) Structure: R²-R¹ᵃ-O-CH₂-[isoxazoline ring with N-O]-C₆H₄-Z¹-CH₂-C(=O)-Y

| Example Number | R² | R¹ᵃ | Z¹ | Y |
|---|---|---|---|---|
| 266 | H | 1-methyl-piperidin-4-yl | CH₂ | OEt |
| 267 | H | 1-methyl-piperidin-4-yl | CH₂ | OEt |
| 268 | H | —NH(CH₂)₂— | CH₂ | OEt |
| 269 | H | —NH(CH₂)₃— | CH₂ | OEt |
| 270 | H | 1-methyl-piperidin-4-yl | O | OEt |
| 271 | H | —NH(CH₂)₂— | O | OEt |
| 272 | H | —NH(CH₂)₃— | O | OEt |
| 273 | Boc | 1-methyl-piperidin-4-yl | CH₂ | OEt |
| 274 | Cbz | 1-methyl-piperidin-4-yl | CH₂ | OEt |

TABLE 5

Structures: amidinophenyl-isoxazoline-CH₂-C(=O)-R (two regioisomers)

| Example Number | R | Y | MS (ESI) (M + H)⁺ |
|---|---|---|---|
| 375 | 1-methyl-piperidin-2-yl-CH₂C(=O)Y | OH | 373 |
| 376 | 1-methyl-pyrrolidin-2-yl-CH₂C(=O)Y | OH | |
| 377 | 1-methyl-azepan-2-yl-CH₂C(=O)Y | OH | 387 |
| 378 | 1-methyl-5-oxo-pyrrolidin-2-yl-CH₂C(=O)Y | OH | |

TABLE 5-continued

Structure: H₂N-C(=NH)-C₆H₄-[4,5-dihydroisoxazol-3-yl]-CH₂-C(=O)-R

| Example Number | R | Y | MS (ESI) (M + H)⁺ |
|---|---|---|---|
| 379 | 1-methyl-6-(CH₂C(=O)Y)-piperidin-2-one | OH | |
| 380 | 1-methyl-7-(CH₂C(=O)Y)-azepan-2-one | OH | |
| 381 | 1-methyl-3-(CH₂C(=O)Y)-piperazin-2-one (NH) | OH | |
| 382 | 1-methyl-5-(CH₂C(=O)Y)-pyrazolidin-3-one | OH | |
| 383 | 2-methyl-1-(CH₂C(=O)Y)-tetrahydropyridazin-3-one | OH | 415 |
| 384 | 2-methyl-1-(CH₂C(=O)Y)-1,2-diazepan-3-one | OH | |
| 385 | 1-methyl-2-(CH₂C(=O)Y)-pyrazolidine | OH | |
| 386 | 1-methyl-2-(CH₂C(=O)Y)-hexahydropyridazine | OH | |
| 387 | 1-methyl-2-(CH₂C(=O)Y)-1,2-diazepane | OH | |
| 388 | 4-methyl-3-(CH₂C(=O)Y)-morpholine | OH | |
| 389 | 4-methyl-5-(CH₂C(=O)Y)-morpholin-3-one | OH | |
| 394 | 1-methyl-2-(CH₂C(=O)Y)-piperidine | OMe | 387 |
| 395 | 1-methyl-2-(CH₂C(=O)Y)-pyrrolidine | OMe | |
| 396 | 1-methyl-2-(CH₂C(=O)Y)-azepane | OMe | |
| 397 | 1-methyl-5-(CH₂C(=O)Y)-pyrrolidin-2-one | OMe | |
| 398 | 1-methyl-6-(CH₂C(=O)Y)-piperidin-2-one | OMe | |

TABLE 5-continued

Structure (left, Examples 399-406):

H₂N-C(=NH)-C₆H₄-[4,5-dihydroisoxazole]-CH₂-C(=O)-R

| Example Number | R | Y | MS (ESI) (M + H)⁺ |
|---|---|---|---|
| 399 | 1-methyl-7-(CH₂C(=O)Y)-azepan-2-one | OMe | |
| 400 | 1-methyl-3-(CH₂C(=O)Y)-piperazin-2-one | OMe | 402 |
| 401 | 1-methyl-2-(CH₂C(=O)Y)-pyrazolidin-3-one | OMe | |
| 402 | 1-methyl-2-(CH₂C(=O)Y)-tetrahydropyridazin-3-one | OMe | |
| 403 | 1-methyl-2-(CH₂C(=O)Y)-[1,2]diazepan-3-one | OMe | |
| 404 | 1-methyl-2-(CH₂C(=O)Y)-pyrazolidine | OMe | |
| 405 | 1-methyl-2-(CH₂C(=O)Y)-hexahydropyridazine | OMe | |
| 406 | 1-methyl-2-(CH₂C(=O)Y)-[1,2]diazepane | OMe | |

TABLE 5-continued

Structure (right, Examples 407-418):

H₂N-C(=NH)-[pyridyl]-[4,5-dihydroisoxazole]-CH₂-C(=O)-R

| Example Number | R | Y | MS (ESI) (M + H)⁺ |
|---|---|---|---|
| 407 | 4-methyl-3-(CH₂C(=O)Y)-morpholine | OMe | |
| 408 | 4-methyl-5-(CH₂C(=O)Y)-morpholin-2-one | OMe | |
| 413 | 1-methyl-2-(CH₂C(=O)Y)-piperidine | OEt | 401 |
| 414 | 1-methyl-2-(CH₂C(=O)Y)-pyrrolidine | OEt | |
| 415 | 1-methyl-2-(CH₂C(=O)Y)-azepane | OEt | 415 |
| 416 | 1-methyl-5-(CH₂C(=O)Y)-pyrrolidin-2-one | OEt | |
| 417 | 1-methyl-6-(CH₂C(=O)Y)-piperidin-2-one | OEt | |
| 418 | 1-methyl-7-(CH₂C(=O)Y)-azepan-2-one | OEt | |

TABLE 5-continued

Structure: H2N-C(=NH)-C6H4-[isoxazoline]-CH2-C(=O)-R

| Example Number | R | Y | MS (ESI) (M + H)+ |
|---|---|---|---|
| 419 | 4-methyl-3-oxopiperazin-2-yl-CH2-C(=O)Y (N-methylpiperazinone, YC(=O)CH2 substituent) | OEt | |
| 420 | 2-methyl-3-oxopyrazolidin-1-yl, CH2C(=O)Y | OEt | |
| 421 | 2-methyl-3-oxo-hexahydropyridazin-1-yl, CH2C(=O)Y | OEt | |
| 422 | 2-methyl-3-oxo-1,2-diazepan-1-yl, CH2C(=O)Y | OEt | |
| 423 | 2-methylpyrazolidin-1-yl, CH2C(=O)Y | OEt | |
| 424 | 2-methylhexahydropyridazin-1-yl, CH2C(=O)Y | OEt | |
| 425 | 2-methyl-1,2-diazepan-1-yl, CH2C(=O)Y | OEt | |
| 426 | 4-methylmorpholin-3-yl, CH2C(=O)Y | OEt | |

TABLE 5-continued

Structure: H2N-C(=NH)-C6H4-[isoxazoline]-CH2-C(=O)-R

| Example Number | R | Y | MS (ESI) (M + H)+ |
|---|---|---|---|
| 427 | 4-methyl-3-oxomorpholin-5-yl, CH2C(=O)Y | OEt | |
| 432 | —NHC(CH3)2—CH2C(=O)Y | OEt. | |
| 433 | —N(CH2C6H5)—(CH2)2C(=O)Y | OEt | |
| 436 | 1-methyl-2-oxopiperidin-5-yl, CH2C(=O)Y | OEt | 387 |
| 437 | 1-methylpiperidin-4-yl, CH2C(=O)Y | OEt | 387 |
| 438 | 1-methyl-4-oxopiperidin-3-yl, CH2C(=O)Y | OMe | 387 |
| 899 | 4-(carboxymethyl)piperazin-1-yl, YC(=O)CH2 | OMe | |
| 900 | 4-(carboxymethyl)piperazin-1-yl, YC(=O)CH2 | OH | |

TABLE 6

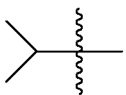

| Ex. No. | R² | R³ | R⁴ᵃ | X | Y | (M + H)⁺ ESI |
|---|---|---|---|---|---|---|
| 950 | H | H | 3-methyl-phenyl-sulfonyl | 2-fluoro-phen-1,4-diyl | OCH₃ | 521 |
| 951 | H | H | 3-methyl-phenyl-sulfonyl | 2-fluoro-phen-1,4-diyl | OH | 507 |
| 952 | 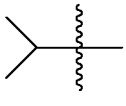 | H | 3-methyl-phenyl-sulfonyl | -phen-1,4-diyl | OCH₃ | 545 |
| 953 | 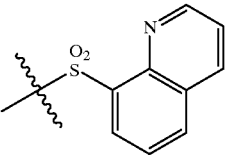 | H | 3-methyl-phenyl-sulfonyl | -phen-1,4-diyl | OH | 532 |
| 954 | H | H | n-butoxy-carbonyl | -phen-1,4-diyl | OH | 435 |
| 955 | H | H | 3-methyl-phenyl-sulfonyl | -phen-1,4-diyl | OCH₃ | 503 |
| 956 | H | H | 3-methyl-phenyl-sulfonyl | -phen-1,4-diyl | OH | 489 |
| 957 | H | H | 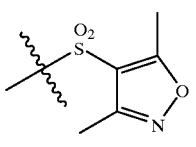 | -phen-1,4-diyl | OH | 527 |
| 958 | H | H | 4-CF₃-phenyl-sulfonyl | -phen-1,4-diyl | OH | 543 |
| 959 | H | H | 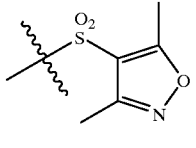 | -phen-1,4-diyl | OH | |
| 960 | o-CH₃O-benzyl | H | 3-methyl-phenyl-sulfonyl | -phen-1,4-diyl | OH | |
| 961 | o-CH₃O-benzyl | H |  | -phen-1,4-diyl | OH | |

TABLE 6-continued

| Ex. No. | R² | R³ | R⁴ᵃ | X | Y | (M + H)⁺ ESI |
|---|---|---|---|---|---|---|
| 962 | o-CH₃O-benzyl | CH₃ | 4-(3,5-dimethylisoxazolyl)sulfonyl | -phen-1,4-diyl | OH | |
| 963 | o-CH₃O-benzyl | CH₃ | 3-methyl-phenyl-sulfonyl | -phen-1,4-diyl | OH | |
| 964 | H | H | 2-fluoro-phenyl-sulfonyl | -phen-1,4-diyl | OH | 493 |
| 965 | H | H | 4-CF₃-phenyl-sulfonyl | -phen-1,4-diyl | OH | 543 |
| 966 | H | H | 4-Cl-phenyl-sulfonyl | -phen-1,4-diyl | OH | 509 |
| 967 | H | H | 2-naphthylsulfonyl | -phen-1,4-diyl | OH | 525 |
| 968 | 3-(CF₃)-benzyl | H | 4-(3,5-dimethylisoxazolyl)sulfonyl | -phen-1,4-diyl | OH | |
| 969 | 3-(CF₃)-benzyl | H | 3-methylphenylsulfonyl | -phen-1,4-diyl | OH | |
| 970 | 3-(CF₃)-benzyl | CH₃ | 3-methyl phenyl-sulfonyl | -phen-1,4-diyl | OH | |
| 971 | 3-(CF₃)-benzyl | CH₃ | 4-(3,5-dimethylisoxazolyl)sulfonyl | -phen-1,4-diyl | OH | |
| 972 | nBu- | H | 3-methyl-phenyl-sulfonyl | -phen-1,4-diyl | OH | |

TABLE 6-continued

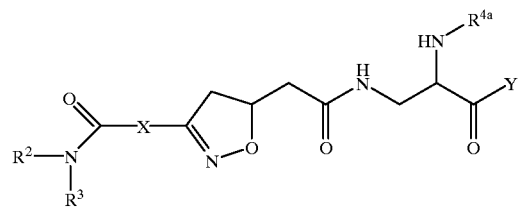

| Ex. No. | R[2] | R[3] | R[4a] | X | Y | (M + H)+ ESI |
|---|---|---|---|---|---|---|
| 973 | nBu- | H | (4-SO2-3,5-dimethylisoxazolyl-methyl) | -phen-1,4-diyl | OH | |
| 974 | nBu- | CH3 | 3-methyl-phenyl-sulfonyl | -phen-1,4-diyl | OH | |
| 975 | nBu- | CH3 | (4-SO2-3,5-dimethylisoxazolyl-methyl) | -phen-1,4-diyl | OH | |
| 976 | CH3 | CH3 | (4-SO2-3,5-dimethylisoxazolyl-methyl) | -phen-1,4-diyl | OH | |
| 977 | CH3 | CH3 | 3-methyl phenyl-sulfonyl | -phen-1,4-diyl | OH | |
| 978 | H | H | 3-methyl-phenyl-sulfonyl | 5-carboxamido pyrid-2-yl | OMe | 490 |
| 979 | H | H | 4-ethyl-phenyl-sulfonyl | -phen-1,4-diyl | OH | 503 |

TABLE 7

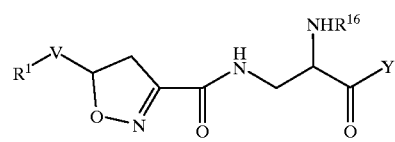

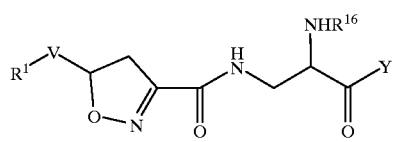

| Ex No. | R[1]-V | R[16] | Y | MS (M + H)+ |
|---|---|---|---|---|
| 980 | 4-amidinophenyl | H | OH | |
| 981 | 4-amidinophenyl | benzyloxycarbonyl | OH | |
| 982 | 4-amidinophenyl | t-butyloxycarbonyl | OH | |
| 983 | 4-amidinophenyl | n-butyloxycarbonyl | OH | |
| 984 | 4-amidinophenyl | ethyloxycarbonyl | OH | |
| 985 | 4-amidinophenyl | methyloxycarbonyl | OH | |
| 986 | 4-amidinophenyl | phenylethylcarbonyl | OH | |
| 987 | 4-amidinophenyl | 2,2-dimethyl-propylcarbonyl | OH | |
| 988 | 4-amidinophenyl | n-pentylcarbonyl | OH | |
| 989 | 4-amidinophenyl | n-butylcarbonyl | OH | |
| 990 | 4-amidinophenyl | propionyl | OH | |
| 991 | 4-amidinophenyl | acetyl | OH | |
| 992 | 4-amidinophenyl | methylsulfonyl | OH | |
| 993 | 4-amidinophenyl | ethylsulfonyl | OH | |
| 994 | 4-amidinophenyl | n-butylsulfonyl | OH | |
| 995 | 4-amidinophenyl | phenylsulfonyl | OH | |
| 996 | 4-amidinophenyl | 4-methylphenyl-sulfonyl | OH | 474 |
| 997 | 4-amidinophenyl | benzylsulfonyl | OH | |
| 998 | 4-amidinophenyl | 2-pyridylcarbonyl | OH | |
| 999 | 4-amidinophenyl | 3-pyridylcarbonyl | OH | |

TABLE 7-continued $$R^1-V \diagdown \text{[isoxazoline]} -C(=O)-NH-CH(NHR^{16})-C(=O)-Y$$

| Ex No. | R¹-V | R¹⁶ | Y | MS (M + H)⁺ |
|---|---|---|---|---|
| 1000 | 4-amidinophenyl | 4-pyridylcarbonyl | OH | |
| 1001 | 4-amidinophenyl | 2-pyridylmethyl-carbonyl | OH | |
| 1002 | 4-amidinophenyl | 3-pyridylmethyl-carbonyl | OH | |
| 1003 | 4-amidinophenyl | 4-pyridylmethyl-carbonyl | OH | |
| 1004 | 4-amidinophenyl | 2-pyridylmethoxy-carbonyl | OH | |
| 1005 | 4-amidinophenyl | 3-pyridylmethoxy-carbonyl | OH | |
| 1006 | 4-amidinophenyl | 4-pyridylmethoxy-carbonyl | OH | |
| 1007 | 4-amidinophenyl | H | OMe | |
| 1008 | 4-amidinophenyl | benzyloxycarbonyl | OMe | |
| 1009 | 4-amidinophenyl | t-butyloxycarbonyl | OMe | |
| 1010 | 4-amidinophenyl | n-butyloxycarbonyl | OMe | |
| 1011 | 4-amidinophenyl | ethyloxycarbonyl | OMe | |
| 1012 | 4-amidinophenyl | methyloxycarbonyl | OMe | |
| 1013 | 4-amidinophenyl | phenylethylcarbonyl | OMe | |
| 1014 | 4-amidinophenyl | 2,2-dimethyl-propylcarbonyl | OMe | |
| 1015 | 4-amidinophenyl | n-pentylcarbonyl | OMe | |
| 1016 | 4-amidinophenyl | n-butylcarbonyl | OMe | |
| 1017 | 4-amidinophenyl | propionyl | OMe | |
| 1018 | 4-amidinophenyl | acetyl | OMe | |
| 1019 | 4-amidinophenyl | methylsulfonyl | OMe | |
| 1020 | 4-amidinophenyl | ethylsulfonyl | OMe | |
| 1021 | 4-amidinophenyl | n-butylsulfonyl | OMe | |
| 1022 | 4-amidinophenyl | phenylsulfonyl | OMe | |
| 1023 | 4-amidinophenyl | 4-methylphenyl-sulfonyl | OMe | |
| 1024 | 4-amidinophenyl | benzylfulfonyl | OMe | |
| 1025 | 4-amidinophenyl | 2-pyridylcarbonyl | OMe | |
| 1026 | 4-amidinophenyl | 3-pyridylcarbonyl | OMe | |
| 1027 | 4-amidinophenyl | 4-pyridylcarbonyl | OMe | |
| 1029 | 4-amidinophenyl | 2-pyridylmethyl-carbonyl | OMe | |
| 1030 | 4-amidinophenyl | 3-pyridylmethyl-carbonyl | OMe | |
| 1031 | 4-amidinophenyl | 4-pyridylmethyl-carbonyl | OMe | |
| 1032 | 4-amidinophenyl | 2-pyridylmethoxy-carbonyl | OMe | |
| 1033 | 4-amidinophenyl | 3-pyridylmethoxy-carbonyl | OMe | |
| 1034 | 4-amidinophenyl | 4-pyridylmethoxy-carbonyl | OMe | |
| 1035 | 4-piperidinylethyl | benzylcarbonyl | OMe | |
| 1036 | 4-(BOCamidino)phenyl | benzyloxycarbonyl | OMe | |
| 1037 | 4-(BOCamidino)phenyl | n-butyloxycarbonyl | OMe | |
| 1038 | 4-amidinophenyl | 1-naphthylsulfonyl | OMe | |
| 1039 | 4-amidinophenyl | 2-naphthylsulfonyl | OMe | |
| 1040 | 4-amidinophenyl | styrylsulfonyl | OMe | |
| 1041 | 4-piperidinylethyl | n-butyloxycarbonyl | OMe | |
| 1042 | 4-amidinophenyl | 4-butyloxyphenyl-sulfonyl | OMe | |
| 1043 | 4-amidinophenyl | 2-thienylsulfonyl | OMe | |
| 1044 | 4-amidinophenyl | 3-methylphenyl-sulfonyl | OMe | |
| 1045 | 4-amidinophenyl | 4-iodophenyl | OMe | |
| 1046 | 4-amidinophenyl | 3-trifluoromethyl-phenylsulfonyl | OMe | |
| 1047 | 4-amidinophenyl | 3-chlorophenyl-sulfonyl | OMe | |
| 1048 | 4-amidinophenyl | 2-methoxycarbonyl-phenylsulfonyl | OMe | |
| 1050 | 4-amidinophenyl | 2,4,6-trimethyl-phenylsulfonyl | OMe | |
| 1051 | 4-amidinophenyl | 2-chlorophenyl-sulfonyl | OMe | |
| 1052 | 4-amidinophenyl | 2-trifluoromethyl-phenylsulfonyl | OMe | |
| 1053 | 4-amidinophenyl | 4-trifluoromethyl-phenylsulfonyl | OMe | |
| 1054 | 4-amidinophenyl | 2-fluorophenyl-sulfonyl | OMe | |
| 1055 | 4-amidinophenyl | 4-fluorophenyl-sulfonyl | OMe | |
| 1056 | 4-amidinophenyl | 4-methoxyphenyl-sulfonyl | OMe | |
| 1057 | 4-amidinophenyl | 2,3,4,5,6-tetramethyl-phenylsulfonyl | OMe | |
| 1058 | 4-amidinophenyl | 4-cyanophenyl-sulfonyl | OMe | |
| 1059 | 4-amidinophenyl | 4-chlorophenyl-sulfonyl | OMe | |
| 1060 | 4-amidinophenyl | 4-ethylphenyl-sulfonyl | OMe | |
| 1061 | 4-amidinophenyl | 4-propylphenyl-sulfonyl | OMe | |
| 1062 | 4-amidinophenyl | n-propylsulfonyl | OMe | |
| 1063 | 4-amidinophenyl | 2-phenylethyl-sulfonyl | OMe | |
| 1064 | 4-amidinophenyl | 4-isopropylphenyl-sulfonyl | OMe | |
| 1065 | 4-amidinophenyl | 3-phenylpropyl-sulfonyl | OMe | |
| 1066 | 4-amidinophenyl | 3-pyridylsulfonyl | OMe | |
| 1068 | 4-amidinophenyl | 2-pyridylsulfonyl | OMe | |
| 1069 | 4-amidinophenyl | 2,2-diphenyl-1-ethenylsulfonyl | OMe | |
| 1070 | 4-amidinophenyl | 2-pyrimidinyl-sulfonyl | OMe | |
| 1071 | 4-amidinophenyl | 4-methyl-2-pyrimidinylsulfonyl | OMe | |
| 1072 | 4-amidinophenyl | 4,6-dimethyl-2-pyrimidinylsulfonyl | OMe | |
| 1073 | 4-amidinophenyl | 1,2,4-triazol-3-ylsulfonyl | OMe | |
| 1074 | 4-amidinophenyl | 1-methyl-1,3,4-trizol-5-ylsulfonyl | OMe | |
| 1075 | 4-amidinophenyl | 3,5-dimethyl-4-pyrazolylsulfonyl | OMe | |
| 1076 | 4-amidinophenyl | 1-phenyl-4-pyrazolylsulfonyl | OMe | |
| 1077 | 4-amidinophenyl | n-butylaminosulfonyl | OMe | |
| 1078 | 4-amidinophenyl | i-butylaminosulfonyl | OMe | |
| 1079 | 4-amidinophenyl | t-butylaminosulfonyl | OMe | |
| 1080 | 4-amidinophenyl | i-propylamino-sulfonyl | OMe | |
| 1081 | 4-amidinophenyl | cyclohexylamino-sulfonyl | OMe | |
| 1082 | 4-amidinophenyl | phenylaminosulfonyl | OMe | |
| 1083 | 4-amidinophenyl | benzylaminosulfonyl | OMe | |
| 1084 | 4-amidinophenyl | dimethylamino-sulfonyl | OMe | |
| 1085 | 4-amidino-2-fluoro-phenyl | 3-methylphenyl-sulfonyl | OMe | |
| 1086 | 2-amidino-5-pyridyl | n-butyloxycarbonyl | OMe | |
| 1088 | 2-amidino-5-pyridyl | 3-methylphenyl-sulfonyl | OMe | |
| 1089 | 3-amidino-6-pyridyl | n-butyloxycarbonyl | OMe | |

TABLE 7-continued

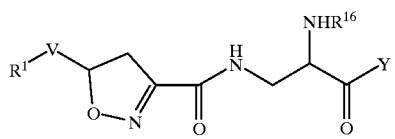

| Ex No. | R¹-V | R¹⁶ | Y | MS (M + H)⁺ |
|---|---|---|---|---|
| 1090 | 3-amidino-6-pyridyl | 3-methylphenylsulfonyl | OMe | |
| 1091 | 4-amidinophenyl | phenylaminocarbonyl | OMe | |
| 1092 | 4-amidinophenyl | 4-fluorophenylaminocarbonyl | OMe | |
| 1093 | 4-amidinophenyl | 1-naphthylaminocarbonyl | OMe | |
| 1094 | 4-amidinophenyl | benzylaminocarbonyl | OMe | |
| 1095 | 4-amidinophenyl | n-butylaminocarbonyl | OMe | |
| 1096 | 4-amidinophenyl | 4-ethylphenylcarbonyl | OMe | |
| 1097 | 4-amidinophenyl | biphenylcarbonyl | OMe | |
| 1098 | 4-amidinophenyl | 2-naphthylcarbonyl | OMe | |
| 1099 | 4-amidinophenyl | (2-chlorophenyl)methoxycarbonyl | OMe | |
| 1100 | 4-amidinophenyl | (2-chlorophenyl)methoxycaronyl | OH | |
| 1101 | 4-amidinophenyl | (2-bromophenyl)methoxycarbonyl | OMe | |
| 1102 | 4-amidinophenyl | (2-bromophenyl)methoxycarbonyl | OH | |
| 1103 | 4-amidinophenyl | n-hexyloxycarbonyl | OMe | |
| 1104 | 4-amidinophenyl | n-hexyloxycarbonyl | OH | |
| 1105 | 4-amidinophenyl | isobutyloxycarbonyl | OMe | |
| 1106 | 4-amidinophenyl | isobutyloxycarbonyl | OH | |
| 1107 | 4-amidinophenyl | 2-cyclopropylethoxycarbonyl | OMe | |
| 1108 | 4-amidinophenyl | 2-cyclopropylethoxycarbonyl | OH | |
| 1110 | 4-amidinophenyl | 2-cyclopentylethoxycarbonyl | OMe | |
| 1111 | 4-amidinophenyl | 2-cyclopentylethoxycarbonyl | OH | |
| 1112 | 4-amidinophenyl | 4,4,4-trifluorobutyloxycarbonyl | OMe | |
| 1113 | 4-amidinophenyl | 4,4,4-trifluorobutyloxycarbonyl | OH | |
| 1114 | 4-amidinophenyl | n-propylsulfonyl | OH | |
| 1115 | 4-amidinophenyl | 2-methylphenylsulfonyl | OMe | |
| 1116 | 4-amidinophenyl | 4-chloro-2,5-dimethylphenylsulfonyl | OH | 536 |
| 1117 | 4-amidinophenyl | 2,3-dichlorophenylsulfonyl | OMe | |
| 1118 | 4-amidinophenyl | 2-bromophenylsulfonyl | OMe | |
| 1119 | 4-amidinophenyl | 3-bromophenylsulfonyl | OMe | |
| 1120 | 4-amidinophenyl | 4-bromophenylsulfonyl | OMe | |
| 1121 | 4-amidinophenyl | biphenylsulfonyl | OMe | |
| 1122 | 4-amidinophenyl | 5-chloro-1,3-dimethyl-4-pyrazolyl | OMe | |
| 1123 | 4-amidinophenyl | 3-bromo-2-thienylsulfonyl | OMe | |
| 1124 | 4-amidinophenyl | 5-bromo-2-thienylsulfonyl | OMe | |
| 1125 | 4-amidinophenyl | 5-[1-methyl-5-trifluoromethyl-3-pyrazolyl]-2-thienylsulfonyl | OMe | |
| 1127 | 4-amidinophenyl | 5-(3-isoxazolyl)-2-thienylsulfonyl | OMe | |
| 1128 | 4-amidinophenyl | 5-(2-pyridinyl)-2-thienylsulfonyl | OMe | |

TABLE 7-continued

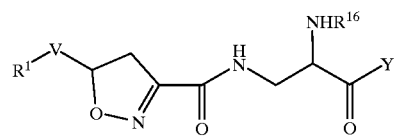

| Ex No. | R¹-V | R¹⁶ | Y | MS (M + H)⁺ |
|---|---|---|---|---|
| 1129 | 4-amidinophenyl | 4-methyl-2-methylcarbonylamino-5-thiazolylsulfonyl | OMe | |
| 1130 | 4-amidinophenyl | 2-benzothienylsulfonyl | OMe | |
| 1131 | 4-amidinophenyl | 2-benzothienylsulfonyl | OMe | |
| 1132 | 4-amidinophenyl | 3-methyl-2-benzothienylsulfonyl | OMe | |
| 1133 | 4-amidinophenyl | 8-quinolinylsulfonyl | OMe | |
| 1134 | 4-amidinophenyl | 8-quinolinylsulfonyl | OH | |
| 1135 | 4-amidinophenyl | 2,1,3-benzothiadiazol-4-ylsulfonyl | OMe | |
| 1136 | 4-amidinophenyl | 2,1,3-benzothiadiazol-4-ylsulfonyl | OH | |
| 1137 | 4-amidinophenyl | 4-N,N-dimethylamino-1-naphthylsulfonyl | OMe | |
| 1138 | 4-amidinophenyl | 4-N,N-dimethylamino-1-haphthylsulfonyl | OH | |
| 1139 | 4-amidinophenyl | 2,1,3-benzoxadiazol-4-ylsulfonyl | OMe | |
| 1140 | 4-amidinophenyl | 2,1,3-benzoxadiazol-4-ylsulfonyl | OH | |
| 1141 | 4-amidinophenyl | 2,2,5,7,8-pentamethyl 3,4-dihydro-2Hbenxopyran-6-ylsulfonyl | OMe | |
| 1143 | 4-amidinophenyl | 2,2,5,7,8-pentamethyl 3,4-dihydro-2Hbenzopyran-6-ylsulfonyl | OH | |
| 1144 | 4-N-methylamidino phenyl | 3-methylphenylsulfonyl | OMe | |
| 1145 | 4-N-ethylamidino phenyl | 3-methylphenylsulfonyl | OMe | |
| 1146 | 4-N-n-propylamidino phenyl | 3-methylphenylsulfonyl | OMe | |
| 1147 | 4-N-benzylamidino phenyl | 3-methylphenylsulfonyl | OMe | |
| 1148 | 4-N-n-butylamidino phenyl | 3-methylphenylsulfonyl | OMe | |
| 1149 | 4-N-methylamidino phenyl | 3-methylphenylsulfonyl | OH | |
| 1150 | 4-N-ethylamidino phenyl | 3-methylphenylsulfonyl | OH | |
| 1151 | 4-N-n-propylamidino phenyl | 3-methylphenylsulfonyl | OH | |
| 1152 | 4-N-benzylamidino phenyl | 3-methylphenylsulfonyl | OH | |
| 1153 | 4-N-n-butylamidino phenyl | 3-methylphenylsulfonyl | OH | |
| 1154 | 4-N-methylamidino-phenyl | n-butyloxycarbonyl | OMe | |
| 1155 | 4-N-ethylamidinophenyl | n-butyloxycarbonyl | OMe | |
| 1156 | 4-N-npropylamidino-phenyl | n-butyloxycarbonyl | OMe | |
| 1157 | 4-N-n-butylamidino-phenyl | n-butyloxycarbonyl | OMe | |
| 1158 | 4-N-benzylamidino-phenyl | n-butyloxycarbonyl | OMe | |
| 1160 | 4-N-methylamidino-phenyl | n-butyloxycarbonyl | OH | |
| 1161 | 4-N-ethylamidino-phenyl | n-butyloxycarbonyl | OH | |
| 1162 | 4-N-n-propylamidino-phenyl | n-butyloxycarbonyl | OH | |
| 1163 | 4-N-n-butylamidino-phenyl | n-butyloxycarbonyl | OH | |

TABLE 7-continued

| Ex No. | R¹-V | R¹⁶ | Y | MS (M + H)⁺ |
|---|---|---|---|---|
| 1164 | 4-N-benzylamidino-phenyl | n-butyloxycarbonyl | OH | |
| 1165 | 4-(acetoxyamidino)-phenyl | n-butyloxycarbonyl | OMe | |
| 1166 | 4-(acetoxyamidino)-phenyl | n-butyloxycarbonyl | OH | |
| 1167 | 4-(acetoxyamidino)-phenyl | isobutyloxycarbonyl | OMe | |
| 1168 | 4-(acetoxyamidino)-phenyl | isobutyloxycarbonyl | OH | |
| 1169 | 4-(acetoxyamidino)-phenyl | cyclopropylethoxy-carbonyl | OMe | |
| 1170 | 4-(acetoxyamidino)-phenyl | cyclopropylethoxy-carbonyl | OH | |
| 1171 | 4-(acetoxyamidino)-phenyl | benzyloxycarboyl | OMe | |
| 1172 | 4-(acetoxyamidino)-phenyl | benzyloxycarbonyl | OH | |
| 1173 | 4-(acetoxyamidino)-phenyl | 4-methylphenylsulfonyl | OMe | |
| 1174 | 4-(acetoxyamidino)-phenyl | 4-methylphenylsulfonyl | OH | |
| 1175 | 4-piperidinylethyl | n-butyloxycarbonyl | OMe | |
| 1176 | 4-piperidinylethyl | benzyloxycarbonyl | OMe | |
| 1177 | 4-piperidinylethyl | n-propyloxycarbonyl | OMe | |
| 1178 | 4-piperidinylethyl | isobutyloxycarbonyl | OMe | |
| 1179 | 4-piperidinylethyl | 2-methylphenylsulfonyl | OMe | |
| 1180 | 4-piperidinylethyl | 3-methylphenylsulfonyl | OMe | |
| 1181 | 4-piperidinylethyl | 4-methylphenylsulfonyl | OMe | |
| 1182 | 4-piperidinylethyl | 2-bromophenylsulfonyl | OMe | |
| 1183 | 4-piperidinylethyl | 3-bromophenylsulfonyl | OMe | |
| 1184 | 4-piperidinylethyl | 2-methoxy-phenylsulfonyl | | |
| 1185 | 4-piperidinylethyl | 3-methoxy-phenylsulfonyl | OMe | |
| 1186 | 4-piperidinylethyl | 3-trifluoromethylphenylsulfonyl | OMe | |
| 1187 | 4-piperidinylethyl | n-propylsulfonyl | OMe | |
| 1188 | 4-piperidinylethyl | n-butylsulfonyl | OMe | |
| 1189 | 4-piperidinylethyl | isopropylsulfonyl | OMe | |
| 1190 | 4-piperidinylethyl | isobutylsulfonyl | OMe | |
| 1191 | 4-piperidinylethyl | 3,5-dimethyl-isoxazolylsulfonyl | OMe | |
| 1192 | 4-piperidinylethyl | 2,4-dimethyl-thiazolylsulfonyl | OMe | |
| 1193 | 4-piperidinylpropyl | n-butyloxycarbonyl | OMe | |
| 1194 | 4-piperidinylpropyl | n-propyloxycarbonyl | OMe | |
| 1195 | 4-piperidinylpropyl | benzyloxycarbonyl | OMe | |
| 1196 | 4-piperidinylpropyl | isobutyloxycarbonyl | OMe | |
| 1197 | 4-piperidinylpropyl | 2-methylphenyl-sulfonyl | OMe | |
| 1198 | 4-piperidinylpropyl | 3-methylphenyl-sulfonyl | OMe | |
| 1199 | 4-piperidinylpropyl | 4-methylphenyl-sulfonyl | OMe | |
| 1200 | 4-piperidinylpropyl | 2-bromophenylsulfonyl | OMe | |
| 1201 | 4-piperidinylpropyl | n-butylsulfonyl | OMe | |
| 1202 | 4-piperidinylpropyl | isobutylsulfonyl | OMe | |
| 1203 | 4-piperidinylpropyl | 3,5-dimethyl-isoxazolylsulfonyl | OMe | |
| 1204 | 4-piperidinylpropyl | 2,4-dimethyl-thiazoylsulfonyl | OMe | |
| 1205 | 4-piperidinylethyl | n-butyloxycarbonyl | OH | |
| 1206 | 4-piperidinylethyl | n-propyloxycarbonyl | OH | |
| 1207 | 4-piperidinylethyl | benyloxycarbonyl | OH | |
| 1208 | 4-piperidinylethyl | isobutyloxycarbonyl | OH | |
| 1209 | 4-piperidinylethyl | 2-methylphenyl-sulfonyl | OH | |
| 1210 | 4-piperidinylethyl | 3-methylphenyl-sulfonyl | OH | |
| 1211 | 4-piperidinylethyl | 4-methylphenyl-sulfonyl | OH | |
| 1212 | 4-piperidinylethyl | 2-bromophenylsulfonyl | OH | |
| 1213 | 4-piperidinylethyl | 3,5-dimethyl-isoxazolylsulfonyl | OH | |
| 1214 | 4-piperidinylethyl | 2,4-dimethyl-thiazolylsulfonyl | OH | |
| 1215 | 4-piperidinylethyl | n-butylsulfonyl | OH | |
| 1216 | 4-piperidinylethyl | isobutylsulfonyl | OH | |
| 1217 | 4-piperidinylpropyl | n-butyloxycarbonyl | OH | |
| 1218 | 4-piperidinylpropyl | n-propyloxycarbonyl | OH | |
| 1219 | 4-piperidinylpropyl | isobutyloxycarbonyl | OH | |
| 1220 | 4-piperidinylpropyl | 2-methylphenyl-carbonyl | OH | |
| 1221 | 4-piperidinylpropyl | 4-methylphenyl-carbonyl | OH | |
| 1222 | 4-piperidinylpropyl | 2-bromophenyl-carbonyl | OH | |
| 1223 | 4-piperidinylpropyl | 3,5-dimethyl-isoxazolylsulfonyl | OH | |
| 1224 | 4-piperidinylpropyl | n-butylsulfonyl | OH | |
| 1225 | 4-piperidinylpropyl | isobutylsulfonyl | OH | |
| 1226 | 4-amidinopiperidinyl | n-butyloxycarbonyl | OMe | |
| 1227 | 4-amidinopiperidinyl | isobutyloxycarbonyl | OMe | |
| 1228 | 4-amidinopiperidinyl | n-propyloxycarbonyl | OMe | |
| 1229 | 4-amidinopiperidinyl | benzyloxycarbonyl | OMe | |
| 1230 | 4-amidinopiperidinyl | n-butylsulfonyl | OMe | |
| 1231 | 4-amidinopiperidinyl | isobutylsulfonyl | OMe | |
| 1232 | 4-amidinopiperidinyl | n-propylsulfonyl | OMe | |
| 1233 | 4-amidinopiperidinyl | 2-methylphenyl-sulfonyl | OMe | |
| 1234 | 4-amidinopiperidinyl | 4-methylphenyl-sulfonyl | OMe | |
| 1235 | 4-amidinopiperidinyl | benzylsulfonyl | OMe | |
| 1236 | 4-amidinopiperidinyl | 3,5-dimethyl-isoxazolylsulfonyl | OMe | |
| 1237 | 4-amidinopiperidinyl | 2,4-dimethyl-thiazolylsulfonyl | OMe | |
| 1238 | 4-amidinopiperidinyl | 4-methylphenyl-sulfonyl | OH | |
| 1239 | 4-amidinopiperidinyl | n-butyloxycarbonyl | OH | |
| 1240 | 4-amidinopiperidinyl | isobutyloxycarbonyl | OH | |
| 1241 | 4-amidinopiperidinyl | n-propyloxycarbonyl | OH | |
| 1242 | 4-amidinopiperidinyl | benzyloxycarbonyl | OH | |
| 1243 | 4-amidinopiperidinyl | n-butylsulfonyl | OH | |
| 1244 | 4-amidinopiperidinyl | isobutylsulfonyl | OH | |
| 1245 | 4-amidinopiperidinyl | 2-methylphenyl-sulfonyl | OH | |
| 1246 | 4-amidinopiperidinyl | 3-methylphenyl-sulfonyl | OH | |
| 1247 | 4-amidinopiperidinyl | 4-methylphenyl-sulfonyl | OH | |
| 1248 | 4-amidinopiperidinyl | 2-bromophenylsulfonyl | OH | |
| 1249 | 4-amidinopiperidinyl | 3-bromophenylsulfonyl | OH | |

TABLE 7-continued

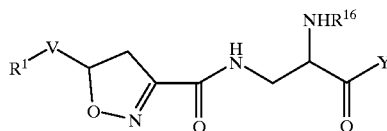

| Ex No. | R¹-V | R¹⁶ | Y | MS (M + H)⁺ |
|---|---|---|---|---|
| 1250 | 4-amidinopiperidinyl | 3,5-dimethyl-isoxazolylsulfonyl | OH | |
| 1251 | 4-amidinopiperidinyl | 2,4-dimethyl-thiazolylsulfonyl | OH | |
| 1252 | 4-amidino-piperidinylmethyl | n-butyloxycarbonyl | OMe | |
| 1253 | 4-amidino-piperidinylmethyl | n-propyloxycarbonyl | OMe | |
| 1254 | 4-amidino-piperidinylmethyl | benzyloxycarbonyl | OMe | |
| 1255 | 4-amidino-piperidinylmethyl | n-butylsulfonyl | OMe | |
| 1256 | 4-amidino-piperidinylmethyl | n-propylsulfonyl | OMe | |
| 1257 | 4-amidino-piperidinylmethyl | 2-methylphenyl-sulfonyl | OMe | |
| 1258 | 4-amidino-piperidinylmethyl | 3-methylphenyl-sulfonyl | OMe | |
| 1259 | 4-amidino-piperidinylmethyl | 4-methylphenyl-sulfonyl | OMe | |
| 1260 | 4-amidino-piperidinylmethyl | 2-bromophenylsulfonyl | OMe | |
| 1261 | 4-amidino-piperidinylmethyl | 3-bromophenylsulfonyl | OMe | |
| 1262 | 4-amidino-piperidinylmethyl | 3,5-dimethyl-isoxazolylsulfonyl | OMe | |
| 1263 | 4-amidino-piperidinylmethyl | 4-methylphenyl-sulfonyl | OH | |
| 1264 | 4-amidino-piperidinylmethyl | n-butyloxycarbonyl | OH | |
| 1265 | 4-amidino-piperidinylmethyl | n-propyloxycarbonyl | OH | |
| 1266 | 4-amidino-piperidinylmethyl | benzyloxycarbonyl | OH | |
| 1267 | 4-amidino-piperidinylmethyl | n-butylsulfonyl | OH | |
| 1268 | 4-amidino-piperidinylmethyl | 2-methylphenyl-sulfonyl | OH | |
| 1269 | 4-amidino-piperidinylmethyl | 3-methylphenyl-sulfonyl | OH | |
| 1270 | 4-amidino-piperidinylmethyl | 2-bromophenyl-sulfonyl | OH | |
| 1271 | 4-amidino-piperidinylmethyl | 3-bromophenyl-sulfonyl | OH | |
| 1272 | 4-amidino-piperidinylmethyl | 3,5-dimethyl-isoxazolylsulfonyl | OH | |
| 1273 | 4-quinuclidinylethyl | n-butyloxycarbonyl | OH | |
| 1274 | 4-quinuclidinylethyl | n-propyloxycarbonyl | OH | |
| 1275 | 4-quinuclidinylethyl | benzyloxycarbonyl | OH | |
| 1276 | 4-quinuclidinylethyl | n-butylsulfonyl | OH | |
| 1277 | 4-quinuclidinylethyl | 2-methylphenyl-sulfonyl | OH | |
| 1278 | 4-quinuclidinylethyl | 4-methylphenyl-sulfonyl | OH | |
| 1279 | 4-quinuclidinylethyl | 2-bromophenylsulfonyl | OH | |
| 1280 | 4-quinuclidinylethyl | 3-bromophenylsulfonyl | OH | |
| 1281 | 4-quinuclidinylethyl | 3,5-dimethyl-isoxazolylsulfonyl | OH | |
| 1282 | guanidinopropyl | n-butyloxycarbonyl | OMe | |
| 1283 | guanidinopropyl | n-propyloxycarbonyl | OMe | |
| 1284 | guanidinopropyl | benzyloxycarbonyl | OH | 435 |
| 1285 | guanidinopropyl | n-butylsulfonyl | OMe | |
| 1286 | guanidinopropyl | 2-methylphenyl-sulfonyl | OMe | |

TABLE 7-continued

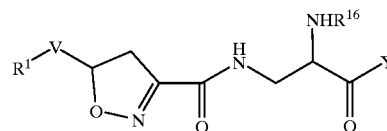

| Ex No. | R¹-V | R¹⁶ | Y | MS (M + H)⁺ |
|---|---|---|---|---|
| 1287 | guanidinopropyl | 3-methylphenyl-sulfonyl | OMe | |
| 1288 | guanidinopropyl | 2-bromophenylsulfonyl | OMe | |
| 1289 | guanidinopropyl | 3-bromophenylsulfonyl | OMe | |
| 1290 | guanidinopropyl | 3,5-dimethyl-isoxazolylsulfonyl | OMe | |
| 1291 | guanidinopropyl | benzylsulfonyl | OMe | |
| 1292 | guanidinopropyl | styrylsulfonyl | OMe | |
| 1293 | guanidinopropyl | 2-benzothiophene-sulfonyl | OMe | |
| 1294 | guanidinopropyl | n-butyloxycarbonyl | OH | |
| 1295 | guanidinopropyl | n-propyloxycarbonyl | OH | |
| 1296 | guanidinopropyl | benzyloxycarbonyl | OH | |
| 1297 | guanidinopropyl | n-butylsulfonyl | OH | |
| 1298 | guanidinopropyl | 2-methylphenyl-sulfonyl | OH | |
| 1299 | guanidinopropyl | 3-methylphenyl-sulfonyl | OH | |
| 1300 | guanidinopropyl | 4-methylphenyl-sulfonyl | OH | |
| 1301 | guanidinopropyl | 2-bromophenylsulfonyl | OH | |
| 1302 | guanidinopropyl | 3-bromophenylsulfonyl | OH | |
| 1303 | guanidinopropyl | 3,5-dimethyl-isoxazolylsulfonyl | OH | |
| 1304 | guanidinopropyl | 2,4-dimethyl-thiazolylsulfonyl | OH | |
| 1305 | guanidinopropyl | benzylsulfonyl | OH | |
| 1306 | guanidinopropyl | styrylsulfonyl | OH | |
| 1307 | guanidinopropyl | 2-benzothiophene-sulfonyl | OH | |
| 1308 | guanidinobutyl | n-butyloxycarbonyl | OH | |
| 1309 | guanidinobutyl | n-butylsulfonyl | OH | |
| 1310 | guanidinobutyl | phenylsulfonyl | OH | |
| 1311 | guanidinobutyl | 2-methylphenyl-sulfonyl | OH | |
| 1312 | guanidinobutyl | 4-methylphenyl-sulfonyl | OH | |
| 1313 | guanidinobutyl | 2-bromophenylsulfonyl | OH | |
| 1314 | guanidinobutyl | 3,5-dimethyl-isoxazolylsulfonyl | OH | |
| 1315 | guanidinobutyl | 2,4-dimethyl-thiazolylsulfonyl | OH | |
| 1316 | guanidinobutyl | benzylsulfonyl | OH | |
| 1317 | guanidinobutyl | styrylsulfonyl | OH | |
| 1318 | guanidinobutyl | 3-fluorophenyl-sulfonyl | OH | |
| 1319 | guanidinobutyl | n-butyloxycarbonyl | OMe | |
| 1320 | guanidinobutyl | n-butylsulfonyl | OMe | |
| 1321 | guanidinobutyl | benzyloxycarbonyl | OH | 449 |
| 1322 | guanidinobutyl | phenylsulfonyl | OMe | |
| 1323 | guanidinobutyl | 2-methylphenyl-sulfonyl | OMe | |
| 1324 | guanidinobutyl | 2-bromophenylsulfonyl | OMe | |
| 1325 | guanidinobutyl | 3-bromophenylsulfonyl | OMe | |
| 1326 | guanidinobutyl | 3,5-dimethyl-isoxazolyl sufonyl | OMe | |
| 1327 | guanidinobutyl | benzylsulfonyl | OMe | |
| 1328 | guanidinobutyl | n-butyloxycarbonyl | OH | |
| 1329 | guanidinobutyl | isobutyloxycarbonyl | OH | |
| 1330 | guanidinobutyl | n-propyloxycarbonyl | OH | |

TABLE 7-continued

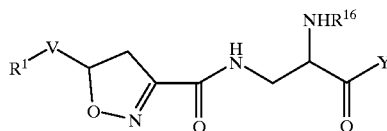

| Ex No. | R¹-V | R¹⁶ | Y | MS (M + H)⁺ |
|---|---|---|---|---|
| 1331 | guanidinobutyl | phenylsulfonyl | OH | |
| 1332 | guanidinobutyl | n-butylsulfonyl | OH | |
| 1333 | guanidinobutyl | 2-methylphenyl-sulfonyl | OH | |
| 1334 | guanidinobutyl | 3-methylphenyl-sulfonyl | OH | |
| 1335 | guanidinobutyl | 4-methylphenyl-sulfonyl | OH | |
| 1336 | guanidinobutyl | 2-bromophenylsulfonyl | OH | |
| 1337 | 4-piperidinylmethyl-aminocarbonyl | n-butyloxycarbonyl | OH | |
| 1338 | 4-piperidinylmethyl-amino-carbonyl | n-butyloxycarbonyl | OMe | |
| 1339 | 4-piperidinylmethyl-amino-carbonyl | benzyloxycarbonyl | OH | |
| 1340 | 4-piperidinylmethyl-amino-carbonyl | benzyloxycarbonyl | OMe | |
| 1341 | 4-piperidinylmethyl-amino-carbonyl | n-butylsulfonyl | OH | |
| 1342 | 4-piperidinylmethyl-amino-carbonyl | n-butylsulfonyl | OMe | |
| 1343 | 4-piperidinylmethyl-amino-carbonyl | 2-methylphenyl-sulfonyl | OH | |
| 1344 | 4-piperidinylmethyl-amino-carbonyl | 2-methylphenyl-sulfonyl | OMe | |
| 1345 | 4-piperidinylmethyl-amino-carobnyl | 3-methylphenyl-sulfonyl | OH | |
| 1346 | 4-piperidinylmethyl-amino-carbonyl | 4-methylphenyl-sulfonyl | OH | |
| 1347 | 4-piperidinylmethyl-amino-carbonyl | 3-methylphenyl-sulfonyl | OMe | |
| 1348 | 4-piperidinylmethyl-amino-carbonyl | 3,5-dimethyl-isoxazolylsulfonyl | OH | |
| 1349 | 4-piperidinylmethyl-amino-carbonyl | 3,5-dimethyl-isoxazolylsulfonyl | OMe | |
| 1350 | N-(4-piperidinyl-methyl)-N-methyl-aminocarbonyl | n-butyloxycarbonyl | OH | |
| 1351 | N-(4-piperidinyl-methyl)-N-methyl-aminocarbonyl | n-butyloxycarbonyl | OMe | |
| 1352 | N-(4-piperdinyl-methyl)-N-methyl-aminocarbonyl | benzyloxycarbonyl | OH | |
| 1353 | N-(4-piperidinyl-methyl)-N-methyl-aminocarbonyl | benzyloxycarbonyl | OMe | |
| 1354 | N-(4-piperidinyl-methyl)-N-methyl-aminocarbonyl | n-butylsulfonyl | OH | |
| 1355 | N-(4-piperidinyl-methyl)-N-methylaminocarbonyl | n-butylsulfonyl | OMe | |
| 1356 | N-(4-piperidinyl-methyl)-N-methyl-aminocarbonyl | 2-methylphenyl-sulfonyl | OH | |
| 1357 | N-(4-piperidinyl-methyl)-N-methyl-aminocarbonyl | 2-methylphenyl-sulfonyl | OMe | |
| 1358 | N-(4-piperidinyl-methyl)-N-methyl-aminocarbonyl | 3-methylphenyl-sulfonyl | OH | |
| 1359 | N-(4-N-piperidinyl-methyl)-N-methyl-aminocarbonyl | 4-methylphenyl-sulfonyl | OH | |

TABLE 7-continued

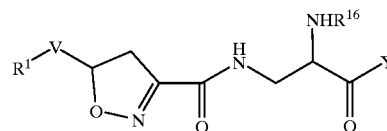

| Ex No. | R¹-V | R¹⁶ | Y | MS (M + H)⁺ |
|---|---|---|---|---|
| 1360 | N-(4-piperidinyl-methyl)-N-methyl-aminocarbonyl | 3-methylphenyl-sulfonyl | OMe | |
| 1361 | N-(4-piperidinyl-methyl)-N-methyl-aminocarbonyl | 3,5-dimethyl-isoxazolylsulfonyl | OH | |
| 1362 | N-(4-piperidinyl-methyl)-N-methyl-aminocarbonyl | 3,5-dimethyl-isoxazolylsulfonyl | OMe | |
| 1363 | 4-piperidinyl-aminocarbonyl | n-butyloxycarbonyl | OH | |
| 1364 | 4-piperidinyl-aminocarbonyl | 4-methylphenyl-sulfonyl | OH | |
| 1365 | 4-guanidinophenyl | 2-methylphenyl-sulfonyl | OH | |
| 1366 | 4-guanidinophenyl | 2-methylphenyl-sulfonyl | OMe | |
| 1367 | 4-guanidinophenyl | 2-bromophenylsulfonyl | OH | |
| 1368 | 4-guanidinophenyl | 2-bromophenylsulfonyl | OMe | |
| 1369 | 4-guanidinophenyl | 3-methylphenyl-sulfonyl | OH | |
| 1370 | 4-guanidinophenyl | 3,5-dimethyl-isoxazolylsulfonyl | OH | |
| 1371 | 4-guanidinophenyl | 3,5-dimethyl-isoxazolylsulfonyl | OMe | |
| 1372 | 4-guanidinophenyl | 2,4-dimethyl-thiazolylsulfonyl | OH | |
| 1373 | 4-guanidinophenyl | 2,4-dimethyl-thiazolylsulfonyl | OMe | |
| 1374 | 4-guanidinophenyl | benzylsulfonyl | OH | |
| 1375 | 4-guanidinophenyl | benzylsulfonyl | OMe | |
| 1376 | 4-guanidinophenyl | styrylsulfonyl | OH | |
| 1377 | 4-guanidinophenyl | styrylsulfonyl | OMe | |
| 1378 | 4-guanidinophenyl | 2-benzothiophene-sulfonyl | OH | |
| 1379 | 3-guanidinophenyl | n-butyloxycarbonyl | OH | |
| 1380 | 3-guanidinophenyl | n-butyloxycarbonyl | OMe | |
| 1381 | 3-guanidinophenyl | n-propyloxycarbonyl | OH | |
| 1382 | 3-guanidinophenyl | 2-bromophenylsulfonyl | OH | |
| 1383 | 3-guanidinophenyl | 2-bromophenylsulfonyl | OMe | |
| 1384 | 3-guanidinophenyl | 2-methylphenyl-sulfonyl | OH | |
| 1385 | 3-guanidinophenyl | 4-methylphenyl-sulfonyl | OH | |
| 1386 | 3-guanidinophenyl | 4-methylphenyl-sulfonyl | OMe | |
| 1387 | 3-guanidinophenyl | n-butylsulfonyl | OH | |
| 1388 | 3-guanidinophenyl | n-butylsulfonyl | OMe | |
| 1389 | 3-guanidinophenyl | styrylsulfonyl | OH | |
| 1390 | 3-guanidinophenyl | benzyloxycarbonyl | OH | |
| 1391 | 3-guanidinophenyl | benzyloxycarbonyl | OMe | |
| 1392 | 4-amidinophenylmethyl | 2-methylphenyl-sulfonyl | OH | |
| 1393 | 4-amidinophenylmethyl | 2-methylphenyl-sulfonyl | OMe | |
| 1394 | 4-amidinophenylmethyl | phenylsulfonyl | OH | |
| 1395 | 4-amidinophenylmethyl | phenylsulfonyl | OMe | |
| 1396 | 4-amidinophenylmethyl | 3,5-dimethyl-isoxazolylsulfonyl | OH | |
| 1397 | 4-amidinophenylmethyl | 3,5-dimethyl-isoxazolylsulfonyl | OMe | |
| 1398 | 4-amidinophenylmethyl | 2,4-dimethyl-thiazolylsulfonyl | OH | |

TABLE 7-continued

![Structure: R¹-V group attached to isoxazoline ring with carboxamide linkage to CH(NHR¹⁶)-C(=O)-Y]

| Ex No. | R¹-V | R¹⁶ | Y | MS (M + H)⁺ |
|---|---|---|---|---|
| 1399 | 4-amidinophenylmethyl | 2,4-dimethyl-thiazolylsulfonyl | OMe | |
| 1400 | 4-amidinophenylmethyl | p-toluylsulfonyl | OH | |
| 1401 | 3-amidinophenylmethyl | n-butyloxycarbonyl | OH | |
| 1402 | 3-amidinophenylmethyl | n-butyloxycarbonyl | OMe | |
| 1403 | 3-amidinophenylmethyl | phenylsulfonyl | OH | |
| 1404 | 3-amidinophenylmethyl | phenylsulfonyl | OMe | |
| 1405 | 3-amidinophenylmethyl | 2-bromophenylsulfonyl | OH | |
| 1406 | 3-amidinophenylmethyl | 2-bromophenylsulfonyl | OMe | |
| 1407 | 3-amidinophenylmethyl | 2-methylphenyl-sulfonyl | OH | |
| 1408 | 3-amidinophenylmethyl | 2-methylphenyl-sulfonyl | OMe | |
| 1409 | 3-amidinophenylmethyl | 4-methylphenyl-sulfonyl | OH | |
| 1410 | 3-amidinophenylmethyl | 4-methylphenyl-sulfonyl | OMe | |
| 1411 | 3-amidinophenylmethyl | styrylsulfonyl | OH | |
| 1412 | 3-amidinophenylmethyl | styrylsulfonyl | OMe | |
| 1413 | 3-amidinophenylmethyl | benzyloxycarbonyl | OH | |
| 1414 | 3-amidinophenylmethyl | benzyloxycarbonyl | OMe | |
| 1415 | 3-amidinophenylmethyl | 3,5-dimethyl-isoxazolylsulfonyl | OH | |
| 1416 | 3-amidinophenylmethyl | 3,5-dimethyl-isoxazolylsulfonyl | OMe | |
| 1417 | 3-amidinophenylmethyl | 2,4-dimethyl-thiazolylsulfonyl | OH | |
| 1418 | 3-amidinophenylmethyl | benzylsulfonyl | OH | |
| 1419 | 4-pyridylethyl | n-benzyloxycarbonyl | OMe | |
| 1420 | 4-pyridylethyl | n-benzyloxycarbonyl | OH | |
| 1421 | 4-pyridylethyl | n-butyloxyoxycarbonyl | OMe | |
| 1422 | 4-pyridylethyl | n-butyloxyoxycarbonyl | OH | |
| 1423 | 4-pyridylethyl | 2-methylphenylsulfonyl | OH | |
| 1424 | 4-pyridylethyl | 2-methylphenyl-sulfonyl | OMe | |
| 1425 | 4-pyridylethyl | 2-bromophenylsulfonyl | OH | |
| 1426 | 4-pyridylethyl | 2-bromophenylsulfonyl | OMe | |
| 1427 | 4-pyridylethyl | 3-methylphenyl-sulfonyl | OH | |
| 1428 | 4-pyridylethyl | 3,5-dimethyl-isoxazolylsulfonyl | OH | |
| 1429 | 4-pyridylethyl | 3,5-dimethyl-isoxazolylsulfonyl | OMe | |
| 1430 | 4-pyridylethyl | 2,4-dimethyl-thiazolylsulfonyl | OH | |
| 1431 | 4-pyridylethyl | 2,4-dimethyl-thiazolylsulfonyl | OMe | |
| 1432 | 4-pyridylethyl | benzylsulfonyl | OH | |
| 1433 | 4-pyridylethyl | styrylsulfonyl | OH | |
| 1434 | 4-pyridylethyl | styrylsulfonyl | OMe | |
| 1435 | 4-pyridylethyl | 2-benzothiophene-sulfonyl | OH | |
| 1436 | 3-pyridylethyl | n-benzyloxycarbonyl | OMe | |
| 1437 | 3-pyridylethyl | n-benzyloxycarbonyl | OH | |
| 1438 | 3-pyridylethyl | n-butyloxyoxycarbonyl | OMe | |
| 1439 | 3-pyridylethyl | n-butyloxyoxycarbonyl | OH | |
| 1440 | 3-pyridylethyl | 2-methylphenyl-sulfonyl | OH | |
| 1441 | 3-pyridylethyl | 2-methylphenyl-sulfonyl | OMe | |
| 1442 | 3-pyridylethyl | 2-bromophenylsulfonyl | OH | |
| 1443 | 3-pyridylethyl | 2-bromophenylsulfonyl | OMe | |
| 1444 | 3-pyridylethyl | 3-methylphenyl-sulfonyl | OH | |
| 1445 | 3-pyridylethyl | 3,5-dimethyl-isoxazolylsulfonyl | OH | |
| 1446 | 3-pyridylethyl | 3,5-dimethyl-isoxazolylsulfonyl | OMe | |
| 1447 | 3-pyridylethyl | 2,4-dimethyl-thiazolylsulfonyl | OH | |
| 1448 | 3-pyridylethyl | 2,4-dimethyl-thiazolylsulfonyl | OMe | |
| 1449 | 3-pyridylethyl | benzylsulfonyl | OH | |
| 1450 | 3-pyridylethyl | styrylsulfonyl | OH | |
| 1451 | 3-pyridylethyl | styrylsulfonyl | OMe | |
| 1452 | 3-pyridylethyl | 2-benzothiophene-sulfonyl | OH | |
| 1453 | 2-amino-4-pyridylethyl | n-benzyloxycarbonyl | OMe | |
| 1454 | 2-amino-4-pyridylethyl | n-benzyloxycarbonyl | OH | |
| 1455 | 2-amino-4-pyridylethyl | n-butyloxyoxycarbonyl | OMe | |
| 1456 | 2-amino-4-pyridylethyl | n-butyloxyoxycarbonyl | OH | |
| 1457 | 2-amino-4-pyridylethyl | 2-methylphenyl-sulfonyl | OH | |
| 1458 | 2-amino-4-pyridylethyl | 2-methylphenyl-sulfonyl | OMe | |
| 1459 | 2-amino-4-pyridylethyl | 2-bromophenylsulfonyl | OH | |
| 1460 | 2-amino-4-pyridylethyl | 2-bromophenylsulfonyl | OMe | |
| 1461 | 2-amino-4-pyridylethyl | 3-methylphenyl-sulfonyl | OH | |
| 1462 | 2-amino-4-pyridylethyl | 3,5-dimethyl-isoxazolylsulfonyl | OH | |
| 1463 | 2-amino-4-pyridylethyl | 3,5-dimethyl-isoxazolylsulfonyl | OMe | |
| 1464 | 2-amino-4-pyridylethyl | 2,4-dimethyl-thiazolylsulfonyl | OH | |
| 1465 | 2-amino-4-pyridylethyl | 2,4-dimethyl-thiazolylsulfonyl | OMe | |
| 1466 | 2-amino-4-pyridylethyl | benzylsulfonyl | OH | |
| 1467 | 2-amino-4-pyridylethyl | benzylsulfonyl | OMe | |
| 1468 | 2-amino-4-pyridylethyl | styrylsulfonyl | OH | |
| 1469 | 2-amino-4-pyridylethyl | styrylsulfonyl | OMe | |
| 1470 | 2-amino-4-pyridylethyl | 2-benzothiophene-sulfonyl | OH | |
| 1471 | 6-amino-3-pyridylethyl | n-benzyloxycarbonyl | OMe | |
| 1472 | 6-amino-3-pyridylethyl | n-benzyloxycarbonyl | OH | |
| 1473 | 6-amino-3-pyridylethyl | n-butyloxyoxycarbonyl | OMe | |
| 1474 | 6-amino-3-pyridylethyl | n-butyloxyoxycarbonyl | OH | |
| 1475 | 6-amino-3-pyridylethyl | 2-methylphenyl-sulfonyl | OH | |
| 1476 | 6-amino-3-pyridylethyl | 2-methylphenyl-sulfonyl | OMe | |
| 1477 | 6-amino-3-pyridylethyl | 2-bromophenylsulfonyl | OH | |
| 1478 | 6-amino-3-pyridylethyl | 2-bromophenylsulfonyl | OMe | |
| 1479 | 6-amino-3-pyridylethyl | 3-methylphenyl-sulfonyl | OH | |
| 1480 | 6-amino-3-pyridylethyl | 3,5-dimethyl-isoxazolylsulfonyl | OH | |
| 1481 | 6-amino-3-pyridylethyl | 3,5-dimethyl-isoxazolylsulfonyl | OMe | |
| 1482 | 6-amino-3-pyridylethyl | 2,4-dimethyl-thiazolylsulfonyl | OH | |
| 1483 | 6-amino-3-pyridylethyl | 2,4-dimethyl-thiazolylsulfonyl | OMe | |

TABLE 7-continued

Structure: $R^1$-V-[isoxazoline]-C(O)-NH-CH(CH$_2$-NHR$^{16}$)-C(O)-Y

| Ex No. | R$^1$-V | R$^{16}$ | Y | MS (M + H)$^+$ |
|---|---|---|---|---|
| 1484 | 6-amino-3-pyridylethyl | benzylsulfonyl | OH | |
| 1485 | 6-amino-3-pyridylethyl | benzylsulfonyl | OMe | |
| 1486 | 6-amino-3-pyridylethyl | styrylsulfonyl | OH | |
| 1487 | 6-amino-3-pyridylethyl | styrylsulfonyl | OMe | |
| 1488 | 6-amino-4-pyridylethyl | 2-benzothiophene-sulfonyl | OH | |
| 1489 | 2-amidino-4-pyridylethyl | n-benzyloxycarbonyl | OMe | |
| 1490 | 2-amidino-4-pyridylethyl | n-benzyloxycarbonyl | OH | |
| 1491 | 2-amidino-4-pyridylethyl | n-butyloxyoxycarbonyl | OMe | |
| 1492 | 2-amidino-4-pyridylethyl | n-butyloxyoxycarbonyl | OH | |
| 1493 | 2-amidino-4-pyridylethyl | 2-methylphenyl-sulfonyl | OH | |
| 1494 | 2-amidino-4-pyridylethyl | 2-methylphenyl-sulfonyl | OMe | |
| 1495 | 2-amidino-4-pyridylethyl | 2-bromophenylsulfonyl | OH | |
| 1496 | 2-amidino-4-pyridylethyl | 2-bromophenylsulfonyl | OMe | |
| 1497 | 2-amidino-4-pyridylethyl | 3-methylphenyl-sulfonyl | OH | |
| 1498 | 2-amidino-4-pyridylethyl | 3,5-dimethyl-isoxazolylsulfonyl | OH | |
| 1499 | 2-amidino-4-pyridylethyl | 3,5-dimethyl-isoxazolylsulfonyl | OMe | |
| 1500 | 2-amidino-4-pyridylethyl | 2,4-dimethyl-thiazolylsulfonyl | OH | |
| 1501 | 2-amidino-4-pyridylethyl | 2,4-dimethyl-thiazolylsulfonyl | OMe | |
| 1502 | 2-amidino-4-pyridylethyl | benzylsulfonyl | OH | |
| 1503 | 2-amidino-4-pyridylethyl | benzylsulfonyl | OMe | |
| 1504 | 2-amidino-4-pyridylethyl | styrylsulfonyl | OH | |
| 1505 | 2-amidino-4-pyridylethyl | styrylsulfonyl | OMe | |
| 1506 | 2-amidino-4-pyridylethyl | 2-benzothiophene-sulfonyl | OH | |
| 1507 | 6-amidino-3-pyridylethyl | n-benzyloxycarbonyl | OMe | |
| 1508 | 6-amidino-3-pyridylethyl | n-benzyloxycarbonyl | OH | |
| 1509 | 6-amidino-3-pyridylethyl | n-butyloxyoxycarbonyl | OMe | |
| 1510 | 6-amidino-3-pyridylethyl | n-butyloxyoxycarbonyl | OH | |
| 1511 | 6-amidino-3-pyridylethyl | 2-methylphenyl-sulfonyl | OH | |
| 1512 | 6-amidino-3-pyridylethyl | 2-methylphenyl-sulfonyl | OMe | |
| 1513 | 6-amidino-3-pyridylethyl | 2-bromophenylsulfonyl | OH | |
| 1514 | 6-amidino-3-pyridylethyl | 2-bromophenylsulfonyl | OMe | |
| 1515 | 6-amidino-3-pyridylethyl | 3-methylphenyl-sulfonyl | OH | |
| 1516 | 6-amidino-3-pyridylethyl | 3,5-dimethyl-isoxazolylsulfonyl | OH | |
| 1517 | 6-amidino-3-pyridylethyl | 3,5-dimethyl-isoxazolylsulfonyl | OMe | |
| 1518 | 6-amidino-3-pyridylethyl | 2,4-dimethyl-thiazolylsulfonyl | OH | |
| 1519 | 6-amidino-3-pyridylethyl | 2,4-dimethyl-thiazolylsulfonyl | OMe | |
| 1520 | 6-amidino-3-pyridylethyl | benzylsulfonyl | OH | |
| 1521 | 6-amidino-3-pyridylethyl | benzylsulfonyl | Me | |
| 1522 | 6-amidino-3-pyridylethyl | styrylsulfonyl | OH | |
| 1523 | 6-amidino-3-pyridylethyl | styrylsulfonyl | OMe | |
| 1524 | 6-amidino-3-pyridylethyl | 2-benzothiophene-sulfonyl | OH | |
| 1525 | guanidinoethyl | benzyloxycarbonyl | OH | 421 |

TABLE 8

Structure: $R^1$-V-[spiro isoxazoline/pyrrolidine]-(CH$_2$)$_{p1}$-N-(CH$_2$)$_{p2}$ with CH(NHR$^{16}$)-COY

| Ex. No. | R$^1$—V | p$^1$ | p$^2$ | R$^{16}$ | Y | MS M + H |
|---|---|---|---|---|---|---|
| 1540 | 4-amidinophenyl | 2 | 1 | n-butyloxycarbonyl | OH | 446 |
| 1541 | 4-amidinophenyl | 2 | 1 | 3-methylphenyl-sulfonyl | OH | 448 |
| 1542 | 4-amidinophenyl | 1 | 1 | benzyloxycarbonyl | OMe | |
| 1543 | 4-amidinophenyl | 1 | 1 | (2-methylphenyl)-methoxycarbonyl | OH | |
| 1544 | 4-amidinophenyl | 1 | 1 | (3-methylphenyl)-methoxycarbonyl | OH | |
| 1545 | 4-amidinophenyl | 1 | 2 | i-butyloxycarbonyl | OMe | |
| 1546 | 4-amidinophenyl | 1 | 2 | 4-methylphenyl-sulfonyl | OH | |
| 1547 | 4-amidinophenyl | 1 | 2 | 2-methylphenyl-sulfonyl | OH | |
| 1548 | 4-amidinophenyl | 2 | 1 | 3,5-dimethylpyra-zoylsulfonyl | OH | |
| 1549 | 4-amidinophenyl | 2 | 1 | 3,5-dimethylisox-azolylsulfonyl | OH | |
| 1550 | 4-amidinophenyl | 2 | 1 | i-butylamino-sulfonyl | OH | |
| 1551 | 4-amidinophenyl | 2 | 1 | 2-bromophenyl-sulfonyl | OH | |
| 1552 | 4-piperidinylethyl | 1 | 1 | n-propyloxy-carbonyl | OMe | |
| 1553 | 4-piperidinylethyl | 1 | 2 | n-butylsulfonyl | OH | |
| 1554 | 4-piperidinylethyl | 1 | 2 | (3-bromophenyl)-methylsulfonyl | OH | |
| 1555 | 4-piperidinylethyl | 2 | 1 | (3-methylphenyl)-methoxycarbonyl | OMe | |
| 1556 | 4-piperidinylethyl | 2 | 1 | 2-phenylethoxy-carbonyl | OH | |
| 1557 | 4-(N-benzylamid-ino)phenyl | 1 | 1 | n-butyloxycarbonyl | OH | |
| 1558 | 4-[N-(2-methyl-phenyl)-methyl-amidino]phenyl | 1 | 1 | 3-methylphenyl-sulfonyl | OH | |
| 1559 | 4-[N-(2-bromo-phenyl)-methyl-amidino]phenyl | 1 | 2 | 2-bromophenyl-sulfonyl | OH | |
| 1560 | 4-(N-butyl-amidino)phenyl | 2 | 1 | 3,5-dimethylpyra-zoylsulfonyl | OH | |
| 1561 | 4-[N-(2-methoxyphenyl)-methyl-amidino]phenyl | 2 | 1 | 3-methylphenyl-sulfonyl | OH | |
| 1562 | 4-[N-(3-[trifluoro-methyl]phen-yl)methyl-amidino]phenyl | 2 | 1 | 2,5-dimethyl-thiazolylsulfonyl | OH | |
| 1563 | 4-amidino-2-fluorophenyl | 1 | 1 | 3-methylphenyl-sulfonyl | OH | |
| 1564 | 4-amidino-2-fluorophenyl | 1 | 2 | i-butylamino-sulfonyl | OH | |
| 1565 | 4-amidino-2-fluorophenyl | 2 | 1 | 3,5-dimethylisoxa-zoylsulfonyl | OH | |
| 1566 | 5-amidino-2-pyridyl | 1 | 1 | n-butyloxycarbonyl | OMe | |
| 1567 | 5-amidino-2-pyridyl | 1 | 2 | 2-methylphenyl-sulfonyl | OH | |
| 1568 | 5-amidino-2-pyridyl | 1 | 2 | 3-methylphenyl-sulfonyl | OMe | |
| 1569 | 5-amidino-2-pyridyl | 2 | 1 | n-butylsulfonyl | OH | |
| 1570 | 5-amidino-2-pyridyl | 2 | 1 | 3,5-dimethylisoxa-zoylsulfonyl | OH | |
| 1571 | 2-amidino-5-pyridyl | 1 | 1 | 2-bromophenyl-sulfonyl | OH | |
| 1572 | 2-amidino-5-pyridyl | 1 | 1 | 2-(trifluoromethyl)-phenylsulfonyl | OMe | |

TABLE 8-continued

R¹—V—[spiro isoxazoline structure with (CH₂)p1, (CH₂)p2, N-CH₂-CH(NHR¹⁶)-COY]

| Ex. No. | R¹—V | p¹ | p² | R¹⁶ | Y | MS M + H |
|---|---|---|---|---|---|---|
| 1573 | 2-amidino-5-pyridyl | 1 | 2 | n-propylaminocarbonyl | OMe | |
| 1574 | 2-amidino-5-pyridyl | 1 | 2 | 4-methylphenylsulfonyl | OH | |
| 1575 | 2-amidino-5-pyridyl | 2 | 1 | 2-fluorophenylsulfonyl | OH | |

TABLE 9

R¹—V—[isoxazoline]—CH₂—C(O)—NH—CH₂—CH(NHR¹⁶)—C(O)Y

| Example Number | R¹-V | R¹⁶ | Y | MS (M + H)⁺ |
|---|---|---|---|---|
| 1585 | 4-piperidinylethyl | n-butyloxycarbonyl | OMe | 441 |
| 1585A | 4-piperidinylmethyl | n-butyloxycarbonyl | OH | 427 |
| 1586 | 4-piperidinylethyl | benzyloxycarbonyl | OMe | |
| 1587 | 4-piperidinylethyl | n-propyloxycarbonyl | OMe | |
| 1588 | 4-piperidinylethyl | isobutyloxycarbonyl | OMe | |
| 1589 | 4-piperidinylethyl | 2-methylphenylsulfonyl | OMe | |
| 1590 | 4-piperidinylethyl | 3-methylphenylsulfonyl | OMe | |
| 1591 | 4-piperidinylethyl | 4-methylphenylsulfonyl | OMe | |
| 1592 | 4-piperidinylethyl | 2-bromophenylsulfonyl | OMe | |
| 1593 | 4-piperidinylethyl | 3-bromophenylsulfonyl | OMe | |
| 1594 | 4-piperidinylethyl | 2-methoxyphenylsulfonyl | OMe | |
| 1595 | 4-piperidinylethyl | 3-methoxyphenylsulfonyl | OMe | |
| 1596 | 4-piperidinylethyl | 3-trifluoromethylphenylsulfonyl | OMe | |
| 1597 | 4-piperidinylethyl | n-propylsulfonyl | OMe | |
| 1598 | 4-piperidinylethyl | n-butylsulfonyl | OMe | |
| 1599 | 4-piperidinylethyl | isopropylsulfonyl | OMe | |
| 1600 | 4-piperidinylethyl | isobutylsulfonyl | OMe | |
| 1601 | 4-piperidinylethyl | 3,5-dimethylisoxazolylsulfonyl | OMe | |
| 1602 | 4-piperidinylethyl | 2,4-dimethylthiazolylsulfonyl | OMe | |
| 1603 | 4-piperidinylpropyl | n-butyloxycarbonyl | OMe | 455 |
| 1604 | 4-piperidinylpropyl | n-propyloxycarbonyl | OMe | |
| 1605 | 4-piperidinylpropyl | benzyloxycarbonyl | OMe | |
| 1606 | 4-piperidinylpropyl | isobutyloxycarbonyl | OMe | |
| 1607 | 4-piperidinylpropyl | 2-methylphenylsulfonyl | OMe | |
| 1608 | 4-piperidinylpropyl | 3-methylphenylsulfonyl | OMe | |
| 1609 | 4-piperidinylpropyl | 4-methylphenylsulfonyl | OMe | 509 |
| 1610 | 4-piperidinylpropyl | 2-bromophenylsulfonyl | OMe | |
| 1611 | 4-piperidinylpropyl | n-butylsulfonyl | OMe | |
| 1612 | 4-piperidinylpropyl | isobutylsulfonyl | OMe | |
| 1613 | 4-piperidinylpropyl | 3,5-dimethylisoxazolylsulfonyl | OMe | |
| 1614 | 4-piperidinylpropyl | 2,4-dimethylthiazoylsulfonyl | OMe | |
| 1615 | 4-piperidinylethyl | n-butyloxycarbonyl | OH | |
| 1616 | 4-piperidinylethyl | n-propyloxycarbonyl | OH | |

TABLE 9-continued

| Example Number | R¹-V | R¹⁶ | Y | MS (M + H)⁺ |
|---|---|---|---|---|
| 1617 | 4-piperidinylethyl | benyloxycarbonyl | OH | |
| 1618 | 4-piperidinylethyl | isobutyloxycarbonyl | OH | |
| 1619 | 4-piperidinylethyl | 2-methylphenyl-sulfonyl | OH | 481 |
| 1620 | 4-piperidinylethyl | 3-methylphenyl-sulfonyl | OH | 481 |
| 1621 | 4-piperidinylethyl | 4-methylphenyl-sulfonyl | OH | 481 |
| 1622 | 4-piperidinylethyl | 2-bromophenylsulfonyl | OH | 545 |
| 1623 | 4-piperidinylethyl | 3,5-dimethyl-isoxazolylsulfonyl | OH | 486 |
| 1624 | 4-piperidinylethyl | 2,4-dimethyl-thiazolylsulfonyl | OH | 502 |
| 1625 | 4-piperidinylethyl | n-butylsulfonyl | OH | 447 |
| 1626 | 4-piperidinylethyl | isobutylsulfonyl | OH | |
| 1627 | 4-piperidinylpropyl | n-butyloxycarbonyl | OH | 441 |
| 1628 | 4-piperidinylpropyl | n-propyloxycarbonyl | OH | |
| 1629 | 4-piperidinylpropyl | isobutyloxycarbonyl | OH | |
| 1630 | 4-piperidinylpropyl | 2-methylphenyl-carbonyl | OH | |
| 1631 | 4-piperidinylpropyl | 4-methylphenyl-carbonyl | OH | 495 |
| 1632 | 4-piperidinylpropyl | 2-bromophenyl-carbonyl | OH | |
| 1633 | 4-piperidinylpropyl | 3,5-dimethyl-isoxazolylsulfonyl | OH | |
| 1634 | 4-piperidinylpropyl | n-butylsulfonyl | OH | |
| 1635 | 4-piperidinylpropyl | isobutylsulfonyl | OH | |
| 1636 | 4-amidinopiperidinyl | n-butyloxycarbonyl | OMe | |
| 1637 | 4-amidinopiperidinyl | isobutyloxycarbonyl | OMe | |
| 1638 | 4-amidinopiperidinyl | n-propyloxycarbonyl | OMe | |
| 1639 | 4-amidinopiperidinyl | benzyloxycarbonyl | OMe | |
| 1640 | 4-amidinopiperidinyl | n-butylsulfonyl | OMe | |
| 1641 | 4-amidinopiperidinyl | isobutylsulfonyl | OMe | |
| 1642 | 4-amidinopiperidinyl | n-propylsulfonyl | OMe | |
| 1643 | 4-amidinopiperidinyl | 2-methylphenyl-sulfonyl | OMe | |
| 1644 | 4-amidinopiperidinyl | 4-methylphenyl-sulfonyl | OMe | |
| 1645 | 4-amidinopiperidinyl | benzylsulfonyl | OMe | |
| 1646 | 4-amidinopiperidinyl | 3,5-dimethyl-isoxazolylsulfonyl | OMe | |
| 1647 | 4-amidinopiperidinyl | 2,4-dimethyl-thiazolylsulfonyl | OMe | |
| 1648 | 4-amidinopiperidinyl | 4-methylphenyl-sulfonyl | OH | |
| 1649 | 4-amidinopiperidinyl | n-butyloxycarbonyl | OH | |
| 1650 | 4-amidinopiperidinyl | isobutyloxycarbonyl | OH | |
| 1651 | 4-amidinopiperidinyl | n-propyloxycarbonyl | OH | |
| 1652 | 4-amidinopiperidinyl | benzyloxycarbonyl | OH | |
| 1653 | 4-amidinopiperidinyl | n-butylsulfonyl | OH | |
| 1654 | 4-amidinopiperidinyl | isobutylsulfonyl | OH | |
| 1655 | 4-amidinopiperidinyl | 2-methylphenyl-sulfonyl | OH | |
| 1656 | 4-amidinopiperidinyl | 3-methylphenyl-sulfonyl | OH | 495 |
| 1657 | 4-amidinopiperidinyl | 4-methylphenyl-sulfonyl | OH | 495 |
| 1658 | 4-amidinopiperidinyl | 2-bromophenylsulfonyl | OH | |
| 1659 | 4-amidinopiperidinyl | 3-bromophenylsulfonyl | OH | |
| 1660 | 4-amidinopiperidinyl | 3,5-dimethyl-isoxazolylsulfonyl | OH | |
| 1661 | 4-amidinopiperidinyl | 2,4-dimethyl-thiazolylsulfonyl | OH | |
| 1662 | 4-amidino-piperidinylmethyl | n-butyloxycarbonyl | OMe | 427 |
| 1663 | 4-amidino-piperidinylmethyl | n-propyloxycarbonyl | OMe | |

TABLE 9-continued

Structure: R¹—V—[isoxazoline]—CH₂—C(O)—NH—CH(NHR¹⁶)—C(O)—Y

| Example Number | R¹-V | R¹⁶ | Y | MS (M + H)⁺ |
|---|---|---|---|---|
| 1664 | 4-amidino-piperidinylmethyl | benzyloxycarbonyl | OMe | |
| 1665 | 4-amidino-piperidinylmethyl | n-butylsulfonyl | OMe | |
| 1666 | 4-amidino-piperidinylmethyl | n-propylsulfonyl | OMe | |
| 1667 | 4-amidino-piperidinylmethyl | 2-methylphenyl-sulfonyl | OMe | |
| 1668 | 4-amidino-piperidinylmethyl | 3-methylphenyl-sulfonyl | OMe | |
| 1669 | 4-amidino-piperidinylmethyl | 4-methylphenyl-sulfonyl | OMe | |
| 1670 | 4-amidino-piperidinylmethyl | 2-bromophenylsulfonyl | OMe | |
| 1671 | 4-amidino-piperidinylmethyl | 3-bromophenylsulfonyl | OMe | |
| 1672 | 4-amidino-piperidinylmethyl | 3,5-dimethyl-isoxazolylsulfonyl | OMe | |
| 1673 | 4-amidino-piperidinylmethyl | 4-methylphenyl-sulfonyl | OH | 509 |
| 1674 | 4-amidino-piperidinylmethyl | n-butyloxycarbonyl | OH | |
| 1675 | 4-amidino-piperidinylmethyl | n-propyloxycarbonyl | OH | |
| 1676 | 4-amidino-piperidinylmethyl | benzyloxycarbonyl | OH | |
| 1677 | 4-amidino-piperidinylmethyl | n-butylsulfonyl | OH | |
| 1678 | 4-amidino-piperidinylmethyl | 2-methylphenyl-sulfonyl | OH | |
| 1679 | 4-amidino-piperidinylmethyl | 3-methylphenyl-sulfonyl | OH | |
| 1680 | 4-amidino-piperidinylmethyl | 2-bromophenyl-sulfonyl | OH | |
| 1681 | 4-amidino-piperidinylmethyl | 3-bromophenyl-sulfonyl | OH | |
| 1682 | 4-amidino-piperidinylmethyl | 3,5-dimethyl-isoxazolylsulfonyl | OH | |
| 1683 | 4-quinuclidinylethyl | n-butyloxycarbonyl | OH | |
| 1684 | 4-quinuclidinylethyl | n-propyloxycarbonyl | OH | |
| 1685 | 4-quinuclidinylethyl | benzyloxycarbonyl | OH | |
| 1686 | 4-quinuclidinylethyl | n-butylsulfonyl | OH | |
| 1687 | 4-quinuclidinylethyl | 2-methylphenyl-sulfonyl | OH | |
| 1688 | 4-quinuclidinylethyl | 4-methylphenyl-sulfonyl | OH | |
| 1689 | 4-quinuclidinylethyl | 2-bromophenylsulfonyl | OH | |
| 1690 | 4-quinuclidinylethyl | 3-bromophenylsulfonyl | OH | |
| 1691 | 4-quinuclidinylethyl | 3,5-dimethyl-isoxazolylsulfonyl | OH | |
| 1692 | guanidinopropyl | n-butyloxycarbonyl | OMe | |
| 1693 | guanidinopropyl | n-propyloxycarbonyl | OMe | |
| 1694 | guanidinopropyl | benzyloxycarbonyl | OH | 449 |
| 1695 | guanidinopropyl | n-butylsulfonyl | OMe | |
| 1696 | guanidinopropyl | 2-methylphenyl-sulfonyl | OMe | |
| 1697 | guanidinopropyl | 3-methylphenyl-sulfonyl | OMe | |
| 1698 | guanidinopropyl | 2-bromophenylsulfonyl | OMe | |
| 1699 | guanidinopropyl | 3-bromophenylsulfonyl | OMe | |
| 1700 | guanidinopropyl | 3,5-dimethyl-isoxazolylsulfonyl | OMe | |
| 1701 | guanidinopropyl | benzylsulfonyl | OMe | |
| 1702 | guanidinopropyl | styrylsulfonyl | OMe | |
| 1703 | guanidinopropyl | 2-benzothiophene-sulfonyl | OMe | |
| 1704 | guanidinopropyl | n-butyloxycarbonyl | OH | 529 |

TABLE 9-continued

| Example Number | R$^1$-V | R$^{16}$ | Y | MS (M + H)$^+$ |
|---|---|---|---|---|
| 1705 | guanidinopropyl | n-propyloxycarbonyl | OH | |
| 1706 | guanidinopropyl | benzyloxycarbonyl | OH | |
| 1707 | guanidinopropyl | n-butylsulfonyl | OH | |
| 1708 | guanidinopropyl | 2-methylphenyl-sulfonyl | OH | |
| 1709 | guanidinopropyl | 3-methylphenyl-sulfonyl | OH | |
| 1710 | guanidinopropyl | 4-methylphenyl-sulfonyl | OH | |
| 1711 | guanidinopropyl | 2-bromophenylsulfonyl | OH | |
| 1712 | guanidinopropyl | 3-bromophenylsulfonyl | OH | |
| 1713 | guanidinopropyl | 3,5-dimethyl-isoxazolylsulfonyl | OH | |
| 1714 | guanidinopropyl | 2,4-dimethyl-thiazolylsulfonyl | OH | |
| 1715 | guanidinopropyl | benzylsulfonyl | OH | |
| 1716 | guanidinopropyl | styrylsulfonyl | OH | |
| 1717 | guanidinopropyl | 2-benzothiophene-sulfonyl | OH | |
| 1718 | guanidinobutyl | n-butyloxycarbonyl | OH | |
| 1719 | guanidinobutyl | n-butylsulfonyl | OH | |
| 1720 | guanidinobutyl | phenylsulfonyl | OH | |
| 1721 | guanidinobutyl | 2-methylphenyl-sulfonyl | OH | |
| 1722 | guanidinobutyl | 4-methylphenyl-sulfonyl | OH | |
| 1723 | guanidinobutyl | 2-bromophenylsulfonyl | OH | |
| 1724 | guanidinobutyl | 3,5-dimethyl-isoxazolylsulfonyl | OH | |
| 1725 | guanidinobutyl | 2,4-dimethyl-thiazolylsulfonyl | OH | |
| 1726 | guanidinobutyl | benzylsulfonyl | OH | |
| 1727 | guanidinobutyl | styrylsulfonyl | OH | |
| 1728 | guanidinobutyl | 3-fluorophenyl-sulfonyl | OH | |
| 1729 | guanidinobutyl | n-butyloxycarbonyl | OMe | |
| 1730 | guanidinobutyl | n-butylsulfonyl | OMe | |
| 1731 | guanidinobutyl | benzyloxycarbonyl | OH | 463 |
| 1732 | guanidinobutyl | phenylsulfonyl | OMe | |
| 1733 | guanidinobutyl | 2-methylphenyl-sulfonyl | OMe | |
| 1734 | guanidinobutyl | 2-bromophenylsulfonyl | OMe | |
| 1735 | guanidinobutyl | 3-bromophenylsulfonyl | OMe | |
| 1736 | guanidinobutyl | 3,5-dimethyl-isoxazolyl sufonyl | OMe | |
| 1737 | guanidinobutyl | benzylsulfonyl | OMe | |
| 1738 | guanidinobutyl | n-butyloxycarbonyl | OH | |
| 1739 | guanidinobutyl | isobutyloxycarbonyl | OH | |
| 1740 | guanidinobutyl | n-propyloxycarbonyl | OH | |
| 1741 | guanidinobutyl | phenylsulfonyl | OH | |
| 1742 | guanidinobutyl | n-butylsulfonyl | OH | |
| 1743 | guanidinobutyl | 2-methylphenyl-sulfonyl | OH | |
| 1744 | guanidinobutyl | 3-methylphenyl-sulfonyl | OH | |
| 1745 | guanidinobutyl | 4-methylphenyl-sulfonyl | OH | |
| 1746 | guanidinobutyl | 2-bromophenylsulfonyl | OH | |
| 1747 | 4-piperidinylmethyl-aminocarbonyl | n-butyloxycarbonyl | OH | |
| 1748 | 4-piperidinylmethyl-amino-carbonyl | n-butyloxycarbonyl | OMe | |
| 1749 | 4-piperidinylmethyl-amino-carbonyl | benzyloxycarbonyl | OH | |
| 1750 | 4-piperidinylmethyl-amino-carbonyl | benzyloxycarbonyl | OMe | |

TABLE 9-continued

| Example Number | R¹-V | R¹⁶ | Y | MS (M + H)⁺ |
|---|---|---|---|---|
| 1751 | 4-piperidinylmethyl-amino-carbonyl | n-butylsulfonyl | OH | |
| 1752 | 4-piperidinylmethyl-amino-carbonyl | n-butylsulfonyl | OMe | |
| 1753 | 4-piperidinylmethyl-amino-carbonyl | 2-methylphenyl-sulfonyl | OH | |
| 1754 | 4-piperidinylmethyl-amino-carbonyl | 2-methylphenyl-sulfonyl | OMe | |
| 1755 | 4-piperidinylmethyl-amino-carbonyl | 3-methylphenyl-sulfonyl | OH | |
| 1756 | 4-piperidinylmethyl-amino-carbonyl | 4-methylphenyl-sulfonyl | OH | 510 |
| 1757 | 4-piperidinylmethyl-amino-carbonyl | 3-methylphenyl-sulfonyl | OMe | |
| 1758 | 4-piperidinylmethyl-amino-carbonyl | 3,5-dimethyl-isoxazolylsulfonyl | OH | |
| 1759 | 4-piperidinylmethyl-amino-carbonyl | 3,5-dimethyl-isoxazolylsulfonyl | OMe | |
| 1760 | N-(4-piperidinyl-methyl)-N-methyl-aminocarbonyl | n-butyloxycarbonyl | OH | |
| 1761 | N-(4-piperidinyl-methyl)-N-methyl-aminocarbonyl | n-butyloxycarbonyl | OMe | |
| 1762 | N-(4-piperidinyl-methyl)-N-methyl-aminocarbonyl | benzyloxycarbonyl | OH | |
| 1763 | N-(4-piperidinyl-methyl)-N-methyl-aminocarbonyl | benzyloxycarbonyl | OMe | |
| 1764 | N-(4-piperidinyl-methyl)-N-methyl-aminocarbonyl | n-butylsulfonyl | OH | |
| 1765 | N-(4-piperidinyl-methyl)-N-methylaminocarbonyl | n-butylsulfonyl | OMe | |
| 1766 | N-(4-piperidinyl-methyl)-N-methyl-aminocarbonyl | 2-methylphenyl-sulfonyl | OH | |
| 1767 | N-(4-piperidinyl-methyl)-N-methyl-aminocarbonyl | 2-methylphenyl-sulfonyl | OMe | |
| 1768 | N-(4-piperidinyl-methyl)-N-methyl-aminocarbonyl | 3-methylphenyl-sulfonyl | OH | |
| 1769 | N-(4-piperidinyl-methyl)-N-methyl-aminocarbonyl | 4-methylphenyl-sulfonyl | OH | 524 |
| 1770 | N-(4-piperidinyl-methyl)-N-methyl-aminocarbonyl | 3-methylphenyl-sulfonyl | OMe | |
| 1771 | N-(4-piperidinyl-methyl)-N-methyl-aminocarbonyl | 3,5-dimethyl-isoxazolylsulfonyl | OH | |
| 1772 | N-(4-piperidinyl-methyl)-N-methyl-aminocarbonyl | 3,5-dimethyl-isoxazolylsulfonyl | OMe | |
| 1773 | 4-piperidinyl-aminocarbonyl | n-butyloxycarbonyl | OH | |
| 1774 | 4-piperidinyl-aminocarbonyl | 4-methylphenyl-sulfonyl | OH | 496 |
| 1775 | 4-guanidinophenyl | 2-methylphenyl-sulfonyl | OH | |
| 1776 | 4-guanidinophenyl | 2-methylphenyl-sulfonyl | OMe | |
| 1777 | 4-guanidinophenyl | 2-bromophenylsulfonyl | OH | |
| 1778 | 4-guanidinophenyl | 2-bromophenylsulfonyl | OMe | |

TABLE 9-continued

Structure: R¹—V—[isoxazoline]—CH₂—C(=O)—NH—CH(NHR¹⁶)—C(=O)—Y

| Example Number | R¹-V | R¹⁶ | Y | MS (M + H)⁺ |
|---|---|---|---|---|
| 1779 | 4-guanidinophenyl | 3-methylphenylsulfonyl | OH | |
| 1780 | 4-guanidinophenyl | 3,5-dimethyl-isoxazolylsulfonyl | OH | |
| 1781 | 4-guanidinophenyl | 3,5-dimethyl-isoxazolylsulfonyl | OMe | |
| 1782 | 4-guanidinophenyl | 2,4-dimethyl-thiazolylsulfonyl | OH | |
| 1783 | 4-guanidinophenyl | 2,4-dimethyl-thiazolylsulfonyl | OMe | |
| 1784 | 4-guanidinophenyl | benzylsulfonyl | OH | |
| 1785 | 4-guanidinophenyl | benzylsulfonyl | OMe | |
| 1786 | 4-guanidinophenyl | styrylsulfonyl | OH | |
| 1787 | 4-guanidinophenyl | styrylsulfonyl | OMe | |
| 1788 | 4-guanidinophenyl | 2-benzothiophene-sulfonyl | OH | |
| 1789 | 3-guanidinophenyl | n-butyloxycarbonyl | OH | |
| 1790 | 3-guanidinophenyl | n-butyloxycarbonyl | OMe | |
| 1791 | 3-guanidinophenyl | n-propyloxycarbonyl | OH | |
| 1792 | 3-guanidinophenyl | 2-bromophenylsulfonyl | OH | |
| 1793 | 3-guanidinophenyl | 2-bromophenylsulfonyl | OMe | |
| 1794 | 3-guanidinophenyl | 2-methylphenyl-sulfonyl | OH | |
| 1795 | 3-guanidinophenyl | 4-methylphenyl-sulfonyl | OH | |
| 1796 | 3-guanidinophenyl | 4-methylphenyl-sulfonyl | OMe | |
| 1797 | 3-guanidinophenyl | n-butylsulfonyl | OH | |
| 1798 | 3-guanidinophenyl | n-butylsulfonyl | OMe | |
| 1799 | 3-guanidinophenyl | styrylsulfonyl | OH | |
| 1800 | 3-guanidinophenyl | benzyloxycarbonyl | OH | |
| 1801 | 3-guanidinophenyl | benzyloxycarbonyl | OMe | |
| 1802 | 4-amidinophenylmethyl | 2-methylphenyl-sulfonyl | OH | |
| 1803 | 4-amidinophenylmethyl | 2-methylphenyl-sulfonyl | OMe | |
| 1804 | 4-amidinophenylmethyl | phenylsulfonyl | OH | |
| 1805 | 4-amidinophenylmethyl | phenylsulfonyl | OMe | |
| 1806 | 4-amidinophenylmethyl | 3,5-dimethyl-isoxazolylsulfonyl | OH | |
| 1807 | 4-amidinophenylmethyl | 3,5-dimethyl-isoxazolylsulfonyl | OMe | |
| 1898 | 4-amidinophenylmethyl | 2,4-dimethyl-thiazolylsulfonyl | OH | |
| 1809 | 4-amidinophenylmethyl | 2,4-dimethyl-thiazolylsulfonyl | OMe | |
| 1810 | 4-amidinophenylmethyl | p-toluylsulfonyl | OH | |
| 1811 | 3-amidinophenylmethyl | n-butyloxycarbonyl | OH | |
| 1812 | 3-amidinophenylmethyl | n-butyloxycarbonyl | OMe | |
| 1813 | 3-amidinophenylmethyl | phenylsulfonyl | OH | |
| 1814 | 3-amidinophenylmethyl | phenylsulfonyl | OMe | |
| 1815 | 3-amidinophenylmethyl | 2-bromophenylsulfonyl | OH | |
| 1816 | 3-amidinophenylmethyl | 2-bromophenylsulfonyl | OMe | |
| 1817 | 3-amidinophenylmethyl | 2-methylphenyl-sulfonyl | OH | |
| 1818 | 3-amidinophenylmethyl | 2-methylphenyl-sulfonyl | OMe | |
| 1819 | 3-amidinophenylmethyl | 4-methylphenyl-sulfonyl | OH | |
| 1820 | 3-amidinophenylmethyl | 4-methylphenyl-sulfonyl | OMe | |
| 1821 | 3-amidinophenylmethyl | styrylsulfonyl | OH | |
| 1822 | 3-amidinophenylmethyl | styrylsulfonyl | OMe | |
| 1823 | 3-amidinophenylmethyl | benzyloxycarbonyl | OH | |
| 1824 | 3-amidinophenylmethyl | benzyloxycarbonyl | OMe | |
| 1825 | 3-amidinophenylmethyl | 3,5-dimethyl-isoxazolylsulfonyl | OH | |

TABLE 9-continued

| Example Number | R¹-V | R¹⁶ | Y | MS (M + H)⁺ |
|---|---|---|---|---|
| 1826 | 3-amidinophenylmethyl | 3,5-dimethyl-isoxazolylsulfonyl | OMe | |
| 1827 | 3-amidinophenylmethyl | 2,4-dimethyl-thiazolylsulfonyl | OH | |
| 1828 | 3-amidinophenylmethyl | benzylsulfonyl | OH | |
| 1829 | 4-pyridylethyl | n-benzyloxycarbonyl | OMe | |
| 1830 | 4-pyridylethyl | n-benzyloxycarbonyl | OH | |
| 1831 | 4-pyridylethyl | n-butyloxyoxycarbonyl | OMe | |
| 1832 | 4-pyridylethyl | n-butyloxyoxycarbonyl | OH | |
| 1833 | 4-pyridylethyl | 2-methylphenylsulfonyl | OH | |
| 1834 | 4-pyridylethyl | 2-methylphenyl-sulfonyl | OMe | |
| 1835 | 4-pyridylethyl | 2-bromophenylsulfonyl | OH | |
| 1836 | 4-pyridylethyl | 2-bromophenylsulfonyl | OMe | |
| 1837 | 4-pyridylethyl | 3-methylphenyl-sulfonyl | OH | |
| 1838 | 4-pyridylethyl | 3,5-dimethyl-isoxazolylsulfonyl | OH | |
| 1839 | 4-pyridylethyl | 3,5-dimethyl-isoxazolylsulfonyl | OMe | |
| 1840 | 4-pyridylethyl | 2,4-dimethyl-thiazolylsulfonyl | OH | |
| 1841 | 4-pyridylethyl | 2,4-dimethyl-thiazolylsulfonyl | OMe | |
| 1842 | 4-pyridylethyl | benzylsulfonyl | OH | |
| 1843 | 4-pyridylethyl | styrylsulfonyl | OH | |
| 1844 | 4-pyridylethyl | styrylsulfonyl | OMe | |
| 1845 | 4-pyridylethyl | 2-benzothiophene-sulfonyl | OH | |
| 1846 | 3-pyridylethyl | n-benzyloxycarbonyl | OMe | |
| 1847 | 3-pyridylethyl | n-benzyloxycarbonyl | OH | |
| 1848 | 3-pyridylethyl | n-butyloxyoxycarbonyl | OMe | |
| 1849 | 3-pyridylethyl | n-butyloxyoxycarbonyl | OH | |
| 1850 | 3-pyridylethyl | 2-methylphenyl-sulfonyl | OH | |
| 1851 | 3-pyridylethyl | 2-methylphenyl-sulfonyl | OMe | |
| 1852 | 3-pyridylethyl | 2-bromophenylsulfonyl | OH | |
| 1853 | 3-pyridylethyl | 2-bromophenylsulfonyl | OMe | |
| 1854 | 3-pyridylethyl | 3-methylphenyl-sulfonyl | OH | |
| 1855 | 3-pyridylethyl | 3,5-dimethyl-isoxazolylsulfonyl | OH | |
| 1856 | 3-pyridylethyl | 3,5-dimethyl-isoxazolylsulfonyl | OMe | |
| 1857 | 3-pyridylethyl | 2,4-dimethyl-thiazolylsulfonyl | OH | |
| 1858 | 3-pyridylethyl | 2,4-dimethyl-thiazolylsulfonyl | OMe | |
| 1859 | 3-pyridylethyl | benzylsulfonyl | OH | |
| 1860 | 3-pyridylethyl | styrylsulfonyl | OH | |
| 1861 | 3-pyridylethyl | styrylsulfonyl | OMe | |
| 1862 | 3-pyridylethyl | 2-benzothiophene-sulfonyl | OH | |
| 1863 | 2-amino-4-pyridylethyl | n-benzyloxycarbonyl | OMe | |
| 1864 | 2-amino-4-pyridylethyl | n-benzyloxycarbonyl | OH | |
| 1865 | 2-amino-4-pyridylethyl | n-butyloxyoxycarbonyl | OMe | |
| 1866 | 2-amino-4-pyridylethyl | n-butyloxyoxycarbonyl | OH | |
| 1867 | 2-amino-4-pyridylethyl | 2-methylphenyl-sulfonyl | OH | |
| 1868 | 2-amino-4-pyridylethyl | 2-methylphenyl sulfonyl | OMe | |
| 1869 | 2-amino-4-pyridylethyl | 2-bromophenylsulfonyl | OH | |
| 1870 | 2-amino-4-pyridylethyl | 2-bromophenylsulfonyl | OMe | |
| 1871 | 2-amino-4-pyridylethyl | 3-methylphenyl-sulfonyl | OH | |

TABLE 9-continued

[Structure with R¹—V, isoxazoline ring, NH, NHR¹⁶, and Y substituents]

| Example Number | R¹-V | R¹⁶ | Y | MS (M + H)⁺ |
|---|---|---|---|---|
| 1872 | 2-amino-4-pyridylethyl | 3,5-dimethyl-isoxazolylsulfonyl | OH | |
| 1873 | 2-amino-4-Pyridylethyl | 3,5-dimethyl-isoxazolylsulfonyl | OMe | |
| 1874 | 2-amino-4-pyridylethyl | 2,4-dimethyl-thiazolylsulfonyl | OH | |
| 1875 | 2-amino-4-pyridylethyl | 2,4-dimethyl-thiazolylsulfonyl | OMe | |
| 1876 | 2-amino-4-pyridylethyl | benzylsulfonyl | OH | |
| 1877 | 2-amino-4-pyridylethyl | benzylsulfonyl | OMe | |
| 1878 | 2-amino-4-pyridylethyl | styrylsulfonyl | OH | |
| 1879 | 2-amino-4-pyridylethyl | styrylsulfonyl | OMe | |
| 1880 | 2-amino-4-pyridylethyl | 2-benzothiophene-sulfonyl | OH | |
| 1881 | 6-amino-3-pyridylethyl | n-benzyloxycarbonyl | OMe | |
| 1882 | 6-amino-3-pyridylethyl | n-benzyloxycarbonyl | OH | |
| 1883 | 6-amino-3-pyridylethyl | n-butyloxyoxycarbonyl | OMe | |
| 1884 | 6-amino-3-pyridylethyl | n-butyloxyoxycarbonyl | OH | |
| 1885 | 6-amino-3-pyridylethyl | 2-methylphenyl-sulfonyl | OH | |
| 1886 | 6-amino-3-pyridylethyl | 2-methylphenyl-sulfonyl | OMe | |
| 1887 | 6-amino-3-pyridylethyl | 2-bromophenylsulfonyl | OH | |
| 1888 | 6-amino-3-pyridylethyl | 2-bromophenylsulfonyl | OMe | |
| 1889 | 6-amino-3-pyridylethyl | 3-methylphenyl-sulfonyl | OH | |
| 1890 | 6-amino-3-pyridylethyl | 3,5-dimethyl-isoxazolylsulfonyl | OH | |
| 1891 | 6-amino-3-pyridylethyl | 3,5-dimethyl-isoxazolylsulfonyl | OMe | |
| 1892 | 6-amino-3-pyridylethyl | 2,4-dimethyl-thiazolylsulfonyl | OH | |
| 1893 | 6-amino-3-pyridylethyl | 2,4-dimethyl-thiazolylsulfonyl | OMe | |
| 1894 | 6-amino-3-pyridylethyl | benzylsulfonyl | OH | |
| 1895 | 6-amino-3-pyridylethyl | benzylsulfonyl | OMe | |
| 1896 | 6-amino-3-pyridylethyl | styrylsulfonyl | OH | |
| 1897 | 6-amino-3-pyridylethyl | styrylsulfonyl | OMe | |
| 1898 | 6-amino-4-pyridylethyl | 2-benzothiophene-sulfonyl | OH | |
| 1899 | 2-amidino-4-pyridylethyl | n-benzyloxycarbonyl | OMe | |
| 1900 | 2-amidino-4-pyridylethyl | n-benzyloxycarbonyl | OH | |
| 1901 | 2-amidino-4-pyridylethyl | n-butyloxyoxycarbonyl | OMe | |
| 1902 | 2-amidino-4-pyridylethyl | n-butyloxyoxycarbonyl | OH | |
| 1903 | 2-amidino-4-pyridylethyl | 2-methylphenyl-sulfonyl | OH | |
| 1904 | 2-amidino-4-pyridylethyl | 2-methylphenyl-sulfonyl | OMe | |
| 1905 | 2-amidino-4-pyridylethyl | 2-bromophenylsulfonyl | OH | |
| 1906 | 2-amidino-4-pyridylethyl | 2-bromophenylsulfonyl | OMe | |
| 1907 | 2-amidino-4-pyridylethyl | 3-methylphenyl-sulfonyl | OH | |
| 1908 | 2-amidino-4-pyridylethyl | 3,5-dimethyl-isoxazolylsulfonyl | OH | |
| 1909 | 2-amidino-4-pyridylethyl | 3,5-dimethyl-isoxazolylsulfonyl | OMe | |
| 1910 | 2-amidino-4-pyridylethyl | 2,4-dimethyl-thiazolylsulfonyl | OH | |
| 1911 | 2-amidino-4-pyridylethyl | 2,4-dimethyl-thiazolylsulfonyl | OMe | |
| 1912 | 2-amidino-4-pyridylethyl | benzylsulfonyl | OH | |
| 1913 | 2-amidino-4-pyridylethyl | benzylsulfonyl | OMe | |
| 1914 | 2-amidino-4-pyridylethyl | styrylsulfonyl | OH | |
| 1915 | 2-amidino-4-pyridylethyl | styrylsulfonyl | OMe | |
| 1916 | 2-amidino-4-pyridylethyl | 2-benzothiophene-sulfonyl | OH | |
| 1917 | 6-amidino-3-pyridylethyl | n-benzyloxycarbonyl | OMe | |

TABLE 9-continued

Structure: R¹—V—[isoxazoline]—CH₂—C(O)—NH—CH(CH₂NHR¹⁶)—C(O)—Y

| Example Number | R¹-V | R¹⁶ | Y | MS (M + H)⁺ |
|---|---|---|---|---|
| 1918 | 6-amidino-3-pyridylethyl | n-benzyloxycarbonyl | OH | |
| 1919 | 6-amidino-3-pyridylethyl | n-butyloxyoxycarbonyl | OMe | |
| 1920 | 6-amidino-3-pyridylethyl | n-butyloxyoxycarbonyl | OH | |
| 1921 | 6-amidino-3-pyridylethyl | 2-methylphenyl-sulfonyl | OH | |
| 1922 | 6-amidino-3-pyridylethyl | 2-methylphenyl- | OMe | |
| 1923 | 6-amidino-3-pyridylethyl | 2-bromophenylsulfonyl | OH | |
| 1924 | 6-amidino-3-pyridylethyl | 2-bromophenylsulfonyl | OMe | |
| 1925 | 6-amidino-3-pyridylethyl | 3-methylphenyl-sulfonyl | OH | |
| 1926 | 6-amidino-3-pyridylethyl | 3,5-dimethyl-isoxazolylsulfonyl | OH | |
| 1927 | 6-amidino-3-pyridylethyl | 3,5-dimethyl-isoxazolylsulfonyl | OMe | |
| 1928 | 6-amidino-3-pyridylethyl | 2,4-dimethyl-thiazolylsulfonyl | OH | |
| 1929 | 6-amidino-3-pyridylethyl | 2,4-dimethyl-thiazolylsulfonyl | OMe | |
| 1930 | 6-amidino-3-pyridylethyl | benzylsulfonyl | OH | |
| 1931 | 6-amidino-3-pyridylethyl | benzylsulfonyl | Me | |
| 1932 | 6-amidino-3-pyridylethyl | styrylsulfonyl | OH | |
| 1933 | 6-amidino-3-pyridylethyl | styrylsulfonyl | OMe | |
| 1934 | 6-amidino-3-pyridylethyl | 2-benzothiophene-sulfonyl | OH | |
| 1935 | 4-amidino-2-fluoro-phenyl | 2-methylphenylsulfonyl | OH | |
| 1936 | 4-amidino-2-fluoro-phenyl | 3,5-dimethylisoxazolyl-sulfonyl | OH | |
| 1937 | 2-amidino-5-pyridyl | 2-methylphenylsulfonyl | OH | |
| 1938 | 2-amidino-5-pyridyl | 2-bromophenylsulfonyl | OH | |
| 1939 | 2-amidino-5-pyridyl | i-butyloxycarbonyl | OMe | |
| 1940 | 2-amidino-5-pyridyl | 3,5-dimethylisoxazolyl-sulfonyl | OH | |
| 1941 | 3-amidino-6-pyridyl | 2-methylphenylsulfonyl | OH | |
| 1942 | 3-amidino-6-pyridyl | 2-bromophenylsulfonyl | OMe | |
| 1943 | 3-amidino-6-pyridyl | 2,5-dimethylthiazolyl-sulfonyl | OH | |
| 1944 | 3-amidino-6-pyridyl | 3,5-dimethylisoxazolyl-sulfonyl | OH | |
| 1945 | 4-piperidinylethyl | 3-methylphenylsulfonyl | OH | 481 |
| 1946 | 4-(N-2-methoxybenzyl)-amidinophenyl HCl | 2-methylphenylsulfonyl | OMe | 622.3 |
| 1947 | 4-(N-2-methoxybenzyl)-amidinophenyl TFA | 2-methylphenylsulfonyl | OH | 608.3 |
| 1948 | 4-(N-n-butyl)-amidinophenyl | 2-methylphenylsulfonyl | OMe | 558.4 |
| 1949 | 4-(N-n-butyl)-amidinophenyl | 2-methylphenylsulfonyl | OH | 544.4 |
| 1950 | 4-(N-ethyl)-amidinophenyl | 2-methylphenylsulfonyl | OMe | 530.3 |
| 1951 | 4-(N-ethyl)-amidinophenyl | 2-methylphenylsulfonyl | OH | 516.3 |
| 1952 | 4-amidinophenoxymethyl | benzyloxycarbonyl | OMe | |
| 1953 | 4-amidinophenoxymethyl | benzyloxycarbonyl | OH | |
| 1954 | 4-amidinophenoxymethyl | n-butyloxycarbonyl | OMe | |
| 1955 | 4-amidinophenoxymethyl | n-butyloxycarbonyl | OH | |
| 1956 | 4-amidinophenoxymethyl | cyclopropylethoxy carbonyl | OMe | |
| 1957 | 4-amidinophenoxymethyl | cyclopropylethoxy carbonyl | OH | |
| 1958 | 4-amidinophenoxymethyl | 4-methylphenylsulfonyl | OMe | |
| 1959 | 4-amidinophenoxymethyl | 4-methylphenylsulfonyl | OH | |
| 1960 | 4-amidinophenoxymethyl | 3-methylphenylsulfonyl | OMe | |
| 1961 | 4-amidinophenoxymethyl | 3-methylphenylsulfonyl | OH | |
| 1962 | 4-amidinophenoxymethyl | n-butylsulfonyl | OMe | |
| 1963 | 4-amidinophenoxymethyl | n-butylsulfonyl | OH | |
| 1964 | 4-amidinophenoxy | benzyloxycarbonyl | OMe | |

TABLE 9-continued

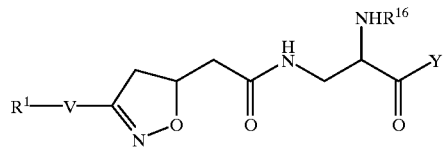

| Example Number | R¹—V | R¹⁶ | Y | MS (M + H)⁺ |
|---|---|---|---|---|
| 1965 | 4-amidinophenoxy | benzyloxycarbonyl | OH | |
| 1967 | 4-amidinophenoxy | n-butyloxycarbonyl | OMe | |
| 1968 | | | | |
| 1969 | 4-amidinophenoxy | n-butyloxycarbonyl | OH | |
| 1970 | 4-amidinophenoxy | cyclopropylethyoxy carbonyl | OHe | |
| 1971 | 4-amidinophenoxy | cyclopropylethoxy carbonyl | OH | |
| 1972 | 4-amidinophenoxy | 4-methylphenylsulfonyl | OMe | |
| 1973 | 4-amidinophenoxy | 4-methylphenylsulfonyl | OH | |
| 1974 | 4-amidinophenoxy | 3-methylphenylsulfonyl | OMe | |
| 1975 | 4-amidinophenoxy | 3-methylphenylsulfonyl | OH | |
| 1976 | 4-amidinophenoxy | n-butylsulfonyl | OMe | |
| 1977 | 4-amidinophenoxy | n-butylsulfonyl | OH | |
| 1978 | 4-amidinophenethyl | benzyloxycarbonyl | OMe | |
| 1979 | 4-amidinophenethyl | benzyloxycarbonyl | OH | |
| 1980 | 4-amidinophenethyl | n-butyloxycarbonyl | OMe | |
| 1981 | 4-amidinophenethyl | n-butyloxycarbonyl | OH | |
| 1982 | 4-amidinophenethyl | cyclopropylethoxy carbonyl | OMe | |
| 1983 | 4-amidinophenethyl | cyclopropylethoxy carbonyl | OH | |
| 1984 | 4-amidinophenethyl | 4-methylphenylsulfonyl | OMe | |
| 1985 | 4-amidinophenethyl | 4-methylphenylsulfonyl | OH | |
| 1986 | 4-amidinophenethyl | 3-methylphenylsulfonyl | OMe | |
| 1987 | 4-amidinophenethyl | 3-methylphenylsulfonyl | OH | |
| 1988 | 4-amidinophenethyl | n-butylsulfonyl | OMe | |
| 1989 | 4-amidinophenethyl | n-butylsulfonyl | OH | |
| 1990 | N-(4-amidinophenyl) aminomethyl | benzyloxycarbonyl | OMe | |
| 1991 | N-(4-amidinophenyl) aminomethyl | benzyloxycarbonyl | OH | |
| 1993 | N-(4-amidinophenyl) aminomethyl | n-butyloxycarbonyl | OMe | |
| 1994 | N-(4-amidinophenyl) aminomethyl | n-butyloxycarbonyl | OH | |
| 1995 | N-(4-amidinophenyl) aminomethyl | cyclopropylethoxy carbonyl | OH | |
| 1996 | N-(4-amidinophenyl) aminomethyl | 4-methylphenylsulfonyl | OMe | |
| 1997 | N-(4-amidinophenyl) aminomethyl | 4-methylphenylsulfonyl | OH | |
| 1998 | N-(4-amidinophenyl) aminomethyl | 3-methylphenylsulfonyl | OMe | |
| 1999 | N-(4-amidinophenyl) aminomethyl | 3-methylphenylsulfonyl | OH | |
| 2000 | N-(4-amidinophenyl) aminomethyl | n-butylsulfonyl | OMe | |
| 2001 | N-(4-amidinophenyl) aminomethyl | n-butylsulfonyl | OH | |
| 2002 | 4-amidinophenyl methylamino | benzyloxycarbonyl | OMe | |
| 2003 | 4-amidinophenyl methylamino | benzyloxycarbonyl | OH | |
| 2004 | 4-amidinophenyl methylamino | n-butyloxycarbonyl | OMe | |
| 2005 | 4-amidinophenyl methylamino | n-butyloxycarbonyl | OH | |
| 2006 | 4-amidinophenyl methylamino | cyclopropylethoxy carbonyl | OMe | |
| 2007 | 4-amidinophenyl methylamino | cyclopropylethoxy carbonyl | OH | |
| 2008 | 4-amidinophenyl methylamino | 4-methylphenylsulfonyl | OMe | |
| 2010 | 4-amidinophenyl methylamino | 4-methylphenylsulfonyl | OH | |

TABLE 9-continued

Structure: R¹—V—[isoxazoline]—CH$_2$—C(=O)—NH—CH(CH$_2$NHR$^{16}$)—C(=O)—Y

| Example Number | R¹-V | R¹⁶ | Y | MS (M + H)⁺ |
|---|---|---|---|---|
| 2011 | 4-amidinophenyl methylamino | 3-methylphenylsulfonyl | OMe | |
| 2012 | 4-amidinophenyl methylamino | n-butylsulfonyl | OMe | |
| 2013 | 4-amidinophenyl methylamino | n-butylsulfonyl | OH | |
| 2014 | N-(4-amidinophenyl) aminocarbonyl | benzyloxycarbonyl | OMe | |
| 2015 | N-(4-amidinophenyl) aminocarbonyl | benzyloxycarbonyl | OH | |
| 2016 | N-(4-amidinophenyl) aminocarbonyl | n-butyloxycarbonyl | OMe | |
| 2017 | N-(4-amidinophenyl) aminocarbonyl | n-butyloxycarbonyl | OH | |
| 2018 | N-(4-amidinophenyl) aminocarbonyl | cyclopropylethoxy carbonyl | OMe | |
| 2019 | N-(4-amidinophenyl) aminocarbonyl | cyclopropylethoxy carbonyl | OH | |
| 2020 | N-(4-amidinophenyl) aminocarbonyl | 4-methylphenylsulfonyl | OMe | |
| 2021 | N-(4-amidinophenyl) aminocarbonyl | 4-methylphenylsulfonyl | OH | |
| 2022 | N-(4-amidinophenyl) aminocarbonyl | 3-methylphenylsulfonyl | OMe | |
| 2023 | N-(4-amidinophenyl) aminocarbonyl | 3-methylphenylsulfonyl | OH | |
| 2024 | N-(4-amidinophenyl) aminocarbonyl | n-butylsulfonyl | OMe | |
| 2025 | N-(4-amidinophenyl) aminocarbonyl | n-butylsulfonyl | OH | |
| 2027 | 4-amidinophenyl carbonylamino | benzyloxycarbonyl | OMe | |
| 2028 | 4-amidinophenyl carbonylamino | benzyloxycarbonyl | OH | |
| 2029 | 4-amidinophenyl carbonylamino | n-butyloxycarbonyl | OMe | |
| 2030 | 4-amidinophenyl carbonylamino | n-butyloxycarbonyl | OH | |
| 2031 | 4-amidinophenyl carbonylamino | cyclopropylethoxy carbonyl | OMe | |
| 2032 | 4-amidinophenyl carbonylamino | cyclopropylethoxy carbonyl | OH | |
| 2033 | 4-amidinophenyl carbonylamino | 4-methylphenylsulfonyl | OMe | |
| 2034 | 4-amidinophenyl carbonylamino | 4-methylphenylsulfonyl | OH | |
| 2035 | 4-amidinophenyl carbonylamino | 3-methylphenylsulfonyl | OMe | |
| 2036 | 4-amidinophenyl carbonylamino | 3-methylphenylsulfonyl | OH | |
| 2037 | 4-amidinophenyl carbonylamino | n-butylsulfonyl | OMe | |
| 2038 | 4-amidinophenyl carbonylamino | n-butylsulfonyl | OH | |
| 2039 | N-(4-amidinophenyl) amino | benzyloxycarbonyl | OMe | |
| 2040 | N-(4-amidinophenyl) amino | benzyloxycarbonyl | OH | |
| 2041 | N-(4-amidinophenyl) amino | n-butyloxycarbonyl | OMe | |
| 2042 | N-(4-amidinophenyl) amino | n-butyloxycarbonyl | OH | |
| 2044 | N-(4-amidinophenyl) amino | cyclopropylethoxy carbonyl | OMe | |
| 2045 | N-(4-amidinophenyl) amino | cyclopropylethoxy carbonyl | OH | |

TABLE 9-continued

| Example Number | R¹-V | R¹⁶ | Y | MS (M + H)⁺ |
|---|---|---|---|---|
| 2046 | N-(4-amidinophenyl)amino | 4-methylphenylsulfonyl | OMe | |
| 2047 | N-(4-amidinophenyl)amino | 4-methylphenylsulfonyl | OH | |
| 2048 | N-(4-amidinophenyl)amino | 3-methylphenylsulfonyl | OMe | |
| 2049 | N-(4-amidinophenyl)amino | 3-methylphenylsulfonyl | OH | |
| 2050 | N-(4-amidinophenyl)amino | n-butylsulfonyl | OMe | |
| 2051 | N-(4-amidinophenyl)amino | n-butylsulfonyl | OH | |
| 2052 | N-(4-amidinophenyl)-N-methylamino | benzyloxycarbonyl | OMe | |
| 2053 | N-(4-amidinophenyl)-N-methylamino | benzyloxycarbonyl | OH | |
| 2054 | N-(4-amidinophenyl)-N-methylamino | n-butyloxycarbonyl | OMe | |
| 2055 | N-(4-amidinophenyl)-N-methylamino | n-butyloxycarbonyl | OH | |
| 2056 | N-(4-amidinophenyl)-N-methylamino | cyclopropylethoxycarbonyl | OMe | |
| 2057 | N-(4-amidinophenyl)-N-methylamino | cyclopropylethoxycarbonyl | OH | |
| 2058 | N-(4-amidinophenyl)-N-methylamino | 4-methylphenylsulfonyl | OMe | |
| 2059 | N-(4-amidinophenyl)-N-methylamino | 4-methylphenylsulfonyl | OH | |
| 2061 | N-(4-amidinophenyl)-N-methylamino | 3-methylphenylsulfonyl | OMe | |
| 2062 | N-(4-amidinophenyl)-N-methylamino | 3-methylphenylsulfonyl | OH | |
| 2063 | N-(4-amidinophenyl)-N-methylamino | n-butylsulfonyl | OMe | |
| 2064 | N-(4-amidinophenyl)-N-methylamino | n-butylsulfonyl | OH | |
| 2065 | 4-amidinobenzoyl | benzyloxycarbonyl | OMe | |
| 2066 | 4-amidinobenzoyl | benzyloxycarbonyl | OH | |
| 2067 | 4-amidinobenzoyl | n-butyloxycarbonyl | OMe | |
| 2068 | 4-amidinobenzoyl | n-butyloxycarbonyl | OH | |
| 2069 | 4-amidinobenzoyl | cyclopropylethoxycarbonyl | OMe | |
| 2070 | 4-amidinobenzoyl | cyclopropylethoxycarbonyl | OH | |
| 2071 | 4-amidinobenzoyl | 4-methylphenylsulfonyl | OMe | |
| 2072 | 4-amidinobenzoyl | 4-methylphenylsulfonyl | OH | |
| 2073 | 4-amidinobenzoyl | 3-methylphenylsulfonyl | OMe | |
| 2074 | 4-amidinobenzoyl | 3-methylphenylsulfonyl | OH | |
| 2075 | 4-amidinobenzoyl | n-butylsulfonyl | OMe | |
| 2076 | 4-amidinobenzoyl | n-butylsulfonyl | OH | |
| 2077 | 4-amidinophenylmethylcarbonyl | benzyloxycarbonyl | OMe | |
| 2078 | 4-amidinophenylmethylcarbonyl | benzyloxycarbonyl | OH | |
| 2079 | 4-amidinophenylmethylcarbonyl | n-butyloxycarbonyl | OMe | |
| 2080 | 4-amidinophenylmethylcarbonyl | n-butyloxycarbonyl | OH | |
| 2081 | 4-amidinophenylmethylcarbonyl | cyclopropylethoxycarbonyl | OMe | |
| 2083 | 4-amidinophenylmethylcarbonyl | cyclopropylethoxycarbonyl | OH | |
| 2084 | 4-amidinophenylmethylcarbonyl | 4-methylphenylsulfonyl | OMe | |
| 2085 | 4-amidinophenylmethylcarbonyl | 4-methylphenylsulfonyl | OH | |

TABLE 9-continued

Structure: R¹—V—[isoxazoline]—CH₂—C(=O)—NH—CH(NHR¹⁶)—C(=O)—Y

| Example Number | R¹-V | R¹⁶ | Y | MS (M + H)⁺ |
|---|---|---|---|---|
| 2086 | 4-amidinophenyl methylcarbonyl | 3-methylphenylsulfonyl | OMe | |
| 2087 | 4-amidinophenyl methylcarbonyl | 3-methylphenylsulfonyl | OH | |
| 2088 | 4-amidinophenyl methylcarbonyl | n-butylsulfonyl | OMe | |
| 2089 | 4-amidinophenyl methylcarbonyl | n-butylsulfonyl | OH | |
| 2090 | 4-amidinophenyl-carbonylmethyl | benzyloxycarbonyl | OMe | |
| 2091 | 4-amidinophenyl-carbonylmethyl | benzyloxycarbonyl | OH | |
| 2092 | 4-amidinophenyl-carbonylmethyl | n-butyloxycarbonyl | OMe | |
| 2093 | 4-amidinophenyl-carbonylmethyl | n-butyloxycarbonyl | OH | |
| 2094 | 4-amidinophenyl carbonylmethyl | cyclopropylethoxy carbonyl | OMe | |
| 2095 | 4-amidinophenyl carbonylmethyl | cyclopropylethoxy carbonyl | OH | |
| 2096 | 4-amidinophenyl carbonylmethyl | 4-methylphenylsulfonyl | OMe | |
| 2097 | 4-amidinophenyl-carbonylmethyl | 4-methylphenylsulfonyl | OH | |
| 2098 | 4-amidinophenyl-carbonylmethyl | 3-methylphenylsulfonyl | OMe | |
| 2100 | 4-amidinophenyl-carbonylmethyl | 3-methylphenylsulfonyl | OH | |
| 2101 | 4-amidinophenyl-carbonylmethyl | n-butylsulfonyl | OMe | |
| 2102 | 4-amidinophenyl-carbonylmethyl | n-butylsulfonyl | OH | |
| 2103 | 4-amidinophenyl HOAc salt, 5(R),N²(S) isomer | 3,5-dimethylisoxazol-4-ylsulfonyl | OMe | HNMR |
| 2104 | 4-amidinophenyl TFA salt, 5(R),N²(S) isomer | 3,5-dimethylisoxazol-4-ylsulfonyl | OH | 493 |
| 2105 | 4-amidinophenyl HOAc salt, 5(S),N²(S) isomer | 3,5-dimethylisoxazol-4-ylsulfonyl | OMe | HNMR |
| 2106 | 4-amidinophenyl TFA salt, 5(S),N²(S) isomer | 3,5-dimethylisoxazol-4-ylsulfonyl | OH | |
| 2107 | 4-amidinophenyl HOAc salt, 5(R),N²(R) isomer | 3,5-dimethylisoxazol-4-ylsulfonyl | OMe | |
| 2108 | 4-amidinophenyl HOAc salt, 5(S),N²(R) isomer | 3,5-dimethylisoxazol-4-ylsulfonyl | OMe | |
| 2109 | 2-guanidinoethyl | carbobenzyloxy | OH | 435 |
| 2110 | 5-guanidinovaleryl | carbobenzyloxy | OH | 477 |
| 2111 | 4-(N-2-methoxybenyzyl)-amidinophenyl ·HCl | 2-methylphenylsulfonyl | OMe | 622 |
| 2112 | 4-(N-2-methoxybenyzyl)-amidinophenyl ·HCl | 2-methylphenylsulfonyl | OH | 608 |
| 2113 | 4-(N-n-butyl)-amidinophenyl ·TFA | 2-methylphenylsulfonyl | OMe | 558 |
| 2114 | 4-(N-n-butyl)-amidinophenyl ·TFA | 2-methylphenylsulfonyl | OH | 544 |
| 2115 | 4-(N-ethyl)-amidinophenyl ·TFA | 2-methylphenylsulfonyl | OMe | 530 |
| 2116 | 4-(N-ethyl)-amidinophenyl ·TFA | 2-methylphenylsulfonyl | OH | 516 |
| 2117 | 4-amidinophenyl | 4-methyl-2-methylcarbonylamino-5-thiazolylsulfonyl ·TFA | OH | 566 |

TABLE 9-continued

Structure: R¹—V—[isoxazoline]—CH₂—C(O)—NH—CH(CH₂NHR¹⁶)—C(O)—Y

| Example Number | R¹-V | R¹⁶ | Y | MS (M + H)⁺ |
|---|---|---|---|---|
| 2118 | 4-amidinophenyl | 5-phenylsulfonyl-2-thienylsulfonyl·TFA | OMe | 634 |
| 2119 | 4-amidinophenyl | 5-phenylsulfonyl-2-thienylsulfonyl·TFA | OMe | 620 |
| 2120 | N-t-butyloxycarbonyl-4-amidinophenyl | 5-phenylsulfonyl-2-thienylsulfonyl·TFA | OH | 720 |

TABLE 10

Structure: R¹—V—[isoxazoline]—CH₂—C(O)—N(R⁵ᵃ)—CH₂—CH(NHR¹⁶)—C(O)—Y

| Ex. No. | R¹—V | R⁵ᵃ | R¹⁶ | Y | MS (M + H) |
|---|---|---|---|---|---|
| 2121 | 4-piperidinylethyl | methyl | benzyloxycarbonyl | OH | |
| 2122 | 4-piperidinylethyl | methyl | 2-methylphenylsulfonyl | OH | |
| 2123 | 4-piperidinylethyl | methyl | 3,5-dimethylisoxazolyl sulfonyl | OH | |
| 2124 | 4-piperidinylethyl | methyl | n-butylsulfonyl | OH | |
| 2125 | 4-piperidinylethyl | methyl | n-butylsulfonyl | OMe | |
| 2126 | 4-piperidinylmethyl | methyl | n-butylsulfonyl | OH | |
| 2127 | 4-piperidinylmethyl | methyl | n-butylsulfonyl | OMe | |
| 2128 | 4-piperidinylmethyl | methyl | 2-methylphenylsulfonyl | OH | |
| 2129 | 4-piperidinylmethyl | methyl | 2-bromophenylsulfonyl | OH | |
| 2130 | 4-piperidinylmethyl | methyl | 3-methylphenylsulfonyl | OH | |
| 2131 | 4-piperidinylmethyl | methyl | 3-methylphenylsulfonyl | OMe | |
| 2132 | 4-piperidinylmethyl | methyl | 3,5-dimethylisoxazolyl sulfonyl | OH | |
| 2133 | 4-piperidinylmethyl | methyl | 3,5-dimethylisoxazolyl sulfonyl | OMe | |
| 2134 | 4-piperidinylmethyl | methyl | styrylsulfonyl | OH | |
| 2135 | 4-piperidinylmethyl | methyl | benzyloxycarbonyl | OH | |
| 2136 | 4-piperidinylmethyl | methyl | benzyloxycarbonyl | OMe | |
| 2137 | 4-piperidinylmethyl | methyl | n-butyloxycarbonyl | OH | |
| 2138 | 4-piperidinylmethyl | methyl | n-butyloxycarbonyl | OMe | |
| 2139 | 4-piperidinylpropyl | methyl | n-butylsulfonyl | OH | |
| 2140 | 4-piperidinylpropyl | methyl | n-butylsulfonyl | OMe | |
| 2141 | 4-piperidinylpropyl | methyl | 2-methylphenylsulfonyl | OH | |
| 2142 | 4-piperidinylpropyl | methyl | 2-bromophenylsulfonyl | OH | |
| 2143 | 4-piperidinylpropyl | methyl | 3-methylphenylsulfonyl | OH | |
| 2144 | 4-piperidinylpropyl | methyl | 3-methylphenylsulfonyl | OMe | |
| 2145 | 4-piperidinylpropyl | methyl | 3,5-dimethylisoxazolyl sulfonyl | OH | |
| 2146 | 4-piperidinylpropyl | methyl | 3,5-dimethylisoxazolyl sulfonyl | OMe | |
| 2147 | 4-piperidinylpropyl | methyl | styrylsulfonyl | OH | |
| 2148 | 4-piperidinylpropyl | methyl | benzyloxycarbonyl | OH | |
| 2149 | 4-piperidinylpropyl | methyl | benzyloxycarbonyl | OMe | |
| 2150 | 4-piperidinylpropyl | methyl | n-butyloxycarbonyl | OH | |
| 2151 | 4-piperidinylpropyl | methyl | n-butyloxycarbonyl | OMe | |
| 2152 | 4-amidinopiperidinyl | methyl | n-butylsulfonyl | OH | |
| 2153 | 4-amidinopiperidinyl | methyl | n-butylsulfonyl | OMe | |
| 2154 | 4-amidinopiperidinyl | methyl | 2-methylphenylsulfonyl | OH | |
| 2155 | 4-amidinopiperidinyl | methyl | 2-bromophenylsulfonyl | OH | |
| 2156 | 4-amidinopiperidinyl | methyl | 3-methylphenylsulfonyl | OH | |
| 2157 | 4-amidinopiperidinyl | methyl | 3-methylphenylsulfonyl | OMe | |
| 2158 | 4-amidinopiperidinyl | methyl | 3,5-dimethylisoxazolyl sulfonyl | OH | |

TABLE 10-continued

Structure: R$^1$—V—[isoxazoline ring]—CH$_2$—C(=O)—N(R$^{5a}$)—CH$_2$—CH(NHR$^{16}$)—C(=O)—Y

| Ex. No. | R$^1$—V | R$^{5a}$ | R$^{16}$ | Y | MS (M + H) |
|---|---|---|---|---|---|
| 2159 | 4-amidinopiperidinyl | methyl | 3,5-dimethylisoxazolyl sulfonyl | OMe | |
| 2160 | 4-amidinopiperidinyl | methyl | styrylsulfonyl | OH | - |
| 2161 | 4-amidinopiperidinyl | methyl | benzyloxycarbonyl | OH | . |
| 2162 | 4-amidinopiperidinyl | methyl | benzyloxycarbonyl | OMe | |
| 2163 | 4-amidinopiperidinyl | methyl | n-butyloxycarbonyl | OH | |
| 2164 | 4-amidinopiperidinyl | methyl | n-butyloxycarbonyl | OMe | |
| 2165 | 4-amidinopiperidinyl-methyl | methyl | n-butylsulfonyl | OH | |
| 2166 | 4-amidinopiperidinyl-methyl | methyl | n-butylsulfonyl | OMe | |
| 2167 | 4-amidinopiperidinyl-methyl | methyl | 2-methylphenylsulfonyl | OH | |
| 2168 | 4-amidinopiperidinyl-methyl | methyl | 2-bromophenylsulfonyl | OH | |
| 2169 | 4-amidinopiperidinyl-methyl | methyl | 3-methylphenylsulfonyl | OH | |
| 2170 | 4-amidinopiperidinyl-methyl | methyl | 3-methylphenylsulfonyl | OMe | |
| 2171 | 4-amidinopiperidinyl-methyl | methyl | 3,5-dimethylisoxazolyl sulfonyl | OH | |
| 2172 | 4-amidinopiperidinyl-methyl | methyl | 3,5-dimethylisoxazolyl sulfonyl | OMe | |
| 2173 | 4-amidinopiperidinyl-methyl | methyl | styrylsulfonyl | OH | |
| 2174 | 4-amidinopiperidinyl-methyl | methyl | benzyloxycarbonyl | OH | |
| 2175 | 4-amidinopiperidinyl-methyl | methyl | benzyloxycarbonyl | OMe | |
| 2176 | 4-amidinopiperidinyl-methyl | methyl | n-butyloxycarbonyl | OH | |
| 2177 | 4-amidinopiperidinyl-methyl | methyl | n-butyloxycarbonyl | OMe | |
| 2178 | 4-amidinophenyl | methyl | phenylcarbonyl | OMe | |
| 2179 | 4-amidinophenyl | methyl | phenylcarbonyl | OH | |
| 2180 | 4-amidinophenyl | methyl | 2,6-methylphenylcarbonyl | OMe | |
| 2181 | 4-amidinophenyl | methyl | 2,6-methylphenylcarbonyl | OH | |
| 2182 | 4-amidinophenyl | methyl | 2-methylphenylcarbonyl | OMe | |
| 2183 | 4-amidinophenyl | methyl | 2-methylphenylcarbonyl | OH | |
| 2184 | 4-amidinophenyl | methyl | 2-bromophenylcarbonyl | OMe | |
| 2185 | 4-amidinophenyl | methyl | 2-bromophenylcarbonyl | OH | |
| 2186 | 4-amidinophenyl | methyl | 3-methylphenylcarbonyl | OMe | |
| 2187 | 4-amidinophenyl | methyl | 3-methylphenylcarbonyl | OH | |
| 2188 | 4-amidinophenyl | methyl | 3,5-dimethyl-isoxazoylcarbonyl | OMe | |
| 2189 | 4-amidinophenyl | methyl | 3,5-dimethyl-isoxazoylcarbonyl | OH | |
| 2190 | 4-piperidinylethyl | methyl | phenylcarbonyl | OMe | |
| 2191 | 4-piperidinylethyl | methyl | phenylcarbonyl | OH | |
| 2192 | 4-piperidinylethyl | methyl | 2,6-methylphenylcarbonyl | OMe | |
| 2193 | 4-piperidinylethyl | methyl | 2,6-methylphenylcarbonyl | OH | |
| 2194 | 4-piperidinylethyl | methyl | 2-methylphenylcarbonyl | OMe | |
| 2195 | 4-piperidinylethyl | methyl | 2-methylphenylcarbonyl | OH | |
| 2196 | 4-piperidinylethyl | methyl | 2-bromophenylcarbonyl | OMe | |
| 2197 | 4-piperidinylethyl | methyl | 2-bromophenylcarbonyl | OH | |
| 2198 | 4-piperidinylethyl | methyl | 3-methylphenylcarbonyl | OMe | |
| 2199 | 4-piperidinylethyl | methyl | 3-methylphenylcarbonyl | OH | |
| 2200 | 4-piperidinylethyl | methyl | 3,5-dimethyl-isoxazoylcarbonyl | OMe | |
| 2201 | 4-piperidinylethyl | methyl | 3,5-dimethyl-isoxazoylcarbonyl | OH | |
| 2202 | 4-piperidinylethyl | methyl | n-butyloxycarbonyl | OH | |

TABLE 11

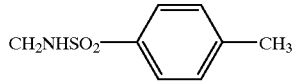

(VI)

| Example Number | R² | R⁸ | Y | MS (M + H)⁺ |
|---|---|---|---|---|
| 2220 | H | CH₂NHCO₂n-C₃H₇ | OH | |
| 2221 | H | CH₂NHCO₂n-C₄H₉ | OH | |
| 2222 | H | CH₂NHCO₂n-C₅H₁₁ | OH | |
| 2223 | H | CH₂NHCO₂CH₂Ph | OH | |
| 2224 | H | CH₂NHCO₂CH₂CH₂Ph | OH | |
| 2225 | H | CH₂NHCO₂i-C₄H₉ | OH | |
| 2226 | H | CH₂NHSO₂CH₂Ph | OH | |
| 2227 | H | 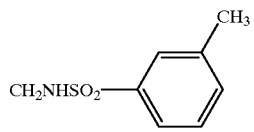 | OH | |
| 2228 | H | 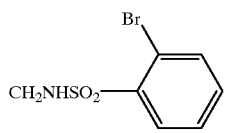 | OH | |
| 2229 | H | 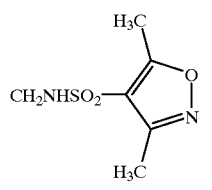 | OH | |
| 2230 | H | 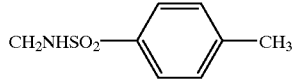 | OH | |
| 2231 | n-Bu | CH₂NHCO₂n-C₃H₇ | OH | |
| 2232 | n-Bu | CH₂NHCO₂n-C₄H₉ | OH | |
| 2233 | n-Bu | CH₂NHCO₂n-C₅H₁₁ | OH | |
| 2234 | n-Bu | CH₂NHCO₂CH₂Ph | OH | |
| 2235 | n-Bu | CH₂NHCO₂CH₂CH₂Ph | OH | |
| 2236 | n-Bu | CH₂NHCO₂i-C₄H₉ | OH | |
| 2237 | n-Bu | CH₂NHSO₂CH₂Ph | OH | |
| 2238 | n-Bu | 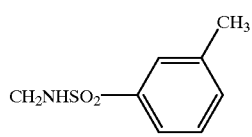 | OH | |
| 2239 | n-Bu | 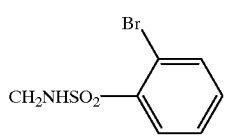 | OH | |
| 2240 | n-Bu |  | OH | |

TABLE 11-continued (VI)

Structure: $R^2N(H_2N)C$-C$_6H_4$-[isoxazoline]-CH$_2$C(O)NH-CH(R$^8$)-C(O)-Y

| Example Number | R² | R⁸ | Y | MS (M + H)⁺ |
|---|---|---|---|---|
| 2241 | n-Bu | CH₂NHSO₂-(3,5-dimethylisoxazol-4-yl) | OH | |
| 2242 | o-methoxybenzyl | —CH₂CH₃ | OH | |
| 2243 | o-methoxybenzyl | —CH=CH₂ | OH | |
| 2244 | o-methoxybenzyl | —C≡CH | OH | |
| 2245 | o-methoxybenzyl | CH₂NHCO₂n-C₃H₇ | OH | |
| 2246 | o-methoxybenzyl | CH₂NHCO₂n-C₄H₉ | OH | |
| 2247 | o-methoxybenzyl | CH₂NHCO₂n-C₅H₁₁ | OH | |
| 2248 | methoxybenzyl | CH₂NHCO₂CH₂Ph | OH | |
| 2249 | o-methoxybenzyl | CH₂NHCO₂CH₂CH₂Ph | OH | |
| 2250 | o-methoxybenzyl | CH₂NHCO₂i-C₄H₉ | OH | |
| 2251 | o-methoxybenzyl | CH₂NHSO₂CH₂Ph | OH | |
| 2252 | o-methoxybenzyl | CH₂NHSO₂-(4-methylphenyl) | OH | |
| 2253 | o-methoxybenzyl | CH₂NHSO₂-(3-methylphenyl) | OH | |
| 2254 | o-methoxybenzyl | CH₂NHSO₂-(2-bromophenyl) | OH | |
| 2255 | o-methoxybenzyl | CH₂NHSO₂-(3,5-dimethylisoxazol-4-yl) | OH | |
| 2256 | o-methoxybenzyl | —CH₂CH₃ | OH | |
| 2257 | o-methoxybenzyl | —CH=CH₂ | OH | |
| 2258 | o-methoxybenzyl | —C≡CH | OH | |

TABLE 12

$$R^1 \diagdown_m \diagdown_{O-N} \diagdown_n \diagdown_H^N \diagdown_O \diagdown^{NHR^{16}}_{OH}$$

| Ex. No. | R¹ | R¹⁶ | m | n | MS (M + H)⁺ |
|---|---|---|---|---|---|
| 2280 | guanidino | benzyloxycarbonyl | 2 | 2 | 449 |
| 2281 | guanidino | benzyloxycarbonyl | 1 | 2 | 435 |
| 2282 | guanidino | benzyloxycarbonyl | | | |
| 2283 | guanidino | benzyloxycarbonyl | | | |
| 2284 | guanidino | benzyloxycarbonyl | | | |
| 2285 | guanidino | benzyloxycarbonyl | | | |

TABLE 13

$$R^1 \diagdown_m \diagdown_{N-O} \diagdown_n \diagdown_H^N \diagdown_O \diagdown^{NHR^{16}}_{OH}$$

| Ex. No. | R¹ | R¹⁶ | m | n | MS (M + H)⁺ |
|---|---|---|---|---|---|
| 2400 | guanidino | benzyloxycarbonyl | 2 | 2 | 449 |
| 2401 | guanidino | benzyloxycarbonyl | 3 | 0 | 435 |
| 2402 | guanidino | benzyloxycarbonyl | 5 | 0 | 463 |
| 2403 | guanidino | benzyloxycarbonyl | 3 | 2 | 463 |
| 2404 | guanidino | benzyloxycarbonyl | 4 | 2 | 477 |
| 2405 | guanidino | benzyloxycarbonyl | 2 | 0 | 421 |
| 2406 | guanidino | benzyloxycarbonyl | 4 | 0 | 449 |

TABLE 14

$$R^1-V \diagdown_{N-O} \diagdown_O \diagdown_H^N \diagdown_O \diagdown^{NHR^{16}}_Y$$

| Ex No. | R¹-V | R¹⁶ | Y | MS (M + H)⁺ |
|---|---|---|---|---|
| 2420 | 4-piperidinylpropyl | n-butyloxycarbonyl | OMe | 441 |
| 2421 | 4-piperidinylpropyl | 4-methylphenylsulfonyl | OMe | 495 |
| 2422 | 4-piperidinylpropyl | 4-methylphenylsulfonyl | OH | 481 |
| 2423 | 4-piperidinylpropyl | n-butyloxycarbonyl | OH | 427 |

Utility

The compounds of this invention possess antiplatelet efficacy, as evidenced by their activity in standard platelet aggregation assays or platelet fibrinogen binding assays, as described below. A compound is considered to be active in these assays if it has an IC$_{50}$ value of less than about 1 mM. Platelet aggregation and fibrinogen binding assays which may be used to demonstrate the antiplatelet activity of the compounds of the invention are described below.

Platelet Aggregation Assay: Venous blood was obtained from the arm of a healthy human donor who was drug-free and aspirin-free for at least two weeks prior to blood collection. Blood was collected into 10 mL citrated Vacutainer tubes. The blood was centrifuged for 15 minutes at 150×g at room temperature, and platelet-rich plasma (PRP) was removed. The remaining blood was centrifuged for 15 minutes at 1500×g at room temperature, and platelet-poor plasma (PPP) was removed. Samples were assayed on a aggregometer (PAP-4 Platelet Aggregation Profiler), using PPP as the blank (100% transmittance). 200 μL of PRP was added to each micro test tube, and transmittance was set to 0%. 20 μL of various agonists (ADP, collagen, arachidonate, epinephrine, thrombin) were added to each tube, and the aggregation profiles were plotted (% transmittance versus time). The results are expressed as % inhibition of agonist-induced platelet aggregation. For the IC$_{50}$ evaluation, the test compounds were added at various concentrations prior to the activation of the platelets.

Ester prodrugs were preincubated (10⁻³ M F.C.) with 100 IU/mL Porcine liver esterase (Sigma Chemical Co., St. Louis, Mo., #E-3128) for 2 hours at 37° C. Aliquots are then diluted in 0.1 M Tris, pH 7.4, to the desired concentrations. Aliquots of 20 μl of the esterase pretreated prodrugs are added to 200 μl of human platelet rich plasma. Samples were placed in platelet profiler (aggregometer) for 8 minutes at 37° C., followed by the addition of 100 μM Adenosine Diphosphate, (Sigma Chemical Co., St. Louis, Mo., #A-6521), to induce platelet aggregation. Platelet aggregation was allowed to proceed for 5 minutes. Percent inhibition is calculated using percent aggregation in the presence of the test compound divided by percent aggregation of control, times 100. This value is subtracted from 100, yielding percent inhibition. Calculation of IC$_{50}$ is performed on a Texas Instruments TI59 with an IC$_{50}$ program.

Purified GPIIb/IIIa-Fibrinogen Binding ELISA

The following reagents are used in the GPIIb/IIIa-fibrinogen binding ELISA:

purified GPIIb/IIIa (148.8 μg/mL);

biotinylated fibrinogen (~1 mg/mL or 3000 nM);

anti-biotin alkaline phosphatase conjugate (Sigma no. A7418);

flat-bottom, high binding, 96-well plates (Costar Cat. no. 3590);

phosphatase substrate (Sigma 104) (40 mg capsules);

bovine serum albumin (BSA) (Sigma no. A3294);

Alkaline Phosphatase buffer–0.1 M glycine-HCl, 1 mM MgCl$_2$.6H$_2$O, 1 mM ZnCl$_2$, pH 10.4;

Binding buffer–20 mM Tris-HCl, 150 mM NaCl, 1 mM CaCl$_2$.2H$_2$O, 0.02% NaN$_3$, pH 7.0;

Buffer A–50 mM Tris-HCl, 100 mM NaCl, 2 mM CaCl$_2$.2H$_2$O, 0.02% NaN$_3$, pH 7.4;

Buffer A+3.5% BSA (Blocking buffer);

Buffer A+0.1% BSA (Dilution buffer); 2N NaOH.

The following method steps are used in the GPIIb/IIIa-fibrinogen binding ELISA:

Coat plates with GPIIb/IIIa in Binding buffer (125 ng/100 μL/well) overnight at 4° C. (Leave first column uncoated for non-specific binding). Cover and freeze plates at −70° C. until used. Thaw plate 1 hour at room temperature or overnight at 4° C. Discard coating solution and wash once with 200 μL Binding buffer per well. Block plate 2 hours at room temperature on shaker with 200 μL Buffer A+3.5% BSA (Blocking buffer) per well. Discard Blocking buffer and wash once with 200 μL Buffer A+0.1% BSA (Dilution buffer) per well. Pipet 11 μL of test compound (10× the concentration to be tested in Dilution buffer) into duplicate wells. Pipet 11 μL Dilution buffer into non-specific and total binding wells. Add 100 μL Biotinylated fibrinogen (⅟₁₃₃ in Dilution buffer, final concentration=20 nM) to each well.

Incubate plates for 3 hours at room temperature on a plate shaker. Discard assay solution and wash twice with 300 μL Binding buffer per well. Add 100 μL Anti-biotin alkaline phosphatase conjugate (1/1500 in Dilution buffer) to each well. Incubate plates for 1 hour at room temperature on plate shaker. Discard conjugate and wash twice with 300 51 Binding buffer per well. Add 100 μL Phosphatase substrate (1.5 mg/mL in Alkaline phosphatase buffer) to each well. Incubate plate at room temperature on shaker until color develops. Stop color development by adding 25 μL 2N NaOH per well. Read plate at 405 nm. Blank against non-specific binding (NSB) well. % Inhibition is calculated as 100−(Test Compound Abs/Total Abs)×100.

Platelet-Fibrinogen Binding Assay: Binding of $^{125}$I-fibrinogen to platelets was performed as described by Bennett et al. (1983) Proc. Natl. Acad. Sci. USA 80: 2417–2422, with some modifications as described below. Human PRP (h-PRP) was applied to a Sepharose column for the purification of platelet fractions. Aliquots of platelets ($5\times10^8$ cells) along with 1 mM calcium chloride were added to removable 96 well plates prior to the activation of the human gel purified platelets (h-GPP). Activation of the human gel purified platelets was achieved using ADP, collagen, arachidonate, epinephrine, and/or thrombin in the presence of the ligand, $^{125}$I-fibrinogen. The $^{125}$I-fibrinogen bound to the activated platelets was separated from the free form by centrifugation and then counted on a gamma counter. For an $IC_{50}$ evaluation, the test compounds were added at various concentrations prior to the activation of the platelets.

The compounds of Formula I of the present invention may also possess thrombolytic efficacy, that is, they are capable of lysing (breaking up) already formed platelet-rich fibrin blood clots, and thus are useful in treating a thrombus formation, as evidenced by their activity in the tests described below. Preferred compounds of the present invention for use in thrombolysis include those compounds having an $IC_{50}$ value (that is, the molar concentration of the compound capable of achieving 50% clot lysis) of less than about 1 μM, more preferably an $IC_{50}$ value of less than about 0.1 μM.

Thrombolytic Assay: Venous blood was obtained from the arm of a healthy human donor who was drug-free and aspirin free for at least two weeks prior to blood collection, and placed into 10 ml citrated Vacutainer tubes. The blood was centrifuged for 15 minutes at 1500×g at room temperature, and platelet rich plasma (PRP) was removed. To the PRP was then added $1\times10^{-3}$ M of the agonist ADP, epinephrine, collagen, arachidonate, serotonin or thrombin, or a mixture thereof, and the PRP incubated for 30 minutes. The PRP was centrifuged for 12 minutes at 2500×g at room temperature. The supernatant was then poured off, and the platelets remaining in the test tube were resuspended in platelet poor plasma (PPP), which served as a plasminogen source. The suspension was then assayed on a Coulter Counter (Coulter Electronics, Inc., Hialeah, Fla.), to determine the platelet count at the zero time point. After obtaining the zero time point, test compounds were added at various concentrations. Test samples were taken at various time points and the platelets were counted using the Coulter Counter. To determine the percent of lysis, the platelet count at a time point subsequent to the addition of the test compound was subtracted from the platelet count at the zero time point, and the resulting number divided by the platelet count at the zero time point. Multiplying this result by 100 yielded the percentage of clot lysis achieved by the test compound. For the $IC_{50}$ evaluation, the test compounds were added at various concentrations, and the percentage of lysis caused by the test compounds was calculated.

The compounds of Formula I of the present invention are also useful for administration in combination with anticoagulant agents such as warfarin or heparin, or antiplatelet agents such as aspirin, piroxicam or ticlopidine, or thrombin inhibitors such as boropeptides, hirudin or argatroban, or thrombolytic agents such as tissue plasminogen activator, anistreplase, urokinase or streptokinase, or combinations thereof.

The compounds of Formula I of the present invention may also be useful as antagonists of other integrins such as for example, the $\alpha_v/\beta_3$ or vitronectin receptor, $\alpha_4/\beta_1$ or $\alpha_5/\beta_1$ and as such may also have utility in the treatment and diagnosis of osteoporosis, cancer metastasis, diabetic retinopathy, rheumatoid arthritis, inflammation, and autoimmune disorders. The compounds of Formula I of the present invention may be useful for the treatment or prevention of other diseases which involve cell adhesion processes, including, but not limited to, inflammation, bone degradation, rheumatoid arthritis, asthma, allergies, adult respiratory distress syndrome, graft versus host disease, organ transplantation, septic shock, psoriasis, eczema, contact dermatitis, osteoporosis, osteoarthritis, atherosclerosis, metastasis, wound healing, diabetic retinopathy, inflammatory bowel disease and other autoimmune diseases.

Table A below sets forth the antiplatelet activity of representative compounds of the present invention. The indicated compounds were tested for their ability to inhibit platelet aggregation (using platelet rich plasma (PRP)). The $IC_{50}$ value (the concentration of antagonist which inhibits platelet aggregation by 50% relative to a control lacking the antagonist) is shown. In Table 5 the $IC_{50}$ values are expressed as: +++=$IC_{50}$ of <10 μM; ++=$IC_{50}$ of 10–50 μM; +=$IC_{50}$ of 50–100 μM (μM=micromolar).

TABLE A

| Example Number | Platelet Aggregation Assay $IC_{50}$ (without esterase) | Platelet Aggregation Assay $IC_{50}$ (with esterase) |
| --- | --- | --- |
| 1 | +++ | |
| 4 (isomer A) | ++ | |
| 4 (isomer B) | ++ | |
| 7 | >100 | |
| 8 | + | |
| 9 (isomer A) | +++ | |
| 9 (isomer B) | +++ | |
| 33 | >100 | |
| 43 | +++ | |
| 89 | | +++ |
| 115 | | +++ |
| 119A (3R) | | +++ |
| 119B (3S) | | +++ |
| 120A (3R) | | +++ |
| 120B (3S) | | +++ |
| 120C (3R)†† | | +++ |
| 166 | | +++ |
| 189 | >100 | |
| 190 | + | |
| 275 | | +++ |
| 276 | | +++ |
| 278 | | +++ |
| 290 | | +++ |
| 300 | | +++ |
| 312 | | +++ |
| 314A (2S)† | | +++ |
| 314B (2S)†† | | +++ |

TABLE A-continued

| Example Number | Platelet Aggregation Assay IC$_{50}$ (without esterase) | Platelet Aggregation Assay IC$_{50}$ (with esterase) |
|---|---|---|
| 323 | | +++ |
| 324 | | +++ |
| 326 | | +++ |
| 327 (2S) | | +++ |
| 328 (2S) | | +++ |
| 338 (3S) | + | +++ |
| 339 (3S) | +++ | |
| 340 (3S) | + | ++ |
| 341 (3S) | +++ | |
| 342 (2S) | +++ | |
| 344 (3R) | | +++ |
| 345 | | +++ |
| 347 (3R)†† | | +++ |
| 348 (3R) | | +++ |
| 350 | | +++ |
| 359 | | +++ |
| 362 | | +++ |
| 365 | | +++ |
| 368 | | +++ |
| 373 | ++ | |
| 371A | | +++ |
| 371B | | +++ |
| 374 (2S) | + | +++ |
| 375* | +++ | |
| 377 | +++ | |
| 394 | | +++ |
| 394Aft | | +++ |
| 400 | +++ | |
| 413* | | +++ |
| 415 | | +++ |
| 435 | | +++ |
| 436 | | +++ |
| 437 | | +++ |
| 438 | | +++ |
| 439 | | +++ |
| 440 | | +++ |
| 441 | +++ | |
| 442 | | +++ |
| 443 (2S) | | +++ |
| 444 (2S) | | +++ |
| 445 (2S) | | +++ |
| 446 | | +++ |
| 449A | | +++ |
| 449B | | +++ |
| 450 | | +++ |
| 451 | | +++ |
| 452 | | +++ |
| 453 | | +++ |
| 454 | | +++ |
| 455 | | +++ |
| 456 | | +++ |
| 457 | | +++ |
| 458A | +++ | |
| 458B | +++ | |
| 460A | +++ | |
| 460B | +++ | |
| 462 | | +++ |
| 463 | +++ | |
| 464 | | +++ |
| 465 | | +++ |
| 466 | | +++ |
| 467 | | +++ |
| 468 | | +++ |
| 469 | | +++ |
| 470 | | +++ |
| 471 | | +++ |
| 472 | | +++ |
| 473A (2S)† | | +++ |
| 473B (2S)†† | | +++ |
| 474 | | +++ |
| 475 | | +++ |
| 476 | | +++ |
| 477 | | +++ |
| 478 | | +++ |
| 479 | | +++ |
| 480 | | +++ |
| 481 | | +++ |
| 482 | | +++ |
| 483 | | +++ |
| 484 | | +++ |
| 485 | | +++ |
| 486 | | +++ |
| 487 | | +++ |
| 488 | | +++ |
| 489 | | +++ |
| 490 | | +++ |
| 491 | | +++ |
| 492 | | +++ |
| 493 | | +++ |
| 494 | | +++ |
| 495 | | +++ |
| 596 | | +++ |
| 504 | | +++ |
| 505 | | +++ |
| 506 | | +++ |
| 507 | | +++ |
| 508 | | +++ |
| 509 | | +++ |
| 510 | | +++ |
| 511 | | +++ |
| 512 | | +++ |
| 513 | | +++ |
| 514 | | +++ |
| 515 | | +++ |
| 516 | | +++ |
| 517 | | +++ |
| 518 | | +++ |
| 519 | | +++ |
| 520 | | +++ |
| 522 | | +++ |
| 523 | | +++ |
| 524 | | +++ |
| 525 | | +++ |
| 526 | +++ | |
| 527 | | +++ |
| 528 | +++ | |
| 529 | | +++ |
| 530 | +++ | |
| 531 | | +++ |
| 532 | +++ | |
| 533 | | +++ |
| 534 | +++ | |
| 535 | | +++ |
| 536 | +++ | |
| 537 | | +++ |
| 538 | +++ | |
| 539 | | +++ |
| 540 | | +++ |
| 541 | | +++ |
| 542 | | +++ |
| 543 | | +++ |
| 544 | | +++ |
| 545 | | +++ |
| 546 | | +++ |
| 547 | | +++ |
| 548 | | +++ |
| 549 | | +++ |
| 550 | | +++ |
| 551 | | +++ |
| 552 | | +++ |
| 553 | | +++ |
| 554 | | +++ |
| 555 | | +++ |
| 556 | | +++ |
| 587A (2S)†† | +++ | |
| 588 | | +++ |
| 602 | | +++ |
| 611 | | +++ |

TABLE A-continued

| Example Number | Platelet Aggregation Assay IC$_{50}$ (without esterase) | Platelet Aggregation Assay IC$_{50}$ (with esterase) |
|---|---|---|
| 612 | | +++ |
| 613 | | +++ |
| 616 | +++ | |
| 642 | | +++ |
| 643 | | +++ |
| 644 | | +++ |
| 651 | | +++ |
| 727 | | +++ |
| 729 | | +++ |
| 798 | | +++ |
| 829 | | +++ |
| 1284 | | +++ |
| 1321 | | +++ |
| 1525 | | +++ |
| 1694 | | +++ |
| 1731 | | +++ |
| 2104 | | +++ |
| 2109 | | +++ |
| 2110 | | +++ |
| 2111 | | +++ |
| 2112 | | +++ |
| 2113 | | +++ |
| 2114 | | +++ |
| 2115 | | +++ |
| 2116 | | +++ |
| 2117 | | +++ |
| 2118 | | +++ |
| 2119 | | +++ |
| 2120 | | +++ |
| 2280 | | +++ |
| 2281 | | +++ |
| 2400 | | +++ |
| 2401 | | +++ |
| 2402 | | +++ |
| 2403 | | +++ |
| 2404 | | +++ |
| 2405 | | +++ |
| 2406 | | +++ |

\* Single diastereomer, racemic
f S isomer at C5 of isoxazoline ring
††R isomer at C5 of isoxazoline ring The compounds of the present invention may be useful for the treatment or prevention of other diseases which involve cell adhesion processes, including, but not limited to, inflammation, bone degradation, thrombosis, rheumatoid arthritis, asthma, allergies, adult respiratory distress syndrome, graft versus host disease, organ transplantation, septic shock, psoriasis, eczema, contact dermatitis, osteoarthritis, atherosclerosis, metastasis, wound healing, diabetic retinopathy, inflammatory bowel disease and other angiogenic disorders.

The compounds of the formulae (Ie) and (If) possess selectivity as antagonists of integrins such as the $\alpha_v/\beta_3$ vitronectin receptor.

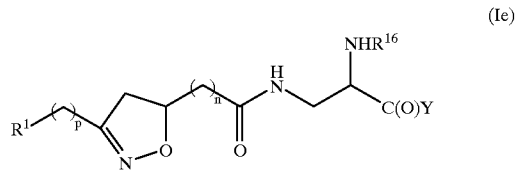
(Ie)

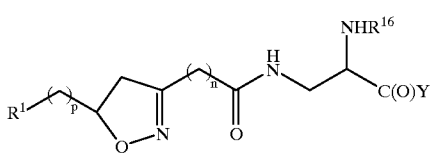
(If)

The integrin antagonist activity of the compounds of the present invention is demonstrated using assays which measure the binding of a specific integrin to a native ligand, for example, using the ELISA assay described below for the binding of vitronectin to the $\alpha_v/\beta_3$ receptor. The compounds provided by this invention are also useful as standards and reagents in determining the ability of a potential pharmaceutical to inhibit integrin-ligand binding. These would be provided in commercial kits comprising a compound of this invention.

Purified $\alpha_v/\beta_3$ (human placenta)—Vitronectin ELISA:

The $\alpha_v/\beta_3$ receptor was isolated from human placental extracts prepared using octylglucoside. The extracts were passed over an affinity column composed of anti-$\alpha_v/\beta_3$ monoclonal antibody (LM609) to Affigel. The column was subsequently washed extensively at pH 7 and pH 4.5 followed by elution at pH 3. The resulting sample was concentrated by wheat germ agglutinin chromatography to provide gave two bands on SDS gel which were confirmed as $\alpha_v/\beta_3$ by western blotting.

Affinity purified protein was diluted at different levels and plated to 96 well plates. ELISA was performed using fixed concentration of biotinylated vitronectin (approximately 80 nM/well). This receptor preparation contains the $\alpha_v/\beta_3$ with no detectable levels of $\alpha_v/\beta_5$ according to the gel ($\alpha_v/\beta_3$) and according to effects of blocking antibodies for the $\alpha_v/\beta_3$ or $\alpha_v/\beta_5$ in the ELISA.

A submaximal concentration of biotinylated vitronectin was selected based on conc. response curve with fixed receptor conc. and variable concentrations of biotinylated vitronectin.

$\alpha_v/\beta_3$-Vitronectin Binding Assay

The purified receptor is diluted with coating buffer (20 mM Tris HCl, 150 mM NaCl, 2.0 mM CaCl$_2$, 1.0 mM MgCl$_2$.6H$_2$O, 1.0 mM MnCl$_2$.4H$_2$O) and coated (100 μl/well) on Costar (3590) high capacity binding plates overnight at 4° C. The coating solution is discarded and the plates washed once with blocking/binding buffer (B/B buffer, 50 mM Tris HCl, 100 mM NaCl, 2.0 mM CaCl$_2$, 1.0 mM MgCl$_2$.6H$_2$O,1.0 mM MnCl$_2$.4H$_2$O). Receptor is then blocked (200 μl/well) with 3.5% BSA in B/B buffer for 2 hours at room temperature. After washing once with 1.0% BSA in B/B buffer, biotinylated vitronectin (100 μl) and either inhibitor (11 μl) or B/B buffer w/1.0% BSA (11 μl) is added to each well. The plates are incubated 2 hours at room temperature. The plates are washed twice with B/B buffer and incubated 1 hour at room temperature with anti-biotin alkaline phosphatase (100 μl/well) in B/B buffer containing 1.0% BSA. The plates are washed twice with B/B buffer and alkaline phosphatase substrate (100 μl) is added. Color is developed at room temperature. Color development is stopped by addition of 2N NaOH (25 μl/well) and absorbance is read at 405 nm. The IC$_{50}$ is the concentration of test substance needed to block 50% of the vitronectin binding to the receptor.

Integrin Cell-Based Adhesion Assays

In the adhesion assays, a 96 well plate was coated with the ligand (i.e., fibrinogen) and incubated overnight at 4° C. The following day, the cells were harvested, washed and loaded with a fluorescent dye. Compounds and cells were added together and then were immediately added to the coated plate. After incubation, loose cells are removed from the plate, and the plate (with adherent cells) is counted on a fluorometer. The ability of test compounds to inhibit cell adhesion by 50% is given by the $IC_{50}$ value and represents a measure of potency of inhibition of integrin mediated binding. Compounds were tested for their ability to block cell adhesion using assays specific for $\alpha_v/\beta_3$, $\alpha_v/\beta_5$ and $\alpha_5/\beta_1$ integrin interactions.

Dosage and Formulation

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an anti-aggregation agent. Finally, the compounds of the invention may also be administered intranasally.

The compounds of this invention can be administered by any means that produces contact of the active agent with the agent's site of action, glycoprotein IIb/IIIa (GPIIb/IIIa), in the body of a mammal. They can be administered by any conventional means available for use in conjunction with pharmaceuticals, either as individual therapeutic agents or in a combination of therapeutic agents, such as a second antiplatelet agent such as aspirin or ticlopidine which are agonist-specific. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

We have unexpectedly found that delivery of Example 327 (and it's free acid Example 300) through the nasal route provided very high bioactivity (inhibition of platelet aggregation) that was similar to that observed after administering the same dose intravenously. Also dog to dog variability was very small. For example, nasal and i.v. administration of 0.025 mg/kg gave similar profiles of platelet aggregation inhibition, however comparable effect after oral administration was only seen at doses equal or greater than 0.4 mg/kg. Therefore, the advantages of delivering Example 327 nasally are to enhance bioavailability and reduce variability. The latter is very important due to the steep dose response of these types of compounds.

The active ingredient can be administered intranasally to a mammal at a dosage range of about 0.01 to 0.5 mg/kg while the preferred dosage range is about 0.01–0.1 mg/kg.

Compositions of the active ingredients can be administered intranasally by preparing a suitable formulation of the active ingredient by procedures well known to those skilled in the art. Preferably the formulations are prepared with suitable nontoxic pharmaceutically acceptable ingredients. These ingredients are known to those skilled in the preparation of nasal dosage forms and some of these can be found in REMINGTON'S PHARMACEUTICAL SCIENCES. 17th edition, 1985 a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, jelling agents, or buffering and other stabilizing and solubilizing agents may also be present. Preferably, the nasal dosage form should be isotonic with nasal secretions.

An example of a nasal solution composition of this invention includes:

| | |
|---|---|
| Active Drug | 0.2–2 g |
| Sorbitol | 0.6 g |
| Benzalkonium chloride | 0.002 g |
| Hydrochloric acid | to adjust pH |
| Sodium hydroxide | to adjust pH |
| Purified water | to 10 mL |

In this example the active drug can be in one vial and the rest of the formulation can be in another vial. The drug can be reconstituted when needed.

The formulation of this invention may be varied to include: (1) other acids and bases to adjust the pH; (2) other tonicity imparting agents such as glycerin and dextrose; (3) other antimicrobial preservatives such as other parahydroxy benzoic acid esters, sorbate, benzoate, propionate, chlorbutanol, phenylethyl alcohol, and mercurials; (4) other viscosity imparting agents such as sodium carboxymethylcellulose microcrystalline cellulose, polyvinylpyrrolidone, polyvinyl alcohol and other gums; (5) suitable absorption enhancers; (6) stabilizing agents such as antioxidants, like bisulfite and ascorbate, metal chelating agents such as sodium edetate and drug solubility enhancers such as polyethylene glycols.

The above formulation can be administered as drops, sprays, aerosols or by any other intranasal dosage form. Optionally, the delivery system can be a unit dose delivery system. The volume of solution or suspension delivered per dose can be anywhere from 5 to 400 µL, and preferably between 50 and 150 µL. Delivery systems for these various dosage forms can be dropper bottles, plastic squeeze units, atomizers, nebulizers or pharmaceutical aerosols in either unit dose or multiple dose packages.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences,* Mack Publishing Company, a standard reference text in this field.

Representative useful pharmaceutical dosage-forms for administration of the compounds of this invention can be illustrated as follows:

Capsules

A large number of unit capsules are prepared by filling standard two-piece hard gelatin capsules each with 1–20 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 1–20 milligrams of the active ingredient. The capsules are washed and dried.

Tablets

A large number of tablets are prepared by conventional procedures so that the dosage unit was 1–20 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 1–20 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent selected from: an anti-coagulant agent such as warfarin or heparin; an anti-platelet agent such as aspirin, piroxicam or ticlopidine; a thrombin inhibitor such as a boropeptide thrombin inhibitor, or hirudin; or a thrombolytic agent such as plasminogen activators, such as tissue plasminogen activator, anistreplase, urokinase or streptokinase. The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent (anti-coagulant agent, anti-platelet agent, thrombin inhibitor, and/or thrombolytic agent) may be administered essentially at the same time, or in any order; for example the compound of Formula I may be administered first, followed by administration of the second agent (anti-coagulant agent, anti-platelet agent, thrombin inhibitor, and/or thrombolytic agent). When not administered at the same time, preferably the administration of the compound of Formula I and the second therapeutic agent occurs less than about one hour apart.

A preferable route of administration of the compound of Formula I is oral. Although it is preferable that the compound of Formula I and the second therapeutic agent (anti-coagulant agent, anti-platelet agent, thrombin inhibitor, and/or thrombolytic agent) are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Although the proper dosage of the compound of Formula I when administered in combination with the second therapeutic agent will be readily ascertainable by a medical practitioner skilled in the art, once armed with the present disclosure, by way of general guidance, where the compounds of this invention are combined with anti-coagulant agents, for example, a daily dosage may be about 0.1 to 100 milligrams of the compound of Formula I and about 1 to 7.5 milligrams of the anti-coagulant, per kilogram of patient body weight. For a tablet dosage form, the novel compounds of this invention generally may be present in an amount of about 1 to 10 milligrams per dosage unit, and the anti-coagulant in an amount of about 1 to 5 milligrams per dosage unit.

Where the compounds of Formula I are administered in combination with a second anti-platelet agent, by way of general guidance, typically a daily dosage may be about 0.01 to 25 milligrams of the compound of Formula I and about 50 to 150 milligrams of the additional anti-platelet agent, preferably about 0.1 to 1 milligrams of the compound of Formula I and about 1 to 3 milligrams of antiplatelet agents, per kilogram of patient body weight.

Further, by way of general guidance, where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced) For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the inhibition of platelet aggregation, the treatment of blood clots, and/or the treatment of thromboembolic disorders, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

What is claimed is:

1. A compound of Formula I:

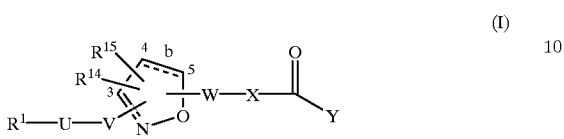

(I)

or pharmaceutically acceptable salt form thereof wherein:

b is a carbon-carbon single or double bond;

$R^1$ is selected from $R^2(R^3)N(CH_2)_qZ-$, $R^2(R^3)N(R^2N=)CN(R^2)(CH_2)_qZ-$, piperazinyl—$(CH_2)_qZ-$ or

;

Z is selected from O, S, S(=O), or S(=O)$_2$;

$R^2$ and $R^3$ are independently selected from: H, $C_1$–$C_{10}$ alkyl, $C_2$–$C_6$ alkenyl, $C_3$–$C_{11}$ cycloalkyl, $C_4$–$C_{11}$ cycloalkylalkyl, $C_6$–$C_{10}$ aryl, $C_7$–$C_{11}$ arylalkyl, $C_2$–$C_7$ alkylcarbonyl, $C_6$–$C_{10}$ arylcarbonyl, $C_2$–$C_{10}$ alkoxycarbonyl, $C_4$–$C_{11}$ cycloalkoxycarbonyl, $C_7$–$C_{11}$ bicycloalkoxycarbonyl, $C_6$–$C_{10}$ aryloxycarbonyl, aryl ($C_1$–$C_{10}$ alkoxy)carbonyl, $C_1$–$C_6$ alkylcarbonyloxy ($C_1$–$C_4$ alkoxy)carbonyl, $C_6$–$C_{10}$ arylcarbonyloxy ($C_1$–$C_4$ alkoxy)carbonyl, $C_4$–$C_{11}$ cycloalkylcarbonyloxy($C_1$–$C_4$ alkoxy)carbonyl;

U is selected from:
a single bond,
—($C_1$–$C_7$ alkyl)—,
—($C_2$–$C_7$ alkenyl)—,
—($C_2$–$C_7$ alkynyl)—,
—(aryl)—substituted with 0–3 $R^{6a}$, or
—(pyridyl)—substituted with 0–3 $R^{6a}$;

V is selected from:
a single bond;
—($C_1$–$C_7$ alkyl)—, substituted with 0–3 groups independently selected from $R^6$ or $R^7$;
—($C_2$–$C_7$ alkenyl)—, substituted with 0–3 groups independently selected from $R^6$ or $R^7$;
—($C_2$–$C_7$ alkynyl)—, substituted with 0–2 groups independently selected from $R^6$ or $R^7$;
-(aryl)-, substituted with 0–2 groups independently selected from $R^6$ or $R^7$;
-(pyridyl)-, substituted with 0–2 groups independently selected from $R^6$ or $R^7$; or
-(pyridazinyl)-, substituted with 0–2 groups independently selected from $R^6$ or $R^7$;

W is selected from:
a single bond,
—($C_1$–$C_7$ alkyl)-,
—($C_2$–$C_7$ alkenyl)-,
—($C_2$–$C_7$ alkynyl)-, or
—(C($R^5$)$_2$)$_n$C(=O) N($R^{5a}$)—;

X is selected from:
a single bond;

—($C_1$–$C_7$ alkyl)-, substituted with 0–3 groups independently selected from $R^4$, $R^8$ or $R^{14}$;
—($C_2$–$C_7$ alkenyl)-, substituted with 0–3 groups independently selected from $R^4$, $R^8$ or $R^{14}$;
—($C_2$–$C_7$ alkynyl)-, substituted with 0–2 groups independently selected from $R^4$, $R^8$ or $R^{14}$; or

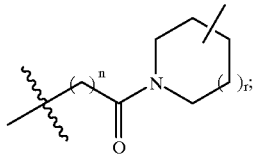

Y is selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ aralkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{10}$ alkoxyalkylcarbonyloxyalkyloxy, $C_5$ to $C_{10}$ (5-alkyl-1,3-dioxa-cyclopenten-2-one-yl)methyloxy, $C_{10}$ to $C_{14}$ (5-aryl-1,3-dioxa-cyclopenten-2-one-yl)methyloxy; or $(R^2)(R^3)N-(C_1-C_{10}$ alkoxy)-;

$R^4$ and $R^{4b}$ are independently selected from H, $C_1$–$C_{10}$ alkyl, hydroxy, $C_1$–$C_{10}$ alkoxy, nitro, $C_1$–$C_{10}$ alkylcarbonyl, or —N($R^{12}$)$R^{13}$;

$R^5$ is selected from H, $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$;

$R^{5a}$ is selected from hydrogen, hydroxy, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_1$–$C_6$ alkoxy, benzyloxy, $C_6$ to $C_{10}$ aryl, heteroaryl, heteroarylalkyl, $C_7$ to $C_{11}$ arylalkyl, adamantylmethyl or $C_1$–$C_{10}$ alkyl substituted with 0–2 $R^{4b}$;

alternately, $R^5$ and $R^5a$ can be taken together to be 3-azabicyclononyl, 1-piperidinyl, 1-morpholinyl or 1-piperazinyl, each being optionally substituted with $C_1$–$C_6$ alkyl, $C_6$–$C_{10}$ aryl, heteroaryl, $C_7$–$C_{11}$ arylalkyl, $C_1$–$C_6$ alkylcarbonyl, $C_3$–$C_7$ cycloalkylcarbonyl, $C_1$–$C_6$ alkoxycarbonyl, $C_7$–$C_{11}$ arylalkoxycarbonyl, $C_1$–$C_6$ alkylsulfonyl or $C_6$–$C_{10}$ arylsulfonyl;

$R^{5b}$ is selected from $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$;

$R^6$ is selected from H, $C_1$–$C_{10}$ alkyl, hydroxy, $C_1$–$C_{10}$ alkoxy, nitro, $C_1$–$C_{10}$ alkylcarbonyl, —N($R^{12}$)$R^{13}$, cyano, halo, $CF_3$, CHO, $CO_2R^5$, $C(=O)R^{5a}$, $CONR^5R^{5a}$, $OC(=O)R^{5a}$, $OC(=O)OR^{5b}$, $OR^{5a}$, $OC(=O)NR^5R^{5a}$, $OCH_2CO_2R^5$, $CO_2CH_2CO_2R^5$, $NO_2$, $NR^{5a}C(=O)R^{5a}$, $NR^{5a}C(=O)OR^{5b}$, $NR^{5a}C(=O)$ $NR^5R^{5a}$, $NR^{5a}SO_2NR^5R^{5a}$, $NR^{5a}SO_2R^5$, $S(O)_pR^{5a}$, $SO_2NR^5R^{5a}$, $C_2$ to $C_6$ alkenyl, $C_3$ to $C_{11}$ cycloalkyl, $C_4$ to $C_{11}$ cycloalkylmethyl;

$C_6$ to $C_{10}$ aryl optionally substituted with 1–3 groups selected from halogen, $C_1$–$C_6$ alkoxy, $C_1$–$C_6$ alkyl, $CF_3$, $S(O)_mMe$, or —$NMe_2$;

$C_7$ to $C_{11}$ arylalkyl, said aryl being optionally substituted with 1–3 groups selected from halogen, $C_1$–$C_6$ alkoxy, $C_1$–$C_6$ alkyl, $CF_3$, $S(O)_mMe$, or —$NMe_2$; methylenedioxy when $R^6$ is a substituent on aryl; or a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^{6a}$ is selected from $C_1$–$C_4$ alkyl, $C_1$–$C_4$ alkoxy, halo, $CF_3$, $NO_2$, or $NR^{12}R^{13}$;

$R^7$ is selected from H, $C_1$–$C_{10}$ alkyl, hydroxy, $C_1$–$C_{10}$ alkoxy, nitro, $C_1$–$C_{10}$ alkylcarbonyl, —$N(R^{12})R^{13}$, cyano, halo, $CF_3$, CHO, $CO_2R^5$, $C(=O)R^{5a}$, $CONR^5R^{5a}$, $OC(=O)R^{5a}$, $OC(=O)OR^{5b}$, $OR^{5a}$, $OC(=O)NR^5R^{5a}$, $OCH_2CO_2R^5$, $CO_2CH_2CO_2R^5$, $NO_2$, $NR^{5a}C(=O)R^{5a}$, $NR^{5a}C(=O)OR^{5b}$, $NR^{5a}C(=O)NR^5R^{5a}$, $NR^{5a}SO_2NR^5R^{5a}$, $NR^{5a}SO_2R^5$, $S(O)_pR^{5a}$, $SO_2NR^5R^{5a}$, $C_2$ to $C_6$ alkenyl, $C_3$ to $C_{11}$ cycloalkyl, $C_4$ to $C_{11}$ cycloalkylmethyl, $C_6$ to $C_{10}$ aryl, or $C_7$ to $C_{11}$ arylalkyl;

$R^8$ is selected from:
H;
$R^6$;
$C_1$–$C_{10}$ alkyl, substituted with 0–3 $R^6$;
$C_2$–$C_{10}$ alkenyl, substituted with 0–3 $R^6$;
$C_2$–$C_{10}$ alkynyl, substituted with 0–3 $R^6$;
$C_3$–$C_8$ cycloalkyl, substituted with 0–3 $R^6$;
$C_5$–$C_6$ cycloalkenyl, substituted with 0–2 $R^6$;
aryl, substituted with 0–2 $R^6$;
5–10 membered heterocyclic ring containing 1–3 N, O, or S heteroatoms, wherein said heterocyclic ring may be saturated, partially saturated, or fully unsaturated, said heterocyclic ring being substituted with 0–2 $R^6$;

$R^{12}$ and $R^{13}$ are independently H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, aryl, $C_2$–$C_6$ alkenyl, $C_3$–$C_{11}$ cycloalkyl, $C_4$–$C_{11}$ cycloalkylalkyl, $C_7$–$C_{11}$ arylalkyl, $C_2$–$C_7$ alkylcarbonyl, $C_7$–$C_{11}$ arylcarbonyl, $C_2$–$C_{10}$ alkoxycarbonyl, $C_4$–$C_{11}$ cycloalkoxycarbonyl, $C_7$–$C_{11}$ bicycloalkoxycarbonyl, $C_7$–$C_{11}$ aryloxycarbonyl, heteroarylcarbonyl, heteroarylsulfonyl, heteroarylalkylcarbonyl or aryl($C_1$–$C_{10}$ alkoxy)carbonyl;

$R^{14}$ is selected from H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or $C_1$–$C_{10}$ alkoxycarbonyl, $CO_2R^5$ or —$C(=O)N(R^5)R^{5a}$;

$R^{15}$ is selected from:
H;
$R^6$;
$C_1$–$C_{10}$ alkyl, substituted with 0–8 $R^6$;
$C_2$–$C_{10}$ alkenyl, substituted with 0–6 $R^6$;
$C_1$–$C_{10}$ alkoxy, substituted with 0–6 $R^6$;
aryl, substituted with 0–5 $R^6$;
5–6 membered heterocyclic ring containing 1–2 N, O, or S heteroatoms, wherein said heterocyclic ring may be saturated, partially saturated, or fully unsaturated, said heterocyclic ring being substituted with 0–5 $R^6$;
$C_1$–$C_{10}$ alkoxycarbonyl substituted with 0–8 $R^6$;
$CO_2R^5$; or
—$C(=O)N(R^5)R^{5a}$;

provided that when b is a double bond, only one of $R^{14}$ or $R^{15}$ is present;
n is 0–4;
q is 2–7;
r is 0–3;

provided that n, q, and r are chosen such that the number of atoms connecting $R^1$ and Y is in the range of 8–18.

2. A compound of claim 1 of Formula II:

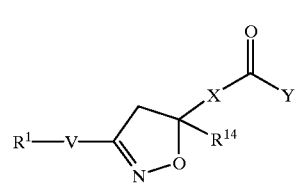

(II)

wherein:
$R^1$ is selected from $R^2HN(CH_2)_qO$—, $R^2HN(R^2N)CNH(CH_2)_qO$—, piperazinyl-$(CH_2)_qO$—, or

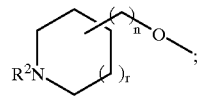

$R^2$ is selected from H, aryl($C_1$–$C_{10}$ alkoxy)carbonyl, $C_1$–$C_{10}$ alkoxycarbonyl;

$R^8$ is selected from H, $C_1$–$C_{10}$ alkyl, $C_2$–$C_{10}$ alkenyl, $C_3$–$C_8$ cycloalkyl, $C_5$–$C_6$ cycloalkenyl, aryl, 5–6 membered heterocyclic ring containing 1–2 N, O, or S heteroatoms, wherein said heterocyclic ring may be saturated, partially saturated, or fully unsaturated;

$R^6$ and $R^7$ are selected from H, $C_1$–$C_{10}$ alkyl, hydroxy, $C_1$–$C_{10}$ alkoxy, nitro, $C_1$–$C_{10}$ alkylcarbonyl, —$N(R^{12})R^{13}$, cyano, or halo.

3. A compound of claim 2 wherein:
X is selected from:
a single bond;
—($C_1$–$C_7$ alkyl)-, substituted with 0–2 groups independently selected from $R^4$, $R^8$ or $R^{14}$;
—($C_2$–$C_7$ alkenyl)-, substituted with 0–2 groups independently selected from $R^4$, $R^8$ or $R^{14}$;
—($C_2$–$C_7$ alkynyl)-, substituted with 0–2 groups independently selected from $R^4$, $R^8$ or $R^{14}$;

$R^8$ is selected from H, $C_1$–$C_6$ alkyl, $C_2$–$C_6$ alkenyl, $C_3$–$C_8$ cycloalkyl, $C_5$–$C_6$ cycloalkenyl, aryl, 5–6 membered heterocyclic ring containing 1–2 N, O, or S heteroatoms, wherein said heterocyclic ring may be saturated, partially saturated, or fully unsaturated.

4. A compound of claim 2 wherein:
$R^1$ is

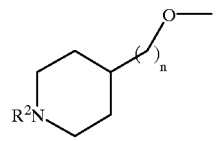

V is phenylene or pyridylene;
n is 1 or 2;
X is —($C_1$–$C_2$)alkyl-substituted with 0–2 $R^4$
Y is selected from:
hydroxy;
$C_1$ to $C_{10}$ alkoxy;
methylcarbonyloxymethoxy-;
ethylcarbonyloxymethoxy-;
t-butylcarbonyloxymethoxy-;

cyclohexylcarbonyloxymethoxy-;
1-(methylcarbonyloxy)ethoxy-;
1-(ethylcarbonyloxy)ethoxy-;
1-(t-butylcarbonyloxy)ethoxy-;
1-(cyclohexylcarbonyloxy)ethoxy-;
i-propyloxycarbonyloxymethoxy-;
t-butyloxycarbonyloxymethoxy-;
1-(i-propyloxycarbonyloxy)ethoxy-;
1-(cyclohexyloxycarbonyloxy)ethoxy-;
1-(t-butyloxycarbonyloxy)ethoxy-;
dimethylaminoethoxy-;
diethylaminoethoxy-;
(5-methyl-1,3-dioxacyclopenten-2-on-4-yl)methoxy-;
(5-(t-butyl)-1,3-dioxacyclopenten-2-on-4-yl)
methoxy-;
(1,3-dioxa-5-phenyl-cyclopenten-2-on-4-yl)methoxy-;
1-(2-(2-methoxypropyl)carbonyloxy)ethoxy-;

$R^4$ is $-NR^{12}R^{13}$;

$R^{12}$ is H, $C_1-C_4$ alkoxycarbonyl, $C_1-C_4$ alkylcarbonyl, $C_1-C_4$ alkylsulfonyl, arylalkylsulfonyl, heteroarylsulfonyl, arylsulfonyl, benzyl, benzoyl, phenoxycarbonyl, benzyloxycarbonyl, arylalkylsulfonyl, pyridylcarbonyl, or pyridylmethylcarbonyl;

$R^{13}$ is H.

5. A compound of claim 1, or a pharmaceutically acceptable salt form thereof, selected from:

5(R,S) -3-[[4-(2-piperidin-4-yl)ethoxyphenyl]isoxazolin-5-yl]acetic acid;

5(R,S)-N-(butanesulfonyl)-L-{3-[4-(2-piperidin-4-yl)ethoxyphenyl]isoxazolin-5-yl}glycine;

5(R,S)-N-(α-toluenesulfonyl)-L-{3-[4-(2-piperidin-4-yl)ethoxyphenyl]isoxazolin-5-yl}glycine;

5(R,S) -N-[(benzyloxy)carbonyl]-L-{3-[4-(2-piperidin-4-yl)ethoxyphenyl]isoxazolin-5-yl}glycine;

5(R,S)-N-(pentanoyl)-L-{3-[4-(2-piperidin-4-yl)ethoxyphenyl]isoxazolin-5-yl}glycine;

5(R,S)-3-{[4-(piperidin-4-yl)methoxyphenyl]isoxazolin-5-yl}propanoic acid;

2(R,S)-5(R,S)-N-(butanesulfonyl)amino-{3-[4-(piperidin-4-yl)methoxyphenyl]isoxazolin-5-yl}propanoic acid;

2(R,S)-5(R,S)-N-(α-toluenesulfonyl)amino-{3-[4-(piperidin-4-yl)methoxyphenyl]isoxazolin-5-yl}propanoic acid;

2(R,S)-5(R,S)-N-[(benzyloxy)carbonyl]amino-{3-[4-(piperidin-4-yl)methoxyphenyl]isoxazolin-5-yl}propanoic acid;

2(R,S)-5(R,S)-N-(pentanoyl)amino-{3-[4-(piperidin-4-yl)methoxyphenyl]isoxazolin-5-yl}propanoic acid.

6. A compound of Formula Id:

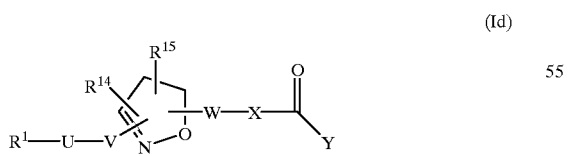

(Id)

or a pharmaceutically acceptable salt form thereof wherein:

$R^1$ is selected from is selected from $R^2(R^3)N-$, $R^2(R^3)N(R^2N=)C-$, $R^2(R^3)N(R^2N=)CN(R^2)-$, $R^2(R^3)N(CH_2)_qZ-$, $R^2(R^3)N(R^2N=)C(CH_2)_qZ-$, $R^2(R^3)N(R^2N=)CN(R^2)(CH_2)_qZ-$, piperazinyl-$(CH_2)_qZ-$, $R^2(R^3)NC(O)-$, $R^2(R^5O)N(R^2N=)C-$, $R^2(R^3)N(R^5ON=)C-$,

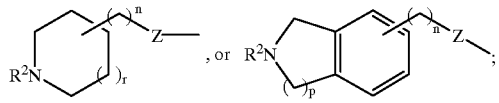

Z is selected from a bond, O, S, S(=O), or S(=O)$_2$;

$R^2$ and $R^3$ are independently selected from: H; $C_1-C_{10}$ alkyl; $C_3-C_6$ alkenyl; $C_3-C_{11}$ cycloalkyl; $C_4-C_{11}$ cycloalkylalkyl; $C_6-C_{10}$ aryl optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; $C_7-C_{11}$ arylalkyl optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; $C_2-C_7$ alkylcarbonyl; $C_7-C_{11}$ arylcarbonyl optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; $C_1-C_{10}$ alkoxycarbonyl; $C_4-C_{11}$ cycloalkoxycarbonyl; $C_7-C_{11}$ bicycloalkoxycarbonyl; $C_7-C_{11}$ aryloxycarbonyl optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; aryl($C_1-C_{10}$ alkoxy)carbonyl where the aryl group is optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; $C_1-C_6$ alkylcarbonyloxy($C_1-C_4$ alkoxy)carbonyl; $C_6-C_{10}$ arylcarbonyloxy($C_1-C_4$ alkoxy)carbonyl where the aryl group is optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; $C_4-C_{11}$ cycloalkylcarbonyloxy($C_1-C_4$ alkoxy)carbonyl; heteroaryl optionally substituted with 0–2 groups from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; or heteroaryl($C_1-C_5$)alkyl where the heteroaryl group is optionally substituted with 0–2 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl;

provided that only one of $R^2$ and $R^3$ may be hydroxy;

U is selected from:
a single bond,
$C_1-C_7$ alkylene,
$C_2-C_7$ alkenylene,
$C_2-C_7$ alkynylene,
arylene substituted with 0–3 $R^{6a}$, or
pyridylene substituted with 0–3 $R^{6a}$;

V is selected from:
a single bond;
$C_1-C_7$ alkylene substituted with 0–6 $R^6$ or $R^7$;
$C_2-C_7$ alkenylene substituted with 0–4 $R^6$ or $R^7$;
$C_2-C_7$ alkynylene substituted with 0–4 $R^6$ or $R^7$;
phenylene substituted with 0–4 $R^6$ or $R^7$;
pyridylene substituted with 0–3 $R^6$ or $R^7$;
pyridazinylene substituted with 0–3 $R^6$ or $R^7$;

X is selected from:
  a single bond;
  —(CH$_2$)$_n$C(=O)N(R$^{12}$)—;
  C$_1$–C$_7$ alkylene substituted with 0–6 R$^4$, R$^8$ or R$^{15}$;
  C$_2$–C$_7$ alkenylene substituted with 0–4 R$^4$, R$^8$ or R$^{15}$;
  C$_2$–C$_7$ alkynylene substituted with 0–4 R$^4$, R$^8$ or R$^{15}$;

Y is selected from:
  hydroxy,
  C$_1$ to C$_{10}$ alkyloxy,
  C$_3$ to C$_{11}$ cycloalkyloxy,
  C$_6$ to C$_{10}$ aryloxy,
  C$_7$ to C$_{11}$ aralkyloxy,
  C$_3$ to C$_{10}$ alkylcarbonyloxyalkyloxy,
  C$_3$ to C$_{10}$ alkoxycarbonyloxyalkyloxy,
  C$_2$ to C$_{10}$ alkoxycarbonylalkyloxy,
  C$_5$ to C$_{10}$ cycloalkylcarbonyloxyalkyloxy,
  C$_5$ to C$_{10}$ cycloalkoxycarbonyloxyalkyloxy,
  C$_5$ to C$_{10}$ cycloalkoxycarbonylalkyloxy,
  C$_7$ to C$_{11}$ aryloxycarbonylalkyloxy,
  C$_8$ to C$_{12}$ aryloxycarbonyloxyalkyloxy,
  C$_8$ to C$_{12}$ arylcarbonyloxyalkyloxy,
  C$_5$ to C$_{10}$ alkoxyalkylcarbonyloxyalkyloxy,
  C$_5$ to C$_{10}$ (5-alkyl-1,3-dioxa-cyclopenten-2-one-yl) methyloxy,
  C$_{10}$ to C$_{14}$ (5-aryl-1,3-dioxa-cyclopenten-2-one-yl) methyloxy;
  (R$^2$) (R$^3$)N—(C$_1$–C$_{10}$ alkoxy)-;

R$^{14}$ and W are attached to the same carbon and taken together to form a spiro-fused, 5–7 membered ring structure of the formula:

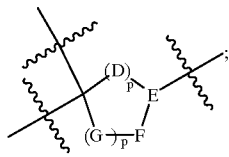

D, E, F and G are each independently selected from:
  C(R$^{6a}$)$_2$;
  carbonyl;
  a heteroatom moiety selected from N, N(R$^{12}$), O, provided that no more than 2 of D, E, F and G are N, N(R$^{12}$), O, S, or C(=O);
  alternatively, the bond between D and E, E and F, or F and G in such spiro-fused ring may be a carbon-nitrogen double bond or a carbon-carbon double bond;

R$^4$ is selected from H, C$_1$–C$_{10}$ alkyl, hydroxy, C$_1$–C$_{10}$ alkoxy, nitro, C$_1$–C$_{10}$ alkylcarbonyl, or —N(R$^{12}$)R$^{13}$;

R$^6$ and R$^7$ are each independently selected from H, C$_1$–C$_{10}$ alkyl, hydroxy, C$_1$–C$_{10}$ alkoxy, nitro, C$_1$–C$_{10}$ alkylcarbonyl, —N(R$^{12}$)R$^{13}$, cyano, halo, CF$_3$, CHO, CO$_2$R$^{5a}$, C(=O)R$^{5a}$, CONHR$^{5a}$, CON(R$^{12}$)$_2$, OC(=O)R$^{5a}$, OC(=O)OR$^{5a}$, OR$^{5a}$, OC(=O)N(R$^{12}$)$_2$, OCH$_2$CO$_2$R$^{5a}$, CO$_2$CH$_2$CO$_2$R$^{5a}$, N(R$^{12}$)$_2$, NO$_2$, NR$^{12}$C(=O) R$^{5a}$, NR$^{12}$C(=O)OR$^{5a}$, NR$^{12}$C(=O)N (R$^{12}$)$_2$, NR$^{12}$SO$_2$N(R$^{12}$)$_2$, NR$^{12}$SO$_2$R$^{5a}$, S(O)$_p$R$^{5a}$, SO$_2$N(R$^{12}$)$_2$, C$_2$ to C$_6$ alkenyl, C$_3$ to C$_{11}$ cycloalkyl, C$_4$ to C$_{11}$ cycloalkylmethyl;
  C$_6$ to C$_{10}$ aryl optionally substituted with 1–3 groups selected from halogen, C$_1$–C$_6$ alkoxy, C$_1$–C$_6$ alkyl, CF$_3$, S(O)$_m$Me, or —NMe$_2$;
  C$_7$ to C$_{11}$ arylalkyl, said aryl being optionally substituted with 1–3 groups selected from halogen, C$_1$–C$_6$ alkoxy, C$_1$–C$_6$ alkyl, CF$_3$, S(O)$_m$Me, or —NMe$_2$;
  methylenedioxy when R$^6$ is a substituent on aryl;

R$^{6a}$ is selected from C$_1$–C$_4$ alkyl, C$_1$–C$_4$ alkoxy, halo, CF$_3$, NO$_2$, or NR$^{12}$R$^{13}$;

R$^8$ is selected from:
  H;
  R$^6$;
  C$_1$–C$_{10}$ alkyl, substituted with 0–8 R$^6$;
  C$_2$–C$_{10}$ alkenyl, substituted with 0–6 R$^6$;
  C$_2$–C$_{10}$ alkynyl, substituted with 0–6 R$^6$;
  C$_3$–C$_8$ cycloalkyl, substituted with 0–6 R$^6$;
  C$_5$–C$_6$ cycloalkenyl, substituted with 0–5 R$^6$;
  aryl, substituted with 0–5 R$^6$;
  5–6 membered heterocyclic ring containing 1–2 N, O, or S heteroatoms, wherein said heterocyclic ring may be saturated, partially saturated, or fully unsaturated, said heterocyclic ring being substituted with 0–5 R$^6$;

R$^{12}$ and R$^{13}$ are independently H, C$_1$–C$_{10}$ alkyl, C$_1$–C$_{10}$ alkoxycarbonyl, C$_1$–C$_{10}$ alkylcarbonyl, C$_1$–C$_{10}$ alkylsulfonyl, aryl(C$_1$–C$_{10}$ alkyl)sulfonyl, arylsulfonyl, aryl, C$_2$–C$_6$ alkenyl, C$_3$–C$_{11}$ cycloalkyl, C$_4$–C$_{11}$ cycloalkylalkyl, C$_7$–C$_{11}$ arylalkyl, C$_2$–C$_7$ alkylcarbonyl, C$_7$–C$_{11}$ arylcarbonyl, C$_2$–C$_{10}$ alkoxycarbonyl, C$_4$–C$_{11}$ cycloalkoxycarbonyl, C$_7$–C$_{11}$ bicycloalkoxycarbonyl, C$_7$–C$_{11}$ aryloxycarbonyl, heteroarylcarbonyl, heteroarylsulfonyl, heteroarylalkylcarbonyl or aryl(C$_1$–C$_{10}$ alkoxy)carbonyl, wherein said aryl groups and heteroaryl groups are optionally substituted with 0–3 substituents selected from: C$_1$–C$_4$ alkyl, C$_1$–C$_4$ alkoxy, halo, CF$_3$, and NO$_2$;

R$^5$ and R$^{5a}$ are selected independently from H, C$_1$ to C$_8$ alkyl, C$_2$ to C$_6$ alkenyl, C$_3$ to C$_{11}$ cycloalkyl, C$_4$ to C$_{11}$ cycloalkylmethyl, C$_6$ to C$_{10}$ aryl, C$_7$ to C$_{11}$ arylalkyl, or C$_1$–C$_{10}$ alkyl substituted with 0–8 R$^4$;

R$^{15}$ is selected from:
  H;
  R$^6$;
  C$_1$–C$_{10}$ alkyl, substituted with 0–8 R$^6$;
  C$_2$–C$_{10}$ alkenyl, substituted with 0–6 R$^6$;
  C$_1$–C$_{10}$ alkoxy, substituted with 0–6 R$^6$;
  aryl, substituted with 0–5 R$^6$;
  5–6 membered heterocyclic ring containing 1–2 N, O, or S heteroatoms, wherein said heterocyclic ring may be saturated, partially saturated, or fully unsaturated, said heterocyclic ring being substituted with 0–5 R$^6$;
  C$_1$–C$_{10}$ alkoxycarbonyl substituted with 0–8 R$^6$;
  CO$_2$R$^5$; or
  —C(=O)N(R$^{12}$)R$^{13}$;

n is 0–4;
p is 1–3;
q is 1–7;
r is 0–3;
provided that n, p, q and r are chosen such that the number of atoms connecting R$^1$ and Y is in the range of 8–17.

7. A compound of claim 6 of Formula III:

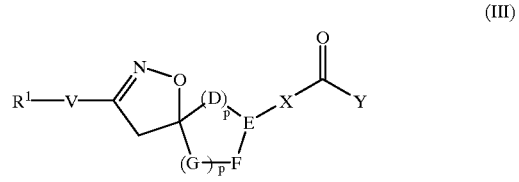

(III)

wherein:
R$^1$ is selected from R$^2$HN—, H$_2$N(R$^2$N=)C—, H$_2$N(R$^2$N=)CNH—, R$^2$HN(CH$_2$)$_q$O—, H$_2$N(R$^2$N=)CNH $-(CH_2)_qO-$, piperazinyl-$(CH_2)_qO-$, $R^2(R^3)NC(O)-$, $R^2(R^5O)N(R^2N=)C-$, $R^2(R^3)N(R^5ON=)C-$,

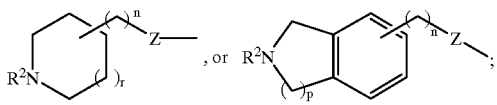

$R^2$ and $R^3$ are selected from H; $C_1-C_6$ alkyl; $C_7-C_{11}$ arylalkyl optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; aryl($C_1-C_{10}$ alkoxy)carbonyl where the aryl group is optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; heteroaryl($C_1-C_5$)alkyl wherein the heteroaryl group is optionally substituted with 0–2 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; or $C_1-C_{10}$ alkoxycarbonyl;

$R^4$ is selected from H, $C_1-C_{10}$ alkyl, hydroxy, $C_1-C_{10}$ alkoxy, nitro, $C_1-C_{10}$ alkylcarbonyl, or $-N(R^{12})R^{13}$;

V is selected from:
  a single bond;
  $C_1-C_7$ alkylene substituted with 0–6 $R^6$ or $R^7$;
  $C_2-C_7$ alkenylene substituted with 0–4 $R^6$ or $R^7$;
  $C_2-C_7$ alkynylene substituted with 0–4 $R^6$ or $R^7$;
  phenylene substituted with 0–3 $R^6$ or $R^7$;
  pyridylene substituted with 0–3 $R^6$ or $R^7$;
  pyridazinylene substituted with 0–3 $R^6$ or $R^7$;

X is selected from $-(CH_2)_nC(=O)N(R^{12})-$, $C_1-C_7$ alkylene substituted with 0–1 $R^4$, $C_2-C_7$ alkenylene, or $C_2-C_7$ alkynylene;

Y is selected from:
  hydroxy,
  $C_1$ to $C_{10}$ alkyloxy,
  $C_3$ to $C_{11}$ cycloalkyloxy,
  $C_6$ to $C_{10}$ aryloxy,
  $C_7$ to $C_{11}$ aralkyloxy,
  $C_3$ to $C_{10}$ alkylcarbonyloxyalkyloxy,
  $C_3$ to $C_{10}$ alkoxycarbonyloxyalkyloxy,
  $C_2$ to $C_{10}$ alkoxycarbonylalkyloxy,
  $C_5$ to $C_{10}$ cycloalkylcarbonyloxyalkyloxy,
  $C_5$ to $C_{10}$ cycloalkoxycarbonyloxyalkyloxy,
  $C_5$ to $C_{10}$ cycloalkoxycarbonylalkyloxy,
  $C_7$ to $C_{11}$ aryloxycarbonylalkyloxy,
  $C_8$ to $C_{12}$ aryloxycarbonyloxyalkyloxy,
  $C_8$ to $C_{12}$ arylcarbonyloxyalkyloxy,
  $C_5$ to $C_{10}$ alkoxyalkylcarbonyloxyalkyloxy,
  $C_5$ to $C_{10}$ (5-alkyl-1,3-dioxa-cyclopenten-2-one-yl)methyloxy, or
  $C_{10}$ to $C_{14}$ (5-aryl-1,3-dioxa-cyclopenten-2-one-yl)methyloxy;

Z is selected from O or $CH_2$;
D, E, F and G are each independently selected from:
  $CH_2$;
  carbonyl;
  a heteroatom moiety selected from N, NH, O, provided that no more than 2 of D, E, F and G are N, NH, O or S;
  alternatively, the bond between D and E, E and F, or F and G in such spiro-fused ring may be a carbon-nitrogen double bond or a carbon-carbon double bond;

$R^6$ and $R^7$ are each independently selected from H, $C_1-C_{10}$ alkyl, hydroxy, $C_1-C_{10}$ alkoxy, nitro, $C_1-C_{10}$ alkylcarbonyl, $-N(R^{12})R_{13}$, cyano, or halo;

$R^{12}$ and $R^{13}$ are each independently selected from H, $C_1-C_{10}$ alkyl, $C_1-C_{10}$ alkoxycarbonyl, $C_1-C_{10}$ alkylcarbonyl, $C_1-C_{10}$ alkylsulfonyl, aryl($C_1-C_{10}$ alkyl)sulfonyl, arylsulfonyl, heteroarylsulfonyl, heteroarylcarbonyl, heteroarylalkylcarbonyl or aryl;

n is 0–4;
p is 1–3;
q is 1–7;
r is 0–3;
provided that n, p, q and r are chosen such that the number of atoms between $R^1$ and Y is in the range of 8–17.

8. A compound of claim 7 wherein:
$R^1$ is $R^2NHC(=NR^2)-$ and V is phenyl or pyridyl or $R^1$ is

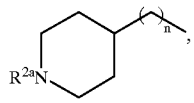

and V is a single bond;
n is 1 or 2;
X is $C_1-C_4$ alkylene substituted with 0–1 $R^4$;
Y is selected from:
  hydroxy;
  $C_1$ to $C_{10}$ alkoxy;
  methylcarbonyloxymethoxy-;
  ethylcarbonyloxymethoxy-;
  t-butylcarbonyloxymethoxy-;
  cyclohexylcarbonyloxymethoxy-;
  1-(methylcarbonyloxy)ethoxy-;
  1-(ethylcarbonyloxy)ethoxy-;
  1-(t-butylcarbonyloxy)ethoxy-;
  1-(cyclohexylcarbonyloxy)ethoxy-;
  i-propyloxycarbonyloxymethoxy-;
  t-butyloxycarbonyloxymethoxy-;
  1-(i-propyloxycarbonyloxy)ethoxy-;
  1-(cyclohexyloxycarbonyloxy)ethoxy-;
  1-(t-butyloxycarbonyloxy)ethoxy-;
  dimethylaminoethoxy-;
  diethylaminoethoxy-;
  (5-methyl-1,3-dioxacyclopenten-2-on-4-yl)methoxy-;
  (5-(t-butyl)-1,3-dioxacyclopenten-2-on-4-yl)methoxy-;
  (1,3-dioxa-5-phenyl-cyclopenten-2-on-4-yl)methoxy-;
  1-(2-(2-methoxypropyl)carbonyloxy)ethoxy-;

$R^{12}$ and $R^{13}$ are each independently selected from H, $C_1-C_6$ alkyl, $C_1-C_4$ alkoxycarbonyl, $C_1-C_4$ alkylcarbonyl, $C_1-C_4$ alkylsulfonyl, aryl($C_1-C_4$ alkyl)sulfonyl, heteroarylsulfonyl, arylsulfonyl, heteroarylcarbonyl, heteroarylalkylcarbonyl or aryl; and
$R^{13}$ is H.

9. A compound of claim 6, or pharmaceutically acceptable salt forms thereof, selected from:
5(R,S)-3-(4-amidinophenyl)-8-(2-carboxyethyl)-1-oxa-2,8-diazaspiro[4.4]non-2-ene-7,9-dione;
5(R,S)-3-(4-amidinophenyl)-8-(3-carboxypropyl)-1-oxa-2,8-diazaspiro[4.4]non-2-ene-7,9-dione;
5(R,S)-3-(4-amidinophenyl)-8-(2-carboxyethyl)-1-oxa-2,8-diazaspiro[4.4]non-2-ene-5-one;
5(R,S)-3-(4-amidinophenyl)-8-(3-carboxypropyl)-1-oxa-2,8-diazaspiro[4.4]non-2-ene-5-one;

5(R,S) -3-(4-amidinophenyl)-8-(2-carboxyethyl)-1-oxa-2-azaspiro[4.4]nona-2,8-diene-5-one;
5(R,S)-3-(4-amidinophenyl)-8-(3-carboxypropyl)-1-oxa-2-azaspiro[4.4]nona-2,8-diene-5-one;
5(R,S) -3-(4-amidinophenyl)-8-(2-carboxyethyl)-1-oxa-2,8-diazaspiro[4.4]dec-2-ene-7,9-dione;
5(R,S)-3-(4-amidinophenyl)-8-(3-carboxypropyl)-1-oxa-2,8-diazaspiro[4.4]dec-2-ene-7,9-dione;
5(R,S) -3-(4-amidinophenyl)-8-(2-carboxyethyl)-1-oxa-2,8-diazaspiro[4.4]dec-2-ene-5-one;
5(R,S)-3-(4-amidinophenyl)-8-(3-carboxypropyl)-1-oxa-2,8-diazaspiro[4.4]dec-2-ene-5-one;
5(R,S)-3-(4-amidinophenyl)-8-(2-carboxyethyl)-1-oxa-2-azaspiro[4.4]deca-2,8-diene-5-one;
5(R,S)-3-(4-amidinophenyl)-8-(3-carboxypropyl)-1-oxa-2-azaspiro[4.4]deca-2,8-diene-5-one;
5(R,S)-3-(4-amidinophenyl)-8-(2-carboxyethyl)-1-oxa-2,8-diazaspiro[4.4]undec-2-ene-7,9-dione;
5(R,S)-3-(4-amidinophenyl)-8-(3-carboxypropyl)-1-oxa-2,8-diazaspiro[4.4]undec-2-ene-7,9-dione;
5(R,S) -3-(4-amidinophenyl)-8-(2-carboxyethyl)-1-oxa-2,8-diazaspiro[4.4]undec-2-ene-5-one;
5(R,S)-3-(4-amidinophenyl)-8-(3-carboxypropyl)-1-oxa-2,8-diazaspiro[4.4]undec-2-ene-5-one;
5(R,S)-3-(4-amidinophenyl)-8-(2-carboxyethyl)-1-oxa-2-azaspiro[4.4]undeca-2,8-diene-5-one;
5(R,S) -3-(4-amidinophenyl)-8-(3-carboxypropyl)-1-oxa-2-azaspiro[4.4]undeca-2,8-diene-5-one;
5(R,S)-3-[2-(piperidin-4-yl)ethyl]-8-(2-carboxyethyl)-1-oxa-2,8-diazaspiro[4.4]non-2-ene-7,9-dione;
5(R,S) -3-[2-(piperidin-4-yl)ethyl]-8-(3-carboxypropyl)-1-oxa-2,8-diazaspiro[4.4]non-2-ene-7,9-dione;
5(R,S)-3-[2-(piperidin-4-yl)ethyl]-8-(2-carboxyethyl)-1-oxa-2,8-diazaspiro[4.4]non-2-ene-5-one;
5(R,S)-3-[2-(piperidin-4-yl)ethyl]-8-(3-carboxypropyl)-1-oxa-2,8-diazaspiro[4.4]non-2-ene-5-one;
5(R,S)-3-[2-(piperidin-4-yl)ethyl]-8-(2-carboxyethyl)-1-oxa-2-azaspiro[4.4]nona-2,8-diene-5-one;
5(R,S)-3-[2-(piperidin-4-yl)ethyl]-8-(3-carboxypropyl)-1-oxa-2-azaspiro[4.4]nona-2,8-diene-5-one;
5(R,S)-3-[2-(piperidin-4-yl)ethyl]-8-(2-carboxyethyl)-1-oxa-2,8-diazaspiro[4.4]dec-2-ene-7,9-dione;
5(R,S)-3-[2-(piperidin-4-yl)ethyl]-8-(3-carboxypropyl)-1-oxa-2,8-diazaspiro[4.4]dec-2-ene-5,7-dione;
5(R,S)-3-[2-(piperidin-4-yl)ethyl]-8-(2-carboxyethyl)-1-oxa-2,8-diazaspiro[4.4]dec-2-ene-5-one;
5(R,S) -3-[2-(piperidin-4-yl)ethyl]-8-(3-carboxypropyl)-1-oxa-2,8-diazaspiro[4.4]dec-2-ene-5-one;
5(R,S)-3-[2-(piperidin-4-yl)ethyl]-8-(2-carboxyethyl)-1-oxa-2-azaspiro[4.4]deca-2,8-diene-5-one;
5(R,S)-3-[2-(piperidin-4-yl)ethyl]-8-(3-carboxypropyl)-1-oxa-2-azaspiro[4.4]deca-2,8-diene-5-one;
5(R,S) -3-[2-(piperidin-4-yl)ethyl]-8-(2-carboxyethyl)-1-oxa-2,8-diazaspiro[4.4]undec-2-ene-7,9-dione;
5(R,S)-3-[2-(piperidin-4-yl)ethyl]-8-(3-carboxypropyl)-1-oxa-2,8-diazaspiro[4.4]undec-2-ene-7,9-dione;
5(R,S)-3-[2-(piperidin-4-yl)ethyl]-8-(2-carboxyethyl)-1-oxa-2,8-diazaspiro[4.4]undec-2-ene-5-one;
5(R,S)-3-[2-(piperidin-4-yl)ethyl]-8-(3-carboxypropyl)-1-oxa-2,8-diazaspiro[4.4]undec-2-ene-5-one;
5(R,S) -3-[2-(piperidin-4-yl)ethyl]-8-(2-carboxyethyl)-1-oxa-2-azaspiro[4.4]undeca-2,8-diene-5-one;
5(R,S)-3-[2-(piperidin-4-yl)ethyl]-8-(3-carboxypropyl)-1-oxa-2-azaspiro[4.4]undeca-2,8-diene-5-one;
5(R,S)-3-(4-amidinophenyl)-8-[2-(benzyloxycarbonylamino)-2-carboxyethyl]-1-oxa-2,8-diazaspiro[4.5]dec-2-ene.

10. A compound of Formula I:

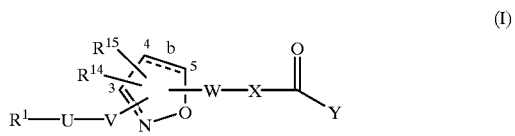

(I)

or pharmaceutically acceptable salt form thereof, wherein:
b is a carbon-carbon single bond or double bond;
$R^1$ is selected from:
$R^2(R^3)N(CH_2)_qZ$—, $R^2(R^3)N(R^2N=)C(CH_2)_qZ$—, $R^2(R^3)N(R^2N=)CN(R^2)(CH_2)_qZ$—, piperazinyl-$(CH_2)_qZ$— or

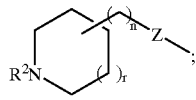

;

Z is selected from O, S, S(=O), S(=O)$_2$;
$R^2$ and $R^3$ are independently selected from: H, $C_1$–$C_{10}$ alkyl, $C_2$–$C_6$ alkenyl, $C_3$–$C_{11}$ cycloalkyl, $C_4$–$C_{11}$ cycloalkylalkyl, $C_6$–$C_{10}$ aryl, $C_7$–$C_{11}$ arylalkyl, $C_2$–$C_7$ alkylcarbonyl, $C_7$–$C_{11}$ arylcarbonyl, $C_2$–$C_{10}$ alkoxycarbonyl, $C_4$–$C_{11}$ cycloalkoxycarbonyl, $C_7$–$C_{10}$ bicycloalkoxycarbonyl, $C_7$–$C_{11}$ aryloxycarbonyl, or aryl($C_1$–$C_{10}$ alkoxy)carbonyl, $C_1$–$C_6$ alkylcarbonyloxy ($C_1$–$C_4$ alkoxy)carbonyl, $C_6$–$C_{10}$ arylcarbonyloxy ($C_1$–$C_4$ alkoxy)carbonyl, $C_4$–$C_{11}$ cycloalkylcarbonyloxy($C_1$–$C_4$ alkoxy)carbonyl;
U is optionally present and is selected from $C_1$–$C_7$ alkylene, $C_2$–$C_7$ alkenylene, $C_2$–$C_7$ alkynylene, arylene, or pyridylene;
V is selected from:
a single bond;
$C_1$–$C_7$ alkylene substituted with 0–6 $R^6$ or $R^7$;
$C_2$–$C_7$ alkenylene substituted with 0–4 $R^6$ or $R^7$;
$C_2$–$C_7$ alkynylene substituted with 0–4 $R^6$ or $R^7$;
phenylene substituted with 0–4 $R^6$ or $R^7$;
pyridylene substituted with 0–3 $R^6$ or $R^7$;
pyridazinylene substituted with 0–3 $R^6$ or $R^7$;
W is -(aryl)-$Z^1$—, wherein said aryl is substituted with 0–6 $R^6$ or $R^7$;
$Z^1$ is selected from a single bond, —$CH_2$—, O or S;
X is selected from:
a single bond;
$C_1$–$C_7$ alkylene substituted with 0–6 $R^4$, $R^8$ or $R^{15}$;
$C_2$–$C_7$ alkenylene substituted with 0–4 $R^4$, $R^8$ or $R^{15}$;
$C_2$–$C_7$ alkynylene substituted with 0–4 $R^4$, $R^8$ or $R^{15}$;
Y is selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ aralkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{10}$ alkoxyalkylcarbonyloxyalkyloxy, $C_5$ to $C_{10}$ (5-alkyl-1,3-dioxa-cyclopenten-2-one-yl)methyloxy, $C_{10}$ to $C_{14}$ (5-aryl-1,3-dioxa-cyclopenten-2-one-yl)methyloxy; $(R^2)(R^3)N$—$(C_1$–$C_{10}$ alkoxy)-;

$R^4$ is selected from H, $C_1-C_{10}$ alkyl, hydroxy, $C_1-C_{10}$ alkoxy, nitro, $C_1-C_{10}$ alkylcarbonyl, or $-N(R^{12})R^{13}$;

$R^6$ and $R^7$ are each independently selected from H, $C_1-C_{10}$ alkyl, hydroxy, $C_1-C_{10}$ alkoxy, nitro, $C_1-C_{10}$ alkylcarbonyl, $-N(R^{12})R^{13}$, cyano, halo, $CF_3$, CHO, $CO_2R^{5a}$, $C(=O)R^{5a}$, $CONHR^{5a}$, $CON(R^{12})_2$, $OC(=O)R^{5a}$, $OC(=O)OR^{5a}$, $OR^{5a}$, $OC(=O)N(R^{12})_2$, $OCH_2CO_2R^{5a}$, $CO_2CH_2CO_2R^{5a}$, $N(R^{12})_2$, $NO_2$, $NR^{12}C(=O)R^{5a}$, $NR^{12}C(=O)OR^{5a}$, $NR^{12}C(=O)N(R^{12})_2$, $NR^{12}SO_2N(R^{12})_2$, $NR^{12}SO_2R^{5a}$, $S(O)_pR^{5a}$, $SO_2N(R^{12})_2$, $C_2$ to $C_6$ alkenyl, $C_3$ to $C_{11}$ cycloalkyl, $C_4$ to $C_{11}$ cycloalkylmethyl;

$C_6$ to $C_{10}$ aryl optionally substituted with halogen, alkoxy, alkyl, $-CF_3$, $S(O)_m$Me, or $-NMe_2$; or $C_7$ to $C_{11}$ arylalkyl said aryl being optionally substituted with halogen, alkoxy, alkyl, $-CF_3$, $S(O)_m$Me, or $-NMe_2$;

$R^8$ is selected from:
  H;
  $R^6$;
  $C_1-C_{10}$ alkyl, substituted with 0–8 $R^6$;
  $C_2-C_{10}$ alkenyl, substituted with 0–6 $R^6$;
  $C_2-C_{10}$ alkynyl, substituted with 0–6 $R^6$;
  $C_3-C_8$ cycloalkyl, substituted with 0–6 $R^6$;
  $C_5-C_6$ cycloalkenyl, substituted with 0–5 $R^6$;
  aryl, substituted with 0–5 $R^6$;
  5–6 membered heterocyclic ring containing 1–2 N, O, or S heteroatoms, wherein said heterocyclic ring may be saturated, partially saturated, or fully unsaturated, said heterocyclic ring being substituted with 0–5 $R^6$;

$R^{12}$ and $R^{13}$ are independently H, $C_1-C_{10}$ alkyl, $C_1-C_{10}$ alkoxycarbonyl, $C_1-C_{10}$ alkylcarbonyl, $C_1-C_{10}$ alkylsulfonyl, aryl($C_1-C_{10}$ alkyl)sulfonyl, heteroarylsulfonyl, arylsulfonyl, aryl, $C_2-C_6$ alkenyl, $C_3-C_{11}$ cycloalkyl, $C_4-C_{11}$ cycloalkylalkyl, $C_7-C_{11}$ arylalkyl, $C_2-C_7$ alkylcarbonyl, $C_7-C_{11}$ arylcarbonyl, $C_2-C_{10}$ alkoxycarbonyl, $C_4-C_{11}$ cycloalkoxycarbonyl, $C_7-C_{11}$ bicycloalkoxycarbonyl, $C_7-C_{11}$ aryloxycarbonyl, heteroarylcarbonyl, heteroarylalkylcarbonyl or aryl ($C_1-C_{10}$ alkoxy) carbonyl;

$R^{14}$ is selected from H, $C_1-C_{10}$ alkyl, $C_2-C_{10}$ alkenyl, $C_2-C_{10}$ alkynyl, $C_1-C_{10}$ alkoxy, aryl, heteroaryl or $C_1-C_{10}$ alkoxycarbonyl, $CO_2R^5$ or $-C(=O)N(R^{12})R^{13}$;

$R^5$ and $R^{5a}$ are selected independently from H, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_6$ to $C_{10}$ aryl, $C_7$ to $C_{11}$ arylalkyl, or $C_1-C_{10}$ alkyl substituted with 0–8 $R^4$;

$R^{15}$ is selected from:
  H;
  $R^6$;
  $C_1-C_{10}$ alkyl, substituted with 0–8 $R^6$;
  $C_2-C_{10}$ alkenyl, substituted with 0–6 $R^6$;
  $C_1-C_{10}$ alkoxy, substituted with 0–6 $R^6$;
  aryl, substituted with 0–5 $R^6$;
  5–6 membered heterocyclic ring containing 1–2 N, O, or S heteroatoms, wherein said heterocyclic ring may be saturated, partially saturated, or fully unsaturated, said heterocyclic ring being substituted with 0–5 $R^6$;
  $C_1-C_{10}$ alkoxycarbonyl substituted with 0–8 $R^6$;
  $CO_2R^5$; or
  $-C(=O)N(R^{12})R^{13}$;

n is 0–4;
q is 2–7;
r is 0–3;

provided that n, q, and r are chosen such that the number of atoms between $R^1$ and Y is about 8–17.

11. A compound of claim 10 of Formula IV:

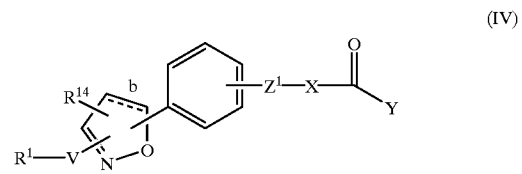

(IV)

wherein:

b is a carbon-carbon single bond or double bond;

$R^1$ is selected from $R^2HN(CH_2)_qO-$, $R^2HN(R^2N=C)NH(CH_2)_qO-$, piperazinyl-$(CH_2)_qO-$, or

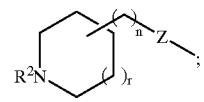

Z is O;

$R^2$ is selected from H, aryl($C_1-C_{10}$)alkoxycarbonyl, $C_1-C_{10}$ alkoxycarbonyl;

V is selected from:
  a single bond;
  $C_1-C_7$ alkylene substituted with 0–6 $R^6$ or $R^7$;
  $C_2-C_7$ alkenylene substituted with 0–4 $R^6$ or $R^7$;
  $C_2-C_7$ alkynylene substituted with 0–4 $R^6$ or $R^7$;
  phenylene substituted with 0–3 $R^6$ or $R^7$;
  pyridylene substituted with 0–3 $R^6$ or $R^7$; pyridazinylene substituted with 0–3 $R^6$ or $R^7$;

$Z^1$ is selected from a single bond, O or S;

X is selected from:
  a single bond;
  $C_1-C_7$ alkylene substituted with 0–4 $R^4$, $R^8$ or $R^{15}$;
  $C_2-C_7$ alkenylene substituted with 0–3 $R^4$, $R^8$ or $R^{15}$;
  $C_2-C_7$ alkynylene substituted with 0–3 $R^4$, $R^8$ or $R^{15}$;

Y selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ aralkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{10}$ alkoxyalkylcarbonyloxyalkyloxy, $C_5$ to $C_{10}$ (5-alkyl-1,3-dioxa-cyclopenten-2-one-yl)methyloxy, or $C_{10}$ to $C_{14}$ (5-aryl-1,3-dioxa-cyclopenten-2-one-yl) methyloxy;

$R^4$ is selected from H, $C_1-C_{10}$ alkyl, hydroxy, $C_1-C_{10}$ alkoxy, nitro, $C_1-C_{10}$ alkylcarbonyl, or $-N(R^{12})R^{13}$;

$R^6$ and $R^7$ are selected from H, $C_1-C_{10}$ alkyl, hydroxy, $C_1-C_{10}$ alkoxy, nitro, $C_1-C_{10}$ alkylcarbonyl, $-N(R^{12})R^{13}$, cyano, or halo;

$R^8$ is selected from H, $C_1-C_{10}$ alkyl, $C_2-C_{10}$ alkenyl, $C_3-C_8$ cycloalkyl, $C_5-C_6$ cycloalkenyl, aryl, 5–6 membered heterocyclic ring containing 1–2 N, O, or S, where said heterocyclic ring may be saturated, partially saturated, or fully unsaturated;

$R^{12}$ and $R^{13}$ are independently selected from H, $C_1-C_{10}$ alkyl, $C_1-C_{10}$ alkoxycarbonyl, $C_1-C_{10}$ alkylcarbonyl, $C_1-C_{10}$ alkylsulfonyl, aryl($C_1-C_{10}$ alkyl)sulfonyl, arylsulfonyl, heteroarylcarbonyl, heteroarylsulfonyl, heteroarylalkylcarbonyl or aryl;

$R^{14}$ is selected from H, $C_1-C_{10}$ alkyl, $C_2-C_{10}$ alkenyl, $C_2-C_{10}$ alkynyl, $C_1-C_{10}$ alkoxy, aryl, heteroaryl or $C_1-C_{10}$ alkoxycarbonyl, $CO_2R^5$ or —C(=O)N($R^{12}$)$R^{13}$;

$R^5$ is selected from H or $C_1-C_{10}$ alkyl substituted with 0–6 $R^4$;

n is 0–4;

q is 2–7;

provided that n and q are chosen such that the number of atoms between $R^1$ and Y is in the range of 8–17.

12. A compound of claim 1, wherein:
$R^1$ is $R^2HN(CH_2)_qO$— or

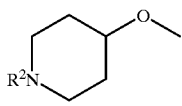

V is $C_1-C_3$ alkylene;

$Z^1$ is a single bond or O;

X is $C_1-C_3$ alkylene substituted with 0–1 $R^4$;

Y is selected from:
hydroxy;
$C_1$ to $C_{10}$ alkoxy;
methylcarbonyloxymethoxy-;
ethylcarbonyloxymethoxy-;
t-butylcarbonyloxymethoxy-;
cyclohexylcarbonyloxymethoxy-;
1-(methylcarbonyloxy)ethoxy-;
1-(ethylcarbonyloxy)ethoxy-;
1-(t-butylcarbonyloxy)ethoxy-;
1-(cyclohexylcarbonyloxy)ethoxy-;
i-propyloxycarbonyloxymethoxy-;
t-butyloxycarbonyloxymethoxy-;
1-(i-propyloxycarbonyloxy)ethoxy-;
1-(cyclohexyloxycarbonyloxy)ethoxy-;
1-(t-butyloxycarbonyloxy)ethoxy-;
dimethylaminoethoxy-;
diethylaminoethoxy-;
(5-methyl-1,3-dioxacyclopenten-2-on-4-yl)methoxy-;
(5-(t-butyl)-1,3-dioxacyclopenten-2-on-4-yl)methoxy-;
(1,3-dioxa-5-phenyl-cyclopenten-2-on-4-yl)methoxy-;
1-(2-(2-methoxypropyl)carbonyloxy)ethoxy-;

$R^{12}$ and $R^{13}$ are independently selected from H, $C_1-C_6$ alkyl, $C_1-C_4$ alkoxycarbonyl, $C_1-C_4$ alkylcarbonyl, $C_1-C_6$ alkylsulfonyl, aryl($C_1-C_4$ alkyl)sulfonyl, arylsulfonyl, heteroarylcarbonyl, heteroarylsulfonyl, heteroarylalkylcarbonyl or aryl;

$R^{13}$ is H.

13. A compound of claim 10, or a pharmaceutically acceptable salt form thereof, selected from:
5(R,S)-4-[3-(piperidin-4-yl)oxymethylisoxazolin-5-yl] hydrocinnamic acid;
5(R,S)-4-[3-(2-aminoethoxymethyl),isoxazolin-5-yl] hydrocinnamic acid;
5(R,S)-4-[3-(3-aminopropyloxymethyl)isoxazolin-5-yl] hydrocinnamic acid;
5(R,S)-4-[3-(piperidin-4-yl)oxymethylisoxazolin-5-yl] phenoxyacetic acid;
5(R,S)-4-[3-(2-aminoethoxymethyl)isoxazolin-5-yl] phenoxyacetic acid;
5(R,S)-4-[3-(3-aminopropyloxymethyl)isoxazolin-5-yl] phenoxyacetic acid.

14. A compound of Formula I:

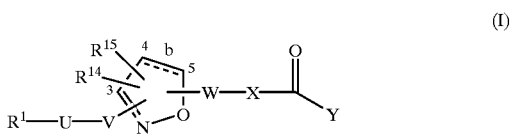

(I)

or a pharmaceutically acceptable salt form thereof wherein:

b is a carbon-carbon single or double bond;

$R^1$ is selected from $R^{2a}(R^3)N$—, $R^2(R^3)N(R^2N=)C$—, $R^{2a}(R^3)N(CH_2)_qZ$—, $R^2(R^3)N(R^2N=)C(CH_2)_qZ$—, $R^2(R^3)NC(O)$—, $R^2(R^5O)N(R^2N=)C$—, $R^2(R^3)N(R^5ON=)C$—;

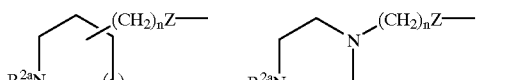

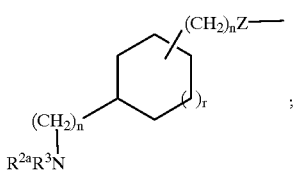

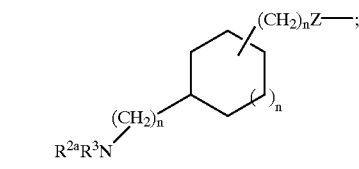

Z is selected from a bond, O, S, S(=O), S(=O)$_2$;

$R^2$ and $R^3$ are independently selected from: H; $C_1-C_{10}$ alkyl; $C_3-C_6$ alkenyl; $C_3-C_{11}$ cycloalkyl; $C_4-C_{11}$ cycloalkylalkyl; $C_6-C_{10}$ aryl optionally substituted with 0–3 groups selected from hydroxy, halogen, $C_1-C_6$ alkoxy, $C_1-C_6$ alkyl, $CF_3$, $S(O)_mCH_3$, —N(CH$_3$)$_2$, $C_1-C_4$ haloalkyl, methylenedioxydiyl, ethylenedioxydiyl; $C_7-C_{11}$ arylalkyl optionally substituted with 0–3 groups selected from hydroxy, halogen, $C_1-C_6$ alkoxy, $C_1-C_6$ alkyl, $CF_3$, $S(O)_mCH_3$, —N(CH$_3$)$_2$, $C_1-C_4$ haloalkyl, methylenedioxydiyl, ethylenedioxydiyl; $C_2-C_7$ alkylcarbonyl; $C_7-C_{11}$ arylcarbonyl optionally substituted with 0–3 groups selected from hydroxy, halogen, $C_1-C_6$ alkoxy, $C_1-C_6$ alkyl, $CF_3$, $S(O)_mCH_3$, —N(CH$_3$)$_2$, $C_1-C_4$ haloalkyl, methylenedioxydiyl, ethylenedioxydiyl; $C_1-C_{10}$ alkoxycarbonyl; $C_4-C_{11}$ cycloalkoxycarbonyl; $C_7-C_{11}$ bicycloalkoxycarbonyl; $C_7-C_{11}$ aryloxycarbonyl optionally substituted with 0–3 groups selected from hydroxy, halogen, $C_1-C_6$ alkoxy, $C_1-C_6$ alkyl, $CF_3$, $S(O)_mCH_3$, —N(CH$_3$)$_2$, $C_1-C_4$ haloalkyl, methylenedioxydiyl, ethylenedioxydiyl; aryl($C_1-C_{10}$ alkoxy)carbonyl where the aryl group is optionally substituted with 0–3 groups selected from hydroxy, halogen, $C_1-C_6$ alkoxy, $C_1-C_6$ alkyl, $CF_3$, $S(O)_mCH_3$, —N(CH$_3$)$_2$, $C_1-C_4$ haloalkyl, methylenedioxydiyl, ethylenedioxydiyl; $C_1-C_6$ alkylcarbonyloxy($C_1-C_4$ alkoxy)carbonyl; $C_6-C_{10}$ arylcarbonyloxy($C_1-C_4$ alkoxy)carbonyl where the aryl group is optionally substituted with 0–3 groups selected from hydroxy, halogen, $C_1-C_6$ alkoxy, $C_1-C_6$ alkyl, $CF_3$, $S(O)_mCH_3$, —N(CH$_3$)$_2$, C$_1$–C$_4$ haloalkyl, methylenedioxydiyl, ethylenedioxydiyl; C$_4$–C$_{11}$ cycloalkylcarbonyloxy(C$_1$–C$_4$ alkoxy)carbonyl; heteroaryl optionally substituted with 0–2 groups selected from hydroxy, halogen, C$_1$–C$_6$ alkoxy, C$_1$–C$_6$ alkyl, CF$_3$, S(O)$_m$CH$_3$, —N(CH$_3$)$_2$, C$_1$–C$_4$ haloalkyl, methylenedioxydiyl, ethylenedioxydiyl; or heteroaryl(C$_1$–C$_5$)alkyl where the heteroaryl group is optionally substituted with 0–2 groups selected from hydroxy, halogen, C$_1$–C$_6$ alkoxy, C$_1$–C$_6$ alkyl, CF$_3$, S(O)$_m$CH$_3$, —N(CH$_3$)$_2$, C$_1$–C$_4$ haloalkyl, methylenedioxydiyl, ethylenedioxydiyl;

provided that only one of R$^2$ and R$^3$ may be hydroxy;

R$^{2a}$ is R$^2$ or R$^2$(R$^3$)N(R$^2$N=)C;

U is selected from:
  a single bond,
  —(C$_1$–C$_7$ alkyl)-,
  —(C$_2$–C$_7$ alkenyl)-,
  —(C$_2$–C$_7$ alkynyl)-,
  -(aryl)- substituted with 0–3 R$^6$-, or
  -(pyridyl)- substituted with 0–3 R$^{6a}$;

V is selected from:
  a single bond;
  —(C$_1$–C$_7$ alkyl)-, substituted with 0–3 groups independently selected from R$^6$ or R$^7$;
  —(C$_2$–C$_7$ alkenyl)-, substituted with 0–3 groups independently selected from R$^6$ or R$^7$;
  —(C$_2$–C$_7$ alkynyl)-, substituted with 0–3 groups independently selected from R$^6$ or R$^7$;
  -(phenyl)-, substituted with 0–2 groups independently selected from R$^6$ or R$^7$;
  -(pyridyl)-, substituted with 0–2 groups independently selected from R$^6$ or R$^7$; or
  -(pyridazinyl)-, substituted with 0–2 groups independently selected from R$^6$ or R$^7$;

W is selected from:

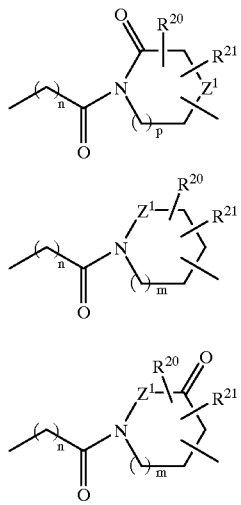
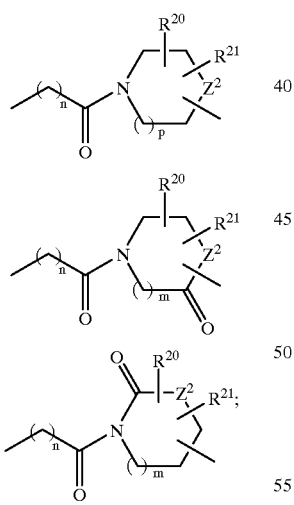

X is selected from:
  a single bond,
  —(C(R$^4$)$_2$)$_n$—C(R$^4$)(R$^8$)—C(R$^4$)(R$^{4a}$)—, with the proviso that when n is 0 or 1, then at least one of R$^{4a}$ or R$^8$ is other than H or methyl;

Y selected from:
  hydroxy,
  C$_1$ to C$_{10}$ alkyloxy,
  C$_3$ to C$_{11}$ cycloalkyloxy,
  C$_6$ to C$_{10}$ aryloxy,
  C$_7$ to C$_{11}$ aralkyloxy,
  C$_3$ to C$_{10}$ alkylcarbonyloxyalkyloxy,
  C$_3$ to C$_{10}$ alkoxycarbonyloxyalkyloxy,
  C$_2$ to C$_{10}$ alkoxycarbonylalkyloxy,
  C$_5$ to C$_{10}$ cycloalkylcarbonyloxyalkyloxy,
  C$_5$ to C$_{10}$ cycloalkoxycarbonyloxyalkyloxy,
  C$_5$ to C$_{10}$ cycloalkoxycarbonylalkyloxy,
  C$_7$ to C$_{11}$ aryloxycarbonylalkyloxy,
  C$_8$ to C$_{12}$ aryloxycarbonyloxyalkyloxy,
  C$_8$ to C$_{12}$ arylcarbonyloxyalkyloxy,
  C$_5$ to C$_{10}$ alkoxyalkylcarbonyloxyalkyloxy,
  C$_5$ to C$_{10}$ (5-alkyl-1,3-dioxa-cyclopenten-2-one-yl)methyloxy,
  C$_{10}$ to C$_{14}$ (5-aryl-1,3-dioxa-cyclopenten-2-one-yl)methyloxy,
  (R$^2$)(R$^3$)N—(C$_1$–C$_{10}$ alkoxy)-;

Z$^1$ is —C—, —O—, or —NR$^{22}$—;

Z$^2$ is —O—, or —NR$^{22}$—;

R$^4$ is selected from H, C$_1$–C$_{10}$ alkyl, C$_1$–C$_{10}$ alkylcarbonyl, aryl, arylalkylene cycloalkyl, or cycloalkylalkylene;

alternately, two R$^4$ groups on adjacent carbon atoms may join to form a bond, thereby to form a carbon-carbon double or triple bond between such adjacent carbon atoms;

R$^{4a}$ is selected from H, hydroxy, C$_1$–C$_{10}$ alkoxy, nitro, N(R$^5$)R$^{5a}$, —N(R$^{12}$)R$^{13}$, —N(R$^{16}$)R$^{17}$, C$_1$–C$_{10}$ alkyl substituted with 0–3 R$^6$, aryl substituted with 0–3 R$^6$, or C$_1$–C$_{10}$ alkylcarbonyl;

R$^{4b}$ is selected from H, C$_1$–C$_6$ alkyl, C$_2$–C$_6$ alkenyl, C$_2$–C$_6$ alkynyl, hydroxy, C$_1$–C$_6$ alkoxy; C$_1$–C$_6$ alkylthio, C$_1$–C$_6$ alkylsulfinyl, C$_1$–C$_6$ alkylsulfonyl, nitro, C$_1$–C$_6$ alkylcarbonyl, C$_6$–C$_{10}$ aryl, —N(R$^{12}$)R$^{13}$; halo, CF$_3$, CN, C$_1$–C$_6$ alkoxycarbonyl, carboxy, piperidinyl, or pyridyl;

R$^5$ is selected from H, C$_1$–C$_8$ alkyl, C$_2$–C$_6$ alkenyl, C$_3$–C$_{11}$ cycloalkyl, C$_4$–C$_{11}$ cycloalkylmethyl, C$_6$–C$_{10}$ aryl, C$_7$–C$_{11}$ arylalkyl, or C$_1$–C$_{10}$ alkyl substituted with 0–2 R$^{4b}$;

R$^{5a}$ is selected from hydrogen, hydroxy, C$_1$ to C$_8$ alkyl, C$_2$ to C$_6$ alkenyl, C$_3$ to C$_{11}$ cycloalkyl, C$_4$ to C$_{11}$ cycloalkylmethyl, C$_1$–C$_6$ alkoxy, benzyloxy, C$_6$ to C$_{10}$ aryl, heteroaryl, C$_7$ to C$_{11}$ arylalkyl, or C$_1$–C$_{10}$ alkyl substituted with 0–2 R$^{4b}$;

alternately, R$^5$ and R$^{5a}$ when both are substituents on the same nitrogen atom (as in —NR$^5$R$^{5a}$) can be taken together with the nitrogen atom to which they are attached to form 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl, each being optionally substituted with C$_1$–C$_6$ alkyl, C$_6$–C$_{10}$ aryl, heteroaryl, C$_7$–C$_{11}$ arylalkyl, C$_1$–C$_6$ alkylcarbonyl, C$_3$–C$_7$ cycloalkylcarbonyl, C$_1$–C$_6$ alkoxycarbonyl, C$_7$–C$_{11}$ arylalkoxycarbonyl, C$_1$–C$_6$ alkylsulfonyl or C$_6$–C$_{10}$ arylsulfonyl;

R$^{5b}$ is selected from C$_1$–C$_8$ alkyl, C$_2$–C$_6$ alkenyl, C$_3$–C$_{11}$ cycloalkyl, C$_4$–C$_{11}$ cycloalkylmethyl, C$_6$–C$_{10}$ aryl, C$_7$–C$_{11}$ arylalkyl, or C$_1$–C$_{10}$ alkyl substituted with 0–2 R$^{4b}$;

R$^6$ is selected from H, C$_1$–C$_{10}$ alkyl, hydroxy, C$_1$–C$_{10}$ alkoxy, nitro, C$_1$–C$_{10}$ alkylcarbonyl, —N(R$^{12}$)R$^{13}$, cyano, halo, CF$_3$, CHO, CO$_2$R$^5$, C(=O)R$^{5a}$, CONR$^5$R$^{5a}$, OC(=O)R$^{5a}$, OC(=O)OR$^{5b}$, OR$^5$, OC(=O)NR$^5$R$^{5a}$, OCH$_2$CO$_2$R$^5$, CO$_2$CH$_2$CO$_2$R$^5$, NO$_2$, NR$^{5a}$C(=O)R$^{5a}$, NR$^{5a}$C(=O)OR$^{5b}$, NR$^{5a}$C(=O) NR$^5$R$^{5a}$, NR$^{5a}$SO$_2$NR$^5$R$^{5a}$, NR$^{5a}$SO$_2$R$^5$, S(O)$_p$R$^5$, SO$_2$NR$^5$R$^{5a}$, C$_2$ to C$_6$ alkenyl, C$_3$ to C$_{11}$ cycloalkyl, C$_4$ to C$_{11}$ cycloalkylmethyl;

C$_6$ to C$_{10}$ aryl optionally substituted with 1–3 groups selected from halogen, C$_1$–C$_6$ alkoxy, C$_1$–C$_6$ alkyl, CF$_3$, S(O)$_m$Me, or —NMe$_2$;

C$_7$ to C$_{11}$ arylalkyl, said aryl being optionally substituted with 1–3 groups selected from halogen, C$_1$–C$_6$ alkoxy, C$_1$–C$_6$ alkyl, CF$_3$, S(O)$_m$Me, or —NMe$_2$;

methylenedioxy when R$^6$ is a substiuent on aryl; or a 5–6 membered heterocyclic ring containing 1–2 N, O, or S heteroatoms, wherein said heterocyclic ring may be saturated, partially saturated, or fully unsaturated, said heterocyclic ring being substituted with 0–2 R$^7$;

R$^{6a}$ is selected from C$_1$–C$_4$ alkyl, C$_1$–C$_4$ alkoxy, halo, CF$_3$, NO$_2$, or NR$^{12}$R$^{13}$;

R$^7$ is selected from H, C$_1$–C$_{10}$ alkyl, hydroxy, C$_1$–C$_{10}$ alkoxy, nitro, C$_1$–C$_{10}$ alkylcarbonyl, —N(R$^{12}$)R$^{13}$, cyano, halo, CF$_3$, CHO, CO$_2$R$^5$, C(=O)R$^{5a}$, CONR$^5$R$^{5a}$, OC(=O)R$^{5a}$, OC(=O)OR$^{5b}$, OR$^{5a}$, OC(=O)NR$^5$R$^{5a}$, OCH$_2$CO$_2$R$^5$, CO$_2$CH$_2$CO$_2$R$^5$, NO$_2$, NR$^{5a}$C(=O)R$^{5a}$, NR$^{5a}$C(=O)OR$^{5b}$, NR$^{5a}$C(=O) NR$^5$R$^{5a}$, NR$^{5a}$SO$_2$NR$^5$R$^{5a}$, NR$^{5a}$SO$_2$R$^5$, S(O)$_m$R$^{5a}$, SO$_2$NR$^5$R$^{5a}$, C$_2$ to C$_6$ alkenyl, C$_3$ to C$_{11}$ cycloalkyl, C$_4$ to C$_{11}$ cycloalkylmethyl, C$_6$ to C$_{10}$ aryl, or C$_7$ to C$_{11}$ arylalkyl;

R$^8$ is selected from:
R$^6$;
C$_2$–C$_{10}$ alkyl, substituted with 0–3 R$^6$;
C$_2$–C$_{10}$ alkenyl, substituted with 0–3 R$^6$;
C$_2$–C$_{10}$ alkynyl, substituted with 0–3 R$^6$;
C$_3$–C$_8$ cycloalkyl, substituted with 0–3 R$^6$;
C$_5$–C$_6$ cycloalkenyl, substituted with 0–3 R$^6$;
aryl, substituted with 0–3 R$^6$;
5–6 membered heterocyclic ring containing 1–2 N, O, or S heteroatoms, wherein said heterocyclic ring may be saturated, partially saturated, or fully unsaturated, said heterocyclic ring being substituted with 0–2 R$^6$;

R$^{12}$ and R$^{13}$ are independently H, C$_1$–C$_{10}$ alkyl, C$_1$–C$_{10}$ alkoxycarbonyl, C$_1$–C$_{10}$ alkylcarbonyl, C$_1$–C$_{10}$ alkylsulfonyl, aryl(C$_1$–C$_{10}$ alkyl)sulfonyl, heteroarylsulfonyl, arylsulfonyl, aryl, C$_2$–C$_6$ alkenyl, C$_3$–C$_{11}$ cycloalkyl, C$_4$–C$_{11}$ cycloalkylalkyl, C$_7$–C$_{11}$ arylalkyl, C$_7$–C$_{11}$ arylcarbonyl, C$_4$–C$_{11}$ cycloalkoxycarbonyl, C$_7$–C$_{11}$ bicycloalkoxycarbonyl, C$_7$–C$_{11}$ aryloxycarbonyl, or aryl(C$_1$–C$_{10}$ alkoxy)carbonyl, wherein said aryls are optionally substituted with 0–3 substituents selected from the group consisting of: C$_1$–C$_4$ alkyl, C$_1$–C$_4$ alkoxy, halo, CF$_3$, and NO$_2$;

R$^{14}$ is selected from H, C$_1$–C$_{10}$ alkyl, C$_2$–C$_{10}$ alkenyl, C$_2$–C$_{10}$ alkynyl, C$_1$–C$_{10}$ alkoxy, aryl, heteroaryl or C$_1$–C$_{10}$ alkoxycarbonyl, CO$_2$R$^5$ or —C(=O)N(R$^5$)R$^{5a}$;

R$^{15}$ is selected from:
H;
R$^6$;
C$_1$–C$_{10}$ alkyl, substituted with 0–3 R$^6$;
C$_2$–C$_{10}$ alkenyl, substituted with 0–3 R$^6$;
C$_1$–C$_{10}$ alkoxy, substituted with 0–3 R$^6$;
aryl, substituted with 0–3 R$^6$;
5–6 membered heterocyclic ring containing 1–2 N, O, or S heteroatoms, wherein said heterocyclic ring may be saturated, partially saturated, or fully unsaturated, said heterocyclic ring being substituted with 0–2 R$^6$;
C$_1$–C$_{10}$ alkoxycarbonyl substituted with 0–2 R$^6$;

—CO$_2$R$^5$; or
—C(=O)N(R$^{12}$)R$^{13}$;

provided that when b is a double bond, only one of R$^{14}$ or R$^{15}$ is present;

R$^{16}$ is selected from:
—C(=O)—O—R$^{18a}$,
—C(=O)—R$^{18b}$,
—C(=O)N(R$^{18b}$)$_2$,
—C(=O)NHSO$_2$R$^{18a}$,
—C(=O)NHC(=O)R$^{18b}$,
—C(=O)NHC(=O)OR$^{18a}$,
—C(=O)NHSO$_2$NHR$^{18b}$,
—C(=S)—NH—R$^{18b}$,
—NH—C(=O)—O—R$^{18a}$,
—NH—C(=O)—R$^{18b}$,
—NH—C(=O)—NH—R$^{18b}$,
—SO$_2$—O—R$^{18a}$,
—SO$_2$—R$^{18a}$,
—SO$_2$—N(18$^b$)$_2$,
—SO$_2$—NHC(=O)O18$^b$,
—P(=S)(OR$^{18a}$)$_2$,
—P(=O)(OR$^{18a}$)$_2$,
—P(=S)(R$^{18a}$)$_2$,

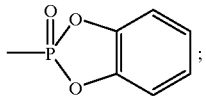

or

R$^{17}$ is selected from: H, C$_1$–C$_{10}$ alkyl, C$_2$–C$_6$ alkenyl, C$_3$–C$_{11}$ cycloalkyl, C$_4$–C$_{15}$ cycloalkylalkyl, aryl, aryl (C$_1$–C$_{10}$ alkyl)-;

R$^{18a}$ is selected from:
C$_1$–C$_8$ alkyl substituted with 0–2 R$^{19}$,
C$_2$–C$_8$ alkenyl substituted with 0–2 R$^{19}$,
C$_2$–C$_8$ alkynyl substituted with 0–2 R$^{19}$,
C$_3$–C$_8$ cycloalkyl substituted with 0–2 R$^{19}$,
aryl substituted with 0–4 R$^{19}$,
aryl(C$_1$–C$_6$ alkyl)- substituted with 0–4 R$^{19}$,
a 5–10 membered heterocyclic ring system having 1–3 heteroatoms selected independently from O, S, and N, said heterocyclic ring being substituted with 0–4 R$^{19}$,
C$_1$–C$_6$ alkyl substituted with a 5–10 membered heterocyclic ring system having 1–3 heteroatoms selected independently from O, S, and N, said heterocyclic ring being substituted with 0–4 R$^{19}$;

R$^{18b}$ is selected from R$^{18a}$ or H;

R$^{19}$ is selected from H, halogen, CF$_3$, CN, NO$_2$, NR$^{12}$R$^{13}$, C$_1$–C$_8$ alkyl, C$_2$–C$_6$ alkenyl, C$_2$–C$_6$ alkynyl, C$_3$–C$_{11}$ cycloalkyl, C$_4$–C$_{11}$ cycloalkylalkyl, aryl, aryl(C$_1$–C$_6$ alkyl)-, C$_1$–C$_6$ alkoxy, or C$_1$–C$_4$ alkoxycarbonyl;

R$^{20}$ and R$^{21}$ are each independently selected from H, C$_1$–C$_{10}$ alkyl, CO$_2$R$^5$, C(=O)R$^{5a}$, CONR$^5$R$^{5a}$, NR$^5$C(=O)R$^{5a}$, NR$^{12}$R$^{13}$, C$_2$–C$_6$ alkenyl, C$_3$–C$_{11}$ cycloalkyl, C$_4$–C$_{11}$ cycloalkylmethyl, C$_6$–C$_{10}$ aryl, or C$_7$–C$_{11}$ arylalkyl;

R$^{22}$ is selected from C$_1$–C$_{10}$ alkyl, C$_2$–C$_6$ alkenyl, C$_3$–C$_{11}$ cycloalkyl, C$_4$–C$_{15}$ cycloalkylalkyl, aryl, aryl(C$_1$–C$_{10}$ alkyl)-; C(=O)R$^{5a}$, CO$_2$R$^{5b}$, —C(=O)N(R$^5$)R$^{5a}$, or a bond to X;

m is 0–2;
n is 0–2;
p is 1–2;

q is 1–7;

r is 0–3;

provided that n, q and r are chosen such that the number of atoms connecting $R^1$ and Y is in the range of 8–17.

15. A compound of claim 14 of Formula Ic:

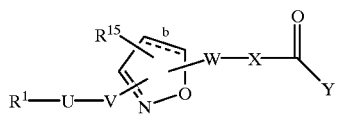

(Ic)

wherein:

Z is selected from a bond, O, or S;

$R^2$ and $R^3$ are independently selected from: H; $C_1$–$C_6$ alkyl; $C_7$–$C_{11}$ arylalkyl optionally substituted with 0–3 groups selected from hydroxy, halogen, $C_1$–$C_6$ alkoxy; $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; $C_1$–$C_{10}$ alkoxycarbonyl; aryl($C_1$–$C_{10}$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; or heteroaryl($C_1$–$C_5$)alkyl wherein the heteroaryl group is optionally substituted with 0–2 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl;

U is a single bond;

X is —$CHR^{4a}$—;

$R^5$ is selected from H or $C_1$–$C_{10}$ alkyl substituted with 0–6 $R^{4b}$;

$R^6$ and $R^7$ are each independently selected from H, $C_1$–$C_{10}$ alkyl, hydroxy, $C_1$–$C_{10}$ alkoxy, nitro, $C_1$–$C_{10}$ alkylcarbonyl, —$N(R^{12})R^{13}$, cyano, or halo;

$R^{12}$ and $R^{13}$ are each independently selected from H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, heteroarylsulfonyl, or aryl, wherein said aryls are optionally substituted with 0–3 substituents selected from the group consisting of: $C_1$–$C_4$ alkyl, $C_1$–$C_4$ alkoxy, halo, $CF_3$, and $NO_2$;

$R^{15}$ is selected from H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or $C_1$–$C_{10}$ alkoxycarbonyl, $CO_2R^5$ or —$C(=O)N(R^5)R^{5a}$;

$R^{16}$ is selected from:
—C(=O)—O—$R^{18a}$,
—C(=O)—$R^{18b}$,
—S(=O)$_2$—$R^{18a}$;

$R^{17}$ is selected from: H or $C_1$–$C_4$ alkyl;

$R^{18a}$ is selected from:
$C_1$–$C_8$ alkyl substituted with 0–2 $R^{19}$,
$C_2$–$C_8$ alkenyl substituted with 0–2 $R^{19}$,
$C_2$–$C_8$ alkynyl substituted with 0–2 $R^{19}$,
$C_3$–$C_8$ cycloalkyl substituted with 0–2 $R^{19}$,
aryl substituted with 0–2 $R^{19}$,
aryl($C_1$–$C_6$ alkyl)- substituted with 0–2 $R^{19}$,
a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyridinyl, 3H-indolyl, carbazolyl, pyrrolidinyl, piperidinyl, indolinyl, or morpholinyl, said heterocyclic ring being substituted with 0–2 $R^{19}$;

$C_1$–$C_6$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, said heterocyclic ring being substituted with 0–2 $R^{19}$.

16. A compound of claim 14 of Formula Ib:

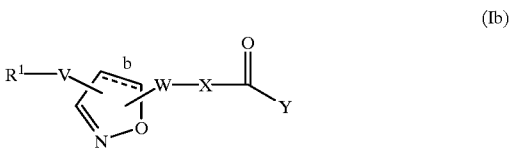

(Ib)

wherein:

$R^1$ is selected from: $R^2(R^3)N$—, $R^2NH(R^2N=)C$—, $R^2R^3N(CH_2)_{p''}Z$—, $R^2NH(R^2N=)CNH(CH_2)_{p'}Z$—, $R^2(R^3)NC(O)$—, $R^2(R^5O)N(R^2N=)C$—, $R^2(R^3)N(R^5ON=)C$—;

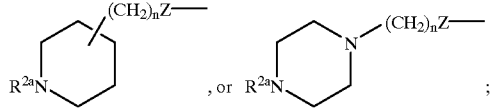

n is 0–1;

p' is 2–4;

p'' is 4–6;

Z is selected from a bond or O;

$R^3$ is H or $C_1$–$C_5$ alkyl;

V is a single bond, or -(phenyl)-;

X is selected from:
—$CH_2$—,
—$CHN(R^{16})R^{17}$—, or
—$CHNR^5R^{5a}$—;

Y is selected from:
hydroxy;
$C_1$ to $C_{10}$ alkoxy;
methylcarbonyloxymethoxy-;
ethylcarbonyloxymethoxy-;
t-butylcarbonyloxymethoxy-;
cyclohexylcarbonyloxymethoxy-;
1-(methylcarbonyloxy)ethoxy-;
1-(ethylcarbonyloxy)ethoxy-;
1-(t-butylcarbonyloxy)ethoxy-;
1-(cyclohexylcarbonyloxy)ethoxy-;
i-propyloxycarbonyloxymethoxy-;
t-butyloxycarbonyloxymethoxy-;
1-(i-propyloxycarbonyloxy)ethoxy-;
1-(cyclohexyloxycarbonyloxy)ethoxy-;
1-(t-butyloxycarbonyloxy)ethoxy-;
dimethylaminoethoxy-;
diethylaminoethoxy-;
(5-methyl-1,3-dioxacyclopenten-2-on-4-yl)methoxy-;
(5-(t-butyl)-1,3-dioxacyclopenten-2-on-4-yl) methoxy-;

(1,3-dioxa-5-phenyl-cyclopenten-2-on-4-yl)methoxy-;
1-(2-(2-methoxypropyl)carbonyloxy)ethoxy-;

$R^{18a}$ is selected from:
  $C_1$–$C_4$ alkyl substituted with 0–2 $R^{19}$,
  $C_2$–$C_4$ alkenyl substituted with 0–2 $R^{19}$,
  $C_2$–$C_4$ alkynyl substituted with 0–2 $R^{19}$,
  $C_3$–$C_4$ cycloalkyl substituted with 0–2 $R^{19}$,
  aryl substituted with 0–2 $R^{19}$,
  aryl($C_1$–$C_4$ alkyl)- substituted with 0–2 $R^{19}$,
  a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyridinyl, 3H-indolyl, carbazolyl, pyrrolidinyl, piperidinyl, indolinyl, or morpholinyl, said heterocyclic ring being substituted with 0–2 $R^{19}$;
  $C_1$–$C_6$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, said heterocyclic ring being substituted with 0–2 $R^{19}$.

17. A compound of claim 16 wherein:
  $R^1$ is $R^2NH(R^2N=)C-$ or $R^2NH(R^2N=)CNH-$ and V is phenyl or pyridyl; or
  $R^1$ is

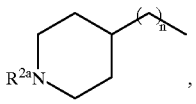

and V is a single bond;
  n is 1–2;
  $R^3$ is H or $C_1$–$C_5$ alkyl;
  X is selected from:
    —$CH_2$—,
    —$CHN(R^{16})R^{17}$—, or
    —$CHNR^5R^{5a}$—;
  W is selected from:

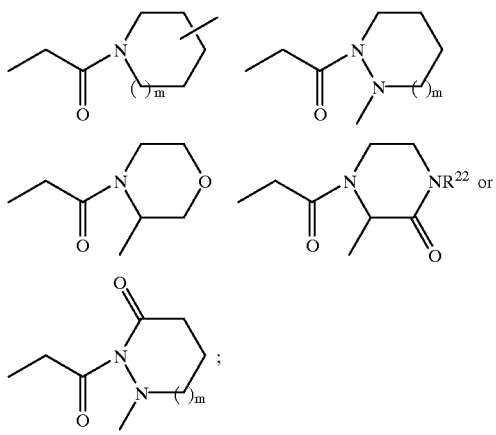

m is 1–3;

Y is selected from:
  hydroxy;
  $C_1$ to $C_{10}$ alkoxy;
  methylcarbonyloxymethoxy-;
  ethylcarbonyloxymethoxy-;
  t-butylcarbonyloxymethoxy-;
  cyclohexylcarbonyloxymethoxy-;
  1-(methylcarbonyloxy)ethoxy-;
  1-(ethylcarbonyloxy)ethoxy-;
  1-(t-butylcarbonyloxy)ethoxy-;
  1-(cyclohexylcarbonyloxy)ethoxy-;
  i-propyloxycarbonyloxymethoxy-;
  t-butyloxycarbonyloxymethoxy-;
  1-(i-propyloxycarbonyloxy)ethoxy-;
  1-(cyclohexyloxycarbonyloxy)ethoxy-;
  1-(t-butyloxycarbonyloxy)ethoxy-;
  dimethylaminoethoxy-;
  diethylaminoethoxy-;
  (5-methyl-1,3-dioxacyclopenten-2-on-4-yl)methoxy-;
  (5-(t-butyl)-1,3-dioxacyclopenten-2-on-4-yl)methoxy-;
  (1,3-dioxa-5-phenyl-cyclopenten-2-on-4-yl)methoxy-;
  1-(2-(2-methoxypropyl)carbonyloxy)ethoxy-;

$R^{19}$ is H, halogen, $C_1$–$C_4$ alkyl, $C_3$–$C_7$ cycloalkyl, cyclopropylmethyl, aryl, or benzyl;
$R^{20}$ and $R^{21}$ are both H;
$R^{22}$ is H, $C_1$–$C_4$ alkyl or benzyl.

18. A compound of claim 14, or a pharmaceutically acceptable salt form thereof, selected from:
  2-(R,S)-2-carboxymethyl-1-{5-(R,S)-N-[3-(4-amidinophenyl)isoxazolin-5-yl acetyl]piperidine;
  2-(R,S)-2-carboxymethyl-1-{5-(R,S)-N-[3-(4-amidinophenyl)isoxazolin-5-yl acetyl]azepine;
  2-(R,S)-2-carboxymethyl-1-{5-(R,S)-N-[3-(4-amidinophenyl)isoxazolin-5-yl acetyl]pyrrolidine;
  3-(R,S)-carboxymethyl-4-{5-(R,S)-N-[3-(4-amidinophenyl)isoxazolin-5-yl acetyl]piperazine-2-one;
  6-(R,S)-carboxymethyl-1-{5-(R,S)-N-[3-(4-amidinophenyl)isoxazolin-5-yl acetyl]piperidine-2-one;
  5-(R,S)-carboxymethyl-1-{5-(R,S)-N-[3-(4-amidinophenyl)isoxazolin-5-yl acetyl]pyrrolidine-2-one;
  7-(R,S)-carboxymethyl-1-{5-(R,S)-N-[3-(4-amidinophenyl)isoxazolin-5-yl acetyl]azetidine-2-one;
  2-(R,S)-carboxymethyl-1-{5-(R,S)-N-[3-(4-amidinophenyl)isoxazolin-5-yl acetyl]pyrazolidine;
  3-(R,S)-carboxymethyl-4-(5-(R,S)-N-[3-(4-amidinophenyl)isoxazolin-5-yl acetyl]morpholine.

19. A method for the prevention or treatment of thrombosis which comprises administering to a host in need of such treatment a therapeutically effective amount of a compound of claim 1.

20. A pharmaceutical composition comprising a therapeutically effective amount of a compound of claim 1, and a pharmaceutically acceptable carrier.

21. A method of inhibiting the aggregation of blood platelets which comprises administering to a host in need of such inhibition a therapeutically effective amount of a compound of claim 1.

22. A method of treating thromboembolic disorders selected from thrombus or embolus formation, harmful platelet aggregation, reocclusion following thrombolysis, reperfusion injury, restenosis, atherosclerosis, stroke, myocardial infarction, and unstable angina, which comprises administering to a host in need of such treatment a therapeutically effective amount of a compound of claim 16.

23. A method for the treatment of thrombosis which comprises administering to a host in need of such treatment a therapeutically effective amount of a compound of claim 16 in combination with one or more additional therapeutic agents selected from: a thrombolytic agent, an anticoagulant agent, or an anti-platelet agent.

24. A method of treating rheumatoid arthritis, asthma, allergies, adult respiratory syndrome, organ transplantation rejection, septic shock, psoriasis, contact dermatitis, osteoporosis, osteoarthritis, tumor metastasis, diabetic retinopathy, inflammatory conditions and inflammatory bowel disease, comprising administering to a host in need of such treatment a therapeutically effective amount of a compound of claim 16.

25. A pharmaceutical composition for intranasal administration, said composition comprising a therapeutically effective amount of a compound of claim 1, a pharmaceutically acceptable excipient, and water.

26. A method of administering a compound of claim 1, said method comprising intranasally administering, to a patient in need of such treatment, a therapeutically effective amount of a pharmaceutical composition containing said compound.

27. A pharmaceutical composition for intranasal administration, said composition comprising a therapeutically effective amount of a compound of claim 1, a pharmaceutically acceptable excipient, and water.

28. A method of administering a compound of claim 1, said method comprising intranasally administering, to a patient in need of such treatment, a therapeutically effective amount of a pharmaceutical composition containing said compound.

29. A pharmaceutical composition for intranasal administration, said composition comprising a therapeutically effective amount of a compound of claim 6, a pharmaceutically acceptable excipient, and water.

30. A method of administering a compound of claim 6, said method comprising intranasally administering, to a patient in need of such treatment, a therapeutically effective amount of a pharmaceutical composition containing said compound.

31. A pharmaceutical composition for intranasal administration, said composition comprising a therapeutically effective amount of a compound of claim 10, a pharmaceutically acceptable excipient, and water.

32. A method of administering a compound of claim 10, said method comprising intranasally administering, to a patient in need of such treatment, a therapeutically effective amount of a pharmaceutical composition containing said compound.

33. A pharmaceutical composition for intranasal administration, said composition comprising a therapeutically effective amount of a compound of claim 14 a pharmaceutically acceptable excipient, and water.

34. A method of administering a compound of claim 14, said method comprising intranasally administering, to a patient in need of such treatment, a therapeutically effective amount of a pharmaceutical composition containing said compound.

35. A method for the prevention or treatment of thrombosis which comprises administering to a host in need of such treatment a therapeutically effective amount of a compound of claim 6.

36. A method for the prevention or treatment of thrombosis which comprises administering to a host in need of such treatment a therapeutical effective amount of a compound of claim 10.

37. A method for the prevention or treatment of thrombosis which comprises administering to a host in need of such treatment a therapeutically effective amount of a compound of claim 11.

38. A pharmaceutical composition comprising a therapeutically effective amount of a compound of claim 6 and a pharmaceutically acceptable carrier.

39. A pharmaceutical composition comprising a therapeutically effective amount of a compound of claim 10 and a pharmaceutically acceptable carrier.

40. A pharmaceutical composition comprising a therapeutically effective amount of a compound of claim 14 and a pharmaceutically acceptable carrier.

41. A method of inhibiting the aggregation of blood platelets which comprises administering to a host in need of such inhibition a therapeutically effective amount of a compound of claim 6.

42. A method of inhibiting the aggregation of blood platelets which comprises administering to a host in need of such inhibition a therapeutically effective amount of a compound of claim 10.

43. A method of inhibiting the aggregation of blood platelets which comprises administering to a host in need of such inhibition a therapeutically effective amount of a compound of claim 14.

44. A pharmaceutical composition for intranasal administration, said composition comprising a therapeutically effective amount of a compound of claim 6, a pharmaceutically acceptable excipient, and water.

45. A pharmaceutical composition for intranasal administration, said composition comprising a therapeutically effective amount of a compound of claim 10, a pharmaceutically acceptable excipient, and water.

46. A pharmaceutical composition for intranasal administration, said composition comprising a therapeutically effective amount of a compound of claim 14, a pharmaceutically acceptable excipient, and water.

47. A method of administering a compound of claim 6 said method comprising intranasally administering, to a patient in need of such treatment, a therapeutically effective amount of a pharmaceutical composition containing said compound.

48. A method of administering a compound of claim 10 said method comprising intranasally administering, to a patient in need of such treatment, a therapeutically effective amount of a pharmaceutical composition containing said compound.

49. A method of administering a compound of claim 19 said method comprising intranasally administering, to a patient in need of such treatment, a therapeutically effective amount of a pharmaceutical composition containing said compound.

* * * * *